US010472643B2

(12) United States Patent
Wei et al.

(10) Patent No.: US 10,472,643 B2
(45) Date of Patent: Nov. 12, 2019

(54) AGENTS FOR ENHANCEMENT OF PRODUCTION OF BIOFUEL PRECURSORS IN MICROALGAE

(71) Applicant: The Regents of the University of California, Oakland, CA (US)

(72) Inventors: Chia-Lin Wei, West Hartford, CT (US); Chew Yee Ngan, West Hartford, CT (US); Chee Hong Wong, West Hartford, CT (US); Cindy Choi, San Ramon, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/222,970

(22) Filed: Dec. 17, 2018

(65) Prior Publication Data

US 2019/0112615 A1 Apr. 18, 2019

Related U.S. Application Data

(60) Division of application No. 15/243,896, filed on Aug. 22, 2016, now Pat. No. 10,155,954, which is a continuation of application No. PCT/US2015/017586, filed on Feb. 25, 2015.

(60) Provisional application No. 62/051,265, filed on Sep. 16, 2014, provisional application No. 61/944,507, filed on Feb. 25, 2014.

(51) Int. Cl.

| | |
|---|---|
| ***C12N 15/82*** | (2006.01) |
| ***C07K 14/40*** | (2006.01) |
| ***C12P 7/64*** | (2006.01) |
| ***C07K 14/405*** | (2006.01) |

(52) U.S. Cl.

CPC ........ *C12N 15/8247* (2013.01); *C07K 14/405* (2013.01); *C12P 7/64* (2013.01)

(58) Field of Classification Search

None

See application file for complete search history.

(56) References Cited

U.S. PATENT DOCUMENTS

| | | | | |
|---|---|---|---|---|
| 7,424,370 | B2 | 9/2008 | Sachdeva et al. | |
| 9,040,264 | B2 | 5/2015 | Kristof et al. | |
| 2005/0288866 | A1 | 12/2005 | Sachdeva et al. | |
| 2010/0255550 | A1* | 10/2010 | Benning .............. | C07K 14/405 435/134 |
| 2012/0252080 | A1 | 10/2012 | Kristof et al. | |

OTHER PUBLICATIONS

Breuer et al 2012 (Bioresource Technology 124: p. 217-226).*

International Search Report and Written Opinion, PCT/US2015/017586, dated Aug. 4, 2015, 12 pages.

Rubio, et al., "A conserved MYB transcription factor involved in phosphate starvation signaling both in vascular plants and in unicellular algae," Genes & Development 15, 2122-2133 (2001).

Wykoff, et al., "Psr1, a nuclear localized protein that regulates phosphorus metabolism in Chlamydomonas," Proceedings of the National Academy of Sciences of the United States of America 96, 15336-15341 (1999).

Shen et al, "Expression of ZmLEC1 and ZmWRI1 Increases Seed Oil Production in Maize," Plant Physiology 153: p. 980-987 (2010).

* cited by examiner

*Primary Examiner* — Matthew R Keogh

(74) *Attorney, Agent, or Firm* — Robin C. Chiang; Lawrence Berkeley National Laboratory

(57) ABSTRACT

We identified 17 transcription factor genes that regulate lipid production and activity in an organism. We subsequently detailed characterization of one of them (psr1). Constructs, methods and systems for enhancing or increasing lipid production in an organism are described.

11 Claims, 46 Drawing Sheets

Figure 1:
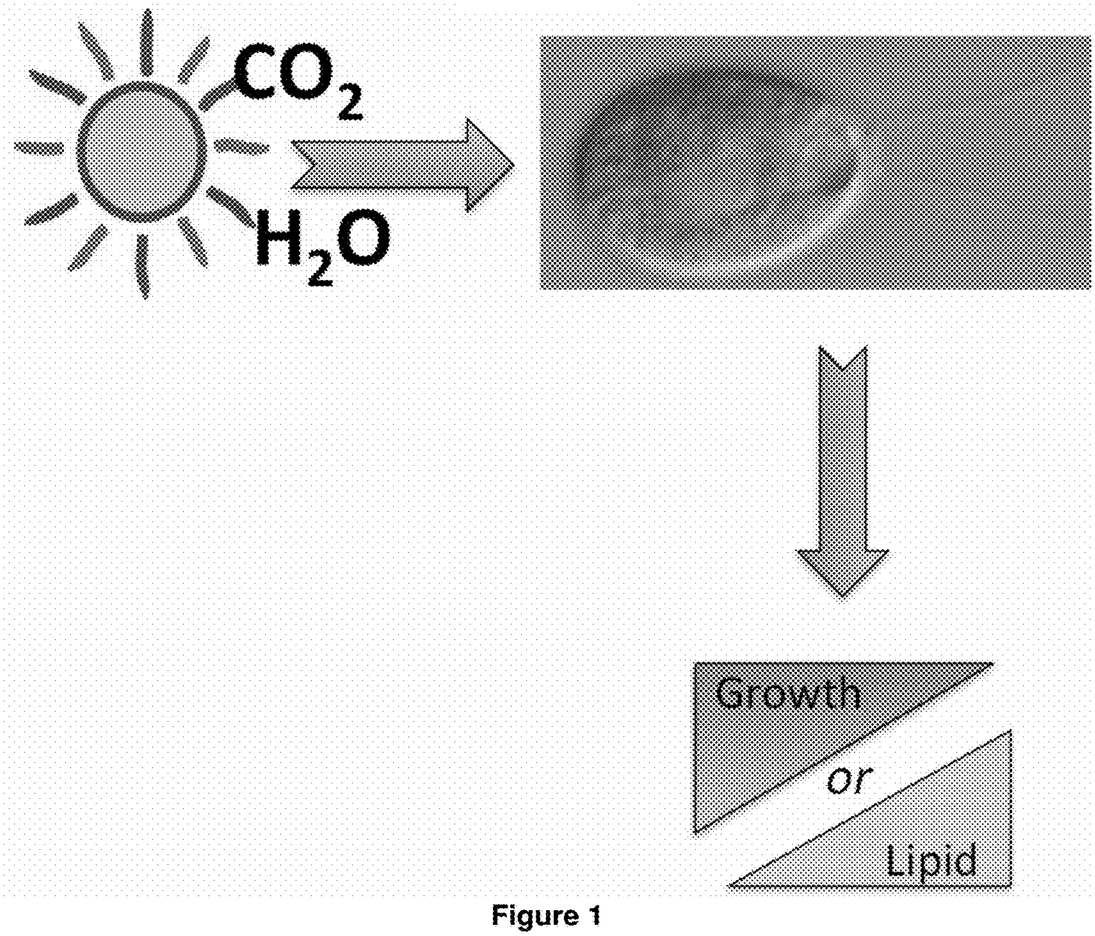

Specification includes a Sequence Listing.

RNA expression

Total 9 time points

Chromatin modifications

Total 2 conditions x 6 marks

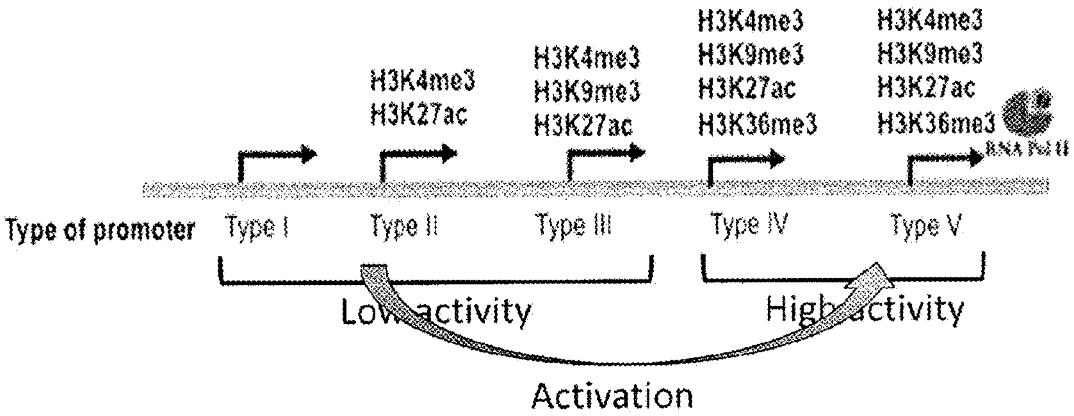
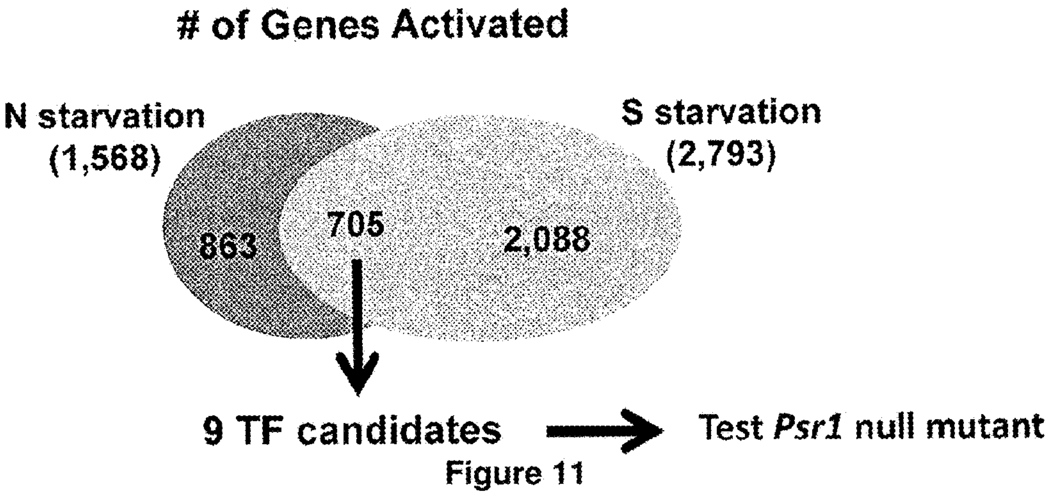
Figure 11

48 WT & 48 *Psr1* over-expressing clones
48 hr growth in rich medium (TAP)
Cell # & total Nile Red fluorescence (C)

(D)

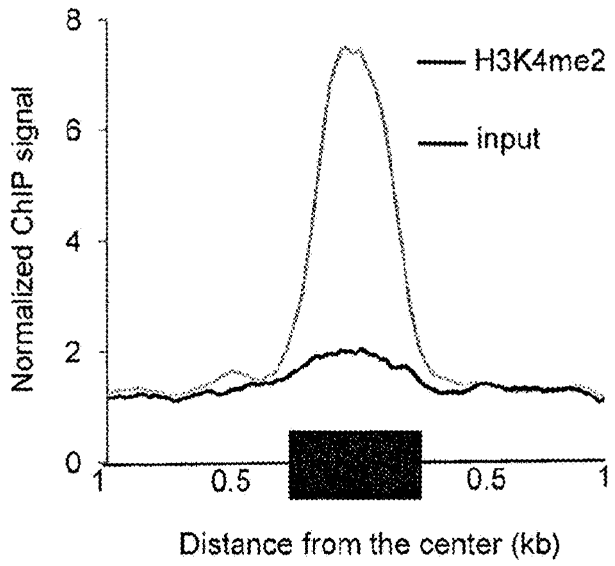
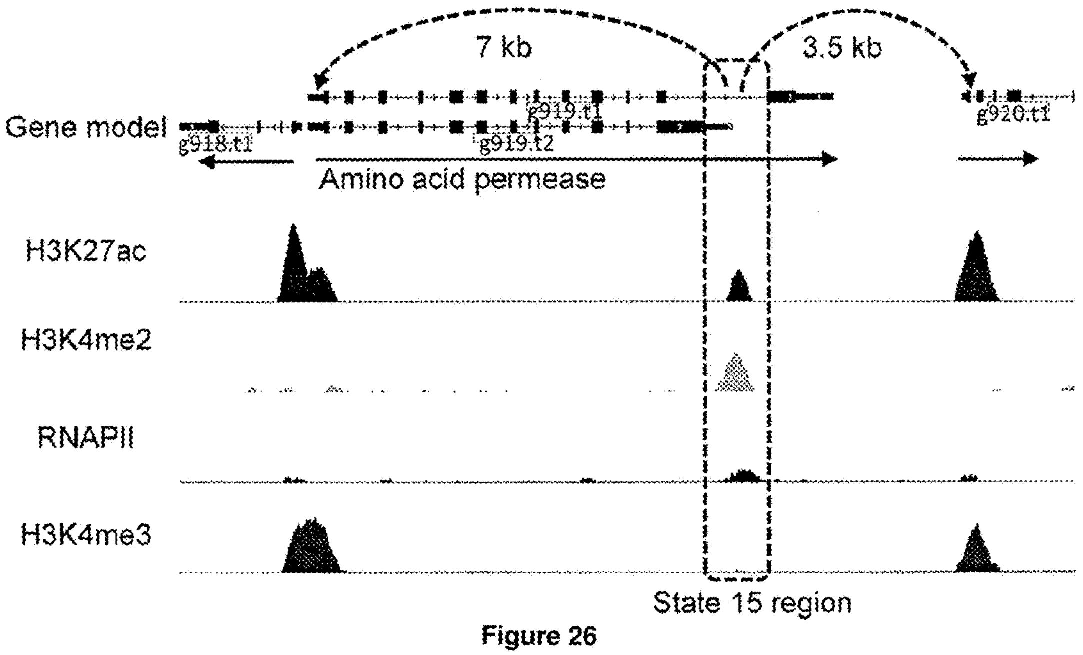
Figure 26

| Gene number | | N- promoter | | |
|---|---|---|---|---|
| | | I+II+III | IV | V |
| TAP promoter | I+II+III | 4,503 | 608 | 82 |
| | IV | 415 | 5,563 | 552 |
| | V | 40 | 1,162 | 1,188 |

| Gene number | | S- promoter | | |
|---|---|---|---|---|
| | | I+II+III | IV | V |
| TAP promoter | I+II+III | 4,689 | 441 | 109 |
| | IV | 410 | 5,475 | 1,656 |
| | V | 17 | 456 | 1,905 |

➡ Inactive to active state in N-  ⇨ Inactive to active state in S-

Chromatin states in WT, N- and S- conditions

| State | H3K27ac | H3K27me3 | H3K36me3 | H3K4me3 | H3K9me3 | RNAPII | % of genome WT | % of genome N- | % of genome S- |
|---|---|---|---|---|---|---|---|---|---|
| CS 1 | | | | | | | 0.19 | 0.51 | 0.07 |
| CS 2 | | | | | | | 0.43 | 0.23 | 0.00 |
| CS 3 | | | | | | | 1.52 | 1.15 | 0.73 |
| CS 4 | | | | | | | 0.28 | 0.18 | 0.19 |
| CS 5 | | | | | | | 0.82 | 0.82 | 1.03 |
| CS 6 | | | | | | | 0.05 | 0.14 | 0.31 |
| CS 7 | | | | | | | 0.00 | 0.05 | 1.66 |
| CS 8 | | | | | | | 0.03 | 0.52 | 3.71 |
| CS 9 | | | | | | | 5.45 | 5.43 | 0.87 |
| CS 10 | | | | | | | 0.16 | 0.21 | 0.11 |
| CS 11 | | | | | | | 1.55 | 1.15 | 0.64 |
| CS12 | | | | | | | 0.08 | 0.03 | 0.00 |
| CS 13 | | | | | | | 1.64 | 0.35 | 0.00 |
| CS 14 | | | | | | | 0.57 | 2.44 | 2.83 |
| CS 15 | | | | | | | 0.52 | 0.13 | 0.15 |
| CS16 | | | | | | | 86.72 | 86.65 | 87.69 |

0 Frequency

```
>sp|P68431|H31_HUMAN Histone H3.1 OS=Homo sapiens
GN=HIST1H3A PE=1 SV=2
>Creinhardtii|Cre06.g265000|Cre06.g265000.t1.2
(histone3, 32 copies in total)

Query coverage=98%, E-value=3e-92
Identities=127/134(95%), Positives=130/134(97%),
Gaps=1/134(0%)

 01 MARTKQTARKSTGGKAPRKQLATKAARKSAPATGGVKKPHRYRPGTVALR(SEQ ID:29)
    ||||||||||||||||||||||||||||+ ||||||||||||||||||||
 01 MARTKQTARKSTGGKAPRKQLATKAARKT-PATGGVKKPHRYRPGTVALR(SEQ ID:30)

 51 EIRRYQKSTELLIRKLPFQRLVREIAQDFKTDLRFQSSAVMALQEACEAY(SEQ ID:31)
    |||+|||||||||||||||||||||||||||||||||| ||+||||| |||
 51 EIRKYQKSTELLIRKLPFQRLVREIAQDFKTDLRFQSQAVLALQEAAEAY(SEQ ID:32)

101 LVGLFEDTNLCAIHAKRVTIMPKDIQLARRIRGERA--------------(SEQ ID:33)
    ||||||||||||||||||||||||||||||||||
101 LVGLFEDTNLCAIHAKRVTIMPKDIQLARRIRGSTPANTYGLLDTAAAGD(SEQ ID:34)

150 -----------------------------------------

150 LLFSVSPRSGSVVVVDVSGGSMASRQLLAAGLPVSSMGLAVAC(SEQ ID:35)
```

Figure 40A

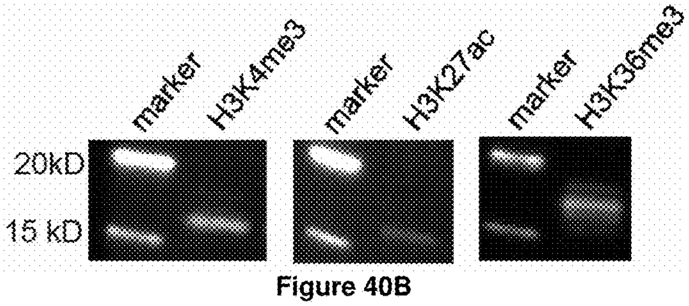

Figure 40B

AGENTS FOR ENHANCEMENT OF PRODUCTION OF BIOFUEL PRECURSORS IN MICROALGAE

CROSS-REFERENCES TO RELATED APPLICATIONS

This application is a divisional of U.S. patent application Ser. No. 15/243,896, filed on Aug. 22, 2016, now U.S. Pat. No. 10,155,954, issued Dec. 18, 2018, which is a continuation of PCT application PCT/US15/17586, filed on Feb. 25, 2015, which is a non-provisional of and claims the benefit of the filing date of U.S. Patent Application No. 61/944,507, filed on Feb. 25, 2014 and U.S. Patent Application No. 62/051,265, filed on Sep. 16, 2014. Each application is herein incorporated by reference in its entirety for all purposes.

STATEMENT OF GOVERNMENTAL SUPPORT

This invention was made with government support under Contract No. DE-ACO2-05CH11231 awarded by the U.S. Department of Energy. The government has certain rights in the invention.

BACKGROUND OF THE INVENTION

Field of the Invention

The present invention relates to synthetic biology, especially using microalgae for the production of biofuels.

Related Art

Biodiesel is one of the most promising renewable transportation fuels that have achieved remarkable success worldwide. However, the current contribution of biodiesel to global transportation fuel consumption is only 0.14%. Oil-rich microalgae have been demonstrated to be a promising alternative source of lipids for biodiesel production. To enhance the economical cost-effectiveness and environmental sustainability, many strategies were proposed and extensive studies have been carried out to attempt lipid overproduction in microalgae. These approaches include, but not limit to, manipulating the nutritional or cultivation conditions and genetic engineering microalgae strain. overexpression key enzymes in the lipid precursor TAG biosynthetic pathways. Nevertheless, significant challenges remain as these approaches seem to be either harmful to cell growth or lack of success due to the emerging of "secondary bottlenecks"

Challenges for algal biofuels include that there is no "ideal" algal species identified. Lipid accumulation tightly coupled to nutrient stress. Lipid pathway gene over-expression is largely unsuccessful. Efficient fuel production will require pathway engineering and there is only a rudimentary understanding of metabolic regulation in algae. Thus, a systems-level understanding of metabolic regulation in microalgae is needed.

BRIEF DESCRIPTION OF THE SEQUENCES

The sequences described in the sequence listing provide the nucleotide and protein sequences of 17 transcription factors which can be used for enhancing or increasing lipid production or activity in an organism.

SEQ ID NO:1 is chr_12:8383195..8384442 forward primer for enhancer assay from Table 7.

SEQ ID NO:2 is chr_12:8383195..8384442 reverse primer for enhancer assay from Table 7.

SEQ ID NO:3 is chr_17:6268127..6269127 forward primer for enhancer assay from Table 7.

SEQ ID NO:4 is chr_17:6268127..6269127 reverse primer for enhancer assay from Table 7.

SEQ ID NO:5 is chr_1:5750235..5751235 forward primer for enhancer assay from Table 7.

SEQ ID NO:6 is chr_1:5750235..5751235 reverse primer for enhancer assay from Table 7.

SEQ ID NO:7 is chr_5:1650592..1651592 forward primer for enhancer assay from Table 7.

SEQ ID NO:8 is chr_5:1650592..1651592 reverse primer for enhancer assay from Table 7.

SEQ ID NO:9 is chr_7:1252718..1253788 forward primer for enhancer assay from Table 7.

SEQ ID NO:10 is chr_7:1252718..1253788 reverse primer for enhancer assay from Table 7.

SEQ ID NO:11 is chr_16:1135475..1136475 forward primer for enhancer assay from Table 7.

SEQ ID NO:12 is chr_16:1135475..1136475 reverse primer for enhancer assay from Table 7.

SEQ ID NO:13 is chr_14:2768740..2769740 forward primer for enhancer assay from Table 7.

SEQ ID NO:14 is chr_14:2768740..2769740 reverse primer for enhancer assay from Table 7.

SEQ ID NO:15 is chr_4:2122753..2123753 forward primer for enhancer assay from Table 7.

SEQ ID NO:16 is chr_4:2122753..2123753 reverse primer for enhancer assay from Table 7.

SEQ ID NO:17 is chr_17:4717149..4718149 forward primer for enhancer assay from Table 7.

SEQ ID NO:18 is chr_17:4717149..4718149 reverse primer for enhancer assay from Table 7.

SEQ ID NO:19 is chr_7:2540672..2541672 forward primer for enhancer assay from Table 7.

SEQ ID NO:20 is chr_7:2540672..2541672 reverse primer for enhancer assay from Table 7.

SEQ ID NO:21 is chr_1:4459808..4460808 forward primer for enhancer assay from Table 7.

SEQ ID NO:22 is chr_1:4459808..4460808 reverse primer for enhancer assay from Table 7.

SEQ ID NO:23 is chr_3:1,064,061..1,065,052 forward primer for enhancer assay from Table 7.

SEQ ID NO:24 is chr_3:1,064,061..1,065,052 reverse primer for enhancer assay from Table 7.

SEQ ID NO:25 is chr_5:2426137..2427133 forward primer for enhancer assay from Table 7.

SEQ ID NO:26 is chr_5:2426137..2427133 reverse primer for enhancer assay from Table 7.

SEQ ID NO:27 is chr_2:1,048,210..1,049,203 forward primer for enhancer assay from Table 7.

SEQ ID NO:28 is chr_2:1,048,210..1,049,203 reverse primer for enhancer assay from Table 7.

SEQ ID NO:29 is human pair-wise alignment sequence of H3 protein sequences between *C. reinhardtii* and human from FIG. 40A.

SEQ ID NO:30 is *C. reinhardtii* pair-wise alignment sequence of H3 protein sequences between *C. reinhardtii* and human from FIG. 40A.

SEQ ID NO:31 is human pair-wise alignment sequence of H3 protein sequences between *C. reinhardtii* and human from FIG. 40A.

SEQ ID NO:32 is *C. reinhardtii* pair-wise alignment sequence of H3 protein sequences between *C. reinhardtii* and human from FIG. 40A.

SEQ ID NO:33 is human pair-wise alignment sequence of H3 protein sequences between *C. reinhardtii* and human from FIG. 40A.

SEQ ID NO:34 is *C. reinhardtii* pair-wise alignment sequence of H3 protein sequences between *C. reinhardtii* and human from FIG. 40A.

SEQ ID NO:35 is *C. reinhardtii* pair-wise alignment sequence of H3 protein sequences between *C. reinhardtii* and human from FIG. 40A.

SEQ ID NO:36 is transcript sequence for activated transcription factor.

SEQ ID NO:37 is coding sequence for activated transcription factor.

SEQ ID NO:38 is protein sequence for activated transcription factor.

SEQ ID NO:39 is transcript sequence for activated transcription factor.

SEQ ID NO:40 is coding sequence for activated transcription factor.

SEQ ID NO:41 is protein sequence for activated transcription factor.

SEQ ID NO:42 is transcript sequence for activated transcription factor.

SEQ ID NO:43 is coding sequence for activated transcription factor.

SEQ ID NO:44 is protein sequence for activated transcription factor.

SEQ ID NO:45 is transcript sequence for activated transcription factor.

SEQ ID NO:46 is coding sequence for activated transcription factor.

SEQ ID NO:47 is protein sequence for activated transcription factor.

SEQ ID NO:48 is transcript sequence for activated transcription factor.

SEQ ID NO:49 is coding sequence for activated transcription factor.

SEQ ID NO:50 is protein sequence for activated transcription factor.

SEQ ID NO:51 is transcript sequence for activated transcription factor.

SEQ ID NO:52 is coding sequence for activated transcription factor.

SEQ ID NO:53 is protein sequence for activated transcription factor.

SEQ ID NO:54 is transcript sequence for activated transcription factor.

SEQ ID NO:55 is coding sequence for activated transcription factor.

SEQ ID NO:56 is protein sequence for activated transcription factor.

SEQ ID NO:57 is transcript sequence for activated transcription factor.

SEQ ID NO:58 is coding sequence for activated transcription factor.

SEQ ID NO:59 is protein sequence for activated transcription factor.

SEQ ID NO:60 is transcript sequence for activated transcription factor.

SEQ ID NO:61 is coding sequence for activated transcription factor.

SEQ ID NO:62 is protein sequence for activated transcription factor.

SEQ ID NO:63 is transcript sequence for inactivated transcription factor.

SEQ ID NO:64 is coding sequence for inactivated transcription factor.

SEQ ID NO:65 is protein sequence for inactivated transcription factor.

SEQ ID NO:66 is transcript sequence for inactivated transcription factor.

SEQ ID NO:67 is coding sequence for inactivated transcription factor.

SEQ ID NO:68 is protein sequence for inactivated transcription factor.

SEQ ID NO:69 is transcript sequence for inactivated transcription factor.

SEQ ID NO:70 is coding sequence for inactivated transcription factor.

SEQ ID NO:71 is protein sequence for inactivated transcription factor.

SEQ ID NO:72 is transcript sequence for inactivated transcription factor.

SEQ ID NO:73 is coding sequence for inactivated transcription factor.

SEQ ID NO:74 is protein sequence for inactivated transcription factor.

SEQ ID NO:75 is transcript sequence for inactivated transcription factor.

SEQ ID NO:76 is coding sequence for inactivated transcription factor.

SEQ ID NO:77 is protein sequence for inactivated transcription factor.

SEQ ID NO:78 is transcript sequence for inactivated transcription factor.

SEQ ID NO:79 is coding sequence for inactivated transcription factor.

SEQ ID NO:80 is protein sequence for inactivated transcription factor.

SEQ ID NO:81 is transcript sequence for inactivated transcription factor.

SEQ ID NO:82 is coding sequence for inactivated transcription factor.

SEQ ID NO:83 is protein sequence for inactivated transcription factor.

SEQ ID NO:84 is transcript sequence for inactivated transcription factor.

SEQ ID NO:85 is coding sequence for inactivated transcription factor.

SEQ ID NO:86 is protein sequence for inactivated transcription factor.

SEQ ID NO:87 is a rabbit polyclonal antibody raised against PSR1 peptide.

SEQ ID NO:88 is a rabbit polyclonal antibody raised against PSR1 peptide.

SEQ ID NO:89 is forward primer for PCR amplification of *C. reinhardtii* PSR1 cDNA.

SEQ ID NO:90 is reverse primer for PCR amplification of *C. reinhardtii* PSR1 cDNA.

SEQ ID NO:91 is forward primer for amplification of psr1 open reading frame fragments.

SEQ ID NO:92 is reverse primer for amplification of psr1 open reading frame fragments.

SEQ ID NO:93 is forward primer for amplification of PSR1 cDNA.

SEQ ID NO:94 is reverse primer for amplification of PSR1 cDNA.

SEQ ID NO:95 is PSR1 forward primer.

SEQ ID NO:96 is PSR1 reverse primer.

SEQ ID NO:97 is CBLP forward primer.

SEQ ID NO:98 is CBLP reverse primer.

SEQ ID NO:99 is XP_001700553.1, phosphorus starvation response 1 protein, transcriptional regulator, *Chlamydomonas reinhardtii.*

SEQ ID NO:100 is 6-base repeats.

SEQ ID NO:101 is palindromic motif.

BRIEF DESCRIPTION OF THE DRAWINGS AND TABLES

FIG. 1: Biofuels from Microalgae: The Current Challenges. Challenges for algal biofuels include that there are no "ideal" algal species identified, lipid accumulation is tightly coupled to nutrient stress, lipid pathway gene over-expression is largely unsuccessful, efficient fuel production will require pathway engineering, and there is a rudimentary understanding of metabolic regulation in algae. A systems-level understanding of metabolic regulation in microalgae is needed.

Figure 2:
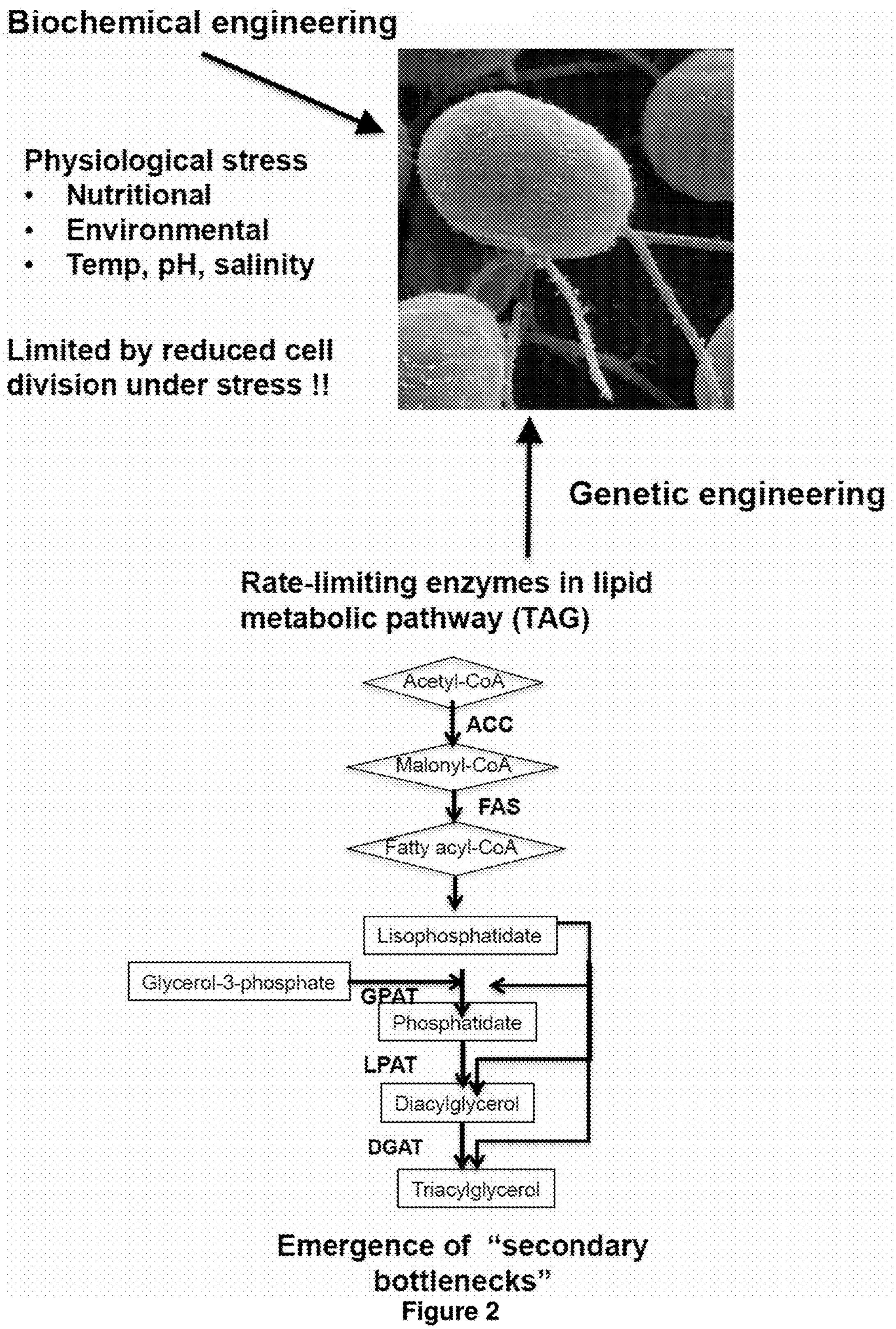

FIG. 2: Schematic describing lipid over-production strategies in microalgae.

Figure 3:
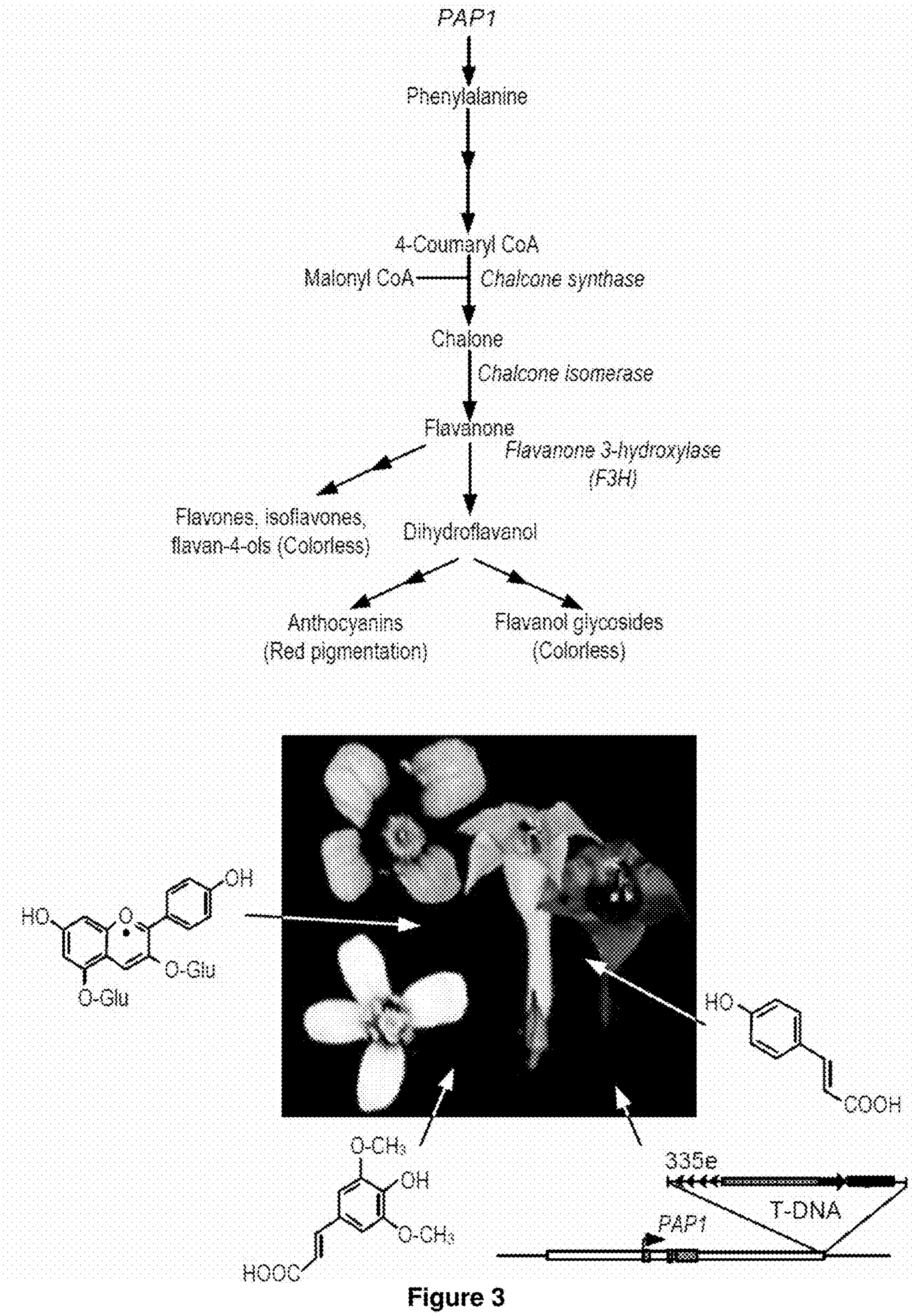

FIG. 3: Transcription Factor Engineering for PAP1 over-expression enhances pigmentation in *Arabidopsis*. Manipulate the transcriptional regulators that control TAG synthesis & storage.

Figure 4:
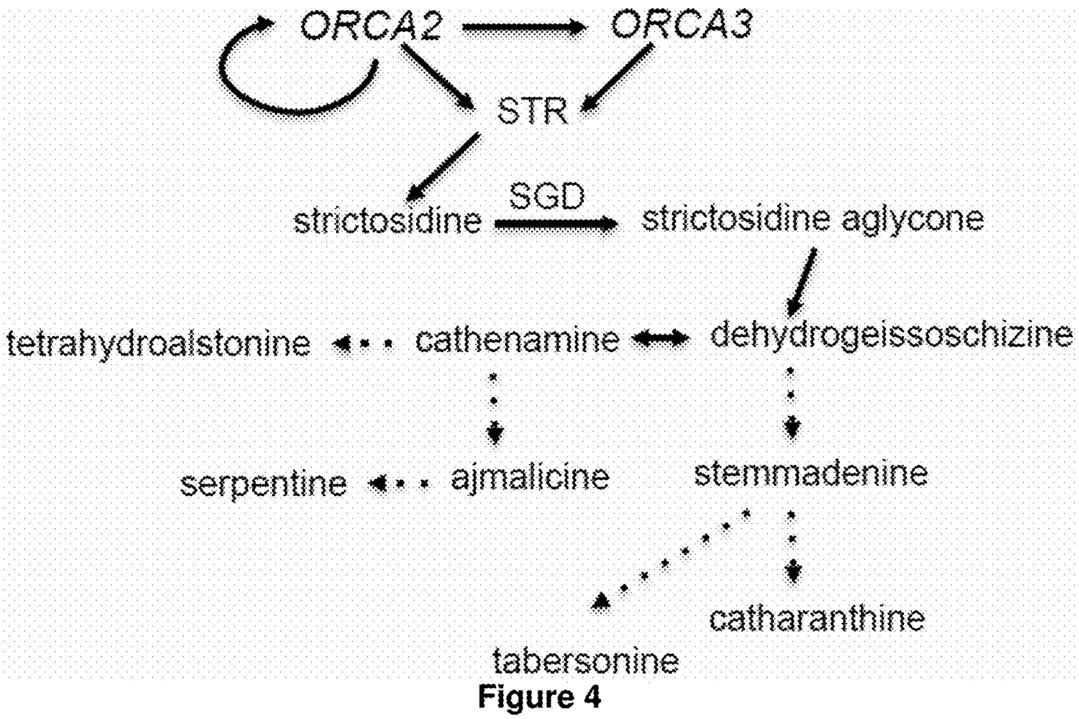

FIG. 4: Transcription Factor Engineering for ORCA3 over-expression enhances TIA biosynthesis in Tobacco. Manipulate the transcriptional regulators that control TAG synthesis & storage.

Figure 5:
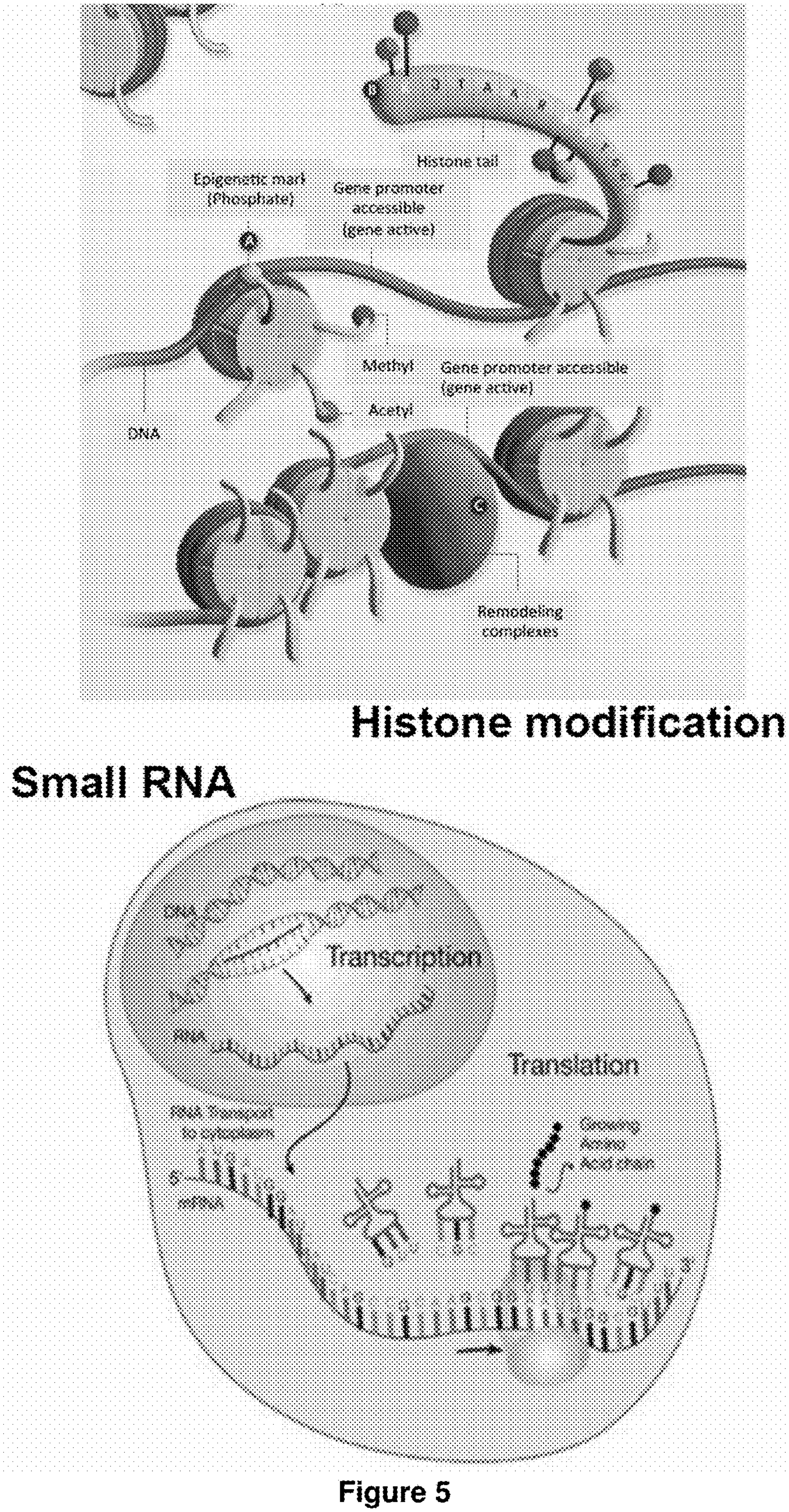

FIG. 5 illustrates Epigenome Analysis-chromatin state directly reflects transcriptional activity.

Figure 6:
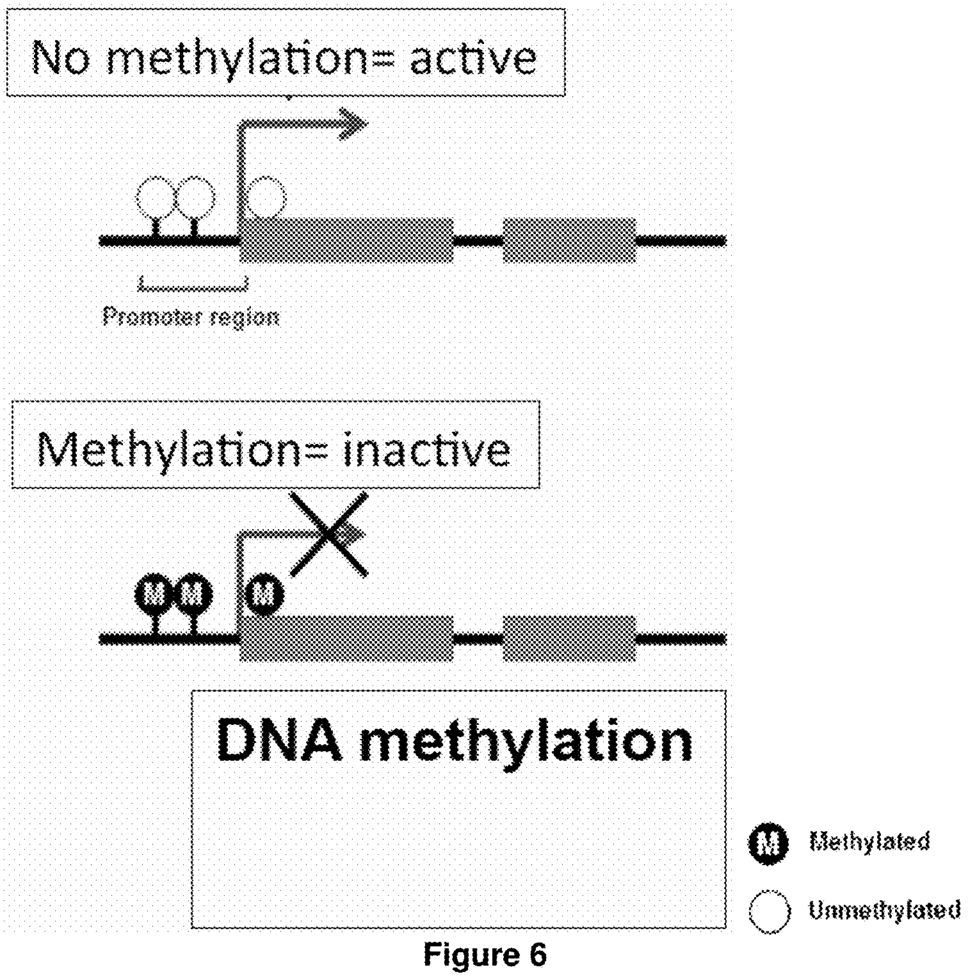

FIG. 6 illustrates Epigenome Analysis-chromatin state directly reflects transcriptional activity. Epigenetic analysis can identify master regulators of lipid accumulation. We hypothesized that TFs acting as master regulators for lipid biosynthetic pathways are induced by the *Chlamydomonas* stress response and that changes in chromatin state can predict TF regulators that standard transcript abundance studies have missed. Our approach was to measure genome-wide changes in chromatin state in *Chlamydomonas* subjected to lipid-inducing conditions, identify genes activated or repressed based on chromatin state & focus on transcription factors and test TF function by gene inactivation and over-expression.

Figure 7:
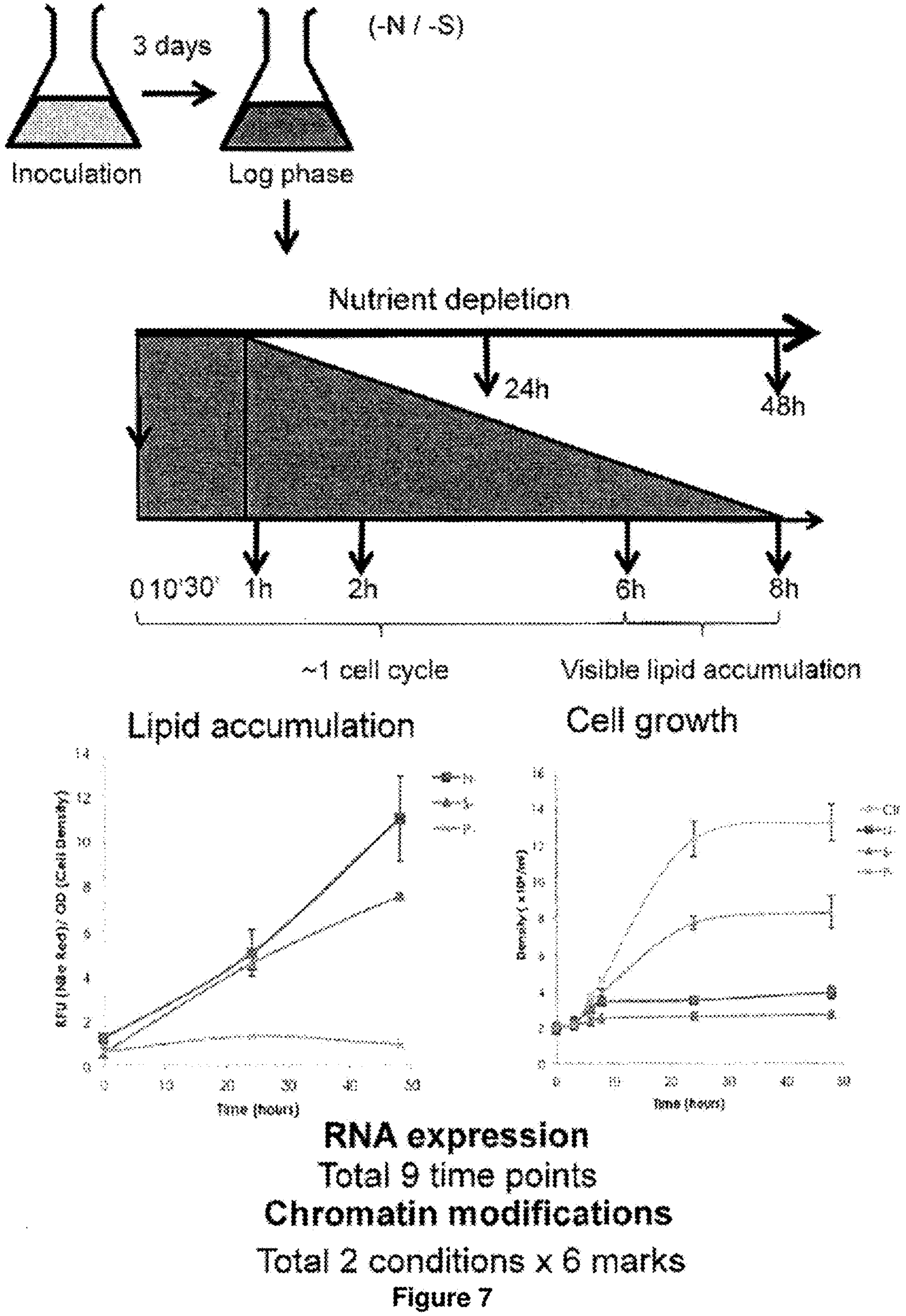

FIG. 7 shows preliminary experiments performed.

Figure 8:
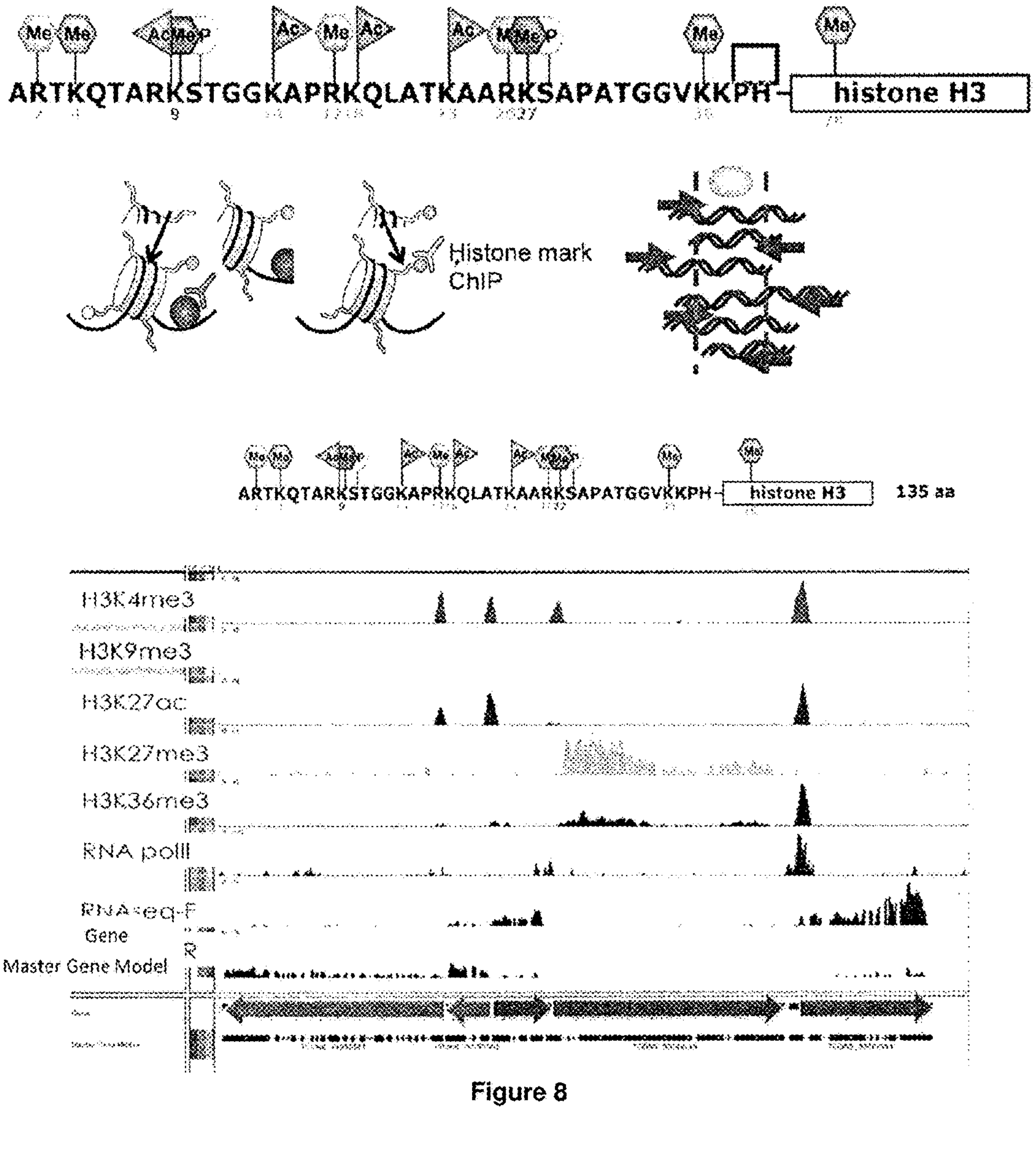

FIG. 8 CHIP-Seq mapping of chromatin modifications. A ChIP-Seq experiment start by fragmenting the sample, follow by enriching with antibody specific to the protein of interest. The DNA fragments bound by the targeted proteins is than released for sequencing. The reads from the sequenced are mapped and extended to construct a combined read density profile. We perform the experiment for 7 PTMs on histone H3 protein and the protein Pol II. This is how the data look like after processing. (ARTKQTARKSTGGKAPRKQLATKAARKSAPATG GVKKPH=SEQ ID NO:103)

Figure 9:
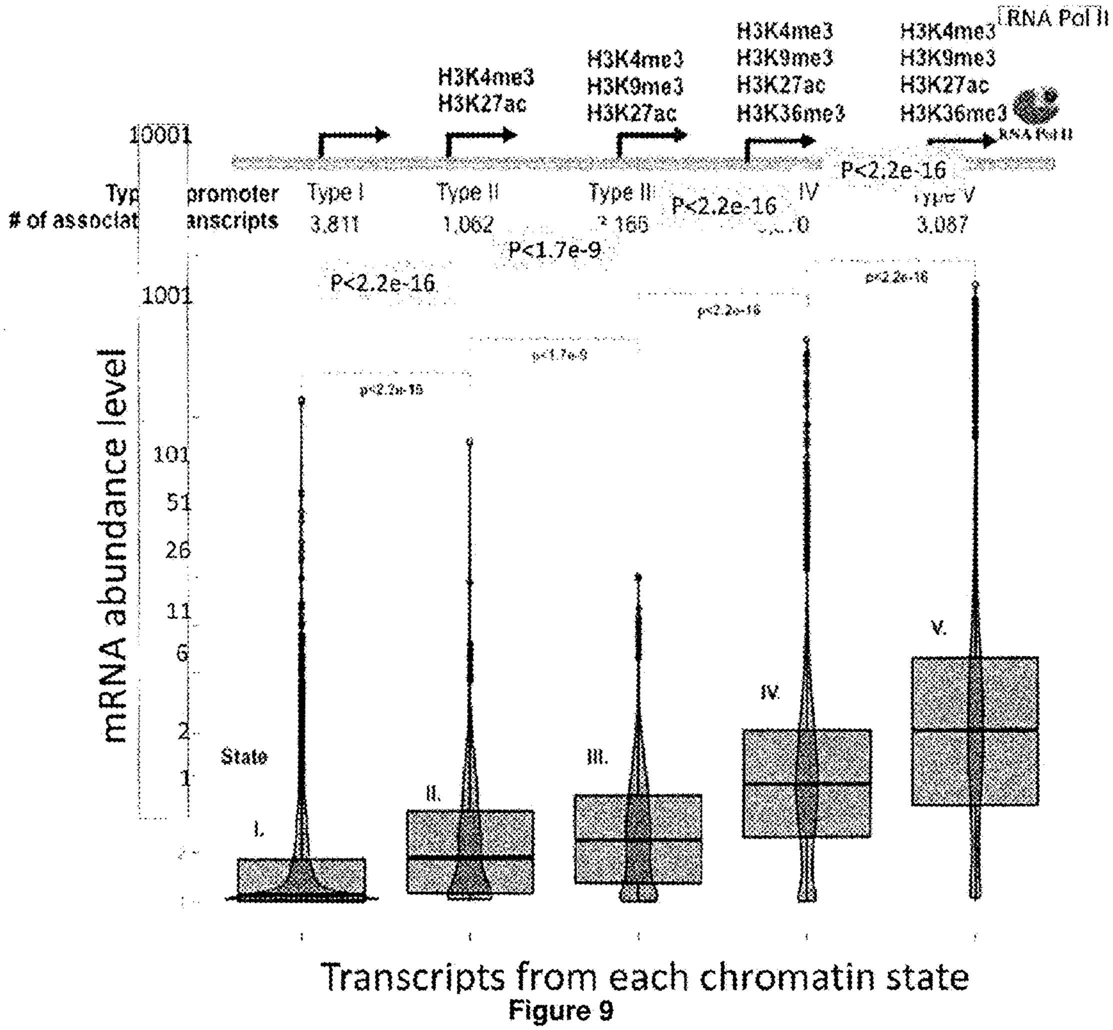

FIG. 9 shows Chromatin state is highly correlated with transcript abundance in *Chlamydomonas*. Chromatin modifications occur in particular patterns and we are able to assign all the gene promoters in the Chlamy genome to one of 5 patterns differing by progressive addition of modifications. These patterns are highly associated with the abundance transcripts driven by these promoters, but note the very wide variation in abundance for each promoter type. The power of chromatin state analysis comes from being able to identify genes encoding relatively low abundance transcripts as transcriptionally activated. Then point to the bottom of range of type Iv and type V promoters.

Figure 10:
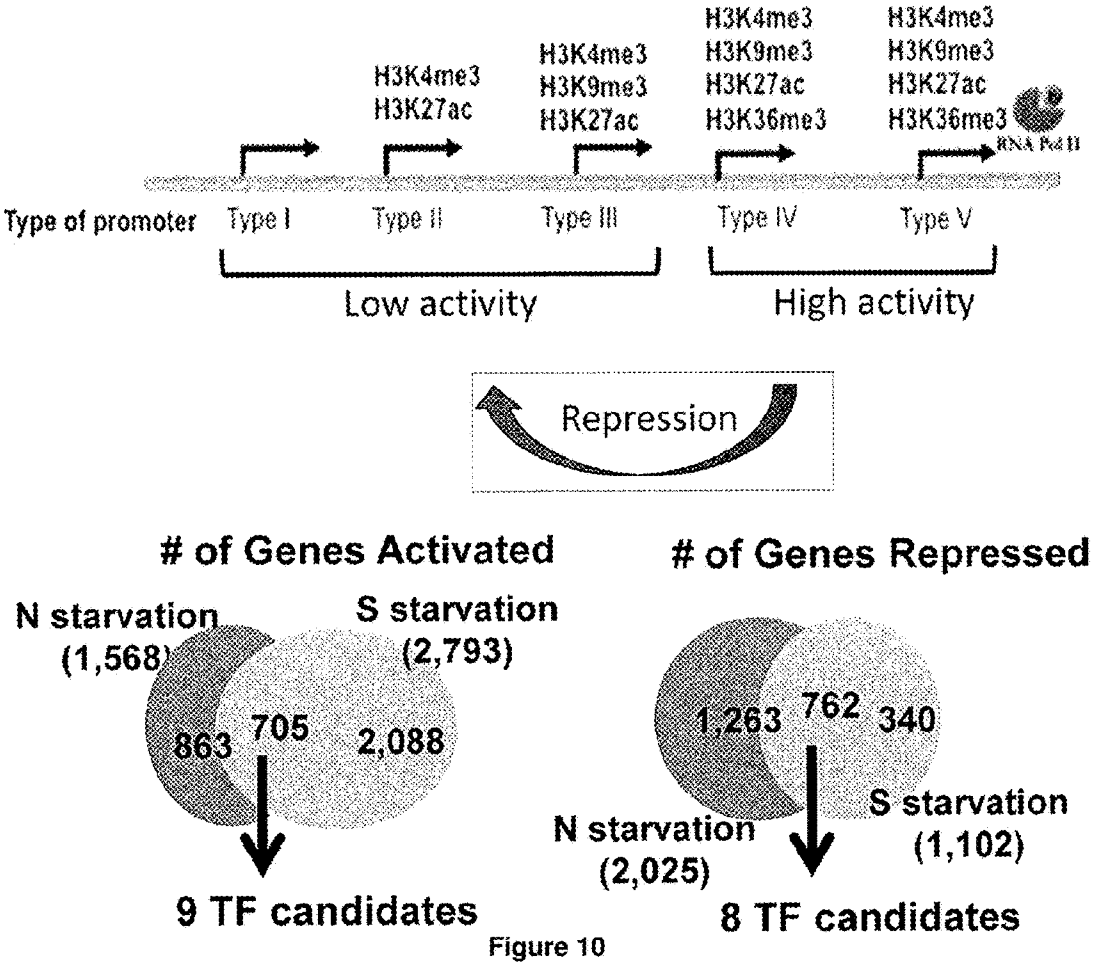

FIG. 10: Candidate regulators inferred from chromatin state transitions.

FIG. 11: Candidate regulators inferred from chromatin state transitions.

Figure 12:
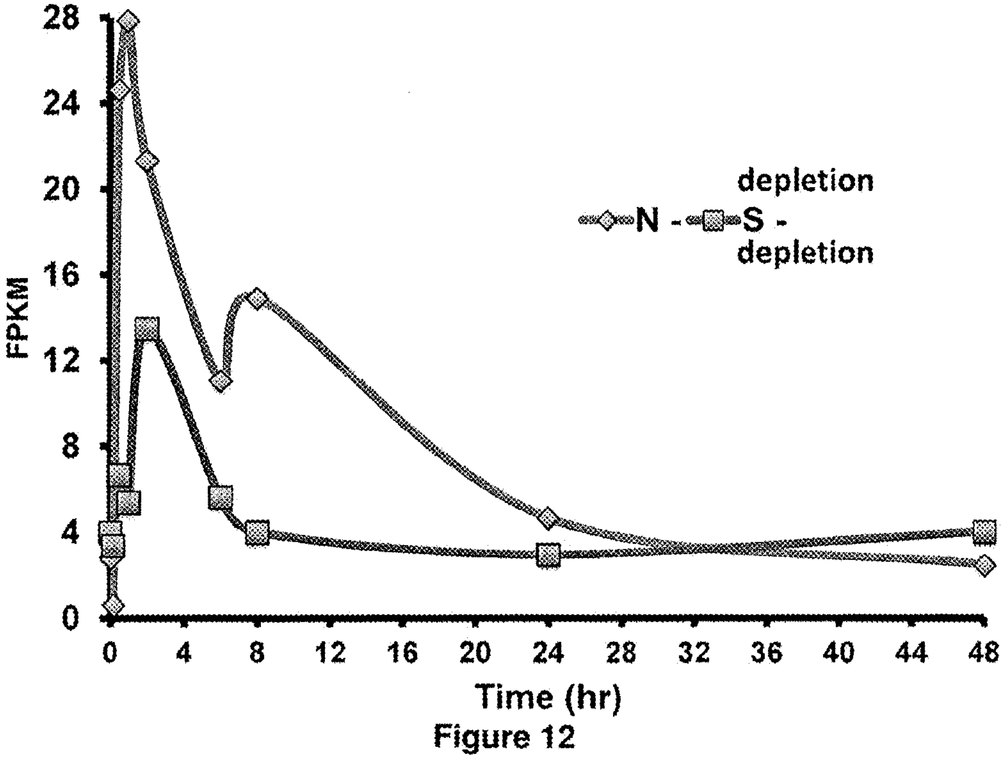

FIG. 12 shows Psr1 mRNA level during stress. Psr1 overlooked from expression data alone. Expression is transient and peak expression is low to modest. This demonstrates the power of epigenomic analysis.

Figure 13:
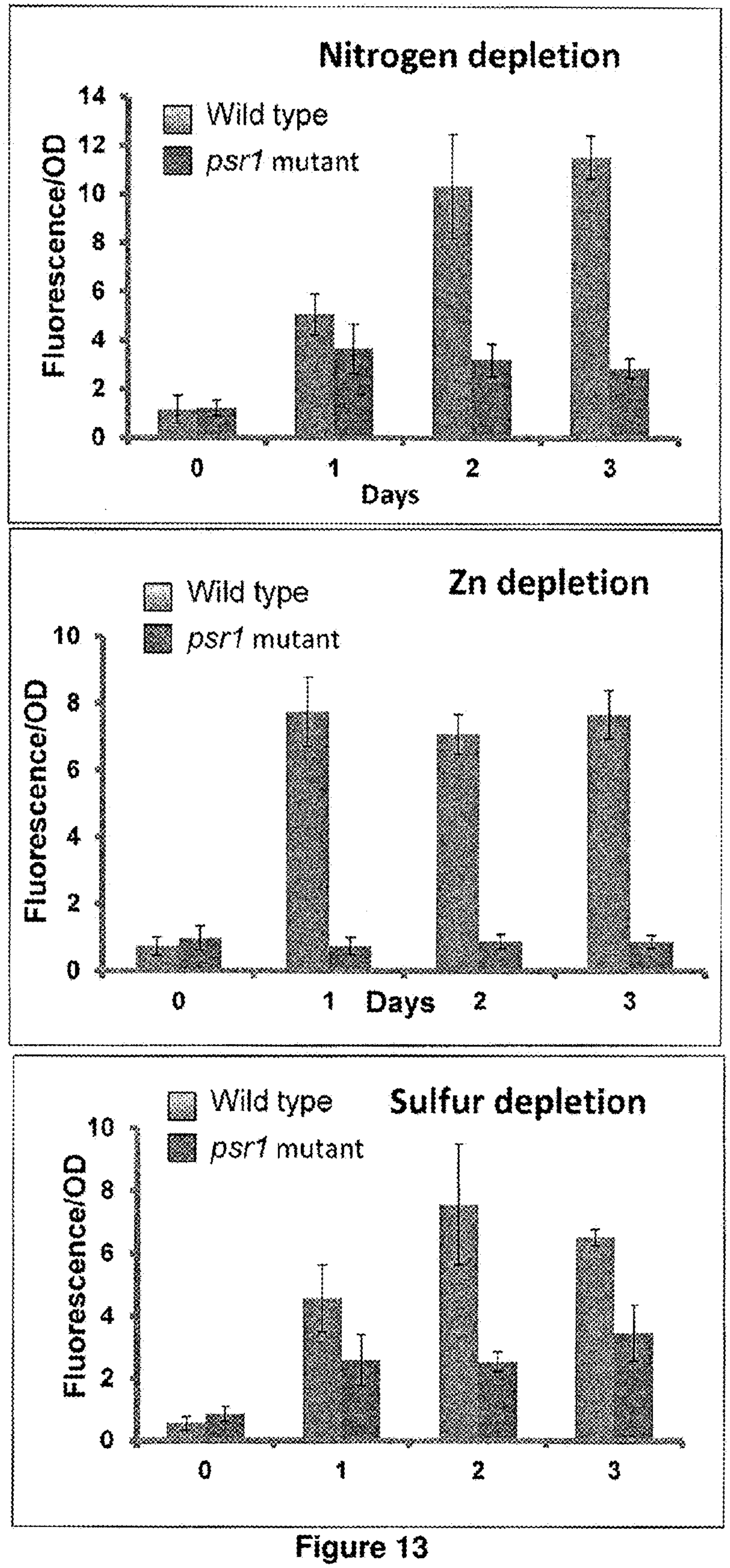

FIG. 13: PSR1 loss-of-function prevents storage lipid accumulation during nutrient stress. Psr1 mutant: 50-90% reductions in lipid accumulation during nutrient stress. 1st TF to be required for lipid storage in multiple conditions.

Figure 14:
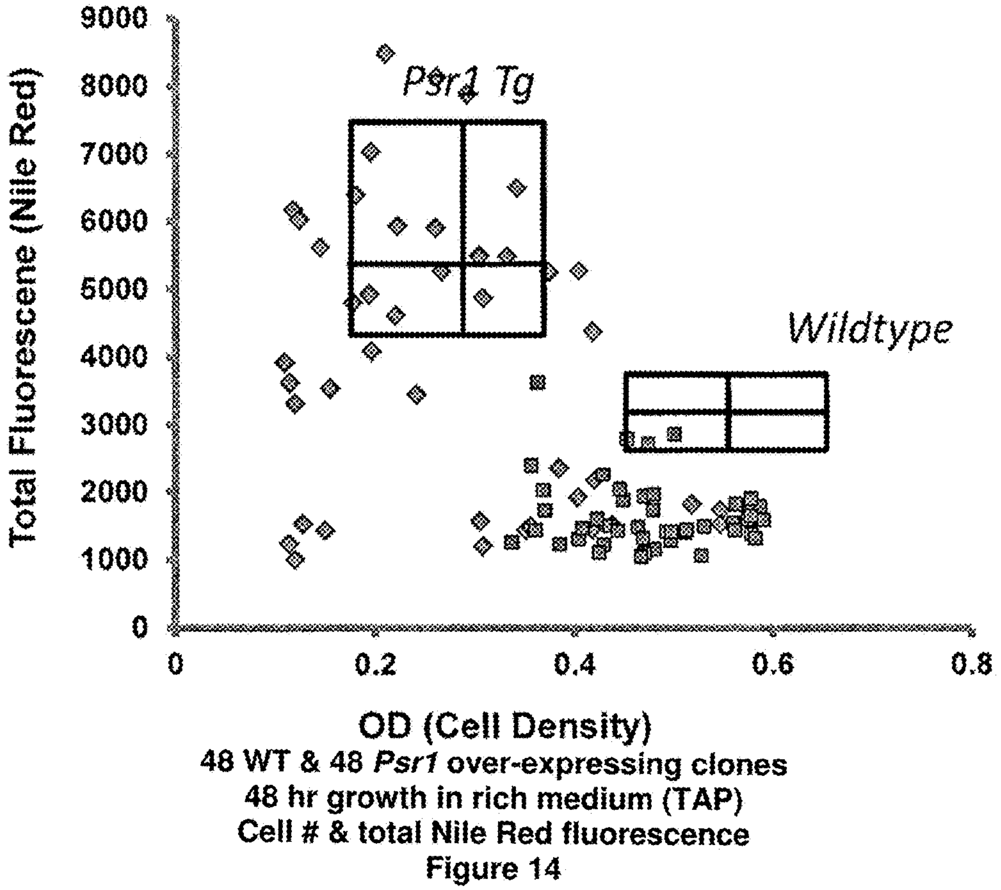

FIG. 14: Psr1 over-expression is sufficient to drive lipid accumulation. Up to 6× increase in total lipid & >12× increase in lipid/cell. Psr1 is necessary & sufficient for storage lipid accumulation. c/w role as a master regulator of lipid accumulation.

Figure 15:
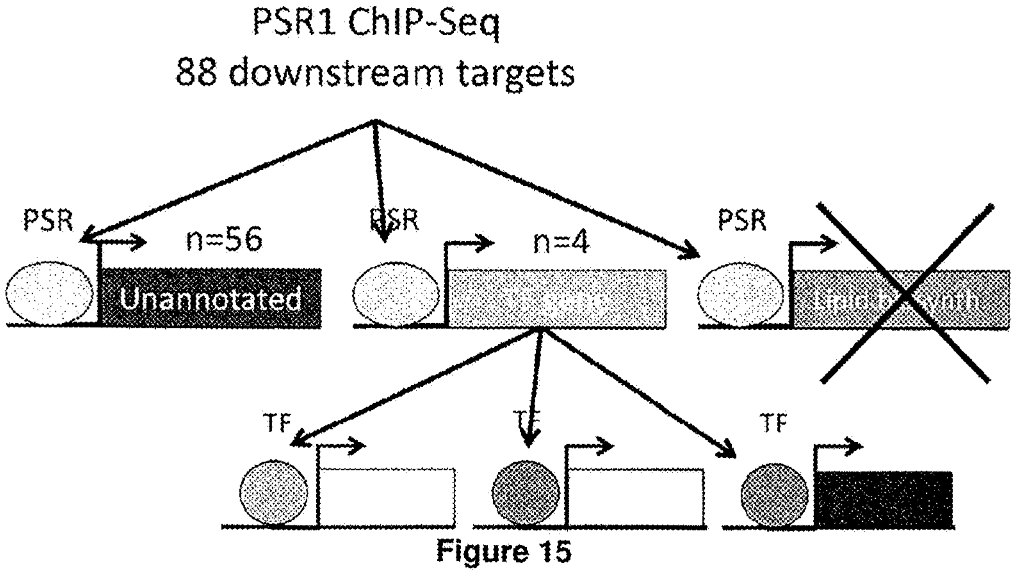

FIG. 15 shows a schematic of Psr1 downstream targets. This suggests Psr1 effects may be pleiotropic which is consistent with proximal regulator of stress response.

Figure 16:
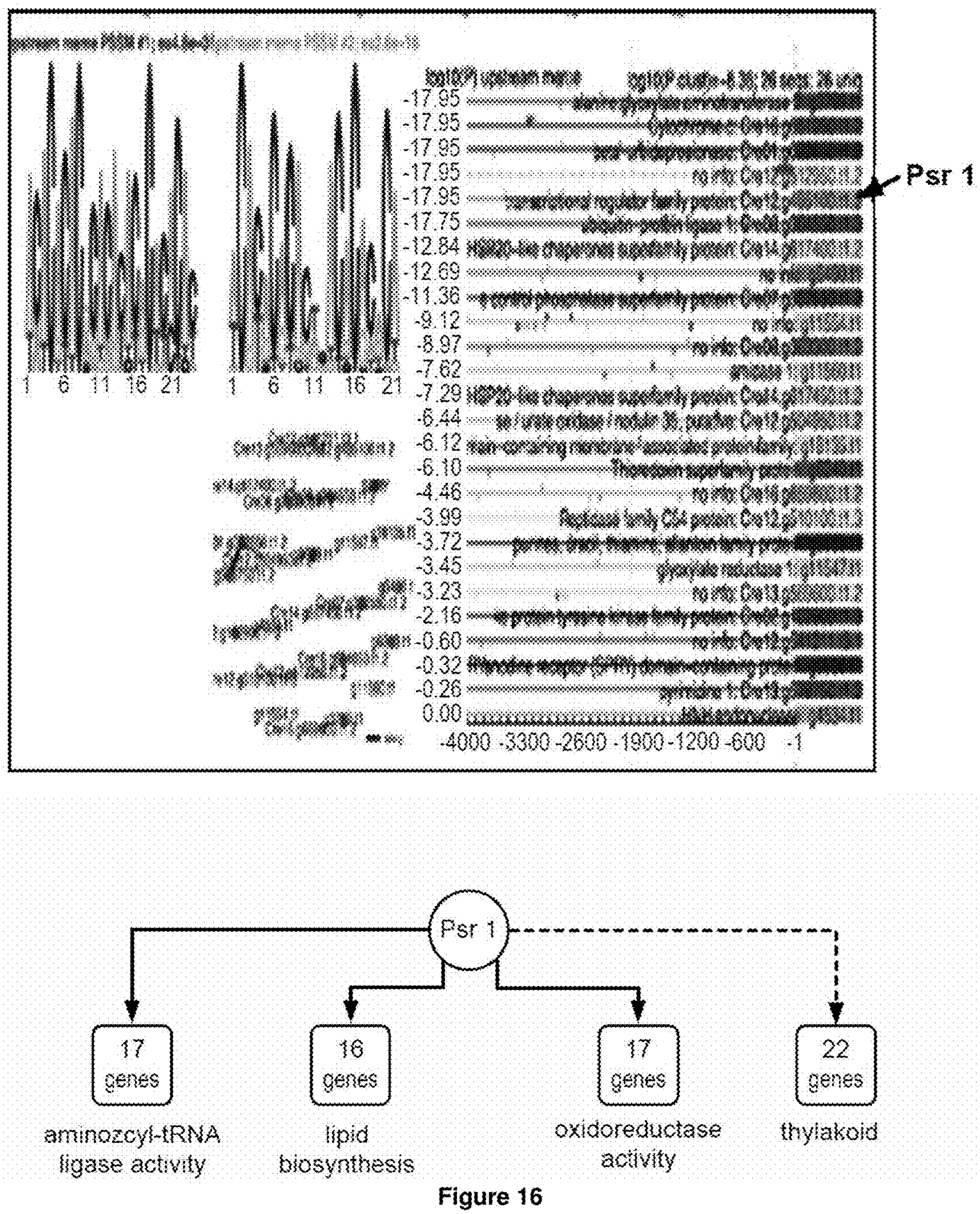

FIG. 16: Computational model of the Psr1 regulatory network.

Figure 17:
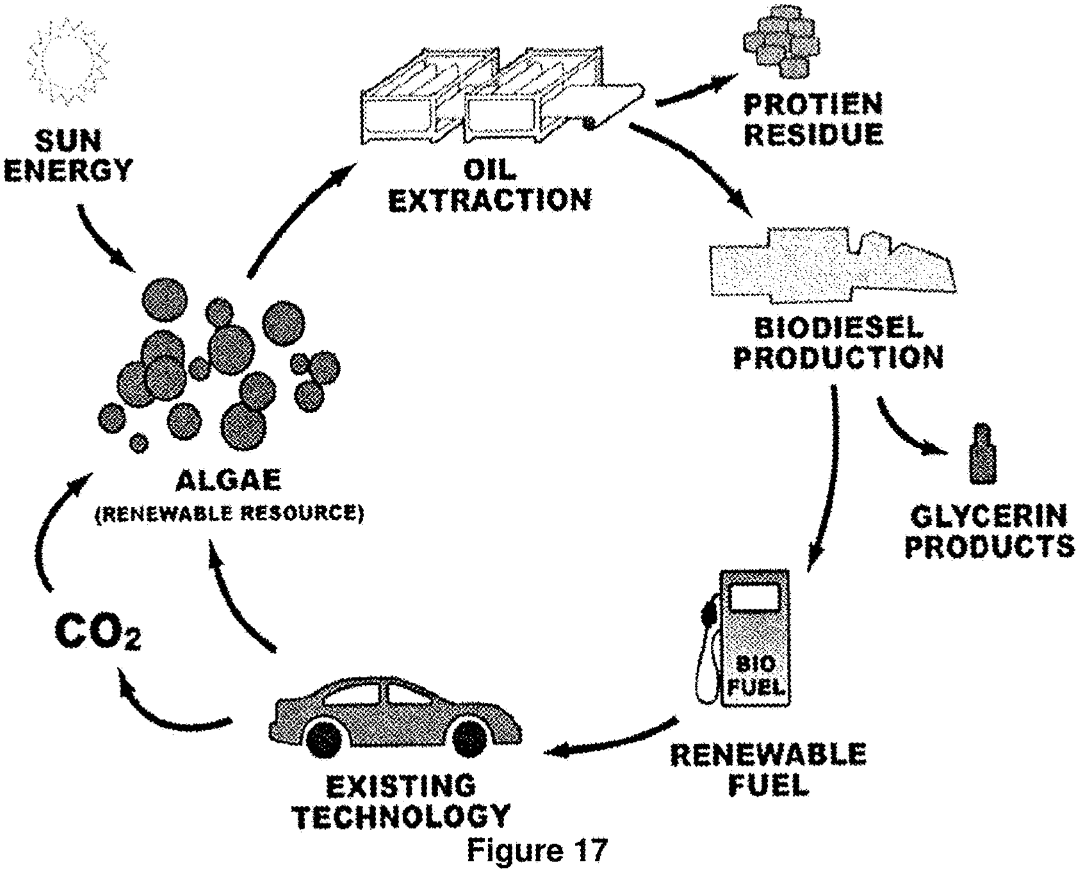

FIG. 17: Many aspects of lipid metabolism must be controlled to enable algal biofuels. Like our understanding of metabolic regulation in Chlamy, our understanding of the lipid biosynthetic pathways is also very limited. If we are ever to produce algal biofuels we need an understanding of the both to be able to do intelligent engineering. Among other things, we need a better understanding of lipid titer, lipid composition, lipid flux, higher value fuels and desire to switch between growth and target lipid production.

Figure 18:
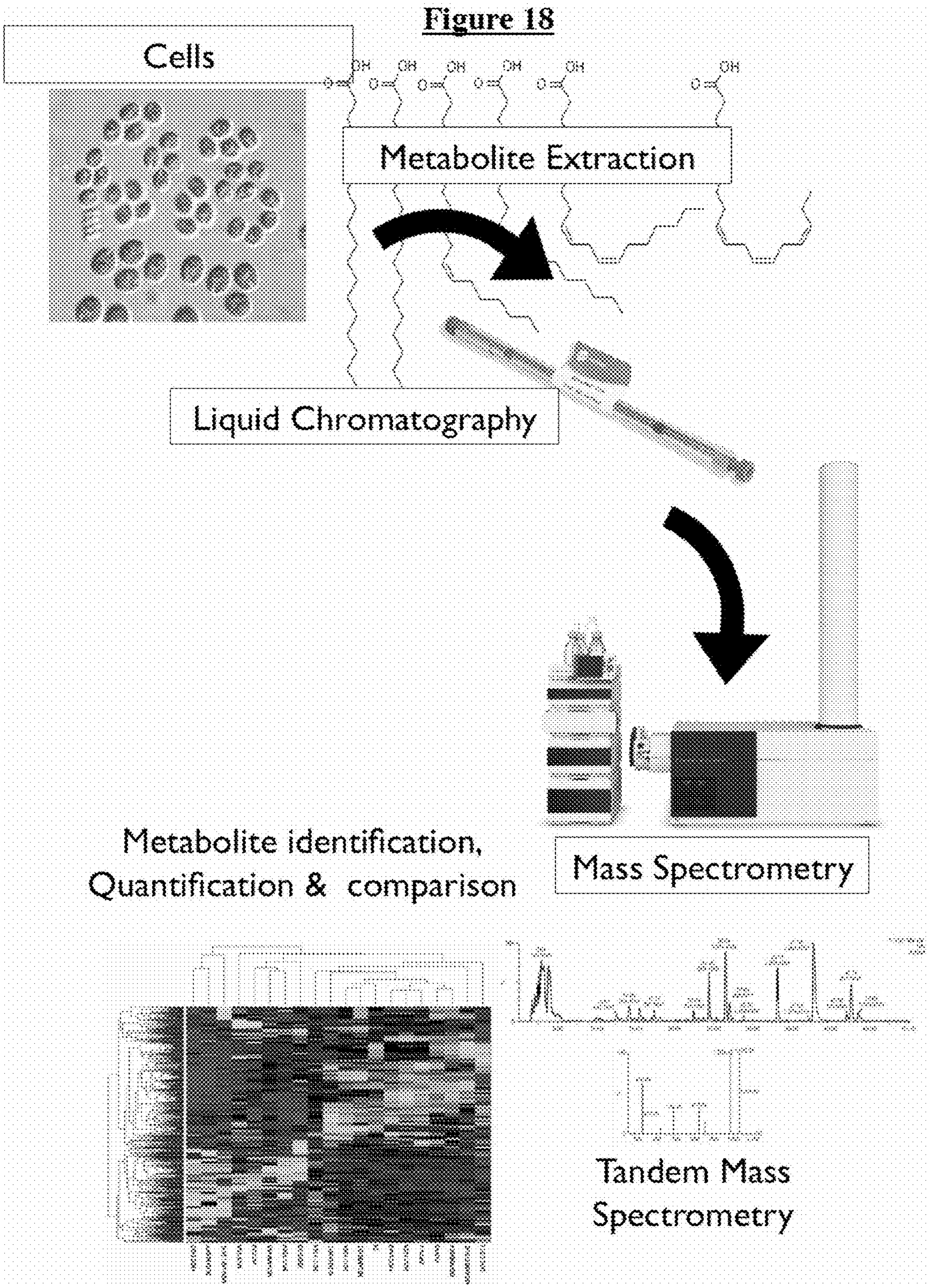

FIG. 18: Algal lipid and metabolite analysis using LC-MS/MS.

Figure 19:
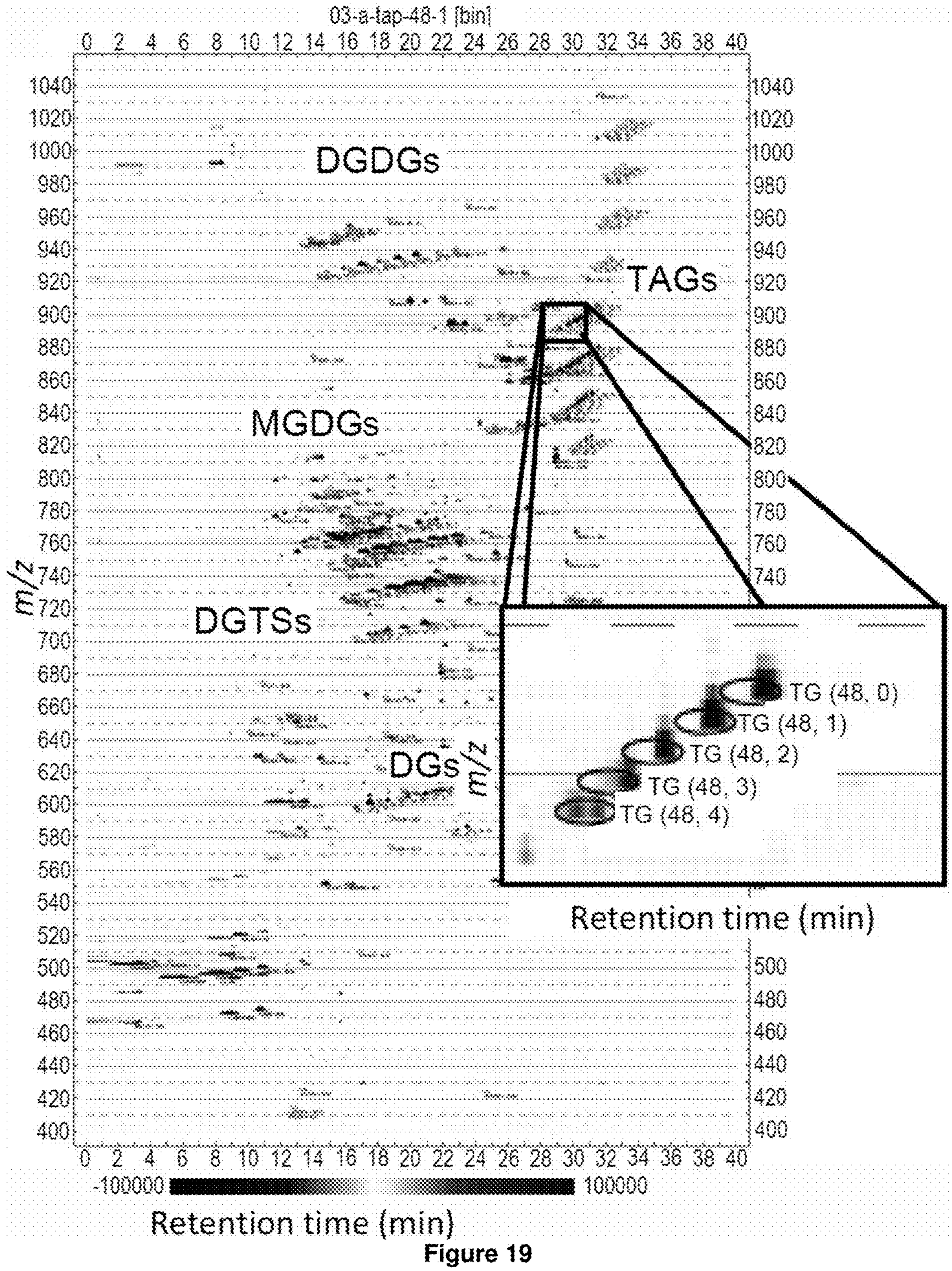

FIG. 19: Preliminary results: LC-MS/MS lipidomics method. WT Chlamy grown rich medium (TAP) produces a wide range of lipid classes. A surprisingly complex >200 lipids total detected. Once developed this can be performed quickly. LC-MS/MS methods will be used to measure lipid precursors including Acyl-ACPs. A database of the lipids and lipid precursors can be made available.

Figure 20:
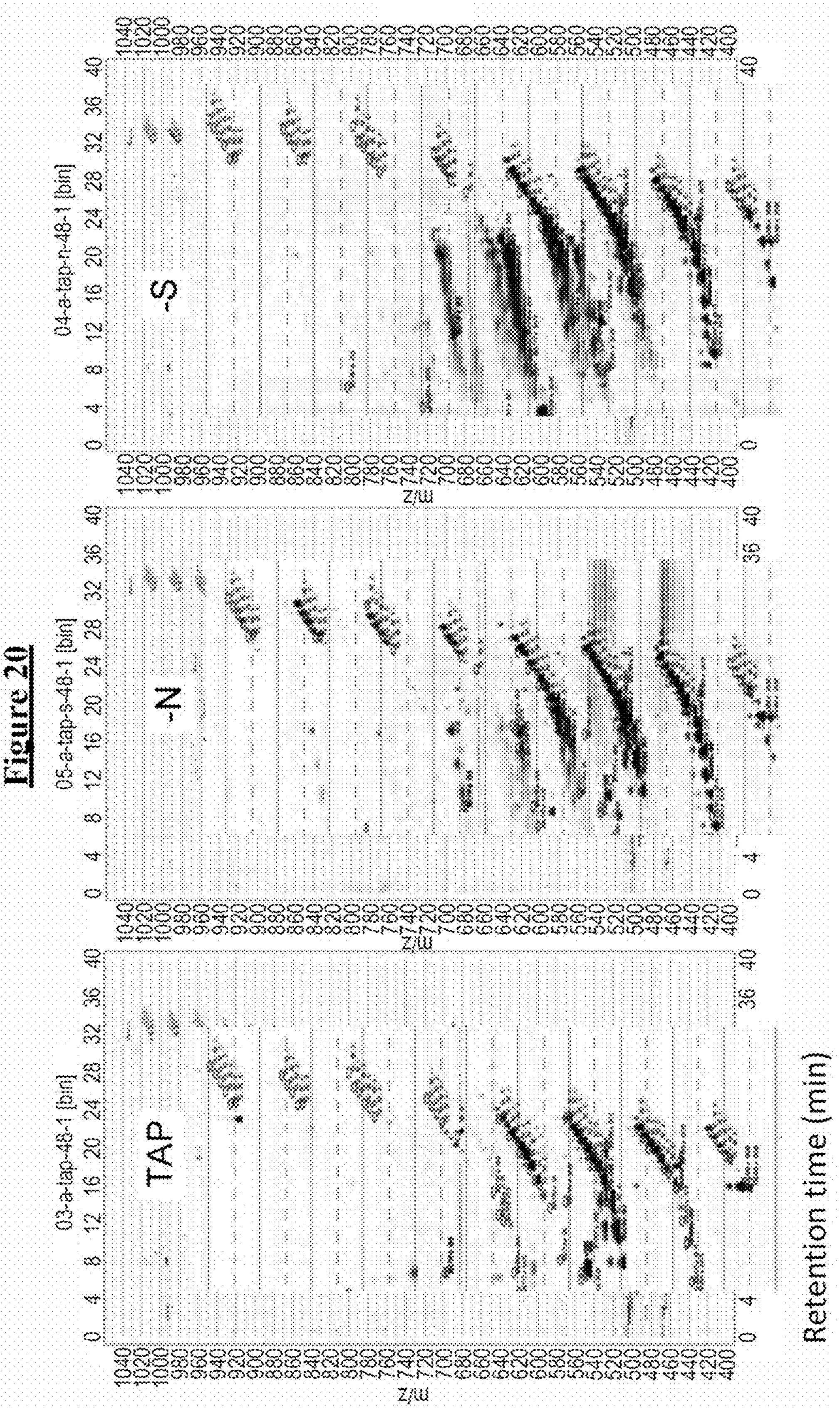

FIG. 20: Preliminary results: wide-spread changes in response to nutrient starvation. Performed 2 experiments characterizing -N and -S. Four replicates per condition in the two experiments (n=8 total). Data are highly reproducible. Observe the expected large-scale changes in lipid composition with nutrient starvation.

Figure 21:
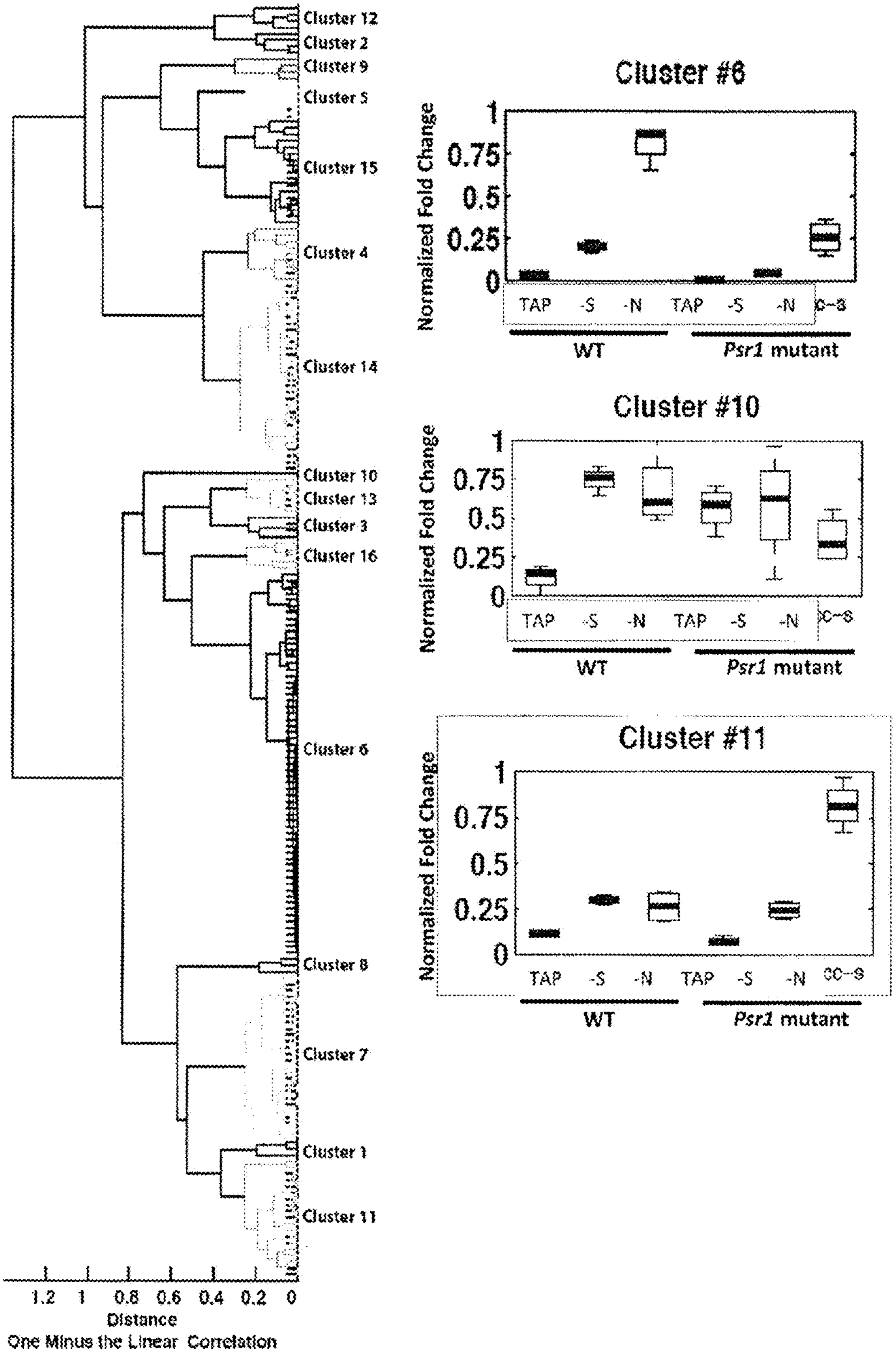

FIG. 21: Global changes in lipid production in Psr1 mutant vs WT. 162/202 lipids were altered in Psr1 mut vs WT. These results are highly reproducible. The largest cluster c/w Nile red staining. We suspected that derangement of lipid metabolism responsible for decreased growth. Specific engineering is required. Psr1 candidate gene summary: Psr1 is required for lipid storage under multiple stresses and is capable of driving lipid accumulation in non-stress conditions, powerful proof-of-concept for all 4 aims and the general concept of TF engineering, evaluation of Psr1 demonstrates effectiveness & synergy of consortium team, complex effects of Psr1 underscore why foundational understanding must precede engineering.

Figure 22:
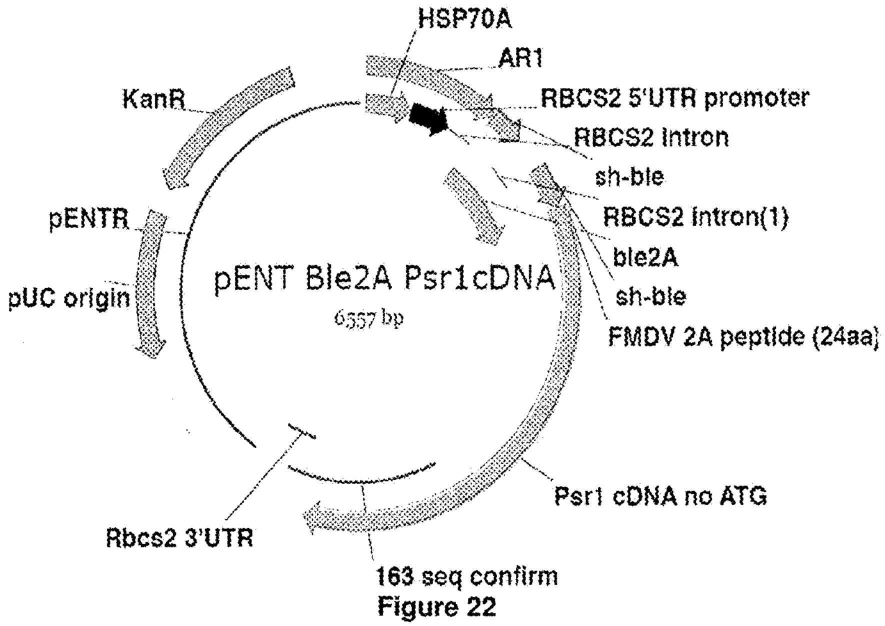

FIG. 22: Schematic of Psr1 cDNA construct and its components

Figure 23A:
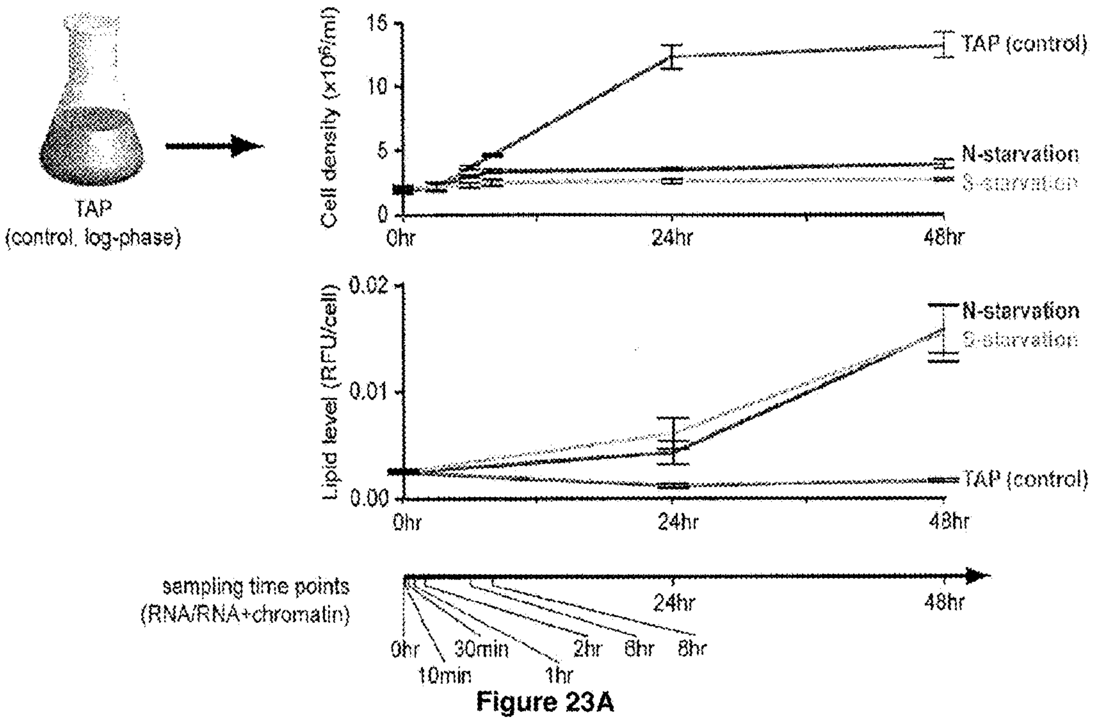

FIG. 23A: An integrative epigenetic and transcriptomic strategy to identify lipid regulators in *C. reinhardtii. C. reinhardtii* cells in log phase were subjected to acute N- and S-depletion for 48 hr. Cell growth and lipid accumulation were measured to confirm the effect of nutrient starvation. RNA expression, histone modifications and RNAPII occupancy were profiled at designated time points.

Figure 23B:
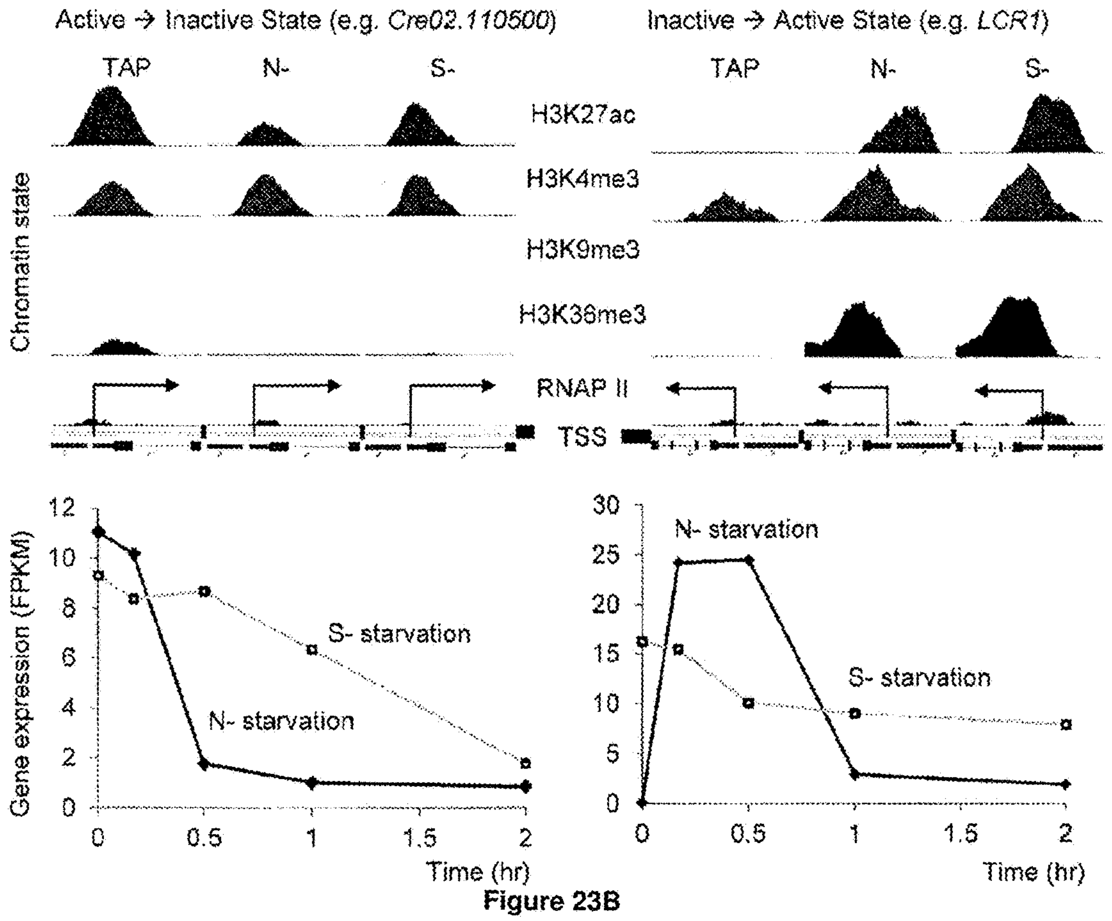

FIG. 23B: An integrative epigenetic and transcriptomic strategy to identify lipid regulators in *C. reinhardtii*. Genes whose TSSs display inactive (left) and active (right) chromatin state changes in response to starvations were selected to evaluate their temporal RNA expression patterns. Inactivated cre02.g110500 (chromosome_2: 5,751,191-5,752,593) and activated LCR1 (chromosome_9:5,231,514-5,245,409) expression are shown as examples.

Figure 24A:
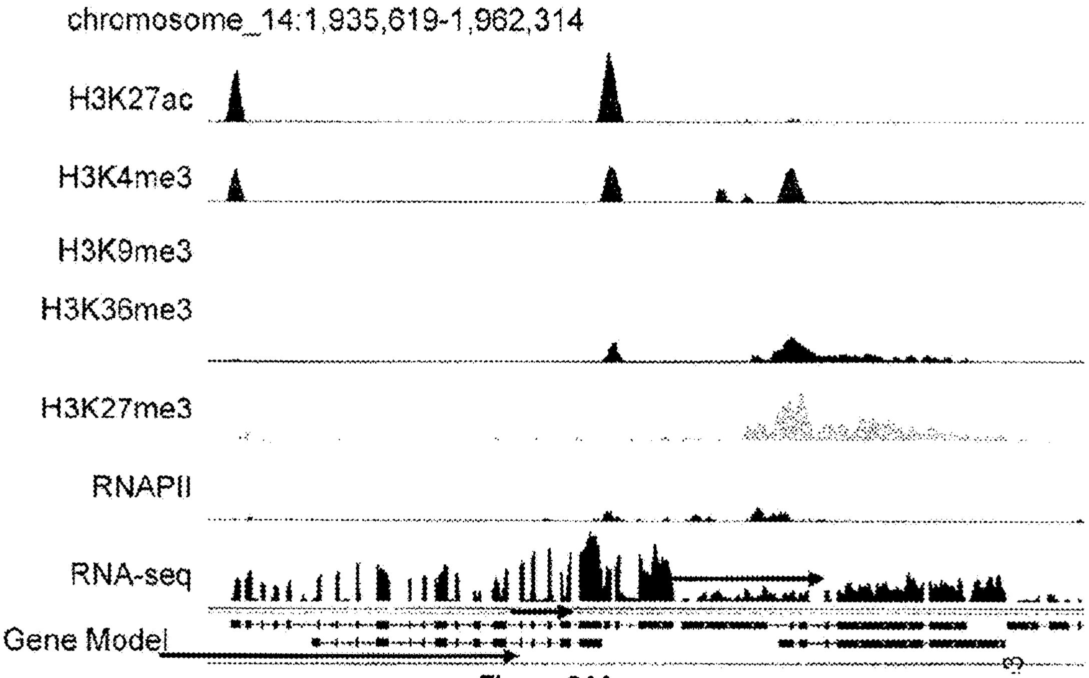

FIG. 24A: Chromatin states analysis reveals unique signatures in *C. reinhardtii*. An overview of histone modification profile in *C. reinhardtii*. Pattern of five histone modifications and RNA polymerase II occupancy as well as RNA expression along genomic region chromosome_14:1,935,619-1,962,314 is shown. Gene model is shown based on the assembled transcripts from this study.

Figure 24B:
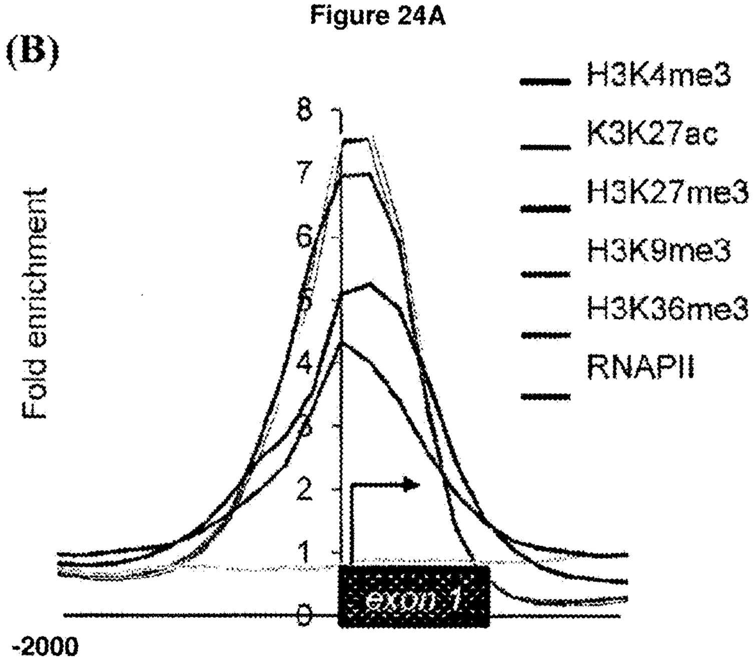

FIG. 24B: Chromatin states analysis reveals unique signatures in *C. reinhardtii*. Enrichment of histone modification signals between ±2 Kb of TSS.

Figure 24C:
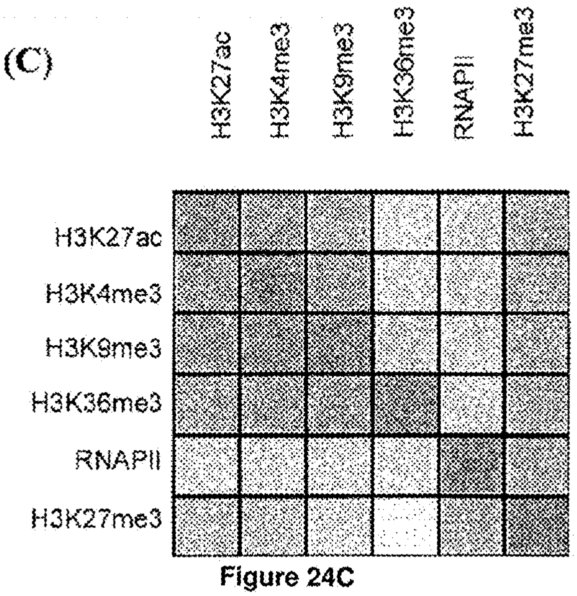

FIG. 24C: Chromatin states analysis reveals unique signatures in *C. reinhardtii*. Pairwise marks co-occurrence in *C. reinhardtii*. Overlap is defined as the ratio of co-occupied regions between the row and column marks over the number of row mark's regions.

Figure 24D:
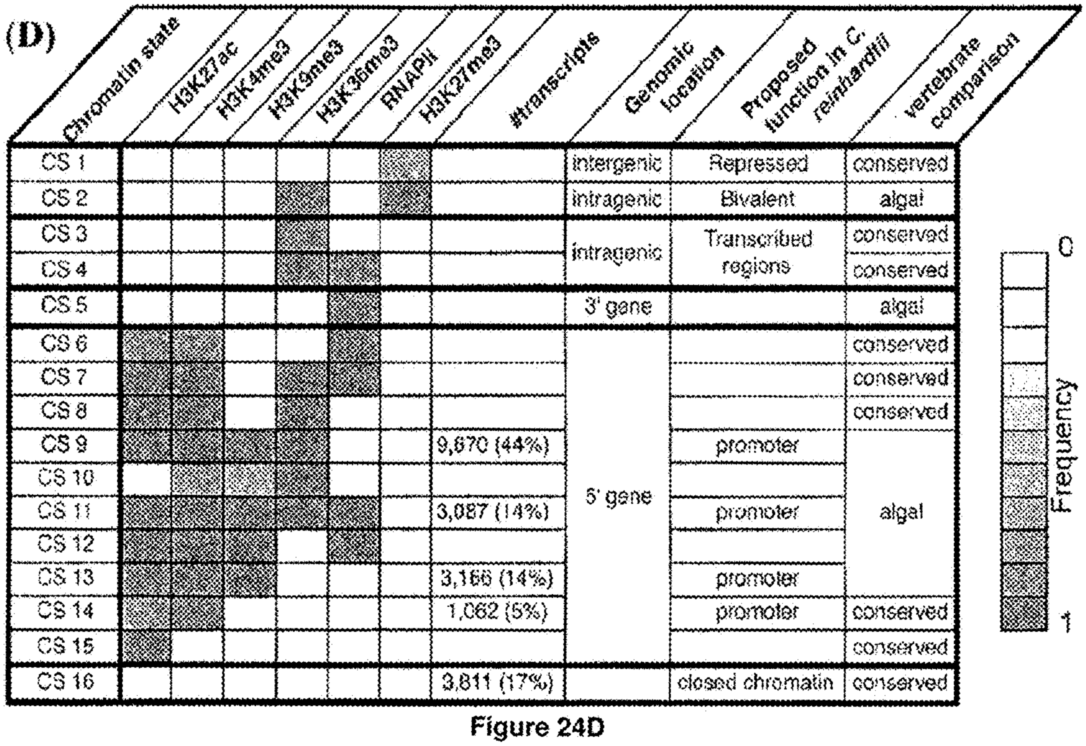

FIG. 24D: Chromatin states analysis reveals unique signatures in *C. reinhardtii*. Predicted chromatin states defined by the combinatory histone modifications, potential functional features and conservation with other species are shown. The representative marks for individual states are highlighted in blue. The fraction of transcripts associated with major promoter states are listed. Similar patterns are also found in the N- and S-cells.

Figure 25:
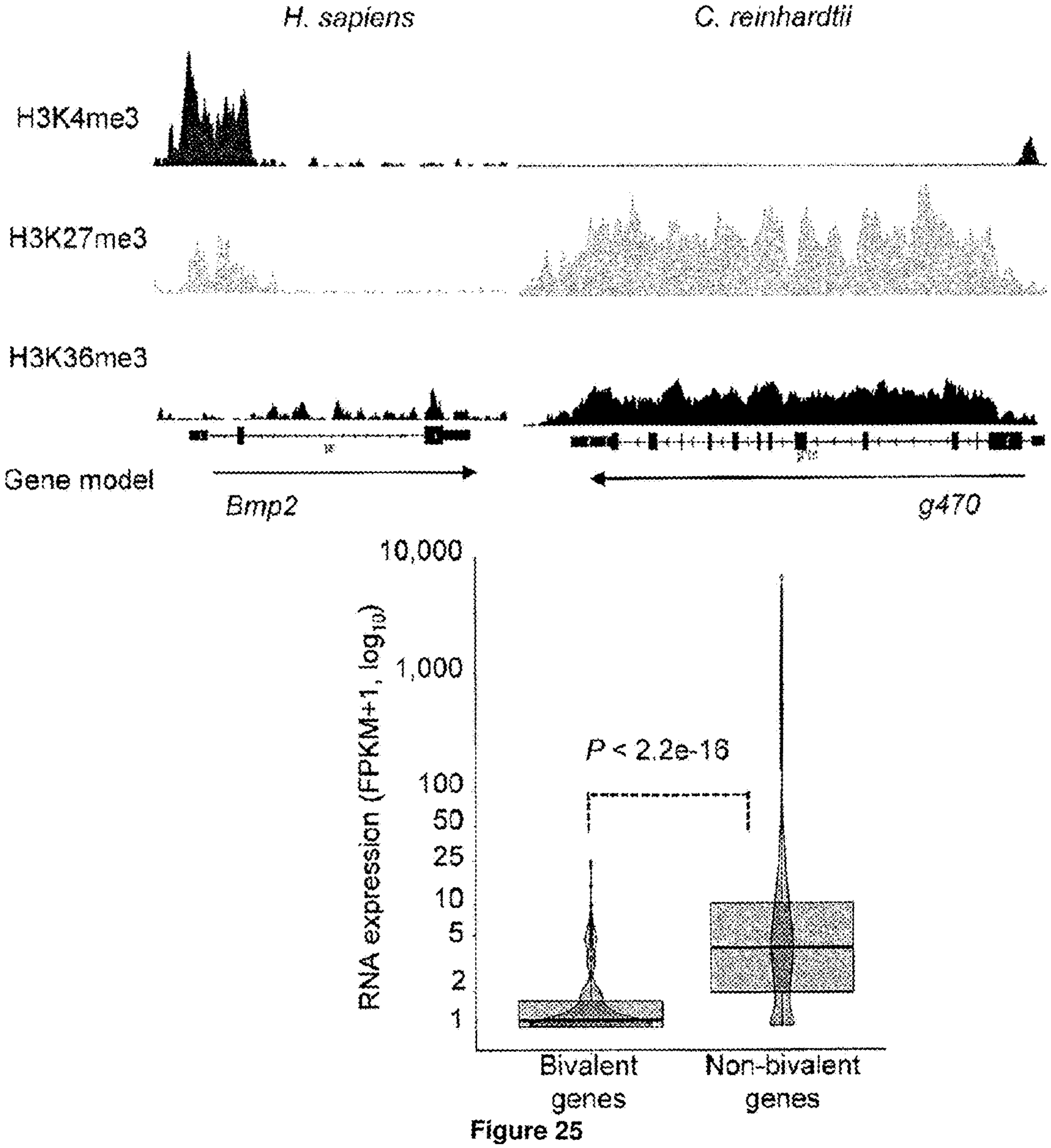

FIG. 25: Distinct chromatin features in *C. reinhardtii* compared to vertebrate. Chromatin state 2: Bivalent domain. Putative bivalent domain defined by chromatin state 2. Different modification patterns between *C. reinhardtii* and *Homo sapiens* (ENCODE data) are shown (Left). Bivalent state-associated transcripts are expressed at a significantly (Wilcoxon rank-sum test) lower level (Right).

FIG. 26: Distinct chromatin features in *C. reinhardtii* compared to vertebrate. Chromatin state 15: Putative enhancer. Putative enhancer state defined by chromatin state 15. H3K4me2 enrichment at distal H3K27ac marked regions (Left). An example of putative enhancer region (chr_1:5,739,311-5,755,673) exhibiting enhancer activity (Figure S2D) is shown (Right). H3K27ac peak is found in the 3' intron of the amino acid permease gene, 7 kb and 3.5 kb away from its neighboring promoters.

Figure 27:
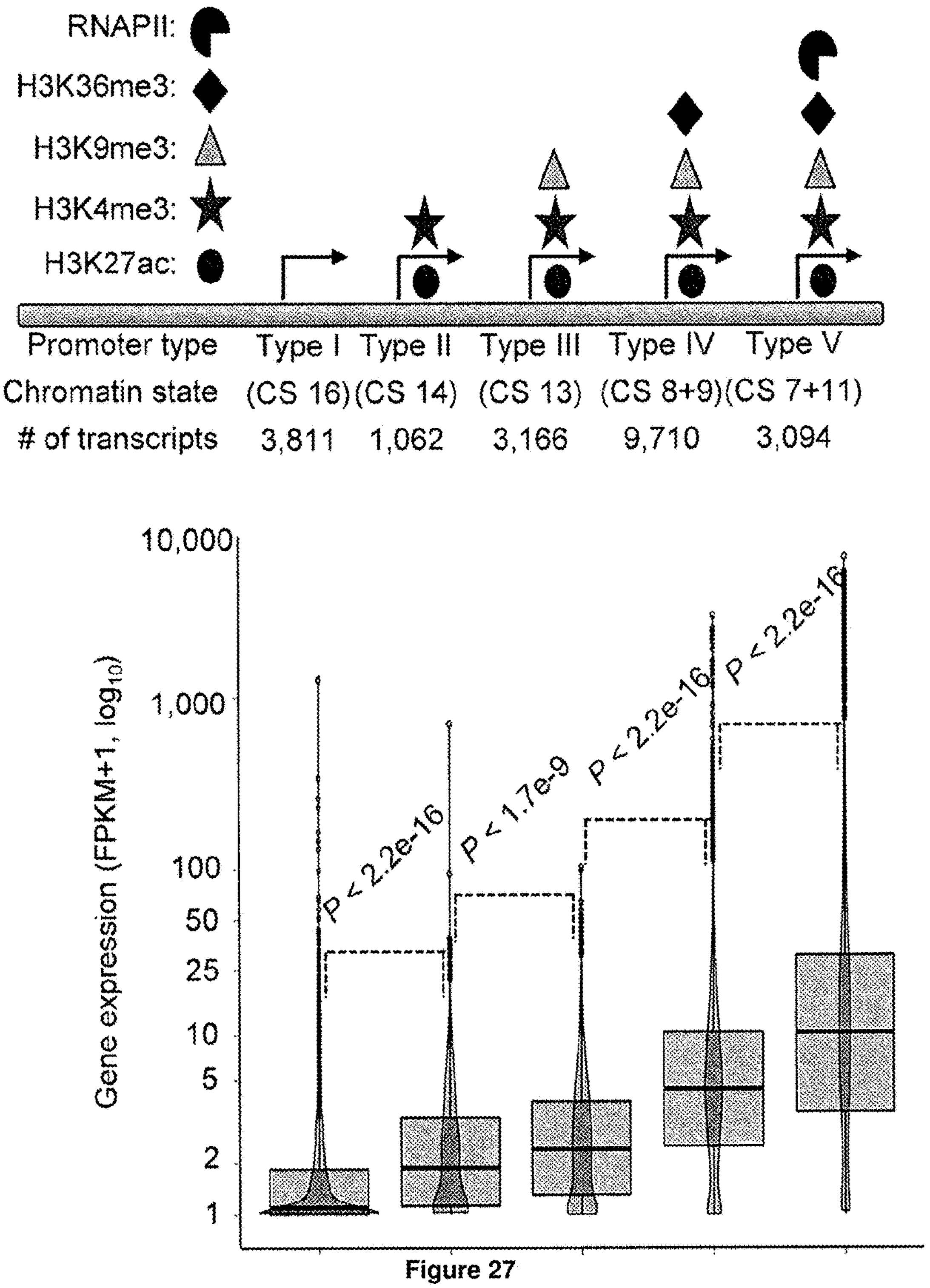

FIG. 27: Chromatin state changes predict regulators of lipid accumulation. Five promoter types are defined by progressive addition of histone modifications (top panel) and are highly correlated with expression levels (bottom panel).

Figures 28A, 28B:
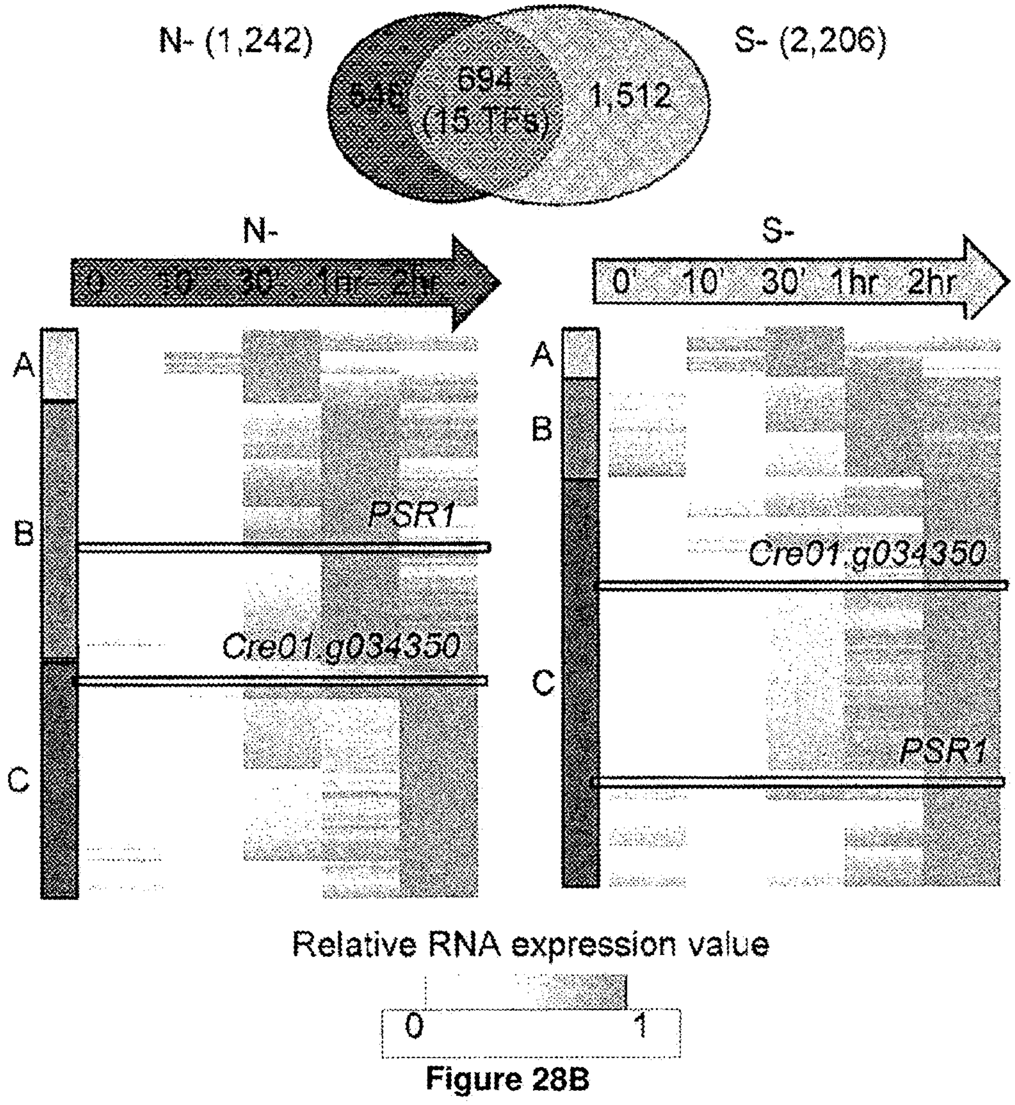

FIG. 28A: Chromatin state changes predict regulators of lipid accumulation. Numbers of genes found in each promoter type during growth in TAP (column) and corresponding state at nutrient depletion (row). Numbers of genes with activated chromatin (Types I+II+III changing to IV or V, plus IV changing to V) are marked in red and green, for N- and S-starvation, respectively.

FIG. 28B: Chromatin state changes predict regulators of lipid accumulation. Venn diagram displays the activated genes found in both N- and S-starvation. Clustering of normalized expression levels from the genes activated during N- (left) and S- (right) cells across different time points. Clusters A, B and C are defined by peak expression at 30 min, 1 hr and 2 hr, respectively. TF genes are highlighted.

Figure 29A:
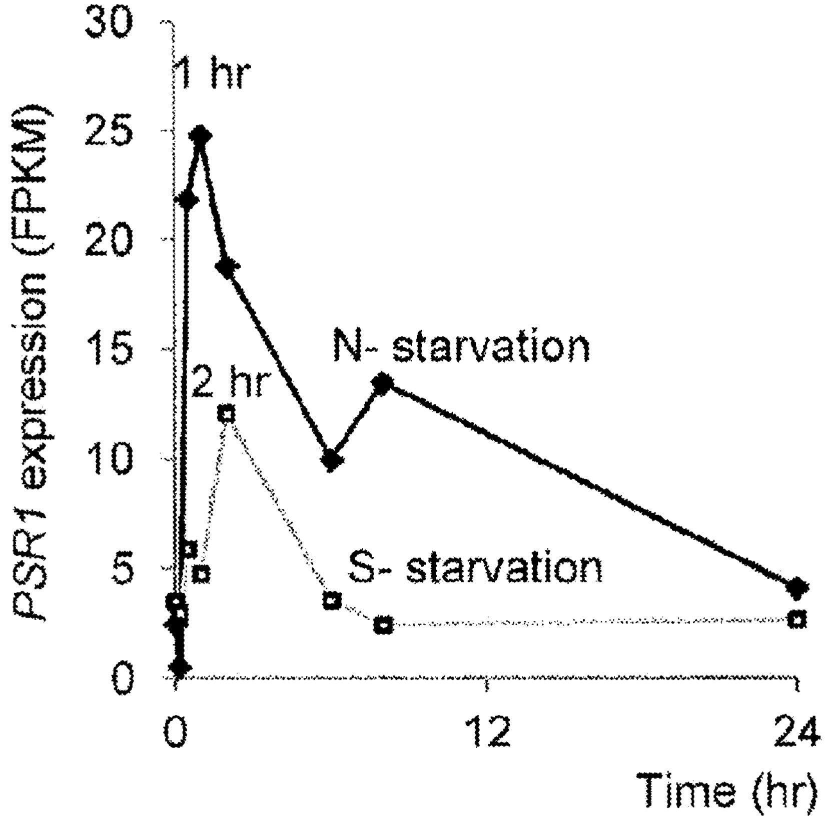

FIG. 29A: Lack of lipid induction in psr1 mutant in response to nutrient deprivation. Temporal expression of PSR1 gene in N- (red) or S-(green) starved cells.

Figure 29B:
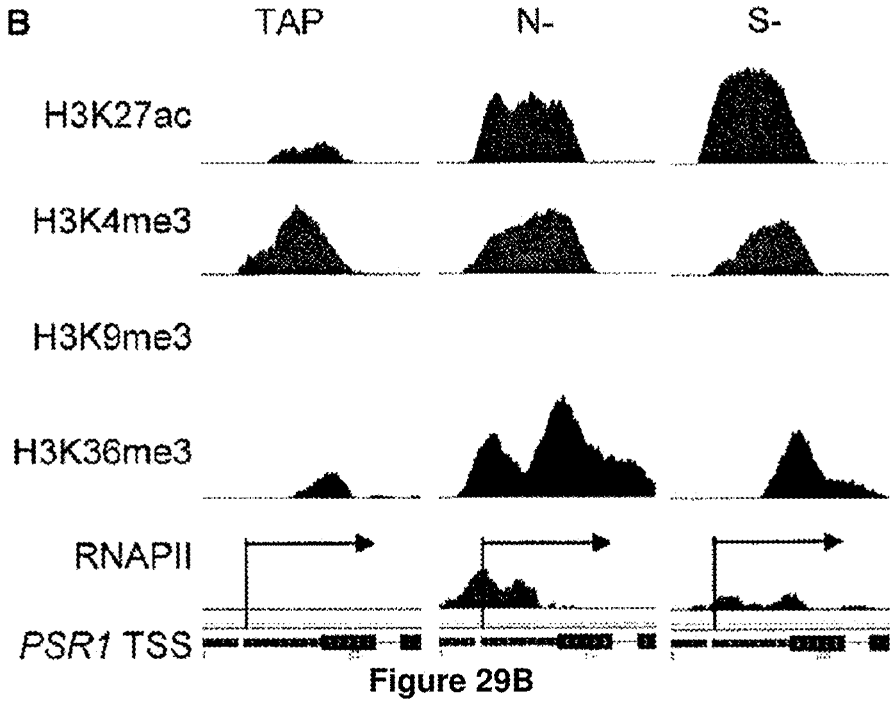

FIG. 29B: Lack of lipid induction in psr1 mutant in response to nutrient deprivation. Chromatin modifications changes at the PSR1 promoter regions following N- and S-starvation.

Figure 29C:
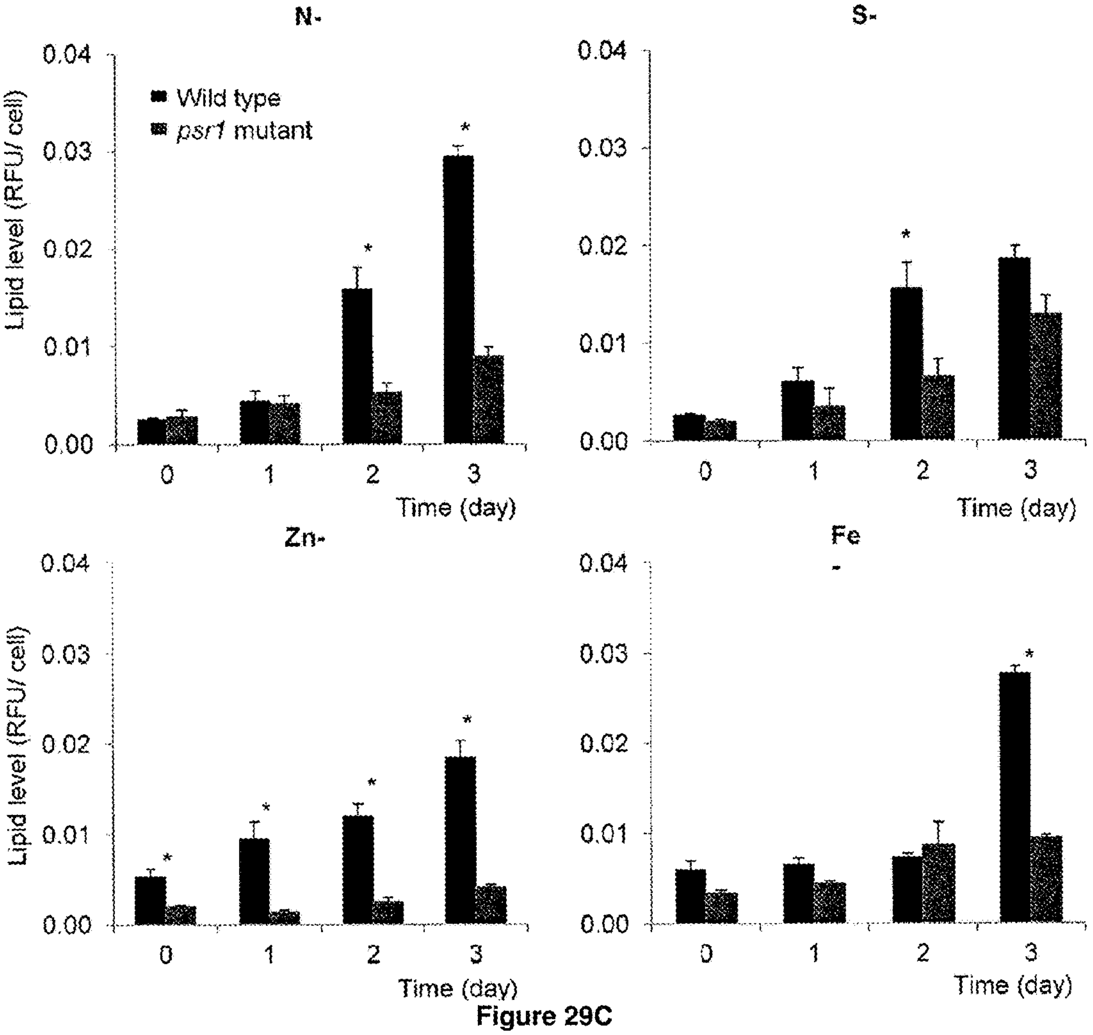

FIG. 29C: Lack of lipid induction in psr1 mutant in response to nutrient deprivation. Lipid accumulation in wild type and psr1 mutant cells in four nutrient starvation regimens. Nile red fluorescence (RFU) normalized per cell is shown during 3 days of nutrient starvation (n=3). Statistical significance by student t-test is indicated as *$P<0.05$. Depletion time course for trace metal depletion (Zn— and Fe—) was performed after a pre-inoculation of cells in depleted media (see details in Experimental Procedures).

Figure 30A:
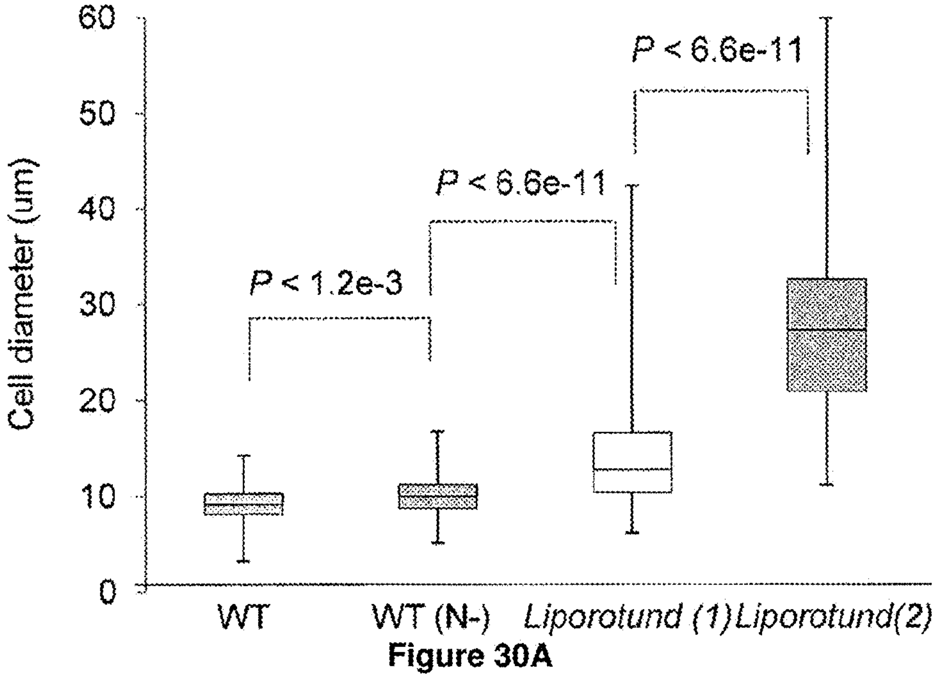

FIG. 30A: Overexpression of PSR1 triggers lipid accumulation in *C. reinhardtii*. Cell size measurement of wild type cells in TAP, N- and two independent clones of liporotund.

Figure 30B:
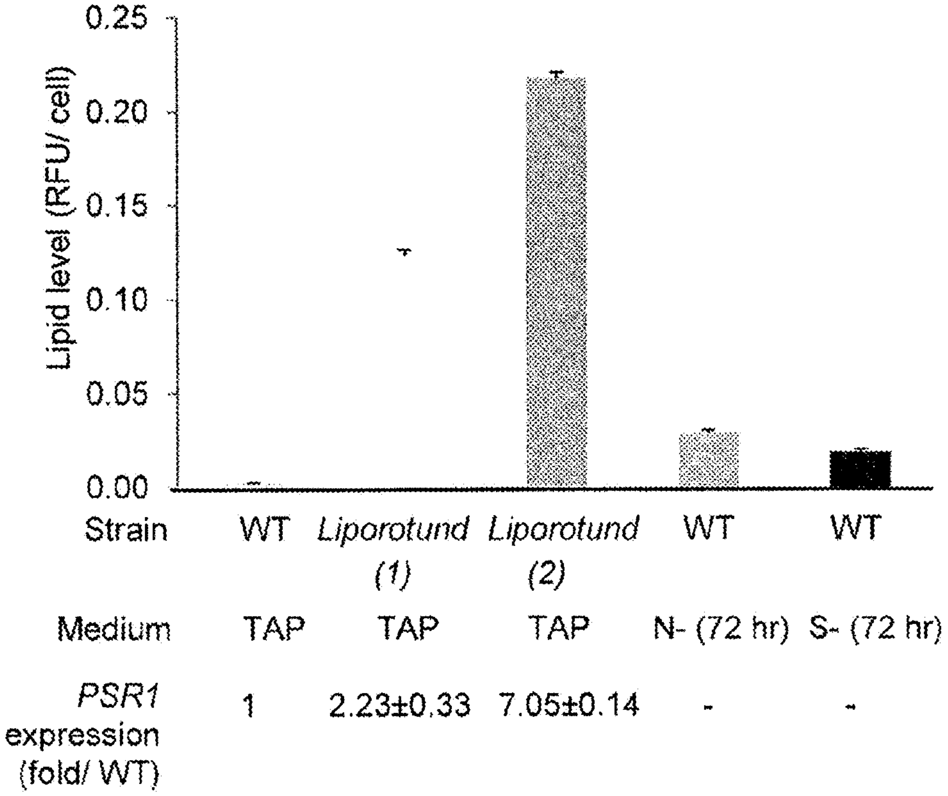

FIG. 30B: Overexpression of PSR1 triggers lipid accumulation in *C. reinhardtii*. Comparison of lipid accumulation in wild type cells (in TAP and during nutrient starvation) and liporotund grown in TAP (n=3). The fold of PSR1 overexpression is shown below.

Figure 31:
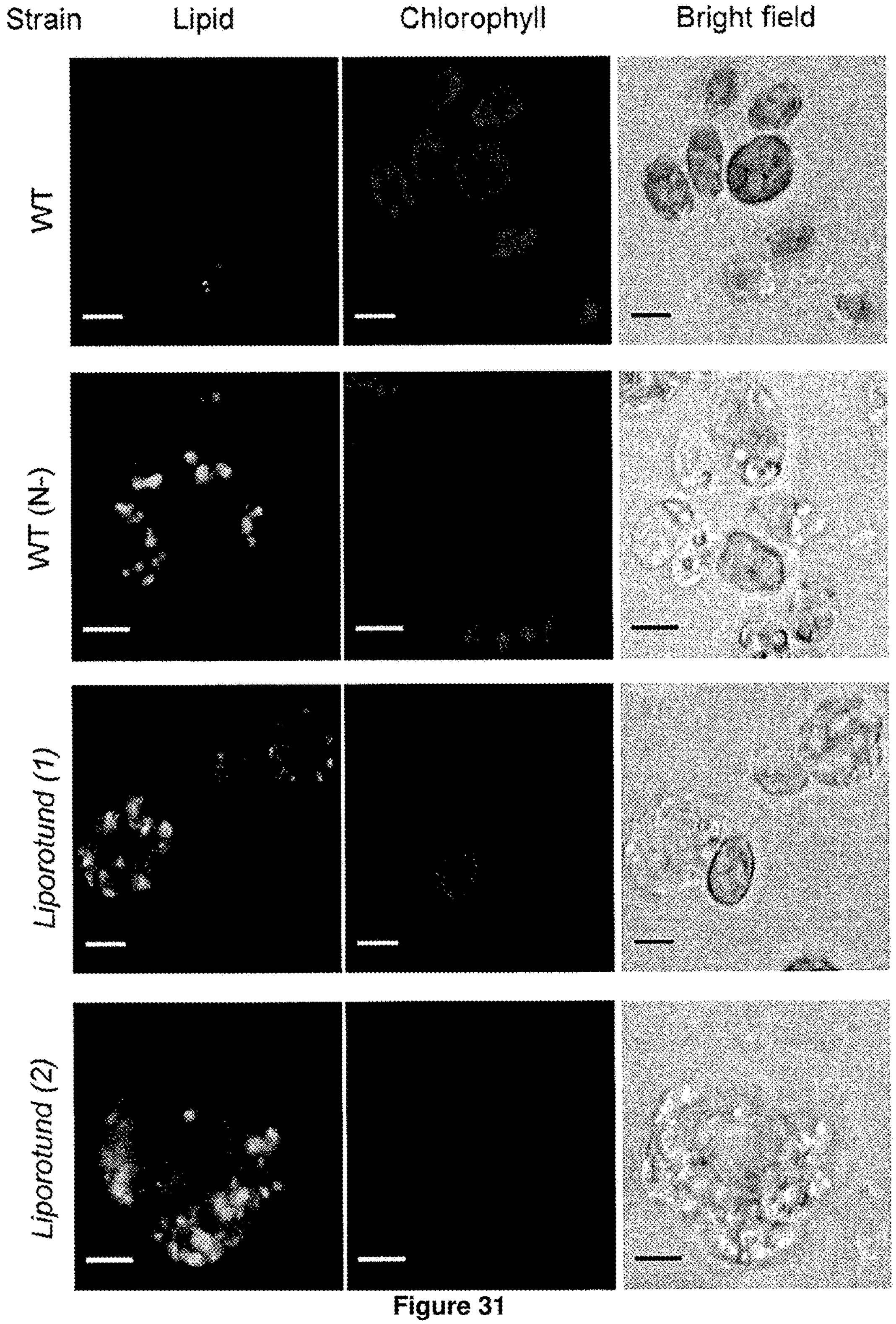

FIG. 31: Overexpression of PSR1 triggers lipid accumulation in *C. reinhardtii*. Images of LipidTOX Green-stained PSR1-overexpressing cells confirmed an increased number of lipid bodies. Chlorophyll autofluorescence and cell morphology images were taken with the same laser power to facilitate cross-comparison (scale bar: 5 um).

Figure 32A:
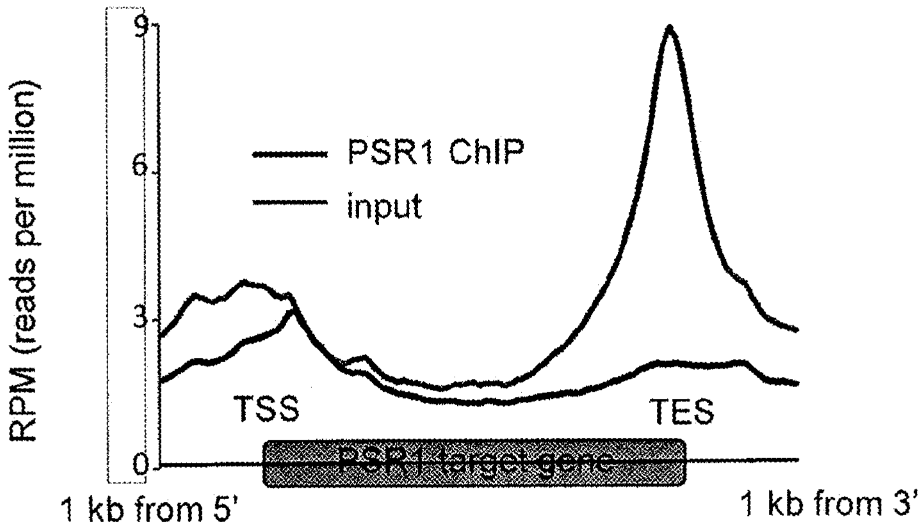

FIG. 32A: Characterization of PSR1 binding and target genes. PSR1 ChIP-seq signal intensity along the bound genes.

Figure 32B:
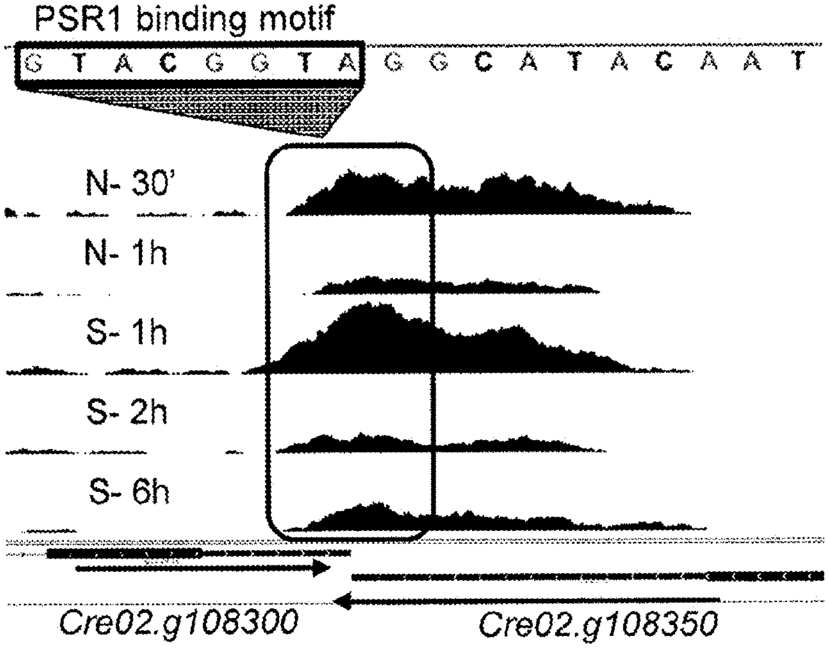

FIG. 32B: Characterization of PSR1 binding and target genes. PSR1 binding profiles across 2 time points in N- and 3 time points in S-cells at TF gene Cre02.g108350. The predicted binding motif is highlighted (SEQ ID NO:104).

Figure 32C:
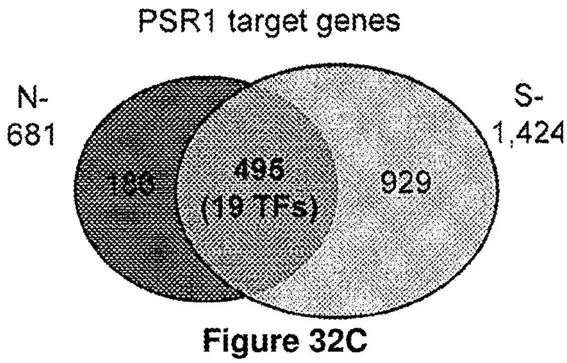

FIG. 32C: Characterization of PSR1 binding and target genes. Number of PSR1 target genes common and specific in N-, S-states.

Figure 33:
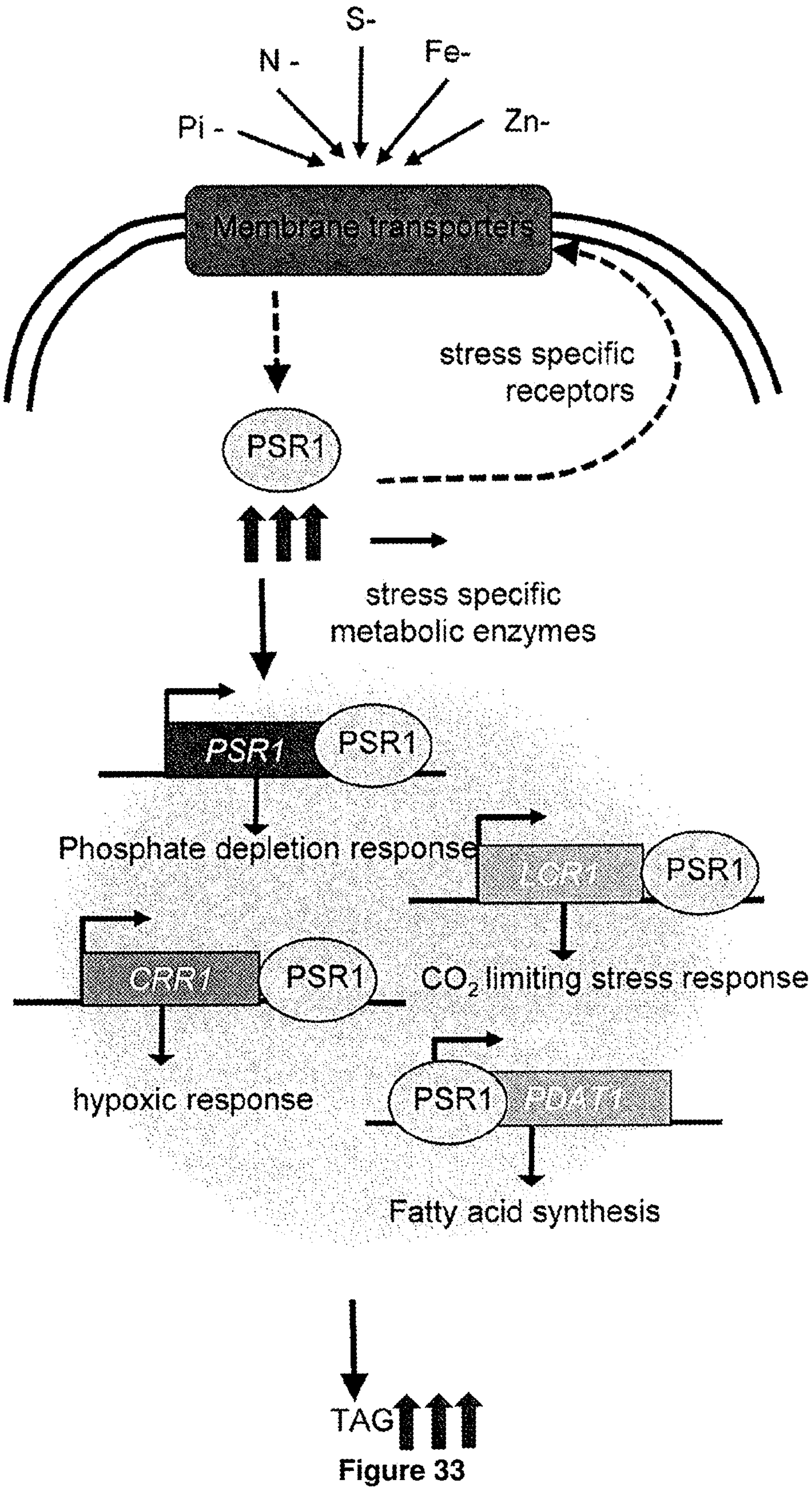

FIG. 33: Characterization of PSR1 binding and target genes. Proposed model of PSR1-mediated lipid regulation.

Figure 34:
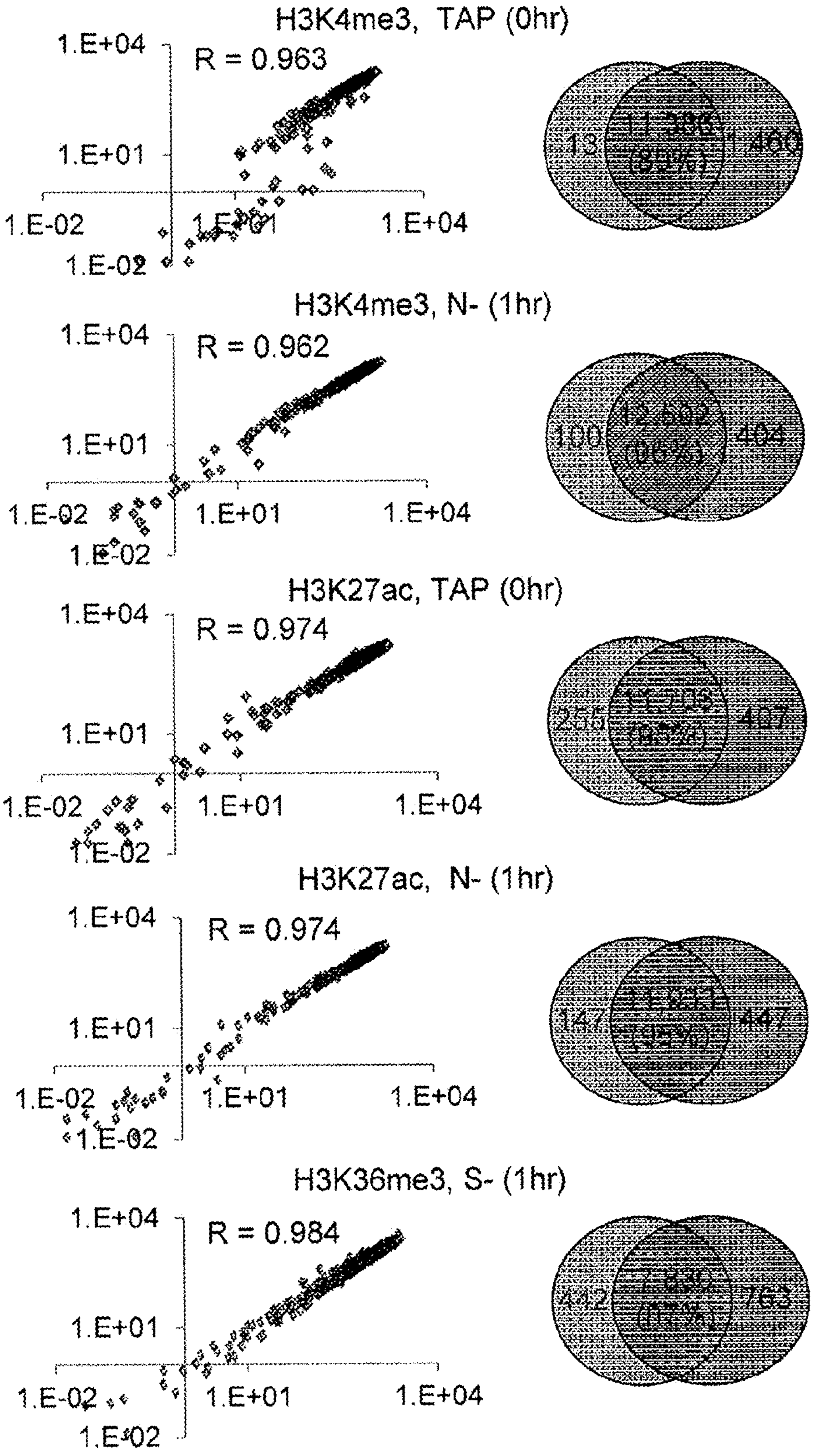

FIG. 34: Data reproducibility of ChIP-seq and RNA-seq analysis, related to FIG. 1. Two biological replicates (BR1 and BR2) were generated for 5 ChIP-seq experiments. Numbers of the mapped reads from each genomic bin (100 kb) were plotted in log scale between two replicates (X-axis: BR1; Y-axis: BR2). R values calculated by Pearson correlation coefficient at 1 kb genomic bin are shown. Venn diagrams display the high % of overlaps between peaks called for each replicate.

Figure 35A:
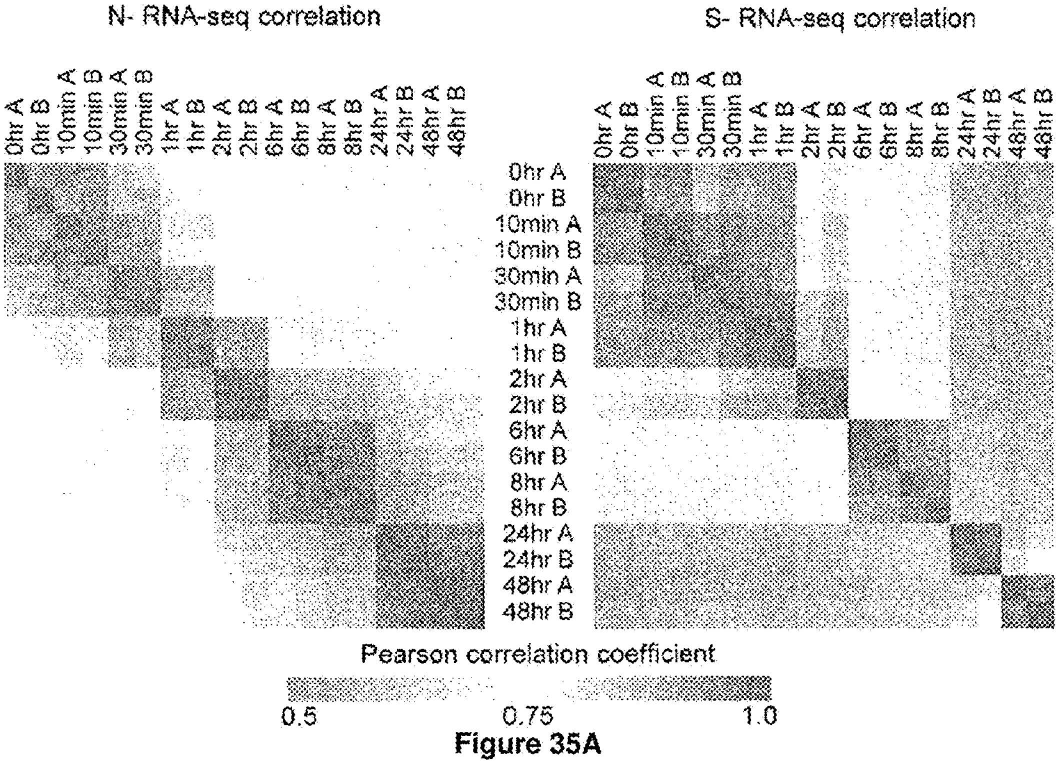

FIG. 35A: Data reproducibility of ChIP-seq and RNA-seq analysis, related to FIG. 1. Pair-wise comparison between 18 RNA-seq libraries of different time points from N- (left panel) and S- (right panel). Replicates for each data point were indicated as A and B. Pearson correlation coefficient (R) calculated from expression value (FPKM) of each transcripts model was shown in color scale.

Figure 35B:
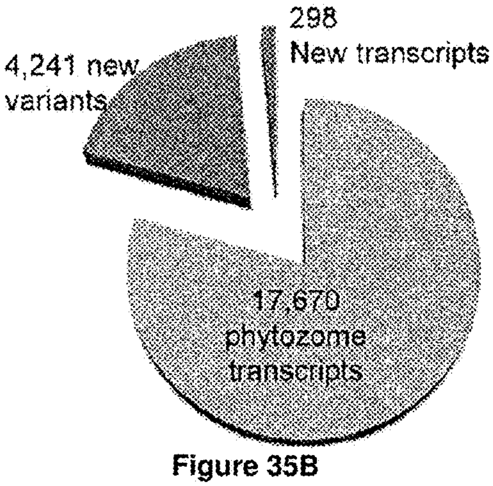

FIG. 35B: Data reproducibility of ChIP-seq and RNA-seq analysis, related to FIG. 1. The classification of 22,209 assembled transcripts among the known, new variant and new transcripts is shown.

Figures 36A, 36B:
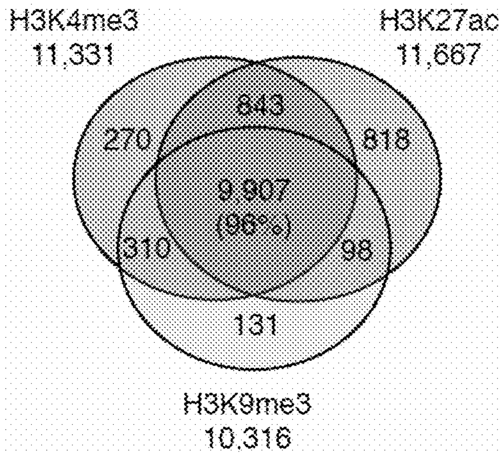

FIG. 36A: Chromatin features in *C. reinhardtii*, related to FIGS. 2 and 3. H3K9me3 co-occupies regions modified by the active H3K4me3 and H3K27ac marks in *C. reinhardtii.*

FIG. 36B: Chromatin features in *C. reinhardtii*, related to FIGS. 2 and 3. Chromatin states defined by ChromHMM for cells cultured in WT (TAP), N- or S-depleted media. The major histone modifications found in each state are highlighted in blue. The % of occupied genome is listed.

Figure 36C:
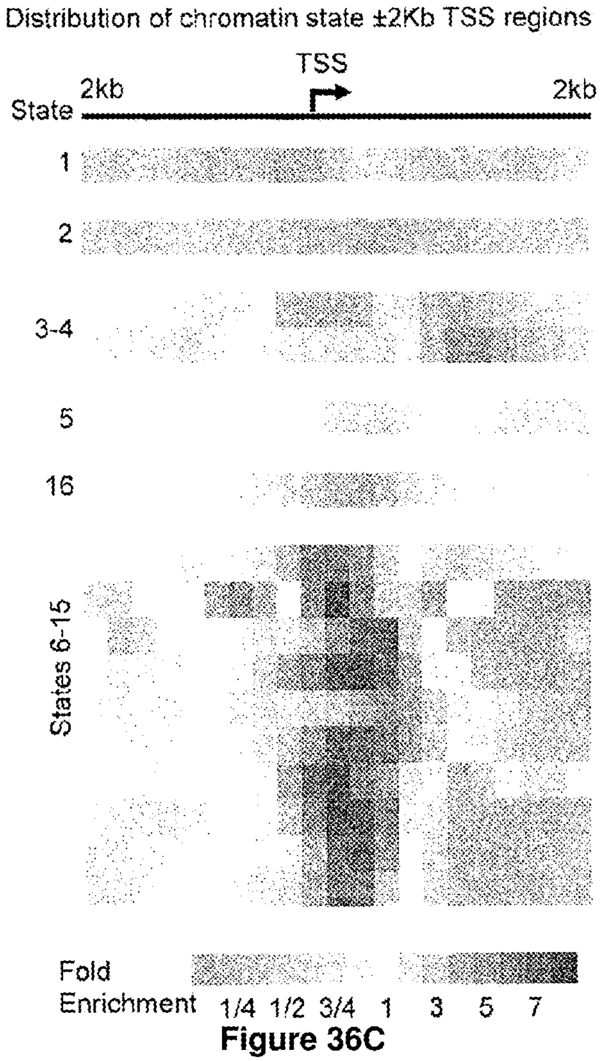

FIG. 36C: Chromatin features in *C. reinhardtii*, related to FIGS. 2 and 3. The enrichment of chromatin state at ±2 kb of transcription start site (TSS). The fold of enrichment of each state is shown in color scale.

Figure 36D:
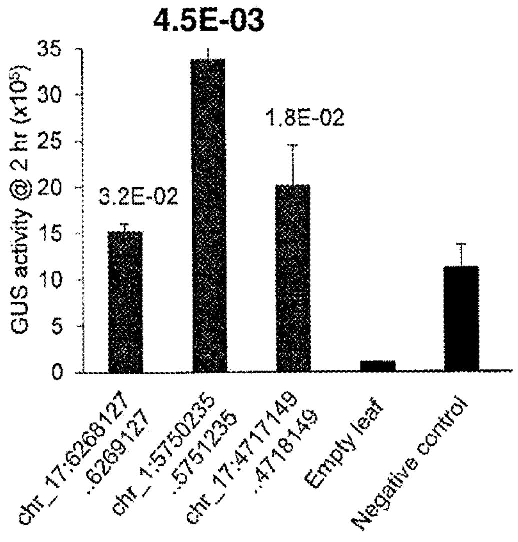

FIG. 36D: Chromatin features in *C. reinhardtii*, related to FIGS. 2 and 3. GUS activity driven by putative enhancer elements predicted by chromatin states. The genomic coordinates of the tested regions and one random negative control are shown in X-axis. GUS activity was measured at 2 hr post inoculation. P-values above indicate the significance of the enhanced activities by Mann-Whitney test (one-tailed).

Figure 37A:
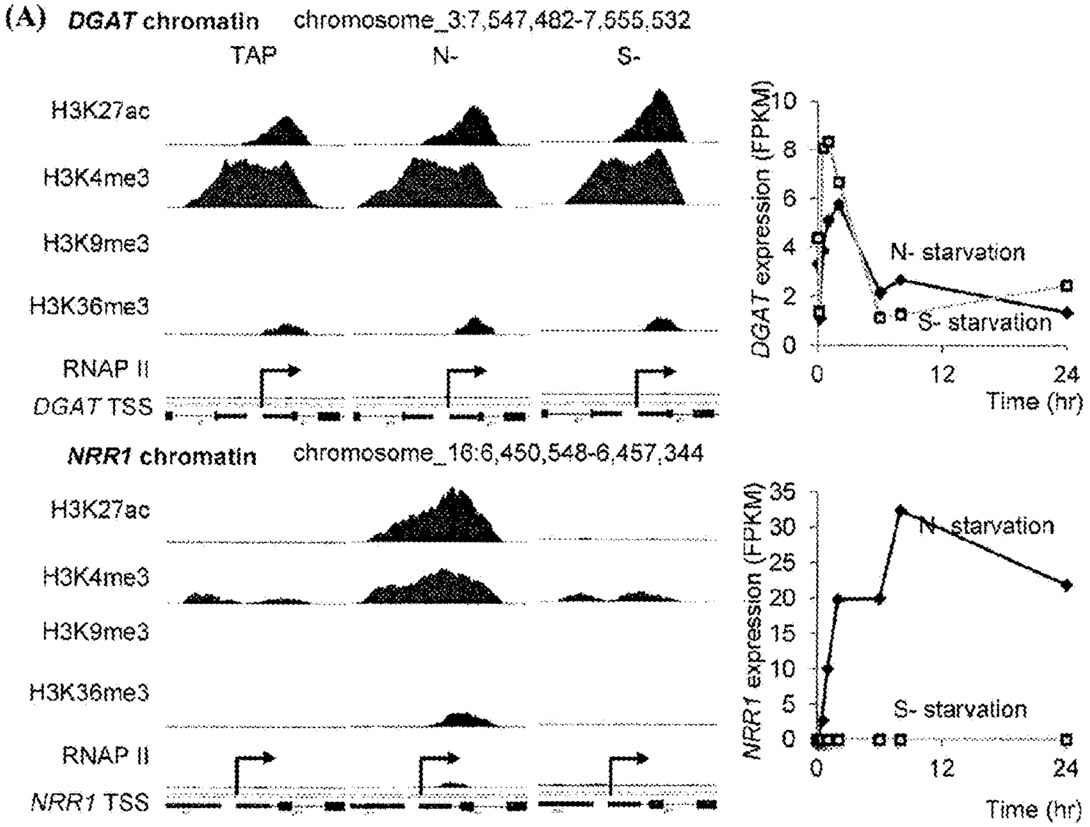

FIG. 37A: Chromatin state accurately predicts transcription activity, related to FIG. 4. Chromatin profile changes found in the TSS of DGAT (upper panel) and NRR1 (lower panel) in N and S starvation.

Figure 37B:
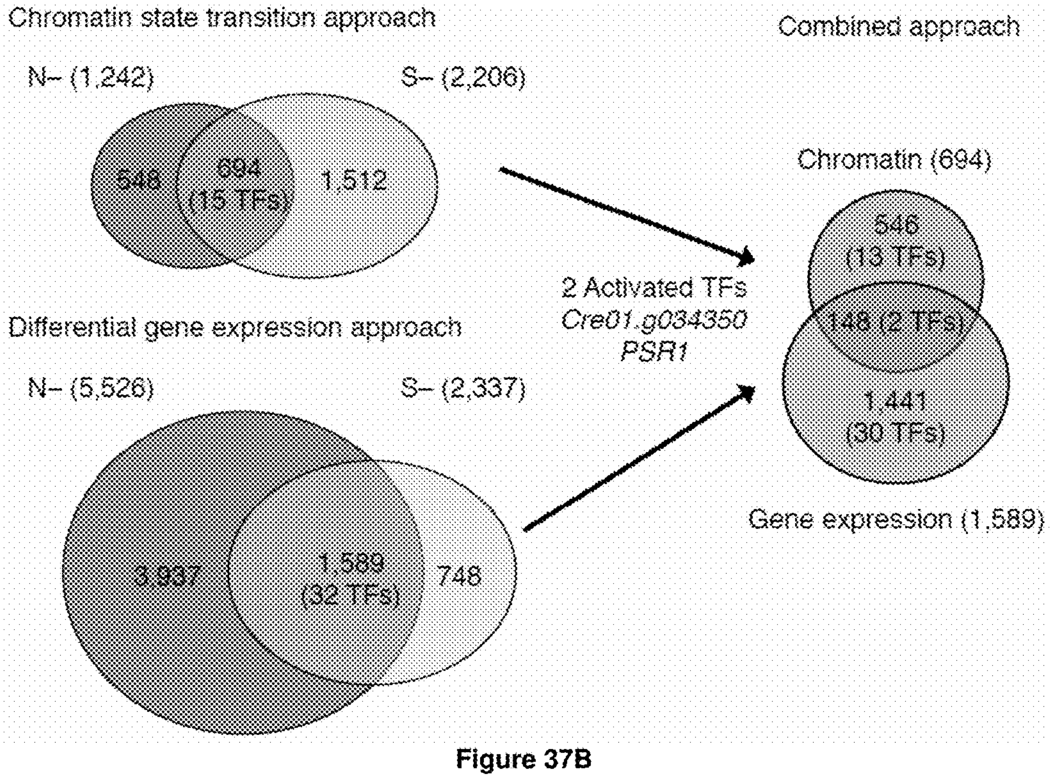

FIG. 37B: Chromatin state accurately predicts transcription activity, related to FIG. 4. Candidate genes activated in both N and S starvation inferred by chromatin state transition (top left), RNA-seq approach (bottom left) and combined approach (right) are shown in the overlap in the Venn Diagrams.

Figure 38A:
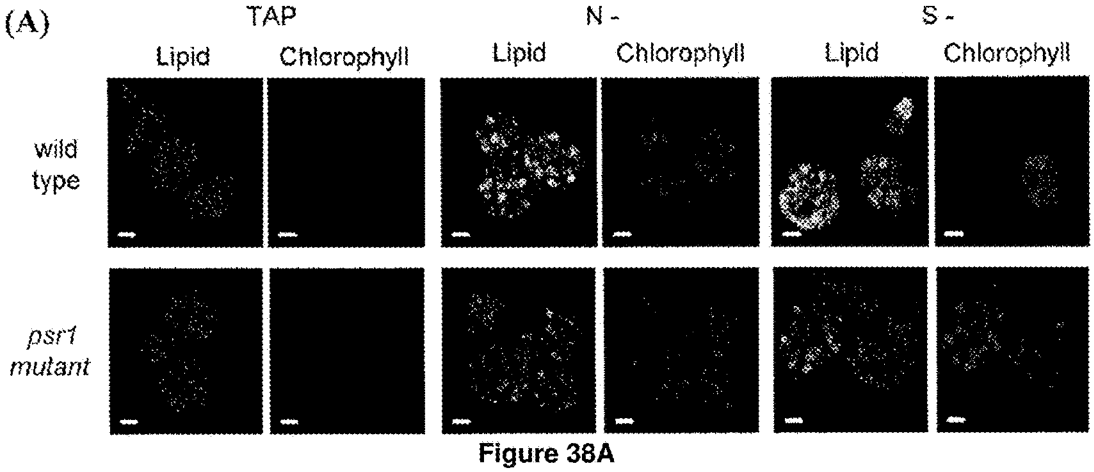

FIG. 38A: PSR1 functions as a lipid trigger in *C. reinhardtii*, related to FIG. 5. Confocal microscopy and lipid specific staining (LipidTOX Green) and chlorophyll autofluorescence of wild type 4a+ cell (upper) and psr1 mutant (lower) cells. Samples were collected 48 h after depletion. Pictures were taken with the same laser power. Scale bar: 2 um.

Figure 38B:
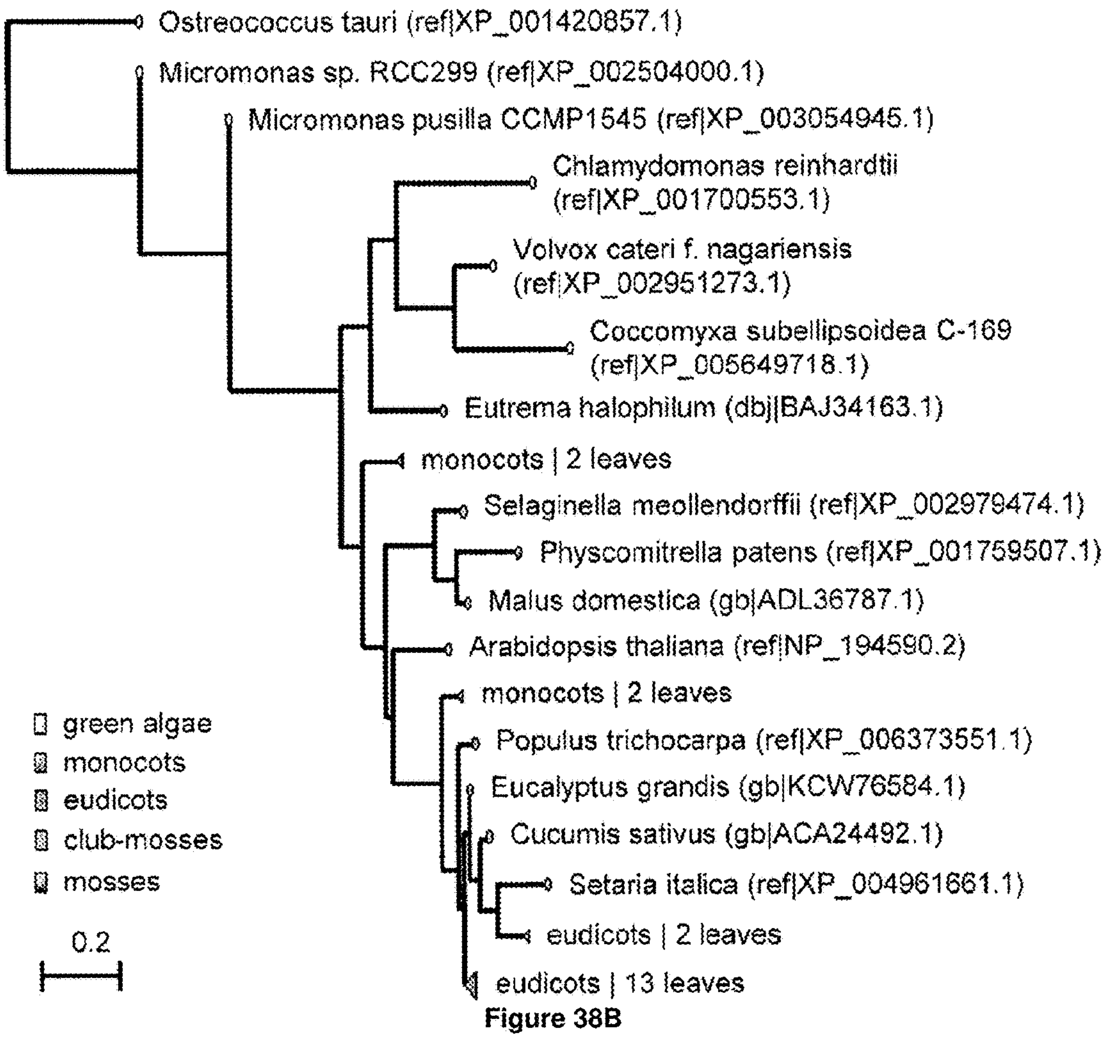

FIG. 38B: PSR1 functions as a lipid trigger in *C. reinhardtii*, related to FIG. 5. PSR1 conservation across multiple plant species in high-level taxonomy categories is shown in a tree view. *C. reinhardtii*'s PSR1 protein sequence's BLAST search returned 2404 hits across different plant and algae species (data not shown).

Figure 39A:
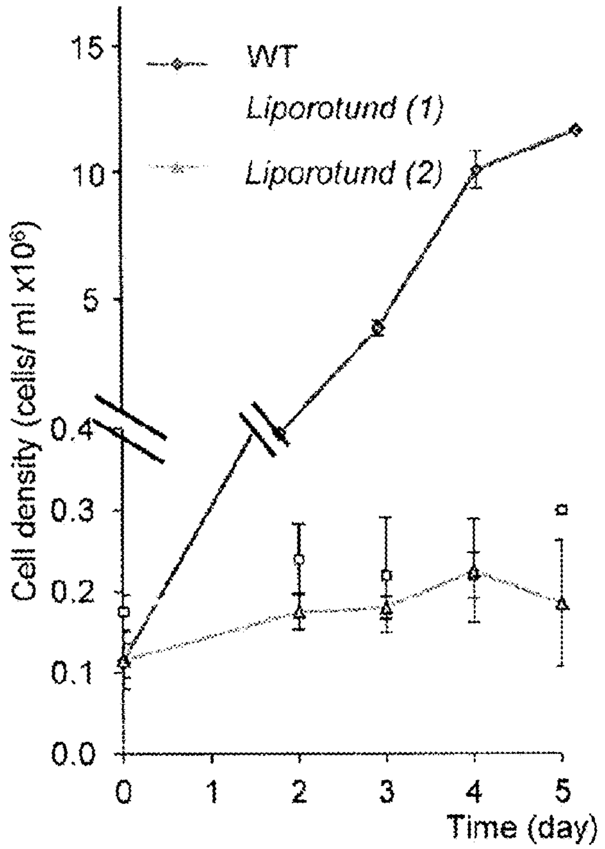

FIG. 39A: PSR1 overexpression and target genes, related to FIG. 6. Growth rate analysis of liporotund along 5 days culture in TAP media.

Figure 39B:
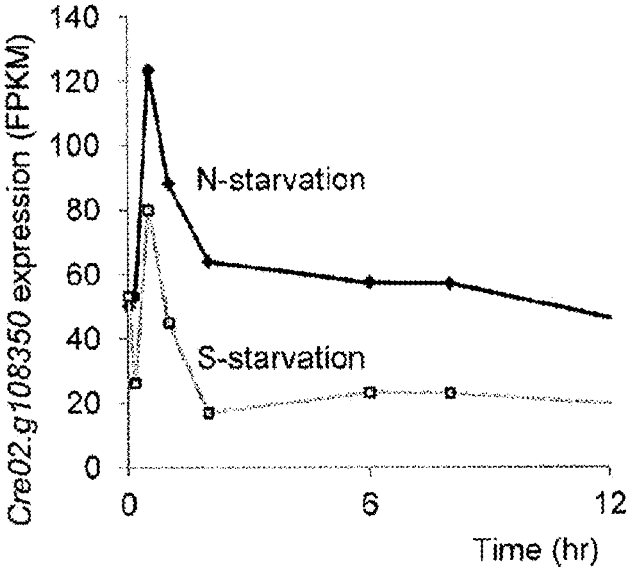

FIG. 39B: PSR1 overexpression and target genes, related to FIG. 6. PSR1 target gene expression profile of Cre02.g108350.

Figure 39C:
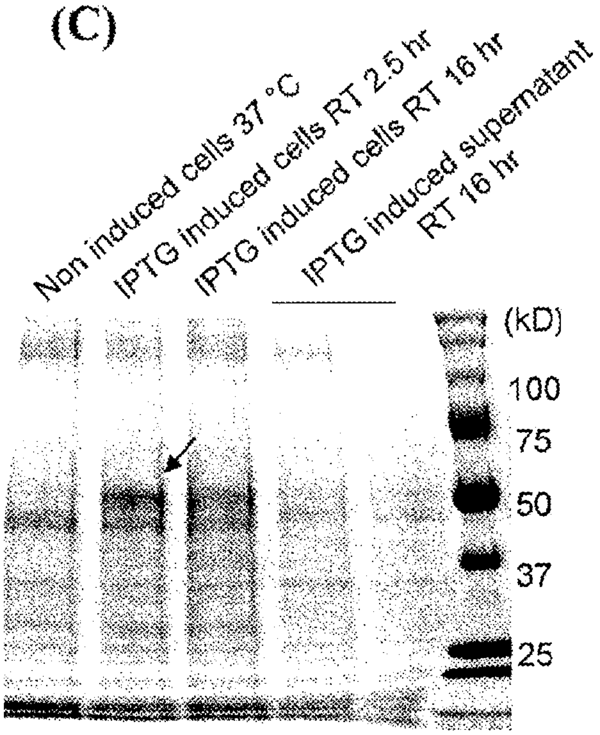

FIG. 39C: PSR1 overexpression and target genes, related to FIG. 6. A truncated form of *C. reinhardtii* PSR1 protein containing target epitopes was expressed in *E. coli.*

Figure 39D:
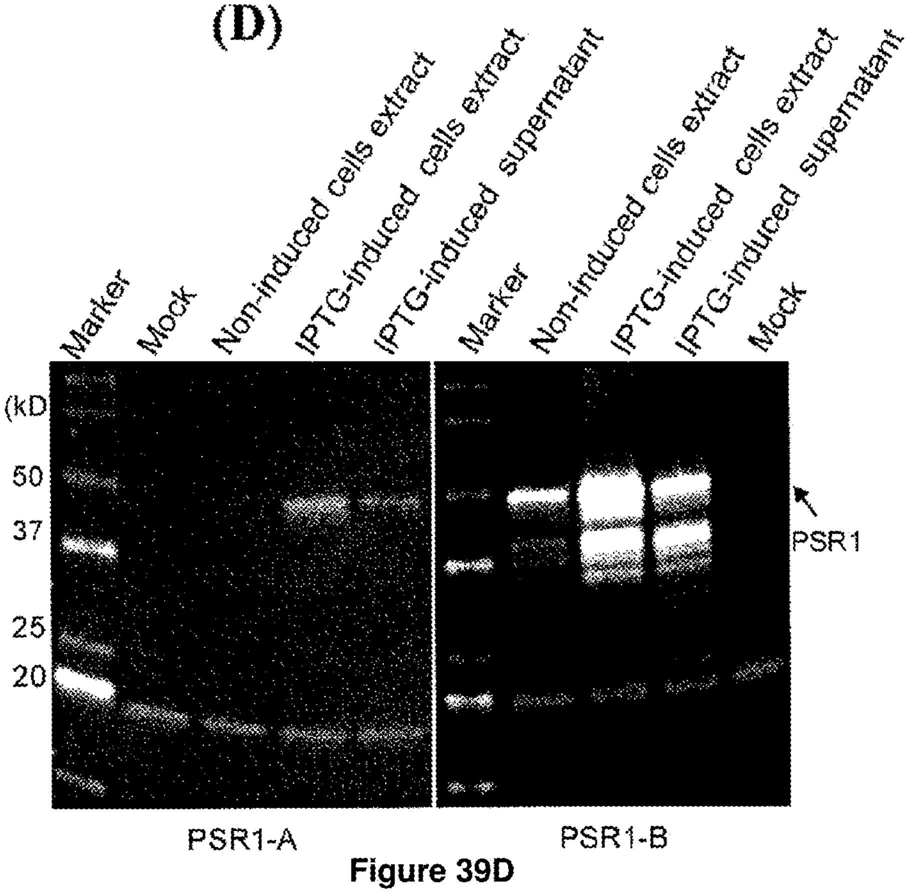

FIG. 39D: PSR1 overexpression and target genes, related to FIG. 6. Two PSR1 antibodies (PSR1-A and PSR1-B) detect a ~47 kD protein of the *E. coli* protein extract.

FIG. 40A: Antibodies validation and states reduction approach, related to Experimental Procedures. Pair-wise alignment of H3 protein sequences between *C. reinhardtii* (amino acids 1-49=SEQ ID NO:30, amino acids 50-99=SEQ ID NO:32, amino acids 100-149=SEQ ID NO:34, amino acids 150-192=SEQ ID NO:35) and human (amino acids 1-50=SEQ ID NO:29, amino acids 51-100=SEQ ID NO:31, amino acids 101-136=SEQ ID NO:33).

FIG. 40B: Antibodies validation and states reduction approach, related to Experimental Procedures. Western blot confirmed antibodies used for ChIP-seq analysis recognize a ~17 kDa protein in *C. reinhardtii*, an expected size for H3.

Figure 41A:
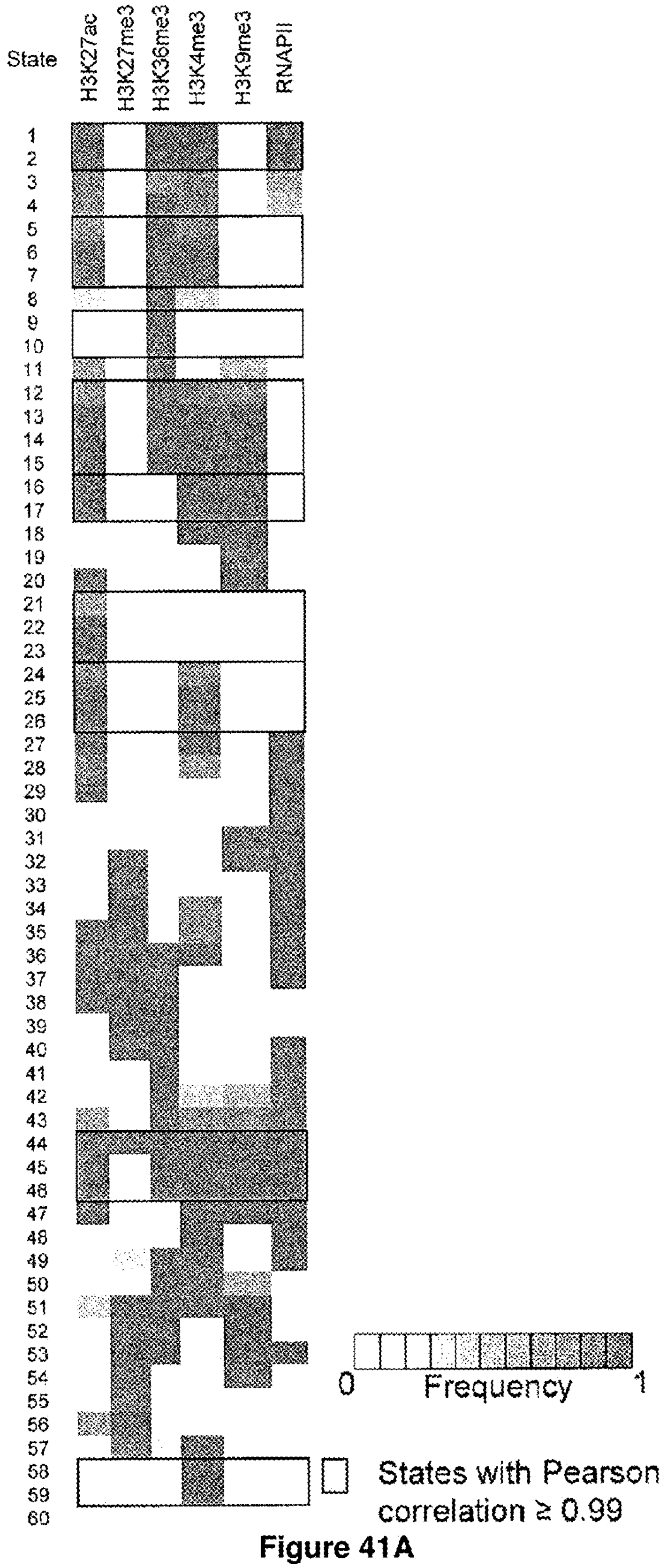

FIG. 41A: Antibodies validation and states reduction approach, related to Experimental Procedures. Additional states captures finer-grain chromatin distinction but introduces state redundancy for biological interpretation. Chromatin mark frequency for each chromatin state of the best HMM amongst 693 HMMs. The frequency is shown in color scale. The red box indicates states with Pearson correlation ≥0.99.

Figure 41B:
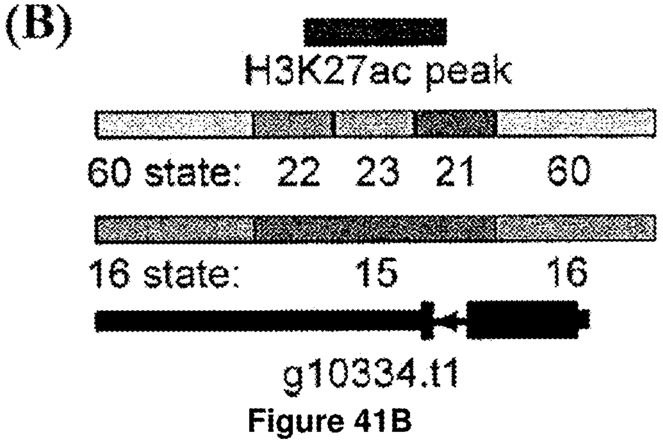

FIG. 41B: Antibodies validation and states reduction approach, related to Experimental Procedures. Examples of state redundancy introduced by spatial consideration in the best HMM and their concise state representation in the final non-redundant 16-states HMM. Each panel shows the detected chromatin peak in a genome region (top), its genome segmentation by the best HMM (60 states) and the final non-redundant 16-state HMM (middle), and the gene model in the vicinity (bottom).

Figure 41C:
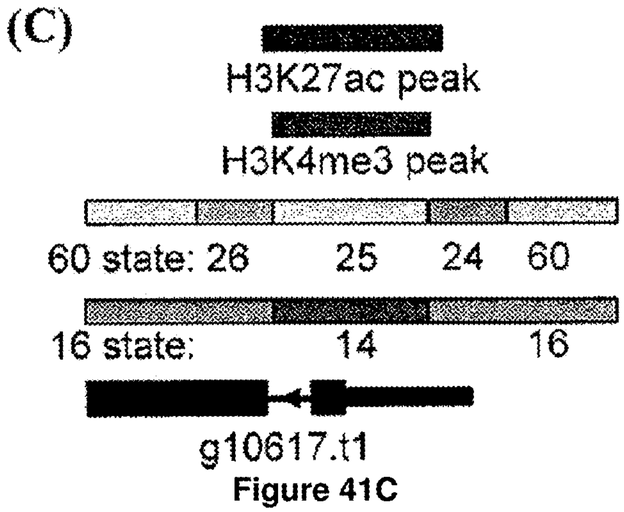

FIG. 41C: Antibodies validation and states reduction approach, related to Experimental Procedures. Examples of state redundancy introduced by spatial consideration in the best HMM and their concise state representation in the final non-redundant 16-states HMM. Each panel shows the detected chromatin peak in a genome region (top), its genome segmentation by the best HMM (60 states) and the final non-redundant 16-state HMM (middle), and the gene model in the vicinity (bottom).

Figure 41D:
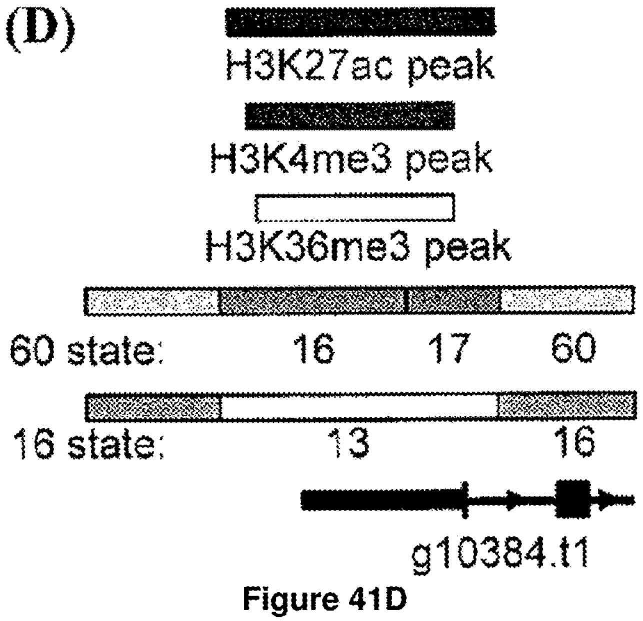

FIG. 41D: Antibodies validation and states reduction approach, related to Experimental Procedures. Examples of state redundancy introduced by spatial consideration in the best HMM and their concise state representation in the final non-redundant 16-states HMM. Each panel shows the detected chromatin peak in a genome region (top), its genome segmentation by the best HMM (60 states) and the final non-redundant 16-state HMM (middle), and the gene model in the vicinity (bottom).

Table 1. ChIP-seq summary, related to FIGS. 23A-23B.

Table 2. ChIP-seq summary, related to FIGS. 23A-23B.

Table 3. RNA-seq data summary and processing, related to FIGS. 23A-23B.

Table 4. Transcript models constructed from RNA-seq data, related to FIGS. 23A-23B.

Table 5. Differential gene expression analysis, related to FIGS. 23A-23B.

Table 6. PSR1 ChIP-seq summary, related to FIGS. 32A-32C and 33.

Table 7. Primers sequences for enhancer assay.

Table 8. H4K3me3 time series ChIP-seq data summary.

SUMMARY OF THE INVENTION

Alga-derived lipids represent an attractive potential source of biofuels. However, lipid accumulation in algae is a stress response tightly coupled to growth arrest, thereby imposing a major limitation on productivity. To identify master regulators of lipid accumulation and decipher the regulation of lipid biosynthetic pathway, we performed an integrative chromatin signature and transcriptomic analysis in the alga *Chlamydomonas reinhardtii*. Genome-wide histone modification profiling revealed remarkable differences in functional chromatin states between algae and higher eukaryotes and uncovered regulatory components at the core of lipid accumulation pathways. We identified the transcription factor PSR1 as a pivotal master switch that triggers cytosolic lipid hyper-accumulation an order of magnitude higher than stress regimens have achieved. Dissection of the PSR1 target network corroborates its central role in coordinating multiple stress responses. The comprehensive maps of functional chromatin signatures in a major clade of eukaryotic life and the discovery of a central regulator of algal lipid metabolism will facilitate targeted engineering strategies in microalgae.

Briefly, we describe genome-wide functional chromatin profiling in a major clade of plant lineage. An integrative chromatin and transcriptome analysis reveals core lipid regulators. PSR1 is a master lipid switch triggering hyper-lipid accumulation in microalgae. PSR1 target gene network coordinates multiple lipid-inducing stress responses

DESCRIPTION OF THE EMBODIMENTS

Introduction

We have discovered and identified key transcription factors (TFs) that act as master regulators of biodiesel precursor pathways in microalgae. Such knowledge will enable one to genetically manipulate microalgae through transgenetic approaches to create lipid over-producing strains. Such capability and resulted strains can be used for the production of renewable biofuels. As described in the earlier section this approach was not possible before because the lack knowledge on the specific regulators and our discovery enables such approach The challenges for identifying key transcriptional regulators include that the key transcription factors (TF) controlling lipid accumulation in microalgae are not known, the TF genes are not well annotated, TF expression may be transient and low level, there is a huge range of mRNA abundance in the cell and measured mRNA levels reflect balance of transcription and degradation rates.

Our discovery was made because we adopted a novel and integrated experimental platform to dissect the genetic regulatory pathways of TAG synthesis. The platform utilized a combinatory experimental interrogation on the genomic, transcriptomic and epigenetic dynamics in microalgae throughout lipid accumulation culture conditions. To do so, we have to develop several related technologies in microalgae and overcome a lot of technical issues during the method development (such as cell lysis for native chromatin isolation, chromatin immunoprecipitation and micro-algae specific antibody characterization).

Herein is described a general strategy for increasing lipid production in a heterologous host environment. Host species such as *Chlamydomonas* may be suitable hosts and used for industrial-scale production Definitions An "expression vector" or "expression cassette" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

By "host cell" is meant a cell that contains an expression vector and supports the replication or expression of the expression vector. Host cells may be prokaryotic cells including but not limited to, algae such as *Chlamydomonas*, cyanobacteria, or eukaryotic cells including but not limited to, yeast, insect, amphibian, or mammalian cells such as CHO, HeLa and the like, e.g., cultured cells, explants, and cells in vivo.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid polymers may comprise entirely L-amino acids, entirely D-amino acids, or a mixture of L and D amino acids. The use of the term "peptide or peptidomimetic" in the current application merely emphasizes that peptides comprising naturally occurring amino acids as well as modified amino acids are contemplated.

Any "gene" is meant to refer to the polynucleotide sequence that encodes a protein, i.e., after transcription and translation of the gene a protein is expressed. As understood in the art, there are naturally occurring polymorphisms for many gene sequences. Genes that are naturally occurring allelic variations for the purposes of this invention are those genes encoded by the same genetic locus. Thus, any "transcription factor gene" as referred to herein is meant to include any polynucleotide that regulates a gene encoding a lipid protein or variants thereof.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel.

The terms "identical" or percent "identity," in the context of two or more polypeptide sequences (or two or more nucleic acids), refer to two or more sequences or subsequences that are the same or have a specified percentage of amino acid residues or nucleotides that are the same e.g., 60% identity, preferably 65%, 70%, 75%, 80%, 85%, 90%, 91%, 92%, 93%, 94%, 95%, 96%, 97%, 98%, 99% or 100% identity over a specified region (such as the first 15 amino acids of each of the transcription factor genes), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are typically used.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides.

Examples of such analogs include, without limitation, phosphorothioates, phosphoramidates, methyl phosphonates, chiral-methyl phosphonates, 2-O-methyl ribonucleotides, polypeptide-nucleic acids (PNAs). Unless otherwise indicated, a particular nucleic acid sequence also encompasses "conservatively modified variants" thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., *J. Biol. Chem.,* 260:2605-2608 (1985); Rossolini et al., *Mol. Cell. Probes,* 8:91-98 (1994)). The term nucleic acid can be used interchangeably with gene, cDNA, mRNA, oligonucleotide, and polynucleotide.

A "label" or "detectable label" is a composition detectable by spectroscopic, photochemical, biochemical, immunochemical, or chemical means. For example, useful labels include radioisotopes (e.g., $^{3}H$, $^{35}S$, $^{32}P$, $^{51}Cr$, or $^{125}I$), fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available (e.g., lipid proteins can be made detectable, e.g., by incorporating a radiolabel into the protein, and used to detect antibodies specifically reactive with the protein).

The present invention provides for the overexpression of regulatory proteins, specifically transcription factors (TFs) to up-regulate the activity of multiple enzymes in the TAG biosynthetic pathway of microalgae. Different from prior strategies, over-expression of transcription factors affects a large number of genes involving multiple pathways, resulting in an integrated regulation of these pathways simultaneously. Thus, such TF-engineered microalgal strains offer as an attractive mean for cost-effective TAG production. Towards this goal, we uncovered key TFs that can be used to use for generating transgenic lipid over-producing microalgae. Such microalgae can be used as green cell-factories to produce commercial biodiesel industry. Thus, our invention describes the use of these genes, their protein products and the transgenic strains as agents to produce biodiesel at economic scale.

In one embodiment, the present invention provides for a construct or an expression cassette comprising a polynucleotide encoding a transcription factor gene selected from the 17 transcription factors in the sequence listing for the expression in a host cell.

The expression cassette can be used to provide a cell comprising in its genome at least one stably incorporated expression cassette, where the expression cassette comprising a heterologous nucleotide sequence or a fragment thereof operably linked to a promoter that drives expression in the cell.

Also provided are methods for enhancing lipid production activity in an organism. In one method, comprising introducing into an organism at least one expression cassette operably linked to a promoter that drives expression in the organism, where the expression cassette comprising a transcription factor gene identified herein.

In one embodiment, lipid overexpression is described and methods for increasing overexpression using the Psr1 transcription factor.

In one embodiment, polynucleotides which regulate lipid expression, are cloned into an appropriate plasmid, inserted into an expression vector, and used to transform cells from any host organism. Suitable host organisms include, but are not limited to, bacteria such as *E. coli, B. subtilis, S. cerevisiae*, cyanobacteria, algae such as *Chlamydomonas*, plants such as *Nicotiana tabacum* and *Camelina sativa*, fungi, or other eukaryotic organisms.

In one embodiment, the polynucleotides are in an inducible expression system which maintains the expression of the inserted genes silent unless an inducer molecule (e.g., IPTG) is added to the medium containing the host cell. The expression vector or construct may be a vector for coexpression or in some embodiments, it may be a neutral site vector for insertion into a host genome such as *Chlamydomonas*. The construct may include either inducible transcription elements or may be constitutively expressed in the host organism.

Bacterial colonies are allowed to grow after gene expression has begun, or if required, after induction of gene expression. Thus, in some embodiments, expression vectors comprising a promoter operably linked to a heterologous nucleotide sequence or a fragment thereof, that regulates expression of a lipid protein are further provided. The expression vectors of the invention find use in generating transformed plants, plant cells, microorganisms, algae, fungi, and other eukaryotic organisms as is known in the art and described herein. The expression vector will include 5' and 3' regulatory sequences operably linked to a polynucleotide of the invention. "Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The vector may additionally contain at least one additional gene to be co-transformed into the organism. Alternatively, the additional gene(s) can be provided on multiple expression vectors or cassettes. Such an expression vectors is provided with a plurality of restriction sites and/or recombination sites for insertion of the polynucleotide that is a transcription factor gene or a regulatory factor of gene expression of lipids. The expression vector may additionally contain selectable marker genes.

In one embodiment, the expression vector will include in the 5'-3' direction of transcription, a transcriptional initiation region (i.e., a promoter), a cluster of bacterial compartment genes each preceded by a translational initiation site (RBS) specific to the organism and type of shell protein and followed by a translation termination signal (stop codon), and, optionally, a transcriptional termination region functional in the host organism. The regulatory regions (i.e., promoters, transcriptional regulatory regions, ribosomal binding sites and translational termination regions) and/or any targeting sequences may be native/analogous to the host cell or to each other. Alternatively, the regulatory regions and/or the targeting regions may be heterologous to the host cell or to each other. As used herein, "heterologous" in reference to a sequence that originates from a foreign species, or, if from the same species, is modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

In other embodiments, the transcription genes described herein can be incorporated into multiple expression vectors and/or under multiple promoter control.

Where appropriate, the polynucleotides may be optimized for increased expression in the transformed organism. For example, the polynucleotides can be synthesized using preferred codons for improved lipid expression.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression vector can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). The above list of selectable marker genes is not meant to be limiting. Any selectable marker gene can be used in the present invention.

In various embodiments, it is beneficial to express the gene from an inducible promoter, particularly from an inducible promoter in order to induce lipid production or overexpression.

In some embodiments, the expression vector comprising multiple copies of the lipid genes and transcription regulatory factors.

In some embodiments, an engineered or non-natural strain whose genome comprises one of the 17 transcription genes, wherein the strain is capable of increased production or overexpression of lipids.

In some embodiments, an engineered or non-natural strain whose genome comprises at least one of the 9 activated transcription genes, wherein the strain is capable of increased production or expression of lipids.

In some embodiments, an engineered or non-natural strain whose genome comprises at least one of the 8 inactivated transcription genes, wherein the strain is capable of increased production or expression of lipids.

In some embodiments, an engineered or non-natural strain whose genome comprises at least one of the 8 inactivated transcription genes and at least one of the 9 activated transcriptions genes, wherein the strain is capable of increase production or expression of lipids.

In some embodiments, an engineered or non-natural strain whose genome comprises overexpression of at least one of the 9 activated transcription genes, wherein the strain is capable of increased production or expression of lipids.

In some embodiments, an engineered or non-natural strain whose genome comprises disruption of at least one of the 8 inactivated transcription genes, wherein the strain is capable of increased production or expression of lipids. Methods of gene disruption include, without limitation, mutation, down-regulation, insertional inactivation of a gene, use of nucleases or recombinases, homologous recombination, and/or siRNA (Guo, Chang □An, O'Neill, Lucas M, and Ntambi, James M (October 2014) Gene Inactivation Strategies: An Update. In: eLS. John Wiley & Sons Ltd, Chichester; Bischof, J. et al., Recombinases and their use in gene activation, gene inactivation, and transgenesis, Methods Mol Biol. 2008; 420:175-95).

In some embodiments, an engineered or non-natural strain whose genome comprises overexpression of at least one of the 9 activated transcription genes and disruption of at least one of the 8 inactivated transcription genes, wherein the strain is capable of increased production or expression of lipids.

EXAMPLE 1: Lineage-Specific Chromatin Signatures Reveal a Master Lipid Switch in Microalgae Algae naturally accumulate energy-dense oils that can be converted into transportation fuels, potentially rendering them an attractive system for large-scale biofuel production (Wijffels and Barbosa, 2010). Algae-derived biofuels offer the promise of high areal productivity, minimal competition with food crops, utilization of a wide variety of water sources, and $CO_2$ capture from stationary emission sources (U.S. DOE 2010. National Algal Biofuels Technology Roadmap. DOE EERE Website for algal-biofuels; Merchant et al., 2012). However, high-yield lipid accumulation in algae is a stress response inducible through conditions like nutrient deprivation, which limits overall yield and thus commercial viability (Chisti, 2013). Extensive research efforts have been aimed at improving algal lipid productivity, but these approaches including metabolic engineering (Blatti et al., 2013), mutant screening (Cagnon et al., 2013) and growth manipulation (Csavina et al., 2011) have yet to substantially boost intracellular lipid levels (Courchesne et al., 2009).

The microalga *Chlamydomonas reinhardtii* is one of the model organisms for studying algal growth and lipid metabolism. This species accumulates substantial amounts of triacylglycerol (TAG) during nutrient stress and is amenable to well-established classical genetic methods (Chisti, 2007). A high quality and functionally annotated genome sequence is available in public repositories (Merchant et al., 2007) and large collections of mutant strains have been produced (on the world wide web at chlamycollection.org). Despite growing amounts of transcriptome and proteome data (Boyle et al., 2012; Castruita et al., 2011), the molecular mechanisms that govern algal lipid production have remained elusive. In particular, it is unclear how various responses to distinct environmental stressors converge into the transcriptional control of a single common TAG biosynthesis pathway.

In higher plants, many stress-elicited responses are controlled at the level of epigenetic (Tanurdzic et al., 2008; Zhong et al., 2013) and transcriptional regulation (Boyle et al., 2012; Hemschemeier et al., 2013), particularly through the activation of master transcription factors (TFs) (Borevitz et al., 2000; Nuruzzaman et al., 2013). Because of substantial variation in transcript stability and degradation rates, transcript levels are an imperfect proxy for the transcriptional status of individual genes. This problem is likely exacerbated by the transient expression and potentially low abundance of stress-responding TF transcripts, rendering their identification through transcription profiling alone difficult. Due to these challenges, only a single algal TF, NRR1, has been functionally implicated in lipid accumulation albeit with moderate effects on lipid accumulation only during nitrogen (N-) starvation and none during other nutrient stresses (Boyle et al., 2012). In contrast to transcriptome profiling, distinct patterns of histone modifications can reveal active or repressed chromatin states (Kouzarides, 2007) and provide information about the transcriptional activity of the associated genes (Li et al., 2008; Wang et al., 2009a). For instance, alterations in histone modifications have been used to identify central regulatory genes in the *Arabidopsis* leaf senescence process (Ay et al., 2009). We thus hypothesized that a combination of chromatin state and transcriptome changes induced by lipid-inducing starvation conditions in *C. reinhardtii* may provide a sensitive and specific readout for detecting key switches controlling the lipid accumulation process.

In this study, we constructed genome-wide maps of chromatin states and their dynamics in *C. reinhardtii*. Compared with patterns found in metazoans (Celniker et al., 2009; Consortium et al., 2012) and land plants (Ben et al., 2011; Roudier et al., 2011), functional chromatin signatures in microalgae are a combination of both conserved and lineage-specific histone codes. We exploited chromatin signature changes to infer master regulators of lipid accumulation and applied targeted genetic perturbation to confirm one of these TF genes, PSR1, as a core switch activating lipid accumulation. Mapping the in vivo PSR1 target genes reveals intricate connectivity between different stress responses and provides insights into the regulation of TAG biosynthetic pathway as well as strategies for their targeted genetic engineering.

Results

Mapping epigenomic changes in response to lipid-inducing conditions. To characterize chromatin states in *C. reinhardtii* and profile their changes in response to stress-induced lipid accumulation, we cultured *C. reinhardtii* cells under two different acute nutrient depletion schemes known to induce TAG accumulation, nitrogen (N-) and sulfur (S-) starvation (Boyle et al., 2012). A slow rate of cell growth and high lipid levels confirmed that the expected stress responses were achieved (FIGS. 23A-23B). We used chromatin immuno-precipitation followed by sequencing (ChIP-seq) to profile the genome-wide distribution of RNA polymerase II (RNAPII), as well as five distinct post-translational modifications of histone H3 including trimethylation of lysine residues 4 (H3K4me3), 9 (H3K9me3), 27 (H3K27me3), 36 (H3K36me3) and lysine 27 acetylation (H3K27ac) in control cells, cultured in Tris-acetate-phosphate (TAP) media and 1 hr post-starvation under both N- and S-conditions (FIGS. 23A-23B). ChIP-seq reads were mapped to the *C. reinhardtii* reference genome and used to determine modified regions with high reproducibility across biological replicates (overall reproducibility Pearson correlation, R>0.96 in all cases, FIG. 34, Tables 1-5).

To monitor the transcriptional responses associated with chromatin changes at high temporal resolution, we also performed deep RNA-seq analysis throughout the course of nutrient depletion up to 48 hr post-starvation when lipid accumulation is pronounced. Comprehensive expression changes in both early (0-8 hr, within one cell cycle) and late (24-48 hr) phases were captured (FIGS. 23A-23B). Similar to the epigenomic data, high correlations between biological replicates were observed (Pearson correlation ≥0.99, FIG. 35A). To ensure that all transcripts specifically expressed in response to N- and S-starvation were included in our analysis, we performed a reference-guided transcript assembly from these deep RNA-seq data sets, which revealed 4,241 new alternative splice variants and 298 previously unannotated transcripts. Across all 22,209 transcripts assembled, approximately half are differentially expressed (>2 fold, P<0.01) in at least one time point along the course of N- or S-starvation (Tables 1-5), suggesting extensive transcriptional changes associated with nutrient starvation and lipid induction.

Plant- and alga-specific histone signatures. Similar to metazoans, histone modifications in *C. reinhardtii* largely exhibit punctuated patterns across the *C. reinhardtii* genome (FIG. 24A) and are primarily clustered within 1 kb of the transcription start sites (TSSs) of annotated genes (FIG. 24B). Examination of individual histone marks revealed similarities, but also marked differences compared to the well-characterized histone code of animals. Overall, H3K4me3, H3K27ac, H3K9me3 and H3K36me3 (to a lesser degree) are co-localized (FIG. 24C). In vertebrates, H3K9me3 is associated with repressed heterochromatin (Peters et al., 2002), but in *C. reinhardtii*, this mark nearly universally (96% of H3K9me3 regions) co-localizes with active marks H3K4me3 or H3K27ac (FIG. 36A). While a general activity-associated and promoter-centric distribution of H3K9me3 was observed in *Arabidopsis* (Roudier et al., 2011), the co-occurrence of H3K9me3 with active marks and mutual exclusion with repressive mark H3K27me3 observed in *C. reinhardtii* may be restricted to algae or could represent a previously unappreciated general plant-specific histone signature. A second mark divergent from vertebrates is H3K36me3, which spans broad regions along actively transcribed genes in vertebrates (Guenther et al., 2007), but is largely confined between active promoters (90%; 7,978 out of 8,873 regions) in *C. reinhardtii* (FIG. 24B). Hence, while the general existence of these histone modifications is highly conserved, their functions appear to have diverged across the different eukaryotic clades.

Because the individual histone patterns were found unique in *C. reinhardtii*, we adopted an unsupervised approach to systematically analyze combinatorial patterns from these histone modifications and RNAPII occupancy through the established ChromHMM (Ernst and Kellis, 2012), which led to the identification of 16 distinct chromatin states (CS). Most of the genomic regions (87%) are devoid of any modification (CS 16). The remaining 15 states contain one or more marks in different combinations and associated with different genomic locations (FIG. 24D, FIG. 36B). CS 1-5 account for 3% of the genome, are mainly defined by H3K27me3, H3K36me3 and RNAPII and distributed among non-promoter regions, while CS 6-15 occupy 10% of the genome, are mainly defined by H3K27ac, H3K4me3 and H3K9me3 and found around promoter regions (FIG. 36C).

Two states, CS 2 and CS 15, are of particular interest in comparison to known animal and plant chromatin signatures (FIG. 25, middle panel). CS 2 represents bivalent domains showing an active mark (H3K36me3) in combination with a repressive mark (H3K27me3). Bivalent domains, initially uncovered in animal cells as the regions co-modified by H3K4me3 and H3K27me3, pervasively associate with developmental regulator genes in early developmental cells (Bernstein et al., 2006) (FIG. 25, left panel). Similar "K4/K27me3" bivalent status was also detected in *Arabidopsis*, including the flowering locus C (Luo et al., 2012). In support of a bivalent status, *C. reinhardtii* transcripts associated with K36/K27me3 are expressed at substantially lower levels than those with non-bivalent marks ($P<2.2e-16$, FIG. 25) and significantly enriched for genes encoding metabolic enzymes and protein kinase activities (P=1.8e-03 & 6.8e-03). In contrast, CS 15 is defined through H3K27ac single modification and, based on what has been observed in metazoan genomes, this signature is overall a characteristic of distal transcriptional enhancers (Creyghton et al., 2010). As expected, a significant portion of these regions is outside ±1 kb of the known TSS. To evaluate this functional feature, we profiled the known enhancer mark H3K4me2 in log-phase *C. reinhardtii* cells and found that CS 15 is enriched for H3K4me2 modification (FIG. 26). Experimental validation of individual sequences identified by this signature confirmed their enhancer activity in 3 out of 11 cases tested (one-tailed Mann-Whitney test with $P<0.05$) by placing them upstream of reporter GUS gene in a heterologous Tobacco enhancer reporter assay, despite it is distally related to algae (FIG. 36D). One such region is shown in FIG. 26 where a H3K27ac peak is found in the 3' of amino acid permease gene; 7 kb and 3.5 kb away from its neighboring promoters. These data indicate the presence of potential distant-acting regulatory elements similar to those extensively characterized in vertebrate genomes (Shlyueva et al., 2014) in algae and possibly other plants.

Promoter histone modification patterns reflect genes transcriptional status.

Among all 16 different chromatin states defined, five types of histone modification patterns were associated with nearly all (20,843; 94%) transcript promoters in *C. reinhardtii* (FIG. 27). These five types differ mainly by progressive addition of modifications ranging from Type I promoter depleted of any mark to Type V promoter with all four active marks (H3K4me3, H3K27ac, H3K9me3 and H3K36me3) and the presence of RNAPII. Transcript abundance levels are highly correlated with the chromatin state of their respective promoters. Each consecutive class is associated with a significant increase in expression (FIG. 27, lower panel) ($P<1.7e-9$ in all cases, Wilcoxon rank sum test). Quantitative increases are most pronounced in Type IV vs. I-III (8.6-fold, $P<2.2e-16$) and V vs. IV (2.4-fold, $P<2.2e-16$), characterized by the addition of H3K36me3 and RNAPII, respectively. For all following analyses, Types IV and V were considered transcriptionally active in *C. reinhardtii* cells. Despite these overall highly significant correlations, within each promoter class a wide range of transcript levels was observed. This variation may result from a combination of inherently different transcription rates from individual promoters ("weak" vs. "strong" promoters) as well as from differences in post-transcriptional RNA stability, highlighting the limitations of transcriptome data alone for inferring the transcriptional status of individual genes. Taken together, histone modification landscape of model algae *C. reinhardtii* reveals chromatin signatures signifying functional elements both homologous to and distinct from those characterized for vertebrates and land plants. *C. reinhardtii* also exhibits unique histone modification states, particularly centered on promoters, suggesting that these promoter chromatin state assignments may provide a substrate for sensitive and accurate identification of regulatory genes like TFs responding changes in lipid metabolism.

Chromatin changes reveal candidate genes transcriptionally regulated in N- and S-conditions.

To infer regulatory gene candidates involved in lipid accumulation, we evaluated genes whose promoters exhibit chromatin state changes during both N- and S-starvations. We focused on promoters transitioning from Types I-III (no/low transcriptional activity) in control medium to Types IV (high) or V (very high transcription activity), i.e., promoters with substantial activation in response to nutrient depletion (FIG. 28A). Among 1,242 and 2,206 promoters transitioning to an active chromatin state under either of the starvation regimens, 694 genes are common to both conditions, including 15 annotated TFs (FIG. 28B). As expected, several genes known to be involved in TAG accumulation and stress responses are found among the 694 candidate genes. For example, the promoter of gene encoding DGAT (diacylglycerol acyltransferase), a critical enzyme converting DAG (diacylglycerol) to TAG (triacylglycerol) in the TAG biosynthesis pathway (Merchant et al., 2012) transitions from Type III to Type IV in both N- and S-, which is accompanied by substantially increased DGAT transcripts in starved cells. In contrast, NRR1 (nitrogen response regulator 1), a plant-specific TF gene involved in nitrogen assimilation and TAG accumulation (Boyle et al., 2012), is not found among the 694 candidates genes because its promoter switches from Type I to Type IV following N-starvation, but remains Type II under S-starvation. This is mirrored by a >25-fold increase in transcript level under N-but not S-starvation (FIG. 37A) (Boyle et al., 2012). To further prioritize this candidate list, we incorporated the RNA expression data of the 694 candidate genes. Because master regulatory genes are expected to function in early stages of the starvation, we focused on a subset of 397 genes that are differentially expressed between 0 and 2 hr under N- and S-starvation (>2-fold, $P<0.01$). These 397 genes were subjected to cluster analysis and grouped by the time point of highest expression for activated transcripts (see Experimental Procedures). Normalized expression values of the genes from the major clusters were displayed in heat maps and confirmed that those with activated promoter types tend to be up-regulated along the course of both starvation treatments (FIG. 28B, Table 7). We observed 3 broad categories of up-regulated expression patterns: clusters of genes with peak expression at 30 min (cluster A), 1 hr (cluster B) or 2 hr (cluster C) after the onset of nutrient starvation. Two of the 15 TF genes behave similarly within 2 hr in the courses of both N- and S-conditions whereas the remaining 13 TFs were either up-regulated after 2 hr or exhibited discordant expression patterns between the courses of N- and S-starvation. Compared to this integrative approach combining chromatin states with expression data, as many as 1,589 (32 TFs) candidate genes were up-regulated between 0 and 2 hr under both N- and S-starvations if only differential expression analysis is used (FIG. 37B). These results highlight how the intersection of orthogonal transcriptomic and epigenomic data sets enabled the stratification of genes into distinct clusters to retrieve a small number of high-confidence candidates.

PSR1 is a master regulator of lipid accumulation. Between the two highest-priority candidate TFs (PSR1 and Cre01.g034350), PSR1 (phosphorus-stress response 1) was the first TF up-regulated at 1 hr under N-starvation (10-fold), with a delayed and less pronounced increase in expression (3-fold) under S-starvation at 2 hr (FIG. 30A). Such expression pattern differences between N- and S-depletion correlate with differences in lipid accumulation, which is higher under N-than S-starvation (FIG. 1). The PSR1 promoter acquires a substantial amount of H3K36me3 and RNAPII binding in nutrient-deficient medium (FIG. 30B).

PSR1 is a member of the MYB-CC (MYB/coiled-coil domain) TF family and was first described as a component of the phosphate starvation response pathway, but initial studies did not suggest a link to lipid accumulation and its genomic targets are unknown (Wykoff et al., 1999). To confirm that PSR1 is a key regulator of lipid accumulation, we examined lipid levels during stress response in a psr1 loss-of-function mutant containing a nonsense mutation (see Extended Experimental Procedures) and the psr1 mRNA is undetectable (Wykoff et al., 1999). Throughout the 3-day starvation period, the psr1 mutant exhibited a 50-90% reduction in lipid accumulation compared to wild type under multiple, well characterized lipid induction regimens (nitrogen, sulfur, zinc, and iron starvation) (FIGS. 34 and 35A-35B). Differences in lipid content were also confirmed by a separate lipid staining (LipidTOX Green). In N-than S-starvation, wild type cells displayed intense green staining while the psr1 mutant showed only red chlorophyll autofluorescence (FIG. 38A). These results indicate that in the absence of PSR1, *C. reinhardtii* shows defects in normal lipid accumulation in response to a range of nutrient stress, raising the possibility that PSR1 may be a key switch of lipid accumulation in *C. reinhardtii.*

To examine if PSR1 alone is sufficient to drive lipid accumulation in the absence of nutrient depletion, we evaluated the consequences of its overexpression by nuclear transformation of a constitutively expressed PSR1 transgene into *C. reinhardtii* cells. Psr1 cDNA was transcriptionally fused to bleomycin (zeocin-resistance) gene sh-ble linked by a self-cleavage peptide 2A from foot-and-mouth-disease-virus (FMDV) under the control of constitutive hsp70/rbcs2 promoter (Rasala et al., 2012). The 2A peptide mediates a self-cleavage reaction to process the fusion protein into two discrete and functional proteins: bleomycin and PSR1. Therefore, the presence zeocin resistant clones indicate overexpression of PSR1 protein. PSR1-overexpressing cells show major morphological differences from wild-type cells grown in control (TAP) medium or under N-starvation. PSR1-overexpressing cells lose their flagella, display an over two-fold increase in diameter, suggesting an ~8-fold increase in cell size, and they have a round shape, termed here “liporotund”, as it appears to be associated with excessive formation of lipid bodies in the cytoplasm. When the quantity of accumulated lipids was compared between two independent PSR1-overexpressing clones, the level of lipid was positively correlated with the amount of PSR1 overexpression determined by quantitative RT-PCR (FIG. 30B). These clonal PSR1-overexpressing, lipid hyper-accumulating “liporotund” cells have substantially higher (70×) levels of intracellular lipid than wild-type cells when grown in TAP medium and 10× higher lipid levels than wild-type cells grown under nutritional starvation regimens (Mann-Whitney P<1.65e-11) (FIG. 30B). This level is also considerably higher than in transgenic strains overexpressing key enzymes of lipid metabolic pathways (Courchesne et al., 2009), cells blocked in starch biosynthesis (Wang et al., 2009b) or lipid hyper-accumulating cells isolated through random mutagenesis screens (Xie et al., 2014). Microscopy of LipidTOX-stained PSR1-overexpressing cells confirmed an increased number of lipid bodies (FIGS. 34 and 35A-35B), which correlates with normalized fluorescence measured by Nile red staining. Similar to the effects of nutrient starvation regimens, increases in lipid content were accompanied by decreases in chlorophyll staining and overall growth delays (FIG. 39A), suggesting that PSR1 alone can convey the common lipid accumulating response from different stress regimens. These results demonstrate that PSR1 is both necessary and sufficient for storage lipid accumulation and confirm its role as a master regulator that uncouples the induction of lipid biosynthesis from specific stress responses.

Deciphering PSR1 target gene circuitry reveals cross-talk between stress responses. Given the properties of structurally related TFs (Prouse and Campbell, 2012), it is expected that PSR1 regulates lipid accumulation by direct binding to specific nucleotide motifs in regulatory sequences near its target genes, thereby altering their transcription. To characterize PSR1 DNA-binding characteristics and determine its genome-wide regulatory targets, we raised polyclonal antibodies against PSR1 peptides and used ChIP-seq to determine the in vivo binding sites of PSR1 at selected time points following nutrient starvation when PSR1 expressions were significantly elevated (30 min and 1 hr in N-; 1 hr, 2 hr and 6 hr in S-) (Table 6). In total, there were 631 and 1,404 PSR1 binding sites found under N- and S-starvation, respectively, with 391 sites shared across conditions. In contrast to the majority of known TFs, PSR1 binding is most frequently observed at the 3' ends of the genes (transcription end site, TES) (FIG. 32A). Among a total 1,644 PSR1-bound regions, 1,234 (75%) are within 1 kb of TES, whereas only 629 (38%) are within 1 kb of TSS, and 101 (6%) in intergenic regions. Besides preferential binding at the 3' ends of genes, PSR1-DNA interactions also appear to be sequence-specific. Using a de novo motif prediction algorithm (Bailey and Elkan, 1994), we found a novel partially palindromic motif ([G/A]TAC[G/A/C]GTA (SEQ ID NO:102)) highly enriched (MEME motif E=9.1e-97 based on genomic background) within the binding regions in N- and S-cells. As an illustrative example, FIG. 7 shows PSR1 binding at the 3' TES of Myb family TF gene Cre02.g108350 through the consensus motif within 1 hr after N- and S-depletion. These results are consistent with the temporal dynamics of Cre02.g108350 up-regulation (FIG. 39B). Taken together, these results suggest that PSR1 regulates its target genes via sequence-specific binding to sites preferentially located at the 3' ends of the genes.

The majority (74%) of PSR1-bound genes showed differential expression in response to N- and S-conditions and was inferred as PSR1 target genes. Overall, 495, 186 and 929 PSR1 targets are defined in N-/S-common, N-specific and S-specific conditions, respectively (FIG. 7; Table 6). Among the N-/S-common PSR1 targets, both transcription regulators (Fisher's Exact Test, P=2.1e-6) and lipid metabolic enzymes (P=2.7e-5) are over-represented, demonstrating that PSR1 acts both upstream and as a direct regulator of lipid metabolism. For example, PDAT1, a gene encoding phospholipid:diacylglycerol acyltransferase is found as a N-/S-common PSR1 target. In *Arabidopsis*, overexpression of PDAT1 enhances fatty acid synthesis and diverting fatty acids from membrane lipids to triacylglycerol. In *C. reinhardtii*, pdat1 mutant accumulates 25% less TAG compared with the parent strain (Boyle et al., 2012; Fan et al., 2013). Besides known key lipid metabolic enzyme, the N-/S-common PSR1 targets also contain an over-representative transcription factors (19 TFs, Fisher's Exact Test p-value=2.047e-6) that could directly or indirectly regulate lipid metabolism; implicating that PSR1 acts upstream of the direct regulators of lipid metabolism. TF genes bound by PSR1 include previously known stress-specific regulators, like Copper response regulator1 (CRR1) (Sommer et al., 2010), Low-$CO_2$ response regulator1 (LCR1) (Ohnishi et al., 2010) and PSR1 itself (Table 6), revealing the potential genetic basis for the integration of different regulatory circuits controlling stress responses (Vischi Winck et al., 2013). Among condition-specific PSR1 target genes, cellular metabolic (P<9e-3) and transporter activities (P<2e-2) are enriched. These genes include ammonium transporter AMT4 in N-cells as well as sulfate anion transporters SUL2 and SLP3 in S-cells. Beyond these enriched functional categories, more than half of the PSR1 targets have no functional annotation, providing a rich collection of direct PSR1 downstream candidate genes for further functional exploration of lipid metabolism.

In summary, these converging lines of evidence support a model (FIGS. 37A-37B) in which PSR1 is a key switch in the transcriptional regulatory network of lipid biosynthesis and has pleiotropic effects on overall cellular stress response including affecting the expression of membrane transporters.

Discussion

Microalgal are considered one of the most promising sources for biofuels (Wijffels and Barbosa, 2010). As such, a detailed characterization of chromatin landscape and transcription regulation, particularly pertinent to stress response and lipid biosynthesis in model algae can offer keys to understand, and eventually manipulate growth and lipid production. By linking epigenomic dynamics and gene expression profiling, we demonstrate an effective approach of using chromatin state changes to reveal potential regulatory components triggering lipid accumulation in *C. reinhardtii*. Furthermore, our study also provides major advancements in understanding the genetic basis for communication between various stress responses and deciphering the target gene pathway inducing lipid accumulation.

Although histone modifications are largely conserved among eukaryotes, differences have been observed between plants and animals in their genomic distribution and biological function. The global chromatin modification maps from the model alga *C. reinhardtii* reveal unique, as well as common epigenetic features between green algae, land plants, and metazoans. Specifically, the classification of genes with different transcription activities through progressive addition of histone modifications at their TSS may be unique to algae. Since algae often have a compact genome with relatively little intergenic space, it is plausible to assume that the chromatin states at promoters reflect most of the transcriptional activities. Hence, the promoter-associated chromatin states can be used as a readout to infer their corresponding transcription activity. We demonstrated that chromatin analysis, coupled with RNA analysis, enables the detection of some known genes involved in TAG biosynthesis, but also the discovery of new candidates that function as master regulators. This strategy could be applied in other plant species to study environmentally elicited metabolic responses. Beyond the unique promoter chromatin states, complex epigenetic features including bivalent domains and enhancer elements that have so far only been observed in vertebrates (Bernstein et al., 2006) and/or land plants (Luo et al., 2012) are also present in *C. reinhardtii*. However, different sets of histone modification are associated with these features, raising the possibility that these functions may have evolved independently in algae.

*C. reinhardtii* has been adopted as a genetically accessible model for characterization of the genetic regulatory process of lipid metabolism in order to guide genetic engineering in other algal species with higher native lipid yield. The level of lipid accumulation achieved in the present study through a single targeted genetic manipulation, overexpression of the master regulator PSR1, results in higher yields than previous strategies including deficiencies in starch biosynthesis (Li et al., 2010), nitrogen starvation or lipid hyper-accumulating mutant screening (Xie et al., 2014). Although not considered as the production strain, PSR1-overexpressing *C. reinhardtii* can serve as a model for engineering of algal lipid production strains as well as for the identification of additional factors that contribute to lipid hyperaccumulation.

PSR1 is the first TF with genome-wide target genes mapped in *C. reinhardtii*. Intriguingly, PSR1 binds to the 3' regions of its target genes. While regulatory elements harbored at the 3' ends of genes in principle exist (Bigler and Eisenman, 1995; Chen et al., 1998), they appear to be uncommon across eukaryotes and could suggest a mechanism like enhancer:promoter chromatin looping events known in metazoans (Zhang et al., 2013). Currently, it is not clear whether transcription regulation through 3' binding is a common property in microalgae, which may be resolved when more TFs and their target gene interactions are characterized.

PSR1 is highly conserved among a wide range of photosynthetic organisms ranging from marine algae to land plants. Beyond sequence conservation, at least some aspects of PSR1 function are also conserved. The *Arabidopsis* homolog PHR1 is involved in the phosphate starvation response (Rubio et al., 2001). This high degree of conservation is consistent with its role in the regulation of fundamental metabolic responses. Thus, we expect that PSR1 and its homologs have similar activities in lipid regulation in other microalgae species, particularly in production strains including *Botryococcus* and *Nannochloropsis* (Li et al., 2014; Vieler et al., 2012). Alignment of transcriptome data suggests that PSR1 homologs are present in *Botryococcus braunii, Nannochloropsis gaditana* and *Dunaliella tertiolecta*. We expect the approaches demonstrated and the knowledge learned in the present study of *C. reinhardtii* to be applicable to other algal species and bioenergy crops, enabling the characterization of additional environment elicited metabolic responses and their targeted engineering.

Experimental Procedures

Cell Growth and Starvation Treatment. *C. reinhardtii* wild type strain 4a+ and psr1 mutant strain cc-4267 were cultured using Tris-acetate-phosphate (TAP) medium. N-free (TAP-N), $SO_4^{2-}$-free (TAP-S), Zn-free and Fe-free media were prepared as described (Boyle et al., 2012; Kropat et al., 2011). For N- and S-starvation conditions, cells were grown to mid-log phase, washed twice with depleted media and re-suspended in TAP-N or TAP-*S media* to a density of $2\times10^6$ cells/ml. For Zn— and Fe— starvation conditions, cells were grown to mid-log phase in Zn— or Fe-free media and then re-inoculate at $2\times10^6$ cells/ml as day 0 for the depletion assays. Cells were counted using the Countess® (Invitrogen) and optical density (OD) at 750 nm at time points indicated.

Lipid Analysis. Two types of dyes; Nile Red (Chen et al., 2009) and LipidTOX Green (Invitrogen) were used to analyze the level of neutral lipid in *C. reinhardtii* cells. Cells were stained with a final concentration of 0.5 ug/ml Nile Red. Wavelength of 530 nm was used for excitation and 570 nm for emission. Fluorescence intensity was normalized with cell count or cell density measured at $OD_{750}$. Data was expressed as mean values from 3 biological replicates with standard deviation. For staining intracellular lipid, cells were fixed at 1% formaldehyde and stained with LipidTOX Green for 30 min in the dark. Images were captured by Zeiss LSM710 Confocal Laser Scanning Microscopes using Zen software.

Chromatin immunoprecipitation sequencing (ChIP-Seq). ChIP-seq was performed as previously described (Chen et al., 2008). Briefly, cross-linked cells were lysed with Lysis Buffer (50 mM Tris-HCl pH8, 5 mM EDTA, 1% SDS) and chromatin was then sheared. 5-50 ug of chromatin was used in each immuno-precipitation. Antibodies for histone modifications including H3K4me2 (ab11946), H3K4me3 (ab8580), H3K9me3 (ab8898), H3K27ac (ab4729), H3K27me3 (ab6002) and H3K36me3 (ab9050) were obtained from Abcam and antibody for RNAPII (clone 8WG16) was obtained from Covance (#MMS-126R). For PSR1 ChIP, two rabbit polyclonal antibodies were raised against PSR1 peptide sequences aa54-69 (peptide A: C-QQQGLALGGYGLTQQP (SEQ ID NO:87)) and aa465-48 (peptide B: C-LQHQPQLLQPQGSLPA (SEQ ID NO:88)) and affinity purified. Chromatin was first pre-cleared and then mixed with beads pre-bound with antibody. Beads were washed and eluted at 37° C. The eluate was then de-crosslinked and DNA was purified by phenol/chloroform extraction, followed by ethanol precipitation. 5-10 ng of purified DNA was used in ChIP-seq library preparation using Truseq DNA Sample Preparation Kit (Illumina) and sequenced on Illumina Miseq.

Strand-specific RNA-seq analysis. Cells were first lysed and total RNA extracted using Trizol and cleaned up using RNeasy column (Qiagen). PolyA$^+$ RNA was isolated and then fragmented using RNA Fragmentation Reagents (Ambion). Strand-specific RNA-seq library (Parkhomchuk et al., 2009) was constructed using Illumina DNA Sample Preparation Kit (Rumina) or the Kapa Library Amplification Kit (Kapa Biosystems) with 10 cycles PCR amplification. Sequencing was done on the Illumina Hiseq platform of 2×100 bp or 2×150 bp.

Psr1 overexpression. PSR1 cDNA was PCR amplified and fused to bleomycin (zeocin-resistance) gene sh-ble linked by a self-cleavage peptide 2A from foot-and-mouth-disease-virus (FMDV) in a expression vector, Bpms4841, a gift from Dr. Rasala, as ble-2A-PSR1 under the control of constitutive hsp70A/rbcs2 promoter (Rasala et al., 2012) and transformed into *C. reinhardtii* cells by electroporation. The zeocin-positive clones were further analyzed for expression of PSR1 and lipid production. For cell size determination, multiple photos were captured using microscope Axio Observer.D1 (Carl Zeiss) at 320× magnification. The longest diameter was determined for each cell by two operators independently using AxioVision re1.4.8 software (Carl Zeiss). A minimum of 200 cells was counted for each condition. Analysis of Variance (ANOVA) was performed which rejected the null hypothesis that the mean diameters were equal between all 4 groups. Tukey's HSD (honest significant difference) test was then performed to find mean diameters that were significantly different from each other. The adjusted P-values were reported.

Informatics Analysis.

Characterization of chromatin state and transcript assignment. ChromHMM v1.0.6 (Ernst and Kellis, 2010) was used to perform unsupervised segmentation of the genome into a certain number of states based on the combination of chromatin modifications. We reduced the number of states by merging the redundant states indicated by correlation ≥0.99. Enrichment analysis of chromatin states was performed with ChromHMM. Based on ChromHMM signal enrichment profile around TSS (FIG. 36A), the chromatin state found between 400 bp upstream to 1000 bp downstream of the TSS was defined as the state for each individual transcript. If multiple chromatin states were found in the TSS region, the state with the most different chromatin modifications was chosen. Transcripts were classified into five types as follow: Type I (state 16), Type II (state 14), Type III (state 13), Type IV (state 8+9) and Type V (state 7+11).

RNA-seq analysis. High quality reads for each of the RNA-seq libraries were mapped to the *C. reinhardtii* genome (Phytozome v5.3.1) using TopHat v2.0.8 (Kim et al., 2013) with Bowtie v2.1.0 (Langmead and Salzberg, 2012). TopHat's parameters were adjusted for the genome characteristics with sensitive and fusion mapping enabled. Next, Cufflinks (modified to work on compact genomes) was used to reconstruct the transcripts guided with the Phytozome v5.3.1 reference transcriptome. Multi-mapped reads were addressed. The remaining transcript assemblies from different time points were merged into a unified set of gene models. Sequential steps of filtering criteria were applied to remove "noise" transcripts. The filtered transcripts were then compared with the reference transcriptome. Differentially expressed transcripts were defined based on the comparison of expression values for each transcript between individual time points and at time 0. The transcripts with significant absolute expression fold change >2, P<0.01 were selected as differentially expressed. Transcripts expression profile clustering was performed for each condition separately.

Accession numbers. All data described in this study will be deposited in the GEO database. The chromatin patterns and assembled transcripts can be visualized and downloaded from the JGI comparative plant genomics portal Phytozome (DOE JGI website).

Chromatin Immunoprecipitation (ChIP) Analysis: Antibody characterization.

Epitopes recognized by antibodies against these seven proteins (H3K4me2, H3K36me3, H3K4me3, H3K27ac, H3K27me3, H3K9me3 and RNAPII) are conserved among *S. cerevisae, C. reinhardtii* and human. These histone modifications were selected based on studies done in metazoans. Genomic regions associated with these histone modifications are known to represent functional chromatin states. Specifically, H3K4me3 and H3K36me3 mark active promoters and transcribed regions, respectively. H3K27ac is enriched at distal enhancer elements while H3K27me3 and H3K9me3 represent transcription repressive regions and heterochromatin.

Antibodies against modified histones were designed based on human histone H3 protein. *C. reinhardtii* H3 peptide sequences are highly conserved with 95% identical. We further confirmed that the target epitopes for H3K4me3 and H3K9m3 match exactly to sequences found in *C. reinhardtii* while H3K27ac/me3 and H3K36me3 showed 95% of identity (data not shown). Western blot results from selected antibodies confirmed their specificity to *C. reinhardtii* histone H3 at the expected size of 17 kDa. For RNAPII, antibody 8WG16 recognizes consensus peptide YSPTSP (Patturajan et al., 1998) present in the carboxy-terminal domain (CTD) repeats in *C. reinhardtii* RNAPII. For PSR1 antibodies, in order to determine the specificity of the two PSR1 rabbit polyclonal antibodies, we performed western blot analysis against the recombinant PSR1 protein generated in *E. coli*. The induced expression of the truncated recombinant PSR1 protein was confirmed by SDS-PAGE followed by Coomassie Brilliant Blue staining (FIG. 41A). As expected, both batches of the polyclonal antibodies reacted with N-terminal 6×His-tagged PSR1 fusion protein and displayed a MW of 47 kDa protein on Western blot analysis (FIG. 41B).

Western Blot. Whole cell protein lysate was prepared using CelLytic M (Sigma-Aldrich) and nuclear lysate was prepared using CelLytic NuCLEAR Extraction kit (Sigma-Aldrich). Protein containing-lysate was mixed with Laemmli sample loading buffer (BioRad) containing 2-mercaptoethanol and denatured for 10 min at 98° C. The samples were then ran on a Mini PROTEAN® TGX™ Gel (BioRad).

Proteins were electrically transferred onto a PVDF membrane using the Transblot® Turbo™ transfer system (Bio-Rad). The membrane was blocked with 5% nonfat milk in TTBS (TBS+0.05% Tween 20) at room temperature for an hour followed by a 1 hr incubation with a primary antibody and another hour of incubation with StrepTactin-HRP conjugated secondary antibody (BioRad) at 4° C. Signal was detected and imaged using the Immun-Star™ WesternC™ Chemiluminescence Kit and ChemiDoc™ (Biorad).

Generation of recombinant PSR1 protein. *C. reinhardtii* PSR1 cDNA was PCR amplified using the forward primer 5'-GGAATTCCATATGCTGTCGCAGCATCAAGAC-3' (SEQ ID NO:89) and reverse primer 5'-ACAGGATCCTCAATGGGCTTCAGAGGAACC-3' (SEQ ID NO:90) including a forward NdeI and reverse BamHI restriction sites, respectively. NdeI-BamHI fragment containing PSR1 coding region from aa38 to aa488, including two target peptide sequences used in raising antibodies, was subcloned into the pET28 (a+) vector (Novagen). The production of 6×His-tagged recombinant PSR1 proteins was induced with 2 mM IPTG and expressed in *E. coli* BL21 (DE3) (Novagen).

Enhancer assay: Target region selection. Of 1339 regions defined in CS 15 (H3K27ac only), we identified 369 potential distal-acting enhancer elements located more than 1 kb upstream or downstream of any known TSS. In order to further dissect the function of these potential enhancers, we applied further filtering criteria to select high confident candidates for screening. We eliminated regions that overlapped with H3K4me3 signals in any of the conditions (TAP, N- or S-depleted) as these regions could be potential novel TSS. We identified 93 candidate enhancers and validated 11 regions randomly selected with the GUS reporter assay. We also included 3 randomly selected regions from CS 16 as negative controls. P-values were calculated against the average of 3 negative controls.

Tobacco GUS (β-glucuronidase) Reporter Assay. GUS-reporter construct driven by a CaMV 35S minimal promoter (−46/+8) was a gift from Dr. John Harada from UC, Davis. The reporter cassette was cloned into pEG301 (Earley et al., 2006) via a Gateway LR reaction (Invitrogen). Putative target enhancer regions of approximately 1 kb in length based on the selection criteria described above were amplified from genomic DNA using KAPA HiFi HotStart DNA Polymerase (Kapa Biosystems, Inc). Genomic location of regions of interest and primers used are listed in Table 7. Fragments were inserted via EcoRI restriction site using Quick Ligase (NEB). Selected clones were transformed into *Agrobacterium tumefaciens* strain GV3101. Transformants were selected on LB agar containing 50 ug/ml gentamycin and 30 ug/ml kanamycin. Agro strains were resuspended in 1 ml induction medium (10 mM $MgCl_2$, 10 mM MES pH5.6, 150 uM acetosyringeone) and incubated for 2 hr at 28° C. The cultures were then diluted to an OD of 0.5 and injected into *Nicotiana benthamiana* leaves (3 replicates per construct). Plants were placed under constant light (~70 uE) for 48 hr. 0.5 $cm^2$ leaf discs were powdered (6.5 m/s for 60 sec) using the cryo rotor of a Fastprep-24 (MP Bio) and resuspended in 150 ul of lysis buffer (50 mM sodium phosphate buffer pH 7.0, 10 mM EDTA, 0.1% Triton X-100, and 10 mM 3-mercaptoethanol). Debris was pelleted and 100 ul of supernatant was collected. 100ul of 1 mM 4-methylumbelliferyl-β-D-glucuronide (MUG) in lysis buffer was added to each well and the plate was placed at 37° C. Fluorescence was read at various time points with a FluoroMax-4 spectrofluormeter (Horiba Scientific) using an excitation of 365 nm and emission of 455 nm.

PSR1 Functional Analysis: Characterization of Psr1 Loss-of-Function Mutant.

We obtained psr1 knockout strain cc-4267 from *Chlamydomonas* Resource Center (chlamycollection.org website). cc-4267 was isolated through UV mutagenesis and screened by failing to activate high-affinity Pi uptake during P starvation with poor growth (growth arrest) and down-regulation of photosynthesis (Shimogawara et al., 1999; Wykoff et al., 1999). In order to identify the exact mutation(s) resided in the psr1 open reading frame in cc-4267, psr1 open reading frame fragments were amplified from both WT 4A+ and mutant cc-4267 genomic DNA using forward primer TGGAGAGCAACCCGGGCCCCCTCGAGGACAAAGCTGAACGCGCTGCT GGTGGCCCTAACG (SEQ ID NO:91) and reverse primer GAGTGGGTCGACGTCGGAGAGGTACCCTATGGCTCCACTCGCTGCCGCTTTGCGCGATC (SEQ ID NO:92). The fragment is cloned into pENTR vector via KpnI and XhoI using In-Fusion system (Clontech) and subjected to sequencing analysis. A single nucleotide cytosine deletion on exon 1 at amino acid 153 was detected from 3 independent clones. This deletion causes a frame-shift and a stop codon in exon 2.

PSR1 overexpression. First strand cDNA was synthesized using Superscript III First-Strand Synthesis SuperMix (Invitrogen) with $dT_{20}$ oligo followed by PCR to amplify PSR1 cDNA with forward primer: GACAAAGCTGAACGCGCTGCTGGT (SEQ ID NO:93) and reverse primer: CTATGGCTCCACTCGCTGCCGCTTT (SEQ ID NO:94). Fragment containing hsp70/rbcs2 promoter, Ble2A and PSR1 cDNA was then built into pENTR backbone vector via NotI restriction site, creating pENT_Ble2A_PSR1 using In-Fusion system (Clontech). *C. reinhardtii* cells grown to mid log phase were resuspended in TAP medium containing 40 mM sucrose to a density of $2\times10^8$ cells/ml. About 1 ug of vector, linearized by AsiSI site, was electroporated with Gene Pulser II (BioRad) at 2000 V/cm with 50 uF capacitance. The transformants were incubated overnight in the dark in TAP media with 40 mM sucrose before spread on 1.5% TAP agar containing 5 ug/ml of zeocin. Upon nuclear transformation of PSR1 transgene, PSR1 were transcriptionally fused with the selection marker through 2A peptide, and the 2A peptide mediates a self-cleavage reaction to process the fusion protein into two discrete and functional proteins: bleomycin and PSR1. Therefore, the presence of zeocin resistance indicates the expression of PSR1 protein.

A total of 264 zeocin-positive clones were selected through multiple transformations. These transformant clones were screened for lipid accumulation using Nile Red assay. A cutoff of OD reading (OD750<0.01 after normalization with blank) was applied to filter off clones that did not grow. PSR1 transformants showed a wide range of lipid accumulation and higher levels of lipid detected in the transformants were significant when compared to log phase grown wild type control cells cultured in TAP media. We further examined a few selected clones with high lipid accumulation. RT-PCR results showed 3 out of 6 clones have more than 2-fold PSR1 expression. Two of these clones, termed liporotund (1) and (2) were further characterized.

Reverse transcription—PCR (RT-PCR). Two μg of total RNA was primed with Oligo $(dT)_{12-18}$ (Invitrogen) and reverse transcribed using the Superscript® First-Strand Synthesis System for RT-PCR kit (Life Technologies). The first strand cDNA was used for qPCR using the LightCycler®480 (Roche), KAPA SYBR® FAST qPCR Kit (Kapa Biosystems). PSR1 forward primer: ATGGGCAGTACTTCATGC (SEQ ID NO:95), reverse primer TGAC- GAAGCGGTTGTG (SEQ ID NO:96). CBLP was used as a housekeeping control (Sommer et al., 2010); forward primer: GCCACACCGAGTGGGTGTCGTGCG (SEQ ID NO:97) and reverse primer: CCTTGCCGCCCGAGGCG-CACAGCG (SEQ ID NO:98).

Informatics analysis: ChIP-seq analysis. ChIP was performed to enrich DNA fragments associated with specific modified histones and RNAPII followed by sequencing analysis. 2.5-7 million raw reads were generated from each ChIP experiments and were mapped to *C. reinhardtii* genome (v5.3.1) by BWA v0.6.2 (Li and Durbin, 2009) with default parameters. Enriched regions in the non-redundant mapped reads were identified by MACS2 v2.0.10 (Zhang et al., 2008) (effective genome size=107270392, FDR<5%) (Tables 1 and 2). Normalized ChIP-Seq signal correlation (Pearson's coefficient) between two biological replicates was computed genome-wide over 1 kb bins. The P-value for the number of overlapped peaks between two replicates was computed using the hypergeometric model. The 5 pairwise comparisons of the biological replicates peak list for H3K4me3 and H3K27ac (at 0 and 1 hr after N-condition) and H3K36me3 (at 1 hr after S-condition) demonstrated both high Pearson correlation (R>0.96) in normalized ChIP-seq signal and high proportion (87-96%) of common peaks (P-value of zero) (FIG. 34).

Determination of time point to capture Maximal chromatin changes. H3K4me3 ChIP-Seq peaks were called as above for the 9 time points across starvation time courses (Table 8). Averagely, 11,837 peaks were called for each of the 9 time points. For time points with replicates (0 hr, 1 hr), peaks present in only one of the replicates were excluded. The peaks called from 9 time points were merged to produce a common unified list of peaks and pair-wise comparison between the 0 hr and each of the remaining 8 time points' peaks were computed. The number of peaks called increased from 0 to 1 hr but remained mostly above the average after 1 hr. The 12,543 peaks called at 1 hr time point covered 97.5% of the 12,868 union peaks from all 9 time points and contained the highest number (1,272) of unique peaks compared to the rest of the starvation conditions. Thus, we conclude that 1 hr time point captures the maximal chromatin changes.

Characterization of chromatin state. ChromHMM v1.0.6 (Ernst and Kellis, 2010) was used to perform unsupervised segmentation of the genome into a certain number of states based on the combination of chromatin modifications. First, the genome was divided into 200 bp bins. For each data set (5 histone modifications and RNAPII in each of the 3 conditions), ChromHMM marked a bin as "1" if it overlapped with the MACS identified enriched regions. Next, ChromHMM learned 10 randomly initialized HMMs and 1 HMM initialized by information initialization strategy for each number of states, from 2 to 64. The Bayesian Information Criterion (BIC) scores of each model were computed as in (Ernst and Kellis, 2010). The model with the best BIC score (, the 60-states HMM initialized by ChromHMM information initialization strategy,) among the 693 models was selected. While additional states enable increasingly finer-grain distinction, we sought after a smaller number of states that allow for appropriate biological interpretations of the chromatin marks. Pearson correlation was computed for all-to-all chromatin states based on their input marks' emission probabilities. There were 15 redundant states reflected by Pearson correlation ≥0.99, indicating that a 45-states HMM could be sufficient by merging them. The additional states captured the spatial distinction besides the presence of chromatin marks (FIG. 41A). For instance, ChromHMM represented the H3K27ac peak that spanned three 200 bp bins by the two flanking bins (State 21 and 22) and the sandwiched bin (State 23). This spatial distinction became more pronounced for wider peaks where the number of sandwiched bins increased (FIG. 41B). Conversely, two states may be sufficient to represent the peak (FIG. 41C). Although the spatial distinctions were meticulously represented by the additional states, they were mostly the consequence of transiting from one chromatin combination to another where the boundary bins shared almost the exact characteristics of the sandwiched bin (FIG. 41D). Thus, they were considered 'biologically' redundant. We then picked the best scored 45-states HMM amongst the eleven 45-states HMMs and repeated the redundancy check. Progressively, we selected HMMs with 45-, 37-, 30-, 26-, 23-, 21-, 18-, and finally 16-states where no two states have high similarity in their emission probabilities. We then ran additional 489 randomly initialized HMMs for the smallest number of states determined (16-states) and picked the best from among these 500 models. This 16-state HMM has a BIC score −937,141 and remained the best model among the total of five hundreds 16-states HMMs learned.

ChromHMM was used to perform enrichment analysis of chromatin states in the neighborhood of an anchor point and overlap with specific genomics features. Features from the transcripts assembled by RNA-Seq analysis (see RNA-Seq analysis below) were prepared in bed format accordingly.

RNA-seq analysis Strand-specific paired-end RNA-seq data was generated for each time point; 9 time points for each of the N- and S-conditions, 2 biological replicates each. From a total of 36 libraries, an average of 44 million mappable paired reads were generated for each sample (Table 3). Trimmed reads with average quality ≥20, ≤3 Ns, and ≥32 bases and not associated with artifacts were kept. These high quality reads for each of the 36 libraries were mapped to the *C. reinhardtii* genome (Phytozome v5.3.1) using TopHat v2.0.8 (Kim et al., 2013) with Bowtie v2.1.0 (Langmead and Salzberg, 2012). TopHat's parameters were adjusted for the genome characteristics with sensitive and fusion mapping enabled. Specifically, valid intron length was 20 bp to 25 kbp and minimum distance between intra-chromosomal fusions was 1 Mbp. The library type "fr-firststrand" stated and read alignments with >3 mismatches were discarded. To assess the quality between replicates, Pearson correlation between each pair of the 18 libraries for each condition was computed based on the expression values of Phytozome transcripts models generated by Cufflinks v2.1.1 (Trapnell et al., 2013). The biological replicates for each time point showed high correlation (≥0.988, Pearson). Next, Cufflinks (modified to work on compact genomes) was used to reconstruct the transcripts guided with the Phytozome v5.3.1 reference transcriptome. Multi-mapped read correction was turned on and transcript composed of >50% multi-mapped reads or <25 reads were discarded. The remaining transcript assemblies from different time points were merged into a unified set of gene models, which was then compared to the annotated transcriptome. In total, 66,561 transcripts were assembled (Table 4). Potential noise was filtered from these predicted transcripts. Sequential steps of filtering criteria were applied as follows; 1). FPKM>0 for both replicates at least at one time point; 2) length of CDS>=50 amino acid; candidate coding regions were predicted based on transcript sequences using TransDecoder script v2013-02-25 from the Trinity package (Grabherr et al., 2011), 3) Remove "noise" transcripts of CuffDiff classes 'E', '0' and 'P' and single exon transcripts of CuffDiff classes '.', 'C' and 'I'. The three-step filtering generated 22,209 high confident transcript models, which were then compared with the reference transcriptome using CuffCompare. 90% of the 19,526 Phytozome annotated transcripts (v5.3.1), 4,241 new variants and 298 new transcripts were found (FIG. 35B, Table 4). 277 and 250 transcripts were assigned to putative TFs and TRs, respectively (Table 4).

Expression was defined by the expression value (FPKM) combining both replicates calculated by statistical model used in CuffDiff with geometric library normalization and per-condition cross-replicate dispersion estimation. Differentially expressed transcripts were defined based on the comparison of expression values for each transcript between individual time points and at time 0. The transcripts with significant absolute expression fold change >2, P<0.01 were selected as differentially expressed. In total, 12,144 and 12,242 transcripts were differentially expressed in N- and S-, respectively; among them, roughly half were up-regulated and half were down-regulated (Table 5). Transcripts expression profile clustering was performed using ClassDiscovery (Coombes, 2013) for each condition separately. Transcript expression profile was first log 10-transformed with a pseudo count 1 before the Min-Max normalization. Complete linkage clustering with Spearman correlation distance threshold ≤0.05 defined clusters of transcripts with similar expression patterns. Clusters were grouped by the time point of highest expression for activated transcripts.

Go Analysis. *C. reinhardtii* GO annotations were downloaded from Phytozome and set up for GOstats (Falcon and Gentleman, 2007). Conditional GO terms over-representation was tested with P<0.05.

Classification of *C. reinhardtii* expressed transcripts as TF and transcription regulator (TR).

An earlier attempt to generate a high quality set of TF annotated gene list from *C. reinhardtii* Phytozome genes Cre 3.0 defined 378 TF genes (Perez-Rodriguez et al., 2010). Since then, the number of annotated genes in *C. reinhardtii* has greatly expanded and, with higher quality of genome sequence and better annotation tools, their predicted protein domains were also changed. Therefore, we decided to generate an improved and updated TF gene list. PFAM (Punta et al., 2012) annotations of the *C. reinhardtii* proteome (v5.3.1) were downloaded from Phytozome. Based on the presence of required and the absence of forbidden domain(s) as defined in PlnTFDB classification rules (Perez-Rodriguez et al., 2010), we classified the proteins and their corresponding transcripts in *C. reinhardtii* into their respective TF or TR family. We found that 7 of the PFAM domain ids used in PlnTFDB have been superseded. In total, we defined 547 TF transcripts expressed from 499 genomic coding loci. Among them, 518 transcripts (277 TFs and 250 TRs) are expressed in our experimental conditions and 344 and 318 are differentially expressed in N- and S-conditions, respectively. They serve as the basis for discovering TFs in this study.

PSR1 ChIP-seq analysis. ChIP was performed to enrich DNA fragments associated with PSR1 followed by sequencing analysis. Two sets of ChIP experiments were performed at selected time points, based on expression data, following nutrient starvation (30 min, 1 hr in N- and 1 hr, 2 hr, 6 hr in S-) targeting peptide A and peptide B separately (Table 6). The time points were selected based on the times when high levels of Psr1 transcript were detected. Paired-end reads generated from each ChIP experiments were treated as 2 sets of single-end read and processed as stated above (see ChIP-seq analysis). Common enriched regions identified by both Read/1 and Read/2 in each experiment were retained. These regions from all 10 experiments were merged to produce the final putative binding regions.

Psr1 conservation. *C. reinhardtii* PSR1 protein sequence (XP_001700553.1 (SEQ ID NO:99)) was searched against non-redundant protein sequences database using NCBI's BLAST (on the world wide web at blast.ncbi.nlm.nih.gov) (Altschul et al., 1997; Altschul et al., 2005) with BLOSUM45 scoring matrix and 5000 maximum target sequences. A Grishin General distance (Grishin, 1995) tree was built using BLAST tree view based on BLAST pairwise alignment results by Neighbor joining method (Saitou and Nei, 1987).

PSR1 binding motif analysis. Merged peaks containing high proportion of 6-base repeats (e.g. (CCCTAA)n (SEQ ID NO:100)) were removed. MEME (Bailey and Elkan, 1994) version 4.9.1 was run with the parameters "-mod anr-bfile Chlre5_CnM.bfile-maxsites 1000-dna-revcomp-evt 0.01-nmotifs 30-minw 8-maxw 9" on the remaining merged peaks. MEME identified multiple motifs enriched within the binding peaks with high significance (E<1e-7). Manual curation was performed to remove motifs containing high proportion of repeat sequences, which resulted in two motifs (a 8-base motif and a 9-base motif). TOMTOM (Gupta et al., 2007) determined that both remaining motifs to be highly similar (E=8.0e-7). The palindromic motif [AG]TACCGTA (SEQ ID NO:101) (E=9.4e-102) with smaller E-value was chosen as the representative. There were 312 motif sites found in the 1625 merged peaks and 158 motif sites were found amongst the 376 common merged peaks between N- and S-depletion conditions.

REFERENCES

1. Ay, N., Irmler, K., Fischer, A., Uhlemann, R., Reuter, G., and Humbeck, K. (2009). Epigenetic programming via histone methylation at WRKY53 controls leaf senescence in *Arabidopsis thaliana*. The Plant journal: for cell and molecular biology 58, 333-346.
2. Bailey, T. L., and Elkan, C. (1994). Fitting a mixture model by expectation maximization to discover motifs in biopolymers. Proceedings/International Conference on Intelligent Systems for Molecular Biology; ISMB International Conference on Intelligent Systems for Molecular Biology 2, 28-36.
3. Bernstein, B. E., Mikkelsen, T. S., Xie, X., Kamal, M., Huebert, D. J., Cuff, J., Fry, B., Meissner, A., Wernig, M., Plath, K., et al. (2006). A bivalent chromatin structure marks key developmental genes in embryonic stem cells. Cell 125, 315-326.
4. Berr, A., Shafiq, S., and Shen, W. H. (2011). Histone modifications in transcriptional activation during plant development. Biochimica et biophysica acta 1809, 567-576.
5. Bigler, J., and Eisenman, R. N. (1995). Novel location and function of a thyroid hormone response element. The EMBO journal 14, 5710-5723.
6. Blatti, J. L., Michaud, J., and Burkart, M. D. (2013). Engineering fatty acid biosynthesis in microalgae for sustainable biodiesel. Current opinion in chemical biology 17, 496-505.
7. Borevitz, J. O., Xia, Y., Blount, J., Dixon, R. A., and Lamb, C. (2000). Activation tagging identifies a conserved MYB regulator of phenylpropanoid biosynthesis. The Plant cell 12, 2383-2394.
8. Boyle, N. R., Page, M. D., Liu, B., Blaby, I. K., Casero, D., Kropat, J., Cokus, S. J., Hong-Hermesdorf, A., Shaw, J., Karpowicz, S. J., et al. (2012). Three acyltransferases and nitrogen-responsive regulator are implicated in nitrogen starvation-induced triacylglycerol accumulation in *Chlamydomonas*. The Journal of biological chemistry 287, 15811-15825.

9. Cagnon, C., *Mirabella*, B., Nguyen, H. M., Beyly-Adriano, A., Bouvet, S., Cuine, S., Beisson, F., Peltier, G., and Li-Beisson, Y. (2013). Development of a forward genetic screen to isolate oil mutants in the green microalga *Chlamydomonas reinhardtii*. Biotechnology for biofuels 6, 178.
10. Castruita, M., Casero, D., Karpowicz, S. J., Kropat, J., Vieler, A., Hsieh, S. I., Yan, W., Cokus, S., Loo, J. A., Benning, C., et al. (2011). Systems biology approach in *Chlamydomonas* reveals connections between copper nutrition and multiple metabolic steps. The Plant cell 23, 1273-1292.
11. Celniker, S. E., Dillon, L. A., Gerstein, M. B., Gunsalus, K. C., Henikoff, S., Karpen, G. H., Kellis, M., Lai, E. C., Lieb, J. D., MacAlpine, D. M., et al. (2009). Unlocking the secrets of the genome. Nature 459, 927-930.
12. Chen, R., Silver, D. L., and de Bruijn, F. J. (1998). Nodule parenchyma-specific expression of the *sesbania rostrata* early nodulin gene SrEnod2 is mediated by its 3' untranslated region. The Plant cell 10, 1585-1602.
13. Chen, W., Zhang, C., Song, L., Sommerfeld, M., and Hu, Q. (2009). A high throughput Nile red method for quantitative measurement of neutral lipids in microalgae. J Microbiol Methods 77, 41-47.
14. Chen, X., Xu, H., Yuan, P., Fang, F., Huss, M., Vega, V. B., Wong, E., Orlov, Y. L., Zhang, W., Jiang, J., et al. (2008). Integration of external signaling pathways with the core transcriptional network in embryonic stem cells. Cell 133, 1106-1117.
15. Chisti, Y. (2007). Biodiesel from microalgae. Biotechnology advances 25, 294-306.
16. Chisti, Y. (2013). Constraints to commercialization of algal fuels. Journal of biotechnology 167, 201-214.
17. Consortium, E. P., Bernstein, B. E., Birney, E., Dunham, I., Green, E. D., Gunter, C., and Snyder, M. (2012). An integrated encyclopedia of DNA elements in the human genome. Nature 489, 57-74.
18. Courchesne, N. M., Parisien, A., Wang, B., and Lan, C. Q. (2009). Enhancement of lipid production using biochemical, genetic and transcription factor engineering approaches. Journal of biotechnology 141, 31-41.
19. Creyghton, M. P., Cheng, A. W., Welstead, G. G., Kooistra, T., Carey, B. W., Steine, E. J., Hanna, J., Lodato, M. A., Frampton, G. M., Sharp, P. A., et al. (2010). Histone H3K27ac separates active from poised enhancers and predicts developmental state. Proceedings of the National Academy of Sciences of the United States of America 107, 21931-21936.
20. Csavina, J. L., Stuart, B. J., Riefler, R. G., and Vis, M. L. (2011). Growth optimization of algae for biodiesel production. Journal of applied microbiology 111, 312-318.
21. Ernst, J., and Kellis, M. (2010). Discovery and characterization of chromatin states for systematic annotation of the human genome. Nature biotechnology 28, 817-825.
22. Ernst, J., and Kellis, M. (2012). ChromHMM: automating chromatin-state discovery and characterization. Nature methods 9, 215-216.
23. Fan, J., Yan, C., Zhang, X., and Xu, C. (2013). Dual role for phospholipid:diacylglycerol acyltransferase: enhancing fatty acid synthesis and diverting fatty acids from membrane lipids to triacylglycerol in *Arabidopsis* leaves. The Plant cell 25, 3506-3518.
24. Guenther, M. G., Levine, S. S., Boyer, L. A., Jaenisch, R., and Young, R. A. (2007). A chromatin landmark and transcription initiation at most promoters in human cells. Cell 130, 77-88.
25. Hemschemeier, A., Casero, D., Liu, B., Benning, C., Pellegrini, M., Happe, T., and Merchant, S. S. (2013). Copper response regulator1-dependent and -independent responses of the *Chlamydomonas reinhardtii* transcriptome to dark anoxia. The Plant cell 25, 3186-3211.
26. Kim, D., Pertea, G., Trapnell, C., Pimentel, H., Kelley, R., and Salzberg, S. L. (2013). TopHat2: accurate alignment of transcriptomes in the presence of insertions, deletions and gene fusions. Genome biology 14, R36.
27. Kouzarides, T. (2007). Chromatin modifications and their function. Cell 128, 693-705.
28. Kropat, J., Hong-Hermesdorf, A., Casero, D., Ent, P., Castruita, M., Pellegrini, M., Merchant, S. S., and Malasarn, D. (2011). A revised mineral nutrient supplement increases biomass and growth rate in *Chlamydomonas reinhardtii*. The Plant journal: for cell and molecular biology 66, 770-780.
29. Langmead, B., and Salzberg, S. L. (2012). Fast gapped-read alignment with Bowtie 2. Nature methods 9, 357-359.
30. Li, J., Han, D., Wang, D., Ning, K., Jia, J., Wei, L., Jing, X., Huang, S., Chen, J., Li, Y., et al. (2014). Choreography of Transcriptomes and Lipidomes of *Nannochloropsis* Reveals the Mechanisms of Oil Synthesis in Microalgae. The Plant cell.
31. Li, X., Wang, X., He, K., Ma, Y., Su, N., He, H., Stolc, V., Tongprasit, W., Jin, W., Jiang, J., et al. (2008). High-resolution mapping of epigenetic modifications of the rice genome uncovers interplay between DNA methylation, histone methylation, and gene expression. The Plant cell 20, 259-276.
32. Li, Y., Han, D., Hu, G., Dauvillee, D., Sommerfeld, M., Ball, S., and Hu, Q. (2010). *Chlamydomonas* starchless mutant defective in ADP-glucose pyrophosphorylase hyper-accumulates triacylglycerol. Metabolic engineering 12, 387-391.
33. Luo, C., Sidote, D. J., Zhang, Y., Kerstetter, R. A., Michael, T. P., and Lam, E. (2012). Integrative analysis of chromatin states in *Arabidopsis* identified potential regulatory mechanisms for natural antisense transcript production. The Plant journal: for cell and molecular biology.
34. Merchant, S. S., Kropat, J., Liu, B., Shaw, J., and Warakanont, J. (2012). TAG, you're it! *Chlamydomonas* as a reference organism for understanding algal triacylglycerol accumulation. Current opinion in biotechnology 23, 352-363.
35. Merchant, S. S., Prochnik, S. E., Vallon, O., Harris, E. H., Karpowicz, S. J., Witman, G. B., Terry, A., Salamov, A., Fritz-Laylin, L. K., Marechal-Drouard, L., et al. (2007). The *Chlamydomonas* genome reveals the evolution of key animal and plant functions. Science 318, 245-250.
36. Nuruzzaman, M., Sharoni, A. M., and Kikuchi, S. (2013). Roles of NAC transcription factors in the regulation of biotic and abiotic stress responses in plants. Frontiers in microbiology 4, 248.
37. Ohnishi, N., Mukherjee, B., Tsujikawa, T., Yanase, M., Nakano, H., Moroney, J. V., and Fukuzawa, H. (2010). Expression of a low CO(2)-inducible protein, LCI1, increases inorganic carbon uptake in the green alga *Chlamydomonas reinhardtii*. The Plant cell 22, 3105-3117.
38. Parkhomchuk, D., Borodina, T., Amstislayskiy, V., Banaru, M., Hallen, L., Krobitsch, S., Lehrach, H., and Soldatov, A. (2009). Transcriptome analysis by strand-specific sequencing of complementary DNA. Nucleic acids research 37, e123.

39. Peters, A. H., Mermoud, J. E., O'Carroll, D., Pagani, M., Schweizer, D., Brockdorff, N., and Jenuwein, T. (2002). Histone H3 lysine 9 methylation is an epigenetic imprint of facultative heterochromatin. Nature genetics 30, 77-80.
40. Prouse, M. B., and Campbell, M. M. (2012). The interaction between MYB proteins and their target DNA binding sites. Biochimica et biophysica acta 1819, 67-77.
41. Rasala, B. A., Lee, P. A., Shen, Z., Briggs, S. P., Mendez, M., and Mayfield, S. P. (2012). Robust expression and secretion of Xylanasel in *Chlamydomonas reinhardtii* by fusion to a selection gene and processing with the FMDV 2A peptide. PloS one 7, e43349.
42. Roudier, F., Ahmed, I., Berard, C., Sarazin, A., Mary-Huard, T., Cortijo, S., Bouyer, D., Caillieux, E., Duvernois-Berthet, E., Al-Shikhley, L., et al. (2011). Integrative epigenomic mapping defines four main chromatin states in *Arabidopsis*. The EMBO journal 30, 1928-1938.
43. Rubio, V., Linhares, F., Solano, R., Martin, A. C., Iglesias, J., Leyva, A., and Paz-Ares, J. (2001). A conserved MYB transcription factor involved in phosphate starvation signaling both in vascular plants and in unicellular algae. Genes & development 15, 2122-2133.
44. Shlyueva, D., Stampfel, G., and Stark, A. (2014). Transcriptional enhancers: from properties to genome-wide predictions. Nature reviews Genetics 15, 272-286.
45. Sommer, F., Kropat, J., Malasarn, D., Grossoehme, N. E., Chen, X., Giedroc, D. P., and Merchant, S. S. (2010). The CRR1 nutritional copper sensor in *Chlamydomonas* contains two distinct metal-responsive domains. The Plant cell 22, 4098-4113.
46. Tanurdzic, M., Vaughn, M. W., Jiang, H., Lee, T. J., Slotkin, R. K., Sosinski, B., Thompson, W. F., Doerge, R. W., and Martienssen, R. A. (2008). Epigenomic consequences of immortalized plant cell suspension culture. PLoS biology 6, 2880-2895.
47. Vieler, A., Wu, G., Tsai, C. H., Bullard, B., Cornish, A. J., Harvey, C., Reca, I. B., Thornburg, C., Achawanantakun, R., Buehl, C. J., et al. (2012). Genome, functional gene annotation, and nuclear transformation of the heterokont oleaginous alga *Nannochloropsis* oceanica CCMP1779. PLoS genetics 8, e1003064.
48. Vischi Winck, F., Arvidsson, S., Riano-Pachon, D. M., Hempel, S., Koseska, A., Nikoloski, Z., Urbina Gomez, D. A., Rupprecht, J., and Mueller-Roeber, B. (2013). Genome-wide identification of regulatory elements and reconstruction of gene regulatory networks of the green alga *Chlamydomonas reinhardtii* under carbon deprivation. PloS one 8, e79909.
49. Wang, X., Elling, A. A., Li, X., Li, N., Peng, Z., He, G., Sun, H., Qi, Y., Liu, X. S., and Deng, X. W. (2009a). Genome-wide and organ-specific landscapes of epigenetic modifications and their relationships to mRNA and small RNA transcriptomes in maize. The Plant cell 21, 1053-1069.
50. Wang, Z. T., Ullrich, N., Joo, S., Waffenschmidt, S., and Goodenough, U. (2009b). Algal lipid bodies: stress induction, purification, and biochemical characterization in wild-type and starchless *Chlamydomonas reinhardtii*. Eukaryotic cell 8, 1856-1868.
51. Wijffels, R. H., and Barbosa, M. J. (2010). An outlook on microalgal biofuels. Science 329, 796-799.
52. Wykoff, D. D., Grossman, A. R., Weeks, D. P., Usuda, H., and Shimogawara, K. (1999). Psr1, a nuclear localized protein that regulates phosphorus metabolism in *Chlamydomonas*. Proceedings of the National Academy of Sciences of the United States of America 96, 15336-15341.
53. Xie, B., Stessman, D., Hart, J. H., Dong, H., Wang, Y., Wright, D. A., Nikolau, B. J., Spalding, M. H., and Halverson, L. J. (2014). High-throughput fluorescence-activated cell sorting for lipid hyperaccumulating *Chlamydomonas reinhardtii* mutants. Plant biotechnology journal.
54. Zhang, Y., Wong, C. H., Birnbaum, R. Y., Li, G., Favaro, R., Ngan, C. Y., Lim, J., Tai, E., Poh, H. M., Wong, E., et al. (2013). Chromatin connectivity maps reveal dynamic promoter-enhancer long-range associations. Nature 504, 306-310.
55. Zhong, S., Fei, Z., Chen, Y. R., Zheng, Y., Huang, M., Vrebalov, J., McQuinn, R., Gapper, N., Liu, B., Xiang, J., et al. (2013). Single-base resolution methylomes of tomato fruit development reveal epigenome modifications associated with ripening. Nature biotechnology 31, 154-159.

SUPPLEMENTAL REFERENCES

56. Altschul, S. F., Madden, T. L., Schaffer, A. A., Zhang, J., Zhang, Z., Miller, W., and Lipman, D. J. (1997). Gapped BLAST and PSI-BLAST: a new generation of protein database search programs. Nucleic acids research 25, 3389-3402.
57. Altschul, S. F., Wootton, J. C., Gertz, E. M., Agarwala, R., Morgulis, A., Schaffer, A. A., and Yu, Y. K. (2005). Protein database searches using compositionally adjusted substitution matrices. The FEBS journal 272, 5101-5109.
58. Coombes, K. R. (2013). ClassDiscovery: Classes and methods for "class discovery" with microarrays or proteomics.
59. Earley, K. W., Haag, J. R., Pontes, O., Opper, K., Juehne, T., Song, K., and Pikaard, C. S. (2006). Gateway-compatible vectors for plant functional genomics and proteomics. The Plant journal: for cell and molecular biology 45, 616-629.
60. Falcon, S., and Gentleman, R. (2007). Using GOstats to test gene lists for GO term association. Bioinformatics 23, 257-258.
61. Grabherr, M. G., Haas, B. J., Yassour, M., Levin, J. Z., Thompson, D. A., Amit, I., Adiconis, X., Fan, L., Raychowdhury, R., Zeng, Q., et al. (2011). Full-length transcriptome assembly from RNA-Seq data without a reference genome. Nature biotechnology 29, 644-652.
62. Grishin, N. V. (1995). Estimation of the number of amino acid substitutions per site when the substitution rate varies among sites. Journal of molecular evolution 41, 675-679.
63. Gupta, S., Stamatoyannopoulos, J. A., Bailey, T. L., and Noble, W. S. (2007). Quantifying similarity between motifs. Genome biology 8, R24.
64. Li, H., and Durbin, R. (2009). Fast and accurate short read alignment with Burrows-Wheeler transform. Bioinformatics 25, 1754-1760.
65. Patturajan, M., Schulte, R. J., Sefton, B. M., Berezney, R., Vincent, M., Bensaude, O., Warren, S. L., and Corden, J. L. (1998). Growth-related changes in phosphorylation of yeast RNA polymerase II. The Journal of biological chemistry 273, 4689-4694.
66. Perez-Rodriguez, P., Riano-Pachon, D. M., Correa, L. G., Rensing, S. A., Kersten, B., and Mueller-Roeber, B. (2010). PlnTFDB: updated content and new features of the plant transcription factor database. Nucleic acids research 38, D822-827.
67. Punta, M., Coggill, P. C., Eberhardt, R. Y., Mistry, J., Tate, J., Boursnell, C., Pang, N., Forslund, K., Ceric, G., Clements, J., et al. (2012). The Pfam protein families database. Nucleic acids research 40, D290-301.
68. Saitou, N., and Nei, M. (1987). The neighbor-joining method: a new method for reconstructing phylogenetic trees. Molecular biology and evolution 4, 406-425.
69. Shimogawara, K., Wykoff, D. D., Usuda, H., and Grossman, A. R. (1999). *Chlamydomonas reinhardtii* mutants abnormal in their responses to phosphorus deprivation. Plant physiology 120, 685-694.

70. Sommer, F., Kropat, J., Malasarn, D., Grossoehme, N. E., Chen, X., Giedroc, D. P., and Merchant, S. S. (2010). The CRR1 nutritional copper sensor in *Chlamydomonas* contains two distinct metal-responsive domains. The Plant cell 22, 4098-4113.

71. Trapnell, C., Hendrickson, D. G., Sauvageau, M., Goff, L., Rinn, J. L., and Pachter, L. (2013). Differential analysis of gene regulation at transcript resolution with RNA-seq. Nature biotechnology 31, 46-53.

72. Zhang, Y., Liu, T., Meyer, C. A., Eeckhoute, J., Johnson, D. S., Bernstein, B. E., Nusbaum, C., Myers, R. M., Brown, M., Li, W., et al. (2008). Model-based analysis of ChIP-Seq (MACS). Genome biology 9, R137.

The figures, sequences and examples are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

TABLE 1

| | | | Baseline (Ohr) | | | | | |
|---|---|---|---|---|---|---|---|---|
| Marks | Replicate | Type | # of reads | Mappable reads | Mapped (%) | # of dedupl unique reads | Dedupl-unique % | #MACS2 peaks* |
| H3K4me2 | | IP | 8,921,796 | 8,720,202 | 97.7% | 7,029,002 | 80.6% | 6,032 |
| | | Input | 7,597,576 | 7,342,003 | 96.6% | 3,596,656 | 49.0% | |
| H3K4me3 | R1 | IP | 6,991,217 | 6,660,886 | 95.3% | 5,146,811 | 77.3% | 11,487 |
| | | Input | 6,743,218 | 6,382,897 | 94.7% | 4,040,258 | 63.3% | |
| | R2 | IP | 5,015,597 | 4,930,521 | 98.3% | 3,780,635 | 76.7% | 12,857 |
| | | Input | 3,973,127 | 3,843,943 | 96.7% | 2,327,899 | 60.6% | |
| H3K27ac | R1 | IP | 4,112,025 | 3,739,326 | 90.9% | 2,924,426 | 78.2% | 11,992 |
| | | Input | 5,394,178 | 4,713,175 | 87.4% | 3,158,292 | 67.0% | |
| | R2 | IP | 6,335,579 | 6,209,650 | 98.0% | 4,389,420 | 70.7% | 12,175 |
| | | Input | 3,973,127 | 3,843,943 | 96.7% | 2,327,899 | 60.6% | |
| H3K9me3 | | IP | 5,174,636 | 4,816,363 | 93.1% | 3,214,285 | 66.7% | 10,575 |
| | | Input | 3,797,702 | 3,608,874 | 95.0% | 2,558,492 | 70.9% | |
| H3K27me3 | | IP | 2,541,255 | 2,337,799 | 92.0% | 1,744,210 | 74.6% | 484 |
| | | Input | 4,099,370 | 3,896,239 | 95.0% | 2,529,618 | 64.9% | |
| H3K36me3 | R1 | IP | 4,339,861 | 4,253,142 | 98.0% | 3,371,955 | 79.3% | 8,873 |
| | | Input | 4,070,390 | 3,929,062 | 96.5% | 2,681,361 | 68.2% | |
| | R2 | IP | n.a | n.a | n.a | n.a | n.a | n.a |
| | | Input | n.a | n.a | n.a | n.a | n.a | n.a |
| RNAPII | | IP | 3,791,640 | 89.2% | 89.2% | 2,077,194 | 61.4% | 3,143 |
| | | Input | 2,475,900 | 93.4% | 93.4% | 1,550,148 | 67.0% | |

Peaks are called with FDR < 0.05

TABLE 2

| # of reads | Mappable reads | Mapped (%) | # of dedupl unique reads | Dedupl-unique % | #MACS2 peaks* |
|---|---|---|---|---|---|
| Nitrogen Depreviation (1 hr) | | | | | |
| n.a | n.a | n.a | n.a | n.a | n.a |
| n.a | n.a | n.a | n.a | n.a | n.a |
| 3,977,733 | 3,859,385 | 97.0% | 3,074,149 | 79.7% | 12,821 |
| 3,719,293 | 3,544,825 | 95.3% | 2,216,073 | 62.5% | |
| 5,733,447 | 5,587,201 | 97.4% | 4,149,765 | 74.3% | 13,048 |
| 3,954,921 | 3,819,769 | 96.6% | 2,672,471 | 70.0% | |
| 4,060,312 | 3,917,846 | 96.5% | 3,028,160 | 77.3% | 12,244 |
| 3,719,293 | 3,544,825 | 95.3% | 2,216,073 | 62.5% | |
| 4,852,751 | 4,747,843 | 97.8% | 3,555,971 | 74.9% | 12,412 |
| 3,954,921 | 3,819,769 | 96.6% | 2,672,471 | 70.0% | |
| 4,091,263 | 3,888,102 | 95.0% | 2,851,236 | 73.3% | 8,120 |
| 4,369,910 | 4,209,239 | 96.3% | 2,942,246 | 69.9% | |
| 5,786,549 | 5,034,533 | 87.0% | 3,321,965 | 66.0% | 521 |
| 3,867,019 | 3,668,587 | 94.9% | 2,411,860 | 65.7% | |
| 4,710,003 | 4,577,918 | 97.2% | 3,554,242 | 77.6% | 9,188 |

TABLE 2-continued

| # of reads | Mappable reads | Mapped (%) | # of dedupl unique reads | Dedupl-unique % | #MACS2 peaks* |
|---|---|---|---|---|---|
| 4,369,910 | 4,209,239 | 96.3% | 2,942,246 | 69.9% | |
| n.a | n.a | n.a | n.a | n.a | n.a |
| n.a | n.a | n.a | n.a | n.a | n.a |
| 3,877,267 | 3,538,792 | 91.3% | 2,119,854 | 59.9% | 3,138 |
| 3,649,425 | 3,492,461 | 95.7% | 2,221,803 | 63.6% | |
| Sulphur Depreviation (1 hr) | | | | | |
| n.a | n.a | n.a | n.a | n.a | n.a |
| n.a | n.a | n.a | n.a | n.a | n.a |
| 6,860,877 | 6,569,112 | 95.7% | 4,651,112 | 70.8% | 12,868 |
| 6,382,232 | 6,139,895 | 96.2% | 3,638,293 | 59.3% | |
| n.a | n.a | n.a | n.a | n.a | n.a |
| n.a | n.a | n.a | n.a | n.a | n.a |
| 7,591,542 | 7,277,309 | 95.9% | 4,914,747 | 67.5% | 12,623 |
| 6,131,473 | 5,855,234 | 95.5% | 2,868,969 | 49.0% | |
| n.a | n.a | n.a | n.a | n.a | n.a |
| n.a | n.a | n.a | n.a | n.a | n.a |
| 8,704,508 | 7,936,605 | 91.2% | 3,107,982 | 39.2% | 2,293 |
| 7,722,693 | 7,383,081 | 95.6% | 3,787,568 | 51.3% | |

TABLE 2-continued

| # of reads | Mappable reads | Mapped (%) | # of dedupl unique reads | Dedupl-unique % | #MACS2 peaks* |
|---|---|---|---|---|---|
| 4,983,273 | 4,253,982 | 85.4% | 1,057,077 | 24.8% | 510 |
| 6,541,621 | 6,247,061 | 95.5% | 3,509,535 | 56.2% | |
| 8,481,474 | 8,125,826 | 95.8% | 4,456,946 | 54.8% | 8,528 |
| 7,722,693 | 7,383,081 | 95.6% | 3,787,568 | 51.3% | |
| 7,940,234 | 6,232,638 | 78.5% | 4,358,067 | 69.9% | 8,647 |
| 7,755,521 | 7,492,746 | 96.6% | 3,867,641 | 51.6% | |
| 6,729,049 | 6,330,305 | 94.1% | 1,945,188 | 30.7% | 4,385 |
| 6,382,232 | 6,139,895 | 96.2% | 3,638,293 | 59.3% | |

TABLE 3

| Treatment | Time Point | Replicate | Raw Pairs | Trimed Pairs | Mapped and Properly paired | % of raw data |
|---|---|---|---|---|---|---|
| Baseline | 0 hr | A | 71,422,643 | 64,747,175 | 47,024,606 | 66% |
| Baseline | 0 hr | B | 110,470,791 | 100,922,597 | 75,531,765 | 68% |
| N- | 10' | A | 61,464,593 | 53,177,133 | 37,727,829 | 61% |
| N- | 10' | B | 49,909,719 | 46,685,339 | 32,188,759 | 64% |
| N- | 30' | A | 75,769,515 | 67,777,184 | 50,055,526 | 66% |
| N- | 30' | B | 97,014,730 | 92,635,222 | 57,015,580 | 59% |
| N- | 1 hr | A | 64,554,510 | 59,103,917 | 41,486,758 | 64% |
| N- | 1 hr | B | 167,115,974 | 149,991,988 | 109,796,223 | 66% |
| N- | 2 hr | A | 78,005,952 | 63,686,449 | 46,538,643 | 60% |
| N- | 2 hr | B | 81,926,123 | 74,193,002 | 53,657,960 | 65% |
| N- | 6 hr | A | 69,255,663 | 63,306,952 | 46,908,149 | 68% |
| N- | 6 hr | B | 81,034,852 | 74,198,626 | 55,391,284 | 68% |
| N- | 8 hr | A | 47,825,305 | 45,149,030 | 33,339,635 | 70% |
| N- | 8 hr | B | 50,370,863 | 48,030,881 | 34,701,013 | 69% |
| N- | 24 hr | A | 62,005,731 | 57,492,037 | 40,931,543 | 66% |
| N- | 24 hr | B | 54,600,205 | 48,711,746 | 33,704,301 | 62% |
| N- | 48 hr | A | 52,092,730 | 48,630,104 | 34,093,344 | 65% |
| N- | 48 hr | B | 46,821,585 | 43,359,198 | 31,827,819 | 68% |
| Baseline | 0 hr | A | 51,484,492 | 49,836,381 | 41,734,327 | 81% |
| Baseline | 0 hr | B | 66,475,777 | 63,977,422 | 52,441,434 | 79% |
| S- | 10' | A | 65,883,075 | 63,261,591 | 52,045,540 | 79% |
| S- | 10' | B | 51,722,869 | 49,157,939 | 40,923,320 | 79% |
| S- | 30' | A | 29,074,565 | 25,247,048 | 20,782,696 | 71% |
| S- | 30' | B | 50,965,858 | 48,907,146 | 40,567,280 | 80% |
| S- | 1 hr | A | 40,992,077 | 38,830,624 | 32,334,403 | 79% |
| S- | 1 hr | B | 54,304,828 | 52,632,770 | 44,342,126 | 82% |
| S- | 2 hr | A | 65,124,047 | 62,126,856 | 48,635,207 | 75% |
| S- | 2 hr | B | 41,780,378 | 39,974,674 | 31,898,329 | 76% |
| S- | 6 hr | A | 45,698,133 | 44,101,007 | 35,598,874 | 78% |
| S- | 6 hr | B | 50,023,019 | 48,175,137 | 38,122,275 | 76% |
| S- | 8 hr | A | 50,546,965 | 48,474,179 | 39,276,801 | 78% |
| S- | 8 hr | B | 71,838,370 | 67,634,921 | 51,761,322 | 72% |
| S- | 24 hr | A | 47,824,291 | 45,437,606 | 35,856,850 | 75% |
| S- | 24 hr | B | 62,820,960 | 60,205,464 | 46,077,329 | 73% |
| S- | 48 hr | A | 50,169,761 | 47,968,838 | 37,328,836 | 74% |
| S- | 48 hr | B | 52,360,125 | 50,226,696 | 39,089,036 | 75% |
| Total | | | 2,270,751,074 | 2,107,974,879 | 1,590,736,722 | |
| Average | | | | | 44,187,131 | |

TABLE 4

| Filtering step/break down | Total | Phytozome annotations v5.3.1 (19,526 transcripts) |
|---|---|---|
| Merged; unfiltered | 66,561 | 19,140 (98%) |
| FPKM > 0 for both BR1/BR2 in ≥ one time point | 24,499 | 18,161 (93%) |
| CDS length ≥ 50 a.a. | 23,169 | 17,670 (90%) |
| Post-filtering on obvious noise by CuffDiff classes | 22,209* | 17,670 (90%) |
| non-reference transcripts | 298 | |
| w/histone mark support~ | 228 (77%) | |
| transcript variants | 4,241 | |
| Transcription factor (TF) | 277 | |
| Transcription regulator (TR) | 250 | |
| TF & TR | 518 | |

*used in assiging ChromoHMM state and differential expression analysis

TABLE 5

| | N starvation | | S starvation | |
|---|---|---|---|---|
| DE | up-regulated | down-regulated | up-regulated | down-regulated |
| o vs 10' | 933 (51) | 1,273 (46)* | 701 (14) | 1,285 (42) |
| 0 vs 30' | 3,002 (128)* | 2,403 (64) | 633 (20) | 1,065 (28) |
| 0 vs 60' | 3,555 (121)* | 2,044 (55) | 723 (23) | 804 (16) |
| 0 vs 2 hr | 4,437 (150)* | 1,721 (41) | 1,658 (42)* | 1,350 (32) |
| 0 vs 6 hr | 2,633 (83)* | 2,084 (49) | 2,629 (56) | 2,603 (56) |
| 0 vs 8 hr | 3,231 (97)* | 2,216 (45) | 2,744 (75) | 2,842 (64) |
| 0 vs 24 hr | 3,339 (103) | 2,351 (45) | 3,458 (92) | 4,484 (125) |
| 0 vs 48 hr | 3,391 (99) | 2,087 (46) | 4,149 (99) | 2,589 (82) |
| Total | 12,144 (344) | | 12,242 (318) | |
| Union | 7,871 (256) | 6,265 (149) | 6,931 (166) | 7,387 (197) |

Cuffdiff, fold change >2, $p < 0.01$
(tf/tr): number of tf/tr in the categories
*containing Psr1

TABLE 6

| | | | | | Peptide A PSR1 ChIP-Seq | | | | | |
|---|---|---|---|---|---|---|---|---|---|---|
| Protein | Condition | Replicate | Read | Type | # of reads | Mappable reads | Mapped (%) | # of dedupl unique reads | Dedupl-unique % | #MACS2 peaks* |
| PSR1 | N-30 min | BR1 | R/1 | IP | 4,536,359 | 2,936,198 | 64.70% | 1,555,304 | 52.97% | 428 |
| | | BR1 | | Input | 9,419,422 | 8,707,412 | 92.40% | 4,886,365 | 56.12% | |

TABLE 6-continued

| Protein | Condition | Replicate | Read | Type | Peptide A PSR1 ChIP-Seq # of reads | Mappable reads | Mapped (%) | # of dedupl unique reads | Dedupl-unique % | #MACS2 peaks* |
|---|---|---|---|---|---|---|---|---|---|---|
| PSR1 | N-30 min | BR1 | R/2 | IP | 4,536,359 | 2,847,120 | 62.80% | 1,509,646 | 53.02% | 396 |
| | | BR1 | | Input | 9,419,422 | 8,368,085 | 88.80% | 4,680,375 | 55.93% | |
| PSR1 | N-1 hr | BR1 | R/1 | IP | 10,443,930 | 8,631,817 | 82.60% | 4,792,817 | 55.53% | 215 |
| | | BR1 | | Input | 7,966,639 | 7,318,997 | 91.90% | 4,457,715 | 60.91% | |
| PSR1 | N-1 hr | BR1 | R/2 | IP | 10,443,930 | 8,322,723 | 79.70% | 4,591,363 | 55.17% | 228 |
| | | BR1 | | Input | 7,966,639 | 7,068,458 | 88.70% | 4,288,024 | 60.66% | |
| PSR1 | S-1 hr | BR1 | R/1 | IP | 5,352,712 | 3,302,972 | 61.70% | 2,069,291 | 62.65% | 645 |
| | | BR1 | | Input | 8,780,319 | 8,088,585 | 92.10% | 4,400,801 | 54.41% | |
| PSR1 | S-1 hr | BR1 | R/2 | IP | 5,352,712 | 3,062,119 | 57.20% | 1,917,072 | 62.61% | 598 |
| | | BR1 | | Input | 8,780,319 | 7,876,621 | 89.70% | 4,274,408 | 54.27% | |
| PSR1 | S-2 hr | BR1 | R/1 | IP | 9,100,455 | 6,942,267 | 76.30% | 3,845,762 | 55.40% | 446 |
| | | BR1 | | Input | 11,085,316 | 10,259,042 | 92.50% | 5,774,503 | 56.29% | |
| PSR1 | S-2 hr | BR1 | R/2 | IP | 9,100,455 | 6,631,646 | 72.90% | 3,669,039 | 55.33% | 438 |
| | | BR1 | | Input | 11,085,316 | 9,832,631 | 88.70% | 5,518,151 | 56.12% | |
| PSR1 | S-6 hr | BR1 | R/1 | IP | 6,198,290 | 4,269,698 | 68.90% | 2,164,926 | 50.70% | 942 |
| | | BR1 | | Input | 8,018,891 | 7,408,931 | 92.40% | 4,641,986 | 62.65% | |
| PSR1 | S-6 hr | BR1 | R/2 | IP | 6,198,290 | 4,086,743 | 65.90% | 2,081,045 | 50.92% | 942 |
| | | BR1 | | Input | 8,018,891 | 7,140,684 | 89.00% | 4,483,476 | 62.79% | |
| PSR1 | N-30 min | BR1 | R/1 | IP | 4,536,359 | 2,936,198 | 64.70% | 1,555,304 | 52.97% | 428 |
| | | BR1 | | Input | 9,419,422 | 8,707,412 | 92.40% | 4,886,365 | 56.12% | |
| PSR1 | N-30 min | BR1 | R/2 | IP | 4,536,359 | 2,847,120 | 62.80% | 1,509,646 | 53.02% | 396 |
| | | BR1 | | Input | 9,419,422 | 8,368,085 | 88.80% | 4,680,375 | 55.93% | |
| PSR1 | N-1 hr | BR1 | R/1 | IP | 10,443,930 | 8,631,817 | 82.60% | 4,792,817 | 55.53% | 215 |
| | | BR1 | | Input | 7,966,639 | 7,318,997 | 91.90% | 4,457,715 | 60.91% | |
| PSR1 | N-1 hr | BR1 | R/2 | IP | 10,443,930 | 8,322,723 | 79.70% | 4,591,363 | 55.17% | 228 |
| | | BR1 | | Input | 7,966,639 | 7,068,458 | 88.70% | 4,288,024 | 60.66% | |
| PSR1 | S-1 hr | BR1 | R/1 | IP | 5,352,712 | 3,302,972 | 61.70% | 2,069,291 | 62.65% | 645 |
| | | BR1 | | Input | 8,780,319 | 8,088,585 | 92.10% | 4,400,801 | 54.41% | |
| PSR1 | S-1 hr | BR1 | R/2 | IP | 5,352,712 | 3,062,119 | 57.20% | 1,917,072 | 62.61% | 598 |
| | | BR1 | | Input | 8,780,319 | 7,876,621 | 89.70% | 4,274,408 | 54.27% | |
| PSR1 | S-2 hr | BR1 | R/1 | IP | 9,100,455 | 6,942,267 | 76.30% | 3,845,762 | 55.40% | 446 |
| | | BR1 | | Input | 11,085,316 | 10,259,042 | 92.50% | 5,774,503 | 56.29% | |
| PSR1 | S-2 hr | BR1 | R/2 | IP | 9,100,455 | 6,631,646 | 72.90% | 3,669,039 | 55.33% | 438 |
| | | BR1 | | Input | 11,085,316 | 9,832,631 | 88.70% | 5,518,151 | 56.12% | |
| PSR1 | S-6 hr | BR1 | R/1 | IP | 6,198,290 | 4,269,698 | 68.90% | 2,164,926 | 50.70% | 942 |
| | | BR1 | | Input | 8,018,891 | 7,408,931 | 92.40% | 4,641,986 | 62.65% | |
| PSR1 | S-6 hr | BR1 | R/2 | IP | 6,198,290 | 4,086,743 | 65.90% | 2,081,045 | 50.92% | 942 |
| | | BR1 | | Input | 8,018,891 | 7,140,684 | 89.00% | 4,483,476 | 62.79% | |

*Peaks are called with FDR < 0.05

TABLE 7

| # | Genomic location | Forward primer | Reverse primer | Region span (bp) |
|---|---|---|---|---|
| 1 | chr_12:8383195..8384442 | ACGAGTCCACTAGGTCAAG TCA (SEQ ID NO: 1) | GTAGGAGGGACACCTGGC A (SEQ ID NO: 2) | 1226 |
| 2 | chr_17:6268127..6269127 | GGGCTGCAAGAAACACACC (SEQ ID NO: 3) | GCTCGAAGCTGCGTGATA TT (SEQ ID NO: 4) | 900 |
| 3 | chr_1:5750235..5751235 | ATTTGGGGATGGCGGCATT TCC (SEQ ID NO: 5) | GAGTGAGCGGAGTGTGTA CGATA (SEQ ID NO: 6) | 873 |
| 4 | chr_5:1650592..1651592 | CGGGCTATGGGTTATGTTCT T (SEQ ID NO: 7) | CTGTCGCTGTTTGCTCCTG (SEQ ID NO: 8) | 961 |
| 5 | chr_7:1252718..1253788 | GATGTCGTGCACGGTTGTG (SEQ ID NO: 9) | CGGATGGTGGAAGCATCA TATAG (SEQ ID NO: 10) | 971 |
| 6 | chr_16:1135475..1136475 | GAGCACGCACATTGCATCA (SEQ ID NO: 11) | AGAGCCTTCGAGGACTTC AC (SEQ ID NO: 12) | 974 |

TABLE 7-continued

| # | Genomic location | Forward primer | Reverse primer | Region span (bp) |
|---|---|---|---|---|
| 7 | chr_14:2768740..2769740 | GTTCTAGCCGCACGAACAG (SEQ ID NO: 13) | TTTGGGATTTCGGCCACT T (SEQ ID NO: 14) | 924 |
| 8 | chr_4:2122753..2123753 | GCGGCCTGTAGTACTGTAA TC (SEQ ID NO: 15) | GATCGCGGTTCCCTGAAT C (SEQ ID NO: 16) | 965 |
| 9 | chr_17:4717149..4718149 | AAGCATGTATCATAGGAAT CTTGGG (SEQ ID NO: 17) | CAAGGGCGAACTTGAACT TACT (SEQ ID NO: 18) | 964 |
| 10 | chr_7:2540672..2541672 | CGGGTAGGAGGGTAGGAAA T (SEQ ID NO: 19) | GACTGGCGTGGTTTCCC (SEQ ID NO: 20) | 978 |
| 11 | chr_1:4459808..4460808 | GTCACACATGCGAATGTAA CAG (SEQ ID NO: 21) | GTTGGACGTGTTTGATGC TG (SEQ ID NO: 22) | 990 |
| Neg ctrl | chr_3:1,064,061..1,065,052 | TGTTTACGTGCGAAAACCT G (SEQ ID NO: 23) | AGCGTACGGTGAGAGGTA CG (SEQ ID NO: 24) | 992 |
| Neg ctrl | chr_5:2426137..2427133 | CCTGGTCCGAAAGACCATC (SEQ ID NO: 25) | GACCTGCACGAAATTCAA GG (SEQ ID NO: 26) | 996 |
| Neg ctrl | chr_2:1,048,210..1,049,203 | AAATGCAACGGCTAGGTCT G (SEQ ID NO: 27) | TTTGCACGCTTGCATAAG TC (SEQ ID NO: 28) | 994 |

TABLE 8

| | | | | Nitrogen Depletion Time Series | | | | | |
|---|---|---|---|---|---|---|---|---|---|
| Time | Marks | Replicate | Type | # of reads | Mappable reads | Mapped (%) | # of dedupl unique reads | Dedupl-unique % | #MACS2 peaks* |
| 0 hr | H3K4me3 | R1 | IP | 6,991,217 | 6,660,886 | 95.30% | 5,146,811 | 77.27% | 11,487 |
| | | | Input | 6,743,218 | 6,382,897 | 94.70% | 4,040,258 | 63.30% | |
| 0 hr | H3K4me3 | R2 | IP | 5,015,597 | 4,930,521 | 98.30% | 3,780,635 | 76.68% | 12,857 |
| | | | Input | 3,973,127 | 3,843,943 | 96.70% | 2,327,899 | 60.56% | |
| 10 min | H3K4me3 | R1 | IP | 6,402,847 | 6,207,514 | 96.90% | 4,370,387 | 70.40% | 11,659 |
| | | | Input | 6,871,315 | 6,616,833 | 96.30% | 2,414,104 | 36.48% | |
| 30 min | H3K4me3 | R1 | IP | 6,771,909 | 6,552,696 | 96.80% | 4,609,518 | 70.35% | 11,856 |
| | | | Input | 7,145,723 | 6,833,261 | 95.60% | 2,831,179 | 41.43% | |
| 1 hr | H3K4me3 | R1 | IP | 3,977,733 | 3,859,385 | 97.00% | 3,074,149 | 79.65% | 12,821 |
| | | | Input | 3,719,293 | 3,544,825 | 95.30% | 2,216,073 | 62.52% | |
| 1 hr | H3K4me3 | R2 | IP | 5,733,447 | 5,587,201 | 97.40% | 4,149,765 | 74.27% | 13,048 |
| | | | Input | 3,954,921 | 3,819,769 | 96.60% | 2,672,471 | 69.96% | |
| 2 hr | H3K4me3 | R1 | IP | 8,556,234 | 8,376,084 | 97.90% | 5,598,650 | 66.84% | 11,971 |
| | | | Input | 7,990,163 | 7,691,362 | 96.30% | 2,765,931 | 35.96% | |
| 6 hr | H3K4me3 | R1 | IP | 8,852,681 | 8,680,042 | 98.00% | 5,684,969 | 65.49% | 12,142 |
| | | | Input | 6,696,078 | 6,465,297 | 96.60% | 3,188,760 | 49.32% | |
| 8 hr | H3K4me3 | R1 | IP | 6,323,140 | 6,198,760 | 98.00% | 4,388,501 | 70.80% | 12,076 |
| | | | Input | 8,392,944 | 8,026,621 | 95.60% | 3,826,305 | 47.67% | |
| 24 hr | H3K4me3 | R1 | IP | 7,649,839 | 7,488,617 | 97.90% | 5,165,870 | 68.98% | 12,053 |
| | | | Input | 8,029,758 | 7,687,005 | 95.70% | 4,466,748 | 58.11% | |
| 48 hr | H3K4me3 | R1 | IP | 6,769,530 | 6,605,952 | 97.60% | 4,899,245 | 74.16% | 11,948 |
| | | | Input | 8,191,636 | 7,914,010 | 96.60% | 4,965,240 | 62.74% | |

| time point | #peaks | % peaks | unique to 0 hr | unique to time point | common | union | #peaks not capture |
|---|---|---|---|---|---|---|---|
| | | | set (0 hr, time point) | | | | |
| 0 hr | 11,310 | 87.89% | n.a. | n.a. | n.a. | n.a. | n.a. |
| 10 min | 11,504 | 89.40% | 262 | 456 | 11,048 | 11,766 | 1,102 |
| 30 min | 11,700 | 90.92% | 201 | 591 | 11,109 | 11,901 | 967 |
| 1 hr | 12,543 | 97.47% | 39 | 1,272 | 11,271 | 12,582 | 286 |

TABLE 8-continued

| | | | | | | | |
|---|---|---|---|---|---|---|---|
| 2 hr | 11,817 | 91.83% | 164 | 671 | 11,146 | 11,981 | 887 |
| 6 hr | 11,985 | 93.14% | 117 | 792 | 11,193 | 12,102 | 766 |
| 8 hr | 11,919 | 92.63% | 170 | 779 | 11,140 | 12,089 | 779 |
| 24 hr | 11,929 | 92.70% | 154 | 773 | 11,156 | 12,083 | 785 |
| 48 hr | 11,822 | 91.87% | 219 | 731 | 11,091 | 12,041 | 827 |
| Union | 12,868 | | | | | | |
| Average | 11,837 | | | | | | |

*Peaks are called with FDR < 0.05

What is claimed is:

1. A method for increasing lipid production in a host organism, said method comprising introducing into an organism an expression vector comprising a heterologous nucleotide sequence comprising (a) an operably linked promoter that drives expression in the organism; and (b) a lipid regulatory transcription factor gene that encodes a polypeptide comprising the amino acid sequence of SEQ ID NO:44; culturing the organism under conditions in which the heterologous nucleotide is expressed; and selecting an organism that produces increased amounts of lipid compared to wildtype.

2. The method of claim 1, wherein the host organism is cyanobacteria, plants, or algae.

3. The method of claim 2, wherein the host organism is microalgae.

4. The method of claim 3, wherein the microalgae into which the expression vector is introduced comprises a wildtype Lcr1 gene.

5. A cell culture that comprises a strain of algae or cyanobacteria that produces increased amounts of lipid compared to wildtype, wherein the strain of algae or cyanbacteria comprises in its genome at least one stably incorporated expression cassette, said expression cassette comprising a heterologous nucleotide sequence comprising a transcription factor regulatory gene that encodes a polypeptide comprising the amino acid sequence of SEQ ID NO:44 linked to a promoter that drives expression, wherein the strain of algae or cyanobacteria is selected by the method of claim 1.

6. The cell culture of claim 5, wherein the cell culture comprises a strain of microalgae.

7. A cell culture comprising a strain of microalgae selected by the method of claim 3.

8. The cell culture of claim 5, wherein the polypeptide comprising amino acid sequence SEQ ID NO:44 is encoded by a nucleic acid sequence of SEQ ID NO:43; or a codon-optimized variant of SEQ ID NO:43.

9. A method for enhancing lipid production in a transgenic strain of microalgae, said method comprising introducing into the microalgae an expression cassette comprising a heterologous nucleotide comprising (a) an operably linked promoter that drives expression in the organism; and (b) a transcription factor gene from a microalgae that encodes a polypeptide comprising the amino acid sequence of SEQ ID NO:44; culturing the microalgae under conditions in which the transcription factor gene is expressed;

and selecting algae that produces increased amounts of lipid compared to wildtype, thereby providing enhanced lipid production in the transgenic strain of microalgae.

10. The method of claim 9, wherein the culturing step comprises a period in which the cells are cultured under nitrogen starvation conditions.

11. A method of obtaining lipids from a cell culture, the method comprising collecting the cells from a cell culture of claim 5; and isolating lipids from the cells.

* * * * *

SEQUENCE LISTING

<160> NUMBER OF SEQ ID NOS: 104

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
acgagtccac taggtcaagt ca 22

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
gtaggaggga cacctggca 19

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
gggctgcaag aaacacacc 19

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gctcgaagct gcgtgatatt 20

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
atttggggat ggcggcattt cc 22

<210> SEQ ID NO 6
<211> LENGTH: 23

<212> TYPE: DNA
<213> ORGANISM: Artificial Sequence
<220> FEATURE:
<223> OTHER INFORMATION: Primer

<400> SEQUENCE: 6
gagtgagcgg agtgtgtacg ata 23

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
cgggctatgg gttatgttct t 21

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
ctgtcgctgt ttgctcctg 19

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
gatgtcgtgc acggttgtg 19

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
cggatggtgg aagcatcata tag 23

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
gagcacgcac attgcatca 19

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12

-continued agagccttcg aggacttcac 20

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
gttctagccg cacgaacag 19

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
tttgggattt cggccactt 19

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gcggcctgta gtactgtaat c 21

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
gatcgcggtt ccctgaatc 19

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
aagcatgtat cataggaatc ttggg 25

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
caagggcgaa cttgaactta ct 22

<210> SEQ ID NO 19
<211> LENGTH: 20
<212> TYPE: DNA
<213> ORGANISM: Artificial Sequence -continued
<220> FEATURE:
<223> OTHER INFORMATION: Primer

<400> SEQUENCE: 19
cgggtaggag ggtaggaaat 20

<210> SEQ ID NO 20
<211> LENGTH: 17
<212> TYPE: DNA
<213> ORGANISM: Artificial Sequence
<220> FEATURE:
<223> OTHER INFORMATION: Primer

<400> SEQUENCE: 20
gactggcgtg gtttccc 17

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
gtcacacatg cgaatgtaac ag 22

<210> SEQ ID NO 22
<211> LENGTH: 20
<212> TYPE: DNA
<213> ORGANISM: Chlamydomonas reinhardtii

<400> SEQUENCE: 22
gttggacgtg tttgatgctg 20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
tgtttacgtg cgaaaacctg 20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
agcgtacggt gagaggtacg 20

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
cctggtccga aagaccatc 19

<210> SEQ ID NO 26

<211> LENGTH: 20
<212> TYPE: DNA
<213> ORGANISM: Artificial Sequence
<220> FEATURE:
<223> OTHER INFORMATION: Primer

<400> SEQUENCE: 26
gacctgcacg aaattcaagg 20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
aaatgcaacg gctaggtctg 20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tttgcacgct tgcataagtc 20

<210> SEQ ID NO 29
<211> LENGTH: 50
<212> TYPE: PRT
<213> ORGANISM: Homo sapiens

<400> SEQUENCE: 29

```
Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg
    50
```

<210> SEQ ID NO 30
<211> LENGTH: 49
<212> TYPE: PRT
<213> ORGANISM: Chlamydomonas reinhardtii

<400> SEQUENCE: 30

```
Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Thr Pro Ala Thr
            20                  25                  30

Gly Gly Val Lys Lys Pro His Arg Tyr Arg Pro Gly Thr Val Ala Leu
        35                  40                  45

Arg
```

<210> SEQ ID NO 31
<211> LENGTH: 50
<212> TYPE: PRT
<213> ORGANISM: Homo sapiens -continued

<400> SEQUENCE: 31

```
Glu Ile Arg Arg Tyr Gln Lys Ser Thr Glu Leu Leu Ile Arg Lys Leu
1               5                   10                  15

Pro Phe Gln Arg Leu Val Arg Glu Ile Ala Gln Asp Phe Lys Thr Asp
            20                  25                  30

Leu Arg Phe Gln Ser Ser Ala Val Met Ala Leu Gln Glu Ala Cys Glu
        35                  40                  45

Ala Tyr
    50
```

<210> SEQ ID NO 32
<211> LENGTH: 50
<212> TYPE: PRT
<213> ORGANISM: Chlamydomonas reinhardtii

<400> SEQUENCE: 32

```
Glu Ile Arg Lys Tyr Gln Lys Ser Thr Glu Leu Leu Ile Arg Lys Leu
1               5                   10                  15

Pro Phe Gln Arg Leu Val Arg Glu Ile Ala Gln Asp Phe Lys Thr Asp
            20                  25                  30

Leu Arg Phe Gln Ser Gln Ala Val Leu Ala Leu Gln Glu Ala Ala Glu
        35                  40                  45

Ala Tyr
    50
```

<210> SEQ ID NO 33
<211> LENGTH: 36
<212> TYPE: PRT
<213> ORGANISM: Homo sapiens

<400> SEQUENCE: 33

```
Leu Val Gly Leu Phe Glu Asp Thr Asn Leu Cys Ala Ile His Ala Lys
1               5                   10                  15

Arg Val Thr Ile Met Pro Lys Asp Ile Gln Leu Ala Arg Arg Ile Arg
            20                  25                  30

Gly Glu Arg Ala
        35
```

<210> SEQ ID NO 34
<211> LENGTH: 50
<212> TYPE: PRT
<213> ORGANISM: Chlamydomonas reinhardtii

<400> SEQUENCE: 34

```
Leu Val Gly Leu Phe Glu Asp Thr Asn Leu Cys Ala Ile His Ala Lys
1               5                   10                  15

Arg Val Thr Ile Met Pro Lys Asp Ile Gln Leu Ala Arg Arg Ile Arg
            20                  25                  30

Gly Ser Thr Pro Ala Asn Thr Tyr Gly Leu Leu Asp Thr Ala Ala Ala
        35                  40                  45

Gly Asp
    50
```

<210> SEQ ID NO 35
<211> LENGTH: 43
<212> TYPE: PRT
<213> ORGANISM: Chlamydomonas reinhardtii

<400> SEQUENCE: 35

-continued

```
Leu Leu Phe Ser Val Ser Pro Arg Ser Gly Ser Val Val Val Val Asp
1               5                   10                  15

Val Ser Gly Gly Ser Met Ala Ser Arg Gln Leu Leu Ala Ala Gly Leu
            20                  25                  30

Pro Val Ser Ser Met Gly Leu Ala Val Ala Cys
        35                  40


<210> SEQ ID NO 36
<211> LENGTH: 8119
<212> TYPE: DNA
<213> ORGANISM: Chlamydomonas reinhardtii

<400> SEQUENCE: 36

aagcattgtg agtttgaacg cgtttgccgt caccatggcg ggcgacacgc ctctgcaggc      60

cgttttccgc gtaagcccaa gggaagtaga tactattgag tagttgtcaa cacttgctta     120

ctatcagcga cttgtcggtg taggcgtagg cgatagctgg cgacgcgagg agttttggag     180

gccagggtta aaggagccaa cgccgtggta tcacgaggta gccgggccag tgccttgtac     240

aagccgggcg cccgcatgtt gacagcaact aggcgttaag aatggaagac gaggttgaag     300

gagcggtggg ggcgcctgcg ggcgggggag gcgggcgcgg gccagacccg cacctgctgc     360

ctccgcccgc accccttcaa cttcccatct caatcgagct gctgccgccg ccgccgcccc     420

tccagctacc ccccaacatg gatccagtgc atagccctga tgcagcagcg ccgggggtgg     480

ggtcggcagc ggaggccctg tcaccgtggc tgttgctgac gcagcaccaa tcgcaacacc     540

cgccacggcg gcccggctcg agcggtgggg gtgcgctgcg ccccccagac atggggctgc     600

ccggcgcggg gagcagcggc ggcgtgctcg gcggtggcgg cggcagcaac agcaccggaa     660

cagctctgcc cgactcgctg ctgctgtcgc ccgagacgtc gtccctgcgg tcacgcctgt     720

tgggccacct gtcttccgac tcaccgcagt tagggctgtc ggctcaggcc agcctgcaac     780

aggcgctgct acagctcggc agcgtgggcg gagcgtcggc ctggagcgag gcacacggca     840

gcggcgctgg cgttggcagt agccacagca acagccagct ggtgccgatg ggggcggcgg     900

gggagttgct gagcatcagc cgaagcagct tgggcgggcc gggaagcgtc agtcagaacg     960

tgttctcaca aggcctccgg agccctgatc acccgagttc ggccgcactg actgcgccct    1020

ggctcgccga cttgcagtcg ccacggccag cgcaacatca gcaacaacgc cagcaggaac    1080

aggagcaggc tggcggcagc agcgcaggcg ccagcagttt ggatgcgccg cagcaagcgt    1140

taacgggcag tctaggcatc ggccccactg caagtccagg gaccggaggc ggcggaccgc    1200

agggtggggg cggcgcggcg gccggcagcg tgcccggggg cagggcgcac ggcagtggcc    1260

ccacgtaccc ttcgctggcg gaggcgctgg cactggctca agccacgcta agggctgagc    1320

gcggcagcca cggaggaggc aacggcagtt caggtggcgg gagcgcaggc ggcaggggcc    1380

agcagcagcc ttcacgcagg cggagcggca actccgatgc cgcggcggcg ctgaccgccc    1440

tgcccgcgcc gcacaactca cgcggcggcg acggtggcag tggcggcggc ggcggcggcg    1500

gggacacgca ctcgcacccg caggcacaca actcggcttt ccgcccctac acagtcgtgg    1560

tgactagcgg gcagctgcgc gcgtcggatg ccgtgcttcg ggctgcggac gttgcgggtg    1620

ccgctgcagg cggcggcggt ggcggcggcg gcacgctcag cggaggcgct ggttcacacg    1680

tcgcccacac gcactctcca gcacggacgc cggagcggct gccgaggtcg ggcgacagcg    1740

gtcggggcgc gcaggcagcg gatcgcatgg ctggcctgac ggcggcggcc gcggcggtgc    1800

ttggcagcgc ctccagcggc ccgggccccg tgacgactgg actcacgcac agcgggcggt    1860
```

-continued

```
caacgccgcc ggggcacgcc acgccgcccg gccaagtgac cccgccaggg cagaccacgc   1920
cggagcgcct gcggggcgcc gctggtgctg cgggcgccgc ggggggcggc ggtggggagg   1980
cttggtcagc ggctggtgcg gcggcgctca ctctacagca cttggcagct agtgactcgg   2040
gtgcgctgca tccgcggccc cggcaggctt tggagccggg acagcagcag cagcagcagc   2100
agcagcagca ggtggcgccc cagttgtcga caccgtttgc cgggagggcg caggctgaat   2160
tactgcagac gctcgggcag cagcagcagc acgcagcgaa gcatcgtgca ccggagcgcg   2220
ggcagtcaac gccagagcgg gggccagcgt ctcaggatgc ggacactgct ggcaagttcg   2280
ctgctgcaga ggccgcagga ccgtccagca cacccacgta cgcagccgca gcacgagtga   2340
cacacgcgat gcctgcaccc cagccgacac cagcgtacgc ccctggacct tctcgaccgg   2400
cgatggctca tcccggcgca gcttcggccc agctccggca cacgcctcaa tggcccactg   2460
gcgacgccgc catgcgtgct ttccatgatg tgccgcgtgg tgcgggggcg gatggcgccg   2520
tcaaggctga cgccgtggcc ggctccacgg cagctggagg cgcaggcagc agcgggcttg   2580
taggcgcagc agtcccgctg acaacgcacg agcatgggcc cggtccccgc ccgcccctct   2640
tacgagcaca ggcgtccaaa tcgctgttct cgcagcagca gcagcagcag cagcagcagc   2700
agcaggcaca aggggctgca ccggcgaccg gcactttgcc cgatctggac acggggccaa   2760
tgcacgagtc agcgggtgaa gacgcagagg aggggccgga tgcatatccc gacgtgcatg   2820
cgccgcccgg tcaggcgcgg cgccctccgc agctgcggcc gccgcccgcg gaccctcagc   2880
agcagcagca gcagcagcag ctgccagagc ccatcttcgt cacggtggcg gcgtcggcct   2940
ccaagcggcc gcgcaacgac cggcccggga cctccggcgc cgaaggcgcc gccgcaggcg   3000
gcggagccgc agccgctgcg gcggagccgc acacggccgc gggtggcggc ggcggcggca   3060
cagactcctc gccgttacgt cgtacggtgg tgttgggcag cttcacgttg cagctgcggt   3120
cggacctggt ttgcgaggtg ctggggctgt tccacccgcg gcgctacgtg gagggcaggg   3180
actgtgtgga gtacccgccg cactcgggca ccttcgtgtc gcgcagccac tttgaaaagg   3240
tgggcggcgc ggtgacggcc aagtggtacc gctccatccg ggtcctgccg cagatggagc   3300
acctcgggga ttggctggag gcgcacgggc tgcaggtctt caagggcacg ggccgcaagc   3360
gcggcggccg ctatggcggc ggcggtagcg gtgatgtgct agccatgctg gctttaggag   3420
ccgccgcagc gggcggcgcc ggcagcactg gcaccggcac ggaagctaca gccgagtccg   3480
agggccccga catgggggcg gcagtagcag ccacaggcgc aggcatgggg ttgggcgccc   3540
ttgcagccat gccgtactcc agccgaggag cagcggcagc ggccttggct cgggccaagc   3600
ctgttgacgg ggacacagcc gccgccgtcg ccgccctggc cgcgctgtcc gccgccgccg   3660
cggaaggggc ggcggccccg ccggcctcct ccgctgcggc agaggcagcg gcggcatcca   3720
ggtgggccgt tgcgccgctg gcggacaggc agtggcacgc tcagcacgcg accccgctgt   3780
cgatgctcca ccccagcgcc catgcggctg cctttgcaca tgcagctggc ccggcagcag   3840
cagcaggggc tgcttctctg cctgcagcgc gaggtgtggc tgcagcctcc ggtcccgccg   3900
gctcgcggcc gcccacgccc gcgtcccctc acgcccggca ggacccgccc gtgctgttgc   3960
atgccccgga gccgctgcct ctgccagaac ccgaggccgg gttggggcac gagtatgctg   4020
acgagcaacc cgagcagccg cggcagccat acgcggcggt gccgcacccc tcctacgcag   4080
ctgtgccctt cccatacccg cacccgcacc cacacccctc ctacccgtac ggtgcctacc   4140
cgtacccgta cccccacgcg ggcgcccgta ggcacagtgt gtggcctccc gcgctgcccc   4200
cgccgccgca aggccacgca ctgggatggc cgccgcacct gccgccgccc tacgccgcac   4260
```

gagccccagg cctgtacgcg ccctatcccc tgcatgggca cccgcagcat ccgcacccgt 4320
accctcagcg tctggcgcgc ccgggggtgc acctgcggcc acgcctatca atgctggccg 4380
ctgggtaccc cggtgcaagc agcgacggct cggaggggcc cgaaggcggc agcggcgacg 4440
aagcagcgac ggcggcgctg gcagcagcgg ctgcgcacgg cagcgacgat gcggctgcag 4500
cggcagaggc gacgtcatcg cacgcgcagc actgggccac agcggcacgc ggcgcgctgc 4560
aaggcaccag gagccgcagc ttcggcgcct cctcgaccgc cgccgccgcc gctgcggccg 4620
tggcggcgga gcactggcgg tcggctgggg gtggtactca gcactggggc agtagcagcg 4680
gcggtgcagg tggcggctac agccacggac aggccgggct gctgctgccc gccgcgtcct 4740
ggccgggtcc gtcgcctctg ggaggaggtc agcgggggca gcacggcgca ccgcctcgcg 4800
tgagtgcccc cgcggccacg ggttccggga gcgagcgtgg gtacgagctg gaggcgcggc 4860
aggccgccgt ggcggccacg gcggctgcgg cggctgcgga ctggctcgat accgagcaca 4920
tgccagagct gcagcagcag cagcagcagc agcagcagca gcagcagcag cccctgctgg 4980
cgcttcccgc accgcccatg acggcggccg cagggccctc gccgccccac gggctgctac 5040
ggggcgcgct ggaggcggct gcggcggccg ccgccagctc tgccgcgcac ggcggcggcc 5100
ggcagggagc caagggcagt gcgacgaggg gtacggcaga gggtgccggc ggcgctcctg 5160
ctgcctcacc agcgcagccc cgcgtaagcg aaagctgtgc caccagtggc ggcagcgatg 5220
tcagctatgc ctcggctgga gccgccgctg ccgctggcgc ggcggcaggc gcggcagcag 5280
gcgcagcggc aggcgcggca gccgcagccg ctgcagcggc agcggcgcat gcgggagggc 5340
aacaggcatc cggctgggcg ggcggagccg cgctcccacc gctgccgcac gcgcacccgc 5400
acgcgcacct ccacccaaat ctccccccgg gtctgcccgg catgcacccg tcgtcgtacg 5460
gtgcaggaac acgcccgtac ggctatgccc tgccgccgcc gcacccgcac ccgcaagcgc 5520
acccgtaccc gcacgtgcac gcgcacatgt acccgcgtgc accgtgggcc ggcagctggg 5580
cgcagcgccc gccaccgtac ggtacggcac ccccatacgg ctacgcgccg ccgccgccgc 5640
cgtcgtacgg ggcgtggccg ccgccgacag ctgtactgcc gccgtatgtg gctgctgctc 5700
ggcctcccgg ccccgccggg gtgctgccgc cgccaccgca tctccgaggt cccgctgtag 5760
cggctgcggc tgcggctgcg gctgcggcgg ctgctggcgg cgcggctcat cacgaggagc 5820
tgccgacccg ggccagcggt gagcggctgt ctgcaggagg ctcgcctcat cactaccagc 5880
cgcaccagta ccaccagcag caccagcagc agcagaggct gcggcgcacg ggtagttcgg 5940
agagggcacc ttcgtcaggc ccacaccgcc agcagcacga gcaacaagga caggagctcc 6000
cgcagcaagg ccagcaggac caacagcaac aacagcagcg caggcgcacc gcggcggctg 6060
tggctgcggc gttggcggcg gcgctggtgg ctgctgttga tccgggcgcg gcgggggagc 6120
cgcccaccca ccgcagcggg ggcggcccta ccggagcagc agcagcagcc gagggagggc 6180
ctggcattgc ggggggcccc tcgacaagcg ctggggccag ggccccgatc ccctcgtcaa 6240
ccccagcaca tcagaaccac ccgcaccacc agcacgcctc gcgcgcgtcg catggcatcg 6300
gggtgtcgca tcccggccag gctgtgacgt ccccaaagccc agccgccgcc acgccgccac 6360
gtcgcagtca cgggatctcg actgaggcgc tgatgcctgc agcggcggcg aacctcctgc 6420
gcagtggcgg cggcggcggc gggcagctgg cgggcgtggg ggacggcggc gcgcttccga 6480
ctgcctttgg tgcgcagctg cagtggccgc cgccgggcct ggagccggga tcgcgtggtg 6540
ctgctgcagg ggcggcggcg gggcaacaca cggctacgcc gtttgcatgg gcggcagctg 6600

-continued

```
cgacggcgcc gggtgtgcag gtgcggccgc tggtgccgcg tgctggcagc aagcggcgtg   6660
cggagggcgc ggaggatggg gaggaggggc agcaataggc aggcacaggg gagcaaagca   6720
gtgcgtgtgg ggtgaagttg caagggcgct ggtcacggag cgcatacaat gtggtaccag   6780
tagctagctt tgacgtgaag gtttggtgtt aaggtacaat tgttgcgtcg gaacgaattg   6840
gtgcaggacg ttcgagttgc agtggtatca aagcaagtgt gtgcggctga ggtgttggca   6900
ggccctagtt gcaggcgtga cacggcgtgt gtgggcgggg ggtttggggc tctcaatcga   6960
tggttgtgga tggatgggtg tacgtgatat ggacgttgag cttattttcc attgaccgct   7020
cgctgctgtg ccaatcaata catgagctga tttccgtaat tgtgtgtcgc gagcagcagc   7080
aggcaggcga agacatgccg ggtccgcata cggcccacca ttgctggctt aacatttttt   7140
gaggggtagc tatagacgcg tcgcattcgt tgttatacgg caggactgct tatgtctcgt   7200
gtgtttgcta ggcgttgatg taggtctcga taccacacac gttctaccca cacaccatgc   7260
tcgaggtggc atttccacgt gctcgttctc gtacagactt ttcgcctcac agcttttttt   7320
atcagcgtgc gcaccagcgt catactcctg cttccaatcg ctgtatctgt tctgctcgcg   7380
agccattctg cccgcgaccg tagtagctgg ggctgtcgtg tgttttacaa ctcccagctg   7440
tgtgggaaga ataaccttgg catcaagcgc aggcacgacg ttttcgcgct aggcgcggtc   7500
aaaagggaaa ggttgcttct gcgacatgca acctgtccag tgcggtcctg tcggccctca   7560
atgccaagtc gtggatgcat ctgtgttatg ttgcgtttgt gttgttgcaa atgtttgtca   7620
tttacgtggg ggggggcgac aggttacgcc aacctcctcc ggtacacggc gcaggagctg   7680
caactccttc gggggcccac gcatgacggg ccaggcgtca ttcttgaaga ctgcatgggg   7740
cggtattgca tggcgcttca tacctttacg cgtgtctaca taattaggga agaaagctcg   7800
cggtctaatg agcgtattgg ctgtgaatta agctgcggcg tctcggctgc ttgcgctgga   7860
tggctggcag cttggctggc aggagttttc aggtgtggct aagatgtggg tacagagcac   7920
aaggggctgg tgaggttacg catacgtgat acgtacacca gtcatgagtc atacatcgtt   7980
atgcagtaaa tggtcgcggt tattgcgtgc acggtacaca agaccacgag gtcacgattg   8040
cgttgtaagg tacatgacta catgaggcag tggtagattg gttagaggct gtgacgtcag   8100
actgtaatga ttggcccgt                                                 8119
```

<210> SEQ ID NO 37
<211> LENGTH: 6417
<212> TYPE: DNA
<213> ORGANISM: Chlamydomonas reinhardtii

<400> SEQUENCE: 37

```
atggaagacg aggttgaagg agcggtgggg gcgcctgcgg gcgggggagg cgggcgcggg     60
ccagacccgc acctgctgcc tccgcccgca ccccttcaac ttcccatctc aatcgagctg    120
ctgccgccgc cgccgcccct ccagctaccc cccaacatgg atccagtgca tagccctgat    180
gcagcagcgc cgggggtggg gtcggcagcg gaggccctgt caccgtggct gttgctgacg    240
cagcaccaat cgcaacaccc gccacggcgg cccggctcga gcggtggggg tgcgctgcgc    300
cccccagaca tggggctgcc cggcgcgggg agcagcggcg gcgtgctcgg cggtggcggc    360
ggcagcaaca gcaccggaac agctctgccc gactcgctgc tgctgtcgcc cgagacgtcg    420
tccctgcggt cacgcctgtt gggccacctg tcttccgact caccgcagtt agggctgtcg    480
gctcaggcca gcctgcaaca ggcgctgcta cagctcggca gcgtgggcgg agcgtcggcc    540
tggagcgagg cacacggcag cggcgctggc gttggcagta gccacagcaa cagccagctg    600
```

-continued

```
gtgccgatgg gggcggcggg ggagttgctg agcatcagcc gaagcagctt gggcgggccg    660
ggaagcgtca gtcagaacgt gttctcacaa ggcctccgga gccctgatca cccgagttcg    720
gccgcactga ctgcgccctg gctcgccgac ttgcagtcgc cacggccagc gcaacatcag    780
caacaacgcc agcaggaaca ggagcaggct ggcggcagca gcgcaggcgc cagcagtttg    840
gatgcgccgc agcaagcgtt aacgggcagt ctaggcatcg gccccactgc aagtccaggg    900
accggaggcg gcggaccgca gggtgggggc ggcgcggcgg ccggcagcgt gcccgggggc    960
agggcgcacg gcagtggccc cacgtaccct tcgctggcgg aggcgctggc actggctcaa   1020
gccacgctaa gggctgagcg cggcagccac ggaggaggca acggcagttc aggtggcggg   1080
agcgcaggcg gcaggggcca gcagcagcct tcacgcaggc ggagcggcaa ctccgatgcc   1140
gcggcggcgc tgaccgccct gcccgcgccg cacaactcac gcggcggcga cggtggcagt   1200
ggcggcggcg gcggcggcgg ggacacgcac tcgcacccgc aggcacacaa ctcggctttc   1260
cgcccctaca cagtcgtggt gactagcggg cagctgcgcg cgtcggatgc cgtgcttcgg   1320
gctgcggacg ttgcgggtgc cgctgcaggc ggcggcggtg gcggcggcgg cacgctcagc   1380
ggaggcgctg gttcacacgt cgcccacacg cactctccag cacggacgcc ggagcggctg   1440
ccgaggtcgg gcgacagcgg tcggggcgcg caggcagcgg atcgcatggc tggcctgacg   1500
gcggcggccg cggcggtgct tggcagcgcc tccagcggcc cgggccccgt gacgactgga   1560
ctcacgcaca gcgggcggtc aacgccgccg gggcacgcca cgccgcccgg ccaagtgacc   1620
ccgccagggc agaccacgcc ggagcgcctg cggggcgccg ctggtgctgc gggcgccgcg   1680
gggggcggcg gtggggaggc ttggtcagcg gctggtgcgg cggcgctcac tctacagcac   1740
ttggcagcta gtgactcggg tgcgctgcat ccgcggcccc ggcaggcttt ggagccggga   1800
cagcagcagc agcagcagca gcagcagcag gtggcgcccc agttgtcgac accgtttgcc   1860
gggagggcgc aggctgaatt actgcagacg ctcgggcagc agcagcagca cgcagcgaag   1920
catcgtgcac cggagcgcgg gcagtcaacg ccagagcggg ggccagcgtc tcaggatgcg   1980
gacactgctg gcaagttcgc tgctgcagag gccgcaggac cgtccagcac acccacgtac   2040
gcagccgcag cacgagtgac acacgcgatg cctgcacccc agccgacacc agcgtacgcc   2100
cctggacctt ctcgaccggc gatggctcat cccggcgcag cttcggccca gctccggcac   2160
acgcctcaat ggcccactgg cgacgccgcc atgcgtgctt tccatgatgt gccgcgtggt   2220
gcgggggcgg atggcgccgt caaggctgac gccgtggccg gctccacggc agctggaggc   2280
gcaggcagca gcgggcttgt aggcgcagca gtcccgctga caacgcacga gcatgggccc   2340
ggtccccgcc cgcccctctt acgagcacag gcgtccaaat cgctgttctc gcagcagcag   2400
cagcagcagc agcagcagca gcaggcacaa ggggctgcac cggcgaccgg cactttgccc   2460
gatctggaca cggggccaat gcacgagtca gcgggtgaag acgcagagga ggggccggat   2520
gcatatcccg acgtgcatgc gccgcccggt caggcgcggc gccctccgca gctgcggccg   2580
ccgcccgcgg accctcagca gcagcagcag cagcagcagc tgccagagcc catcttcgtc   2640
acggtggcgg cgtcggcctc caagcggccg cgcaacgacc ggcccgggac ctccggcgcc   2700
gaaggcgccg ccgcaggcgg cggagccgca gccgctgcgg cggagccgca cacggccgcg   2760
ggtggcggcg gcggcggcac agactcctcg ccgttacgtc gtacggtggt gttgggcagc   2820
ttcacgttgc agctgcggtc ggacctggtt tgcgaggtgc tggggctgtt ccacccgcgg   2880
cgctacgtgg agggcaggga ctgtgtggag tacccgccgc actcgggcac cttcgtgtcg   2940
```

-continued

```
cgcagccact ttgaaaaggt gggcggcgcg gtgacggcca agtggtaccg ctccatccgg   3000
gtcctgccgc agatggagca cctcggggat tggctggagg cgcacgggct gcaggtcttc   3060
aagggcacgg gccgcaagcg cggcggccgc tatggcggcg gcggtagcgg tgatgtgcta   3120
gccatgctgg ctttaggagc cgccgcagcg ggcggcgccg gcagcactgg caccggcacg   3180
gaagctacag ccgagtccga gggccccgac atgggggcgg cagtagcagc cacaggcgca   3240
ggcatggggt tgggcgccct tgcagccatg ccgtactcca gccgaggagc agcggcagcg   3300
gccttggctc gggccaagcc tgttgacggg gacacagccg ccgccgtcgc cgccctggcc   3360
gcgctgtccg ccgccgccgc ggaaggggcg gcggccccgc cggcctcctc cgctgcggca   3420
gaggcagcgg cggcatccag gtgggccgtt gcgccgctgg cggacaggca gtggcacgct   3480
cagcacgcga ccccgctgtc gatgctccac cccagcgccc atgcggctgc ctttgcacat   3540
gcagctggcc cggcagcagc agcaggggct gcttctctgc ctgcagcgcg aggtgtggct   3600
gcagcctccg gtcccgccgg ctcgcggccg cccacgcccg cgtcccctca cgcccggcag   3660
gacccgcccg tgctgttgca tgccccggag ccgctgcctc tgccagaacc cgaggccggg   3720
ttggggcacg agtatgctga cgagcaaccc gagcagccgc ggcagccata cgcggcggtg   3780
ccgcacccct cctacgcagc tgtgcccttc ccatacccgc acccgcaccc acaccccctcc   3840
tacccgtacg gtgcctaccc gtacccgtac ccccacgcgg gcgcccgtag gcacagtgtg   3900
tggcctcccg cgctgccccc gccgccgcaa ggccacgcac tgggatggcc gccgcacctg   3960
ccgccgccct acgccgcacg agccccaggc ctgtacgcgc cctatcccct gcatgggcac   4020
ccgcagcatc cgcacccgta ccctcagcgt ctggcgcgcc cgggggtgca cctgcggcca   4080
cgcctatcaa tgctggccgc tgggtacccc ggtgcaagca gcgacggctc ggaggggccc   4140
gaaggcggca gcggcgacga agcagcgacg gcggcgctgg cagcagcggc tgcgcacggc   4200
agcgacgatg cggctgcagc ggcagaggcg acgtcatcgc acgcgcagca ctgggccaca   4260
gcggcacgcg gcgcgctgca aggcaccagg agccgcagct tcggcgcctc ctcgaccgcc   4320
gccgccgccg ctgcggccgt ggcggcggag cactggcggt cggctggggg tggtactcag   4380
cactggggca gtagcagcgg cggtgcaggt ggcggctaca gccacggaca ggccgggctg   4440
ctgctgcccg ccgcgtcctg gccgggtccg tcgcctctgg gaggaggtca gcgggggcag   4500
cacggcgcac cgcctcgcgt gagtgccccc gcggccacgg gttccgggag cgagcgtggg   4560
tacgagctgg aggcgcggca ggccgccgtg gcggccacgg cggctgcggc ggctgcggac   4620
tggctcgata ccgagcacat gccagagctg cagcagcagc agcagcagca gcagcagcag   4680
cagcagcagc ccctgctggc gcttcccgca ccgcccatga cggcggccgc agggccctcg   4740
ccgccccacg ggctgctacg gggcgcgctg gaggcggctg cggcggccgc cgccagctct   4800
gccgcgcacg gcggcggccg gcagggagcc aagggcagtg cgacgagggg tacggcagag   4860
ggtgccggcg gcgctcctgc tgcctcacca gcgcagcccc gcgtaagcga aagctgtgcc   4920
accagtggcg gcagcgatgt cagctatgcc tcggctggag ccgccgctgc cgctggcgcg   4980
gcggcaggcg cggcagcagg cgcagcggca ggcgcggcag ccgcagccgc tgcagcggca   5040
gcggcgcatg cgggagggca acaggcatcc ggctgggcgg gcggagccgc gctcccaccg   5100
ctgccgcacg cgcacccgca cgcgcacctc cacccaaatc tccccccggg tctgcccggc   5160
atgcacccgt cgtcgtacgg tgcaggaaca cgcccgtacg gctatgccct gccgccgccg   5220
cacccgcacc cgcaagcgca cccgtacccg cacgtgcacg cgcacatgta cccgcgtgca   5280
ccgtgggccg gcagctgggc gcagcgcccg ccaccgtacg gtacggcacc cccatacggc   5340
```

```
tacgcgccgc cgccgccgcc gtcgtacggg gcgtggccgc cgccgacagc tgtactgccg   5400

ccgtatgtgg ctgctgctcg gcctcccggc cccgccgggg tgctgccgcc gccaccgcat   5460

ctccgaggtc ccgctgtagc ggctgcggct gcggctgcgg ctgcggcggc tgctggcggc   5520

gcggctcatc acgaggagct gccgacccgg gccagcggtg agcggctgtc tgcaggaggc   5580

tcgcctcatc actaccagcc gcaccagtac caccagcagc accagcagca gcagaggctg   5640

cggcgcacgg gtagttcgga gagggcacct tcgtcaggcc cacaccgcca gcagcacgag   5700

caacaaggac aggagctccc gcagcaaggc cagcaggacc aacagcaaca acagcagcgc   5760

aggcgcaccg cggcggctgt ggctgcggcg ttggcggcgg cgctggtggc tgctgttgat   5820

ccgggcgcgg cgggggagcc gcccacccac cgcagcgggg gcggccctac cggagcagca   5880

gcagcagccg agggagggcc tggcattgcg ggggggccct cgacaagcgc tggggccagg   5940

gccccgatcc cctcgtcaac cccagcacat cagaaccacc cgcaccacca gcacgcctcg   6000

cgcgcgtcgc atggcatcgg ggtgtcgcat cccggccagg ctgtgacgtc ccaaagccca   6060

gccgccgcca cgccgccacg tcgcagtcac gggatctcga ctgaggcgct gatgcctgca   6120

gcggcggcga acctcctgcg cagtggcggc ggcggcggcg ggcagctggc gggcgtgggg   6180

gacggcggcg cgcttccgac tgcctttggt gcgcagctgc agtggccgcc gccgggcctg   6240

gagccgggat cgcgtggtgc tgctgcaggg gcggcggcgg ggcaacacac ggctacgccg   6300

tttgcatggg cggcagctgc gacggcgccg ggtgtgcagg tgcggccgct ggtgccgcgt   6360

gctggcagca agcggcgtgc ggagggcgcg gaggatgggg aggaggggca gcaatag      6417
```

<210> SEQ ID NO 38
<211> LENGTH: 2138
<212> TYPE: PRT
<213> ORGANISM: Chlamydomonas reinhardtii

<400> SEQUENCE: 38

```
Met Glu Asp Glu Val Glu Gly Ala Val Gly Ala Pro Ala Gly Gly Gly
1               5                   10                  15

Gly Gly Arg Gly Pro Asp Pro His Leu Leu Pro Pro Pro Ala Pro Leu
            20                  25                  30

Gln Leu Pro Ile Ser Ile Glu Leu Leu Pro Pro Pro Pro Pro Leu Gln
        35                  40                  45

Leu Pro Pro Asn Met Asp Pro Val His Ser Pro Asp Ala Ala Ala Pro
    50                  55                  60

Gly Val Gly Ser Ala Ala Glu Ala Leu Ser Pro Trp Leu Leu Leu Thr
65                  70                  75                  80

Gln His Gln Ser Gln His Pro Pro Arg Arg Pro Gly Ser Ser Gly Gly
                85                  90                  95

Gly Ala Leu Arg Pro Pro Asp Met Gly Leu Pro Gly Ala Gly Ser Ser
            100                 105                 110

Gly Gly Val Leu Gly Gly Gly Gly Gly Ser Asn Ser Thr Gly Thr Ala
        115                 120                 125

Leu Pro Asp Ser Leu Leu Leu Ser Pro Glu Thr Ser Ser Leu Arg Ser
    130                 135                 140

Arg Leu Leu Gly His Leu Ser Ser Asp Ser Pro Gln Leu Gly Leu Ser
145                 150                 155                 160

Ala Gln Ala Ser Leu Gln Gln Ala Leu Leu Gln Leu Gly Ser Val Gly
                165                 170                 175

Gly Ala Ser Ala Trp Ser Glu Ala His Gly Ser Gly Ala Gly Val Gly
```

-continued

```
            180                 185                 190

Ser Ser His Ser Asn Ser Gln Leu Val Pro Met Gly Ala Ala Gly Glu
        195                 200                 205

Leu Leu Ser Ile Ser Arg Ser Ser Leu Gly Gly Pro Gly Ser Val Ser
    210                 215                 220

Gln Asn Val Phe Ser Gln Gly Leu Arg Ser Pro Asp His Pro Ser Ser
225                 230                 235                 240

Ala Ala Leu Thr Ala Pro Trp Leu Ala Asp Leu Gln Ser Pro Arg Pro
                245                 250                 255

Ala Gln His Gln Gln Gln Arg Gln Gln Glu Gln Glu Gln Ala Gly Gly
            260                 265                 270

Ser Ser Ala Gly Ala Ser Ser Leu Asp Ala Pro Gln Gln Ala Leu Thr
        275                 280                 285

Gly Ser Leu Gly Ile Gly Pro Thr Ala Ser Pro Gly Thr Gly Gly Gly
    290                 295                 300

Gly Pro Gln Gly Gly Gly Gly Ala Ala Ala Gly Ser Val Pro Gly Gly
305                 310                 315                 320

Arg Ala His Gly Ser Gly Pro Thr Tyr Pro Ser Leu Ala Glu Ala Leu
                325                 330                 335

Ala Leu Ala Gln Ala Thr Leu Arg Ala Glu Arg Gly Ser His Gly Gly
            340                 345                 350

Gly Asn Gly Ser Ser Gly Gly Gly Ser Ala Gly Gly Arg Gly Gln Gln
        355                 360                 365

Gln Pro Ser Arg Arg Arg Ser Gly Asn Ser Asp Ala Ala Ala Ala Leu
    370                 375                 380

Thr Ala Leu Pro Ala Pro His Asn Ser Arg Gly Gly Asp Gly Gly Ser
385                 390                 395                 400

Gly Gly Gly Gly Gly Gly Gly Asp Thr His Ser His Pro Gln Ala His
                405                 410                 415

Asn Ser Ala Phe Arg Pro Tyr Thr Val Val Val Thr Ser Gly Gln Leu
            420                 425                 430

Arg Ala Ser Asp Ala Val Leu Arg Ala Ala Asp Val Ala Gly Ala Ala
        435                 440                 445

Ala Gly Gly Gly Gly Gly Gly Gly Gly Thr Leu Ser Gly Gly Ala Gly
    450                 455                 460

Ser His Val Ala His Thr His Ser Pro Ala Arg Thr Pro Glu Arg Leu
465                 470                 475                 480

Pro Arg Ser Gly Asp Ser Gly Arg Gly Ala Gln Ala Ala Asp Arg Met
                485                 490                 495

Ala Gly Leu Thr Ala Ala Ala Ala Ala Val Leu Gly Ser Ala Ser Ser
            500                 505                 510

Gly Pro Gly Pro Val Thr Thr Gly Leu Thr His Ser Gly Arg Ser Thr
        515                 520                 525

Pro Pro Gly His Ala Thr Pro Pro Gly Gln Val Thr Pro Pro Gly Gln
    530                 535                 540

Thr Thr Pro Glu Arg Leu Arg Gly Ala Ala Gly Ala Ala Gly Ala Ala
545                 550                 555                 560

Gly Gly Gly Gly Gly Glu Ala Trp Ser Ala Ala Gly Ala Ala Ala Leu
                565                 570                 575

Thr Leu Gln His Leu Ala Ala Ser Asp Ser Gly Ala Leu His Pro Arg
            580                 585                 590

Pro Arg Gln Ala Leu Glu Pro Gly Gln Gln Gln Gln Gln Gln Gln Gln
        595                 600                 605
```

Gln Gln Val Ala Pro Gln Leu Ser Thr Pro Phe Ala Gly Arg Ala Gln
610 615 620

Ala Glu Leu Leu Gln Thr Leu Gly Gln Gln Gln Gln His Ala Ala Lys
625 630 635 640

His Arg Ala Pro Glu Arg Gly Gln Ser Thr Pro Glu Arg Gly Pro Ala
645 650 655

Ser Gln Asp Ala Asp Thr Ala Gly Lys Phe Ala Ala Ala Glu Ala Ala
660 665 670

Gly Pro Ser Ser Thr Pro Thr Tyr Ala Ala Ala Ala Arg Val Thr His
675 680 685

Ala Met Pro Ala Pro Gln Pro Thr Pro Ala Tyr Ala Pro Gly Pro Ser
690 695 700

Arg Pro Ala Met Ala His Pro Gly Ala Ala Ser Ala Gln Leu Arg His
705 710 715 720

Thr Pro Gln Trp Pro Thr Gly Asp Ala Ala Met Arg Ala Phe His Asp
725 730 735

Val Pro Arg Gly Ala Gly Ala Asp Gly Ala Val Lys Ala Asp Ala Val
740 745 750

Ala Gly Ser Thr Ala Ala Gly Gly Ala Gly Ser Ser Gly Leu Val Gly
755 760 765

Ala Ala Val Pro Leu Thr Thr His Glu His Gly Pro Gly Pro Arg Pro
770 775 780

Pro Leu Leu Arg Ala Gln Ala Ser Lys Ser Leu Phe Ser Gln Gln Gln
785 790 795 800

Gln Gln Gln Gln Gln Gln Gln Gln Ala Gln Gly Ala Ala Pro Ala Thr
805 810 815

Gly Thr Leu Pro Asp Leu Asp Thr Gly Pro Met His Glu Ser Ala Gly
820 825 830

Glu Asp Ala Glu Glu Gly Pro Asp Ala Tyr Pro Asp Val His Ala Pro
835 840 845

Pro Gly Gln Ala Arg Arg Pro Pro Gln Leu Arg Pro Pro Pro Ala Asp
850 855 860

Pro Gln Gln Gln Gln Gln Gln Gln Gln Leu Pro Glu Pro Ile Phe Val
865 870 875 880

Thr Val Ala Ala Ser Ala Ser Lys Arg Pro Arg Asn Asp Arg Pro Gly
885 890 895

Thr Ser Gly Ala Glu Gly Ala Ala Ala Gly Gly Gly Ala Ala Ala Ala
900 905 910

Ala Ala Glu Pro His Thr Ala Ala Gly Gly Gly Gly Gly Gly Thr Asp
915 920 925

Ser Ser Pro Leu Arg Arg Thr Val Val Leu Gly Ser Phe Thr Leu Gln
930 935 940

Leu Arg Ser Asp Leu Val Cys Glu Val Leu Gly Leu Phe His Pro Arg
945 950 955 960

Arg Tyr Val Glu Gly Arg Asp Cys Val Glu Tyr Pro Pro His Ser Gly
965 970 975

Thr Phe Val Ser Arg Ser His Phe Glu Lys Val Gly Gly Ala Val Thr
980 985 990

Ala Lys Trp Tyr Arg Ser Ile Arg Val Leu Pro Gln Met Glu His Leu
995 1000 1005

Gly Asp Trp Leu Glu Ala His Gly Leu Gln Val Phe Lys Gly Thr
1010 1015 1020

-continued

```
Gly Arg  Lys Arg Gly Gly Arg  Tyr Gly Gly Gly Gly  Ser Gly Asp
    1025                 1030                 1035

Val Leu  Ala Met Leu Ala Leu  Gly Ala Ala Ala Ala  Gly Gly Ala
    1040                 1045                 1050

Gly Ser  Thr Gly Thr Gly Thr  Glu Ala Thr Ala Glu  Ser Glu Gly
    1055                 1060                 1065

Pro Asp  Met Gly Ala Ala Val  Ala Ala Thr Gly Ala  Gly Met Gly
    1070                 1075                 1080

Leu Gly  Ala Leu Ala Ala Met  Pro Tyr Ser Ser Arg  Gly Ala Ala
    1085                 1090                 1095

Ala Ala  Ala Leu Ala Arg Ala  Lys Pro Val Asp Gly  Asp Thr Ala
    1100                 1105                 1110

Ala Ala  Val Ala Ala Leu Ala  Ala Leu Ser Ala Ala  Ala Ala Glu
    1115                 1120                 1125

Gly Ala  Ala Ala Pro Pro Ala  Ser Ser Ala Ala Ala  Glu Ala Ala
    1130                 1135                 1140

Ala Ala  Ser Arg Trp Ala Val  Ala Pro Leu Ala Asp  Arg Gln Trp
    1145                 1150                 1155

His Ala  Gln His Ala Thr Pro  Leu Ser Met Leu His  Pro Ser Ala
    1160                 1165                 1170

His Ala  Ala Ala Phe Ala His  Ala Ala Gly Pro Ala  Ala Ala Ala
    1175                 1180                 1185

Gly Ala  Ala Ser Leu Pro Ala  Ala Arg Gly Val Ala  Ala Ala Ser
    1190                 1195                 1200

Gly Pro  Ala Gly Ser Arg Pro  Pro Thr Pro Ala Ser  Pro His Ala
    1205                 1210                 1215

Arg Gln  Asp Pro Pro Val Leu  Leu His Ala Pro Glu  Pro Leu Pro
    1220                 1225                 1230

Leu Pro  Glu Pro Glu Ala Gly  Leu Gly His Glu Tyr  Ala Asp Glu
    1235                 1240                 1245

Gln Pro  Glu Gln Pro Arg Gln  Pro Tyr Ala Ala Val  Pro His Pro
    1250                 1255                 1260

Ser Tyr  Ala Ala Val Pro Phe  Pro Tyr Pro His Pro  His Pro His
    1265                 1270                 1275

Pro Ser  Tyr Pro Tyr Gly Ala  Tyr Pro Tyr Pro Tyr  Pro His Ala
    1280                 1285                 1290

Gly Ala  Arg Arg His Ser Val  Trp Pro Pro Ala Leu  Pro Pro Pro
    1295                 1300                 1305

Pro Gln  Gly His Ala Leu Gly  Trp Pro Pro His Leu  Pro Pro Pro
    1310                 1315                 1320

Tyr Ala  Ala Arg Ala Pro Gly  Leu Tyr Ala Pro Tyr  Pro Leu His
    1325                 1330                 1335

Gly His  Pro Gln His Pro His  Pro Tyr Pro Gln Arg  Leu Ala Arg
    1340                 1345                 1350

Pro Gly  Val His Leu Arg Pro  Arg Leu Ser Met Leu  Ala Ala Gly
    1355                 1360                 1365

Tyr Pro  Gly Ala Ser Ser Asp  Gly Ser Glu Gly Pro  Glu Gly Gly
    1370                 1375                 1380

Ser Gly  Asp Glu Ala Ala Thr  Ala Ala Leu Ala Ala  Ala Ala Ala
    1385                 1390                 1395

His Gly  Ser Asp Asp Ala Ala  Ala Ala Ala Glu Ala  Thr Ser Ser
    1400                 1405                 1410

His Ala  Gln His Trp Ala Thr  Ala Ala Arg Gly Ala  Leu Gln Gly
```

-continued

```
    1415                1420                1425

Thr Arg  Ser Arg Ser Phe Gly  Ala Ser Ser Thr Ala  Ala Ala Ala
    1430                1435                1440

Ala Ala  Ala Val Ala Ala Glu  His Trp Arg Ser Ala  Gly Gly Gly
    1445                1450                1455

Thr Gln  His Trp Gly Ser Ser  Ser Gly Gly Ala Gly  Gly Gly Tyr
    1460                1465                1470

Ser His  Gly Gln Ala Gly Leu  Leu Leu Pro Ala Ala  Ser Trp Pro
    1475                1480                1485

Gly Pro  Ser Pro Leu Gly Gly  Gly Gln Arg Gly Gln  His Gly Ala
    1490                1495                1500

Pro Pro  Arg Val Ser Ala Pro  Ala Ala Thr Gly Ser  Gly Ser Glu
    1505                1510                1515

Arg Gly  Tyr Glu Leu Glu Ala  Arg Gln Ala Ala Val  Ala Ala Thr
    1520                1525                1530

Ala Ala  Ala Ala Ala Ala Asp  Trp Leu Asp Thr Glu  His Met Pro
    1535                1540                1545

Glu Leu  Gln Gln Gln Gln Gln  Gln Gln Gln Gln Gln  Gln Gln Gln
    1550                1555                1560

Pro Leu  Leu Ala Leu Pro Ala  Pro Pro Met Thr Ala  Ala Ala Gly
    1565                1570                1575

Pro Ser  Pro Pro His Gly Leu  Leu Arg Gly Ala Leu  Glu Ala Ala
    1580                1585                1590

Ala Ala  Ala Ala Ala Ser Ser  Ala Ala His Gly Gly  Gly Arg Gln
    1595                1600                1605

Gly Ala  Lys Gly Ser Ala Thr  Arg Gly Thr Ala Glu  Gly Ala Gly
    1610                1615                1620

Gly Ala  Pro Ala Ala Ser Pro  Ala Gln Pro Arg Val  Ser Glu Ser
    1625                1630                1635

Cys Ala  Thr Ser Gly Gly Ser  Asp Val Ser Tyr Ala  Ser Ala Gly
    1640                1645                1650

Ala Ala  Ala Ala Ala Gly Ala  Ala Ala Gly Ala Ala  Ala Gly Ala
    1655                1660                1665

Ala Ala  Gly Ala Ala Ala Ala  Ala Ala Ala Ala Ala  Ala Ala His
    1670                1675                1680

Ala Gly  Gly Gln Gln Ala Ser  Gly Trp Ala Gly Gly  Ala Ala Leu
    1685                1690                1695

Pro Pro  Leu Pro His Ala His  Pro His Ala His Leu  His Pro Asn
    1700                1705                1710

Leu Pro  Pro Gly Leu Pro Gly  Met His Pro Ser Ser  Tyr Gly Ala
    1715                1720                1725

Gly Thr  Arg Pro Tyr Gly Tyr  Ala Leu Pro Pro Pro  His Pro His
    1730                1735                1740

Pro Gln  Ala His Pro Tyr Pro  His Val His Ala His  Met Tyr Pro
    1745                1750                1755

Arg Ala  Pro Trp Ala Gly Ser  Trp Ala Gln Arg Pro  Pro Pro Tyr
    1760                1765                1770

Gly Thr  Ala Pro Pro Tyr Gly  Tyr Ala Pro Pro Pro  Pro Pro Ser
    1775                1780                1785

Tyr Gly  Ala Trp Pro Pro Pro  Thr Ala Val Leu Pro  Pro Tyr Val
    1790                1795                1800

Ala Ala  Ala Arg Pro Pro Gly  Pro Ala Gly Val Leu  Pro Pro Pro
    1805                1810                1815
```

-continued

```
Pro His  Leu Arg Gly Pro Ala  Val Ala Ala Ala Ala  Ala Ala Ala
    1820                 1825                 1830

Ala Ala  Ala Ala Ala Gly Gly  Ala Ala His His Glu  Glu Leu Pro
    1835                 1840                 1845

Thr Arg  Ala Ser Gly Glu Arg  Leu Ser Ala Gly Gly  Ser Pro His
    1850                 1855                 1860

His Tyr  Gln Pro His Gln Tyr  His Gln Gln His Gln  Gln Gln Gln
    1865                 1870                 1875

Arg Leu  Arg Arg Thr Gly Ser  Ser Glu Arg Ala Pro  Ser Ser Gly
    1880                 1885                 1890

Pro His  Arg Gln Gln His Glu  Gln Gln Gly Gln Glu  Leu Pro Gln
    1895                 1900                 1905

Gln Gly  Gln Gln Asp Gln Gln  Gln Gln Gln Gln Arg  Arg Arg Thr
    1910                 1915                 1920

Ala Ala  Ala Val Ala Ala Ala  Leu Ala Ala Ala Leu  Val Ala Ala
    1925                 1930                 1935

Val Asp  Pro Gly Ala Ala Gly  Glu Pro Pro Thr His  Arg Ser Gly
    1940                 1945                 1950

Gly Gly  Pro Thr Gly Ala Ala  Ala Ala Ala Glu Gly  Gly Pro Gly
    1955                 1960                 1965

Ile Ala  Gly Gly Pro Ser Thr  Ser Ala Gly Ala Arg  Ala Pro Ile
    1970                 1975                 1980

Pro Ser  Ser Thr Pro Ala His  Gln Asn His Pro His  His Gln His
    1985                 1990                 1995

Ala Ser  Arg Ala Ser His Gly  Ile Gly Val Ser His  Pro Gly Gln
    2000                 2005                 2010

Ala Val  Thr Ser Gln Ser Pro  Ala Ala Ala Thr Pro  Pro Arg Arg
    2015                 2020                 2025

Ser His  Gly Ile Ser Thr Glu  Ala Leu Met Pro Ala  Ala Ala Ala
    2030                 2035                 2040

Asn Leu  Leu Arg Ser Gly Gly  Gly Gly Gly Gly Gln  Leu Ala Gly
    2045                 2050                 2055

Val Gly  Asp Gly Gly Ala Leu  Pro Thr Ala Phe Gly  Ala Gln Leu
    2060                 2065                 2070

Gln Trp  Pro Pro Pro Gly Leu  Glu Pro Gly Ser Arg  Gly Ala Ala
    2075                 2080                 2085

Ala Gly  Ala Ala Ala Gly Gln  His Thr Ala Thr Pro  Phe Ala Trp
    2090                 2095                 2100

Ala Ala  Ala Ala Thr Ala Pro  Gly Val Gln Val Arg  Pro Leu Val
    2105                 2110                 2115

Pro Arg  Ala Gly Ser Lys Arg  Arg Ala Glu Gly Ala  Glu Asp Gly
    2120                 2125                 2130

Glu Glu  Gly Gln Gln
    2135
```

```
<210> SEQ ID NO 39
<211> LENGTH: 5955
<212> TYPE: DNA
<213> ORGANISM: Chlamydomonas reinhardtii

<400> SEQUENCE: 39

cacaggcagc actgtagctc gcgcaacctt gctaagcaaa acaaagcgcc gtcgtgcatg     60

caacataaaa accgtttagt tgtatcatgt cgtccttgga atgagcaaag tttcaaggat    120
```

-continued

```
tctgcatagg aagagggaca cagcgcgtgc ggagcgggcg cgcgatgtgc tcgcggccaa    180
gcgggctgcc tccaaacgcg aacggcgtca gcttaggcga gccaaagctt ccagaagaaa    240
gaagaaagga ggtgctgagg cagccgccgg gccggcggac ccgccgcgca acaccgatgc    300
tgagtcgccc agcgtgcggc cgtcgcccgc cctgccggtt cacgcaggcg agccaagtgg    360
ccgtccggca gcgcgcgagg gcagccgcaa tacggcgctg ggtcactgtg tcgacagcgc    420
tccggcacac ccttaccggc agccagcacc tatctgcggc aagcgcaaac agcggagcac    480
cccgctggca cgggccttac ggctggtaca ggcgggggca ccgggcttgc agactggcgt    540
ggaccttgtt gcgggcgtga gaggggcgaa ggaagcgcag caggcgcggc gcccagcgcc    600
cccagttgcc aaagtgcggc tgctgtcctt gcctctggag ccgaaggtgg acggtcaggt    660
tggggggtgc tcacctggcc aggacacgca gccagcaccc agcagtcaag agggcgggcc    720
agcggtgata gtcagaccgg acgtggcggt gctcggccag gaccggggcc tgggggttgc    780
ggaggcagca ggaacttccg ctgccgctgc cgccgctgca gtgagccagc gggatcgcgg    840
cgcaggccgg cagcctggcc aggagccggc tgaatcacgg gacaccagcc tcagcagtga    900
gttgcagcca caaccacaga tgcagacgca gcgccacgag caagggcagc aagggttgca    960
cgaaagcccg ccgtgtgaga gtgaggcagc ggtgtgtgcc agggaggcag ctgtggccgc   1020
agcgaggcta gcagccatta atgcggccgc tgccctgccc ccggacagcc cgtatgttcg   1080
ggcggtgatg gaaacgtgca gcgggcaagc gactgggggt caggcgggac agaatcagct   1140
gtcggcacac ggcctgctgc agccccagca tgagcagcag caacggcggc ggcggagggg   1200
cctgggggcg gtggacagcg agtacgtggc gtgcgccaag cacgccgctg cagccgcggc   1260
acacctagcg gccctggagg ctgcggctgc actgccagcc gacagtccgt acctgaaggc   1320
ggccgtcgag gtgggtcgtg gcgccgggtt cgggtggccg gatgagcggg acagcgacgt   1380
atgggcgcag cagcgcgcac tgctgcagca gcagacggcg cggctgcagc gggcgctggg   1440
ggctgcactg tgcgggcgag gaggggcagc caggtacacc cccgctgggc cagtaccaga   1500
agggcacggc gccggagctt gcagtagcgg cgccgcggcg tcactggagt tccgtgtggg   1560
atcttcgccc gggcacgctg aggcggcgag cggggcgcgc ggtgccgtgc tagcagcaga   1620
agcagcaaca gcagaagcag aagcagcagg tggcattctc gtgcctgccg tggtggcagg   1680
tggcggacct gcgggtagcg gccgcggcgg cggcacagat gaagtccgtg cgcatcacgg   1740
cagcgccgtt accacgatca ccccgggttg cagcgtgtgc agccgcatgc aagccagcag   1800
aaacggagtg caagcggctg acgccccagc cggtacgggt gttggcggcg cggctgaggc   1860
tcctgaggat gcagctgcag tgcctggagc agcgggccag ggtgcgcgtg tcagcgagtg   1920
ggtcggttcg ttactgctgc agagccctca agcggaatcc gcacctcctg ttttccagaa   1980
gtcgaagcca ggcgctgagg ccagcggccc tgcagcggag ggccgggacc ccagccccca   2040
agttcctgca gcaattgggt gtggagctag cagcaccact catgggagcg gcaccaccag   2100
cagtggcaat ggggcgacca ccggcagcag caacagcggc gatgacagcg gtgggagcac   2160
cagtagcggc gggagcttaa cgggcgctgc cgatagcagc catagcggtg gctccggcgg   2220
cgatagagtt cggagcttaa gcggcgccag acgcagcttg catggtatta cagacagcag   2280
cagaagcacc agcagtggcg gcagtgacca gagcacgagc aaggacgtta acgatgccgt   2340
gaccagcagc ggcggcggcg ggcttggcgc aggcggctgc ggtggtgggg cggggattgt   2400
cgcaggcgat gagccctcca cagcagtccc cgaaagcctt cacaggccgg cgtcagagcg   2460
cagccctgga cggtgcgagc tcactgcagc cgcaggcggc ggcgccgagg cgggcagcgc   2520
```

```
agaggcgggc ggaagggcag tagtccctgc gcgcgagtcg cagtcgtggg ctcaacaact   2580
actgccggag cacttgccgc agtgggaaga cgaggtgccg agcgacggca gcagttgcag   2640
cgacactgac agctccgagt ttgaagaggg agactgggag gacgacgatt ggcctggggg   2700
cgcagccgag gctaaagatg gcagccggga caagtcacag cactcagcgg acaagcccgg   2760
cgcctccgac gtcacggacc acatgatggc agccgtgctg tcgcaggctg cgcccgagca   2820
cagcgctggt gtcaaacgtg ctggcggcga ggcagcgatc ctctacgccg atggcagtga   2880
cagccacggt gggcctgacg ctttcgttga caacgattca gcggcgtggg aggcagcact   2940
ggaggctggc gctggcccac atgaaagcca ggcggaggcc ccgcagcagc tggcggcggc   3000
cgtgacagtt tcgactctgg cgcttcttgg gcatggcaca ggtccggtgc agcaatcgcg   3060
gagacggctg ccggcgtcag gaagcgggcc agcagggcat gacacagcag gattaggtgc   3120
tggcgcggtg gccctcgcag aaccccagtt gcagctgccg gagcagtttg atgttaatct   3180
gctggcgccg ccagtgctag tgccggccgg cacgaagctg caagccctgc cgccatggtc   3240
tgtagggtcg cccgtcacca gccccgggtt gacgcaggca gggcctggcc ccagtgcggc   3300
tgcaggcccc agggtggcgc aggtcgtgtc gggcagcccc tacacggacg cctatgagct   3360
gccggacgat ggcggccacc cgcacctggg cggaggcgcc gccccgcagc ccagcagtcg   3420
cgaggacggc gggggtgtgg ctgccggggt cggtgcacac gcgggctgca acgcacagcg   3480
gggcatgaca gcagcagtaa ttggtcctgg tggtactcgg gttggtgctg cctcgcctcc   3540
gcttgtgctt tcagcctcag gctccggggg agggctggcg actccaggtc ggcggcgcgg   3600
ccgtctggtg atgctgcacg gtgccggggc ggcggcatgt ggtacgccca catcgcagcc   3660
ccgtgccggc agggcggcga gcaatacagc aaccgctggg ggtgcgggcc ccagcgcagt   3720
tgcagcggct gggccgggaa tgggcgacct cggccaccag gggcagccac tgccggccga   3780
gccccctgga gcagctacgc gaccggttgg cagggcaggg cgcgcgccac cgcttagccc   3840
tctgcgccgc agcagtcgcg tgcctggcgg acagcagcag cagcagcagc agcagcagca   3900
gcagcagcat gcagctggca tggcggccca gggccagggg cccgcggagc cttcggcaaa   3960
tggtggagca ggcaggagta gagcgtcggc aggcggtggc atgtcgccca gccgtagggc   4020
ggctgtgcgg cttcagcgac agccggtggt cccatcaccg aggctcgtgg aggattcaag   4080
gctgcatcgc tccggccagc agcaggcggt ggttggagta ggcacagcgg ggggaagccg   4140
cgtgggtgat cgcgcacggg gtggttcggg tgcagggttg tcggcagctg caacaggagt   4200
gatcaaggcc gccactgcct caccctcgcg cggccgcacc cgcagcaagc cacctgaacg   4260
ggcgtcgata gccgggcgag ggcgcggcgg gcgtgggcgg cgggcgactg cgcgctctca   4320
ccggcagtcg gaaagcgacc aggaggagac agcagatgcg gtgcgcccgt ctgacccgga   4380
ggaggataag gagaaggagg gcggtgggca gcagactcgc ggcgcccctg ccaggcgccg   4440
agccccgcgc acacccagtg aagtgctcaa ccggctgcag gtgtcggacc tgcggccggt   4500
gctgcacctg cccctcgttg aggcggcacg gcagctgggg ctacaccgca ctagcttcat   4560
gacgcgctgc cgccaactgg ggatcgcgag atggccggcc aagcagctgc gcatgctgga   4620
cttgatggag gagcagctgc aggagctgga ggcgtgcggc gtcgcaaacc actacacggc   4680
caagaagtgc cttgaagaag ctccgggctg gctggcccag gtggccgctg cgcgctcggc   4740
gctgctggag aacccgtgcg gcttcaccat gccgcagccg ctggagctgc tgcgccagcg   4800
ccacgtgaag gtggcgtggg cgcaccgcca aaagtacaag gcggcactgg gcgaggaggg   4860
```

ggaggagggc gaggagggcg atgacctgga ctcgcaggcg cagatgtcac agtagtgtgc 4920
ggcgggctgc ggctgaggga gtgcggagac ctgagggcgt cagctgttgc tgcacatgcg 4980
gtgttggcga gccgtatccg cggcgtagca gcgcgtggag cagtgaagga ctgggcgggg 5040
agtgcagtgt ggcgcaaggg agcacgcagt atgtagaatt ttgcgatggc aggaaggcga 5100
tggcaggggc aacacatgcc agagcttcga cgtaaacacg gttgtcagtg cgccgtgcaa 5160
gtgggcaata caggatgatg cgaacgagct cagaactagc cgggactatc acatggttgc 5220
acctgtcctt gccgtcctcg cctgctaggt cgcatgtgat ttcactgatt tgtgttactg 5280
cattcccctt tgatccacca gctgcgggtt gagttcaggt gtcttgcgta tgtcggctgg 5340
cgagggcgtg ggcgggtcgt tgacggtgaa ctccaccaac accaggtcgg ggcgggcggc 5400
aggtgctggg ccagggctcc gaaatcagaa gatgtaaagg ccgcggtgca tgtagctagt 5460
gaacgatacc ggactcacct cgcgatgggt aatgggtaac gtcgcttgac gccttgaccg 5520
catacggtac cgtgcccgca cacgtgtggg aggggaactc ctaaccagcc tcaaatctta 5580
aggcatcttg cctgcactgg ccctgcataa cttgcagagt accagcggca tggaaaatct 5640
gcggggacaa aaaatgaaag ccagatggat gcagggtttg gtttgggccg ttggggtgtg 5700
tgcggccggg catgcgcagg caacgcaact tagcatagcc ttctgtgatg cggacttgcc 5760
aagggctgcg gacttgacat cagcgtggcc gagctcattt ctggccgttg atgctgaagg 5820
gctgggcttg cacacgtcgt gctggcagta ctcgcccctt atgacagact gtgcaaacca 5880
ggggtagggc ttcccctggt gttttacgcg gcagttcaag ggctttcctg tttctagctc 5940
tcttacttac ttagg 5955

<210> SEQ ID NO 40
<211> LENGTH: 4815
<212> TYPE: DNA
<213> ORGANISM: Chlamydomonas reinhardtii

<400> SEQUENCE: 40
atgagcaaag tttcaaggat tctgcatagg aagagggaca cagcgcgtgc ggagcgggcg 60
cgcgatgtgc tcgcggccaa gcgggctgcc tccaaacgcg aacggcgtca gcttaggcga 120
gccaaagctt ccagaagaaa gaagaaagga ggtgctgagg cagccgccgg gccggcggac 180
ccgccgcgca acaccgatgc tgagtcgccc agcgtgcggc cgtcgcccgc cctgccggtt 240
cacgcaggcg agccaagtgg ccgtccggca gcgcgcgagg gcagccgcaa tacggcgctg 300
ggtcactgtg tcgacagcgc tccggcacac ccttaccggc agccagcacc tatctgcggc 360
aagcgcaaac agcggagcac cccgctggca cgggccttac ggctggtaca ggcgggggca 420
ccgggcttgc agactggcgt ggaccttgtt gcgggcgtga gaggggcgaa ggaagcgcag 480
caggcgcggc gcccagcgcc cccagttgcc aaagtgcggc tgctgtcctt gcctctggag 540
ccgaaggtgg acggtcaggt tggggggtgc tcacctggcc aggacacgca gccagcaccc 600
agcagtcaag agggcgggcc agcggtgata gtcagaccgg acgtggcggt gctcggccag 660
gaccggggcc tgggggttgc ggaggcagca ggaacttccg ctgccgctgc cgccgctgca 720
gtgagccagc gggatcgcgg cgcaggccgg cagcctggcc aggagccggc tgaatcacgg 780
gacaccagcc tcagcagtga gttgcagcca caaccacaga tgcagacgca gcgccacgag 840
caagggcagc aagggttgca cgaaagcccg ccgtgtgaga gtgaggcagc ggtgtgtgcc 900
agggaggcag ctgtggccgc agcgaggcta gcagccatta atgcggccgc tgccctgccc 960
ccggacagcc cgtatgttcg ggcggtgatg gaaacgtgca gcgggcaagc gactgggggt 1020

-continued

```
caggcgggac agaatcagct gtcggcacac ggcctgctgc agccccagca tgagcagcag   1080
caacggcggc ggcggagggg cctgggggcg gtggacagcg agtacgtggc gtgcgccaag   1140
cacgccgctg cagccgcggc acacctagcg gccctggagg ctgcggctgc actgccagcc   1200
gacagtccgt acctgaaggc ggccgtcgag gtgggtcgtg gcgccgggtt cgggtggccg   1260
gatgagcggg acagcgacgt atgggcgcag cagcgcgcac tgctgcagca gcagacggcg   1320
cggctgcagc gggcgctggg ggctgcactg tgcgggcgag gaggggcagc caggtacacc   1380
cccgctgggc cagtaccaga agggcacggc gccggagctt gcagtagcgg cgccgcggcg   1440
tcactggagt tccgtgtggg atcttcgccc gggcacgctg aggcggcgag cggggcgcgc   1500
ggtgccgtgc tagcagcaga agcagcaaca gcagaagcag aagcagcagg tggcattctc   1560
gtgcctgccg tggtggcagg tggcggacct gcgggtagcg gccgcggcgg cggcacagat   1620
gaagtccgtg cgcatcacgg cagcgccgtt accacgatca ccccgggttg cagcgtgtgc   1680
agccgcatgc aagccagcag aaacggagtg caagcggctg acgccccagc cggtacgggt   1740
gttggcggcg cggctgaggc tcctgaggat gcagctgcag tgcctggagc agcgggccag   1800
ggtgcgcgtg tcagcgagtg ggtcggttcg ttactgctgc agagccctca agcggaatcc   1860
gcacctcctg ttttccagaa gtcgaagcca ggcgctgagg ccagcggccc tgcagcggag   1920
ggccgggacc ccagcccca agttcctgca gcaattgggt gtggagctag cagcaccact   1980
catgggagcg gcaccaccag cagtggcaat ggggcgacca ccggcagcag caacagcggc   2040
gatgacagcg gtgggagcac cagtagcggc gggagcttaa cgggcgctgc cgatagcagc   2100
catagcggtg gctccggcgg cgatagagtt cggagcttaa gcggcgccag acgcagcttg   2160
catggtatta cagacagcag cagaagcacc agcagtggcg gcagtgacca gagcacgagc   2220
aaggacgtta acgatgccgt gaccagcagc ggcggcggcg ggcttggcgc aggcggctgc   2280
ggtggtgggg cggggattgt cgcaggcgat gagccctcca cagcagtccc cgaaagcctt   2340
cacaggccgg cgtcagagcg cagccctgga cggtgcgagc tcactgcagc cgcaggcggc   2400
ggcgccgagg cgggcagcgc agaggcgggc ggaagggcag tagtccctgc gcgcgagtcg   2460
cagtcgtggg ctcaacaact actgccggag cacttgccgc agtgggaaga cgaggtgccg   2520
agcgacggca gcagttgcag cgacactgac agctccgagt ttgaagaggg agactgggag   2580
gacgacgatt ggcctggggg cgcagccgag gctaaagatg gcagccggga caagtcacag   2640
cactcagcgg acaagcccgg cgcctccgac gtcacggacc acatgatggc agccgtgctg   2700
tcgcaggctg cgcccgagca cagcgctggt gtcaaacgtg ctggcggcga ggcagcgatc   2760
ctctacgccg atggcagtga cagccacggt gggcctgacg ctttcgttga caacgattca   2820
gcggcgtggg aggcagcact ggaggctggc gctggcccac atgaaagcca ggcggaggcc   2880
ccgcagcagc tggcggcggc cgtgacagtt tcgactctgg cgcttcttgg gcatggcaca   2940
ggtccggtgc agcaatcgcg gagacggctg ccggcgtcag gaagcgggcc agcagggcat   3000
gacacagcag gattaggtgc tggcgcggtg gccctcgcag aaccccagtt gcagctgccg   3060
gagcagtttg atgttaatct gctggcgccg ccagtgctag tgccggccgg cacgaagctg   3120
caagccctgc cgccatggtc tgtagggtcg cccgtcacca gccccgggtt gacgcaggca   3180
gggcctggcc ccagtgcggc tgcaggcccc agggtggcgc aggtcgtgtc gggcagcccc   3240
tacacggacg cctatgagct gccggacgat ggcggccacc cgcacctggg cggaggcgcc   3300
gccccgcagc ccagcagtcg cgaggacggc gggggtgtgg ctgccggggt cggtgcacac   3360
```

-continued

```
gcgggctgca acgcacagcg gggcatgaca gcagcagtaa ttggtcctgg tggtactcgg   3420
gttggtgctg cctcgcctcc gcttgtgctt tcagcctcag gctccggggg agggctggcg   3480
actccaggtc ggcggcgcgg ccgtctggtg atgctgcacg gtgccggggc ggcggcatgt   3540
ggtacgccca catcgcagcc ccgtgccggc agggcggcga gcaatacagc aaccgctggg   3600
ggtgcgggcc ccagcgcagt tgcagcggct gggccgggaa tgggcgacct cggccaccag   3660
gggcagccac tgccggccga gccccctgga gcagctacgc gaccggttgg cagggcaggg   3720
cgcgcgccac cgcttagccc tctgcgccgc agcagtcgcg tgcctggcgg acagcagcag   3780
cagcagcagc agcagcagca gcagcagcat gcagctggca tggcggccca gggccagggg   3840
cccgcggagc cttcggcaaa tggtggagca ggcaggagta gagcgtcggc aggcggtggc   3900
atgtcgccca gccgtagggc ggctgtgcgg cttcagcgac agccggtggt cccatcaccg   3960
aggctcgtgg aggattcaag gctgcatcgc tccggccagc agcaggcggt ggttggagta   4020
ggcacagcgg ggggaagccg cgtgggtgat cgcgcacggg gtggttcggg tgcagggttg   4080
tcggcagctg caacaggagt gatcaaggcc gccactgcct caccctcgcg cggccgcacc   4140
cgcagcaagc cacctgaacg ggcgtcgata gccgggcgag ggcgcggcgg gcgtgggcgg   4200
cgggcgactg cgcgctctca ccggcagtcg gaaagcgacc aggaggagac agcagatgcg   4260
gtgcgcccgt ctgacccgga ggaggataag gagaaggagg gcggtgggca gcagactcgc   4320
ggcgcccctg ccaggcgccg agccccgcgc acacccagtg aagtgctcaa ccggctgcag   4380
gtgtcggacc tgcggccggt gctgcacctg cccctcgttg aggcggcacg gcagctgggg   4440
ctacaccgca ctagcttcat gacgcgctgc cgccaactgg ggatcgcgag atggccggcc   4500
aagcagctgc gcatgctgga cttgatggag gagcagctgc aggagctgga ggcgtgcggc   4560
gtcgcaaacc actacacggc caagaagtgc cttgaagaag ctccgggctg gctggcccag   4620
gtggccgctg cgcgctcggc gctgctggag aacccgtgcg gcttcaccat gccgcagccg   4680
ctggagctgc tgcgccagcg ccacgtgaag gtggcgtggg cgcaccgcca aaagtacaag   4740
gcggcactgg gcgaggaggg ggaggagggc gaggagggcg atgacctgga ctcgcaggcg   4800
cagatgtcac agtag                                                    4815
```

<210> SEQ ID NO 41
<211> LENGTH: 1604
<212> TYPE: PRT
<213> ORGANISM: Chlamydomonas reinhardtii

<400> SEQUENCE: 41

```
Met Ser Lys Val Ser Arg Ile Leu His Arg Lys Arg Asp Thr Ala Arg
1               5                   10                  15

Ala Glu Arg Ala Arg Asp Val Leu Ala Ala Lys Arg Ala Ala Ser Lys
            20                  25                  30

Arg Glu Arg Arg Gln Leu Arg Arg Ala Lys Ala Ser Arg Arg Lys Lys
        35                  40                  45

Lys Gly Gly Ala Glu Ala Ala Ala Gly Pro Ala Asp Pro Pro Arg Asn
    50                  55                  60

Thr Asp Ala Glu Ser Pro Ser Val Arg Pro Ser Pro Ala Leu Pro Val
65                  70                  75                  80

His Ala Gly Glu Pro Ser Gly Arg Pro Ala Ala Arg Glu Gly Ser Arg
                85                  90                  95

Asn Thr Ala Leu Gly His Cys Val Asp Ser Ala Pro Ala His Pro Tyr
            100                 105                 110
```

-continued

```
Arg Gln Pro Ala Pro Ile Cys Gly Lys Arg Lys Gln Arg Ser Thr Pro
        115                 120                 125

Leu Ala Arg Ala Leu Arg Leu Val Gln Ala Gly Ala Pro Gly Leu Gln
    130                 135                 140

Thr Gly Val Asp Leu Val Ala Gly Val Arg Gly Ala Lys Glu Ala Gln
145                 150                 155                 160

Gln Ala Arg Arg Pro Ala Pro Pro Val Ala Lys Val Arg Leu Leu Ser
                165                 170                 175

Leu Pro Leu Glu Pro Lys Val Asp Gly Gln Val Gly Gly Cys Ser Pro
            180                 185                 190

Gly Gln Asp Thr Gln Pro Ala Pro Ser Ser Gln Glu Gly Gly Pro Ala
        195                 200                 205

Val Ile Val Arg Pro Asp Val Ala Val Leu Gly Gln Asp Arg Gly Leu
    210                 215                 220

Gly Val Ala Glu Ala Ala Gly Thr Ser Ala Ala Ala Ala Ala Ala Ala
225                 230                 235                 240

Val Ser Gln Arg Asp Arg Gly Ala Gly Arg Gln Pro Gly Gln Glu Pro
                245                 250                 255

Ala Glu Ser Arg Asp Thr Ser Leu Ser Ser Glu Leu Gln Pro Gln Pro
            260                 265                 270

Gln Met Gln Thr Gln Arg His Glu Gln Gly Gln Gln Gly Leu His Glu
        275                 280                 285

Ser Pro Pro Cys Glu Ser Glu Ala Ala Val Cys Ala Arg Glu Ala Ala
    290                 295                 300

Val Ala Ala Ala Arg Leu Ala Ala Ile Asn Ala Ala Ala Ala Leu Pro
305                 310                 315                 320

Pro Asp Ser Pro Tyr Val Arg Ala Val Met Glu Thr Cys Ser Gly Gln
                325                 330                 335

Ala Thr Gly Gly Gln Ala Gly Gln Asn Gln Leu Ser Ala His Gly Leu
            340                 345                 350

Leu Gln Pro Gln His Glu Gln Gln Gln Arg Arg Arg Arg Arg Gly Leu
        355                 360                 365

Gly Ala Val Asp Ser Glu Tyr Val Ala Cys Ala Lys His Ala Ala Ala
    370                 375                 380

Ala Ala Ala His Leu Ala Ala Leu Glu Ala Ala Ala Ala Leu Pro Ala
385                 390                 395                 400

Asp Ser Pro Tyr Leu Lys Ala Ala Val Glu Val Gly Arg Gly Ala Gly
                405                 410                 415

Phe Gly Trp Pro Asp Glu Arg Asp Ser Asp Val Trp Ala Gln Gln Arg
            420                 425                 430

Ala Leu Leu Gln Gln Gln Thr Ala Arg Leu Gln Arg Ala Leu Gly Ala
        435                 440                 445

Ala Leu Cys Gly Arg Gly Gly Ala Ala Arg Tyr Thr Pro Ala Gly Pro
    450                 455                 460

Val Pro Glu Gly His Gly Ala Gly Ala Cys Ser Ser Gly Ala Ala Ala
465                 470                 475                 480

Ser Leu Glu Phe Arg Val Gly Ser Ser Pro Gly His Ala Glu Ala Ala
                485                 490                 495

Ser Gly Ala Arg Gly Ala Val Leu Ala Ala Glu Ala Ala Thr Ala Glu
            500                 505                 510

Ala Glu Ala Ala Gly Gly Ile Leu Val Pro Ala Val Val Ala Gly Gly
        515                 520                 525

Gly Pro Ala Gly Ser Gly Arg Gly Gly Gly Thr Asp Glu Val Arg Ala
```

```
    530                 535                 540

His His Gly Ser Ala Val Thr Thr Ile Thr Pro Gly Cys Ser Val Cys
545                 550                 555                 560

Ser Arg Met Gln Ala Ser Arg Asn Gly Val Gln Ala Ala Asp Ala Pro
                565                 570                 575

Ala Gly Thr Gly Val Gly Gly Ala Ala Glu Ala Pro Glu Asp Ala Ala
            580                 585                 590

Ala Val Pro Gly Ala Ala Gly Gln Gly Ala Arg Val Ser Glu Trp Val
        595                 600                 605

Gly Ser Leu Leu Leu Gln Ser Pro Gln Ala Glu Ser Ala Pro Pro Val
    610                 615                 620

Phe Gln Lys Ser Lys Pro Gly Ala Glu Ala Ser Gly Pro Ala Ala Glu
625                 630                 635                 640

Gly Arg Asp Pro Ser Pro Gln Val Pro Ala Ala Ile Gly Cys Gly Ala
                645                 650                 655

Ser Ser Thr Thr His Gly Ser Gly Thr Thr Ser Ser Gly Asn Gly Ala
            660                 665                 670

Thr Thr Gly Ser Ser Asn Ser Gly Asp Asp Ser Gly Gly Ser Thr Ser
        675                 680                 685

Ser Gly Gly Ser Leu Thr Gly Ala Ala Asp Ser Ser His Ser Gly Gly
    690                 695                 700

Ser Gly Gly Asp Arg Val Arg Ser Leu Ser Gly Ala Arg Arg Ser Leu
705                 710                 715                 720

His Gly Ile Thr Asp Ser Ser Arg Ser Thr Ser Ser Gly Gly Ser Asp
                725                 730                 735

Gln Ser Thr Ser Lys Asp Val Asn Asp Ala Val Thr Ser Ser Gly Gly
            740                 745                 750

Gly Gly Leu Gly Ala Gly Gly Cys Gly Gly Gly Ala Gly Ile Val Ala
        755                 760                 765

Gly Asp Glu Pro Ser Thr Ala Val Pro Glu Ser Leu His Arg Pro Ala
    770                 775                 780

Ser Glu Arg Ser Pro Gly Arg Cys Glu Leu Thr Ala Ala Ala Gly Gly
785                 790                 795                 800

Gly Ala Glu Ala Gly Ser Ala Glu Ala Gly Gly Arg Ala Val Val Pro
                805                 810                 815

Ala Arg Glu Ser Gln Ser Trp Ala Gln Gln Leu Leu Pro Glu His Leu
            820                 825                 830

Pro Gln Trp Glu Asp Glu Val Pro Ser Asp Gly Ser Ser Cys Ser Asp
        835                 840                 845

Thr Asp Ser Ser Glu Phe Glu Glu Gly Asp Trp Glu Asp Asp Asp Trp
    850                 855                 860

Pro Gly Gly Ala Ala Glu Ala Lys Asp Gly Ser Arg Asp Lys Ser Gln
865                 870                 875                 880

His Ser Ala Asp Lys Pro Gly Ala Ser Asp Val Thr Asp His Met Met
                885                 890                 895

Ala Ala Val Leu Ser Gln Ala Ala Pro Glu His Ser Ala Gly Val Lys
            900                 905                 910

Arg Ala Gly Gly Glu Ala Ala Ile Leu Tyr Ala Asp Gly Ser Asp Ser
        915                 920                 925

His Gly Gly Pro Asp Ala Phe Val Asp Asn Asp Ser Ala Ala Trp Glu
    930                 935                 940

Ala Ala Leu Glu Ala Gly Ala Gly Pro His Glu Ser Gln Ala Glu Ala
945                 950                 955                 960
```

-continued

```
Pro Gln Gln Leu Ala Ala Ala Val Thr Val Ser Thr Leu Ala Leu Leu
                965                 970                 975

Gly His Gly Thr Gly Pro Val Gln Gln Ser Arg Arg Arg Leu Pro Ala
            980                 985                 990

Ser Gly Ser Gly Pro Ala Gly His  Asp Thr Ala Gly Leu  Gly Ala Gly
        995                 1000                1005

Ala Val  Ala Leu Ala Glu Pro  Gln Leu Gln Leu Pro  Glu Gln Phe
    1010                 1015                 1020

Asp Val  Asn Leu Leu Ala Pro  Pro Val Leu Val Pro  Ala Gly Thr
    1025                 1030                 1035

Lys Leu  Gln Ala Leu Pro Pro  Trp Ser Val Gly Ser  Pro Val Thr
    1040                 1045                 1050

Ser Pro  Gly Leu Thr Gln Ala  Gly Pro Gly Pro Ser  Ala Ala Ala
    1055                 1060                 1065

Gly Pro  Arg Val Ala Gln Val  Val Ser Gly Ser Pro  Tyr Thr Asp
    1070                 1075                 1080

Ala Tyr  Glu Leu Pro Asp Asp  Gly Gly His Pro His  Leu Gly Gly
    1085                 1090                 1095

Gly Ala  Ala Pro Gln Pro Ser  Ser Arg Glu Asp Gly  Gly Gly Val
    1100                 1105                 1110

Ala Ala  Gly Val Gly Ala His  Ala Gly Cys Asn Ala  Gln Arg Gly
    1115                 1120                 1125

Met Thr  Ala Ala Val Ile Gly  Pro Gly Gly Thr Arg  Val Gly Ala
    1130                 1135                 1140

Ala Ser  Pro Pro Leu Val Leu  Ser Ala Ser Gly Ser  Gly Gly Gly
    1145                 1150                 1155

Leu Ala  Thr Pro Gly Arg Arg  Arg Gly Arg Leu Val  Met Leu His
    1160                 1165                 1170

Gly Ala  Gly Ala Ala Ala Cys  Gly Thr Pro Thr Ser  Gln Pro Arg
    1175                 1180                 1185

Ala Gly  Arg Ala Ala Ser Asn  Thr Ala Thr Ala Gly  Gly Ala Gly
    1190                 1195                 1200

Pro Ser  Ala Val Ala Ala Ala  Gly Pro Gly Met Gly  Asp Leu Gly
    1205                 1210                 1215

His Gln  Gly Gln Pro Leu Pro  Ala Glu Pro Pro Gly  Ala Ala Thr
    1220                 1225                 1230

Arg Pro  Val Gly Arg Ala Gly  Arg Ala Pro Pro Leu  Ser Pro Leu
    1235                 1240                 1245

Arg Arg  Ser Ser Arg Val Pro  Gly Gly Gln Gln Gln  Gln Gln Gln
    1250                 1255                 1260

Gln Gln  Gln Gln Gln Gln His  Ala Ala Gly Met Ala  Ala Gln Gly
    1265                 1270                 1275

Gln Gly  Pro Ala Glu Pro Ser  Ala Asn Gly Gly Ala  Gly Arg Ser
    1280                 1285                 1290

Arg Ala  Ser Ala Gly Gly Gly  Met Ser Pro Ser Arg  Arg Ala Ala
    1295                 1300                 1305

Val Arg  Leu Gln Arg Gln Pro  Val Val Pro Ser Pro  Arg Leu Val
    1310                 1315                 1320

Glu Asp  Ser Arg Leu His Arg  Ser Gly Gln Gln Gln  Ala Val Val
    1325                 1330                 1335

Gly Val  Gly Thr Ala Gly Gly  Ser Arg Val Gly Asp  Arg Ala Arg
    1340                 1345                 1350
```

-continued

```
Gly Gly  Ser Gly Ala Gly Leu  Ser Ala Ala Ala Thr  Gly Val Ile
    1355                 1360                 1365

Lys Ala  Ala Thr Ala Ser Pro  Ser Arg Gly Arg Thr  Arg Ser Lys
    1370                 1375                 1380

Pro Pro  Glu Arg Ala Ser Ile  Ala Gly Arg Gly Arg  Gly Gly Arg
    1385                 1390                 1395

Gly Arg  Arg Ala Thr Ala Arg  Ser His Arg Gln Ser  Glu Ser Asp
    1400                 1405                 1410

Gln Glu  Glu Thr Ala Asp Ala  Val Arg Pro Ser Asp  Pro Glu Glu
    1415                 1420                 1425

Asp Lys  Glu Lys Glu Gly Gly  Gly Gln Gln Thr Arg  Gly Ala Pro
    1430                 1435                 1440

Ala Arg  Arg Arg Ala Pro Arg  Thr Pro Ser Glu Val  Leu Asn Arg
    1445                 1450                 1455

Leu Gln  Val Ser Asp Leu Arg  Pro Val Leu His Leu  Pro Leu Val
    1460                 1465                 1470

Glu Ala  Ala Arg Gln Leu Gly  Leu His Arg Thr Ser  Phe Met Thr
    1475                 1480                 1485

Arg Cys  Arg Gln Leu Gly Ile  Ala Arg Trp Pro Ala  Lys Gln Leu
    1490                 1495                 1500

Arg Met  Leu Asp Leu Met Glu  Glu Gln Leu Gln Glu  Leu Glu Ala
    1505                 1510                 1515

Cys Gly  Val Ala Asn His Tyr  Thr Ala Lys Lys Cys  Leu Glu Glu
    1520                 1525                 1530

Ala Pro  Gly Trp Leu Ala Gln  Val Ala Ala Ala Arg  Ser Ala Leu
    1535                 1540                 1545

Leu Glu  Asn Pro Cys Gly Phe  Thr Met Pro Gln Pro  Leu Glu Leu
    1550                 1555                 1560

Leu Arg  Gln Arg His Val Lys  Val Ala Trp Ala His  Arg Gln Lys
    1565                 1570                 1575

Tyr Lys  Ala Ala Leu Gly Glu  Glu Gly Glu Glu Gly  Glu Glu Gly
    1580                 1585                 1590

Asp Asp  Leu Asp Ser Gln Ala  Gln Met Ser Gln
    1595                 1600
```

<210> SEQ ID NO 42
<211> LENGTH: 3367
<212> TYPE: DNA
<213> ORGANISM: Chlamydomonas reinhardtii

<400> SEQUENCE: 42

```
gcagctgtaa atcatttgca ccagcataca ccaaaatcta ttcgccttga aaccaacgga     60

ccccttcgat ctctctctgg ccactccaag ctttggtcgt tctgttttct gaccttgaga    120

agcgctgccc tctctacatt gagctagtgt aagggccatt gaacgactgc attttcctgc    180

aagccatata ccgctaggac gcccagtcgc agccgctgga gcaatgacgg agaccgacca    240

ccgccgaagc cgtccggact ggtctcgcgc acagtccctt cgtctaattc agctccacgt    300

caagctgggt aacagttgga ccgagatcgc taagcagctg cccggccgca ctcagaatga    360

ctgcaagaat ttcttcttcg gagccctgcg cgcaaagcgc ggctaccgtg acaacctggt    420

ctacgcctac gcgcgcgcgt tgccgcccgc ctccgcctct gcttgcgggt cgtgggagca    480

ggacaagcgc ggccccgacg ccctcacccg tgccgccgcc tacaaggcag ccatgcaaca    540

agtggcggcg caagaagtgg ccgagcagat ggagaagcag cagcgtagcc agcagcaaga    600
```

-continued

```
gggagaggac ggcggctgcg gctcgggtgc cgctggtgct actgccgagg acggcgggga    660
gccgggtgct gtagccgctg ccagccgccg cagtagcagt gtgtcagtgg gcgctgacgg    720
cgcggcgccc acggctcagg gcgacggcat ggacacgcaa gaggacgccg cgtccgcgcc    780
tgcctgcccc gcctcggctg ccgcgagccc ggttggtcct ggtgacgtca gcgtccgccg    840
gctctcatcc actggtgata ccgtcgtcac tgatgccgcc ggcaccagga ctgttgttgc    900
cgctggtgtt gttgctggcg gttggcgctc cgttgccgcc gcggcgtcaa tgccggccca    960
ccctgccgcc gtggtgtcga tgccgccggt ggtgcccgcc tctgttgtgg cggcggccag   1020
cggcgtgctt ggcgccgccg cggtgcccgc tgctggtgcc cctggtgacc ggctgtccct   1080
gcagtcgctg cagccgccgc cgcacggctt cgccgccctt ccgcagtcgg cggcgccggc   1140
gatcggcagc agcagcgcca gtcccttctg gcagcaccag cagcagcacc acctcatggg   1200
cccccgggtg cagcttctgt ctcacgagtc gctggccctc ctgcaccagc agcaccagca   1260
ggcgcagcag cactcgcacg tggtcctgca cgtggcgccg ccgttcctgc agcagcacca   1320
ccagaacccg caccaccagc acctgatggt gcagctggaa ggcgccggcg ccggtgcacc   1380
tgccggcgcc ttccagctgc aacaccacca gcacctgcac ccgcaccacg tccagggctc   1440
aggccctgcc gacggcagca gcggccccgt cctgctcatg ggccccgccg gcccccacgc   1500
cgcggcgctg cagctgctgg gctcccaccc gcaccaccag caccagcacc accagcagct   1560
cgtgctcctg ccctcgtctg tccccggtgc acctccgcag catgtgctgc tgcctatggc   1620
cgtccgcccg ccgcacctgc ttcagtacgg cggtgcacac ggtgccagtg ccgctgcatc   1680
tgctgccgcc gctgctccgt ctgcgggcat gggcgccttc gtcttccacc ctcacccgca   1740
gcagcagcag ctgccgcctg ctgccgccgc tgcctttgct gccgcctccg ccgcgccgtc   1800
gcagcccgcc gcagttgcgg ccgccgtgca ctcgctggca cccgccgcct ccgcagccct   1860
gtccctcagc ggcagctcgg tcctggaggc gaccaccacc accacccgca tcacaaccac   1920
cactgccgcg gctgttgcgg ccgctgctgc tggcgccgca gtggctgctg gggtcaagac   1980
cgagcccgcc tcagccgagg cggccactgg ctgggcccag cagcagcaac agaaggcgca   2040
tgctggcgtt agccgcagct gcagtagcag cagcagcagc agcgccgcct gcggcgcctg   2100
cagcacatgc accgccggtg tcggcgctac tcctgccaca gcaacccagc tgccgcaaca   2160
ccagcaggat caccagcttc tgggcgacga ctggtgcgcc ggtgacgagg agtgggccga   2220
gctcgggcgc atcctgcttg gctgaagcag tgctgatgat ggtggcacct tgcgaaggtt   2280
gcatgaacga atgacacaaa cgcatactag tgtactgtag cctaaatggc cggcctgaat   2340
tctttgaaga caataagtaa tttttgagcg tgagcgttct atggtaccta gggcgccacc   2400
atgcaaactc cacatgagtg agtggtatat tacaaggcct ggtccggaca ctgtgaaacc   2460
ggttgaccta ccgaacctaa atgtgagttg ctcaaattcg gagtagcttg aggtaggcgc   2520
atgaatgcat atggttcctg cagctgactt gctgcagcgt gggatgggat ggcaaacgag   2580
ttgtgtagcc agcagcccaa gggtgtctgg atgtgttcaa cctcctaatc gcatgcatgc   2640
gtgttggagt ttgcaagcat gctcgcatgc cgcactagcc gcacacatac acaagaagac   2700
tggagcaggc gagaattgca ctgacacaga gccaagcaag cccataaaaa gtggtagctg   2760
tataagatga ggtgtacagt ggatgggcag tgcccaaagc aagcaggggc gacagtgcaa   2820
gccgcgggca ctgccgtaca gagtgctgtg tactgctgag atgctgcaaa cggcagaagt   2880
agagcagccg ggaaggctgt gggcggggaa gagcgaacgt cggcatgtgt gagcgtcggt   2940
gtttacctag tgcggatgtg atgacgagcg agagagttga ccacagcgga catgcacggc   3000
```

```
cttcggcccc accccatttt tagggctgga gttttcccac catctctgga gttgactcgc   3060
gaatgtgtca accacccgaa agaatggtcg catgcttgtg agagttgctg gaagactgct   3120
gagagcgaga ccggatcccg cgtcaggggt gaaggtgcaa acggcacgaa tgaacgcact   3180
tcatccaagg ctcggaacag cacgcacgca tgtgcagttg taaggcgctg cagcgatacg   3240
atgtaacttc cttctcatgc agtcgtgtca cattgggctc agagcagcct tgaaagacgc   3300
agtggtgcgg gcagcaggtg cgcctggggc ctctctggct gcccacggac tgtaaatgta   3360
cggcgcc                                                              3367
```

```
<210> SEQ ID NO 43
<211> LENGTH: 2022
<212> TYPE: DNA
<213> ORGANISM: Chlamydomonas reinhardtii

<400> SEQUENCE: 43

atgacggaga ccgaccaccg ccgaagccgt ccggactggt ctcgcgcaca gtcccttcgt     60
ctaattcagc tccacgtcaa gctgggtaac agttggaccg agatcgctaa gcagctgccc    120
ggccgcactc agaatgactg caagaatttc ttcttcggag ccctgcgcgc aaagcgcggc    180
taccgtgaca acctggtcta cgcctacgcg cgcgcgttgc cgcccgcctc cgcctctgct    240
tgcgggtcgt gggagcagga caagcgcggc cccgacgccc tcacccgtgc cgccgcctac    300
aaggcagcca tgcaacaagt ggcggcgcaa gaagtggccg agcagatgga gaagcagcag    360
cgtagccagc agcaagaggg agaggacggc ggctgcggct cgggtgccgc tggtgctact    420
gccgaggacg gcggggagcc gggtgctgta gccgctgcca gccgccgcag tagcagtgtg    480
tcagtgggcg ctgacggcgc ggcgcccacg gctcagggcg acggcatgga cacgcaagag    540
gacgccgcgt ccgcgcctgc ctgccccgcc tcggctgccg cgagcccggt tggtcctggt    600
gacgtcagcg tccgccggct ctcatccact ggtgataccg tcgtcactga tgccgccggc    660
accaggactg ttgttgccgc tggtgttgtt gctggcggtt ggcgctccgt tgccgccgcg    720
gcgtcaatgc cggcccaccc tgccgccgtg gtgtcgatgc cgccggtggt gcccgcctct    780
gttgtggcgg cggccagcgg cgtgcttggc gccgccgcgg tgcccgctgc tggtgcccct    840
ggtgaccggc tgtccctgca gtcgctgcag ccgccgccgc acggcttcgc cgcccttccg    900
cagtcggcgg cgccggcgat cggcagcagc agcgccagtc ccttctggca gcaccagcag    960
cagcaccacc tcatgggccc ccgggtgcag cttctgtctc acgagtcgct ggccctcctg   1020
caccagcagc accagcaggc gcagcagcac tcgcacgtgg tcctgcacgt ggcgccgccg   1080
ttcctgcagc agcaccacca gaacccgcac caccagcacc tgatggtgca gctggaaggc   1140
gccggcgccg gtgcacctgc cggcgccttc cagctgcaac accaccagca cctgcacccg   1200
caccacgtcc agggctcagg ccctgccgac ggcagcagcg gccccgtcct gctcatgggc   1260
cccgccggcc cccacgccgc ggcgctgcag ctgctgggct cccacccgca ccaccagcac   1320
cagcaccacc agcagctcgt gctcctgccc tcgtctgtcc ccggtgcacc tccgcagcat   1380
gtgctgctgc ctatggccgt ccgcccgccg cacctgcttc agtacggcgg tgcacacggt   1440
gccagtgccg ctgcatctgc tgccgccgct gctccgtctg cgggcatggg cgccttcgtc   1500
ttccaccctc acccgcagca gcagcagctg ccgcctgctg ccgccgctgc ctttgctgcc   1560
gcctccgccg cgccgtcgca gcccgccgca gttgcggccg ccgtgcactc gctggcaccc   1620
gccgcctccg cagccctgtc cctcagcggc agctcggtcc tggaggcgac caccaccacc   1680
```

-continued

```
acccgcatca caaccaccac tgccgcggct gttgcggccg ctgctgctgg cgccgcagtg   1740

gctgctgggg tcaagaccga gcccgcctca gccgaggcgg ccactggctg ggcccagcag   1800

cagcaacaga aggcgcatgc tggcgttagc cgcagctgca gtagcagcag cagcagcagc   1860

gccgcctgcg gcgcctgcag cacatgcacc gccggtgtcg gcgctactcc tgccacagca   1920

acccagctgc cgcaacacca gcaggatcac cagcttctgg gcgacgactg gtgcgccggt   1980

gacgaggagt gggccgagct cgggcgcatc ctgcttggct ga                       2022
```

<210> SEQ ID NO 44
<211> LENGTH: 673
<212> TYPE: PRT
<213> ORGANISM: Chlamydomonas reinhardtii

<400> SEQUENCE: 44

```
Met Thr Glu Thr Asp His Arg Arg Ser Arg Pro Asp Trp Ser Arg Ala
1               5                   10                  15

Gln Ser Leu Arg Leu Ile Gln Leu His Val Lys Leu Gly Asn Ser Trp
            20                  25                  30

Thr Glu Ile Ala Lys Gln Leu Pro Gly Arg Thr Gln Asn Asp Cys Lys
        35                  40                  45

Asn Phe Phe Phe Gly Ala Leu Arg Ala Lys Arg Gly Tyr Arg Asp Asn
    50                  55                  60

Leu Val Tyr Ala Tyr Ala Arg Ala Leu Pro Pro Ala Ser Ala Ser Ala
65                  70                  75                  80

Cys Gly Ser Trp Glu Gln Asp Lys Arg Gly Pro Asp Ala Leu Thr Arg
                85                  90                  95

Ala Ala Ala Tyr Lys Ala Ala Met Gln Gln Val Ala Ala Gln Glu Val
            100                 105                 110

Ala Glu Gln Met Glu Lys Gln Gln Arg Ser Gln Gln Gln Glu Gly Glu
        115                 120                 125

Asp Gly Gly Cys Gly Ser Gly Ala Ala Gly Ala Thr Ala Glu Asp Gly
    130                 135                 140

Gly Glu Pro Gly Ala Val Ala Ala Ala Ser Arg Arg Ser Ser Ser Val
145                 150                 155                 160

Ser Val Gly Ala Asp Gly Ala Ala Pro Thr Ala Gln Gly Asp Gly Met
                165                 170                 175

Asp Thr Gln Glu Asp Ala Ala Ser Ala Pro Ala Cys Pro Ala Ser Ala
            180                 185                 190

Ala Ala Ser Pro Val Gly Pro Gly Asp Val Ser Val Arg Arg Leu Ser
        195                 200                 205

Ser Thr Gly Asp Thr Val Val Thr Asp Ala Ala Gly Thr Arg Thr Val
    210                 215                 220

Val Ala Ala Gly Val Val Ala Gly Gly Trp Arg Ser Val Ala Ala Ala
225                 230                 235                 240

Ala Ser Met Pro Ala His Pro Ala Ala Val Val Ser Met Pro Pro Val
                245                 250                 255

Val Pro Ala Ser Val Val Ala Ala Ala Ser Gly Val Leu Gly Ala Ala
            260                 265                 270

Ala Val Pro Ala Ala Gly Ala Pro Gly Asp Arg Leu Ser Leu Gln Ser
        275                 280                 285

Leu Gln Pro Pro Pro His Gly Phe Ala Ala Leu Pro Gln Ser Ala Ala
    290                 295                 300

Pro Ala Ile Gly Ser Ser Ser Ala Ser Pro Phe Trp Gln His Gln Gln
305                 310                 315                 320
```

```
Gln His His Leu Met Gly Pro Arg Val Gln Leu Leu Ser His Glu Ser
                325                 330                 335

Leu Ala Leu Leu His Gln Gln His Gln Gln Ala Gln Gln His Ser His
            340                 345                 350

Val Val Leu His Val Ala Pro Pro Phe Leu Gln Gln His His Gln Asn
        355                 360                 365

Pro His His Gln His Leu Met Val Gln Leu Glu Gly Ala Gly Ala Gly
    370                 375                 380

Ala Pro Ala Gly Ala Phe Gln Leu Gln His His Gln His Leu His Pro
385                 390                 395                 400

His His Val Gln Gly Ser Gly Pro Ala Asp Gly Ser Ser Gly Pro Val
                405                 410                 415

Leu Leu Met Gly Pro Ala Gly Pro His Ala Ala Ala Leu Gln Leu Leu
            420                 425                 430

Gly Ser His Pro His His Gln His Gln His His Gln Gln Leu Val Leu
        435                 440                 445

Leu Pro Ser Ser Val Pro Gly Ala Pro Pro Gln His Val Leu Leu Pro
    450                 455                 460

Met Ala Val Arg Pro Pro His Leu Leu Gln Tyr Gly Gly Ala His Gly
465                 470                 475                 480

Ala Ser Ala Ala Ala Ser Ala Ala Ala Ala Ala Pro Ser Ala Gly Met
                485                 490                 495

Gly Ala Phe Val Phe His Pro His Pro Gln Gln Gln Gln Leu Pro Pro
            500                 505                 510

Ala Ala Ala Ala Ala Phe Ala Ala Ala Ser Ala Ala Pro Ser Gln Pro
        515                 520                 525

Ala Ala Val Ala Ala Ala Val His Ser Leu Ala Pro Ala Ala Ser Ala
    530                 535                 540

Ala Leu Ser Leu Ser Gly Ser Ser Val Leu Glu Ala Thr Thr Thr Thr
545                 550                 555                 560

Thr Arg Ile Thr Thr Thr Thr Ala Ala Ala Val Ala Ala Ala Ala Ala
                565                 570                 575

Gly Ala Ala Val Ala Ala Gly Val Lys Thr Glu Pro Ala Ser Ala Glu
            580                 585                 590

Ala Ala Thr Gly Trp Ala Gln Gln Gln Gln Gln Lys Ala His Ala Gly
        595                 600                 605

Val Ser Arg Ser Cys Ser Ser Ser Ser Ser Ser Ser Ala Ala Cys Gly
    610                 615                 620

Ala Cys Ser Thr Cys Thr Ala Gly Val Gly Ala Thr Pro Ala Thr Ala
625                 630                 635                 640

Thr Gln Leu Pro Gln His Gln Gln Asp His Gln Leu Leu Gly Asp Asp
                645                 650                 655

Trp Cys Ala Gly Asp Glu Glu Trp Ala Glu Leu Gly Arg Ile Leu Leu
            660                 665                 670

Gly
```

<210> SEQ ID NO 45
<211> LENGTH: 4772
<212> TYPE: DNA
<213> ORGANISM: Chlamydomonas reinhardtii

<400> SEQUENCE: 45

```
ctgacgcgac ctactttcga tttccaaaga gtcgtctgaa acccccgtat tggcccatgc      60
```

-continued

```
ctgatgcccc acgatttatg cgccagctgg gcgccggttc tgcttccggg agcgggagcg    120
ggacgcagca tgtgtgctca aaacacctca gctttccaat tcggaaatcg agtgcggtga    180
aagtgaaacc ccacgtggtg ccattcagag cacttaggcg cctaacgcag ggttaaatca    240
cgctcagacc cggtaaccga taggcacgta tgtgcggacc attgaaggct gaacggattg    300
tactgcgcct aactatgcaa aaaggcctgt gtaatcctaa gccctagacc tgaacgctca    360
cgcgttctct cgcttactgc attattggtg gcagggctac atacacgctc cgagtgaagt    420
ctataccgct caggagctcc gccaagggag cgcgagcaag ttttgagcaa acgcgcagtt    480
aggacgccgt acgccataga ttccattctg atgccttgcg cagagtcctt tgcaaaggtg    540
gtgtacgcgc caagttgacg actggcatgc gtctgcgggg ccgcagcaag ctttcgatcc    600
aggcgacgtt ccaatttcac gaactagcgc cgcttgtcag tttcaaggtc gcacctatcg    660
ctatgcaacg atctacgttt tgcggccttc ttatacttga tagagcatag aacggatgga    720
agcgagctgg ttggaatcgc catttagtag acctgccctg gggcccgatg gacaaagctg    780
aacgcgctgc tggtggccct aacgctgcaa gcgaggacga ctggctgctg gagttttggc    840
cggagcctgc agcggacttt cctgcaccgg tcgctccgat gctgtcgcag catcaagacg    900
cagcacagct gcctgaggcc atgccgcagc agcaaggact ggcgctgggt ggatatggtc    960
tcacgcagca gccttctgac tttatgcaaa cgggcatgcc cggcttcgac gcgttcagca   1020
gcgggaaggc tgcaaccctc gggctgcccc tgcttgccga cccccagcgc gcctccaccg   1080
acggcgcctc tgcgcttatg aacgcggcgc agcagtcctc agagtacatg ctggcccccg   1140
gcatgggcgg catgccgcat ctactagcac cgagcgttgg cacggcgctg cccggcactg   1200
ggcacaccgg cttcgcggac ctgtccatgg ggggcatggc ggggggcatc ccgggcctcg   1260
gggggccagg cattatgcat gggcagtact tcatgcagcc gcagcgagca gccacgggcc   1320
ccgccaagag ccggctgcgc tggacgccgg agctgcacaa ccgcttcgtc aacgcggtga   1380
actcgctggg ggggccggac aaggccacgc ccaagggcat ccttaagctc atgggcgtcg   1440
acggcctcac catctaccac atcaagtcgc acctgcagaa gtaccgcctc aacatccggc   1500
tgccgggaga gagcggcctc gcgggcgact cggcggacgg ctcggacggc gagcgctcgg   1560
acggcgaggg cggcgtgcgg cgcgccacct cgctggagcg ggcagacacc atgtcgggga   1620
tggcgggagg ggccgccgca gcgttaggga gagcgggcgg gacgccgggc ggtgcgctaa   1680
tctcccccgg ccttgccggc gggacgtcaa gcaccggtgg gatggcagcc ggcggcggcg   1740
ggggtggcgg cttggtgact gagcccagca tctctagggg cacggtcctc aacgcggccg   1800
gcgcagttgc caccgccgcg ccggctgcgg cggcgcctgc cggcgggtcc gccgccgtga   1860
agcggccggc gggtacgtct ctgagcagcg gcagcactgc ctcggctact cggcgcaatc   1920
tggaggaggc gctgctgttc caaatggagc tgcagaagaa gctgcacgag cagctggaga   1980
cgcagcgtca actgcagctg agcttggagg cgcacgggcg ctacatcgcc agcctcatgg   2040
agcaggaggg actcacctcg cgactgcccg agctcagcgg cggcgcgccg gcggcggcgc   2100
ctgtggccgc aggcggcgca gcgggcggca tgattgcgcc gccgccaccg cagcagcagc   2160
tgcagcacca gccgcagctg ctgcagccgc agggcagctt gccagccggc ggttcctctg   2220
aagcccatgc cgcagccggc gccggcacga tggtggtgca ccagcagcag cagcagcacg   2280
tgcaccatca tcaccagcag cagcaggtgc agatgcagca gcatgcccgc cactgcgaca   2340
cgtgtggcgc cggtggcgct gggggtgcgc ccagcggcgg cagcagcatg cagcagcttc   2400
aggctgcgga gcagcagcgc acggagcttg ttgtggcggg gcggctaggc tccatgccgg   2460
```

-continued

```
cgcccgcctc ttcgtcgccg ctagcagggc aggcacacca gcagcagccg ctggccggcg   2520
gggcggcgca cttggtgcac gtgcactcgc acacgcctgg ggggcagccg cacgtgcagc   2580
accaggacgc gtttgccggc gcggctacgg cggcagcgca cgcttcgccg gggctgccgc   2640
agtcacattc gcacctgctc ccagccgacc tctccagcaa cgccggtcct gacacaagcg   2700
cggggcagat taagcctgag cctgatatgt cgcagcaaca gcagcaacaa gagcaacagg   2760
aggcggagca gcttgcgcag ggtttgctca atgacagcag cgctggcgcg ggggctgtca   2820
gcggcagcga tggtgggggc cttggggact ttgacttcgg tgatttcggg gacctggacg   2880
ggggagccca gggcggccta ctaggccccg gagacctcat tggcatcgcc gagctggagg   2940
cagcggccgc gcacgagcag cagcaagagc aagagcacga cccactagat gcggatcgcg   3000
caaagcggca gcgagtggag ccataggttc agagctagca ggtgtgttag gcagcggaac   3060
agcagctgtt gcgctcccga caggctaacc agccaagcca cagacgtctg gtgccccagt   3120
cggttgcgcg tgcagctgtg gcgccagggg cccctgcctg gtagacagag cccctcgtcc   3180
gctgaaagga gagcgagcac gggacgcgac gagccgtcgc caagttggca gaaggcacct   3240
gcgcatgcat ctgttgactc tgtctttctg ttgttggctg atgtcttgaa gtgtcattga   3300
ctaccgtcct gcatacgttc acgtggtaca tgctgggtgc cgccgccatc tggcgctccc   3360
gccgttttga gctgattgcg ctcggcgcca gacagcggtt ggcccttgct ttggggctcg   3420
tgtcgattgc gtttgtatgc cgctcgtttg gccggcagag cgcgccggcc cacggggccg   3480
tgcggacgtt acgtgtgtga ggccccagcc gaagtaccgc agtgtgctgt cgctcactcg   3540
cgcactgccg ctcgacttgc ggtgtgtgga cgggtgctct caggtgcctg cgcatgctgc   3600
gtagttgcat tgcgcccgct ccgcgcttga ggtcagaggc ggggctgtgc agcctgctgg   3660
agtgtgcggc agggggtgcg tgtgccagga ccctcacgac aggaggagga cgcgttgcgc   3720
cccgctggtg tggccggctg ctcgggccgg ccattgtacc attcttaccg gtttgtactg   3780
ttcacggcag ccgtgcgcac ggggtggccg gccgcgaggc ctcagtattt gaggctgaca   3840
tgcgtgtgtg tttggtgcgt cgtggtgcga ttgactcaga gcctgccggt tgagactcag   3900
gagggcccag tgtgcatgga aaggttgcat gagagtccgg cggccgcttt gcgacgagtt   3960
gccagtcgaa tcatagttgg tggggcttct ggcggagcga tgggtgaggc atggttgtgt   4020
gaacaggaag gggttgagt cgccaatgac cgccaatgaa cgatgatcac gaaacattag    4080
taagtggaac gcgttggttg gcatgtgtgc cgattaggag ccggtagggg aaattataac   4140
gtcatggcaa acatgagggg aggaacaaac tggatgcggg gcatagtcaa cagctgaaca   4200
acctagcatt tgctttttat cggggacgac gctcaatcga aagggcaatg cacggaaagg   4260
tcacagcatg ggcaagggac tgggagaggg cgctgtgtga gtcgctcctg cgagctggtg   4320
gccacagggg ctcctggcac aggcgagcgg ctgaagttgt gcgcgcggcc ggcgtctgga   4380
tggcgtgtca acactgcacg tgcatctaga tgtcgacact gcggccgaat aacattgcag   4440
gagcaacggt aatgagggag cgctaaggag agagcgtcct cggagtgttc gaaggcggca   4500
aggcatgggc atgggctgtt gcgcctgcat gcgtggtcag caggctgctt ctcaatgcca   4560
gggggttgcg gtgaggtatg cgccggcgcc acgctcggag caccgcgccg agtcgcctca   4620
gaagtcaggc gtgttggatt tgctgcgaga ggagagggag cggaattgga gacgcgctat   4680
tgtcatgaca catgcgtgcg ccgtacaccg tgcgtgcggt tccaggagtt caggtcgaat   4740
gtaagggagc ccgtgaatgt ctttccgcgc gg                                 4772
```

<210> SEQ ID NO 46
<211> LENGTH: 2259
<212> TYPE: DNA
<213> ORGANISM: Chlamydomonas reinhardtii

<400> SEQUENCE: 46
atggacaaag ctgaacgcgc tgctggtggc cctaacgctg caagcgagga cgactggctg 60
ctggagtttt ggccggagcc tgcagcggac tttcctgcac cggtcgctcc gatgctgtcg 120
cagcatcaag acgcagcaca gctgcctgag gccatgccgc agcagcaagg actggcgctg 180
ggtggatatg gtctcacgca gcagccttct gactttatgc aaacgggcat gcccggcttc 240
gacgcgttca gcagcgggaa ggctgcaacc ctcgggctgc ccctgcttgc cgacccccag 300
cgcgcctcca ccgacggcgc ctctgcgctt atgaacgcgg cgcagcagtc ctcagagtac 360
atgctggccc ccggcatggg cggcatgccg catctactag caccgagcgt tggcacggcg 420
ctgcccggca ctgggcacac cggcttcgcg gacctgtcca tggggggcat ggcgggggc 480 atcccgggcc tcgggggcc aggcattatg catgggcagt acttcatgca gccgcagcga 540
gcagccacgg gccccgccaa gagccggctg cgctggacgc cggagctgca caaccgcttc 600
gtcaacgcgg tgaactcgct gggggggccg gacaaggcca cgcccaaggg catccttaag 660
ctcatgggcg tcgacggcct caccatctac cacatcaagt cgcacctgca gaagtaccgc 720
ctcaacatcc ggctgccggg agagagcggc ctcgcgggcg actcggcgga cggctcggac 780
ggcgagcgct cggacggcga gggcggcgtg cggcgcgcca cctcgctgga gcgggcagac 840
accatgtcgg ggatggcggg aggggccgcc gcagcgttag ggagagcggg cgggacgccg 900
ggcggtgcgc taatctcccc cggccttgcc ggcgggacgt caagcaccgg tgggatggca 960
gccggcggcg gcgggggtgg cggcttggtg actgagccca gcatctctag gggcacggtc 1020
ctcaacgcgg ccggcgcagt tgccaccgcc gcgccggctg cggcggcgcc tgccggcggg 1080
tccgccgccg tgaagcggcc ggcgggtacg tctctgagca gcggcagcac tgcctcggct 1140
actcggcgca atctggagga ggcgctgctg ttccaaatgg agctgcagaa gaagctgcac 1200
gagcagctgg agacgcagcg tcaactgcag ctgagcttgg aggcgcacgg gcgctacatc 1260
gccagcctca tggagcagga gggactcacc tcgcgactgc ccgagctcag cggcggcgcg 1320
ccggcggcgg cgcctgtggc cgcaggcggc gcagcgggcg gcatgattgc gccgccgcca 1380
ccgcagcagc agctgcagca ccagccgcag ctgctgcagc cgcagggcag cttgccagcc 1440
ggcggttcct ctgaagccca tgccgcagcc ggcgccggca cgatggtggt gcaccagcag 1500
cagcagcagc acgtgcacca tcatcaccag cagcagcagg tgcagatgca gcagcatgcc 1560
cgccactgcg acacgtgtgg cgccggtggc gctgggggtg cgcccagcgg cggcagcagc 1620
atgcagcagc ttcaggctgc ggagcagcag cgcacggagc ttgttgtggc ggggcggcta 1680
ggctccatgc cggcgcccgc ctcttcgtcg ccgctagcag ggcaggcaca ccagcagcag 1740
ccgctggccg gcggggcggc gcacttggtg cacgtgcact cgcacacgcc tgggggggcag 1800 ccgcacgtgc agcaccagga cgcgtttgcc ggcgcggcta cggcggcagc gcacgcttcg 1860
ccggggctgc cgcagtcaca ttcgcacctg ctcccagccg acctctccag caacgccggt 1920
cctgacacaa gcgcggggca gattaagcct gagcctgata tgtcgcagca acagcagcaa 1980
caagagcaac aggaggcgga gcagcttgcg cagggtttgc tcaatgacag cagcgctggc 2040
gcgggggctg tcagcggcag cgatggtggg ggccttgggg actttgactt cggtgatttc 2100
ggggacctgg acgggggagc ccagggcggc ctactaggcc ccggagacct cattggcatc 2160
gccgagctgg aggcagcggc cgcgcacgag cagcagcaag agcaagagca cgacccacta 2220
gatgcggatc gcgcaaagcg gcagcgagtg gagccatag 2259

<210> SEQ ID NO 47
<211> LENGTH: 752
<212> TYPE: PRT
<213> ORGANISM: Chlamydomonas reinhardtii

<400> SEQUENCE: 47

```
Met Asp Lys Ala Glu Arg Ala Ala Gly Gly Pro Asn Ala Ala Ser Glu
1               5                   10                  15

Asp Asp Trp Leu Leu Glu Phe Trp Pro Glu Pro Ala Ala Asp Phe Pro
            20                  25                  30

Ala Pro Val Ala Pro Met Leu Ser Gln His Gln Asp Ala Ala Gln Leu
        35                  40                  45

Pro Glu Ala Met Pro Gln Gln Gln Gly Leu Ala Leu Gly Gly Tyr Gly
    50                  55                  60

Leu Thr Gln Gln Pro Ser Asp Phe Met Gln Thr Gly Met Pro Gly Phe
65                  70                  75                  80

Asp Ala Phe Ser Ser Gly Lys Ala Ala Thr Leu Gly Leu Pro Leu Leu
                85                  90                  95

Ala Asp Pro Gln Arg Ala Ser Thr Asp Gly Ala Ser Ala Leu Met Asn
            100                 105                 110

Ala Ala Gln Gln Ser Ser Glu Tyr Met Leu Ala Pro Gly Met Gly Gly
        115                 120                 125

Met Pro His Leu Leu Ala Pro Ser Val Gly Thr Ala Leu Pro Gly Thr
    130                 135                 140

Gly His Thr Gly Phe Ala Asp Leu Ser Met Gly Gly Met Ala Gly Gly
145                 150                 155                 160

Ile Pro Gly Leu Gly Gly Pro Gly Ile Met His Gly Gln Tyr Phe Met
                165                 170                 175

Gln Pro Gln Arg Ala Ala Thr Gly Pro Ala Lys Ser Arg Leu Arg Trp
            180                 185                 190

Thr Pro Glu Leu His Asn Arg Phe Val Asn Ala Val Asn Ser Leu Gly
        195                 200                 205

Gly Pro Asp Lys Ala Thr Pro Lys Gly Ile Leu Lys Leu Met Gly Val
    210                 215                 220

Asp Gly Leu Thr Ile Tyr His Ile Lys Ser His Leu Gln Lys Tyr Arg
225                 230                 235                 240

Leu Asn Ile Arg Leu Pro Gly Glu Ser Gly Leu Ala Gly Asp Ser Ala
                245                 250                 255

Asp Gly Ser Asp Gly Glu Arg Ser Asp Gly Glu Gly Gly Val Arg Arg
            260                 265                 270

Ala Thr Ser Leu Glu Arg Ala Asp Thr Met Ser Gly Met Ala Gly Gly
        275                 280                 285

Ala Ala Ala Ala Leu Gly Arg Ala Gly Gly Thr Pro Gly Gly Ala Leu
    290                 295                 300

Ile Ser Pro Gly Leu Ala Gly Gly Thr Ser Ser Thr Gly Gly Met Ala
305                 310                 315                 320

Ala Gly Gly Gly Gly Gly Gly Gly Leu Val Thr Glu Pro Ser Ile Ser
                325                 330                 335

Arg Gly Thr Val Leu Asn Ala Ala Gly Ala Val Ala Thr Ala Ala Pro
            340                 345                 350
```

```
Ala Ala Ala Ala Pro Ala Gly Gly Ser Ala Ala Val Lys Arg Pro Ala
        355                 360                 365

Gly Thr Ser Leu Ser Ser Gly Ser Thr Ala Ser Ala Thr Arg Arg Asn
    370                 375                 380

Leu Glu Glu Ala Leu Leu Phe Gln Met Glu Leu Gln Lys Lys Leu His
385                 390                 395                 400

Glu Gln Leu Glu Thr Gln Arg Gln Leu Gln Leu Ser Leu Glu Ala His
                405                 410                 415

Gly Arg Tyr Ile Ala Ser Leu Met Glu Gln Glu Gly Leu Thr Ser Arg
            420                 425                 430

Leu Pro Glu Leu Ser Gly Gly Ala Pro Ala Ala Ala Pro Val Ala Ala
        435                 440                 445

Gly Gly Ala Ala Gly Gly Met Ile Ala Pro Pro Pro Pro Gln Gln Gln
    450                 455                 460

Leu Gln His Gln Pro Gln Leu Leu Gln Pro Gln Gly Ser Leu Pro Ala
465                 470                 475                 480

Gly Gly Ser Ser Glu Ala His Ala Ala Ala Gly Ala Gly Thr Met Val
                485                 490                 495

Val His Gln Gln Gln Gln Gln His Val His His His His Gln Gln Gln
            500                 505                 510

Gln Val Gln Met Gln Gln His Ala Arg His Cys Asp Thr Cys Gly Ala
        515                 520                 525

Gly Gly Ala Gly Gly Ala Pro Ser Gly Gly Ser Ser Met Gln Gln Leu
    530                 535                 540

Gln Ala Ala Glu Gln Gln Arg Thr Glu Leu Val Val Ala Gly Arg Leu
545                 550                 555                 560

Gly Ser Met Pro Ala Pro Ala Ser Ser Ser Pro Leu Ala Gly Gln Ala
                565                 570                 575

His Gln Gln Gln Pro Leu Ala Gly Gly Ala Ala His Leu Val His Val
            580                 585                 590

His Ser His Thr Pro Gly Gly Gln Pro His Val Gln His Gln Asp Ala
        595                 600                 605

Phe Ala Gly Ala Ala Thr Ala Ala Ala His Ala Ser Pro Gly Leu Pro
    610                 615                 620

Gln Ser His Ser His Leu Leu Pro Ala Asp Leu Ser Ser Asn Ala Gly
625                 630                 635                 640

Pro Asp Thr Ser Ala Gly Gln Ile Lys Pro Glu Pro Asp Met Ser Gln
                645                 650                 655

Gln Gln Gln Gln Gln Glu Gln Gln Glu Ala Glu Gln Leu Ala Gln Gly
            660                 665                 670

Leu Leu Asn Asp Ser Ser Ala Gly Ala Gly Ala Val Ser Gly Ser Asp
        675                 680                 685

Gly Gly Gly Leu Gly Asp Phe Asp Phe Gly Asp Phe Gly Asp Leu Asp
    690                 695                 700

Gly Gly Ala Gln Gly Gly Leu Leu Gly Pro Gly Asp Leu Ile Gly Ile
705                 710                 715                 720

Ala Glu Leu Glu Ala Ala Ala Ala His Glu Gln Gln Gln Glu Gln Glu
                725                 730                 735

His Asp Pro Leu Asp Ala Asp Arg Ala Lys Arg Gln Arg Val Glu Pro
            740                 745                 750
```

<210> SEQ ID NO 48
<211> LENGTH: 4592
<212> TYPE: DNA

<213> ORGANISM: Chlamydomonas reinhardtii

<400> SEQUENCE: 48
gaacatcaag ctgttgggca aaactctcga tgcagcgaat ttctccattc caagggtcag 60
gcacgcgcat ccgattccca ggcaaactgg aagggcttgc tagtacctct gaggcacctg 120
tgatgcaaat acaaacatag acataatgca catttaagat gccatagggc tcaccgcaag 180
aacttcttcc caaccgaaaa ccctgtgctg ctgcgctggc cctggccagg agctggccat 240
ctaggacagc cgcaatcatt gcggaacaat tggcgaaaac catcagatag cctagatttg 300
gcctgtgggc accgacaatc ggcagggtgt tgcgcaacac agccttgggc ttgtcgcgtg 360
catttcggcc aaaactagtc attttgtgcc cattgcgcat gcgcgcaccg gcacggtagc 420
agcgccgagc tggagcagcc gtgcgaaccc gcgcccggac tgggagggat gtcgcgccgg 480
tccgcagctg gtggcccgcc gcggcaccca actgccaaac ttaaaggtgg atggagcccg 540
gaggaagatg ccctgctcac caggctggtt aagaagttcg gcgagggcaa ctggagcccc 600
atcgcgcgcg ccctgaacga ggccaccggc aagaccgagg ccactggccg catcggcaag 660
cagtgccgcg agcgatggaa ccaccacctg tcgccggggc tgcgcaagga cccctggacg 720
ccggaggagg aggtgctggt ggtggatgct cacaagaggc ttggcaacag gtggagcgac 780
atcgcgcgct gcatccccgg acgtagcgag aacgcagtca agaaccactg gaacgccacg 840
ctgcgcaagc gcgtcacgcc cgagaacccg gcgggcccat tgaaggagta ccttgactca 900
ctcaacctga cagtggcgcc acgcaagagg ggcggcggcg gcggcggcgg cggcggtgga 960
ggcggcggcg ccaagcgcaa gcgcaacaac aggggcagcc aggaggagga cacgtccgag 1020
gaccctgacg aggacctgct gcctgacgac ctggatgact ctctggacga ctccaccacc 1080
agccgcaccg cacacaccgc agcagcggcc gcggcatcag gcggaggaag aggccggact 1140
gccagccgcg ctacaaccac tggcggcggc ggcggcagcc gcgctgcaca cgccgccgcc 1200
gcggcccgca caacctcggc gccgactgcc gccgccgccg tcactgccgc caccgtcgcc 1260
gccaacagcc cggacagctc gtcggctggc ggcgccgttg gcccggccgc ggccgacgcc 1320
gcgcactcgg ctggcggcgg cgccgttgtt tgcggcggcg cctacagcag cggcggcgtg 1380
gtcaccttcg ccggcgccgg cttgctgtgc agcgccgctg tccccaccac caccgtcacc 1440
accgcggcgg tgccgctggc gtcagacgcg ggtgtgggtg tggacgacgg tgcggacgac 1500
ctggcgcctg gcgtgcgccg ctcctcccgc cgcgccgcac agctgagcag ccagcgcctg 1560
cgcgacatgg tggaggcgga gcgccgcctg atggacgagc tggccgagga cgaggaggcg 1620
caggagcagc agcagatgca ggccgcagag gcggcggagg cggctgcagg ggcggccgca 1680
gaggcggcag aggcggcaga gatgcaggct gagatgcagg tgaagcgagc ggaggcgggc 1740
gagcctgcgg gcgccagcgt cggctccggc cgcggccacg gcggcggcgg cggcggcggc 1800
ggcggcggcg gcgccagggc cgagtacggc gctgaggcgg aggtgtccag cggcggcgcg 1860
gccaagaggc ggcgccgcga cggcggaggt gcggcggcgg cggcggcggc gcaacgtgcc 1920
ggtgcgccgc agcggcgccc gcccgcccgc agcgagagtg tgtgcgacag cgccggcatc 1980
cgcatggccc cgctccagaa gccgccgcag cccgccctgc ccagccagca tcaacagcaa 2040
gcgctccacc accaactcca gcaccagcat cagcagccag cgatgtcgcc ctttggctac 2100
gccgccagcc aggccgaacc caccgctgcc gccgccgcag cagccgccgc cggctgcatg 2160
gtaatgcccc gcgtcgcgtc cagcgccgcc ctggcgcctg gcgccgacgc cagcggcggc 2220
ggtggcgacc gtgcggccct ggcacccccc ggcagcatgc tggcgcacgc cgctactgcc 2280

-continued

```
gcctccggct tcccggcggc agcagctgct accgctgcta cagccggcag cccctaccac   2340
ccgcaccacc cgcaccagca gcagcagcac ccgggggggtg gcggcggcgg ctggacgtcc   2400
atgctgccgt acaactggag caccaacaac atgcaacaca tggcggcggt ggcggcggcg   2460
cctggcggcc cggcgggcga ggaggacgag ttccaagcct atcgccgcag cagcagcggt   2520
ggcggcgggt gctacagcgg cggcggcggc ggcaaggtcc gacccaaggg ctcaccgcaa   2580
cacgagtcgg ccgcgccggc catgcgccac gtgagcagca gccaccgcct gcacggcccc   2640
gccgcctcgg cccagctgtc cctctccctg gaccccatgc ccgccgccac caccgtcacc   2700
acagccaccg gcgccggcgc ggccgccgcc gccgccgccg ctgccgccac cgcccctggc   2760
gccgccggcg ccagggcggc cgccgccgcc gtggccgccg ccggccctgc tgacgacgac   2820
gacgagacgt gtctgttcct gtcgccggcc gctactgaga tgacgacggc gggtggcggc   2880
ggcggcctgc gccacgtggc cagcggcagc gccctgttca gctacgacac ctcggcgccg   2940
ccggccccgc ccctggcgcc gccgccggcc ccggctcagg aggccaggca gcagcccacc   3000
atgcctgctg agcagcagca ggagctgcag cggcagccgt cagcgattgc ctgcccgcgg   3060
ccctccctgg cgcagccgca gcagcagcag ccgtacgcga acagcctgtg gcagcagcag   3120
ccgcaacagc cgcagcagcc gcaacagctg cagccgcagc accacatgca gcaccagcac   3180
atgcagcaca tgcacctgca acaataccag cagcgccagc agccgcaaca gcagcgccct   3240
caacagcagc accagcagcc gcaccagcac cagcagcacc agcagcagca ccaggcgggc   3300
ggccgccagc aacacgcgct ggcccacctg ttgcacctgg ctcccacgcc gctgccgctg   3360
cgcgcctgga cgccgcccaa cctgttcgac accgcccacc tgcacctgga ctttggctgc   3420
cccgactcgc cgctcctgga cgccctggga gggtccggcg gcggcactgc cgcagccgcc   3480
ggcgccggca gcggcggcgc ggccgccact gcctgtaccg ctggtgcggc tgctgctgct   3540
gctgctgctg aggcagctgc tgccgcggtg cctgctccag gtgcgggtgt tggtgcgggc   3600
ggtgacggca gcagctccac cagctcagcc ccgtcgggtg aggccggcgg cagcggcagc   3660
ggcagcggcg gggccgagcc cggcaccgcc cgcagcgtgc aggctggcgc agcagcagag   3720
gcggcggcgg accgcagcga cgcagccgtg atgcagatga tgaagcggga gagcagcttc   3780
ggcttccttg ctaacgccgc cggggctgcc gccgccgcca cgggcagcct tacggtcggc   3840
agcgcggccc ctgctgctgc tgctggtacg gctgctgccg cgccctctgc ggcttggccc   3900
ggggccctgc aggcctgcaa cgccgccgcc accgccgccg ctgctgcggc cgcaagcgct   3960
accgcctccg ccgccagctc gcaggccatg ccgtcagcgc cttcctcgcc gggcgtctgg   4020
ccgccggctg cgacggcggc gccagcgctg ccctacctgc cgccgctggc gcctctgggc   4080
gggccgccgg cgctgccgtc gccgccgtgc tcgccgctga tctggaacgg gctgggcatg   4140
gcggcgccgc tgccgccgca gatgcaccac gcgctgctcg gcagcacgtc ggcgccgccg   4200
cctcaacacc agcagcagca gcagcagcag cagcaccacc agcaggcagc gacggctgcg   4260
tctgccgacg ctgctgctag taccgctggt gcgggtgcgg gtgcgggtgc cgctcctgcc   4320
gcaccgtaca tgctgcctgc cggctactac taccaccccg gccccgtgcc gacttggcac   4380
caccccgtca gcagcttcca cggccccctg tacgggcccg tgacttaccc gcccatgccg   4440
gctgcagccg ctgcagtgcc cgcggctgcg gctgcggcag tgccgcagta aacagccagc   4500
ggcagctgcg ctgctgccgc caacaggcac tgggcgcgag tgctggcagg cggggtggtt   4560
cgccgtgtga gcgtatgtaa taatagacca gc                                 4592
```

<210> SEQ ID NO 49
<211> LENGTH: 4023
<212> TYPE: DNA
<213> ORGANISM: Chlamydomonas reinhardtii

<400> SEQUENCE: 49

```
atgtcgcgcc ggtccgcagc tggtggcccg ccgcggcacc caactgccaa acttaaaggt     60
ggatggagcc cggaggaaga tgccctgctc accaggctgg ttaagaagtt cggcgagggc    120
aactggagcc ccatcgcgcg cgccctgaac gaggccaccg gcaagaccga ggccactggc    180
cgcatcggca agcagtgccg cgagcgatgg aaccaccacc tgtcgccggg gctgcgcaag    240
gacccctgga cgccggagga ggaggtgctg gtggtggatg ctcacaagag gcttggcaac    300
aggtggagcg acatcgcgcg ctgcatcccc ggacgtagcg agaacgcagt caagaaccac    360
tggaacgcca cgctgcgcaa gcgcgtcacg cccgagaacc cggcgggccc attgaaggag    420
taccttgact cactcaacct gacagtggcg ccacgcaaga ggggcggcgg cggcggcggc    480
ggcggcggtg gaggcggcgg cgccaagcgc aagcgcaaca acaggggcag ccaggaggag    540
gacacgtccg aggaccctga cgaggacctg ctgcctgacg acctggatga ctctctggac    600
gactccacca ccagccgcac cgcacacacc gcagcagcgg ccgcggcatc aggcggagga    660
agaggccgga ctgccagccg cgctacaacc actggcggcg gcggcggcag ccgcgctgca    720
cacgccgccg ccgcggcccg cacaacctcg gcgccgactg ccgccgccgc cgtcactgcc    780
gccaccgtcg ccgccaacag cccggacagc tcgtcggctg gcggcgccgt tggcccggcc    840
gcggccgacg ccgcgcactc ggctggcggc ggcgccgttg tttgcggcgg cgcctacagc    900
agcggcggcg tggtcacctt cgccggcgcc ggcttgctgt gcagcgccgc tgtccccacc    960
accaccgtca ccaccgcggc ggtgccgctg gcgtcagacg cgggtgtggg tgtggacgac   1020
ggtgcggacg acctggcgcc tggcgtgcgc cgctcctccc gccgcgccgc acagctgagc   1080
agccagcgcc tgcgcgacat ggtggaggcg gagcgccgcc tgatggacga gctggccgag   1140
gacgaggagg cgcaggagca gcagcagatg caggccgcag aggcggcgga ggcggctgca   1200
ggggcggccg cagaggcggc agaggcggca gagatgcagg ctgagatgca ggtgaagcga   1260
gcggaggcgg gcgagcctgc gggcgccagc gtcggctccg gccgcggcca cggcggcggc   1320
ggcggcggcg gcggcggcgg cggcgccagg gccgagtacg gcgctgaggc ggaggtgtcc   1380
agcggcggcg cggccaagag gcggcgccgc gacggcggag gtgcggcggc ggcggcggcg   1440
gcgcaacgtg ccggtgcgcc gcagcggcgc ccgcccgccc gcagcgagag tgtgtgcgac   1500
agcgccggca tccgcatggc cccgctccag aagccgccgc agcccgccct gcccagccag   1560
catcaacagc aagcgctcca ccaccaactc cagcaccagc atcagcagcc agcgatgtcg   1620
ccctttggct acgccgccag ccaggccgaa cccaccgctg ccgccgccgc agcagccgcc   1680
gccggctgca tggtaatgcc ccgcgtcgcg tccagcgccg ccctggcgcc tggcgccgac   1740
gccagcggcg gcggtggcga ccgtgcggcc ctggcacccc ccggcagcat gctggcgcac   1800
gccgctactg ccgcctccgg cttcccggcg gcagcagctg ctaccgctgc tacagccggc   1860
agcccctacc acccgcacca cccgcaccag cagcagcagc acccgggggg tggcggcggc   1920
ggctggacgt ccatgctgcc gtacaactgg agcaccaaca acatgcaaca catggcggcg   1980
gtggcggcgg cgcctggcgg cccggcgggc gaggaggacg agttccaagc ctatcgccgc   2040
agcagcagcg gtggcggcgg gtgctacagc ggcggcggcg gcggcaaggt ccgacccaag   2100
ggctcaccgc aacacgagtc ggccgcgccg gccatgcgcc acgtgagcag cagccaccgc   2160
```

ctgcacggcc ccgccgcctc ggcccagctg tccctctccc tggaccccat gcccgccgcc 2220
accaccgtca ccacagccac cggcgccggc gcggccgccg ccgccgccgc cgctgccgcc 2280
accgcccctg gcgccgccgg cgccagggcg gccgccgccg ccgtggccgc cgccggccct 2340
gctgacgacg acgacgagac gtgtctgttc ctgtcgccgg ccgctactga gatgacgacg 2400
gcgggtggcg gcggcggcct gcgccacgtg gccagcggca gcgccctgtt cagctacgac 2460
acctcggcgc cgccggcccc gcccctggcg ccgccgccgg ccccggctca ggaggccagg 2520
cagcagccca ccatgcctgc tgagcagcag caggagctgc agcggcagcc gtcagcgatt 2580
gcctgcccgc ggccctccct ggcgcagccg cagcagcagc agccgtacgc gaacagcctg 2640
tggcagcagc agccgcaaca gccgcagcag ccgcaacagc tgcagccgca gcaccacatg 2700
cagcaccagc acatgcagca catgcacctg caacaatacc agcagcgcca gcagccgcaa 2760
cagcagcgcc ctcaacagca gcaccagcag ccgcaccagc accagcagca ccagcagcag 2820
caccaggcgg gcggccgcca gcaacacgcg ctggcccacc tgttgcacct ggctcccacg 2880
ccgctgccgc tgcgcgcctg gacgccgccc aacctgttcg acaccgccca cctgcacctg 2940
gactttggct gccccgactc gccgctcctg gacgccctgg gagggtccgg cggcggcact 3000
gccgcagccg ccggcgccgg cagcggcggc gcggccgcca ctgcctgtac cgctggtgcg 3060
gctgctgctg ctgctgctgc tgaggcagct gctgccgcgg tgcctgctcc aggtgcgggt 3120
gttggtgcgg gcggtgacgg cagcagctcc accagctcag ccccgtcggg tgaggccggc 3180
ggcagcggca gcggcagcgg cggggccgag cccggcaccg cccgcagcgt gcaggctggc 3240
gcagcagcag aggcggcggc ggaccgcagc gacgcagccg tgatgcagat gatgaagcgg 3300
gagagcagct tcggcttcct tgctaacgcc gccggggctg ccgccgccgc cacgggcagc 3360
cttacggtcg gcagcgcggc ccctgctgct gctgctggta cggctgctgc cgcgccctct 3420
gcggcttggc ccggggccct gcaggcctgc aacgccgccg ccaccgccgc cgctgctgcg 3480
gccgcaagcg ctaccgcctc cgccgccagc tcgcaggcca tgccgtcagc gccttcctcg 3540
ccgggcgtct ggccgccggc tgcgacggcg gcgccagcgc tgccctacct gccgccgctg 3600
gcgcctctgg gcgggccgcc ggcgctgccg tcgccgccgt gctcgccgct gatctggaac 3660
gggctgggca tggcggcgcc gctgccgccg cagatgcacc acgcgctgct cggcagcacg 3720
tcggcgccgc cgcctcaaca ccagcagcag cagcagcagc agcagcacca ccagcaggca 3780
gcgacggctg cgtctgccga cgctgctgct agtaccgctg gtgcgggtgc gggtgcgggt 3840
gccgctcctg ccgcaccgta catgctgcct gccggctact actaccaccc cggccccgtg 3900
ccgacttggc accaccccgt cagcagcttc cacggccccc tgtacgggcc cgtgacttac 3960
ccgcccatgc cggctgcagc cgctgcagtg cccgcggctg cggctgcggc agtgccgcag 4020
taa 4023

<210> SEQ ID NO 50
<211> LENGTH: 1340
<212> TYPE: PRT
<213> ORGANISM: Chlamydomonas reinhardtii

<400> SEQUENCE: 50

Met Ser Arg Arg Ser Ala Ala Gly Gly Pro Pro Arg His Pro Thr Ala
1 5 10 15

Lys Leu Lys Gly Gly Trp Ser Pro Glu Glu Asp Ala Leu Leu Thr Arg
20 25 30

```
Leu Val Lys Lys Phe Gly Glu Gly Asn Trp Ser Pro Ile Ala Arg Ala
        35                  40                  45

Leu Asn Glu Ala Thr Gly Lys Thr Glu Ala Thr Gly Arg Ile Gly Lys
    50                  55                  60

Gln Cys Arg Glu Arg Trp Asn His His Leu Ser Pro Gly Leu Arg Lys
65                  70                  75                  80

Asp Pro Trp Thr Pro Glu Glu Glu Val Leu Val Val Asp Ala His Lys
                85                  90                  95

Arg Leu Gly Asn Arg Trp Ser Asp Ile Ala Arg Cys Ile Pro Gly Arg
            100                 105                 110

Ser Glu Asn Ala Val Lys Asn His Trp Asn Ala Thr Leu Arg Lys Arg
        115                 120                 125

Val Thr Pro Glu Asn Pro Ala Gly Pro Leu Lys Glu Tyr Leu Asp Ser
    130                 135                 140

Leu Asn Leu Thr Val Ala Pro Arg Lys Arg Gly Gly Gly Gly Gly Gly
145                 150                 155                 160

Gly Gly Gly Gly Gly Gly Gly Ala Lys Arg Lys Arg Asn Asn Arg Gly
                165                 170                 175

Ser Gln Glu Glu Asp Thr Ser Glu Asp Pro Asp Glu Asp Leu Leu Pro
            180                 185                 190

Asp Asp Leu Asp Asp Ser Leu Asp Asp Ser Thr Thr Ser Arg Thr Ala
        195                 200                 205

His Thr Ala Ala Ala Ala Ala Ala Ser Gly Gly Gly Arg Gly Arg Thr
    210                 215                 220

Ala Ser Arg Ala Thr Thr Thr Gly Gly Gly Gly Gly Ser Arg Ala Ala
225                 230                 235                 240

His Ala Ala Ala Ala Ala Arg Thr Thr Ser Ala Pro Thr Ala Ala Ala
                245                 250                 255

Ala Val Thr Ala Ala Thr Val Ala Ala Asn Ser Pro Asp Ser Ser Ser
            260                 265                 270

Ala Gly Gly Ala Val Gly Pro Ala Ala Ala Asp Ala Ala His Ser Ala
        275                 280                 285

Gly Gly Gly Ala Val Val Cys Gly Gly Ala Tyr Ser Ser Gly Gly Val
    290                 295                 300

Val Thr Phe Ala Gly Ala Gly Leu Leu Cys Ser Ala Ala Val Pro Thr
305                 310                 315                 320

Thr Thr Val Thr Thr Ala Ala Val Pro Leu Ala Ser Asp Ala Gly Val
                325                 330                 335

Gly Val Asp Asp Gly Ala Asp Asp Leu Ala Pro Gly Val Arg Arg Ser
            340                 345                 350

Ser Arg Arg Ala Ala Gln Leu Ser Ser Gln Arg Leu Arg Asp Met Val
        355                 360                 365

Glu Ala Glu Arg Arg Leu Met Asp Glu Leu Ala Glu Asp Glu Glu Ala
    370                 375                 380

Gln Glu Gln Gln Gln Met Gln Ala Ala Glu Ala Ala Glu Ala Ala Ala
385                 390                 395                 400

Gly Ala Ala Ala Glu Ala Ala Glu Ala Ala Glu Met Gln Ala Glu Met
                405                 410                 415

Gln Val Lys Arg Ala Glu Ala Gly Glu Pro Ala Gly Ala Ser Val Gly
            420                 425                 430

Ser Gly Arg Gly His Gly Gly Gly Gly Gly Gly Gly Gly Gly Gly Gly
        435                 440                 445

Ala Arg Ala Glu Tyr Gly Ala Glu Ala Glu Val Ser Ser Gly Gly Ala
```

```
    450                 455                 460

Ala Lys Arg Arg Arg Arg Asp Gly Gly Gly Ala Ala Ala Ala Ala Ala
465                 470                 475                 480

Ala Gln Arg Ala Gly Ala Pro Gln Arg Arg Pro Pro Ala Arg Ser Glu
                485                 490                 495

Ser Val Cys Asp Ser Ala Gly Ile Arg Met Ala Pro Leu Gln Lys Pro
            500                 505                 510

Pro Gln Pro Ala Leu Pro Ser Gln His Gln Gln Gln Ala Leu His His
        515                 520                 525

Gln Leu Gln His Gln His Gln Gln Pro Ala Met Ser Pro Phe Gly Tyr
    530                 535                 540

Ala Ala Ser Gln Ala Glu Pro Thr Ala Ala Ala Ala Ala Ala Ala Ala
545                 550                 555                 560

Ala Gly Cys Met Val Met Pro Arg Val Ala Ser Ser Ala Ala Leu Ala
                565                 570                 575

Pro Gly Ala Asp Ala Ser Gly Gly Gly Gly Asp Arg Ala Ala Leu Ala
            580                 585                 590

Pro Pro Gly Ser Met Leu Ala His Ala Ala Thr Ala Ala Ser Gly Phe
        595                 600                 605

Pro Ala Ala Ala Ala Ala Thr Ala Ala Thr Ala Gly Ser Pro Tyr His
    610                 615                 620

Pro His His Pro His Gln Gln Gln Gln His Pro Gly Gly Gly Gly Gly
625                 630                 635                 640

Gly Trp Thr Ser Met Leu Pro Tyr Asn Trp Ser Thr Asn Asn Met Gln
                645                 650                 655

His Met Ala Ala Val Ala Ala Ala Pro Gly Gly Pro Ala Gly Glu Glu
            660                 665                 670

Asp Glu Phe Gln Ala Tyr Arg Arg Ser Ser Ser Gly Gly Gly Gly Cys
        675                 680                 685

Tyr Ser Gly Gly Gly Gly Gly Lys Val Arg Pro Lys Gly Ser Pro Gln
    690                 695                 700

His Glu Ser Ala Ala Pro Ala Met Arg His Val Ser Ser Ser His Arg
705                 710                 715                 720

Leu His Gly Pro Ala Ala Ser Ala Gln Leu Ser Leu Ser Leu Asp Pro
                725                 730                 735

Met Pro Ala Ala Thr Thr Val Thr Thr Ala Thr Gly Ala Gly Ala Ala
            740                 745                 750

Ala Ala Ala Ala Ala Ala Ala Ala Thr Ala Pro Gly Ala Ala Gly Ala
        755                 760                 765

Arg Ala Ala Ala Ala Ala Val Ala Ala Ala Gly Pro Ala Asp Asp Asp
    770                 775                 780

Asp Glu Thr Cys Leu Phe Leu Ser Pro Ala Ala Thr Glu Met Thr Thr
785                 790                 795                 800

Ala Gly Gly Gly Gly Gly Leu Arg His Val Ala Ser Gly Ser Ala Leu
                805                 810                 815

Phe Ser Tyr Asp Thr Ser Ala Pro Pro Ala Pro Pro Leu Ala Pro Pro
            820                 825                 830

Pro Ala Pro Ala Gln Glu Ala Arg Gln Gln Pro Thr Met Pro Ala Glu
        835                 840                 845

Gln Gln Gln Glu Leu Gln Arg Gln Pro Ser Ala Ile Ala Cys Pro Arg
    850                 855                 860

Pro Ser Leu Ala Gln Pro Gln Gln Gln Gln Pro Tyr Ala Asn Ser Leu
865                 870                 875                 880
```

-continued

```
Trp Gln Gln Gln Pro Gln Gln Pro Gln Gln Pro Gln Gln Leu Gln Pro
                885                 890                 895

Gln His His Met Gln His Gln His Met Gln His Met His Leu Gln Gln
            900                 905                 910

Tyr Gln Gln Arg Gln Gln Pro Gln Gln Gln Arg Pro Gln Gln Gln His
        915                 920                 925

Gln Gln Pro His Gln His Gln Gln His Gln Gln Gln His Gln Ala Gly
    930                 935                 940

Gly Arg Gln Gln His Ala Leu Ala His Leu Leu His Leu Ala Pro Thr
945                 950                 955                 960

Pro Leu Pro Leu Arg Ala Trp Thr Pro Pro Asn Leu Phe Asp Thr Ala
                965                 970                 975

His Leu His Leu Asp Phe Gly Cys Pro Asp Ser Pro Leu Leu Asp Ala
            980                 985                 990

Leu Gly Gly Ser Gly Gly Gly Thr  Ala Ala Ala Ala Gly  Ala Gly Ser
        995                 1000                1005

Gly Gly  Ala Ala Ala Thr Ala  Cys Thr Ala Gly Ala  Ala Ala Ala
    1010                 1015                1020

Ala Ala  Ala Ala Glu Ala Ala  Ala Ala Ala Val Pro  Ala Pro Gly
    1025                 1030                1035

Ala Gly  Val Gly Ala Gly Gly  Asp Gly Ser Ser Ser  Thr Ser Ser
    1040                 1045                1050

Ala Pro  Ser Gly Glu Ala Gly  Gly Ser Gly Ser Gly  Ser Gly Gly
    1055                 1060                1065

Ala Glu  Pro Gly Thr Ala Arg  Ser Val Gln Ala Gly  Ala Ala Ala
    1070                 1075                1080

Glu Ala  Ala Ala Asp Arg Ser  Asp Ala Ala Val Met  Gln Met Met
    1085                 1090                1095

Lys Arg  Glu Ser Ser Phe Gly  Phe Leu Ala Asn Ala  Ala Gly Ala
    1100                 1105                1110

Ala Ala  Ala Ala Thr Gly Ser  Leu Thr Val Gly Ser  Ala Ala Pro
    1115                 1120                1125

Ala Ala  Ala Ala Gly Thr Ala  Ala Ala Ala Pro Ser  Ala Ala Trp
    1130                 1135                1140

Pro Gly  Ala Leu Gln Ala Cys  Asn Ala Ala Ala Thr  Ala Ala Ala
    1145                 1150                1155

Ala Ala  Ala Ala Ser Ala Thr  Ala Ser Ala Ala Ser  Ser Gln Ala
    1160                 1165                1170

Met Pro  Ser Ala Pro Ser Ser  Pro Gly Val Trp Pro  Pro Ala Ala
    1175                 1180                1185

Thr Ala  Ala Pro Ala Leu Pro  Tyr Leu Pro Pro Leu  Ala Pro Leu
    1190                 1195                1200

Gly Gly  Pro Pro Ala Leu Pro  Ser Pro Pro Cys Ser  Pro Leu Ile
    1205                 1210                1215

Trp Asn  Gly Leu Gly Met Ala  Ala Pro Leu Pro Pro  Gln Met His
    1220                 1225                1230

His Ala  Leu Leu Gly Ser Thr  Ser Ala Pro Pro Pro  Gln His Gln
    1235                 1240                1245

Gln Gln  Gln Gln Gln Gln Gln  His His Gln Gln Ala  Ala Thr Ala
    1250                 1255                1260

Ala Ser  Ala Asp Ala Ala Ala  Ser Thr Ala Gly Ala  Gly Ala Gly
    1265                 1270                1275
```

-continued

Ala Gly Ala Ala Pro Ala Ala Pro Tyr Met Leu Pro Ala Gly Tyr
1280 1285 1290

Tyr Tyr His Pro Gly Pro Val Pro Thr Trp His His Pro Val Ser
1295 1300 1305

Ser Phe His Gly Pro Leu Tyr Gly Pro Val Thr Tyr Pro Pro Met
1310 1315 1320

Pro Ala Ala Ala Ala Ala Val Pro Ala Ala Ala Ala Ala Ala Val
1325 1330 1335

Pro Gln
1340

<210> SEQ ID NO 51
<211> LENGTH: 1873
<212> TYPE: DNA
<213> ORGANISM: Chlamydomonas reinhardtii

<400> SEQUENCE: 51
gacaccataa gaacacatat attgtattca taacctagga aagcatgttc gcaacctctt 60
tcggcctggc gcattcaggc cgggtgcttc ttgccccctc gcacaatgct gccgcatgca 120
gcacaagcta tattactcaa cgcgggcatc ctctacgagc gatcctgggc cattggcggt 180
ctgcgctgac gctagctcga agaaccctct cgagaggttg cgcgtcacgc ctctgactga 240
gcgcggtgcg cgggcggctc ttctgcagga gcttgacctg acctggtcag agtgggagga 300
gcggtaccag cccacgccag cagagcgctg tctcgctgag gagctggggg tggggcaatc 360
cactgtgatg ctggcggcgg tgcagaaccc gggactgagt gctcttgacg cggccagcca 420
ggtccttccc tcggtgcggg cgctgcgctc ggccggcatt ggggcgcagg acgcctggtt 480
cctggtgtcc aagcgctggc agctcctggc acagccggcg gcgctgtcgc gctggctgga 540
cttcctgggg gtgtacggca tgcagccgcg cgactgccag aacttcctcc tgcgctccca 600
gccgtccttc ctggcggcca ccacactgta ccaggctggc caggtggtga ccttcctcaa 660
aggactgggc ctcaaagacg acatgctggc ggcgcgtgtg ctgtgcgtgt ggccggagct 720
gctggggcgg gacgtggacg cgcagctgcg cccagtggtc accttcctca tgagcctggg 780
gctggaggtg gcaggcgtgg gccgggcggt ggtgctgtgg cctgagatcc tgctcaagga 840
cgtggagggg cagttggcgc cctgggtggc atacctgcga ggactgggct gcaccaccgc 900
ccaggtggcc gaggtcgtct gcctgtgccc acacctgctg ggcttcaagc ctgaggaggt 960
gtttggcggc gtgctggcgg cgctgtcaga cgtgggcatc agcgccgccg acgtgcgaga 1020
catggtgtcg gcctcgctcg cattcctcat cacgccctcc gcctccgcgg cggtgcgcgc 1080
ggcagtggac tgcctgcagc agcagggctt cacaaaggag cagattcgcg ccatggccct 1140
gacgcggccg gagctgctgg ccgtcaagcc gcatgacctg gatcgctcgc tgcgcttcgt 1200
gcgcgagacc atcggcggcg acaacggcac ggtgctgtcc tgcccgctgc tgttggccaa 1260
gccgctgggg caggtgctgg ggccgaggta cagcttcatc cagaagcagg gcctcgcgca 1320
caagtacacc aagagagacg tcgtcgccgg cggagccgac cgaactgacg gcgccagcgg 1380
cagcggcagt gacggcagtg ccagcagcag cggcaacagc acgggcgggt ttgagttcta 1440
caagctgctg atggcggagg acgatgcctg gtgtgcctcc ctgggcctgt ccgtaaacga 1500
gtaccagggc tttaaactgg tgtgggatga ggagtacagt ctgcagctgc accaggaggc 1560
ggcatcagag ttccaggctg aactcaaaaa gctgggcatt tacgagggta tctaggcact 1620
attgcccaag tgattgcatg cagctttcct tgggttcggg gtgaattttc aaaccgattg 1680
gggattacac ggaagatgtg tggattggcc tgtacggtga cggtgctact aagtaggagc 1740
aatcagcctg cccattgggc gggattgcca ttcatgtcgg gctgtgactg gttagcctgg 1800
ctgcttagct tggctgctta gcttcgactc gcggtagtta gcatgtcagc tacccttgta 1860
acaaacacac acg 1873

<210> SEQ ID NO 52
<211> LENGTH: 1500
<212> TYPE: DNA
<213> ORGANISM: Chlamydomonas reinhardtii

<400> SEQUENCE: 52
atgcagcaca agctatatta ctcaacgcgg gcatcctcta cgagcgatcc tgggccattg 60
gcggtctgcg ctgacgctag ctcgaagaac cctctcgaga ggttgcgcgt cacgcctctg 120
actgagcgcg gtgcgcgggc ggctcttctg caggagcttg acctgacctg gtcagagtgg 180
gaggagcggt accagcccac gccagcagag cgctgtctcg ctgaggagct gggggtgggg 240
caatccactg tgatgctggc ggcggtgcag aacccgggac tgagtgctct tgacgcggcc 300
agccaggtcc ttccctcggt gcgggcgctg cgctcggccg gcattggggc gcaggacgcc 360
tggttcctgg tgtccaagcg ctggcagctc ctggcacagc cggcggcgct gtcgcgctgg 420
ctggacttcc tgggggtgta cggcatgcag ccgcgcgact gccagaactt cctcctgcgc 480
tcccagccgt ccttcctggc ggccaccaca ctgtaccagg ctggccaggt ggtgaccttc 540
ctcaaaggac tgggcctcaa agacgacatg ctggcggcgc gtgtgctgtg cgtgtggccg 600
gagctgctgg ggcgggacgt ggacgcgcag ctgcgcccag tggtcacctt cctcatgagc 660
ctggggctgg aggtggcagg cgtgggccgg gcggtggtgc tgtggcctga gatcctgctc 720
aaggacgtgg aggggcagtt ggcgccctgg gtggcatacc tgcgaggact gggctgcacc 780
accgcccagg tggccgaggt cgtctgcctg tgcccacacc tgctgggctt caagcctgag 840
gaggtgtttg gcggcgtgct ggcggcgctg tcagacgtgg gcatcagcgc cgccgacgtg 900
cgagacatgg tgtcggcctc gctcgcattc ctcatcacgc cctccgcctc cgcggcggtg 960
cgcgcggcag tggactgcct gcagcagcag ggcttcacaa aggagcagat tcgcgccatg 1020
gccctgacgc ggccggagct gctggccgtc aagccgcatg acctggatcg ctcgctgcgc 1080
ttcgtgcgcg agaccatcgg cggcgacaac ggcacggtgc tgtcctgccc gctgctgttg 1140
gccaagccgc tggggcaggt gctggggccg aggtacagct tcatccagaa gcagggcctc 1200
gcgcacaagt acaccaagag agacgtcgtc gccggcggag ccgaccgaac tgacggcgcc 1260
agcggcagcg gcagtgacgg cagtgccagc agcagcggca acagcacggg cgggtttgag 1320
ttctacaagc tgctgatggc ggaggacgat gcctggtgtg cctccctggg cctgtccgta 1380
aacgagtacc agggctttaa actggtgtgg gatgaggagt acagtctgca gctgcaccag 1440
gaggcggcat cagagttcca ggctgaactc aaaaagctgg gcatttacga gggtatctag 1500

<210> SEQ ID NO 53
<211> LENGTH: 499
<212> TYPE: PRT
<213> ORGANISM: Chlamydomonas reinhardtii

<400> SEQUENCE: 53

Met Gln His Lys Leu Tyr Tyr Ser Thr Arg Ala Ser Ser Thr Ser Asp
1 5 10 15

Pro Gly Pro Leu Ala Val Cys Ala Asp Ala Ser Ser Lys Asn Pro Leu
20 25 30

-continued

```
Glu Arg Leu Arg Val Thr Pro Leu Thr Glu Arg Gly Ala Arg Ala Ala
        35                  40                  45

Leu Leu Gln Glu Leu Asp Leu Thr Trp Ser Glu Trp Glu Glu Arg Tyr
    50                  55                  60

Gln Pro Thr Pro Ala Glu Arg Cys Leu Ala Glu Glu Leu Gly Val Gly
65                  70                  75                  80

Gln Ser Thr Val Met Leu Ala Ala Val Gln Asn Pro Gly Leu Ser Ala
                85                  90                  95

Leu Asp Ala Ala Ser Gln Val Leu Pro Ser Val Arg Ala Leu Arg Ser
            100                 105                 110

Ala Gly Ile Gly Ala Gln Asp Ala Trp Phe Leu Val Ser Lys Arg Trp
        115                 120                 125

Gln Leu Leu Ala Gln Pro Ala Ala Leu Ser Arg Trp Leu Asp Phe Leu
    130                 135                 140

Gly Val Tyr Gly Met Gln Pro Arg Asp Cys Gln Asn Phe Leu Leu Arg
145                 150                 155                 160

Ser Gln Pro Ser Phe Leu Ala Ala Thr Thr Leu Tyr Gln Ala Gly Gln
                165                 170                 175

Val Val Thr Phe Leu Lys Gly Leu Gly Leu Lys Asp Asp Met Leu Ala
            180                 185                 190

Ala Arg Val Leu Cys Val Trp Pro Glu Leu Leu Gly Arg Asp Val Asp
        195                 200                 205

Ala Gln Leu Arg Pro Val Val Thr Phe Leu Met Ser Leu Gly Leu Glu
    210                 215                 220

Val Ala Gly Val Gly Arg Ala Val Val Leu Trp Pro Glu Ile Leu Leu
225                 230                 235                 240

Lys Asp Val Glu Gly Gln Leu Ala Pro Trp Val Ala Tyr Leu Arg Gly
                245                 250                 255

Leu Gly Cys Thr Thr Ala Gln Val Ala Glu Val Val Cys Leu Cys Pro
            260                 265                 270

His Leu Leu Gly Phe Lys Pro Glu Glu Val Phe Gly Gly Val Leu Ala
        275                 280                 285

Ala Leu Ser Asp Val Gly Ile Ser Ala Ala Asp Val Arg Asp Met Val
    290                 295                 300

Ser Ala Ser Leu Ala Phe Leu Ile Thr Pro Ser Ala Ser Ala Ala Val
305                 310                 315                 320

Arg Ala Ala Val Asp Cys Leu Gln Gln Gln Gly Phe Thr Lys Glu Gln
                325                 330                 335

Ile Arg Ala Met Ala Leu Thr Arg Pro Glu Leu Leu Ala Val Lys Pro
            340                 345                 350

His Asp Leu Asp Arg Ser Leu Arg Phe Val Arg Glu Thr Ile Gly Gly
        355                 360                 365

Asp Asn Gly Thr Val Leu Ser Cys Pro Leu Leu Leu Ala Lys Pro Leu
    370                 375                 380

Gly Gln Val Leu Gly Pro Arg Tyr Ser Phe Ile Gln Lys Gln Gly Leu
385                 390                 395                 400

Ala His Lys Tyr Thr Lys Arg Asp Val Val Ala Gly Gly Ala Asp Arg
                405                 410                 415

Thr Asp Gly Ala Ser Gly Ser Gly Ser Asp Gly Ser Ala Ser Ser Ser
            420                 425                 430

Gly Asn Ser Thr Gly Gly Phe Glu Phe Tyr Lys Leu Leu Met Ala Glu
        435                 440                 445
```

```
Asp Asp Ala Trp Cys Ala Ser Leu Gly Leu Ser Val Asn Glu Tyr Gln
    450                 455                 460

Gly Phe Lys Leu Val Trp Asp Glu Glu Tyr Ser Leu Gln Leu His Gln
465                 470                 475                 480

Glu Ala Ala Ser Glu Phe Gln Ala Glu Leu Lys Lys Leu Gly Ile Tyr
                485                 490                 495

Glu Gly Ile


<210> SEQ ID NO 54
<211> LENGTH: 2263
<212> TYPE: DNA
<213> ORGANISM: Chlamydomonas reinhardtii

<400> SEQUENCE: 54

ggagtgatgc aggtcggcat gccgtgcata cgacttggtc gctctaccga gttcaccggt     60

cgcattcaag tcacctgtat gaaacaatga gagcgcttgt aggacaacgt tgtttggcgc    120

cacaacgcgc accaggttcg cttcatggca cgcttcgtgc ggtgcccagc gcggtggcgc    180

tgcggcgagc gcgtgctagc tgctcttatc cagaatcatc atcgaaccac tcggcgacag    240

cgaccaccac cacgctggag tcgcagctgt ctgaggtgaa cgccagcccg gtgctggtgc    300

tcggcagtcc tgcactgcag ggcgcagacc atgctcagat gtgtgccgcg ctggaggcgc    360

tgcgcgatgc tgtgccgcgg cgctccctgg gcgggctgct ggagcgctac cccgccatcc    420

tcaccgcccc cgtggccacg tgggtggact tcctgggctc cttcggcttc cagcgactgg    480

ccgtgcagga gctgctgttg aattcgccgg acgtgttggc caactcgtcc gtcttccggg    540

cgggccaggt gttcctgttc ctgaagcggc tgggtgtgcc caacgaccaa attgttggcc    600

ccatattcaa gtggcgggcg ctgctgtcgg agcaggtcga cttcgaggcg gccgccgact    660

tcctggctag cgaggctggc atcgcacccg agctgctggg tcaggtggcg tgccagtacc    720

cggcactgct ggcagccccc gttgccaccg agctggcccc ccggctggcc ttcctgcgcg    780

gcctcggccc cgaggcgccg ggcctgttgc gtggcgtgct gcatgaggac tggtacggct    840

gggtgcacgg cctggcgaac tggcccaccg cggtggcgcc caagttggcg gcgctggagg    900

cggtggtgga gggcgggccg caggcggcgg cggcgctgct gcggcgagtg cccgaggcgc    960

tcaaataccc ccccgagagc cgcctggtgc ccaacctgag gctcttgcag ggagccatgg   1020

ggctggacca gcagtcgctg gcggcgctgc tgcgcggcgc ccccgagatc ctgtccctgg   1080

cgccggagca gctggagagc cgctggacct tcctgaccga ggccgcgaac ggcggagagg   1140

ctgacctgct cgcatacccg ccctacctgc tggccagcct ggccaagacc tccgggcccc   1200

ggctcatgtt tgtggcgaca cgcggcctgg cggcacgcct ggcgacgccg ccggcgccgg   1260

cagctgtgca ggagggctcg gcggcagcgg ctgacgaggc ggggcaaagt gggagatggg   1320

gggaagcgga tgaggaggat ggggatgagg gcggtgacgt gggccagggg gcggtgctgg   1380

acctgagatg gttggtggag ggcagcgacg aggacttcct gcggcgggcg gcgctggagc   1440

tgcgacgggc cggcgggcgg cgctcgcctt cgttgtcagc gggggcgttg ctgtacgcct   1500

cgtcaacctt ctcatcttca tcccgagcat caagcccagt gtctgggtct gcatctgggt   1560

cagcagcagc attggggtca ggggcaaggg caggagcggc gggtggggag gaggtgagtg   1620

aggaggagct gttattggtg cggggcgagt acgagacggc ggcggcagag tgggaatcgc   1680

tgttgggctg gtgcgcggac agggcgttca caaaggcggg gcggaagaag tttgaggagc   1740

agctttcgct gttttatttg ctagtgcagg gttgatgatg ttgcgggtgg tgctttgttt   1800
```

gttgtgcttg catgcttttg tgttcacgga ttgagctcga tgccggcgga ctgacgggga 1860
ggacgtagcg gggccagcgc ttgtggcgtg cagtgctggc tgctgccggg cgcatctgtc 1920
ttaggctgat ttatacctag caatcctagt cagatgacta tctgtgtgcg tggcgtggtg 1980
gggcggtcag gcgcagggga gggtcaggcg gttgcagctg cggtgaagca gcgtggcgcc 2040
gtgacatcat gccacatccg aaaggctgta atttttgcca actgcttaaa taagtgggcg 2100
tgtgaggtag tgaagctgtg aagcgccgta cactgccgtg gatggccgat ccaagtacgt 2160
tgccggtgcg tgtgtgcgga tacgtggcgg atactggcgg atatcattgt ggagcttcac 2220
gcggacgtgc cccgtagggt cccaaggcca gctacaacat ctt 2263

<210> SEQ ID NO 55
<211> LENGTH: 1689
<212> TYPE: DNA
<213> ORGANISM: Chlamydomonas reinhardtii

<400> SEQUENCE: 55
atgagagcgc ttgtaggaca acgttgtttg gcgccacaac gcgcaccagg ttcgcttcat 60
ggcacgcttc gtgcggtgcc cagcgcggtg gcgctgcggc gagcgcgtgc tagctgctct 120
tatccagaat catcatcgaa ccactcggcg acagcgacca ccaccacgct ggagtcgcag 180
ctgtctgagg tgaacgccag cccggtgctg gtgctcggca gtcctgcact gcagggcgca 240
gaccatgctc agatgtgtgc cgcgctggag gcgctgcgcg atgctgtgcc gcggcgctcc 300
ctgggcgggc tgctggagcg ctaccccgcc atcctcaccg cccccgtggc cacgtgggtg 360
gacttcctgg gctccttcgg cttccagcga ctggccgtgc aggagctgct gttgaattcg 420
ccggacgtgt tggccaactc gtccgtcttc cgggcgggcc aggtgttcct gttcctgaag 480
cggctgggtg tgcccaacga ccaaattgtt ggccccatat tcaagtggcg ggcgctgctg 540
tcggagcagg tcgacttcga ggcggccgcc gacttcctgg ctagcgaggc tggcatcgca 600
cccgagctgc tgggtcaggt ggcgtgccag tacccggcac tgctggcagc ccccgttgcc 660
accgagctgg ccccccggct ggccttcctg cgcggcctcg gccccgaggc gccgggcctg 720
ttgcgtggcg tgctgcatga ggactggtac ggctgggtgc acggcctggc gaactggccc 780
accgcggtgg cgcccaagtt ggcggcgctg gaggcggtgg tggagggcgg gccgcaggcg 840
gcggcggcgc tgctgcggcg agtgcccgag gcgctcaaat acccccccga gagccgcctg 900
gtgcccaacc tgaggctctt gcagggagcc atggggctgg accagcagtc gctggcggcg 960
ctgctgcgcg gcgcccccga gatcctgtcc ctggcgccgg agcagctgga gagccgctgg 1020
accttcctga ccgaggccgc gaacggcgga gaggctgacc tgctcgcata cccgccctac 1080
ctgctggcca gcctggccaa gacctccggg ccccggctca tgtttgtggc gacacgcggc 1140
ctggcggcac gcctggcgac gccgccggcg ccggcagctg tgcaggaggg ctcggcggca 1200
gcggctgacg aggcggggca aagtgggaga tgggggggaag cggatgagga ggatggggat 1260
gagggcggtg acgtgggcca gggggcggtg ctggacctga gatggttggt ggagggcagc 1320
gacgaggact tcctgcggcg ggcggcgctg gagctgcgac gggccggcgg gcggcgctcg 1380
ccttcgttgt cagcgggggc gttgctgtac gcctcgtcaa ccttctcatc ttcatcccga 1440
gcatcaagcc cagtgtctgg gtctgcatct gggtcagcag cagcattggg gtcaggggca 1500
agggcaggag cggcgggtgg ggaggaggtg agtgaggagg agctgttatt ggtgcggggc 1560
gagtacgaga cggcggcggc agagtgggaa tcgctgttgg gctggtgcgc ggacagggcg 1620
ttcacaaagg cggggcggaa gaagtttgag gagcagcttt cgctgtttta tttgctagtg 1680
cagggttga 1689

<210> SEQ ID NO 56
<211> LENGTH: 562
<212> TYPE: PRT
<213> ORGANISM: Chlamydomonas reinhardtii

<400> SEQUENCE: 56

Met Arg Ala Leu Val Gly Gln Arg Cys Leu Ala Pro Gln Arg Ala Pro
1 5 10 15

Gly Ser Leu His Gly Thr Leu Arg Ala Val Pro Ser Ala Val Ala Leu
20 25 30

Arg Arg Ala Arg Ala Ser Cys Ser Tyr Pro Glu Ser Ser Ser Asn His
35 40 45

Ser Ala Thr Ala Thr Thr Thr Thr Leu Glu Ser Gln Leu Ser Glu Val
50 55 60

Asn Ala Ser Pro Val Leu Val Leu Gly Ser Pro Ala Leu Gln Gly Ala
65 70 75 80

Asp His Ala Gln Met Cys Ala Ala Leu Glu Ala Leu Arg Asp Ala Val
85 90 95

Pro Arg Arg Ser Leu Gly Gly Leu Leu Glu Arg Tyr Pro Ala Ile Leu
100 105 110

Thr Ala Pro Val Ala Thr Trp Val Asp Phe Leu Gly Ser Phe Gly Phe
115 120 125

Gln Arg Leu Ala Val Gln Glu Leu Leu Leu Asn Ser Pro Asp Val Leu
130 135 140

Ala Asn Ser Ser Val Phe Arg Ala Gly Gln Val Phe Leu Phe Leu Lys
145 150 155 160

Arg Leu Gly Val Pro Asn Asp Gln Ile Val Gly Pro Ile Phe Lys Trp
165 170 175

Arg Ala Leu Leu Ser Glu Gln Val Asp Phe Glu Ala Ala Ala Asp Phe
180 185 190

Leu Ala Ser Glu Ala Gly Ile Ala Pro Glu Leu Leu Gly Gln Val Ala
195 200 205

Cys Gln Tyr Pro Ala Leu Leu Ala Ala Pro Val Ala Thr Glu Leu Ala
210 215 220

Pro Arg Leu Ala Phe Leu Arg Gly Leu Gly Pro Glu Ala Pro Gly Leu
225 230 235 240

Leu Arg Gly Val Leu His Glu Asp Trp Tyr Gly Trp Val His Gly Leu
245 250 255

Ala Asn Trp Pro Thr Ala Val Ala Pro Lys Leu Ala Ala Leu Glu Ala
260 265 270

Val Val Glu Gly Gly Pro Gln Ala Ala Ala Ala Leu Leu Arg Arg Val
275 280 285

Pro Glu Ala Leu Lys Tyr Pro Pro Glu Ser Arg Leu Val Pro Asn Leu
290 295 300

Arg Leu Leu Gln Gly Ala Met Gly Leu Asp Gln Gln Ser Leu Ala Ala
305 310 315 320

Leu Leu Arg Gly Ala Pro Glu Ile Leu Ser Leu Ala Pro Glu Gln Leu
325 330 335

Glu Ser Arg Trp Thr Phe Leu Thr Glu Ala Ala Asn Gly Gly Glu Ala
340 345 350

Asp Leu Leu Ala Tyr Pro Pro Tyr Leu Leu Ala Ser Leu Ala Lys Thr
355 360 365

```
Ser Gly Pro Arg Leu Met Phe Val Ala Thr Arg Gly Leu Ala Ala Arg
    370                 375                 380

Leu Ala Thr Pro Pro Ala Pro Ala Ala Val Gln Glu Gly Ser Ala Ala
385                 390                 395                 400

Ala Ala Asp Glu Ala Gly Gln Ser Gly Arg Trp Gly Glu Ala Asp Glu
                405                 410                 415

Glu Asp Gly Asp Glu Gly Gly Asp Val Gly Gln Gly Ala Val Leu Asp
            420                 425                 430

Leu Arg Trp Leu Val Glu Gly Ser Asp Glu Asp Phe Leu Arg Arg Ala
        435                 440                 445

Ala Leu Glu Leu Arg Arg Ala Gly Gly Arg Arg Ser Pro Ser Leu Ser
    450                 455                 460

Ala Gly Ala Leu Leu Tyr Ala Ser Ser Thr Phe Ser Ser Ser Ser Arg
465                 470                 475                 480

Ala Ser Ser Pro Val Ser Gly Ser Ala Ser Gly Ser Ala Ala Ala Leu
                485                 490                 495

Gly Ser Gly Ala Arg Ala Gly Ala Ala Gly Gly Glu Glu Val Ser Glu
            500                 505                 510

Glu Glu Leu Leu Leu Val Arg Gly Glu Tyr Glu Thr Ala Ala Ala Glu
        515                 520                 525

Trp Glu Ser Leu Leu Gly Trp Cys Ala Asp Arg Ala Phe Thr Lys Ala
    530                 535                 540

Gly Arg Lys Lys Phe Glu Glu Gln Leu Ser Leu Phe Tyr Leu Leu Val
545                 550                 555                 560

Gln Gly
```

<210> SEQ ID NO 57
<211> LENGTH: 9174
<212> TYPE: DNA
<213> ORGANISM: Chlamydomonas reinhardtii

<400> SEQUENCE: 57

```
cgtcttattg cacgaccggc gcaaccctcc acctctcgcg tcgtctcgct tgcgtgacag     60

aggcttgaca acttgtcttt ttcctggtcc catgggagac tgaccttcac aaggcaatac    120

ctatgatgta cctataaggc agctgactct tgagtccgcg ttagccccac gcaaactttg    180

agcgcgcgac ggggatcgtt gtcttggccg ggtcgcttca ccagcgtaga cgaaaatgcg    240

gcggcgtcaa ggccagctgc atccatgggg ttttctgctg cggcagcgcg atggcgggct    300

cgccgcgcca cccgtggcgt tagtccacga ccacgtcgcg ttaggtcgcg gcacggcgcc    360

tcccccgggc gcggcacatg ccgttgcggg catgcagcag tgccccctcc agttcattac    420

tatcgacgat gagcgcgtga gccgcctgca cgccgcgctc acagtgcact gcaacagcag    480

ccggtggccg ccgctggtga ctgtggagga ccgcagccgc aacggtacct acctcaacgg    540

ctcgccgctg cgccccggcg cccccgccgt cctgtccagc ggcgacgtgc tgtcgctggt    600

gctgtgcgtc aaccccctca cgcagctgtg cttcgtgttt gaggagtgcc ccgtgccgcc    660

gcccaactgg acacgagccg ccaacgccca agaaggcgcc ggctcatcag cgcagagcgg    720

caacactgct gtccggcgac caaccgccac cggcggtgat gcgctgggag caggcggagc    780

agcaggagca gcggcagggg cagctcccta tccggtactg ccagtcggcc tgcctcgcgc    840

cagcggcaac ctgaacgcgg ccctgagcgc tgcagctgtt gctgctgcgc tggcggccgg    900

ccgtggcacg tcgcgcaaca gccgcggcca ccgcgccggc cgcagcaacc ggtctcccgc    960
```

-continued

```
cgccgccgcc acgtcgactg ctggcaccga gacgctgggg ctggtggacc cgctggcggc   1020
ggcggcgccg caccggctga gcggcacggg cttctctgag ggcggcgtgg agcagtggcc   1080
gtcgggagct gggccgcgcg aggtgaccag cccccagccg tcgctgccgc cggcctcgct   1140
gccgcagtcg cccgaccgcc gccgtatcac acggcagtcc acgggcagtg gtgtgcctcg   1200
ctcgctgtcg cctgacagca gtcccacctc ggtggtgggc gagtcggcac atggcttccc   1260
cctggaaggc ggcggcgggc ggcgccacag cgtcccggtc ggcggtgcct cctgggaccg   1320
gcacgacgac cactggccgg agccgcacag ccccactgcc actccccgct cgcgcgtgca   1380
caatcacacc gttgcgcagg tcctggcggc gctgcacccc aacccgctgt acgccgacca   1440
cctcaccgcg ctggagctag cgcccggcac ggcgccgccc gcctcgccgc cgcgcagccc   1500
ccgctcgacg cccctgcgtg cgcccgtcac tggcgccgcc gcccgcgcca gccgccccag   1560
ccgccgcagc accggcagcg gcatggccgc ggctgacggc caccaccagc ggcaccagcg   1620
gcaccgccgc tcccggacag cgcacctggg agctcacctg cttgccttcg ccgcagcggg   1680
cgtggccgcg ccggcggact cggcggtgtc tgcggctcgc ggcggcattt cgctgagccg   1740
ctcgctcccc caactgctcc ccgtcgattt ggtcggcaac caccagtttc acgagctgcg   1800
gctgcagcag cactcgtccg cccaagccgg cggctacatg tcggctgcgg cggtgccctc   1860
gctgtcgtca gtgtccgact ccacacctgc ctacgccggc tggcccgtcc atggcctggc   1920
cggcagcgga ggcagtgccc ccgctaccag cgccgccacg agcacgagca gcagcagccg   1980
gcacagcttg cacagcccgc ttagtcagcc cagcctgcac agccgctacc tactgaccgg   2040
cggcgcggag gctgtgctca acagcccgcg gcgccagcgc ttcagcactg gcagcggctt   2100
tggaccgccg ctgccggtgt tgccgccgcc gcccttgtca tcggcacctt cggcgtcatc   2160
tgcgtttgca gatccgaccc aggccgaagc cctggcccag gcccatcgcc gtccgcgcgc   2220
tctgtcctac ggctctggca gctttggcct ggaggaagag aacagcggtg gcggcagcgg   2280
cggcagcggc acccacacag ccctggttcc gaggatttca gcccccacgc tggacgcgtt   2340
tgggtccgtg tccgatgccc ccatgctgac accggcgccg ccgtctgcgc ccctgccagc   2400
ctgcggctcc ggctccggct ctcctcgttc cgcccccgcc gccgccgcag tcatcgtggg   2460
cggcggccca aggtccagcc gcagctcggc gtcgcggccg cagtcccgcc tgctgcgcgt   2520
cagccgcccc aactcgccgc tgcctgggta cgagaacagc ggtggcgtgg gctcaaccgg   2580
cttcgccgct gcatgggctg caggcggcgc tggtgctgct agctgccgcg gcggtgatgt   2640
tggtaccgct ggtgctggtg ctgtggatga gctggcgtat ggcatggaca tgcaagggca   2700
tgagggcgga aacaactgcg agctgctggc tccgttgcca agctcgccgc gctttgggcc   2760
tggaggccgc ggcggcgctg ggtcgttgcc tgatgctgca tcggagtttg gccagggtgc   2820
cagtggtgca ggttctggcg tggctggggc tggagtaggg gggacggcga ccgccgtgcc   2880
gctgcgtcgg ctgtgctccg cagcggtggc cgcgctggcg gccgccgccg aggccactgc   2940
gagtgagagc gacactccca gcgagatcac ttgcaaggag ttctccttct cctccctgtc   3000
ccgtcccaca ctctccgcgc ccgccgccgc cagcagcccg cccggtgcca accgcgaccc   3060
ctgctgcagc ccttcagtgc cggccatcgc gctcgagccc gcagcctccg tccctactgc   3120
cgccgccgcc tctgtcaacc ttgaggctag gctgcacacc gccgcagctg acggcggcag   3180
cgggggcagc ccgcgcttcc tccgccgcac ggtctccgcg aacgacggcc cgcaggcaca   3240
gaccctgcac aggcaacagc agctacagct tcagcagcag cagcactttg gtaatgcctc   3300
tgatgcattt ctggtggcgg cggcggcggc aggagctcct ccaactctcc gtgtgtcagc   3360
```

-continued

```
gtcttccgta agggctgctg caccaggccc gcagcgcagc gtaagcgccg gctcgcacgg   3420
atgcagtagc agaagcgtgg ccagcagcgc ggactgtgct gctgccagtg aggtcagcgg   3480
cgcctacccg gaggggccgt ggctccagcg gggcggcgtg gaggcggcgc tccagcactc   3540
cccacaagcc gcaatggtgg ctgtagcagc cgcagcagca cagctgtacg gtggcggcgc   3600
cgccactggt ggcgccgcta gcagcctgcc cacggccagc cgccagctac agtgccgctg   3660
cagcggcact ggcggcggtg gtgagagcag cggcagcggc acggggctga gtgacgcgtc   3720
catgccctca cccaggtggg ctggggcaca tggcgctgga gaggacgggg gctccagcag   3780
cacccccagt agcggccgcc cgcagcgcct ggccgcaggc cgccacccca accgccgcct   3840
cacgcgctac ggcgagtgcc tcgacacgcc ctcgccgcgc agccccgccg tcaccagcag   3900
tagccatgct ggcgccggcg cctcaccctt ccgtcacgca gactcgtatc gcctggcggc   3960
actcgcggct cttgccgctg cctccccggc cgccgccagc ccggtgccgg tgccagcggc   4020
tgcggcagta gctgcagcgg ctacccaggc ggcgccgtcg tggccgtcac cggcgcgcgc   4080
cacccggccg cgcggcgccg cctcccccgc ctgccgccga ctgcggctgg agggcgctga   4140
gccgcacgac gctgcggcgc cgtcgccttg ctctggggca agaagcagcc gcagctggct   4200
acagcatgat ctcagtggcg ggggcgccgt ggcggaaccg gcgcgcccgc tggcgcctgg   4260
agtggtgaca ttgcctgtat atgtggctcg ctccgagtcg gagggctcgg cgttgcggtc   4320
cgccgcgccg ccaccggcat ggccccgcgc gcaggccgct gccgcctgtc cctcgctgcc   4380
gtacacgccg tcctcgctgg tgcgatacct ggactcgcgc ctgggctccc tggcggcggc   4440
ggcggaggcg gcggtggcgg aggcgggtga agagattggc gcgcagctgg cgtcactgga   4500
ggcggctgca gctgtggctg cggctggcgg tgccgcgggc ggcggcgcac gctcacagtc   4560
gcgctcagcc gcggcgccgg gtctaaattt ggagctaggt ttggatctgg acctacctgc   4620
gttgccgccg gttccgatgc cgacagccat cggctttggc ggcgacggca ctctcggcaa   4680
ccgccgcttc aatgcggctg cgcccagctt ccgcggctac cagtcaccgg aggggatgct   4740
gacgcgtgcc ggcggcggcg gtgatgaggc cctgacgcca cggagtggcc atggcagtgt   4800
ctgtggcagc accggaggcg ccgccgcagc ttcttttgat gaggcccgca gctctggcgc   4860
cggaggcgac ggtggccgca gccccgtcgg cagcagcggc agctgcgcgc gtagctgcgt   4920
gggcaacgcg gctgccggtg gcgcagcgtc gcgcttggcg cttggccgcg ccttgagcac   4980
aagcgcgaca gtgggctcgc cgcgcgcagg ccggcgtgct ccgctggcag cagccacgga   5040
cagcggctgt gacctggacc acagcccgcc gcacaagccc atcaactcta cctgcgccac   5100
cccgcgcaag caaagcccgc cgcacaagcc catcacgtcc acctgtgcca cgccgcggaa   5160
gcacacgccg cgcgcttcgt tcagccaaag ccactcccag gtattccacg aggaccaagg   5220
ctgcgaccac caccaccacg gccaccaccg ccagctctcc cggggcggcg gggactgcct   5280
gctgctgcac gaccaggccc agggacacag ccggacggct gctgcagcgg cggcctcagt   5340
cacggccgcc aggagcggca gcagctcaca gggcctgccc ctccagccct cgccctcagg   5400
ccgccctccc accgccgagt ccgacacact gccgctgcac gacgccggca gcggcagctg   5460
cggcaacagc agcggcggcg gctggagtgc gcaggccagc agccgcgagg ggtatgctta   5520
tgcgtacggc agcgccggct ggcccggcga gcagtgctac ccgcctgctg cccactacca   5580
ctaccagcag caccaggacc gacaggtgct gcagctgcac agccgtcggg tcagcggcgg   5640
cgcggccagc acactggagg cgccgccgcc gtcagaggtg gacgtggcca gggcgatgag   5700
```

-continued

```
caccggccgc ggctgcgaca acgccgaggg cgatggcggt ctcagtgtcg gtatgggcca   5760
cgcaggttgg gggccacagg cgcaggcggc ggcacagcag cagcagcagc agcagcagcg   5820
ccgtgtgtca ggtgtttcgc gtggcagcag cagcagctgt cggcccagca cgagcggcag   5880
cggctgtagc agcgagttct gggcggcggc ggttgtgccg gtggaccaat cccccgctgc   5940
cgccgccggt gcccgcggcg tggtgcagct ggcagttgcg cctgcgctgt cgcgctcgag   6000
cctgagcccc ctcaaggtgg acgtgcggca ggaggacggc gtcccagggg cggaggggcc   6060
cgccaccggc aggctggctg ggtccccagg tagctcgcag ctggtgtgcg gcctgtgtgc   6120
tggcggcttg cgggctgcgg tggcgctgac gccgtgcggc cactccttct gcgccgagtg   6180
tctggcaggg cacctggggt cggcagtgct gggcggatcg cgcgtgggct gccccaaccg   6240
gtgccctgct tttgaggcgg tcgtcatcaa ccatccggcc cgccgcctgg aaagcaagcg   6300
gtccaacgcg accaccgcta cagccgcccc acgctcccac gcccccgccc gtgcccagcc   6360
cgacggtcaa tgtgagtcat ctccctttga agccccggct gcggctgccg ccgtcgcggc   6420
gcacgccgcc gcacgcgcaa gcgccgcctc gacgcccgtg cgcggtgcac gcggcggctc   6480
tgaccccggg cctgccgcat cacccgcgct gcgtgcggct ggtggcgcca ccagcaggct   6540
gcgcacgcgc atgggcagcc gcggcagtgg ctacggcccc agccccagcc ggcgccggga   6600
gggggcgggc acgggcagcg agccaggggc gtggtcggag atgctggcgg acgcagcact   6660
gcccgtgccc gccatccgcc tgcacctgca gcagggcgag gtgctgctgc gcgccctcag   6720
ccagctcctg gacgacacgc cccagctgcc gccgcccccg ccgccctcca tccccgccgc   6780
cacagccacc accaccacaa ccagcaccgc cgcagctgct gccgccgcgg caaccaccca   6840
ggcggcgaca gcagcggtgc gcgaggcccg tgctgcggtg gtggagtggc ggcgtgtggt   6900
gctggacgtg ttgggctgcc tgggccgcct ggcactggag cacgtgcggg tgcgggaggc   6960
gcttggcgcg gcgggcgcgt cccagggctg cgtgctggcg ctgcgggcgg tgcaggcgca   7020
gatggcggcg gcggagctgt gcaccaaggg cggcgagcgg agtcttgtcg acaaggatgg   7080
cattgtcaag aagccaacag tggcggaagc cgagaaggag gcagaggctg cgctggtagc   7140
ggaggagcgg gcgacggcgc aggacaccag ccgcgcggcg tgtgtgctgc tgtgccacct   7200
gctgaaccca ccggcgccgt cgccgccggc cgagacgggt gccacagatt cggagcaagc   7260
ggtgtgccgg cagcagtcca accaatgggc gctggcgcgc atgggcggcg cagaggcctt   7320
gctggcgctg ctcctgcctg cgcaggagcc aggcaagggg gccaccgacg ctggtggcga   7380
gggcgccggt ggcaatggca acgcggagcg gcggcggtgg tcagggcaga tggcggcggc   7440
gctgacggcg cttcagagga tggtcgtggg gaacatcatg actcagaccc acgtggccga   7500
gtgtgggtct gccgccgtca tccgcacgct ggccgccgcc acccgcgccg ccgccgcctc   7560
gggcgatgag gccgtacagg cggcggcgct gcggctgctg gctgacgtgg cccgtggcgg   7620
cgacgccgca cacgccgcag tgcggcagat gctgctagag gccggcgcac tgggggcggc   7680
gctggcggcg ctgcgcgaca gcgtggctgc tttcggcggc tgcaatggag gaagagaagg   7740
atctgggaat agcggatgcg ctgacggcgg tagcgccgcc agctcgggga tggaggtcag   7800
cccggtgctg atggcggcgc tggacgcgat tcatgtgttg atgggtccgt cggagcagca   7860
cgtggacgga tctgagccgc cgctggcgct tcaggcggtg gtgcggcggg agttgcggcg   7920
gctgggcgcg ccgcgcctgc tggcggactg cgtgcgggag ctgcggctgc aacaggagga   7980
cgagcagggc gagggccggg cccaggagga gtgggagcgg gcgagcgggc gcacgggcca   8040
cagcaggcat gcccctgatg gtcgcgtgct tcccggagca gtagcaggag caggagggaa   8100
```

gcagccgcat ccacggccct gggacgggtc gcggtcgcgg gaggagcggg gttcggcggg 8160
tggcgattgc ctcgggtgca gccccgtgct tcgggcgatg gccgagctgc aggcgcgcgt 8220
gtgtgcagta gcaggtggta cgggctgggt gcgttgtgtg gtgcagatgt tgggcgcaag 8280
tcccgacgga gtggggcagg ctgggcgtgg tggcgttgat ggcggtggtg cggcgatggc 8340
agcggtggcg gcgcataggg tgcagttgcg ccttctcgcg gtggcagcag gtggcgggtt 8400
tgcgctcggt gccgcggtga cgggggcagt ggcagcgatg tggatggctt gattttgggg 8460
tggtgctagc aagtgcgttt gcgactttgg tgtgacattg caccttcagg agaaggcagg 8520
caagggttga ggtgtaggtt tggccgttgt ccggttggca agtgctggcc tgtttgttga 8580
gctgttgact ttatagtggc tgtacctttg gggggtcggc tttgttgaac acacgcccac 8640
cacattgttt gcgcatcggg acgctaagtt ggcgcaagcc acggttgccc acccaaaagc 8700
cggcagctgg tagggccatg tgcagcgtgg aagttgctct gctggtaggg ccgtatgcag 8760
atttgaaata gctctggtgt tggccgagga aggctgcgga ggggtccatg ggtgcggctg 8820
tgttggggca ggtgctagcc cgggggactc cccgtgggga ctccctggac atgccgccgt 8880
gtgaatggtc atttgcagga cattgggttg cggggcgtag gggattctag tagatggatg 8940
caggcaggac agctctgaca ttcatcaatt gatgataggc tgcaggacgc agtatacggc 9000
tgtacttgca tgtgtgttga gccgatgggt tgttgacgtc tcctgatgcg ttgggtggct 9060
gggtcgccac ggagcaatta gcgccacggg ccaatcgtaa aggttacatg ttttgctaga 9120
caaaatgaat gaagagaaaa ccattgtcat tggtaggaaa acttctccgt cgag 9174

<210> SEQ ID NO 58
<211> LENGTH: 8217
<212> TYPE: DNA
<213> ORGANISM: Chlamydomonas reinhardtii

<400> SEQUENCE: 58
atgcggcggc gtcaaggcca gctgcatcca tggggttttc tgctgcggca gcgcgatggc 60
gggctcgccg cgccacccgt ggcgttagtc cacgaccacg tcgcgttagg tcgcggcacg 120
gcgcctcccc cgggcgcggc acatgccgtt gcgggcatgc agcagtgccc cctccagttc 180
attactatcg acgatgagcg cgtgagccgc ctgcacgccg cgctcacagt gcactgcaac 240
agcagccggt ggccgccgct ggtgactgtg gaggaccgca gccgcaacgg tacctacctc 300
aacggctcgc cgctgcgccc cggcgccccc gccgtcctgt ccagcggcga cgtgctgtcg 360
ctggtgctgt gcgtcaaccc cctcacgcag ctgtgcttcg tgtttgagga gtgccccgtg 420
ccgccgccca actggacacg agccgccaac gcccaagaag gcgccggctc atcagcgcag 480
agcggcaaca ctgctgtccg gcgaccaacc gccaccggcg gtgatgcgct gggagcaggc 540
ggagcagcag gagcagcggc aggggcagct ccctatccgg tactgccagt cggcctgcct 600
cgcgccagcg gcaacctgaa cgcggccctg agcgctgcag ctgttgctgc tgcgctggcg 660
gccggccgtg gcacgtcgcg caacagccgc ggccaccgcg ccggccgcag caaccggtct 720
cccgccgccg ccgccacgtc gactgctggc accgagacgc tggggctggt ggacccgctg 780
gcggcggcgg cgccgcaccg gctgagcggc acgggcttct ctgagggcgg cgtggagcag 840
tggccgtcgg gagctgggcc gcgcgaggtg accagccccc agccgtcgct gccgccggcc 900
tcgctgccgc agtcgcccga ccgccgccgt atcacacggc agtccacggg cagtggtgtg 960
cctcgctcgc tgtcgcctga cagcagtccc acctcggtgg tgggcgagtc ggcacatggc 1020

-continued

```
ttccccctgg aaggcggcgg cgggcggcgc cacagcgtcc cggtcggcgg tgcctcctgg   1080
gaccggcacg acgaccactg gccggagccg cacagcccca ctgccactcc ccgctcgcgc   1140
gtgcacaatc acaccgttgc gcaggtcctg gcggcgctgc accccaaccc gctgtacgcc   1200
gaccacctca ccgcgctgga gctagcgccc ggcacggcgc cgcccgcctc gccgccgcgc   1260
agcccccgct cgacgcccct gcgtgcgccc gtcactggcg ccgccgcccg cgccagccgc   1320
cccagccgcc gcagcaccgg cagcggcatg gccgcggctg acggccacca ccagcggcac   1380
cagcggcacc gccgctcccg gacagcgcac ctgggagctc acctgcttgc cttcgccgca   1440
gcgggcgtgg ccgcgccggc ggactcggcg gtgtctgcgg ctcgcggcgg catttcgctg   1500
agccgctcgc tcccccaact gctccccgtc gatttggtcg gcaaccacca gtttcacgag   1560
ctgcggctgc agcagcactc gtccgcccaa gccggcggct acatgtcggc tgcggcggtg   1620
ccctcgctgt cgtcagtgtc cgactccaca cctgcctacg ccggctggcc cgtccatggc   1680
ctggccggca gcggaggcag tgcccccgct accagcgccg ccacgagcac gagcagcagc   1740
agccggcaca gcttgcacag cccgcttagt cagcccagcc tgcacagccg ctacctactg   1800
accggcggcg cggaggctgt gctcaacagc ccgcggcgcc agcgcttcag cactggcagc   1860
ggctttggac cgccgctgcc ggtgttgccg ccgccgccct tgtcatcggc accttcggcg   1920
tcatctgcgt ttgcagatcc gacccaggcc gaagccctgg cccaggccca tcgccgtccg   1980
cgcgctctgt cctacggctc tggcagcttt ggcctggagg aagagaacag cggtggcggc   2040
agcggcggca gcggcaccca cacagccctg gttccgagga tttcagcccc cacgctggac   2100
gcgtttgggt ccgtgtccga tgcccccatg ctgacaccgg cgccgccgtc tgcgcccctg   2160
ccagcctgcg gctccggctc cggctctcct cgttccgccc ccgccgccgc cgcagtcatc   2220
gtgggcggcg gcccaaggtc cagccgcagc tcggcgtcgc ggccgcagtc ccgcctgctg   2280
cgcgtcagcc gccccaactc gccgctgcct gggtacgaga acagcggtgg cgtgggctca   2340
accggcttcg ccgctgcatg ggctgcaggc ggcgctggtg ctgctagctg ccgcggcggt   2400
gatgttggta ccgctggtgc tggtgctgtg gatgagctgg cgtatggcat ggacatgcaa   2460
gggcatgagg gcggaaacaa ctgcgagctg ctggctccgt tgccaagctc gccgcgcttt   2520
gggcctggag gccgcggcgg cgctgggtcg ttgcctgatg ctgcatcgga gtttggccag   2580
ggtgccagtg gtgcaggttc tggcgtggct ggggctggag taggggggac ggcgaccgcc   2640
gtgccgctgc gtcggctgtg ctccgcagcg gtggccgcgc tggcggccgc cgccgaggcc   2700
actgcgagtg agagcgacac tcccagcgag atcacttgca aggagttctc cttctcctcc   2760
ctgtcccgtc ccacactctc cgcgcccgcc gccgccagca gcccgcccgg tgccaaccgc   2820
gacccctgct gcagcccttc agtgccggcc atcgcgctcg agcccgcagc ctccgtccct   2880
actgccgccg ccgcctctgt caaccttgag gctaggctgc acaccgccgc agctgacggc   2940
ggcagcgggg gcagcccgcg cttcctccgc cgcacggtct ccgcgaacga cggcccgcag   3000
gcacagaccc tgcacaggca acagcagcta cagcttcagc agcagcagca ctttggtaat   3060
gcctctgatg catttctggt ggcggcggcg gcggcaggag ctcctccaac tctccgtgtg   3120
tcagcgtctt ccgtaagggc tgctgcacca ggcccgcagc gcagcgtaag cgccggctcg   3180
cacggatgca gtagcagaag cgtggccagc agcgcggact gtgctgctgc cagtgaggtc   3240
agcggcgcct acccggaggg gccgtggctc cagcggggcg gcgtggaggc ggcgctccag   3300
cactccccac aagccgcaat ggtggctgta gcagccgcag cagcacagct gtacggtggc   3360
ggcgccgcca ctggtggcgc cgctagcagc ctgcccacgg ccagccgcca gctacagtgc   3420
```

-continued

```
cgctgcagcg gcactggcgg cggtggtgag agcagcggca gcggcacggg gctgagtgac   3480
gcgtccatgc cctcacccag gtgggctggg gcacatggcg ctggagagga cgggggctcc   3540
agcagcaccc ccagtagcgg ccgcccgcag cgcctggccg caggccgcca ccccaaccgc   3600
cgcctcacgc gctacggcga gtgcctcgac acgccctcgc cgcgcagccc cgccgtcacc   3660
agcagtagcc atgctggcgc cggcgcctca cccttccgtc acgcagactc gtatcgcctg   3720
gcggcactcg cggctcttgc cgctgcctcc ccggccgccg ccagcccggt gccggtgcca   3780
gcggctgcgg cagtagctgc agcggctacc caggcggcgc cgtcgtggcc gtcaccggcg   3840
cgcgccaccc ggccgcgcgg cgccgcctcc cccgcctgcc gccgactgcg gctggagggc   3900
gctgagccgc acgacgctgc ggcgccgtcg ccttgctctg gggcaagaag cagccgcagc   3960
tggctacagc atgatctcag tggcgggggc gccgtggcgg aaccggcgcg cccgctggcg   4020
cctggagtgg tgacattgcc tgtatatgtg gctcgctccg agtcggaggg ctcggcgttg   4080
cggtccgccg cgccgccacc ggcatggccc cgcgcgcagg ccgctgccgc ctgtccctcg   4140
ctgccgtaca cgccgtcctc gctggtgcga tacctggact cgcgcctggg ctccctggcg   4200
gcggcggcgg aggcggcggt ggcggaggcg ggtgaagaga ttggcgcgca gctggcgtca   4260
ctggaggcgg ctgcagctgt ggctgcggct ggcggtgccg cgggcggcgg cgcacgctca   4320
cagtcgcgct cagccgcggc gccgggtcta aatttggagc taggtttgga tctggaccta   4380
cctgcgttgc cgccggttcc gatgccgaca gccatcggct ttggcggcga cggcactctc   4440
ggcaaccgcc gcttcaatgc ggctgcgccc agcttccgcg gctaccagtc accggagggg   4500
atgctgacgc gtgccggcgg cggcggtgat gaggccctga cgccacggag tggccatggc   4560
agtgtctgtg gcagcaccgg aggcgccgcc gcagcttctt ttgatgaggc ccgcagctct   4620
ggcgccggag gcgacggtgg ccgcagcccc gtcggcagca gcggcagctg cgcgcgtagc   4680
tgcgtgggca acgcggctgc cggtggcgca gcgtcgcgct tggcgcttgg ccgcgccttg   4740
agcacaagcg cgacagtggg ctcgccgcgc gcaggccggc gtgctccgct ggcagcagcc   4800
acggacagcg gctgtgacct ggaccacagc ccgccgcaca agcccatcaa ctctacctgc   4860
gccaccccgc gcaagcaaag cccgccgcac aagcccatca cgtccacctg tgccacgccg   4920
cggaagcaca cgccgcgcgc ttcgttcagc caaagccact cccaggtatt ccacgaggac   4980
caaggctgcg accaccacca ccacggccac caccgccagc tctcccgggg cggcggggac   5040
tgcctgctgc tgcacgacca ggcccaggga cacagccgga cggctgctgc agcggcggcc   5100
tcagtcacgg ccgccaggag cggcagcagc tcacagggcc tgcccctcca gccctcgccc   5160
tcaggccgcc ctcccaccgc cgagtccgac acactgccgc tgcacgacgc cggcagcggc   5220
agctgcggca acagcagcgg cggcggctgg agtgcgcagg ccagcagccg cgaggggtat   5280
gcttatgcgt acggcagcgc cggctggccc ggcgagcagt gctacccgcc tgctgcccac   5340
taccactacc agcagcacca ggaccgacag gtgctgcagc tgcacagccg tcgggtcagc   5400
ggcggcgcgg ccagcacact ggaggcgccg ccgccgtcag aggtggacgt ggccagggcg   5460
atgagcaccg gccgcggctg cgacaacgcc gagggcgatg gcggtctcag tgtcggtatg   5520
ggccacgcag gttgggggcc acaggcgcag gcggcggcac agcagcagca gcagcagcag   5580
cagcgccgtg tgtcaggtgt ttcgcgtggc agcagcagca gctgtcggcc cagcacgagc   5640
ggcagcggct gtagcagcga gttctgggcg gcggcggttg tgccggtgga ccaatccccc   5700
gctgccgccg ccggtgcccg cggcgtggtg cagctggcag ttgcgcctgc gctgtcgcgc   5760
```

-continued

```
tcgagcctga gccccctcaa ggtggacgtg cggcaggagg acggcgtccc aggggcggag   5820
gggcccgcca ccggcaggct ggctgggtcc ccaggtagct cgcagctggt gtgcggcctg   5880
tgtgctggcg gcttgcgggc tgcggtggcg ctgacgccgt gcggccactc cttctgcgcc   5940
gagtgtctgg cagggcacct ggggtcggca gtgctgggcg gatcgcgcgt gggctgcccc   6000
aaccggtgcc ctgcttttga ggcggtcgtc atcaaccatc cggcccgccg cctggaaagc   6060
aagcggtcca acgcgaccac cgctacagcc gccccacgct cccacgcccc cgcccgtgcc   6120
cagcccgacg gtcaatgtga gtcatctccc tttgaagccc cggctgcggc tgccgccgtc   6180
gcggcgcacg ccgccgcacg cgcaagcgcc gcctcgacgc ccgtgcgcgg tgcacgcggc   6240
ggctctgacc ccgggcctgc cgcatcaccc gcgctgcgtg cggctggtgg cgccaccagc   6300
aggctgcgca cgcgcatggg cagccgcggc agtggctacg gccccagccc cagccggcgc   6360
cgggaggggg cgggcacggg cagcgagcca ggggcgtggt cggagatgct ggcggacgca   6420
gcactgcccg tgcccgccat ccgcctgcac ctgcagcagg gcgaggtgct gctgcgcgcc   6480
ctcagccagc tcctggacga cacgccccag ctgccgccgc ccccgccgcc ctccatcccc   6540
gccgccacag ccaccaccac cacaaccagc accgccgcag ctgctgccgc cgcggcaacc   6600
acccaggcgg cgacagcagc ggtgcgcgag gcccgtgctg cggtggtgga gtggcggcgt   6660
gtggtgctgg acgtgttggg ctgcctgggc cgcctggcac tggagcacgt gcgggtgcgg   6720
gaggcgcttg gcgcggcggg cgcgtcccag ggctgcgtgc tggcgctgcg ggcggtgcag   6780
gcgcagatgg cggcggcgga gctgtgcacc aagggcggcg agcggagtct tgtcgacaag   6840
gatggcattg tcaagaagcc aacagtggcg gaagccgaga aggaggcaga ggctgcgctg   6900
gtagcggagg agcgggcgac ggcgcaggac accagccgcg cggcgtgtgt gctgctgtgc   6960
cacctgctga acccaccggc gccgtcgccg ccggccgaga cgggtgccac agattcggag   7020
caagcggtgt gccggcagca gtccaaccaa tgggcgctgg cgcgcatggg cggcgcagag   7080
gccttgctgg cgctgctcct gcctgcgcag gagccaggca agggggccac cgacgctggt   7140
ggcgagggcg ccggtggcaa tggcaacgcg gagcggcggc ggtggtcagg gcagatggcg   7200
gcggcgctga cggcgcttca gaggatggtc gtggggaaca tcatgactca gacccacgtg   7260
gccgagtgtg ggtctgccgc cgtcatccgc acgctggccg ccgccacccg cgccgccgcc   7320
gcctcgggcg atgaggccgt acaggcggcg gcgctgcggc tgctggctga cgtggcccgt   7380
ggcggcgacg ccgcacacgc cgcagtgcgg cagatgctgc tagaggccgg cgcactgggg   7440
gcggcgctgg cggcgctgcg cgacagcgtg gctgctttcg gcggctgcaa tggaggaaga   7500
gaaggatctg ggaatagcgg atgcgctgac ggcggtagcg ccgccagctc ggggatggag   7560
gtcagcccgg tgctgatggc ggcgctggac gcgattcatg tgttgatggg tccgtcggag   7620
cagcacgtgg acggatctga gccgccgctg gcgcttcagg cggtggtgcg gcgggagttg   7680
cggcggctgg gcgcgccgcg cctgctggcg gactgcgtgc gggagctgcg gctgcaacag   7740
gaggacgagc agggcgaggg ccgggcccag gaggagtggg agcgggcgag cgggcgcacg   7800
ggccacagca ggcatgcccc tgatggtcgc gtgcttcccg gagcagtagc aggagcagga   7860
gggaagcagc cgcatccacg gccctgggac gggtcgcggt cgcgggagga gcggggttcg   7920
gcgggtggcg attgcctcgg gtgcagcccc gtgcttcggg cgatggccga gctgcaggcg   7980
cgcgtgtgtg cagtagcagg tggtacgggc tgggtgcgtt gtgtggtgca gatgttgggc   8040
gcaagtcccg acggagtggg gcaggctggg cgtggtggcg ttgatggcgg tggtgcggcg   8100
atggcagcgg tggcggcgca tagggtgcag ttgcgccttc tcgcggtggc agcaggtggc   8160
```

-continued gggtttgcgc tcggtgccgc ggtgacgggg gcagtggcag cgatgtggat ggcttga 8217

<210> SEQ ID NO 59
<211> LENGTH: 2738
<212> TYPE: PRT
<213> ORGANISM: Chlamydomonas reinhardtii

<400> SEQUENCE: 59

Met Arg Arg Arg Gln Gly Gln Leu His Pro Trp Gly Phe Leu Leu Arg
1 5 10 15

Gln Arg Asp Gly Gly Leu Ala Ala Pro Pro Val Ala Leu Val His Asp
20 25 30

His Val Ala Leu Gly Arg Gly Thr Ala Pro Pro Pro Gly Ala Ala His
35 40 45

Ala Val Ala Gly Met Gln Gln Cys Pro Leu Gln Phe Ile Thr Ile Asp
50 55 60

Asp Glu Arg Val Ser Arg Leu His Ala Ala Leu Thr Val His Cys Asn
65 70 75 80

Ser Ser Arg Trp Pro Pro Leu Val Thr Val Glu Asp Arg Ser Arg Asn
85 90 95

Gly Thr Tyr Leu Asn Gly Ser Pro Leu Arg Pro Gly Ala Pro Ala Val
100 105 110

Leu Ser Ser Gly Asp Val Leu Ser Leu Val Leu Cys Val Asn Pro Leu
115 120 125

Thr Gln Leu Cys Phe Val Phe Glu Glu Cys Pro Val Pro Pro Pro Asn
130 135 140

Trp Thr Arg Ala Ala Asn Ala Gln Glu Gly Ala Gly Ser Ser Ala Gln
145 150 155 160

Ser Gly Asn Thr Ala Val Arg Arg Pro Thr Ala Thr Gly Gly Asp Ala
165 170 175

Leu Gly Ala Gly Gly Ala Ala Gly Ala Ala Ala Gly Ala Ala Pro Tyr
180 185 190

Pro Val Leu Pro Val Gly Leu Pro Arg Ala Ser Gly Asn Leu Asn Ala
195 200 205

Ala Leu Ser Ala Ala Ala Val Ala Ala Ala Leu Ala Ala Gly Arg Gly
210 215 220

Thr Ser Arg Asn Ser Arg Gly His Arg Ala Gly Arg Ser Asn Arg Ser
225 230 235 240

Pro Ala Ala Ala Ala Thr Ser Thr Ala Gly Thr Glu Thr Leu Gly Leu
245 250 255

Val Asp Pro Leu Ala Ala Ala Ala Pro His Arg Leu Ser Gly Thr Gly
260 265 270

Phe Ser Glu Gly Gly Val Glu Gln Trp Pro Ser Gly Ala Gly Pro Arg
275 280 285

Glu Val Thr Ser Pro Gln Pro Ser Leu Pro Pro Ala Ser Leu Pro Gln
290 295 300

Ser Pro Asp Arg Arg Arg Ile Thr Arg Gln Ser Thr Gly Ser Gly Val
305 310 315 320

Pro Arg Ser Leu Ser Pro Asp Ser Ser Pro Thr Ser Val Val Gly Glu
325 330 335

Ser Ala His Gly Phe Pro Leu Glu Gly Gly Gly Gly Arg Arg His Ser
340 345 350

Val Pro Val Gly Gly Ala Ser Trp Asp Arg His Asp Asp His Trp Pro
355 360 365

```
Glu Pro His Ser Pro Thr Ala Thr Pro Arg Ser Arg Val His Asn His
    370                 375                 380

Thr Val Ala Gln Val Leu Ala Ala Leu His Pro Asn Pro Leu Tyr Ala
385                 390                 395                 400

Asp His Leu Thr Ala Leu Glu Leu Ala Pro Gly Thr Ala Pro Pro Ala
                405                 410                 415

Ser Pro Pro Arg Ser Pro Arg Ser Thr Pro Leu Arg Ala Pro Val Thr
            420                 425                 430

Gly Ala Ala Ala Arg Ala Ser Arg Pro Ser Arg Arg Ser Thr Gly Ser
        435                 440                 445

Gly Met Ala Ala Ala Asp Gly His His Gln Arg His Gln Arg His Arg
    450                 455                 460

Arg Ser Arg Thr Ala His Leu Gly Ala His Leu Leu Ala Phe Ala Ala
465                 470                 475                 480

Ala Gly Val Ala Ala Pro Ala Asp Ser Ala Val Ser Ala Ala Arg Gly
                485                 490                 495

Gly Ile Ser Leu Ser Arg Ser Leu Pro Gln Leu Leu Pro Val Asp Leu
            500                 505                 510

Val Gly Asn His Gln Phe His Glu Leu Arg Leu Gln Gln His Ser Ser
        515                 520                 525

Ala Gln Ala Gly Gly Tyr Met Ser Ala Ala Ala Val Pro Ser Leu Ser
    530                 535                 540

Ser Val Ser Asp Ser Thr Pro Ala Tyr Ala Gly Trp Pro Val His Gly
545                 550                 555                 560

Leu Ala Gly Ser Gly Gly Ser Ala Pro Ala Thr Ser Ala Ala Thr Ser
                565                 570                 575

Thr Ser Ser Ser Ser Arg His Ser Leu His Ser Pro Leu Ser Gln Pro
            580                 585                 590

Ser Leu His Ser Arg Tyr Leu Leu Thr Gly Gly Ala Glu Ala Val Leu
        595                 600                 605

Asn Ser Pro Arg Arg Gln Arg Phe Ser Thr Gly Ser Gly Phe Gly Pro
    610                 615                 620

Pro Leu Pro Val Leu Pro Pro Pro Pro Leu Ser Ser Ala Pro Ser Ala
625                 630                 635                 640

Ser Ser Ala Phe Ala Asp Pro Thr Gln Ala Glu Ala Leu Ala Gln Ala
                645                 650                 655

His Arg Arg Pro Arg Ala Leu Ser Tyr Gly Ser Gly Ser Phe Gly Leu
            660                 665                 670

Glu Glu Glu Asn Ser Gly Gly Gly Ser Gly Gly Ser Gly Thr His Thr
        675                 680                 685

Ala Leu Val Pro Arg Ile Ser Ala Pro Thr Leu Asp Ala Phe Gly Ser
    690                 695                 700

Val Ser Asp Ala Pro Met Leu Thr Pro Ala Pro Pro Ser Ala Pro Leu
705                 710                 715                 720

Pro Ala Cys Gly Ser Gly Ser Gly Ser Pro Arg Ser Ala Pro Ala Ala
                725                 730                 735

Ala Ala Val Ile Val Gly Gly Gly Pro Arg Ser Ser Arg Ser Ser Ala
            740                 745                 750

Ser Arg Pro Gln Ser Arg Leu Leu Arg Val Ser Arg Pro Asn Ser Pro
        755                 760                 765

Leu Pro Gly Tyr Glu Asn Ser Gly Gly Val Gly Ser Thr Gly Phe Ala
    770                 775                 780
```

-continued

```
Ala Ala Trp Ala Ala Gly Gly Ala Gly Ala Ala Ser Cys Arg Gly Gly
785                 790                 795                 800

Asp Val Gly Thr Ala Gly Ala Gly Ala Val Asp Glu Leu Ala Tyr Gly
                805                 810                 815

Met Asp Met Gln Gly His Glu Gly Gly Asn Asn Cys Glu Leu Leu Ala
            820                 825                 830

Pro Leu Pro Ser Ser Pro Arg Phe Gly Pro Gly Gly Arg Gly Gly Ala
        835                 840                 845

Gly Ser Leu Pro Asp Ala Ala Ser Glu Phe Gly Gln Gly Ala Ser Gly
    850                 855                 860

Ala Gly Ser Gly Val Ala Gly Ala Gly Val Gly Gly Thr Ala Thr Ala
865                 870                 875                 880

Val Pro Leu Arg Arg Leu Cys Ser Ala Ala Val Ala Ala Leu Ala Ala
                885                 890                 895

Ala Ala Glu Ala Thr Ala Ser Glu Ser Asp Thr Pro Ser Glu Ile Thr
            900                 905                 910

Cys Lys Glu Phe Ser Phe Ser Ser Leu Ser Arg Pro Thr Leu Ser Ala
        915                 920                 925

Pro Ala Ala Ala Ser Ser Pro Pro Gly Ala Asn Arg Asp Pro Cys Cys
    930                 935                 940

Ser Pro Ser Val Pro Ala Ile Ala Leu Glu Pro Ala Ala Ser Val Pro
945                 950                 955                 960

Thr Ala Ala Ala Ala Ser Val Asn Leu Glu Ala Arg Leu His Thr Ala
                965                 970                 975

Ala Ala Asp Gly Gly Ser Gly Gly Ser Pro Arg Phe Leu Arg Arg Thr
            980                 985                 990

Val Ser Ala Asn Asp Gly Pro Gln  Ala Gln Thr Leu His  Arg Gln Gln
        995                 1000                1005

Gln Leu  Gln Leu Gln Gln Gln  Gln His Phe Gly Asn  Ala Ser Asp
    1010                1015                1020

Ala Phe  Leu Val Ala Ala Ala  Ala Ala Gly Ala Pro  Pro Thr Leu
    1025                1030                1035

Arg Val  Ser Ala Ser Ser Val  Arg Ala Ala Ala Pro  Gly Pro Gln
    1040                1045                1050

Arg Ser  Val Ser Ala Gly Ser  His Gly Cys Ser Ser  Arg Ser Val
    1055                1060                1065

Ala Ser  Ser Ala Asp Cys Ala  Ala Ala Ser Glu Val  Ser Gly Ala
    1070                1075                1080

Tyr Pro  Glu Gly Pro Trp Leu  Gln Arg Gly Gly Val  Glu Ala Ala
    1085                1090                1095

Leu Gln  His Ser Pro Gln Ala  Ala Met Val Ala Val  Ala Ala Ala
    1100                1105                1110

Ala Ala  Gln Leu Tyr Gly Gly  Gly Ala Ala Thr Gly  Gly Ala Ala
    1115                1120                1125

Ser Ser  Leu Pro Thr Ala Ser  Arg Gln Leu Gln Cys  Arg Cys Ser
    1130                1135                1140

Gly Thr  Gly Gly Gly Gly Glu  Ser Ser Gly Ser Gly  Thr Gly Leu
    1145                1150                1155

Ser Asp  Ala Ser Met Pro Ser  Pro Arg Trp Ala Gly  Ala His Gly
    1160                1165                1170

Ala Gly  Glu Asp Gly Gly Ser  Ser Ser Thr Pro Ser  Ser Gly Arg
    1175                1180                1185

Pro Gln  Arg Leu Ala Ala Gly  Arg His Pro Asn Arg  Arg Leu Thr
```

```
    1190                1195                1200

Arg Tyr  Gly Glu Cys Leu Asp  Thr Pro Ser Pro Arg  Ser Pro Ala
    1205                1210                1215

Val Thr  Ser Ser Ser His Ala  Gly Ala Gly Ala Ser  Pro Phe Arg
    1220                1225                1230

His Ala  Asp Ser Tyr Arg Leu  Ala Ala Leu Ala Ala  Leu Ala Ala
    1235                1240                1245

Ala Ser  Pro Ala Ala Ala Ser  Pro Val Pro Val Pro  Ala Ala Ala
    1250                1255                1260

Ala Val  Ala Ala Ala Ala Thr  Gln Ala Ala Pro Ser  Trp Pro Ser
    1265                1270                1275

Pro Ala  Arg Ala Thr Arg Pro  Arg Gly Ala Ala Ser  Pro Ala Cys
    1280                1285                1290

Arg Arg  Leu Arg Leu Glu Gly  Ala Glu Pro His Asp  Ala Ala Ala
    1295                1300                1305

Pro Ser  Pro Cys Ser Gly Ala  Arg Ser Ser Arg Ser  Trp Leu Gln
    1310                1315                1320

His Asp  Leu Ser Gly Gly Gly  Ala Val Ala Glu Pro  Ala Arg Pro
    1325                1330                1335

Leu Ala  Pro Gly Val Val Thr  Leu Pro Val Tyr Val  Ala Arg Ser
    1340                1345                1350

Glu Ser  Glu Gly Ser Ala Leu  Arg Ser Ala Ala Pro  Pro Pro Ala
    1355                1360                1365

Trp Pro  Arg Ala Gln Ala Ala  Ala Ala Cys Pro Ser  Leu Pro Tyr
    1370                1375                1380

Thr Pro  Ser Ser Leu Val Arg  Tyr Leu Asp Ser Arg  Leu Gly Ser
    1385                1390                1395

Leu Ala  Ala Ala Ala Glu Ala  Ala Val Ala Glu Ala  Gly Glu Glu
    1400                1405                1410

Ile Gly  Ala Gln Leu Ala Ser  Leu Glu Ala Ala Ala  Ala Val Ala
    1415                1420                1425

Ala Ala  Gly Gly Ala Ala Gly  Gly Gly Ala Arg Ser  Gln Ser Arg
    1430                1435                1440

Ser Ala  Ala Ala Pro Gly Leu  Asn Leu Glu Leu Gly  Leu Asp Leu
    1445                1450                1455

Asp Leu  Pro Ala Leu Pro Pro  Val Pro Met Pro Thr  Ala Ile Gly
    1460                1465                1470

Phe Gly  Gly Asp Gly Thr Leu  Gly Asn Arg Arg Phe  Asn Ala Ala
    1475                1480                1485

Ala Pro  Ser Phe Arg Gly Tyr  Gln Ser Pro Glu Gly  Met Leu Thr
    1490                1495                1500

Arg Ala  Gly Gly Gly Gly Asp  Glu Ala Leu Thr Pro  Arg Ser Gly
    1505                1510                1515

His Gly  Ser Val Cys Gly Ser  Thr Gly Gly Ala Ala  Ala Ala Ser
    1520                1525                1530

Phe Asp  Glu Ala Arg Ser Ser  Gly Ala Gly Gly Asp  Gly Gly Arg
    1535                1540                1545

Ser Pro  Val Gly Ser Ser Gly  Ser Cys Ala Arg Ser  Cys Val Gly
    1550                1555                1560

Asn Ala  Ala Ala Gly Gly Ala  Ala Ser Arg Leu Ala  Leu Gly Arg
    1565                1570                1575

Ala Leu  Ser Thr Ser Ala Thr  Val Gly Ser Pro Arg  Ala Gly Arg
    1580                1585                1590
```

-continued

```
Arg Ala Pro Leu Ala Ala Ala Thr Asp Ser Gly Cys Asp Leu Asp
    1595                1600                1605

His Ser Pro Pro His Lys Pro Ile Asn Ser Thr Cys Ala Thr Pro
    1610                1615                1620

Arg Lys Gln Ser Pro Pro His Lys Pro Ile Thr Ser Thr Cys Ala
    1625                1630                1635

Thr Pro Arg Lys His Thr Pro Arg Ala Ser Phe Ser Gln Ser His
    1640                1645                1650

Ser Gln Val Phe His Glu Asp Gln Gly Cys Asp His His His His
    1655                1660                1665

Gly His His Arg Gln Leu Ser Arg Gly Gly Gly Asp Cys Leu Leu
    1670                1675                1680

Leu His Asp Gln Ala Gln Gly His Ser Arg Thr Ala Ala Ala Ala
    1685                1690                1695

Ala Ala Ser Val Thr Ala Ala Arg Ser Gly Ser Ser Ser Gln Gly
    1700                1705                1710

Leu Pro Leu Gln Pro Ser Pro Ser Gly Arg Pro Pro Thr Ala Glu
    1715                1720                1725

Ser Asp Thr Leu Pro Leu His Asp Ala Gly Ser Gly Ser Cys Gly
    1730                1735                1740

Asn Ser Ser Gly Gly Gly Trp Ser Ala Gln Ala Ser Ser Arg Glu
    1745                1750                1755

Gly Tyr Ala Tyr Ala Tyr Gly Ser Ala Gly Trp Pro Gly Glu Gln
    1760                1765                1770

Cys Tyr Pro Pro Ala Ala His Tyr His Tyr Gln Gln His Gln Asp
    1775                1780                1785

Arg Gln Val Leu Gln Leu His Ser Arg Arg Val Ser Gly Gly Ala
    1790                1795                1800

Ala Ser Thr Leu Glu Ala Pro Pro Pro Ser Glu Val Asp Val Ala
    1805                1810                1815

Arg Ala Met Ser Thr Gly Arg Gly Cys Asp Asn Ala Glu Gly Asp
    1820                1825                1830

Gly Gly Leu Ser Val Gly Met Gly His Ala Gly Trp Gly Pro Gln
    1835                1840                1845

Ala Gln Ala Ala Ala Gln Gln Gln Gln Gln Gln Gln Gln Arg Arg
    1850                1855                1860

Val Ser Gly Val Ser Arg Gly Ser Ser Ser Ser Cys Arg Pro Ser
    1865                1870                1875

Thr Ser Gly Ser Gly Cys Ser Ser Glu Phe Trp Ala Ala Ala Val
    1880                1885                1890

Val Pro Val Asp Gln Ser Pro Ala Ala Ala Ala Gly Ala Arg Gly
    1895                1900                1905

Val Val Gln Leu Ala Val Ala Pro Ala Leu Ser Arg Ser Ser Leu
    1910                1915                1920

Ser Pro Leu Lys Val Asp Val Arg Gln Glu Asp Gly Val Pro Gly
    1925                1930                1935

Ala Glu Gly Pro Ala Thr Gly Arg Leu Ala Gly Ser Pro Gly Ser
    1940                1945                1950

Ser Gln Leu Val Cys Gly Leu Cys Ala Gly Gly Leu Arg Ala Ala
    1955                1960                1965

Val Ala Leu Thr Pro Cys Gly His Ser Phe Cys Ala Glu Cys Leu
    1970                1975                1980
```

-continued

Ala Gly His Leu Gly Ser Ala Val Leu Gly Gly Ser Arg Val Gly
1985 1990 1995

Cys Pro Asn Arg Cys Pro Ala Phe Glu Ala Val Val Ile Asn His
2000 2005 2010

Pro Ala Arg Arg Leu Glu Ser Lys Arg Ser Asn Ala Thr Thr Ala
2015 2020 2025

Thr Ala Ala Pro Arg Ser His Ala Pro Ala Arg Ala Gln Pro Asp
2030 2035 2040

Gly Gln Cys Glu Ser Ser Pro Phe Glu Ala Pro Ala Ala Ala Ala
2045 2050 2055

Ala Val Ala Ala His Ala Ala Ala Arg Ala Ser Ala Ala Ser Thr
2060 2065 2070

Pro Val Arg Gly Ala Arg Gly Gly Ser Asp Pro Gly Pro Ala Ala
2075 2080 2085

Ser Pro Ala Leu Arg Ala Ala Gly Gly Ala Thr Ser Arg Leu Arg
2090 2095 2100

Thr Arg Met Gly Ser Arg Gly Ser Gly Tyr Gly Pro Ser Pro Ser
2105 2110 2115

Arg Arg Arg Glu Gly Ala Gly Thr Gly Ser Glu Pro Gly Ala Trp
2120 2125 2130

Ser Glu Met Leu Ala Asp Ala Ala Leu Pro Val Pro Ala Ile Arg
2135 2140 2145

Leu His Leu Gln Gln Gly Glu Val Leu Leu Arg Ala Leu Ser Gln
2150 2155 2160

Leu Leu Asp Asp Thr Pro Gln Leu Pro Pro Pro Pro Pro Pro Ser
2165 2170 2175

Ile Pro Ala Ala Thr Ala Thr Thr Thr Thr Thr Ser Thr Ala Ala
2180 2185 2190

Ala Ala Ala Ala Ala Ala Thr Thr Gln Ala Ala Thr Ala Ala Val
2195 2200 2205

Arg Glu Ala Arg Ala Ala Val Val Glu Trp Arg Arg Val Val Leu
2210 2215 2220

Asp Val Leu Gly Cys Leu Gly Arg Leu Ala Leu Glu His Val Arg
2225 2230 2235

Val Arg Glu Ala Leu Gly Ala Ala Gly Ala Ser Gln Gly Cys Val
2240 2245 2250

Leu Ala Leu Arg Ala Val Gln Ala Gln Met Ala Ala Ala Glu Leu
2255 2260 2265

Cys Thr Lys Gly Gly Glu Arg Ser Leu Val Asp Lys Asp Gly Ile
2270 2275 2280

Val Lys Lys Pro Thr Val Ala Glu Ala Glu Lys Glu Ala Glu Ala
2285 2290 2295

Ala Leu Val Ala Glu Glu Arg Ala Thr Ala Gln Asp Thr Ser Arg
2300 2305 2310

Ala Ala Cys Val Leu Leu Cys His Leu Leu Asn Pro Pro Ala Pro
2315 2320 2325

Ser Pro Pro Ala Glu Thr Gly Ala Thr Asp Ser Glu Gln Ala Val
2330 2335 2340

Cys Arg Gln Gln Ser Asn Gln Trp Ala Leu Ala Arg Met Gly Gly
2345 2350 2355

Ala Glu Ala Leu Leu Ala Leu Leu Leu Pro Ala Gln Glu Pro Gly
2360 2365 2370

Lys Gly Ala Thr Asp Ala Gly Gly Glu Gly Ala Gly Gly Asn Gly

```
    2375                2380                2385

Asn Ala  Glu Arg Arg Arg Trp  Ser Gly Gln Met Ala  Ala Ala Leu
    2390                2395                2400

Thr Ala  Leu Gln Arg Met Val  Val Gly Asn Ile Met  Thr Gln Thr
    2405                2410                2415

His Val  Ala Glu Cys Gly Ser  Ala Ala Val Ile Arg  Thr Leu Ala
    2420                2425                2430

Ala Ala  Thr Arg Ala Ala Ala  Ala Ser Gly Asp Glu  Ala Val Gln
    2435                2440                2445

Ala Ala  Ala Leu Arg Leu Leu  Ala Asp Val Ala Arg  Gly Gly Asp
    2450                2455                2460

Ala Ala  His Ala Ala Val Arg  Gln Met Leu Leu Glu  Ala Gly Ala
    2465                2470                2475

Leu Gly  Ala Ala Leu Ala Ala  Leu Arg Asp Ser Val  Ala Ala Phe
    2480                2485                2490

Gly Gly  Cys Asn Gly Gly Arg  Glu Gly Ser Gly Asn  Ser Gly Cys
    2495                2500                2505

Ala Asp  Gly Gly Ser Ala Ala  Ser Ser Gly Met Glu  Val Ser Pro
    2510                2515                2520

Val Leu  Met Ala Ala Leu Asp  Ala Ile His Val Leu  Met Gly Pro
    2525                2530                2535

Ser Glu  Gln His Val Asp Gly  Ser Glu Pro Pro Leu  Ala Leu Gln
    2540                2545                2550

Ala Val  Val Arg Arg Glu Leu  Arg Arg Leu Gly Ala  Pro Arg Leu
    2555                2560                2565

Leu Ala  Asp Cys Val Arg Glu  Leu Arg Leu Gln Gln  Glu Asp Glu
    2570                2575                2580

Gln Gly  Glu Gly Arg Ala Gln  Glu Glu Trp Glu Arg  Ala Ser Gly
    2585                2590                2595

Arg Thr  Gly His Ser Arg His  Ala Pro Asp Gly Arg  Val Leu Pro
    2600                2605                2610

Gly Ala  Val Ala Gly Ala Gly  Gly Lys Gln Pro His  Pro Arg Pro
    2615                2620                2625

Trp Asp  Gly Ser Arg Ser Arg  Glu Glu Arg Gly Ser  Ala Gly Gly
    2630                2635                2640

Asp Cys  Leu Gly Cys Ser Pro  Val Leu Arg Ala Met  Ala Glu Leu
    2645                2650                2655

Gln Ala  Arg Val Cys Ala Val  Ala Gly Gly Thr Gly  Trp Val Arg
    2660                2665                2670

Cys Val  Val Gln Met Leu Gly  Ala Ser Pro Asp Gly  Val Gly Gln
    2675                2680                2685

Ala Gly  Arg Gly Gly Val Asp  Gly Gly Gly Ala Ala  Met Ala Ala
    2690                2695                2700

Val Ala  Ala His Arg Val Gln  Leu Arg Leu Leu Ala  Val Ala Ala
    2705                2710                2715

Gly Gly  Gly Phe Ala Leu Gly  Ala Ala Val Thr Gly  Ala Val Ala
    2720                2725                2730

Ala Met  Trp Met Ala
    2735
```

<210> SEQ ID NO 60
<211> LENGTH: 2780
<212> TYPE: DNA
<213> ORGANISM: Chlamydomonas reinhardtii

<400> SEQUENCE: 60
ttagttatca tatcctttga agcagacttg ctattcgcaa cccaccgcca cgctgtgctg 60
tgtgcgaaac acagtacgct cactttggca cggagagagc gcgcagctgc ttaactactc 120
tgtatttgct ctagaatgcg acatggtatt aaccggtttg atctttgctc gcactgataa 180
ttgtcggcat ttggtttcct cgcaaactgg acgcatgctg taattcacac ctgagatggc 240
gcacgagcag cagctcataa caaaacgcgc ctggctgggc ccgggcggtc cggagggcta 300
cctcacggtc gcgagcgcca gcctaaagtg gcagcctgca gccagcggag ccacgggtgt 360
gcaggagctg cgcattcccc tgtcatgcat tacaaataat cagcgcgcca aggacaagcc 420
gctggtgcgc atcactttca ccaatggcac cggcggcgcc gcggcgcatg tgttccagtt 480
tgagagcgtg gcggaccgtg atgcggccct ggacgtgctc acaaaggtca ttgcggcggt 540
ggcggcagcg gcgtcaggca gcggcacggc agccagtggc ggcggcggcg gtggtgatgc 600
tgggccagca gtggcgggcg gcttcaccag gcagcagcgg cagcagatgg ttgcacggga 660
cgctgacctc aaggccctgt acgacgagct ggtgggcggc ggggtggtgg gcgaggccga 720
cttctggggc ggcgtggcgg cacggctggc ggcggcgaag ccggccagct ggggcacggc 780
ggcggcgggg ccggcggggg cgggcgggct gccggggcgg cggcgcctgg gcctgagcaa 840
catcctgcag cgagtggagg ccgaggtgga cgggcggcac caacgtgtgc tgcgtgtgag 900
cctgacgccc gagcaggtgg cgcagatctt tgcggagcag ccggcggtgc tgcgcgccta 960
ccgcgagcac gtgccgcacc gcatggcgga ggaggacttc tggcggcgat acgtccggca 1020
tgagatgcac aaggagtcga agcgcaaggc ccgggctgag ggcatcaacc ccaatgccgc 1080
ggcggcgggc ggcggcgcca tggcggatga cgccggcggc gacatcttca gggaggcggc 1140
ggcggcggtg gcggcggagg cggcgcggcg gccgggccag gcggcggcgc accgtgaggc 1200
agtggatccg gagctggacc tggcggcggc ggcggcggag aggtacagcg gacacggcac 1260
cgcacacgcg gcagcccggg accccgagat ggagctggcg gcgggcagtg gcggcggagg 1320
cagcgggggc catcaccacc cgctggccgc cgaccccgac ccggacgacc tggcggccgc 1380
catcaacaag cacggcgagg tggtgctgca gggtgtggag gctttggccc gggtggaggc 1440
gcagctcaaa ggcaccgcac cggcagcagc aggcggccac cacggccacc acggacatca 1500
ccaacacaac caccacaacc acaaccacaa ccaccataga gcggacggcg cggacccggg 1560
gccaggcagc aacggcggcg acccacacgg ggaggggcag ggcggcgggg ggctgctggg 1620
tcggcggcgg cggcgacaca gcgcgggtct tgaggacctg cacgagccgc ccgcacgcca 1680
gttggacgcc ctcagcattg ccgacccccg caggtacttt gagcgcagcg ggcagcaggg 1740
cggcggggcg gcgccagcag cacacatggg cggcggctgg ggtggggccg gcggaggtgg 1800
gggcggcggg ccgggcctgt cgggcgctgc agcggtgctg ggctgtgtgt ctcccggctg 1860
cctgccgctg ccgccgctgc aggggtgtgc ggcggaggag gcgctgctgg aggccacacc 1920
gctggcccga gcgctggcgg aggaggaggc tgcgggtccg ggcggcgccg cgactgcctc 1980
tggcccgggc ggcgccagtg cgctgctgcg cgaccccgcc tcctccgtgc cgcccgagac 2040
actggccttc ctgcggcgca ccgtgctgtc cgtcaacgag gcgtgccggc acctgtggcg 2100
ctgcctgccc gccaacacac ccgcgcggag agacaaggcc gggcggctgg ctcgtctgct 2160
tgagtccaag cgcggcgagg tggaggccct gaacgaccgc gcccggggag tggaggggcg 2220
cttcatccgg cagctgctca agccgcccat ggacatgctg ctggcggcgc tggtcaggtg 2280

-continued

```
ggatgaggag cagcagaagc ggccggccgg agcgtcatga tgaacggcct gacggcagca   2340

gcgcggggta tgactctggc gtgggcggct cagtgatgcg gcgctggacg ttggcatgtg   2400

caggcataag gaactgggag cagggttgag cgcgcttggt tatgtgagcg tactagctcg   2460

gagctctttg acctggggct aggtgcatgc cgtctgcccc gatgagttgt gacccagata   2520

tgtctgaact ggccggactg agggcgagag gagttacaga gagtcgtgac atcgcctcct   2580

ctagcaagat caagtgcgta agctacgcac agtctgcctt gtgacctgct tacggtgccc   2640

caggcgcctg acacacgcga ccatctccct gttccgtggt acaacgacca ctttctctgt   2700

cggccggcta tgacggaagt attgacagct tgaagccttc gcaccgaagt caagatgcat   2760

ctacatatcc acttcaacgg                                                2780
```

```
<210> SEQ ID NO 61
<211> LENGTH: 2085
<212> TYPE: DNA
<213> ORGANISM: Chlamydomonas reinhardtii

<400> SEQUENCE: 61
```

```
atggcgcacg agcagcagct cataacaaaa cgcgcctggc tgggcccggg cggtccggag     60

ggctacctca cggtcgcgag cgccagccta aagtggcagc ctgcagccag cggagccacg    120

ggtgtgcagg agctgcgcat tcccctgtca tgcattacaa ataatcagcg cgccaaggac    180

aagccgctgg tgcgcatcac tttcaccaat ggcaccggcg gcgccgcggc gcatgtgttc    240

cagtttgaga gcgtggcgga ccgtgatgcg gccctggacg tgctcacaaa ggtcattgcg    300

gcggtggcgg cagcggcgtc aggcagcggc acggcagcca gtggcggcgg cggcggtggt    360

gatgctgggc cagcagtggc gggcggcttc accaggcagc agcggcagca gatggttgca    420

cgggacgctg acctcaaggc cctgtacgac gagctggtgg gcggcggggt ggtgggcgag    480

gccgacttct ggggcggcgt ggcggcacgg ctggcggcgg cgaagccggc cagctggggc    540

acggcggcgg cggggccggc gggggcgggc gggctgccgg ggcggcggcg cctgggcctg    600

agcaacatcc tgcagcgagt ggaggccgag gtggacgggc ggcaccaacg tgtgctgcgt    660

gtgagcctga cgcccgagca ggtggcgcag atctttgcgg agcagccggc ggtgctgcgc    720

gcctaccgcg agcacgtgcc gcaccgcatg gcggaggagg acttctggcg gcgatacgtc    780

cggcatgaga tgcacaagga gtcgaagcgc aaggcccggg ctgagggcat caaccccaat    840

gccgcggcgg cgggcggcgg cgccatggcg gatgacgccg gcggcgacat cttcagggag    900

gcggcggcgg cggtggcggc ggaggcggcg cggcggccgg gccaggcggc ggcgcaccgt    960

gaggcagtgg atccggagct ggacctggcg gcggcggcgg cggagaggta cagcggacac   1020

ggcaccgcac acgcggcagc ccgggacccc gagatggagc tggcggcggg cagtggcggc   1080

ggaggcagcg gggccatca ccacccgctg gccgccgacc ccgacccgga cgacctggcg   1140

gccgccatca acaagcacgg cgaggtggtg ctgcagggtg tggaggcttt ggcccgggtg   1200

gaggcgcagc tcaaaggcac cgcaccggca gcagcaggcg gccaccacgg ccaccacgga   1260

catcaccaac acaaccacca caaccacaac cacaaccacc atagagcgga cggcgcggac   1320

ccggggccag gcagcaacgg cggcgaccca cacggggagg ggcagggcgg cggggggctg   1380

ctgggtcggc ggcggcggcg acacagcgcg ggtcttgagg acctgcacga gccgcccgca   1440

cgccagttgg acgccctcag cattgccgac cccccgcaggt actttgagcg cagcgggcag   1500

cagggcggcg gggcggcgcc agcagcacac atgggcggcg gctggggtgg ggccggcgga   1560

ggtgggggcg gcgggccggg cctgtcgggc gctgcagcgg tgctgggctg tgtgtctccc   1620
```

```
ggctgcctgc cgctgccgcc gctgcagggg tgtgcggcgg aggaggcgct gctggaggcc   1680

acaccgctgg cccgagcgct ggcggaggag gaggctgcgg gtccgggcgg cgccgcgact   1740

gcctctggcc cgggcggcgc cagtgcgctg ctgcgcgacc ccgcctcctc cgtgccgccc   1800

gagacactgg ccttcctgcg gcgcaccgtg ctgtccgtca acgaggcgtg ccggcacctg   1860

tggcgctgcc tgcccgccaa cacacccgcg cggagagaca aggccgggcg gctggctcgt   1920

ctgcttgagt ccaagcgcgg cgaggtggag gccctgaacg accgcgcccg gggagtggag   1980

gggcgcttca tccggcagct gctcaagccg cccatggaca tgctgctggc ggcgctggtc   2040

aggtgggatg aggagcagca gaagcggccg gccggagcgt catga                   2085
```

```
<210> SEQ ID NO 62
<211> LENGTH: 694
<212> TYPE: PRT
<213> ORGANISM: Chlamydomonas reinhardtii

<400> SEQUENCE: 62

Met Ala His Glu Gln Gln Leu Ile Thr Lys Arg Ala Trp Leu Gly Pro
1               5                   10                  15

Gly Gly Pro Glu Gly Tyr Leu Thr Val Ala Ser Ala Ser Leu Lys Trp
            20                  25                  30

Gln Pro Ala Ala Ser Gly Ala Thr Gly Val Gln Glu Leu Arg Ile Pro
        35                  40                  45

Leu Ser Cys Ile Thr Asn Asn Gln Arg Ala Lys Asp Lys Pro Leu Val
    50                  55                  60

Arg Ile Thr Phe Thr Asn Gly Thr Gly Gly Ala Ala Ala His Val Phe
65                  70                  75                  80

Gln Phe Glu Ser Val Ala Asp Arg Asp Ala Ala Leu Asp Val Leu Thr
                85                  90                  95

Lys Val Ile Ala Ala Val Ala Ala Ala Ala Ser Gly Ser Gly Thr Ala
            100                 105                 110

Ala Ser Gly Gly Gly Gly Gly Gly Asp Ala Gly Pro Ala Val Ala Gly
        115                 120                 125

Gly Phe Thr Arg Gln Gln Arg Gln Gln Met Val Ala Arg Asp Ala Asp
    130                 135                 140

Leu Lys Ala Leu Tyr Asp Glu Leu Val Gly Gly Gly Val Val Gly Glu
145                 150                 155                 160

Ala Asp Phe Trp Gly Gly Val Ala Ala Arg Leu Ala Ala Ala Lys Pro
                165                 170                 175

Ala Ser Trp Gly Thr Ala Ala Ala Gly Pro Ala Gly Ala Gly Gly Leu
            180                 185                 190

Pro Gly Arg Arg Arg Leu Gly Leu Ser Asn Ile Leu Gln Arg Val Glu
        195                 200                 205

Ala Glu Val Asp Gly Arg His Gln Arg Val Leu Arg Val Ser Leu Thr
    210                 215                 220

Pro Glu Gln Val Ala Gln Ile Phe Ala Glu Gln Pro Ala Val Leu Arg
225                 230                 235                 240

Ala Tyr Arg Glu His Val Pro His Arg Met Ala Glu Glu Asp Phe Trp
                245                 250                 255

Arg Arg Tyr Val Arg His Glu Met His Lys Glu Ser Lys Arg Lys Ala
            260                 265                 270

Arg Ala Glu Gly Ile Asn Pro Asn Ala Ala Ala Ala Gly Gly Gly Ala
        275                 280                 285
```

-continued

```
Met Ala Asp Asp Ala Gly Gly Asp Ile Phe Arg Glu Ala Ala Ala Ala
    290                 295                 300

Val Ala Ala Glu Ala Ala Arg Arg Pro Gly Gln Ala Ala Ala His Arg
305                 310                 315                 320

Glu Ala Val Asp Pro Glu Leu Asp Leu Ala Ala Ala Ala Ala Glu Arg
                325                 330                 335

Tyr Ser Gly His Gly Thr Ala His Ala Ala Ala Arg Asp Pro Glu Met
            340                 345                 350

Glu Leu Ala Ala Gly Ser Gly Gly Gly Gly Ser Gly Gly His His His
        355                 360                 365

Pro Leu Ala Ala Asp Pro Asp Pro Asp Asp Leu Ala Ala Ala Ile Asn
    370                 375                 380

Lys His Gly Glu Val Val Leu Gln Gly Val Glu Ala Leu Ala Arg Val
385                 390                 395                 400

Glu Ala Gln Leu Lys Gly Thr Ala Pro Ala Ala Ala Gly Gly His His
                405                 410                 415

Gly His His Gly His His Gln His Asn His His Asn His Asn His Asn
            420                 425                 430

His His Arg Ala Asp Gly Ala Asp Pro Gly Pro Gly Ser Asn Gly Gly
        435                 440                 445

Asp Pro His Gly Glu Gly Gln Gly Gly Gly Gly Leu Leu Gly Arg Arg
    450                 455                 460

Arg Arg Arg His Ser Ala Gly Leu Glu Asp Leu His Glu Pro Pro Ala
465                 470                 475                 480

Arg Gln Leu Asp Ala Leu Ser Ile Ala Asp Pro Arg Arg Tyr Phe Glu
                485                 490                 495

Arg Ser Gly Gln Gln Gly Gly Gly Ala Ala Pro Ala Ala His Met Gly
            500                 505                 510

Gly Gly Trp Gly Gly Ala Gly Gly Gly Gly Gly Gly Gly Pro Gly Leu
        515                 520                 525

Ser Gly Ala Ala Ala Val Leu Gly Cys Val Ser Pro Gly Cys Leu Pro
    530                 535                 540

Leu Pro Pro Leu Gln Gly Cys Ala Ala Glu Glu Ala Leu Leu Glu Ala
545                 550                 555                 560

Thr Pro Leu Ala Arg Ala Leu Ala Glu Glu Glu Ala Ala Gly Pro Gly
                565                 570                 575

Gly Ala Ala Thr Ala Ser Gly Pro Gly Gly Ala Ser Ala Leu Leu Arg
            580                 585                 590

Asp Pro Ala Ser Ser Val Pro Pro Glu Thr Leu Ala Phe Leu Arg Arg
        595                 600                 605

Thr Val Leu Ser Val Asn Glu Ala Cys Arg His Leu Trp Arg Cys Leu
    610                 615                 620

Pro Ala Asn Thr Pro Ala Arg Arg Asp Lys Ala Gly Arg Leu Ala Arg
625                 630                 635                 640

Leu Leu Glu Ser Lys Arg Gly Glu Val Glu Ala Leu Asn Asp Arg Ala
                645                 650                 655

Arg Gly Val Glu Gly Arg Phe Ile Arg Gln Leu Leu Lys Pro Pro Met
            660                 665                 670

Asp Met Leu Leu Ala Ala Leu Val Arg Trp Asp Glu Glu Gln Gln Lys
        675                 680                 685

Arg Pro Ala Gly Ala Ser
    690
```

-continued

<210> SEQ ID NO 63
<211> LENGTH: 2293
<212> TYPE: DNA
<213> ORGANISM: Chlamydomonas reinhardtii

<400> SEQUENCE: 63
cttactccca aactcaaaag aagcactgaa tttaactaca actgatagcc atatgttcgg 60
ctcagacgta gggcaccgtg cttagaccca cgcccaagac aatcggtccc cagttataag 120
ggcctgaagg cccgagcgtt cccttagagc ggcaatggac tctgatagcg acgatgagcg 180
tgcggcgggc tacgtgccag tgttggcagc atcaatgcca cgagctgctg cagcggcggc 240
agtggccagc cccgcggcga agcaaccttc caacgttcta caagatggtg tttcgcttta 300
caccaatgag ctgttcaccg acaacaacgg ggatgtgctg ggcgagggtc ctgggctcgc 360
gtctcccagc ggagcggcgc ccggcagcgc acgaaaaggc ctggctgcga aacggcagga 420
gcggttgcag gggaacgcat acacgccaaa ctcgctccta aagaacgcct cactgcgtaa 480
ccccggtgcc cctgcgtcgc cgggtatgcg ggactcgccc tcctccttcc ggccatccac 540
cctgtcgcaa acggggaccg ccaccacagt ggaaacgaca ttggtcagcc ccaaccgcaa 600
cagcaacaac cagggcatcg ccgggggcgt gggaatggtg cacggcttgc gcgccagcta 660
cgaccccaac gaggggcagg aggagcctgt gccctccacg cggtacgtgg cgccggcagc 720
ggtgccggtg gcacgcgccg tgccccagct ggacctttca gacatgccgg cattcctgca 780
gcagccgggg cctaagaatg ggccggtgca gtgcgtcatc gtgcgcgacc gcgggtctgc 840
aaagatgtac ccgcggtact cgctgttcct ggaggagggg cggcgctttc tgctgtcagc 900
gcgcaagcgg aagaagcaga ccaccagcaa ctacatcata tccatggact acgaggacct 960
cagccgggag agcgggtcgt tctttgggaa ggtccgcgcc aacttcgtgg gtacggagtt 1020
cacggtgtat gaccgggggg ttaaggcggg caagaaggac gcccagggcg acggccagcg 1080
cgaggagctg gggggcggtga cgtaccagta caacgtgctg ggcacgcggg ggccgcgcaa 1140
gatgatggcg gccatccccg gggtggacgg cagcgggcgg cgcatgttca accccagcgg 1200
cgacgcggac accatcctgg agcggctcaa acaccggaag ggactggagg agctggtggt 1260
gatgggcaac aagccgccgc gctggaatga cgagctgaac gcctactgcc tgaacttcaa 1320
cgggcgcgtg acggaggcgt ccgtgaagaa cttccagctg gtgtcggacg acaaccacaa 1380
ccacgtcatc ctgcagttcg gcaaggtcgg caaggacacg ttcaccatgg actaccagtg 1440
gcccatctcc gcgtttcagg cgttcgccat ctgcatgtcg tcctttgaca acaagctggc 1500
gtgcgagtaa tgaagtggtg atgcagcagt cagcggcaga atgtggctgg gagtcgcgtg 1560
gaggagcgca gagcggaggg tgctgcagat tttggagcct aaagtggact cgtgatggag 1620
ccggaggttg gccatctggc cggaggtaca tctggcagct gccagggctt ggggagcttg 1680
ggtaggaatg ccgccgtgtg ctgtaaggcg caggttacag gctcgggagc tttgtctaga 1740
caaatgatag caacccgtgc ctacacttgg gtgtgcatgg ctgaagagcg gtgcatacgg 1800
taggacagat cagggcgtgg cgatggggtg ttaggtagct cggaggtaac gggtgcagcg 1860
gcttgggacg gcccgatggg caaggtttgc tgcatgtact gccgacaggg gcacaagaag 1920
aaattgtata atgtatgttc taggacagct ccgactaacc cccaactaac tcgcgtacgg 1980
caccctcagc cgtacaggag ttgactaggg agtcggcagc tgcgcgagtg ggagcgggta 2040
gttgtacggt tgcccagctc gcaagctacc tgactgtcgt gacgcacacg ggcagttgcc 2100
acgagtcagc aggcgcgcga gtgggagctg gcactcagta gagagctcac gcgtgtggga 2160

-continued

```
agctgcggtt gagcataatg gagcacggcg gaggctgccg gttggcgcgg cgcgcgattg   2220

gtagtgcata gtcgcgcgcg tgcgtgctgt gtgggaagcc ccgtgtgtga gctacgtgta   2280

aactcagaga gac                                                      2293


<210> SEQ ID NO 64
<211> LENGTH: 1356
<212> TYPE: DNA
<213> ORGANISM: Chlamydomonas reinhardtii

<400> SEQUENCE: 64

atggactctg atagcgacga tgagcgtgcg gcgggctacg tgccagtgtt ggcagcatca     60

atgccacgag ctgctgcagc ggcggcagtg gccagccccg cggcgaagca accttccaac    120

gttctacaag atggtgtttc gctttacacc aatgagctgt tcaccgacaa caacggggat    180

gtgctgggcg agggtcctgg gctcgcgtct cccagcggag cggcgcccgg cagcgcacga    240

aaaggcctgg ctgcgaaacg gcaggagcgg ttgcagggga acgcatacac gccaaactcg    300

ctcctaaaga acgcctcact gcgtaacccc ggtgcccctg cgtcgccggg tatgcgggac    360

tcgccctcct ccttccggcc atccaccctg tcgcaaacgg ggaccgccac cacagtggaa    420

acgacattgg tcagccccaa ccgcaacagc aacaaccagg gcatcgccgg gggcgtggga    480

atggtgcacg gcttgcgcgc cagctacgac cccaacgagg ggcaggagga gcctgtgccc    540

tccacgcggt acgtggcgcc ggcagcggtg ccggtggcac gcgccgtgcc ccagctggac    600

ctttcagaca tgccggcatt cctgcagcag ccggggccta agaatgggcc ggtgcagtgc    660

gtcatcgtgc gcgaccgcgg gtctgcaaag atgtacccgc ggtactcgct gttcctggag    720

gaggggcggc gctttctgct gtcagcgcgc aagcggaaga agcagaccac cagcaactac    780

atcatatcca tggactacga ggacctcagc cgggagagcg ggtcgttctt tgggaaggtc    840

cgcgccaact tcgtgggtac ggagttcacg gtgtatgacc ggggggttaa ggcgggcaag    900

aaggacgccc agggcgacgg ccagcgcgag gagctggggg cggtgacgta ccagtacaac    960

gtgctgggca cgcgggggcc gcgcaagatg atggcggcca tccccggggt ggacggcagc   1020

gggcggcgca tgttcaaccc cagcggcgac gcggacacca tcctggagcg gctcaaacac   1080

cggaagggac tggaggagct ggtggtgatg ggcaacaagc cgccgcgctg gaatgacgag   1140

ctgaacgcct actgcctgaa cttcaacggg cgcgtgacgg aggcgtccgt gaagaacttc   1200

cagctggtgt cggacgacaa ccacaaccac gtcatcctgc agttcggcaa ggtcggcaag   1260

gacacgttca ccatggacta ccagtggccc atctccgcgt ttcaggcgtt cgccatctgc   1320

atgtcgtcct ttgacaacaa gctggcgtgc gagtaa                             1356


<210> SEQ ID NO 65
<211> LENGTH: 451
<212> TYPE: PRT
<213> ORGANISM: Chlamydomonas reinhardtii

<400> SEQUENCE: 65

Met Asp Ser Asp Ser Asp Asp Glu Arg Ala Ala Gly Tyr Val Pro Val
1               5                   10                  15

Leu Ala Ala Ser Met Pro Arg Ala Ala Ala Ala Ala Ala Val Ala Ser
            20                  25                  30

Pro Ala Ala Lys Gln Pro Ser Asn Val Leu Gln Asp Gly Val Ser Leu
        35                  40                  45

Tyr Thr Asn Glu Leu Phe Thr Asp Asn Asn Gly Asp Val Leu Gly Glu
    50                  55                  60
```

```
Gly Pro Gly Leu Ala Ser Pro Ser Gly Ala Ala Pro Gly Ser Ala Arg
65                  70                  75                  80

Lys Gly Leu Ala Ala Lys Arg Gln Glu Arg Leu Gln Gly Asn Ala Tyr
                85                  90                  95

Thr Pro Asn Ser Leu Leu Lys Asn Ala Ser Leu Arg Asn Pro Gly Ala
            100                 105                 110

Pro Ala Ser Pro Gly Met Arg Asp Ser Pro Ser Ser Phe Arg Pro Ser
        115                 120                 125

Thr Leu Ser Gln Thr Gly Thr Ala Thr Thr Val Glu Thr Thr Leu Val
    130                 135                 140

Ser Pro Asn Arg Asn Ser Asn Asn Gln Gly Ile Ala Gly Gly Val Gly
145                 150                 155                 160

Met Val His Gly Leu Arg Ala Ser Tyr Asp Pro Asn Glu Gly Gln Glu
                165                 170                 175

Glu Pro Val Pro Ser Thr Arg Tyr Val Ala Pro Ala Ala Val Pro Val
            180                 185                 190

Ala Arg Ala Val Pro Gln Leu Asp Leu Ser Asp Met Pro Ala Phe Leu
        195                 200                 205

Gln Gln Pro Gly Pro Lys Asn Gly Pro Val Gln Cys Val Ile Val Arg
    210                 215                 220

Asp Arg Gly Ser Ala Lys Met Tyr Pro Arg Tyr Ser Leu Phe Leu Glu
225                 230                 235                 240

Glu Gly Arg Arg Phe Leu Leu Ser Ala Arg Lys Arg Lys Lys Gln Thr
                245                 250                 255

Thr Ser Asn Tyr Ile Ile Ser Met Asp Tyr Glu Asp Leu Ser Arg Glu
            260                 265                 270

Ser Gly Ser Phe Phe Gly Lys Val Arg Ala Asn Phe Val Gly Thr Glu
        275                 280                 285

Phe Thr Val Tyr Asp Arg Gly Val Lys Ala Gly Lys Lys Asp Ala Gln
    290                 295                 300

Gly Asp Gly Gln Arg Glu Glu Leu Gly Ala Val Thr Tyr Gln Tyr Asn
305                 310                 315                 320

Val Leu Gly Thr Arg Gly Pro Arg Lys Met Met Ala Ala Ile Pro Gly
                325                 330                 335

Val Asp Gly Ser Gly Arg Arg Met Phe Asn Pro Ser Gly Asp Ala Asp
            340                 345                 350

Thr Ile Leu Glu Arg Leu Lys His Arg Lys Gly Leu Glu Glu Leu Val
        355                 360                 365

Val Met Gly Asn Lys Pro Pro Arg Trp Asn Asp Glu Leu Asn Ala Tyr
    370                 375                 380

Cys Leu Asn Phe Asn Gly Arg Val Thr Glu Ala Ser Val Lys Asn Phe
385                 390                 395                 400

Gln Leu Val Ser Asp Asp Asn His Asn His Val Ile Leu Gln Phe Gly
                405                 410                 415

Lys Val Gly Lys Asp Thr Phe Thr Met Asp Tyr Gln Trp Pro Ile Ser
            420                 425                 430

Ala Phe Gln Ala Phe Ala Ile Cys Met Ser Ser Phe Asp Asn Lys Leu
        435                 440                 445

Ala Cys Glu
    450
```

<210> SEQ ID NO 66
<211> LENGTH: 3036

<212> TYPE: DNA
<213> ORGANISM: Chlamydomonas reinhardtii

<400> SEQUENCE: 66
gtatcagtcg tgggcaattg tagaagacgc cctgactgtg cgataggaca catttgctta 60
ggcttcttct tcagccggaa attgtggtcg ccaccgactt gcgctttctc acaccagcaa 120
acatggcgct tccaggctcc acaatgaacc ttacaacccg ctgctctact acaccgcggt 180
cggctgtggt tgcgcgcgcg gtggctgcgc ccacgcgacc caccaccaag tctgcggtgc 240
cagagctgct ggatagccgg ccaggcgagc gcaatctcaa cttcatggag tatgctcagg 300
cgactcagat gctggaccgg ctcaagggcc aggcctctga cctggaattg ctgctggacc 360
agctcaacgc gctggaggcc agcctcgacg agagcgttct ggcgccgccc acggtggacg 420
accccaagga gcgggctgcg cgacaagcac ggcgcgctgc caagcgtgca gagcgtaggg 480
cccaggcgac atccgcaaca gtcgcggccg cggctgggcc ggcaatgtca gcagtggtct 540
cgcattccac gccgacgaag gctgctgctg cgccggccac gtcaacagcg agcagcagct 600
ccagcgatag tggtttgcta gacctggtga gctttgttgg cggctttgac acgcggccga 660
tcccggcaac gacgtctgca ccccctgctg gcgccagcag ctccgacgtg cagcacctgg 720
aggacctctt caaactcagc gtcggcgagc ccgacatccc ccgggcctcc gcttcagcag 780
cgcctgcggt gctgcggcca cgcaagctca caccaaagaa gccctctgcg gcaccctccg 840
cggcggtgac ggcagcaccc tcgccggcac ccacgctccc cagcacgccc agcaccagcg 900
cgcgcattgc gcccgcgccc ggctccctcg cggatgagct ggagcggtta ctggggccca 960
ccacgtcacg ggaggcggct gagtctgagg acgaggacag cttcgcgggg ccgtctgagg 1020
acgacctgct ggcgctggag caggaggtgt cgcgcaagtc gtcacggctg cctgtgctag 1080
acgaggaaga cgaggaggat gagcagcagc agctggagga caacgaggag gacgcggtgg 1140
cggggcccgg ctctttggag gcgtcggcaa tggcgactcg gacgtccagc cagctgtcca 1200
tcatgcagac ggggccgtcg ctgcttagcc tggtcccagc atccgcggcg ccaggccgca 1260
gcgccaaggc gcgcgcctcc cggcgcgcgg cgcgcaacgg tcacgctagc gggcggctgg 1320
gtggcgcgac agctaacgcg gcggggcggg gcaaggtggg cagcaaggac gggaccatga 1380
acttcctggg caaggtggag tcattgtcaa cgctggacgt ggagaaggaa cgcgaggtga 1440
cggcagtttg ccgcgacttc ctgttcctgg agaaggtgaa gcggcagtgc gagaagacgc 1500
tgcaccggcc cgccacgtct gaggagattg cggcggccgt ggccatggat gtcgagagcc 1560
tgaagctccg ctatgacgcc ggtctgaagg ccaaggagct gctgctcaag tccaactaca 1620
agctggtcat gacggtgtgc aagtcgtttg tgggcaaggg cccgcacatc caggacctgg 1680
tgtcggaggg cgtcaagggc ctgctcaagg gcgtggaaaa gtacgacgcc accaagggct 1740
tccgcttcgg cacgtacgcg cactggtgga tccgccaggc cgtgtcgcgc tcgctggcgg 1800
agacgggccg cgcagtcagg ctgcccatgc acatgatcga gcagctgacg cggctcaaga 1860
acctgtccgc caagctgcag acgcagctgg cgcgagagcc cacgctgccc gagctggcca 1920
aggcggctgg tctgcctgtg acgcgcgttc agatgctcat ggagacggcg cgctccgccg 1980
cgtccctgga cacgcccatc ggcggcaacg agctgggccc gaccgtgaag gactccgtgg 2040
aggacgagcg cgaggcggcg gacgaggagt ttggcagcga cagtctgcgc aacgacatgg 2100
aggcgatgtt gttggagctg ccggagcgcg aggcgcgcgt ggtgcggctg cgcttcgggc 2160
tggacgacgg caaggagtgg acgctggagg agattggaga ggcgctgaac gtaacacgcg 2220

-continued agcgcatccg tcagattgag gccaaggcgc tgcgcaagct gcgtgtgaag actattgacg 2280
tgagcggcaa gctgatggag tacggcgaga acctggagat gctgatggac ggctcgcgcg 2340
agatggctgc gcgcaccagc agcggcaccc gcaagacgta agctggctgc tgtaggaggc 2400
ggaggcggca ggaggcggag gcagcaatag ggatgtcaac agtagctgag gtagcgggtg 2460
atgcgtgggt tggtggcggt aatagcagca tgtagcgtgc aggcttgggc cgggaagcta 2520
gattcccgtg aggttctatg cgctggtagc gagtgcgttc atagctagcc gtccatgtct 2580
tgtaggatgt agtcattgca tgaggtagcg tgccacgggg tcaaatgtgc catcctgaat 2640
cagcggtgcg ttgctcgcat ataaatgaga gcaagattgc aggccctgcg ctatgccagg 2700
ccgcagacag tgtcagcact aagagagcgt tagagcacct gagcgcgggt aagggacacc 2760
gtgtatgtgc ttgtttaatc aggataccgt atgctatggc atgggatcgg tcagctgcaa 2820
gtgggagata tagtgtatgc actcacgccc ggattcgagg gctgtataac atgattgctg 2880
atttctgaaa ctatgccaat cctgaattta gtttctcacg atggacatgg gcggcagttg 2940
agacagatac gttcccgacg agaaattgac catccatagc tgcttttgtc tgcagccaag 3000
ttgcttttgc atgatggctt gtaaattcat gccgac 3036

<210> SEQ ID NO 67
<211> LENGTH: 2259
<212> TYPE: DNA
<213> ORGANISM: Chlamydomonas reinhardtii

<400> SEQUENCE: 67
atggcgcttc caggctccac aatgaacctt acaacccgct gctctactac accgcggtcg 60
gctgtggttg cgcgcgcggt ggctgcgccc acgcgaccca ccaccaagtc tgcggtgcca 120
gagctgctgg atagccggcc aggcgagcgc aatctcaact tcatggagta tgctcaggcg 180
actcagatgc tggaccggct caagggccag gcctctgacc tggaattgct gctggaccag 240
ctcaacgcgc tggaggccag cctcgacgag agcgttctgg cgccgcccac ggtggacgac 300
cccaaggagc gggctgcgcg acaagcacgg cgcgctgcca agcgtgcaga gcgtagggcc 360
caggcgacat ccgcaacagt cgcggccgcg gctgggccgg caatgtcagc agtggtctcg 420
cattccacgc cgacgaaggc tgctgctgcg ccggccacgt caacagcgag cagcagctcc 480
agcgatagtg gtttgctaga cctggtgagc tttgttggcg gctttgacac gcggccgatc 540
ccggcaacga cgtctgcacc ccctgctggc gccagcagct ccgacgtgca gcacctggag 600
gacctcttca aactcagcgt cggcgagccc gacatccccc gggcctccgc ttcagcagcg 660
cctgcggtgc tgcggccacg caagctcaca ccaaagaagc cctctgcggc accctccgcg 720
gcggtgacgg cagcaccctc gccggcaccc acgctcccca gcacgcccag caccagcgcg 780
cgcattgcgc ccgcgcccgg ctccctcgcg gatgagctgg agcggttact ggggcccacc 840
acgtcacggg aggcggctga gtctgaggac gaggacagct tcgcggggcc gtctgaggac 900
gacctgctgg cgctggagca ggaggtgtcg cgcaagtcgt cacggctgcc tgtgctagac 960
gaggaagacg aggaggatga gcagcagcag ctggaggaca acgaggagga cgcggtggcg 1020
gggcccggct ctttggaggc gtcggcaatg gcgactcgga cgtccagcca gctgtccatc 1080
atgcagacgg ggccgtcgct gcttagcctg gtcccagcat ccgcggcgcc aggccgcagc 1140
gccaaggcgc gcgcctcccg gcgcgcggcg cgcaacggtc acgctagcgg gcggctgggt 1200
ggcgcgacag ctaacgcggc ggggcggggc aaggtgggca gcaaggacgg gaccatgaac 1260
ttcctgggca aggtggagtc attgtcaacg ctggacgtgg agaaggaacg cgaggtgacg 1320

-continued

```
gcagtttgcc gcgacttcct gttcctggag aaggtgaagc ggcagtgcga gaagacgctg   1380

caccggcccg ccacgtctga ggagattgcg gcggccgtgg ccatggatgt cgagagcctg   1440

aagctccgct atgacgccgg tctgaaggcc aaggagctgc tgctcaagtc caactacaag   1500

ctggtcatga cggtgtgcaa gtcgtttgtg ggcaagggcc cgcacatcca ggacctggtg   1560

tcggagggcg tcaagggcct gctcaagggc gtggaaaagt acgacgccac caagggcttc   1620

cgcttcggca cgtacgcgca ctggtggatc cgccaggccg tgtcgcgctc gctggcggag   1680

acgggccgcg cagtcaggct gcccatgcac atgatcgagc agctgacgcg gctcaagaac   1740

ctgtccgcca agctgcagac gcagctggcg cgagagccca cgctgcccga gctggccaag   1800

gcggctggtc tgcctgtgac gcgcgttcag atgctcatgg agacggcgcg ctccgccgcg   1860

tccctggaca cgcccatcgg cggcaacgag ctgggcccga ccgtgaagga ctccgtggag   1920

gacgagcgcg aggcggcgga cgaggagttt ggcagcgaca gtctgcgcaa cgacatggag   1980

gcgatgttgt tggagctgcc ggagcgcgag gcgcgcgtgg tgcggctgcg cttcgggctg   2040

gacgacggca aggagtggac gctggaggag attggagagg cgctgaacgt aacacgcgag   2100

cgcatccgtc agattgaggc caaggcgctg cgcaagctgc gtgtgaagac tattgacgtg   2160

agcggcaagc tgatggagta cggcgagaac ctggagatgc tgatggacgg ctcgcgcgag   2220

atggctgcgc gcaccagcag cggcacccgc aagacgtaa                           2259
```

<210> SEQ ID NO 68
<211> LENGTH: 752
<212> TYPE: PRT
<213> ORGANISM: Chlamydomonas reinhardtii

<400> SEQUENCE: 68

```
Met Ala Leu Pro Gly Ser Thr Met Asn Leu Thr Thr Arg Cys Ser Thr
1               5                   10                  15

Thr Pro Arg Ser Ala Val Val Ala Arg Ala Val Ala Ala Pro Thr Arg
            20                  25                  30

Pro Thr Thr Lys Ser Ala Val Pro Glu Leu Leu Asp Ser Arg Pro Gly
        35                  40                  45

Glu Arg Asn Leu Asn Phe Met Glu Tyr Ala Gln Ala Thr Gln Met Leu
    50                  55                  60

Asp Arg Leu Lys Gly Gln Ala Ser Asp Leu Glu Leu Leu Leu Asp Gln
65                  70                  75                  80

Leu Asn Ala Leu Glu Ala Ser Leu Asp Glu Ser Val Leu Ala Pro Pro
                85                  90                  95

Thr Val Asp Asp Pro Lys Glu Arg Ala Ala Arg Gln Ala Arg Arg Ala
            100                 105                 110

Ala Lys Arg Ala Glu Arg Arg Ala Gln Ala Thr Ser Ala Thr Val Ala
        115                 120                 125

Ala Ala Ala Gly Pro Ala Met Ser Ala Val Val Ser His Ser Thr Pro
    130                 135                 140

Thr Lys Ala Ala Ala Ala Pro Ala Thr Ser Thr Ala Ser Ser Ser Ser
145                 150                 155                 160

Ser Asp Ser Gly Leu Leu Asp Leu Val Ser Phe Val Gly Gly Phe Asp
                165                 170                 175

Thr Arg Pro Ile Pro Ala Thr Thr Ser Ala Pro Pro Ala Gly Ala Ser
            180                 185                 190

Ser Ser Asp Val Gln His Leu Glu Asp Leu Phe Lys Leu Ser Val Gly
        195                 200                 205
```

```
Glu Pro Asp Ile Pro Arg Ala Ser Ala Ser Ala Ala Pro Ala Val Leu
    210                 215                 220

Arg Pro Arg Lys Leu Thr Pro Lys Lys Pro Ser Ala Ala Pro Ser Ala
225                 230                 235                 240

Ala Val Thr Ala Ala Pro Ser Pro Ala Pro Thr Leu Pro Ser Thr Pro
                245                 250                 255

Ser Thr Ser Ala Arg Ile Ala Pro Ala Pro Gly Ser Leu Ala Asp Glu
            260                 265                 270

Leu Glu Arg Leu Leu Gly Pro Thr Thr Ser Arg Glu Ala Ala Glu Ser
        275                 280                 285

Glu Asp Glu Asp Ser Phe Ala Gly Pro Ser Glu Asp Asp Leu Leu Ala
    290                 295                 300

Leu Glu Gln Glu Val Ser Arg Lys Ser Ser Arg Leu Pro Val Leu Asp
305                 310                 315                 320

Glu Glu Asp Glu Glu Asp Glu Gln Gln Gln Leu Glu Asp Asn Glu Glu
                325                 330                 335

Asp Ala Val Ala Gly Pro Gly Ser Leu Glu Ala Ser Ala Met Ala Thr
            340                 345                 350

Arg Thr Ser Ser Gln Leu Ser Ile Met Gln Thr Gly Pro Ser Leu Leu
        355                 360                 365

Ser Leu Val Pro Ala Ser Ala Ala Pro Gly Arg Ser Ala Lys Ala Arg
    370                 375                 380

Ala Ser Arg Arg Ala Ala Arg Asn Gly His Ala Ser Gly Arg Leu Gly
385                 390                 395                 400

Gly Ala Thr Ala Asn Ala Ala Gly Arg Gly Lys Val Gly Ser Lys Asp
                405                 410                 415

Gly Thr Met Asn Phe Leu Gly Lys Val Glu Ser Leu Ser Thr Leu Asp
            420                 425                 430

Val Glu Lys Glu Arg Glu Val Thr Ala Val Cys Arg Asp Phe Leu Phe
        435                 440                 445

Leu Glu Lys Val Lys Arg Gln Cys Glu Lys Thr Leu His Arg Pro Ala
    450                 455                 460

Thr Ser Glu Glu Ile Ala Ala Ala Val Ala Met Asp Val Glu Ser Leu
465                 470                 475                 480

Lys Leu Arg Tyr Asp Ala Gly Leu Lys Ala Lys Glu Leu Leu Leu Lys
                485                 490                 495

Ser Asn Tyr Lys Leu Val Met Thr Val Cys Lys Ser Phe Val Gly Lys
            500                 505                 510

Gly Pro His Ile Gln Asp Leu Val Ser Glu Gly Val Lys Gly Leu Leu
        515                 520                 525

Lys Gly Val Glu Lys Tyr Asp Ala Thr Lys Gly Phe Arg Phe Gly Thr
    530                 535                 540

Tyr Ala His Trp Trp Ile Arg Gln Ala Val Ser Arg Ser Leu Ala Glu
545                 550                 555                 560

Thr Gly Arg Ala Val Arg Leu Pro Met His Met Ile Glu Gln Leu Thr
                565                 570                 575

Arg Leu Lys Asn Leu Ser Ala Lys Leu Gln Thr Gln Leu Ala Arg Glu
            580                 585                 590

Pro Thr Leu Pro Glu Leu Ala Lys Ala Ala Gly Leu Pro Val Thr Arg
        595                 600                 605

Val Gln Met Leu Met Glu Thr Ala Arg Ser Ala Ala Ser Leu Asp Thr
    610                 615                 620
```

-continued

```
Pro Ile Gly Gly Asn Glu Leu Gly Pro Thr Val Lys Asp Ser Val Glu
625                 630                 635                 640

Asp Glu Arg Glu Ala Ala Asp Glu Glu Phe Gly Ser Asp Ser Leu Arg
                645                 650                 655

Asn Asp Met Glu Ala Met Leu Leu Glu Leu Pro Glu Arg Glu Ala Arg
            660                 665                 670

Val Val Arg Leu Arg Phe Gly Leu Asp Asp Gly Lys Glu Trp Thr Leu
        675                 680                 685

Glu Glu Ile Gly Glu Ala Leu Asn Val Thr Arg Glu Arg Ile Arg Gln
    690                 695                 700

Ile Glu Ala Lys Ala Leu Arg Lys Leu Arg Val Lys Thr Ile Asp Val
705                 710                 715                 720

Ser Gly Lys Leu Met Glu Tyr Gly Glu Asn Leu Glu Met Leu Met Asp
                725                 730                 735

Gly Ser Arg Glu Met Ala Ala Arg Thr Ser Ser Gly Thr Arg Lys Thr
            740                 745                 750


<210> SEQ ID NO 69
<211> LENGTH: 8296
<212> TYPE: DNA
<213> ORGANISM: Chlamydomonas reinhardtii

<400> SEQUENCE: 69

atgactgggc gtacacacgt aacgtgtgag tctgcgaggc tcgggggcg attgccctca      60

ctccgaagac gggcattggc gtctaccagt attgcgctct aatatgagtc caggtttgaa     120

gctatgtgga gattttcaga tggagcgagc ggctggcagc gctctggcta gcggggcgtg     180

aacgccggca gcgacgacgg tgcgcaaagc tatctgggca ccaccggtgc aatcatggac     240

atgtttatgc atggaggctc gccagagcct caaggtcggg gcggctatga agacgaccgc     300

gctggcacaa acgaacttgc agcaaatcga tgccaggccg atggctgcat ggcggacctc     360

tcaggactga agcgctactt ccgccgctac catgtgtgcg agatgcacat ccgggcgcag     420

gtggtgttga tctcggggcg tcaggtgcgc ttctgcgacc agtgcagcac attccacccc     480

ctggccttct ttgacggagt gcgcaggacg tgtcgtgaga agctggagca caaccgacaa     540

aagcggcgcg cgcgcaaggc tgcgcacggc ggcggcggtg gtggcggcgg aggcggcgct     600

gagcgcacaa caggcggcgg cggcggcggt cggcccgctg gctccggccg cggcgcacgc     660

agcggcggcg ccggaaacga cgacgatgac gatggtggcg gcgagtctga aggagagccg     720

ggtggcggcg gcagtgacga tggcggctcg gggtctgggc gggggcaggc gcgcaagcgg     780

ccgccgagcg tgtcgtcgtc gcaacagcag caggcggctg cggcggcgca gcggcggcgc     840

atgggcagcg gcccaatgcc gggctccgcg caggacctag ctctggcggc ggcggtggcg     900

gcggcggcgg cggcgggcat gtcagttgcc agccctggtg ccggcgccgg cgccggacct     960

gggcccggcg cgggggcgct gggcttgggt ccgggctata gccgtatggg gtcggaggca    1020

cggaccggtg cgatgccggg gccggcgccg gggccggggc cgcgtggtgt ctcgcccggg    1080

tttgagggcg aggatgacga gtactacgcc ggccgcaccg gccacccgca cacgtacacg    1140

catcatcaac atccgcatcc acagcagctg ccgcagcagc agcaatcacg agagggctac    1200

atggggggcg ccaacgcgcg ggactccttg tcgggcgggc ccgtggtggc ggggcagggc    1260

gggtcggctg gcgcacaccc gcacccgcac ctgccggcac agggcgggcc gccgccgccg    1320

ccaccgaggg cagggctatt cgggggcccg ctcgggtcag cggcgggagc caacggcgca    1380

gccgctgcgg cggggctgct gcgcggcggc tccggccccg gtgcagagca cctgcggccg    1440
```

```
ccgctgaggg aggctagcgg cgtgctgggg gcgccgtcgg gcgatggcct tggtggtggt   1500
ggtggcggtg gtggtggtgg tggtggtggt ggtggtggcg gtggtgtgct gcctgcggga   1560
ctgagtgagg aggaggcgct gcagcggcag ttggaggagc tgcgcagtgc gatcacgtgg   1620
cgtcagcagg agctgcagca gcaccagcac cagcgctacc aacatcatca ccaacagcaa   1680
caacaacatc aacaacaaca ccagcaacag caacagcagc accaacagat tggcttgaag   1740
caggaggggc gggagcagga agcctgggcg cgcgggccgg ggccggggcc gggagggggac  1800
gagccgcgct ggcagcagca gcagcagcag cagcagcagc aggcgcggca tgggtacccg   1860
gcaccaggca tggggcaagg gccggggctc ggcctggggc ggcagggagc gcctgtgccc   1920
gcaatgccgg caattgcagg cgccgccaat ggcgccaacg gtgtcggtgg cgtcaatggc   1980
gttcgcgtgg cacgtgacgg cgcgtttgca ccgccgccgc tagaccctgc gcgccggcgg   2040
ccgggggcac ccggcggccc ccctccgccg ccgcacctgc cacagcaccc gcaccaccac   2100
catcaccacc accaagatgt ggagatggcg ctgcaggagc agcagctgct gcaggagctg   2160
cgccggcagc aacaacagca gcagcagcag cagcaacaac aacaacaaga acaacaacaa   2220
cggcagcagc aacaacaaca acggcagcag caacagttgc aggagcagca caacatgcag   2280
cacgggcatc agcagcagct gcggccgccg ccgccggttc caggggcgac tgcgggctgg   2340
agttacgccc acacggggac tcgcccgcca gtggaggtga agatggaggt ggaggcagac   2400
gttggggcag gcggcggcgg cctgggcggg accggcggct tgcgcaagga actaacactc   2460
ggccccgccg gcttcaccag cgccggcgct ccgcctccct accacccccca acacccctcg  2520
ccgcacgctt cctcgcctcg tggccccctc gtgggccgct cctgggacgg ccgcggccca   2580
ccgtcagatc cctcggcgcg accgccgccg ccgccgccgc cgggcgtgtc gctggccggc   2640
tttccctccg acgtaccagc ccggctgcag ctgccgggct cggcccgcgg cccggcgccc   2700
ggcgccgccg ccgggaggcc caccggagat ggcatggcgg cggcggcggc ggccgtgcga   2760
cagcaccagc agcaccagta ccagctgcac caacagcagc aagagcacca acagcaacag   2820
cagcaccaac agcaacagca ccagcagcat caccagcacc aacagcagtt gctcctggcg   2880
gaggcggagg cggagctgca gcggcagcgg cagctgcagg cgatggcggc ggcgggcggc   2940
cccatggcgg cggcgatgcg actgcgcgcc ggcgccggcc tcggcggcgc gtggcagcag   3000
caccagcacc agcacccgca gcaccagcac cagcagcaac agccgcagca acagccgcag   3060
ccgcaatcga gccggcggtc agaggactgg acgccgctca cggacgtgcc cacgcttggc   3120
gcggctctgc ctgagggtct cagcctggaa ctcagcttcg gcggcgccgc cggcgccgca   3180
ggtgccgccg gtctcacgcc tctgggtggc ggcggcggcg gcgccgccgc caccgccggg   3240
ctgctgccta gcgccggcag cctgatcagc ctgccgttga gtgtgctaca ggaggactcg   3300
tcgttgtgga gcgacggcga cctggcgcgg ctgatggcgg cgggcagtgt cctgccgccg   3360
ccgccggcct cggcgacgtc gtcgttgtac acggctgacg acgacggcca cctgcgcggc   3420
gaggacggcg aggaggtgga gatggcggtg gcggcggcgg tggggccggt ggggccggtg   3480
gggatggtgg ggatggggat gcctggcggc gccctggcgg cggcggcggc ggcggcggtg   3540
gacgccgagg cggcggagtt ggaattggac agcctagcgg cggcgggcgc gcatttgggc   3600
caccggccgt cgtttggcgg cggcggcggc ggtggcggcg gcggcttgca tcggctgatg   3660
gcgctgcgcg ccctgcccag cggcggcagc agcgcgcagt cgcttgcgca cctggccctc   3720
ccgcaccagg ccccctatgc acacggccac ggtggcggcg gcgccgccgc cgcgtacggc   3780
```

agcggcggcg gaagtggcgg cggcgcagcg ctggcggagg cctactccac caggagcgag 3840
gccagcgagg ctccggagat ctgcctcacg gaatctttta aggcggaggt gctgtcgctg 3900
cagcggctgg cgcaggcgca gcaggggcat ccagggccgc atggctcgga gttcgggccg 3960
cagcatggac cgcacggctt ccccggcccg catgctgggg ccgccgcggc agcaacgccc 4020
aaccagctgc cgccgtcggt acggctacac ctgccgccca gcattttggg gcgcggcggt 4080
accagctacg gcggcggcag cggccctggc gggcccgacg gcggcggcgc cgtataccac 4140
cagcaccagc accagccgta ccagctgcag taccagcacc agctccagca gcagcagcgc 4200
gtggcgctga tgcagcacca ccatcagcaa caacagtacc agcagcagca cttgcaatac 4260
aggccgcctc tgcagcagca gcaccagcag cagcagcagc tgcaccagca gccggccgcg 4320
gcgccgccgc tgttcggcga ggggcgggtg tccgccttcc acctgctggg gccgggggac 4380
ctggacgatg aagaagagga cgggcccgcc ctcgggcccg gctggcagct gcacccgcac 4440
cagcacccgc acccgcagca gccgtatggc ggcatggggc gcccccagca gcaaccgcag 4500
cagcaccagc aaccgcagca ccagcaccag cagcaggctg gcgggctgga ctcgcgccct 4560
tcccacctcg ccggcgccgg cttcggtgcc ggcactggtg cgcgtgcagg tggcggcggc 4620
gccgccgcag ttgcctcagc cggggctggg gctggggctg gggctggggc gccgcagatc 4680
ctgttgctgc ccggcggccc ggcggcgggg agtcagccgg ggcgactgct gggctcggcg 4740
gcggcgctgg gcctaggcgg tgcgcgaggc ggcggcggcg gcggcggtgg cgagcacacg 4800
ctcgtgcagc ctagcctgcg ccgcctcagc caacaggagc aggacggccg cggggcgcag 4860
ggggcggcgt cggctgacag cgagccgccg ccgccggcgc agcagcagca gatgcagcag 4920
cagcagcagc agcagcagac tgccaacggc ccgactggaa aagtaggagg agggggcccg 4980
ggcgctgggt tggcgcgggc gccggcggcg ccgcgggagg cgcctcagca ggcgcagcag 5040
ccgcgcgcaa acggggaagt gcgccacccc acaggcgcgg cgcaggcgtg gagcggcggc 5100
gtcgcttctg gcggcccggc ggcagcggct gacggcaacc tgggcagcgc ggcggcggtg 5160
gcggcggtgg cggcggcggc ggcggaagca gaggcggacg gcgaggtggg tgaggaggag 5220
gaggaggtgg atccttctga gctgttgcgt caggcctact ccgccggact cacagagctg 5280
cctgggatgc tgggggatgc ggaggcggag gaggaggagg agcaggaggc ggccgcggcg 5340
gcgggcgatg aggtgacgga tccggggacg ggtccgggt cgggccaggc aggccgccgc 5400
cgcggcggtg gtggtggggg cagcggcagc gctcaggcgg cggatgccac gccgcctcct 5460
gagggcgagg gcacggagat cgtcggctcc gtcggcagcg gccgtgccgc cactggctta 5520
cgcagtggcg gcggcgccgt cggcgacgcg tccttcatcc ggcccggcgg cggcggcggc 5580
atgtctttcc tggccagtgc cgttggtggt ggcggcggcg gcggcggagg gcaacagatg 5640
acgacgacgg ttgacttttc gggattggat ggaggcggcg gcggctcgtg gtggctcagc 5700
aagggcagtg gcgagggcga gggcgaggag aggagtgtgg tgtcgtcagg cgctatggcg 5760
gcggtggcgg cgggggcacg gcgggagggg ctcagtggtg gcggcggcgt tggcggcggc 5820
gtggtcatgg atgctgagga tgtggacatg gatgacacaa cgtcactggc cgctgaggcg 5880
gcggcggcgg cggcggctga cctggcggcg gcggcggcag gtccggctgt cggcgccgtt 5940
ggggttcgct cgtgaaccgt tgttgggagg agtgcattca agttggtgat gacggtggct 6000
gactgcatgg ctgcatgcct gcatggctgc acaaggcggc atgcctgcac ggctgctcaa 6060
ggcgcgccgc tggggcaggc agatgcatat gtgggcgggc gcagcggtgg cgacagcgcg 6120
gacgcagctg tgcccgacac aatgcggcgg cggcggcgtc tgctccgata ctgccaccgt 6180

-continued ctgcaccccg ttggcatccc gtcggatcag catacaggca tagggccagg gatggcgtgt 6240
caactgcgtg aactgctttc cctggcgttt cccacccggg ttcccacaca cttcacttgc 6300
taccacgctg ctgcgacgac ttggcgtggg cgcaaacagg tgtggcaagg acgtacagta 6360
ccggggtgat gtgttgctgc acctaaggcg ctgagttgtt cataaggaat tttggcgtgt 6420
cactcgtgct tcatgggctt gatgaacgtg atgcctggaa attgcgaagt tgcggccacc 6480
aagggccggc acgactgcac gagcacagga agcggtgaat tgtattgcgg agggggttgt 6540
tgccatgcct cgtatgttgg gagctgccgc gggaagccat acctcttcca gtgcgcatcg 6600
ggaaaaccgg gaggcacaac aaaaaactac tacacggtac cggggcttgt cccggcgcaa 6660
gcgagggaga aagtatacgg catgcaaatt tattgatgat cgaacgccca tgcaggacaa 6720
gaacgatgac ttgtctgcgg cggggttgcc attgtgttct tgtaattgtt gttggctggg 6780
gcgtgctgtg cgggtcgttg caagctgtgt aatttgcatg tcctgctcgc taggactctg 6840
tgggctcaag cgggagacgg tggcggcgcg gggcttggcg gtagctgcgc atgcgccagg 6900
cgtgttgggc ggttgtgggc acggccgcat acaaggggcg cgaatggagc tgctgttcac 6960
gaggcggcgc cggccggcac ctgcacttga gccggccgct gttcctgcac cccagccggc 7020
cgcgggctat agcagagctg gggtgggggc atggccgtgg ggccaattgg caggacgcag 7080
cagaggcaga ggcgtggggg taccttgttt gctgctgtgg ctcctctgcg ctgttggctg 7140
cggtcgggca tgtcgtaagc atttgggggc gggcggcgct tgtggtgcca attcatcagg 7200
ctttgccgcg ggcacgtgcg gcgcagctgg cggacccgcg ggctgagact ttggaggtcg 7260
tgtgggcgtg tgcgtgcagc ccatttcttg cgtgcttgcg cggaaagcgt tactgcattt 7320
gttcttaatg atgactgtgg tgttggtgtt gctggggtcc gggagtggcg gcacggcgga 7380
gagcctgttt gcgctgcacc tgcgacccat gccattaccg cggactcttg ggcgccctac 7440
attgtgggct tggtgttggt gccggttgag gggatggccc gcaatgcaac aaggcttgag 7500
gagtcggcga tgtttaatta agttctttca tgcgaccggg tggtgtgttg gcaagttgtc 7560
acatacactg tatcgcttgg aacgatttgg ggcttctgtg tgtgtatgtc tttatgtggt 7620
ctgttaaagc tgtggtctgt taaagctgga gcggcgaggg gcgagggcgc gaatgtgatg 7680
agggttgagg gctgcaaatt gcggagggaa gatgcgcact tgtccgagat gcgtcccagg 7740
gtaccaaggc actggcagtg tgcgcattgg gtgttgacac atgctggggg ccgcgctgcg 7800
gggggtgggg cgtgtggggg ttaccgaaat gcgggcgcag caggggtgaa acgaggacac 7860
ccctggctgg agcagagctg agaaacgtcg ggggccggca gcaacaacgt gaatgatgat 7920
tgtcccaaca cacggcatgc aatgctagat gtatggtaaa tttgggaccc atcgcaaaga 7980
tgtgcgatat aatgcaactg gtggcaacga ttctaggggc gtcacagcgg ccgcacttgg 8040
gaattacacg ggcaacgcta acagcatgcc gcaggcgatg cggcggggca gatccgcaga 8100
tgcggtcggg tgggtagtgg gcaacccgct ttggagtggt gtgtgtgtgt gtgtgtgtgt 8160
gtgtgtgtgt gtgtgtgtgt gtgtgtgtgt gtgtgtgtgt gtgtgtgtgt gtgtgtgtgt 8220
gtgtgtgtgt gtgtgtgtgt gtgtgtgtgt gtgtgtgtgt gtgtgcattt gtatacaact 8280
gtaaatgccg ggcaat 8296

<210> SEQ ID NO 70
<211> LENGTH: 5721
<212> TYPE: DNA
<213> ORGANISM: Chlamydomonas reinhardtii -continued

<400> SEQUENCE: 70
atggacatgt ttatgcatgg aggctcgcca gagcctcaag gtcggggcgg ctatgaagac 60
gaccgcgctg gcacaaacga acttgcagca aatcgatgcc aggccgatgg ctgcatggcg 120
gacctctcag gactgaagcg ctacttccgc cgctaccatg tgtgcgagat gcacatccgg 180
gcgcaggtgg tgttgatctc ggggcgtcag gtgcgcttct gcgaccagtg cagcacattc 240
cacccccctgg ccttctttga cggagtgcgc aggacgtgtc gtgagaagct ggagcacaac 300
cgacaaaagc ggcgcgcgcg caaggctgcg cacggcggcg gcggtggtgg cggcggaggc 360
ggcgctgagc gcacaacagg cggcggcggc ggcggtcggc ccgctggctc cggccgcggc 420
gcacgcagcg gcggcgccgg aaacgacgac gatgacgatg gtggcggcga gtctgaagga 480
gagccgggtg gcggcggcag tgacgatggc ggctcggggt ctgggcgggg gcaggcgcgc 540
aagcggccgc cgagcgtgtc gtcgtcgcaa cagcagcagg cggctgcggc ggcgcagcgg 600
cggcgcatgg gcagcggccc aatgccgggc tccgcgcagg acctagctct ggcggcggcg 660
gtggcggcgg cggcggcggc gggcatgtca gttgccagcc ctggtgccgg cgccggcgcc 720
ggacctgggc ccggcgcggg ggcgctgggc ttgggtccgg gctatagccg tatggggtcg 780
gaggcacgga ccggtgcgat gccggggccg gcgccggggc cggggccgcg tggtgtctcg 840
cccgggtttg agggcgagga tgacgagtac tacgccggcc gcaccggcca cccgcacacg 900
tacacgcatc atcaacatcc gcatccacag cagctgccgc agcagcagca atcacgagag 960
ggctacatgg ggggcgccaa cgcgcgggac tccttgtcgg gcgggcccgt ggtggcgggg 1020
cagggcgggt cggctggcgc acacccgcac ccgcacctgc cggcacaggg cgggccgccg 1080
ccgccgccac cgagggcagg gctattcggg ggcccgctcg ggtcagcggc gggagccaac 1140
ggcgcagccg ctgcggcggg gctgctgcgc ggcggctccg gccccggtgc agagcacctg 1200
cggccgccgc tgagggaggc tagcggcgtg ctgggggcgc cgtcgggcga tggccttggt 1260
ggtggtggtg gcggtggtgg tggtggtggt ggtggtggtg gtggcggtgg tgtgctgcct 1320
gcgggactga gtgaggagga ggcgctgcag cggcagttgg aggagctgcg cagtgcgatc 1380
acgtggcgtc agcaggagct gcagcagcac cagcaccagc gctaccaaca tcatcaccaa 1440
cagcaacaac aacatcaaca acaacaccag caacagcaac agcagcacca acagattggc 1500
ttgaagcagg aggggcggga gcaggaagcc tgggcgcgcg ggccggggcc ggggccggga 1560
ggggacgagc cgcgctggca gcagcagcag cagcagcagc agcagcaggc gcggcatggg 1620
tacccggcac caggcatggg gcaagggccg gggctcggcc tggggcggca gggagcgcct 1680
gtgcccgcaa tgccggcaat tgcaggcgcc gccaatggcg ccaacggtgt cggtggcgtc 1740
aatggcgttc gcgtggcacg tgacggcgcg tttgcaccgc cgccgctaga ccctgcgcgc 1800
cggcggccgg gggcacccgg cggcccccct ccgccgccgc acctgccaca gcacccgcac 1860
caccaccatc accaccacca agatgtggag atggcgctgc aggagcagca gctgctgcag 1920
gagctgcgcc ggcagcaaca acagcagcag cagcagcagc aacaacaaca acaagaacaa 1980
caacaacggc agcagcaaca acaacaacgg cagcagcaac agttgcagga gcagcacaac 2040
atgcagcacg ggcatcagca gcagctgcgg ccgccgccgc cggttccagg ggcgactgcg 2100
ggctggagtt acgcccacac ggggactcgc ccgccagtgg aggtgaagat ggaggtggag 2160
gcagacgttg gggcaggcgg cggcggcctg ggcgggaccg gcggcttgcg caaggaacta 2220
acactcggcc ccgccggctt caccagcgcc ggcgctccgc ctccctacca cccccaacac 2280
ccctcgccgc acgcttcctc gcctcgtggg cccctcgtgg gccgctcctg ggacggccgc 2340

-continued

```
ggcccaccgt cagatccctc ggcgcgaccg ccgccgccgc cgccgccggg cgtgtcgctg   2400
gccggctttc cctccgacgt accagcccgg ctgcagctgc cgggctcggc ccgcggcccg   2460
gcgcccggcg ccgccgccgg gaggcccacc ggagatggca tggcggcggc ggcggcggcc   2520
gtgcgacagc accagcagca ccagtaccag ctgcaccaac agcagcaaga gcaccaacag   2580
caacagcagc accaacagca acagcaccag cagcatcacc agcaccaaca gcagttgctc   2640
ctggcggagg cggaggcgga gctgcagcgg cagcggcagc tgcaggcgat ggcggcggcg   2700
ggcggcccca tggcggcggc gatgcgactg cgcgccggcg ccggcctcgg cggcgcgtgg   2760
cagcagcacc agcaccagca cccgcagcac cagcaccagc agcaacagcc gcagcaacag   2820
ccgcagccgc aatcgagccg gcggtcagag gactggacgc cgctcacgga cgtgcccacg   2880
cttggcgcgg ctctgcctga gggtctcagc ctggaactca gcttcggcgg cgccgccggc   2940
gccgcaggtg ccgccggtct cacgcctctg ggtggcggcg gcggcggcgc cgccgccacc   3000
gccgggctgc tgcctagcgc cggcagcctg atcagcctgc cgttgagtgt gctacaggag   3060
gactcgtcgt tgtggagcga cggcgacctg gcgcggctga tggcggcggg cagtgtcctg   3120
ccgccgccgc cggcctcggc gacgtcgtcg ttgtacacgg ctgacgacga cggccacctg   3180
cgcggcgagg acggcgagga ggtggagatg gcggtggcgg cggcggtggg gccggtgggg   3240
ccggtgggga tggtggggat ggggatgcct ggcggcgccc tggcggcggc ggcggcggcg   3300
gcggtggacg ccgaggcggc ggagttggaa ttggacagcc tagcggcggc gggcgcgcat   3360
ttgggccacc ggccgtcgtt tggcggcggc ggcggcggtg gcggcggcgg cttgcatcgg   3420
ctgatggcgc tgcgcgccct gcccagcggc ggcagcagcg cgcagtcgct tgcgcacctg   3480
gccctcccgc accaggcccc ctatgcacac ggccacggtg gcggcggcgc cgccgccgcg   3540
tacggcagcg gcggcggaag tggcggcggc gcagcgctgg cggaggccta ctccaccagg   3600
agcgaggcca gcgaggctcc ggagatctgc ctcacggaat cttttaaggc ggaggtgctg   3660
tcgctgcagc ggctggcgca ggcgcagcag gggcatccag ggccgcatgg ctcggagttc   3720
gggccgcagc atggaccgca cggcttcccc ggcccgcatg ctggggccgc cgcggcagca   3780
acgcccaacc agctgccgcc gtcggtacgg ctacacctgc cgcccagcat tttggggcgc   3840
ggcggtacca gctacggcgg cggcagcggc cctggcgggc ccgacggcgg cggcgccgta   3900
taccaccagc accagcacca gccgtaccag ctgcagtacc agcaccagct ccagcagcag   3960
cagcgcgtgg cgctgatgca gcaccaccat cagcaacaac agtaccagca gcagcacttg   4020
caatacaggc cgcctctgca gcagcagcac cagcagcagc agcagctgca ccagcagccg   4080
gccgcggcgc cgccgctgtt cggcgagggg cgggtgtccg ccttccacct gctggggccg   4140
ggggacctgg acgatgaaga agaggacggg cccgccctcg ggcccggctg gcagctgcac   4200
ccgcaccagc acccgcaccc gcagcagccg tatggcggca tggggcgccc ccagcagcaa   4260
ccgcagcagc accagcaacc gcagcaccag caccagcagc aggctggcgg gctggactcg   4320
cgcccttccc acctcgccgg cgccggcttc ggtgccggca ctggtgcgcg tgcaggtggc   4380
ggcggcgccg ccgcagttgc ctcagccggg gctggggctg gggctggggc tggggcgccg   4440
cagatcctgt tgctgcccgg cggcccggcg gcggggagtc agccggggcg actgctgggc   4500
tcggcggcgg cgctgggcct aggcggtgcg cgaggcggcg gcggcggcgg cggtggcgag   4560
cacacgctcg tgcagcctag cctgcgccgc ctcagccaac aggagcagga cggccgcggg   4620
gcgcaggggg cggcgtcggc tgacagcgag ccgccgccgc cggcgcagca gcagcagatg   4680
```

-continued

```
cagcagcagc agcagcagca gcagactgcc aacggcccga ctggaaaagt aggaggaggg   4740

ggcccgggcg ctgggttggc gcgggcgccg gcggcgccgc gggaggcgcc tcagcaggcg   4800

cagcagccgc gcgcaaacgg ggaagtgcgc caccccacag gcgcggcgca ggcgtggagc   4860

ggcggcgtcg cttctggcgg cccggcggca gcggctgacg gcaacctggg cagcgcggcg   4920

gcggtggcgg cggtggcggc ggcggcggcg gaagcagagg cggacggcga ggtgggtgag   4980

gaggaggagg aggtggatcc ttctgagctg ttgcgtcagg cctactccgc cggactcaca   5040

gagctgcctg ggatgctggg ggatgcggag gcggaggagg aggaggagca ggaggcggcc   5100

gcggcggcgg gcgatgaggt gacggatccg ggacggggt ccgggtcggg ccaggcaggc    5160

cgccgccgcg gcggtggtgg tgggggcagc ggcagcgctc aggcggcgga tgccacgccg   5220

cctcctgagg gcgagggcac ggagatcgtc ggctccgtcg gcagcggccg tgccgccact   5280

ggcttacgca gtggcggcgg cgccgtcggc gacgcgtcct tcatccggcc cggcggcggc   5340

ggcggcatgt ctttcctggc cagtgccgtt ggtggtggcg gcggcggcgg cggagggcaa   5400

cagatgacga cgacggttga cttttcggga ttggatggag gcggcggcgg ctcgtggtgg   5460

ctcagcaagg gcagtggcga gggcgagggc gaggagagga gtgtggtgtc gtcaggcgct   5520

atggcggcgg tggcggcggg ggcacggcgg gaggggctca gtggtggcgg cggcgttggc   5580

ggcggcgtgg tcatggatgc tgaggatgtg gacatggatg acacaacgtc actggccgct   5640

gaggcggcgg cggcggcggc ggctgacctg gcggcggcgg cggcaggtcc ggctgtcggc   5700

gccgttgggg ttcgctcgtg a                                              5721
```

<210> SEQ ID NO 71
<211> LENGTH: 1906
<212> TYPE: PRT
<213> ORGANISM: Chlamydomonas reinhardtii

<400> SEQUENCE: 71

```
Met Asp Met Phe Met His Gly Gly Ser Pro Glu Pro Gln Gly Arg Gly
1               5                   10                  15

Gly Tyr Glu Asp Asp Arg Ala Gly Thr Asn Glu Leu Ala Ala Asn Arg
            20                  25                  30

Cys Gln Ala Asp Gly Cys Met Ala Asp Leu Ser Gly Leu Lys Arg Tyr
        35                  40                  45

Phe Arg Arg Tyr His Val Cys Glu Met His Ile Arg Ala Gln Val Val
    50                  55                  60

Leu Ile Ser Gly Arg Gln Val Arg Phe Cys Asp Gln Cys Ser Thr Phe
65                  70                  75                  80

His Pro Leu Ala Phe Phe Asp Gly Val Arg Arg Thr Cys Arg Glu Lys
                85                  90                  95

Leu Glu His Asn Arg Gln Lys Arg Arg Ala Arg Lys Ala Ala His Gly
            100                 105                 110

Gly Gly Gly Gly Gly Gly Gly Gly Gly Ala Glu Arg Thr Thr Gly Gly
        115                 120                 125

Gly Gly Gly Gly Arg Pro Ala Gly Ser Gly Arg Gly Ala Arg Ser Gly
    130                 135                 140

Gly Ala Gly Asn Asp Asp Asp Asp Asp Gly Gly Gly Glu Ser Glu Gly
145                 150                 155                 160

Glu Pro Gly Gly Gly Gly Ser Asp Asp Gly Gly Ser Gly Ser Gly Arg
                165                 170                 175

Gly Gln Ala Arg Lys Arg Pro Pro Ser Val Ser Ser Ser Gln Gln Gln
            180                 185                 190
```

-continued

Gln Ala Ala Ala Ala Ala Gln Arg Arg Arg Met Gly Ser Gly Pro Met
195 200 205

Pro Gly Ser Ala Gln Asp Leu Ala Leu Ala Ala Ala Val Ala Ala Ala
210 215 220

Ala Ala Ala Gly Met Ser Val Ala Ser Pro Gly Ala Gly Ala Gly Ala
225 230 235 240

Gly Pro Gly Pro Gly Ala Gly Ala Leu Gly Leu Gly Pro Gly Tyr Ser
245 250 255

Arg Met Gly Ser Glu Ala Arg Thr Gly Ala Met Pro Gly Pro Ala Pro
260 265 270

Gly Pro Gly Pro Arg Gly Val Ser Pro Gly Phe Glu Gly Glu Asp Asp
275 280 285

Glu Tyr Tyr Ala Gly Arg Thr Gly His Pro His Thr Tyr Thr His His
290 295 300

Gln His Pro His Pro Gln Gln Leu Pro Gln Gln Gln Gln Ser Arg Glu
305 310 315 320

Gly Tyr Met Gly Gly Ala Asn Ala Arg Asp Ser Leu Ser Gly Gly Pro
325 330 335

Val Val Ala Gly Gln Gly Gly Ser Ala Gly Ala His Pro His Pro His
340 345 350

Leu Pro Ala Gln Gly Gly Pro Pro Pro Pro Pro Pro Arg Ala Gly Leu
355 360 365

Phe Gly Gly Pro Leu Gly Ser Ala Ala Gly Ala Asn Gly Ala Ala Ala
370 375 380

Ala Ala Gly Leu Leu Arg Gly Gly Ser Gly Pro Gly Ala Glu His Leu
385 390 395 400

Arg Pro Pro Leu Arg Glu Ala Ser Gly Val Leu Gly Ala Pro Ser Gly
405 410 415

Asp Gly Leu Gly Gly Gly Gly Gly Gly Gly Gly Gly Gly Gly Gly Gly
420 425 430

Gly Gly Gly Gly Gly Val Leu Pro Ala Gly Leu Ser Glu Glu Glu Ala
435 440 445

Leu Gln Arg Gln Leu Glu Glu Leu Arg Ser Ala Ile Thr Trp Arg Gln
450 455 460

Gln Glu Leu Gln Gln His Gln His Gln Arg Tyr Gln His His His Gln
465 470 475 480

Gln Gln Gln Gln His Gln Gln Gln His Gln Gln Gln Gln Gln Gln His
485 490 495

Gln Gln Ile Gly Leu Lys Gln Glu Gly Arg Glu Gln Glu Ala Trp Ala
500 505 510

Arg Gly Pro Gly Pro Gly Pro Gly Gly Asp Glu Pro Arg Trp Gln Gln
515 520 525

Gln Gln Gln Gln Gln Gln Gln Gln Ala Arg His Gly Tyr Pro Ala Pro
530 535 540

Gly Met Gly Gln Gly Pro Gly Leu Gly Leu Gly Arg Gln Gly Ala Pro
545 550 555 560

Val Pro Ala Met Pro Ala Ile Ala Gly Ala Ala Asn Gly Ala Asn Gly
565 570 575

Val Gly Gly Val Asn Gly Val Arg Val Ala Arg Asp Gly Ala Phe Ala
580 585 590

Pro Pro Pro Leu Asp Pro Ala Arg Arg Arg Pro Gly Ala Pro Gly Gly
595 600 605

-continued

```
Pro Pro Pro Pro Pro His Leu Pro Gln His Pro His His His His His
    610                 615                 620

His His Gln Asp Val Glu Met Ala Leu Gln Glu Gln Gln Leu Leu Gln
625                 630                 635                 640

Glu Leu Arg Arg Gln Gln Gln Gln Gln Gln Gln Gln Gln Gln Gln Gln
                645                 650                 655

Gln Gln Glu Gln Gln Gln Arg Gln Gln Gln Gln Gln Gln Arg Gln Gln
            660                 665                 670

Gln Gln Leu Gln Glu Gln His Asn Met Gln His Gly His Gln Gln Gln
        675                 680                 685

Leu Arg Pro Pro Pro Pro Val Pro Gly Ala Thr Ala Gly Trp Ser Tyr
    690                 695                 700

Ala His Thr Gly Thr Arg Pro Pro Val Glu Val Lys Met Glu Val Glu
705                 710                 715                 720

Ala Asp Val Gly Ala Gly Gly Gly Gly Leu Gly Gly Thr Gly Gly Leu
                725                 730                 735

Arg Lys Glu Leu Thr Leu Gly Pro Ala Gly Phe Thr Ser Ala Gly Ala
            740                 745                 750

Pro Pro Pro Tyr His Pro Gln His Pro Ser Pro His Ala Ser Ser Pro
        755                 760                 765

Arg Gly Pro Leu Val Gly Arg Ser Trp Asp Gly Arg Gly Pro Pro Ser
    770                 775                 780

Asp Pro Ser Ala Arg Pro Pro Pro Pro Pro Pro Pro Gly Val Ser Leu
785                 790                 795                 800

Ala Gly Phe Pro Ser Asp Val Pro Ala Arg Leu Gln Leu Pro Gly Ser
                805                 810                 815

Ala Arg Gly Pro Ala Pro Gly Ala Ala Ala Gly Arg Pro Thr Gly Asp
            820                 825                 830

Gly Met Ala Ala Ala Ala Ala Ala Val Arg Gln His Gln Gln His Gln
        835                 840                 845

Tyr Gln Leu His Gln Gln Gln Gln Glu His Gln Gln Gln Gln His
    850                 855                 860

Gln Gln Gln Gln His Gln Gln His His Gln His Gln Gln Gln Leu Leu
865                 870                 875                 880

Leu Ala Glu Ala Glu Ala Glu Leu Gln Arg Gln Arg Gln Leu Gln Ala
                885                 890                 895

Met Ala Ala Ala Gly Gly Pro Met Ala Ala Ala Met Arg Leu Arg Ala
            900                 905                 910

Gly Ala Gly Leu Gly Gly Ala Trp Gln Gln His Gln His Gln His Pro
        915                 920                 925

Gln His Gln His Gln Gln Gln Gln Pro Gln Gln Gln Pro Gln Pro Gln
    930                 935                 940

Ser Ser Arg Arg Ser Glu Asp Trp Thr Pro Leu Thr Asp Val Pro Thr
945                 950                 955                 960

Leu Gly Ala Ala Leu Pro Glu Gly Leu Ser Leu Glu Leu Ser Phe Gly
                965                 970                 975

Gly Ala Ala Gly Ala Ala Gly Ala Ala Gly Leu Thr Pro Leu Gly Gly
            980                 985                 990

Gly Gly Gly Gly Ala Ala Ala Thr  Ala Gly Leu Leu Pro  Ser Ala Gly
        995                 1000                1005

Ser Leu  Ile Ser Leu Pro Leu  Ser Val Leu Gln Glu  Asp Ser Ser
    1010                1015                1020

Leu Trp  Ser Asp Gly Asp Leu  Ala Arg Leu Met Ala  Ala Gly Ser
```

-continued

```
    1025                1030                1035

Val Leu  Pro Pro Pro Pro Ala  Ser Ala Thr Ser Ser  Leu Tyr Thr
    1040                1045                1050

Ala Asp  Asp Asp Gly His Leu  Arg Gly Glu Asp Gly  Glu Glu Val
    1055                1060                1065

Glu Met  Ala Val Ala Ala Ala  Val Gly Pro Val Gly  Pro Val Gly
    1070                1075                1080

Met Val  Gly Met Gly Met Pro  Gly Gly Ala Leu Ala  Ala Ala Ala
    1085                1090                1095

Ala Ala  Ala Val Asp Ala Glu  Ala Ala Glu Leu Glu  Leu Asp Ser
    1100                1105                1110

Leu Ala  Ala Ala Gly Ala His  Leu Gly His Arg Pro  Ser Phe Gly
    1115                1120                1125

Gly Gly  Gly Gly Gly Gly Gly  Gly Gly Leu His Arg  Leu Met Ala
    1130                1135                1140

Leu Arg  Ala Leu Pro Ser Gly  Gly Ser Ser Ala Gln  Ser Leu Ala
    1145                1150                1155

His Leu  Ala Leu Pro His Gln  Ala Pro Tyr Ala His  Gly His Gly
    1160                1165                1170

Gly Gly  Gly Ala Ala Ala Ala  Tyr Gly Ser Gly Gly  Gly Ser Gly
    1175                1180                1185

Gly Gly  Ala Ala Leu Ala Glu  Ala Tyr Ser Thr Arg  Ser Glu Ala
    1190                1195                1200

Ser Glu  Ala Pro Glu Ile Cys  Leu Thr Glu Ser Phe  Lys Ala Glu
    1205                1210                1215

Val Leu  Ser Leu Gln Arg Leu  Ala Gln Ala Gln Gln  Gly His Pro
    1220                1225                1230

Gly Pro  His Gly Ser Glu Phe  Gly Pro Gln His Gly  Pro His Gly
    1235                1240                1245

Phe Pro  Gly Pro His Ala Gly  Ala Ala Ala Ala Ala  Thr Pro Asn
    1250                1255                1260

Gln Leu  Pro Pro Ser Val Arg  Leu His Leu Pro Pro  Ser Ile Leu
    1265                1270                1275

Gly Arg  Gly Gly Thr Ser Tyr  Gly Gly Gly Ser Gly  Pro Gly Gly
    1280                1285                1290

Pro Asp  Gly Gly Gly Ala Val  Tyr His Gln His Gln  His Gln Pro
    1295                1300                1305

Tyr Gln  Leu Gln Tyr Gln His  Gln Leu Gln Gln Gln  Gln Arg Val
    1310                1315                1320

Ala Leu  Met Gln His His His  Gln Gln Gln Gln Tyr  Gln Gln Gln
    1325                1330                1335

His Leu  Gln Tyr Arg Pro Pro  Leu Gln Gln Gln His  Gln Gln Gln
    1340                1345                1350

Gln Gln  Leu His Gln Gln Pro  Ala Ala Ala Pro Pro  Leu Phe Gly
    1355                1360                1365

Glu Gly  Arg Val Ser Ala Phe  His Leu Leu Gly Pro  Gly Asp Leu
    1370                1375                1380

Asp Asp  Glu Glu Glu Asp Gly  Pro Ala Leu Gly Pro  Gly Trp Gln
    1385                1390                1395

Leu His  Pro His Gln His Pro  His Pro Gln Gln Pro  Tyr Gly Gly
    1400                1405                1410

Met Gly  Arg Pro Gln Gln Gln  Pro Gln Gln His Gln  Gln Pro Gln
    1415                1420                1425
```

-continued

```
His Gln His Gln Gln Gln Ala Gly Gly Leu Asp Ser Arg Pro Ser
    1430                1435                1440

His Leu Ala Gly Ala Gly Phe Gly Ala Gly Thr Gly Ala Arg Ala
    1445                1450                1455

Gly Gly Gly Gly Ala Ala Ala Val Ala Ser Ala Gly Ala Gly Ala
    1460                1465                1470

Gly Ala Gly Ala Gly Ala Pro Gln Ile Leu Leu Leu Pro Gly Gly
    1475                1480                1485

Pro Ala Ala Gly Ser Gln Pro Gly Arg Leu Leu Gly Ser Ala Ala
    1490                1495                1500

Ala Leu Gly Leu Gly Gly Ala Arg Gly Gly Gly Gly Gly Gly Gly
    1505                1510                1515

Gly Glu His Thr Leu Val Gln Pro Ser Leu Arg Arg Leu Ser Gln
    1520                1525                1530

Gln Glu Gln Asp Gly Arg Gly Ala Gln Gly Ala Ala Ser Ala Asp
    1535                1540                1545

Ser Glu Pro Pro Pro Pro Ala Gln Gln Gln Gln Met Gln Gln Gln
    1550                1555                1560

Gln Gln Gln Gln Gln Thr Ala Asn Gly Pro Thr Gly Lys Val Gly
    1565                1570                1575

Gly Gly Gly Pro Gly Ala Gly Leu Ala Arg Ala Pro Ala Ala Pro
    1580                1585                1590

Arg Glu Ala Pro Gln Gln Ala Gln Gln Pro Arg Ala Asn Gly Glu
    1595                1600                1605

Val Arg His Pro Thr Gly Ala Ala Gln Ala Trp Ser Gly Gly Val
    1610                1615                1620

Ala Ser Gly Gly Pro Ala Ala Ala Ala Asp Gly Asn Leu Gly Ser
    1625                1630                1635

Ala Ala Ala Val Ala Ala Val Ala Ala Ala Ala Ala Glu Ala Glu
    1640                1645                1650

Ala Asp Gly Glu Val Gly Glu Glu Glu Glu Glu Val Asp Pro Ser
    1655                1660                1665

Glu Leu Leu Arg Gln Ala Tyr Ser Ala Gly Leu Thr Glu Leu Pro
    1670                1675                1680

Gly Met Leu Gly Asp Ala Glu Ala Glu Glu Glu Glu Glu Gln Glu
    1685                1690                1695

Ala Ala Ala Ala Ala Gly Asp Glu Val Thr Asp Pro Gly Thr Gly
    1700                1705                1710

Ser Gly Ser Gly Gln Ala Gly Arg Arg Arg Gly Gly Gly Gly Gly
    1715                1720                1725

Gly Ser Gly Ser Ala Gln Ala Ala Asp Ala Thr Pro Pro Pro Glu
    1730                1735                1740

Gly Glu Gly Thr Glu Ile Val Gly Ser Val Gly Ser Gly Arg Ala
    1745                1750                1755

Ala Thr Gly Leu Arg Ser Gly Gly Gly Ala Val Gly Asp Ala Ser
    1760                1765                1770

Phe Ile Arg Pro Gly Gly Gly Gly Gly Met Ser Phe Leu Ala Ser
    1775                1780                1785

Ala Val Gly Gly Gly Gly Gly Gly Gly Gly Gly Gln Gln Met Thr
    1790                1795                1800

Thr Thr Val Asp Phe Ser Gly Leu Asp Gly Gly Gly Gly Gly Ser
    1805                1810                1815
```

-continued

Trp Trp Leu Ser Lys Gly Ser Gly Glu Gly Glu Gly Glu Glu Arg
1820 1825 1830

Ser Val Val Ser Ser Gly Ala Met Ala Ala Val Ala Ala Gly Ala
1835 1840 1845

Arg Arg Glu Gly Leu Ser Gly Gly Gly Gly Val Gly Gly Gly Val
1850 1855 1860

Val Met Asp Ala Glu Asp Val Asp Met Asp Asp Thr Thr Ser Leu
1865 1870 1875

Ala Ala Glu Ala Ala Ala Ala Ala Ala Ala Asp Leu Ala Ala Ala
1880 1885 1890

Ala Ala Gly Pro Ala Val Gly Ala Val Gly Val Arg Ser
1895 1900 1905

<210> SEQ ID NO 72
<211> LENGTH: 12099
<212> TYPE: DNA
<213> ORGANISM: Chlamydomonas reinhardtii

<400> SEQUENCE: 72
gagcaacacg catcaaccaa gaaagataca agcttgcaga ggtcgccgtg aggaaatagt 60
cccagctaaa atgcgtgcag gtctcaacct gccacgactc ccagtttcgg cgaattaacc 120
gctgtcaccc tcgtcaaggc ttccctacgc gtttacgtat actcctatgt aacttagttg 180
tagtgggcgt gctttcagac gcgtatacga gcgttgtgtc ggttttggaa cgtggtgaat 240
ccagcagtct gccacgccga acgccggaga cgctctctcg tcttgccaac actgccgcga 300
gtaaagtcct cagaattgag cttaaatata tcattaaagt gggcgtcgtc gctggtctgg 360
cgccacaccg ctttgggagt tgggtgttgc gcaaggcgct aatcgaattc gttccgcctg 420
catatcgcac atatcggggt acatgtgaag gtatacattg aactctagcc actcagtaac 480
tccatgctac cagtgcaagg cgctccgtac aggtattagc ggcactagtg caagcggagg 540
ggaagaggac ggaagcctgc ctactaccgc cgcgatagcc gtcgtgtgac ctactagctc 600
catgcaaaag atatagaaaa tggaaggcga atgctcagac acttgcactc cgcaatttgt 660
gacgagcttt tacatactag tattcagtca caagggtagt ggccctaggt cacgacgctt 720
atgcatatca ttgtgagttg tcgaaccagg aagtcctggc gagcgtgctg ccgcggacag 780
gagggctaaa ggcagagcat ggccacggtc ggtgaaccgc cgctggagca gctccgcgag 840
ctcttccatc tttcggctcg cgacgcctgc atcacgctaa atatcagcca atcgcggctt 900
aagaagatat gccgtcagca cggcatctcg cgatggccgc accgcaagct ggccagcctg 960
gactcgctgc ggcagcagct gaagggcgac agcggcctta ccacgcagga cagagcggtg 1020
cttctggcgc ggctggaggc ccaggtggcg gcggtcattg cggagccgga caggccgctg 1080
gagaagctgt tcgaggacat gcggcagacc agctacaagg tgcgttacca cgcacgcaac 1140
aagctgcgtc gcggcacggg agcagctggg gagggcgctg atgatggtga tgctgccggc 1200
accgcttctg gggcgacgc atcctctcca gcggggcgcg ccctgtcgac ggagcgcggc 1260
ggaggcaggc ggggccggcg cggcgctgcc agtccccgta gggggccgca gcgccgggcg 1320
gcgtcctcgg gcccagccag cggcagccgg cttagacggg ccgggagacg tcgaggcagt 1380
gattggggcg gctcctcagg cgaggaagag gcggcatcgg actcgactga agccgcctcg 1440
gatgacgagg agcaggcggc gggtggcgct gcagccggcg gctactcgga gcgggacgat 1500
gacgaagacg acgagggcga tgacggcgag gacagcgatg aggatgacga ggacgacgag 1560
gaggatgagg actgggtggc gggcggcagg gctggcaagg caggggccg ccaggcacgt 1620 gcggacatgg cggcagctgc tacagccggg ggcagtgctg ggcgagccga tcgccttcgc 1680
cgccgggcga cagggttaca ggggctgcgt gtgccggcgg cggcatcccc cgcaactcca 1740
cgcagccggc ggcggcggcg aagcgccgcc ccgctggact cgggggacac agagccttcg 1800
ccaggcggaa ggagcgccgc cgctgcagcc ccgcttgcga caaccgcctg tggtggaggc 1860
gataccaaca gcagtgacag cgcaggcagg agcctggagc agcggcagcc ggcggcaagg 1920
gagggtgccg gtgacgcagc cggacggccg cctacggcgc cacagccgca gctgagcggc 1980
cgctcccgca cagtggcctc ccgctcggcg tccgcccgcg cgggcgcgcc agcggggctg 2040
cccggcttca gccctgtgcg cgatgcggcc acgcccagca gccacaccgg ccctgccgct 2100
gccagccgcg gccggctgca ctccggggga cacgggcacg ggcacgcaca cgggcgcgcc 2160
gccaagccgg agcgcggcgg cgcagccgcc acactgtcag cctttgcggc ggcggagcgc 2220
gcagtggccg gtgcatctgc tgcaggtgct gctggtggtg gtggtggtgg tggtggtggt 2280
ggtggttctg ctgtgaagca ggagcgggag cagagtgctg ggcagctggt gggcccgggc 2340
ggcggtggcg gcgttgccgg cgctgctggc cgcggggccg acggcgcggc ggcaagggac 2400
gacgctcgtg cggcagctgg tgacgttgct gttgaggcag gtgccggtac aggcggatcg 2460
agccagctgg acgggtccag ccagtggggc atgaagcgag cccggtctgc gccgcagccc 2520
cagcctctgg gcgcagctgg tgtggcgggc acgacttcct cccaccagac cacctcttca 2580
gatcgctcgc agcaccagca gcaacaggcg ccgctgccgc cgctccaggc caggacgtcg 2640
agggaatggc cgcccatgga catgatgccc tcaggctggc agcagcccta ccgtcagccc 2700
atgccgctgg acgcaacccg cactacgcct gcaacggcca ccaccgccac gactgctgct 2760
ggcggaggtg ccgacgttgg ctcgggccgc caccaagacc gccgcttaga ccacccgtcg 2820
cacctgcagc aggcgccgca gcaccccac cctcaggaac ccctgcatca gcgggcgcag 2880
cgccctgcct cgtcgcccac ggcctccatg ggcgggcctg caacaaagca gcaggcccac 2940
ggcagctacg gcgccgcagc gcccctccat cacacggcgg cccaaagcca tagccatagc 3000
tacagccacg ccccgccgac ggcaaccacc gcgccgccgg cggagccgca tcctttcttt 3060
tcaccagccg cagccgcagc cgcggccgct gctgccggac cgggaatcga atctagcctg 3120
ggcctggggt cgtctgtgcc caggtcaggg gcgctggagc atggtgttga ggactgggag 3180
tggcgctggc gggaggaagg ccagcagcgg catcagcgcg ccctcctgca gcagcaacaa 3240
cagcagcagg agtacatgcc gccagcaccg caccaccaca tgcctcatga acagcagcag 3300
cggcatcaac agctgctgca gtcacagtcg cagtcgcagt cacagtcgca gtcgcagcca 3360
cagtcacagc agcaacgcca tgacttgcac cgggagcagc tgccaccgct gccgccgcaa 3420
ccagaggcgc tgtcgcgtca acagcaggag cagcggcaac aggagcactt tgagttgcag 3480
cagctgcagt tgctgcagca acagcagcag tcgcagcagc tgcagcagcc gcaacagcac 3540
ctgatgccgt cgtcctcctc cttccaacgc gactggatcc cgccgccgca gccggatccg 3600
cagcctctgc cgtcctggcg ccagtcagag ccgctgcatg ctgaaccgca gccacgtgcc 3660
agccggtcgc agcaacagcc tcaacagctg cagagcccgg ggcatgtgca gcagggccag 3720
ccgctacaac acggcggcgc gtccggcagc gctcctacgt accgcggcgg cggcttcggc 3780
tcagagctgg atggcggttg gcactggcag cagcagcagc agcagcagca acagcagcag 3840
cagctgctgc agcaacaaca ggcggcatct ctgtcgcacc aactgcagga acgtgaacag 3900
caggagctgc agcggcaaca ggcgcaagcc cgacaccaca tgcagctgca gcagcaacaa 3960

-continued

```
caaggcgctc cgccgtcttc gtcatggcac gggcagtacc cgccactcca ccagcgcccc   4020
gaccaggcgc acgcgcagta cccccacctg cagcagccgc aagagcacca gcacccacag   4080
caagagcggt acccgccact gcaccagcag acgcaacagc agctgcagca gcagcagcag   4140
cagccacagc tgcaacagca gcaacaggca cagtggccag gtgcggaccc tcgcctgctt   4200
gcgcctggca ggcagccact gccgcccccg ccttcctggt cagcccgcca aggtcccggc   4260
tcggcgccgc cgtctacctc tgccggccac ccgacactgc agcagcaact gtacccgcca   4320
atgtaccaac agcagacgca acagcagccg cagccgcaac aacaaaacgc aggccagcaa   4380
cccgcctatc accaccaccc gcttttgtcg ccgcactctc cgcagtacca gcagcggatg   4440
caggcgtcgg cgcccgtcgg cagcggcggt gctcaccgac agagccaaag catcatcccg   4500
ggacctccaa gcgctctgct gtcgctgccg agccccgcct ccaatgagcc cagcccccga   4560
gacttcgcct acccctcgcc cctgcctccg catcaccagc caccgcacca accccacccg   4620
caccaccact ctctgtcggg cagcggcttc gactcggagg gcggcgctga cgccgcggct   4680
gctgcccgcc gcccgtccaa ccagtcccag tcctttgacc agcagcacca ggcggcggcg   4740
attgcgagcg gcacgctgcg caattggtcg tcctcctcct cggcctcatc gctgctggtg   4800
tggggctcgg cgtggccccc gggcagcggg ctcggcggca tgggccctgg aggcatgggc   4860
cccggaggcg tgggttctgg aggcatgggc cccgggccgc tggggccggg cggctcgaac   4920
ccacacggcg ctgcgggcag cggcggcggc agcgcctacg gcgcggctgg cttccgcagc   4980
ggcctacaca gcggcggcgg tgtgggtggt gccggaggcg ccggtttcgg cggctcagcg   5040
ggcggcgggt atgggtggag ctctgggggc agttcatatt cgggcggcgg ctttgcgcat   5100
gcaatgggcc ttccgtcgtc gggcggcggc gcagcggctg ccagcggcac cggtggtgac   5160
ggcggcggtg gagacgagaa ccggatgctg cacgaggggc tgcgggggcg cagtgcttac   5220
gtgtccgatg caggggaccg gcgggatgag gcggtggcag aggcggccgc agccgcagcc   5280
gccacggttg cggctggacc cggcggtgga cgcatgggcg gaagggatgc cgcaggcact   5340
cgtggcggtg gtggcggaac tggcagcggc gcggccacaa ccgcagccgt ggcagccgcc   5400
gccgctgcgg ctgcggccgt ggcagcggtt gcggctacct cgggcgctgc cgaccatgaa   5460
acgcgccatc gctcgccagc actgcagcca ccgacgcacc atggcgcccc caccgacctg   5520
ctctcaagtc ggcaccacgc gcgccattcg cacgtgctgc cgcccgccgg aatgaactac   5580
gccgcctacc tgcctccgcc cttgtcactg cctccggcgt tggactcgcc gcaccagccg   5640
ccatacagcg cgtcccacgg accggcccac ggccggctca acccggccgc ctactcccgt   5700
gtcgtctcca ccggcttccc tgggattcac cccgggtcgc tgcctggcag cagcagccca   5760
agccccagcg gcggcggcgg tggcggaggt gccaatgcag gcggaggtcg tgtcggtggc   5820
ggctcgggca ccgccgcccg ccgccgcggt ggtgatcgtg cagccagccc gcttggctcg   5880
tatggcagcg gtgctgctgg cggcgggggc ggtatcgctg ccggcgtaaa ggcagaggac   5940
aggggcccta gcggcggcag cggcggcgat ggcggctttg gcggggacga cactcgggac   6000
gtggagccac atcttggtca cgtagcattc catggcggca atgcagggca gcagcaaaca   6060
gccgcctacc gccgcacgtc ggccccagca gccgcagctg ccgccacggc ggacccacga   6120
gcgcaatctg ccagcggcga gcgcgacagc ggcggcggcg tggcagtaga ccttcggcgc   6180
gtgccgtaca cggggcggct cagcgagccc gtgatgcggg cgccgcttcg ggcattgctg   6240
gggcttgggt ccgacctggc tgacgagggc gagggcgagg cggagctcgc ggcgtccatg   6300
gcggcggcgg cgcgtgatga agagcggttc cgcatgctga gcaccggcag cagcaccgtc   6360
```

-continued

```
gcgatatttg caccggaggc tcagccccag ccgcaccagc aaacgcagca ccaacagccg   6420
caccagccgt cacggccggt ggagggacgg ccgcaccacg gctacggttt gccgcggctg   6480
cagcagggcg cgcccgaggg ccgtgtggct agcgccagtg ctgcagacag aggcggcagg   6540
cgcaccagcg gcgacatgga aaggggcggt aacggcggcc ggcggcccca cactgtgccg   6600
gacgcccgcg gctgggctgg gcccgctgac ctgctgctag cctgccagga aacggacgcc   6660
attgcgcagg ccgaggcggc agacggcgta cgcggcgccg ttggccacct acaccaagca   6720
acgtaccaag ccgccgcttc gcttcacgta gcgcagcagc cgcgcggtgg ggctgcttat   6780
gaggaaccac ccccgcgtcg tcagccccac caggcagcgg gtgcaggcgg gccctcacct   6840
gtgtgctccg ccgacctcac cacacccacc gcagcccatc aacgccccca gcagctacgg   6900
ccgcacgccg cagcgccgcc ttctgccacc tccagccgcc accaagtctc gcgccgcgct   6960
gcggctgctg aggctgcagt cgttactgcc acgcccgtgg cggcgaccgg ctcctcgggt   7020
cggccgggtc ccgctgcagg cccctctcct gccgcagccc ctgttaccgc cgctgcagct   7080
tctggtgccg ccttcctgtc gccagtcgcc tcggtggctg cgggcagcgg cgtggcgggt   7140
ggccctgcca ccagcagcgc cagcagcggc cgccgtagca gcggtggcgg cagtagcagc   7200
agcggcggca ggacgctgct ggtgtggacg ggatcacagc cgcgctgggg gcaggtgctg   7260
ccgccgctgc aacaccagtc acagccacag cagcagcagc cacagcagca gcagcagcca   7320
cagcagcagc cggagctgca gtccccaagt atgcggccgc cgcagctaca gccgctgccc   7380
ctgatgccgt cctcggcgcc gctgcgcacc ggcccccagc gccgcatcag tggcgccggc   7440
gcagctggtg ctgaggtcac caccggcaca gcgactgcat ctggcccagg gcaggagtcc   7500
accagcgcag cagccgcagg cgccgccggt gcgcttccgc ccatgccgcc tctgccagca   7560
tcgctgctag cagcgctggc tgccggcggc ggcgcaggcg gcgacctctc cccagatgcc   7620
taccccgtga cggcgctgca gccgccggca gttggcgccg ctgaccgcgg cactgatgcc   7680
ggtcagcgcg aacaggaccg cccgcagggc cgcagggcct cgccgcctcc cgccgccacc   7740
gaccccgcca acgccacaac cgcgggcgga gtgccactgt ccattctgga gtacctgcgc   7800
catggatccg gatccgagcc gccgctggat ctcgaggcgc tggaggacct ggacatggat   7860
ctggatctgg attttcagac gccgcaggcc ggcgacgcgg ccgccgcgct ggcgctgatg   7920
cggccgtggc tgacgagcac accgggtttg ggccccacgc caatggagat atcgccgcgt   7980
gctgctttgc cggctacgcg ccgtatcagt gccgcgggaa cagaggcacc tgcgccccag   8040
cgccagcagg cgccgccagc aaccgggcag cctacttgtg aggacgccgc tggctcaact   8100
gctgccggcg ggggcactgc tgcagcacct gctgcgcgca tgacgtcagc gggccaagcg   8160
gctgccagca ccgccctgtc gctttctgcc tctgccgccg gcccaagccg gccgccccat   8220
gccacctgtg ccgctgcaga cgctacaacg tttgcctcac ctgtcgccgc ggccgcagct   8280
gacgccgcac ggcagcacga gttcgcatct cccgccccgc acgccgcagc agccacggca   8340
gcagcacccg cggcagtgtc accctgcacg cctgcagccg ccgtgatacc gggtagcggg   8400
gccggtgggg ccgctggtgc cggtgcgccc gcgtcgccgc cgccggcgcc cgtcaagcga   8460
cctccgccgg cgcggctgtt cttgcacacc gtgcggcggc actcgggtac aggcgaaggg   8520
cctgctgctg agcccacggc tgcgcgtgcg catgcccctg cagctcatgc ggagggtggc   8580
ggcatggacg cgcctccgct gccacaccac cagtcacagc agcagcacca gtcacagcag   8640
cacccccagc accaccacca gcaggcatcc ccgtacggag gcgcagcggc gcacatgtac   8700
```

-continued

```
gcggcctggt gcagcagtcc tgccgccacg cccacccgcc acaacgcatc tggtggcggc   8760
gccgccgccg ctgccgcagg cagcaccgga ggcgctgcct tcgctgccgc gcccgcgccg   8820
ccacaggcgc ccagggccgc agccgcagcc gacgctgata cgcggagcgt cagcgtcacc   8880
gggggcctcg gtgggagcgg cagtggaggc tctgcacacg gcgggggcac tgggggtctc   8940
ggaggcgtct caccgcgcag ccgcgctgcg ctcttggtgg atgtggccga gcctcttggc   9000
ccgtacgggc cccagcagcc cacaactgcc acctcgactg ctgcagctgc tgtagctgcg   9060
ggtgaggcgg gtggcgcaag cggcaggcag ctccagccgg ctccggcacc tccaactgcg   9120
gccagccgct acccgtggaa catgggctgg ggtgcggggg caagcggtgc agcgggcagg   9180
gagaacacac cgctgcgcca gcttccgccc ttcccgccgc cgcagcctga gctggcagcc   9240
ctgccgctgc accgtgcgca agcgacgggc acagtggcga caggcaccgc tggacctgga   9300
gagcaggggc cgcaagggta ccagcaacgt agtggcggcg gcgacacgac ggaggcccat   9360
gtgccaccac cgctgctgca gccgccgcca cgcgccacct cgcctaccgg ctacgcggtt   9420
gcgtcctatc gccgggacag tgagggcggc ggcgtcatac cggtggtgtc gccgccgccg   9480
cagctgatgc cgcagtcggt gcggccgccg ccgcgcctgg cgccgctagt ggcgccgact   9540
gccgcggcgg gaccgcctca gccgccgccg ctgacgtcgc cacctgcgcc gcgcaagcca   9600
gccaagcagc ccgcgctcat ggctcctggg ccgccggcgg gccagcgtcg cagtagtggc   9660
ggcagtgtcg acaccggcgg cagtgccgga ggtgcggctg gccgcaactc cccagcatcg   9720
cttgccgggg cgggcaccgg cgcggctggg ccgctgccca agctaccacc acacgtgctg   9780
gagcggccgc tgccgccgcg tatgcaggtg cacatgcccg cgcccgcgcc ttcgccggca   9840
gccgtccaag ggcctgtcgg cgcaacagct cactctggcg cagcagctcc cggcagccgg   9900
ctactagcgg cggccatgtc gcctgtcggt ggcacaaacg cgggtggggc agccgccggc   9960
gcatcgccgc cgcccctgct caaggtaacc attggcggcc gcccaggctc gctgcagtca  10020
gccataggca gcttctccgt gcagcctacg cagctgccgc agccgccgca gctgccggca  10080
ttgcctcagt cacagcacca gtcacagcga cagcaccagg tcgcagagca ggggcgtttt  10140
gggatgccag gcgcggcggg ctgggccgtg ccgggcgctg ctgtgggcgc ggccggctcc  10200
cacctgccgc agctgcacca gcaccagcat gccgctgcag ggatcttgga cggcgataca  10260
cagtctgccg gcggtactgg tggcggtggc gtcagcagca agcgcaagcg ggagggcgat  10320
tcagagtagg atgggcgaca tgggtcttca cgcgcggtgc acattgatgc aaacgcatga  10380
gtggggcaac atgaatgccg gcagcactac ctgtcgaaga tcgtgagtcg attgcatgtg  10440
gccgtgtgac tagcaagcac ttatatccgt gcatggaaag catggcaggt tggtgcattg  10500
gaatgcaaat acggtacact cggcggtagc tgttcaggcg gtggccctgc aactggacga  10560
gaatgtgtgt agactgaagt caggcagcat ttagatcggc tgctgacaac ataccttccc  10620
attcaagggg attcatggga cagtagcgat gccttgaact cgtattgacg tagttggtgg  10680
cgagcgtgtg aggaccagca gcaggtttag cgcaggatgc aaagcgcatc aacgtccagg  10740
cacatgtcat actcacattt gttgacgcgt aatcaagcaa cgcagaaaga gcaagcggcg  10800
cagggtgacc acacaaccag cacgatgtca ctacgcggtg aggatgcgag gtactgctgt  10860
cacaggtcgc gcgcgtacgt tcgcagatgt agggggttgc atgcatgtcc tgccagctgt  10920
aaaggcgcat ggcgtcaatt gcaccatgtg cggcgccgtg ccaccacaga cccatgggcc  10980
tggactgggc ctgagcgcct tggacatggc cgtctattct gccctgtgta tggggtcagg  11040
gaaaatgtgg gtccgggtgc ttgtatgttg acttgggccg cggcacgtaa gccgtcatgc  11100
```

```
cgtctgcatt catagcacag ccatggtgtg caggccgggg gcttttcgat ggcacgtttt  11160

tgcgctgtcg gcgtgtgttc aggcttgggg acgtggttgc atcggtttgc attaaaagcg  11220

aaggctggtg tgaggcgcgc gctcatatca tcagcccagc aagccacgcg gtcgctctgg  11280

cccctactat cgccgttgct catcaggcat gctgtcataa ggtttcgctc tctttctttg  11340

gactgcgctc actccctctt cttctctcaa gcagcatact ggtgctctca tgtttgacag  11400

ggtcatacag ccccggcaag cagagaacct ctttctaact attatgcgtg tgttttgtgc  11460

actgcaatgg tctatgcgta gtcttgatta gcctgtgggc agtccatgaa tgactcattg  11520

gtgttatgcg tcttgcaagt gagggtagag aggttcactg atcaagggca taagatcagg  11580

cccaccagca cgtaattcaa gtctttgcgg caccgcattc ctaagcgttt tgcaagctgt  11640

ctgtaggtgc gcgtgggctg gcgtgcctgt ggtgcgtgaa acattactgc cattctgaga  11700

ctggagctgg ggctgcatcc cctgtgtcac acgcggtgac tagtatgttg tatcaagtcg  11760

tagcaagtaa aactctgctt attctggctt gtcttccgta gcatgcaccg gcctgatgcc  11820

aatttgtgct ggtgttggaa ttgcgcactg atgaaggagg catggtctgt cggttaggcg  11880

tcggcggtag ctggacatgc cagcaccgcc tcacaccaga tcgatgaaga actttgcaca  11940

atcaaaatga ttagcagcta gcactggcac gtcgtgtggc atgggatgtt gagtgttgtg  12000

gcctcgcgaa tggatgtagg gagcagtgta ctgctttccg tgctgtgggg cacttcacat  12060

gttgtggcgg gccgggtggc catgtaattt caagtccga                         12099


<210> SEQ ID NO 73
<211> LENGTH: 9531
<212> TYPE: DNA
<213> ORGANISM: Chlamydomonas reinhardtii

<400> SEQUENCE: 73

atggccacgg tcggtgaacc gccgctggag cagctccgcg agctcttcca tctttcggct     60

cgcgacgcct gcatcacgct aaatatcagc caatcgcggc ttaagaagat atgccgtcag    120

cacggcatct cgcgatggcc gcaccgcaag ctggccagcc tggactcgct gcggcagcag    180

ctgaagggcg acagcggcct taccacgcag gacagagcgg tgcttctggc gcggctggag    240

gcccaggtgg cggcggtcat tgcggagccg gacaggccgc tggagaagct gttcgaggac    300

atgcggcaga ccagctacaa ggtgcgttac cacgcacgca acaagctgcg tcgcggcacg    360

ggagcagctg gggagggcgc tgatgatggt gatgctgccg gcaccgcttc tgggggcgac    420

gcatcctctc cagcggggcg cgccctgtcg acggagcgcg gcggaggcag gcggggccgg    480

cgcggcgctg ccagtccccg tagggggccg cagcgccggg cggcgtcctc gggcccagcc    540

agcggcagcc ggcttagacg ggccgggaga cgtcgaggca gtgattgggg cggctcctca    600

ggcgaggaag aggcggcatc ggactcgact gaagccgcct cggatgacga ggagcaggcg    660

gcgggtggcg ctgcagccgg cggctactcg gagcgggacg atgacgaaga cgacgagggc    720

gatgacggcg aggacagcga tgaggatgac gaggacgacg aggaggatga ggactgggtg    780

gcgggcggca gggctggcaa ggcagggggc cgccaggcac gtgcggacat ggcggcagct    840

gctacagccg gggcagtgc tgggcgagcc gatcgccttc gccgccgggc gacagggtta    900

caggggctgc gtgtgccggc ggcggcatcc cccgcaactc cacgcagccg gcggcggcgg    960

cgaagcgccg ccccgctgga ctcgggggac acagagcctt cgccaggcgg aaggagcgcc   1020

gccgctgcag ccccgcttgc gacaaccgcc tgtggtggag gcgataccaa cagcagtgac   1080
```

-continued agcgcaggca ggagcctgga gcagcggcag ccggcggcaa gggagggtgc cggtgacgca 1140
gccggacggc cgcctacggc gccacagccg cagctgagcg gccgctcccg cacagtggcc 1200
tcccgctcgg cgtccgcccg cgcgggcgcg ccagcggggc tgcccggctt cagccctgtg 1260
cgcgatgcgg ccacgcccag cagccacacc ggccctgccg ctgccagccg cggccggctg 1320
cactccgggg gacacgggca cgggcacgca cacgggcgcg ccgccaagcc ggagcgcggc 1380
ggcgcagccg ccacactgtc agcctttgcg gcggcggagc gcgcagtggc cggtgcatct 1440
gctgcaggtg ctgctggtgg tggtggtggt ggtggtggtg gtggtggttc tgctgtgaag 1500
caggagcggg agcagagtgc tgggcagctg gtgggcccgg gcggcggtgg cggcgttgcc 1560
ggcgctgctg gccgcggggc cgacggcgcg gcggcaaggg acgacgctcg tgcggcagct 1620
ggtgacgttg ctgttgaggc aggtgccggt acaggcggat cgagccagct ggacgggtcc 1680
agccagtggg gcatgaagcg agcccggtct gcgccgcagc cccagcctct gggcgcagct 1740
ggtgtggcgg gcacgacttc ctcccaccag accacctctt cagatcgctc gcagcaccag 1800
cagcaacagg cgccgctgcc gccgctccag gccaggacgt cgagggaatg gccgcccatg 1860
gacatgatgc cctcaggctg gcagcagccc taccgtcagc ccatgccgct ggacgcaacc 1920
cgcactacgc ctgcaacggc caccaccgcc acgactgctg ctggcggagg tgccgacgtt 1980
ggctcgggcc gccaccaaga ccgccgctta gaccacccgt cgcacctgca gcaggcgccg 2040
cagcaccccc accctcagga accccctgcat cagcgggcgc agcgccctgc ctcgtcgccc 2100
acggcctcca tgggcgggcc tgcaacaaag cagcaggccc acggcagcta cggcgccgca 2160
gcgcccctcc atcacacggc ggcccaaagc catagccata gctacagcca cgccccgccg 2220
acggcaacca ccgcgccgcc ggcggagccg catcctttct tttcaccagc cgcagccgca 2280
gccgcggccg ctgctgccgg accgggaatc gaatctagcc tgggcctggg gtcgtctgtg 2340
cccaggtcag gggcgctgga gcatggtgtt gaggactggg agtggcgctg gcgggaggaa 2400
ggccagcagc ggcatcagcg cgccctcctg cagcagcaac aacagcagca ggagtacatg 2460
ccgccagcac cgcaccacca catgcctcat gaacagcagc agcggcatca acagctgctg 2520
cagtcacagt cgcagtcgca gtcacagtcg cagtcgcagc cacagtcaca gcagcaacgc 2580
catgacttgc accgggagca gctgccaccg ctgccgccgc aaccagaggc gctgtcgcgt 2640
caacagcagg agcagcggca acaggagcac tttgagttgc agcagctgca gttgctgcag 2700
caacagcagc agtcgcagca gctgcagcag ccgcaacagc acctgatgcc gtcgtcctcc 2760
tccttccaac gcgactggat cccgccgccg cagccggatc cgcagcctct gccgtcctgg 2820
cgccagtcag agccgctgca tgctgaaccg cagccacgtg ccagccggtc gcagcaacag 2880
cctcaacagc tgcagagccc ggggcatgtg cagcagggcc agccgctaca acacggcggc 2940
gcgtccggca gcgctcctac gtaccgcggc ggcggcttcg gctcagagct ggatggcggt 3000
tggcactggc agcagcagca gcagcagcag caacagcagc agcagctgct gcagcaacaa 3060
caggcggcat ctctgtcgca ccaactgcag gaacgtgaac agcaggagct gcagcggcaa 3120
caggcgcaag cccgacacca catgcagctg cagcagcaac aacaaggcgc tccgccgtct 3180
tcgtcatggc acgggcagta cccgccactc caccagcgcc ccgaccaggc gcacgcgcag 3240
tacccccacc tgcagcagcc gcaagagcac cagcacccac agcaagagcg gtacccgcca 3300
ctgcaccagc agacgcaaca gcagctgcag cagcagcagc agcagccaca gctgcaacag 3360
cagcaacagg cacagtggcc aggtgcggac cctcgcctgc ttgcgcctgg caggcagcca 3420
ctgccgcccc cgccttcctg gtcagcccgc caaggtcccg gctcggcgcc gccgtctacc 3480

```
tctgccggcc acccgacact gcagcagcaa ctgtacccgc caatgtacca acagcagacg   3540
caacagcagc cgcagccgca acaacaaaac gcaggccagc aacccgccta tcaccaccac   3600
ccgcttttgt cgccgcactc tccgcagtac cagcagcgga tgcaggcgtc ggcgcccgtc   3660
ggcagcggcg gtgctcaccg acagagccaa agcatcatcc cgggacctcc aagcgctctg   3720
ctgtcgctgc cgagccccgc ctccaatgag cccagccccc gagacttcgc ctacccctcg   3780
cccctgcctc cgcatcacca gccaccgcac caaccccacc cgcaccacca ctctctgtcg   3840
ggcagcggct tcgactcgga gggcggcgct gacgccgcgg ctgctgcccg ccgcccgtcc   3900
aaccagtccc agtcctttga ccagcagcac caggcggcgg cgattgcgag cggcacgctg   3960
cgcaattggt cgtcctcctc ctcggcctca tcgctgctgg tgtggggctc ggcgtggccc   4020
ccgggcagcg ggctcggcgg catgggccct ggaggcatgg gccccggagg cgtgggttct   4080
ggaggcatgg gccccgggcc gctggggccg ggcggctcga acccacacgg cgctgcgggc   4140
agcggcggcg gcagcgccta cggcgcggct ggcttccgca gcggcctaca cagcggcggc   4200
ggtgtgggtg gtgccggagg cgccggtttc ggcggctcag cgggcggcgg gtatgggtgg   4260
agctctgggg gcagttcata ttcgggcggc ggctttgcgc atgcaatggg ccttccgtcg   4320
tcgggcggcg gcgcagcggc tgccagcggc accggtggtg acggcggcgg tggagacgag   4380
aaccggatgc tgcacgaggg gctgcggggg cgcagtgctt acgtgtccga tgcaggggac   4440
cggcgggatg aggcggtggc agaggcggcc gcagccgcag ccgccacggt tgcggctgga   4500
cccggcggtg gacgcatggg cggaagggat gccgcaggca ctcgtggcgg tggtggcgga   4560
actggcagcg gcgcggccac aaccgcagcc gtggcagccg ccgccgctgc ggctgcggcc   4620
gtggcagcgg ttgcggctac ctcgggcgct gccgaccatg aaacgcgcca tcgctcgcca   4680
gcactgcagc caccgacgca ccatggcgcc cccaccgacc tgctctcaag tcggcaccac   4740
gcgcgccatt cgcacgtgct gccgcccgcc ggaatgaact acgccgccta cctgcctccg   4800
cccttgtcac tgcctccggc gttggactcg ccgcaccagc cgccatacag cgcgtcccac   4860
ggaccggccc acggccggct caacccggcc gcctactccc gtgtcgtctc caccggcttc   4920
cctgggattc accccgggtc gctgcctggc agcagcagcc caagccccag cggcggcggc   4980
ggtggcggag gtgccaatgc aggcggaggt cgtgtcggtg gcggctcggg caccgccgcc   5040
cgccgccgcg gtggtgatcg tgcagccagc ccgcttggct cgtatggcag cggtgctgct   5100
ggcggcgggg gcggtatcgc tgccggcgta aaggcagagg acaggggccc tagcggcggc   5160
agcggcggcg atggcggctt tggcggggac gacactcggg acgtggagcc acatcttggt   5220
cacgtagcat tccatggcgg caatgcaggg cagcagcaaa cagccgccta ccgccgcacg   5280
tcggccccag cagccgcagc tgccgccacg gcggacccac gagcgcaatc tgccagcggc   5340
gagcgcgaca gcggcggcgg cgtggcagta gaccttcggc gcgtgccgta cacggggcgg   5400
ctcagcgagc ccgtgatgcg ggcgccgctt cgggcattgc tggggcttgg gtccgacctg   5460
gctgacgagg gcgagggcga ggcggagctc gcggcgtcca tggcggcggc ggcgcgtgat   5520
gaagagcggt tccgcatgct gagcaccggc agcagcaccg tcgcgatatt tgcaccggag   5580
gctcagcccc agccgcacca gcaaacgcag caccaacagc cgcaccagcc gtcacggccg   5640
gtggagggac ggccgcacca cggctacggt ttgccgcggc tgcagcaggg cgcgcccgag   5700
ggccgtgtgg ctagcgccag tgctgcagac agaggcggca ggcgcaccag cggcgacatg   5760
gaaaggggcg gtaacggcgg ccggcggccc cacactgtgc cggacgcccg cggctgggct   5820
```

-continued

```
gggcccgctg acctgctgct agcctgccag gaaacggacg ccattgcgca ggccgaggcg   5880
gcagacggcg tacgcggcgc cgttggccac ctacaccaag caacgtacca agccgccgct   5940
tcgcttcacg tagcgcagca gccgcgcggt ggggctgctt atgaggaacc acccccgcgt   6000
cgtcagcccc accaggcagc gggtgcaggc gggccctcac ctgtgtgctc cgccgacctc   6060
accacaccca ccgcagccca tcaacgcccc cagcagctac ggccgcacgc cgcagcgccg   6120
ccttctgcca cctccagccg ccaccaagtc tcgcgccgcg ctgcggctgc tgaggctgca   6180
gtcgttactg ccacgcccgt ggcggcgacc ggctcctcgg gtcggccggg tcccgctgca   6240
ggcccctctc ctgccgcagc ccctgttacc gccgctgcag cttctggtgc cgccttcctg   6300
tcgccagtcg cctcggtggc tgcgggcagc ggcgtggcgg gtggccctgc caccagcagc   6360
gccagcagcg gccgccgtag cagcggtggc ggcagtagca gcagcggcgg caggacgctg   6420
ctggtgtgga cgggatcaca gccgcgctgg gggcaggtgc tgccgccgct gcaacaccag   6480
tcacagccac agcagcagca gccacagcag cagcagcagc cacagcagca gccggagctg   6540
cagtccccaa gtatgcggcc gccgcagcta cagccgctgc ccctgatgcc gtcctcggcg   6600
ccgctgcgca ccggccccca gcgccgcatc agtggcgccg gcgcagctgg tgctgaggtc   6660
accaccggca cagcgactgc atctggccca gggcaggagt ccaccagcgc agcagccgca   6720
ggcgccgccg gtgcgcttcc gcccatgccg cctctgccag catcgctgct agcagcgctg   6780
gctgccggcg gcggcgcagg cggcgacctc tccccagatg cctaccccgt gacggcgctg   6840
cagccgccgg cagttggcgc cgctgaccgc ggcactgatg ccggtcagcg cgaacaggac   6900
cgcccgcagg gccgcagggc ctcgccgcct cccgccgcca ccgaccccgc caacgccaca   6960
accgcgggcg gagtgccact gtccattctg gagtacctgc gccatggatc cggatccgag   7020
ccgccgctgg atctcgaggc gctggaggac ctggacatgg atctggatct ggattttcag   7080
acgccgcagg ccggcgacgc ggccgccgcg ctggcgctga tgcggccgtg gctgacgagc   7140
acaccgggtt tgggccccac gccaatggag atatcgccgc gtgctgcttt gccggctacg   7200
cgccgtatca gtgccgcggg aacagaggca cctgcgcccc agcgccagca ggcgccgcca   7260
gcaaccgggc agcctacttg tgaggacgcc gctggctcaa ctgctgccgg cgggggcact   7320
gctgcagcac ctgctgcgcg catgacgtca gcgggccaag cggctgccag caccgccctg   7380
tcgctttctg cctctgccgc cggcccaagc cggccgcccc atgccacctg tgccgctgca   7440
gacgctacaa cgtttgcctc acctgtcgcc gcggccgcag ctgacgccgc acggcagcac   7500
gagttcgcat ctcccgcccc gcacgccgca gcagccacgg cagcagcacc cgcggcagtg   7560
tcaccctgca cgcctgcagc cgccgtgata ccgggtagcg gggccggtgg ggccgctggt   7620
gccggtgcgc ccgcgtcgcc gccgccggcg cccgtcaagc gacctccgcc ggcgcggctg   7680
ttcttgcaca ccgtgcggcg gcactcgggt acaggcgaag ggcctgctgc tgagcccacg   7740
gctgcgcgtg cgcatgcccc tgcagctcat gcggagggtg gcggcatgga cgcgcctccg   7800
ctgccacacc accagtcaca gcagcagcac cagtcacagc agcaccccca gcaccaccac   7860
cagcaggcat ccccgtacgg aggcgcagcg gcgcacatgt acgcggcctg gtgcagcagt   7920
cctgccgcca cgcccacccg ccacaacgca tctggtggcg gcgccgccgc cgctgccgca   7980
ggcagcaccg gaggcgctgc cttcgctgcc gcgcccgcgc cgccacaggc gcccagggcc   8040
gcagccgcag ccgacgctga tacgcggagc gtcagcgtca ccgggggcct cggtgggagc   8100
ggcagtggag gctctgcaca cggcgggggc actgggggtc tcggaggcgt ctcaccgcgc   8160
agccgcgctg cgctcttggt ggatgtggcc gagcctcttg gcccgtacgg gccccagcag   8220
```

cccacaactg ccacctcgac tgctgcagct gctgtagctg cgggtgaggc gggtggcgca 8280
agcggcaggc agctccagcc ggctccggca cctccaactg cggccagccg ctacccgtgg 8340
aacatgggct ggggtgcggg ggcaagcggt gcagcgggca gggagaacac accgctgcgc 8400
cagcttccgc ccttcccgcc gccgcagcct gagctggcag ccctgccgct gcaccgtgcg 8460
caagcgacgg gcacagtggc gacaggcacc gctggacctg gagagcaggg gccgcaaggg 8520
taccagcaac gtagtggcgg cggcgacacg acggaggccc atgtgccacc accgctgctg 8580
cagccgccgc cacgcgccac ctcgcctacc ggctacgcgg ttgcgtccta tcgccgggac 8640
agtgagggcg gcggcgtcat accggtggtg tcgccgccgc cgcagctgat gccgcagtcg 8700
gtgcggccgc cgccgcgcct ggcgccgcta gtggcgccga ctgccgcggc gggaccgcct 8760
cagccgccgc cgctgacgtc gccacctgcg ccgcgcaagc cagccaagca gcccgcgctc 8820
atggctcctg ggccgccggc gggccagcgt cgcagtagtg gcggcagtgt cgacaccggc 8880
ggcagtgccg gaggtgcggc tggccgcaac tccccagcat cgcttgccgg ggcgggcacc 8940
ggcgcggctg ggccgctgcc caagctacca ccacacgtgc tggagcggcc gctgccgccg 9000
cgtatgcagg tgcacatgcc cgcgcccgcg ccttcgccgg cagccgtcca agggcctgtc 9060
ggcgcaacag ctcactctgg cgcagcagct cccggcagcc ggctactagc ggcggccatg 9120
tcgcctgtcg gtggcacaaa cgcgggtggg gcagccgccg gcgcatcgcc gccgcccctg 9180
ctcaaggtaa ccattggcgg ccgcccaggc tcgctgcagt cagccatagg cagcttctcc 9240
gtgcagccta cgcagctgcc gcagccgccg cagctgccgg cattgcctca gtcacagcac 9300
cagtcacagc gacagcacca ggtcgcagag caggggcgtt ttgggatgcc aggcgcggcg 9360
ggctgggccg tgccgggcgc tgctgtgggc gcggccggct cccacctgcc gcagctgcac 9420
cagcaccagc atgccgctgc agggatcttg gacggcgata cacagtctgc cggcggtact 9480
ggtggcggtg gcgtcagcag caagcgcaag cgggagggcg attcagagta g 9531

<210> SEQ ID NO 74
<211> LENGTH: 3176
<212> TYPE: PRT
<213> ORGANISM: Chlamydomonas reinhardtii

<400> SEQUENCE: 74

Met Ala Thr Val Gly Glu Pro Pro Leu Glu Gln Leu Arg Glu Leu Phe
1               5                   10                  15

His Leu Ser Ala Arg Asp Ala Cys Ile Thr Leu Asn Ile Ser Gln Ser
            20                  25                  30

Arg Leu Lys Lys Ile Cys Arg Gln His Gly Ile Ser Arg Trp Pro His
        35                  40                  45

Arg Lys Leu Ala Ser Leu Asp Ser Leu Arg Gln Gln Leu Lys Gly Asp
    50                  55                  60

Ser Gly Leu Thr Thr Gln Asp Arg Ala Val Leu Leu Ala Arg Leu Glu
65                  70                  75                  80

Ala Gln Val Ala Ala Val Ile Ala Glu Pro Asp Arg Pro Leu Glu Lys
                85                  90                  95

Leu Phe Glu Asp Met Arg Gln Thr Ser Tyr Lys Val Arg Tyr His Ala
            100                 105                 110

Arg Asn Lys Leu Arg Arg Gly Thr Gly Ala Ala Gly Glu Gly Ala Asp
        115                 120                 125

Asp Gly Asp Ala Ala Gly Thr Ala Ser Gly Gly Asp Ala Ser Ser Pro
    130                 135                 140

-continued

```
Ala Gly Arg Ala Leu Ser Thr Glu Arg Gly Gly Gly Arg Arg Gly Arg
145                 150                 155                 160

Arg Gly Ala Ala Ser Pro Arg Arg Gly Pro Gln Arg Arg Ala Ala Ser
                165                 170                 175

Ser Gly Pro Ala Ser Gly Ser Arg Leu Arg Arg Ala Gly Arg Arg Arg
            180                 185                 190

Gly Ser Asp Trp Gly Gly Ser Ser Gly Glu Glu Glu Ala Ala Ser Asp
        195                 200                 205

Ser Thr Glu Ala Ala Ser Asp Asp Glu Glu Gln Ala Ala Gly Gly Ala
    210                 215                 220

Ala Ala Gly Gly Tyr Ser Glu Arg Asp Asp Asp Glu Asp Asp Glu Gly
225                 230                 235                 240

Asp Asp Gly Glu Asp Ser Asp Glu Asp Asp Glu Asp Asp Glu Glu Asp
                245                 250                 255

Glu Asp Trp Val Ala Gly Gly Arg Ala Gly Lys Ala Gly Gly Arg Gln
            260                 265                 270

Ala Arg Ala Asp Met Ala Ala Ala Ala Thr Ala Gly Gly Ser Ala Gly
        275                 280                 285

Arg Ala Asp Arg Leu Arg Arg Arg Ala Thr Gly Leu Gln Gly Leu Arg
    290                 295                 300

Val Pro Ala Ala Ala Ser Pro Ala Thr Pro Arg Ser Arg Arg Arg Arg
305                 310                 315                 320

Arg Ser Ala Ala Pro Leu Asp Ser Gly Asp Thr Glu Pro Ser Pro Gly
                325                 330                 335

Gly Arg Ser Ala Ala Ala Ala Ala Pro Leu Ala Thr Thr Ala Cys Gly
            340                 345                 350

Gly Gly Asp Thr Asn Ser Ser Asp Ser Ala Gly Arg Ser Leu Glu Gln
        355                 360                 365

Arg Gln Pro Ala Ala Arg Glu Gly Ala Gly Asp Ala Ala Gly Arg Pro
    370                 375                 380

Pro Thr Ala Pro Gln Pro Gln Leu Ser Gly Arg Ser Arg Thr Val Ala
385                 390                 395                 400

Ser Arg Ser Ala Ser Ala Arg Ala Gly Ala Pro Ala Gly Leu Pro Gly
                405                 410                 415

Phe Ser Pro Val Arg Asp Ala Ala Thr Pro Ser Ser His Thr Gly Pro
            420                 425                 430

Ala Ala Ala Ser Arg Gly Arg Leu His Ser Gly Gly His Gly His Gly
        435                 440                 445

His Ala His Gly Arg Ala Ala Lys Pro Glu Arg Gly Gly Ala Ala Ala
    450                 455                 460

Thr Leu Ser Ala Phe Ala Ala Ala Glu Arg Ala Val Ala Gly Ala Ser
465                 470                 475                 480

Ala Ala Gly Ala Ala Gly Gly Gly Gly Gly Gly Gly Gly Gly Gly Gly
                485                 490                 495

Ser Ala Val Lys Gln Glu Arg Glu Gln Ser Ala Gly Gln Leu Val Gly
            500                 505                 510

Pro Gly Gly Gly Gly Gly Val Ala Gly Ala Ala Gly Arg Gly Ala Asp
        515                 520                 525

Gly Ala Ala Ala Arg Asp Asp Ala Arg Ala Ala Ala Gly Asp Val Ala
    530                 535                 540

Val Glu Ala Gly Ala Gly Thr Gly Gly Ser Ser Gln Leu Asp Gly Ser
545                 550                 555                 560
```

-continued

```
Ser Gln Trp Gly Met Lys Arg Ala Arg Ser Ala Pro Gln Pro Gln Pro
                565                 570                 575

Leu Gly Ala Ala Gly Val Ala Gly Thr Thr Ser Ser His Gln Thr Thr
            580                 585                 590

Ser Ser Asp Arg Ser Gln His Gln Gln Gln Gln Ala Pro Leu Pro Pro
        595                 600                 605

Leu Gln Ala Arg Thr Ser Arg Glu Trp Pro Pro Met Asp Met Met Pro
    610                 615                 620

Ser Gly Trp Gln Gln Pro Tyr Arg Gln Pro Met Pro Leu Asp Ala Thr
625                 630                 635                 640

Arg Thr Thr Pro Ala Thr Ala Thr Thr Ala Thr Thr Ala Ala Gly Gly
                645                 650                 655

Gly Ala Asp Val Gly Ser Gly Arg His Gln Asp Arg Arg Leu Asp His
            660                 665                 670

Pro Ser His Leu Gln Gln Ala Pro Gln His Pro His Pro Gln Glu Pro
        675                 680                 685

Leu His Gln Arg Ala Gln Arg Pro Ala Ser Ser Pro Thr Ala Ser Met
    690                 695                 700

Gly Gly Pro Ala Thr Lys Gln Gln Ala His Gly Ser Tyr Gly Ala Ala
705                 710                 715                 720

Ala Pro Leu His His Thr Ala Ala Gln Ser His Ser His Ser Tyr Ser
                725                 730                 735

His Ala Pro Pro Thr Ala Thr Thr Ala Pro Pro Ala Glu Pro His Pro
            740                 745                 750

Phe Phe Ser Pro Ala Ala Ala Ala Ala Ala Ala Ala Ala Ala Gly Pro
        755                 760                 765

Gly Ile Glu Ser Ser Leu Gly Leu Gly Ser Ser Val Pro Arg Ser Gly
    770                 775                 780

Ala Leu Glu His Gly Val Glu Asp Trp Glu Trp Arg Trp Arg Glu Glu
785                 790                 795                 800

Gly Gln Gln Arg His Gln Arg Ala Leu Leu Gln Gln Gln Gln Gln Gln
                805                 810                 815

Gln Glu Tyr Met Pro Pro Ala Pro His His His Met Pro His Glu Gln
            820                 825                 830

Gln Gln Arg His Gln Gln Leu Leu Gln Ser Gln Ser Gln Ser Gln Ser
        835                 840                 845

Gln Ser Gln Ser Gln Pro Gln Ser Gln Gln Gln Arg His Asp Leu His
    850                 855                 860

Arg Glu Gln Leu Pro Pro Leu Pro Pro Gln Pro Glu Ala Leu Ser Arg
865                 870                 875                 880

Gln Gln Gln Glu Gln Arg Gln Gln Glu His Phe Glu Leu Gln Gln Leu
                885                 890                 895

Gln Leu Leu Gln Gln Gln Gln Gln Ser Gln Gln Leu Gln Gln Pro Gln
            900                 905                 910

Gln His Leu Met Pro Ser Ser Ser Ser Phe Gln Arg Asp Trp Ile Pro
        915                 920                 925

Pro Pro Gln Pro Asp Pro Gln Pro Leu Pro Ser Trp Arg Gln Ser Glu
    930                 935                 940

Pro Leu His Ala Glu Pro Gln Pro Arg Ala Ser Arg Ser Gln Gln Gln
945                 950                 955                 960

Pro Gln Gln Leu Gln Ser Pro Gly His Val Gln Gln Gly Gln Pro Leu
                965                 970                 975

Gln His Gly Gly Ala Ser Gly Ser Ala Pro Thr Tyr Arg Gly Gly Gly
```

-continued

```
            980                 985                 990

Phe Gly Ser Glu Leu Asp Gly Gly  Trp His Trp Gln Gln  Gln Gln Gln
        995                 1000                1005

Gln Gln  Gln Gln Gln Gln Gln  Leu Leu Gln Gln Gln  Gln Ala Ala
    1010                 1015                 1020

Ser Leu  Ser His Gln Leu Gln  Glu Arg Glu Gln Gln  Glu Leu Gln
    1025                 1030                 1035

Arg Gln  Gln Ala Gln Ala Arg  His His Met Gln Leu  Gln Gln Gln
    1040                 1045                 1050

Gln Gln  Gly Ala Pro Pro Ser  Ser Ser Trp His Gly  Gln Tyr Pro
    1055                 1060                 1065

Pro Leu  His Gln Arg Pro Asp  Gln Ala His Ala Gln  Tyr Pro His
    1070                 1075                 1080

Leu Gln  Gln Pro Gln Glu His  Gln His Pro Gln Gln  Glu Arg Tyr
    1085                 1090                 1095

Pro Pro  Leu His Gln Gln Thr  Gln Gln Gln Leu Gln  Gln Gln Gln
    1100                 1105                 1110

Gln Gln  Pro Gln Leu Gln Gln  Gln Gln Gln Ala Gln  Trp Pro Gly
    1115                 1120                 1125

Ala Asp  Pro Arg Leu Leu Ala  Pro Gly Arg Gln Pro  Leu Pro Pro
    1130                 1135                 1140

Pro Pro  Ser Trp Ser Ala Arg  Gln Gly Pro Gly Ser  Ala Pro Pro
    1145                 1150                 1155

Ser Thr  Ser Ala Gly His Pro  Thr Leu Gln Gln Gln  Leu Tyr Pro
    1160                 1165                 1170

Pro Met  Tyr Gln Gln Gln Thr  Gln Gln Gln Pro Gln  Pro Gln Gln
    1175                 1180                 1185

Gln Asn  Ala Gly Gln Gln Pro  Ala Tyr His His His  Pro Leu Leu
    1190                 1195                 1200

Ser Pro  His Ser Pro Gln Tyr  Gln Gln Arg Met Gln  Ala Ser Ala
    1205                 1210                 1215

Pro Val  Gly Ser Gly Gly Ala  His Arg Gln Ser Gln  Ser Ile Ile
    1220                 1225                 1230

Pro Gly  Pro Pro Ser Ala Leu  Leu Ser Leu Pro Ser  Pro Ala Ser
    1235                 1240                 1245

Asn Glu  Pro Ser Pro Arg Asp  Phe Ala Tyr Pro Ser  Pro Leu Pro
    1250                 1255                 1260

Pro His  His Gln Pro Pro His  Gln Pro His Pro His  His His Ser
    1265                 1270                 1275

Leu Ser  Gly Ser Gly Phe Asp  Ser Glu Gly Gly Ala  Asp Ala Ala
    1280                 1285                 1290

Ala Ala  Ala Arg Arg Pro Ser  Asn Gln Ser Gln Ser  Phe Asp Gln
    1295                 1300                 1305

Gln His  Gln Ala Ala Ala Ile  Ala Ser Gly Thr Leu  Arg Asn Trp
    1310                 1315                 1320

Ser Ser  Ser Ser Ser Ala Ser  Ser Leu Leu Val Trp  Gly Ser Ala
    1325                 1330                 1335

Trp Pro  Pro Gly Ser Gly Leu  Gly Gly Met Gly Pro  Gly Gly Met
    1340                 1345                 1350

Gly Pro  Gly Gly Val Gly Ser  Gly Gly Met Gly Pro  Gly Pro Leu
    1355                 1360                 1365

Gly Pro  Gly Gly Ser Asn Pro  His Gly Ala Ala Gly  Ser Gly Gly
    1370                 1375                 1380
```

Gly Ser Ala Tyr Gly Ala Ala Gly Phe Arg Ser Gly Leu His Ser
1385 1390 1395

Gly Gly Gly Val Gly Gly Ala Gly Gly Ala Gly Phe Gly Gly Ser
1400 1405 1410

Ala Gly Gly Gly Tyr Gly Trp Ser Ser Gly Gly Ser Ser Tyr Ser
1415 1420 1425

Gly Gly Gly Phe Ala His Ala Met Gly Leu Pro Ser Ser Gly Gly
1430 1435 1440

Gly Ala Ala Ala Ala Ser Gly Thr Gly Gly Asp Gly Gly Gly Gly
1445 1450 1455

Asp Glu Asn Arg Met Leu His Glu Gly Leu Arg Gly Arg Ser Ala
1460 1465 1470

Tyr Val Ser Asp Ala Gly Asp Arg Arg Asp Glu Ala Val Ala Glu
1475 1480 1485

Ala Ala Ala Ala Ala Ala Ala Thr Val Ala Ala Gly Pro Gly Gly
1490 1495 1500

Gly Arg Met Gly Gly Arg Asp Ala Ala Gly Thr Arg Gly Gly Gly
1505 1510 1515

Gly Gly Thr Gly Ser Gly Ala Ala Thr Thr Ala Ala Val Ala Ala
1520 1525 1530

Ala Ala Ala Ala Ala Ala Ala Val Ala Ala Val Ala Ala Thr Ser
1535 1540 1545

Gly Ala Ala Asp His Glu Thr Arg His Arg Ser Pro Ala Leu Gln
1550 1555 1560

Pro Pro Thr His His Gly Ala Pro Thr Asp Leu Leu Ser Ser Arg
1565 1570 1575

His His Ala Arg His Ser His Val Leu Pro Pro Ala Gly Met Asn
1580 1585 1590

Tyr Ala Ala Tyr Leu Pro Pro Pro Leu Ser Leu Pro Pro Ala Leu
1595 1600 1605

Asp Ser Pro His Gln Pro Pro Tyr Ser Ala Ser His Gly Pro Ala
1610 1615 1620

His Gly Arg Leu Asn Pro Ala Ala Tyr Ser Arg Val Val Ser Thr
1625 1630 1635

Gly Phe Pro Gly Ile His Pro Gly Ser Leu Pro Gly Ser Ser Ser
1640 1645 1650

Pro Ser Pro Ser Gly Gly Gly Gly Gly Gly Gly Ala Asn Ala Gly
1655 1660 1665

Gly Gly Arg Val Gly Gly Gly Ser Gly Thr Ala Ala Arg Arg Arg
1670 1675 1680

Gly Gly Asp Arg Ala Ala Ser Pro Leu Gly Ser Tyr Gly Ser Gly
1685 1690 1695

Ala Ala Gly Gly Gly Gly Gly Ile Ala Ala Gly Val Lys Ala Glu
1700 1705 1710

Asp Arg Gly Pro Ser Gly Gly Ser Gly Gly Asp Gly Gly Phe Gly
1715 1720 1725

Gly Asp Asp Thr Arg Asp Val Glu Pro His Leu Gly His Val Ala
1730 1735 1740

Phe His Gly Gly Asn Ala Gly Gln Gln Gln Thr Ala Ala Tyr Arg
1745 1750 1755

Arg Thr Ser Ala Pro Ala Ala Ala Ala Ala Ala Thr Ala Asp Pro
1760 1765 1770

-continued

```
Arg Ala  Gln Ser Ala Ser Gly  Glu Arg Asp Ser Gly  Gly Gly Val
    1775                 1780                 1785

Ala Val  Asp Leu Arg Arg Val  Pro Tyr Thr Gly Arg  Leu Ser Glu
    1790                 1795                 1800

Pro Val  Met Arg Ala Pro Leu  Arg Ala Leu Leu Gly  Leu Gly Ser
    1805                 1810                 1815

Asp Leu  Ala Asp Glu Gly Glu  Gly Glu Ala Glu Leu  Ala Ala Ser
    1820                 1825                 1830

Met Ala  Ala Ala Ala Arg Asp  Glu Glu Arg Phe Arg  Met Leu Ser
    1835                 1840                 1845

Thr Gly  Ser Ser Thr Val Ala  Ile Phe Ala Pro Glu  Ala Gln Pro
    1850                 1855                 1860

Gln Pro  His Gln Gln Thr Gln  His Gln Gln Pro His  Gln Pro Ser
    1865                 1870                 1875

Arg Pro  Val Glu Gly Arg Pro  His His Gly Tyr Gly  Leu Pro Arg
    1880                 1885                 1890

Leu Gln  Gln Gly Ala Pro Glu  Gly Arg Val Ala Ser  Ala Ser Ala
    1895                 1900                 1905

Ala Asp  Arg Gly Gly Arg Arg  Thr Ser Gly Asp Met  Glu Arg Gly
    1910                 1915                 1920

Gly Asn  Gly Gly Arg Arg Pro  His Thr Val Pro Asp  Ala Arg Gly
    1925                 1930                 1935

Trp Ala  Gly Pro Ala Asp Leu  Leu Leu Ala Cys Gln  Glu Thr Asp
    1940                 1945                 1950

Ala Ile  Ala Gln Ala Glu Ala  Ala Asp Gly Val Arg  Gly Ala Val
    1955                 1960                 1965

Gly His  Leu His Gln Ala Thr  Tyr Gln Ala Ala Ala  Ser Leu His
    1970                 1975                 1980

Val Ala  Gln Gln Pro Arg Gly  Gly Ala Ala Tyr Glu  Glu Pro Pro
    1985                 1990                 1995

Pro Arg  Arg Gln Pro His Gln  Ala Ala Gly Ala Gly  Gly Pro Ser
    2000                 2005                 2010

Pro Val  Cys Ser Ala Asp Leu  Thr Thr Pro Thr Ala  Ala His Gln
    2015                 2020                 2025

Arg Pro  Gln Gln Leu Arg Pro  His Ala Ala Ala Pro  Pro Ser Ala
    2030                 2035                 2040

Thr Ser  Ser Arg His Gln Val  Ser Arg Arg Ala Ala  Ala Ala Glu
    2045                 2050                 2055

Ala Ala  Val Val Thr Ala Thr  Pro Val Ala Ala Thr  Gly Ser Ser
    2060                 2065                 2070

Gly Arg  Pro Gly Pro Ala Ala  Gly Pro Ser Pro Ala  Ala Ala Pro
    2075                 2080                 2085

Val Thr  Ala Ala Ala Ala Ser  Gly Ala Ala Phe Leu  Ser Pro Val
    2090                 2095                 2100

Ala Ser  Val Ala Ala Gly Ser  Gly Val Ala Gly Gly  Pro Ala Thr
    2105                 2110                 2115

Ser Ser  Ala Ser Ser Gly Arg  Arg Ser Ser Gly Gly  Gly Ser Ser
    2120                 2125                 2130

Ser Ser  Gly Gly Arg Thr Leu  Leu Val Trp Thr Gly  Ser Gln Pro
    2135                 2140                 2145

Arg Trp  Gly Gln Val Leu Pro  Pro Leu Gln His Gln  Ser Gln Pro
    2150                 2155                 2160

Gln Gln  Gln Gln Pro Gln Gln  Gln Gln Gln Pro Gln  Gln Gln Pro
```

2165 2170 2175

Glu Leu Gln Ser Pro Ser Met Arg Pro Pro Gln Leu Gln Pro Leu
2180 2185 2190

Pro Leu Met Pro Ser Ser Ala Pro Leu Arg Thr Gly Pro Gln Arg
2195 2200 2205

Arg Ile Ser Gly Ala Gly Ala Ala Gly Ala Glu Val Thr Thr Gly
2210 2215 2220

Thr Ala Thr Ala Ser Gly Pro Gly Gln Glu Ser Thr Ser Ala Ala
2225 2230 2235

Ala Ala Gly Ala Ala Gly Ala Leu Pro Pro Met Pro Pro Leu Pro
2240 2245 2250

Ala Ser Leu Leu Ala Ala Leu Ala Ala Gly Gly Gly Ala Gly Gly
2255 2260 2265

Asp Leu Ser Pro Asp Ala Tyr Pro Val Thr Ala Leu Gln Pro Pro
2270 2275 2280

Ala Val Gly Ala Ala Asp Arg Gly Thr Asp Ala Gly Gln Arg Glu
2285 2290 2295

Gln Asp Arg Pro Gln Gly Arg Arg Ala Ser Pro Pro Pro Ala Ala
2300 2305 2310

Thr Asp Pro Ala Asn Ala Thr Thr Ala Gly Gly Val Pro Leu Ser
2315 2320 2325

Ile Leu Glu Tyr Leu Arg His Gly Ser Gly Ser Glu Pro Pro Leu
2330 2335 2340

Asp Leu Glu Ala Leu Glu Asp Leu Asp Met Asp Leu Asp Leu Asp
2345 2350 2355

Phe Gln Thr Pro Gln Ala Gly Asp Ala Ala Ala Ala Leu Ala Leu
2360 2365 2370

Met Arg Pro Trp Leu Thr Ser Thr Pro Gly Leu Gly Pro Thr Pro
2375 2380 2385

Met Glu Ile Ser Pro Arg Ala Ala Leu Pro Ala Thr Arg Arg Ile
2390 2395 2400

Ser Ala Ala Gly Thr Glu Ala Pro Ala Pro Gln Arg Gln Gln Ala
2405 2410 2415

Pro Pro Ala Thr Gly Gln Pro Thr Cys Glu Asp Ala Ala Gly Ser
2420 2425 2430

Thr Ala Ala Gly Gly Gly Thr Ala Ala Ala Pro Ala Ala Arg Met
2435 2440 2445

Thr Ser Ala Gly Gln Ala Ala Ala Ser Thr Ala Leu Ser Leu Ser
2450 2455 2460

Ala Ser Ala Ala Gly Pro Ser Arg Pro Pro His Ala Thr Cys Ala
2465 2470 2475

Ala Ala Asp Ala Thr Thr Phe Ala Ser Pro Val Ala Ala Ala Ala
2480 2485 2490

Ala Asp Ala Ala Arg Gln His Glu Phe Ala Ser Pro Ala Pro His
2495 2500 2505

Ala Ala Ala Ala Thr Ala Ala Ala Pro Ala Ala Val Ser Pro Cys
2510 2515 2520

Thr Pro Ala Ala Ala Val Ile Pro Gly Ser Gly Ala Gly Gly Ala
2525 2530 2535

Ala Gly Ala Gly Ala Pro Ala Ser Pro Pro Pro Ala Pro Val Lys
2540 2545 2550

Arg Pro Pro Pro Ala Arg Leu Phe Leu His Thr Val Arg Arg His
2555 2560 2565

-continued

Ser Gly Thr Gly Glu Gly Pro Ala Ala Glu Pro Thr Ala Ala Arg
2570 2575 2580

Ala His Ala Pro Ala Ala His Ala Glu Gly Gly Gly Met Asp Ala
2585 2590 2595

Pro Pro Leu Pro His His Gln Ser Gln Gln Gln His Gln Ser Gln
2600 2605 2610

Gln His Pro Gln His His His Gln Gln Ala Ser Pro Tyr Gly Gly
2615 2620 2625

Ala Ala Ala His Met Tyr Ala Ala Trp Cys Ser Ser Pro Ala Ala
2630 2635 2640

Thr Pro Thr Arg His Asn Ala Ser Gly Gly Gly Ala Ala Ala Ala
2645 2650 2655

Ala Ala Gly Ser Thr Gly Gly Ala Ala Phe Ala Ala Ala Pro Ala
2660 2665 2670

Pro Pro Gln Ala Pro Arg Ala Ala Ala Ala Ala Asp Ala Asp Thr
2675 2680 2685

Arg Ser Val Ser Val Thr Gly Gly Leu Gly Gly Ser Gly Ser Gly
2690 2695 2700

Gly Ser Ala His Gly Gly Gly Thr Gly Gly Leu Gly Gly Val Ser
2705 2710 2715

Pro Arg Ser Arg Ala Ala Leu Leu Val Asp Val Ala Glu Pro Leu
2720 2725 2730

Gly Pro Tyr Gly Pro Gln Gln Pro Thr Thr Ala Thr Ser Thr Ala
2735 2740 2745

Ala Ala Ala Val Ala Ala Gly Glu Ala Gly Gly Ala Ser Gly Arg
2750 2755 2760

Gln Leu Gln Pro Ala Pro Ala Pro Pro Thr Ala Ala Ser Arg Tyr
2765 2770 2775

Pro Trp Asn Met Gly Trp Gly Ala Gly Ala Ser Gly Ala Ala Gly
2780 2785 2790

Arg Glu Asn Thr Pro Leu Arg Gln Leu Pro Pro Phe Pro Pro Pro
2795 2800 2805

Gln Pro Glu Leu Ala Ala Leu Pro Leu His Arg Ala Gln Ala Thr
2810 2815 2820

Gly Thr Val Ala Thr Gly Thr Ala Gly Pro Gly Glu Gln Gly Pro
2825 2830 2835

Gln Gly Tyr Gln Gln Arg Ser Gly Gly Gly Asp Thr Thr Glu Ala
2840 2845 2850

His Val Pro Pro Pro Leu Leu Gln Pro Pro Pro Arg Ala Thr Ser
2855 2860 2865

Pro Thr Gly Tyr Ala Val Ala Ser Tyr Arg Arg Asp Ser Glu Gly
2870 2875 2880

Gly Gly Val Ile Pro Val Val Ser Pro Pro Pro Gln Leu Met Pro
2885 2890 2895

Gln Ser Val Arg Pro Pro Pro Arg Leu Ala Pro Leu Val Ala Pro
2900 2905 2910

Thr Ala Ala Ala Gly Pro Pro Gln Pro Pro Pro Leu Thr Ser Pro
2915 2920 2925

Pro Ala Pro Arg Lys Pro Ala Lys Gln Pro Ala Leu Met Ala Pro
2930 2935 2940

Gly Pro Pro Ala Gly Gln Arg Arg Ser Ser Gly Gly Ser Val Asp
2945 2950 2955

Thr Gly Gly Ser Ala Gly Gly Ala Ala Gly Arg Asn Ser Pro Ala
2960 2965 2970

Ser Leu Ala Gly Ala Gly Thr Gly Ala Ala Gly Pro Leu Pro Lys
2975 2980 2985

Leu Pro Pro His Val Leu Glu Arg Pro Leu Pro Pro Arg Met Gln
2990 2995 3000

Val His Met Pro Ala Pro Ala Pro Ser Pro Ala Ala Val Gln Gly
3005 3010 3015

Pro Val Gly Ala Thr Ala His Ser Gly Ala Ala Ala Pro Gly Ser
3020 3025 3030

Arg Leu Leu Ala Ala Ala Met Ser Pro Val Gly Gly Thr Asn Ala
3035 3040 3045

Gly Gly Ala Ala Ala Gly Ala Ser Pro Pro Pro Leu Leu Lys Val
3050 3055 3060

Thr Ile Gly Gly Arg Pro Gly Ser Leu Gln Ser Ala Ile Gly Ser
3065 3070 3075

Phe Ser Val Gln Pro Thr Gln Leu Pro Gln Pro Pro Gln Leu Pro
3080 3085 3090

Ala Leu Pro Gln Ser Gln His Gln Ser Gln Arg Gln His Gln Val
3095 3100 3105

Ala Glu Gln Gly Arg Phe Gly Met Pro Gly Ala Ala Gly Trp Ala
3110 3115 3120

Val Pro Gly Ala Ala Val Gly Ala Ala Gly Ser His Leu Pro Gln
3125 3130 3135

Leu His Gln His Gln His Ala Ala Ala Gly Ile Leu Asp Gly Asp
3140 3145 3150

Thr Gln Ser Ala Gly Gly Thr Gly Gly Gly Gly Val Ser Ser Lys
3155 3160 3165

Arg Lys Arg Glu Gly Asp Ser Glu
3170 3175

<210> SEQ ID NO 75
<211> LENGTH: 3470
<212> TYPE: DNA
<213> ORGANISM: Chlamydomonas reinhardtii

<400> SEQUENCE: 75
aaaaaccagg tatactgtat gctttaggtt cttgcgcaac ctgacgagtc aggcagactc 60
ctgtccttgc tttatcaaaa acacgcactg tacatagtta tacacgaaga ctgatttgat 120
tttatcgtaa gcacgcttgg gcgcaagctg aggtcaggtt cgctcacaag gcaggcaagc 180
tttccgttca tcctggagct aacaggagag ctgtggagag aaatgggcac aatgacctga 240
gactggcccg agcgcaaaat ggactcggag cagcagccgg ccagcccgag ggctgcgcct 300
ggtgcaagcg gaggccgacg cttgcctggt cggacacctt ctggtctatt gggacaggca 360
gcgcaggggc cgcagcaacc tcagccccaa cttggcaagg gagcacttca gctcaatcag 420
tccagcagcg cagcgacaac cgcgttgccg gtgaaacgtc gggggagttt ccagcagttg 480
aagaaaatag gtgccgccgg ggggcgagat ggcagctctt cgcacctgga ctcggactcg 540
gcaccatcaa ttttcgccat tgtgaaaaag tccacacact gggaaaagta tggcacggtg 600
ctcgtgctgc tcgttgccga cgagctcagc agtgacaagg aggcggtggt gcagatgctg 660
agcgcagagg gatacgatga ccagacgtcg gacagcatcg aggaggcggt gaagttgttt 720
tcggaaaggg aggtgtaccc ggacattgtt attgttgatt cagacaatga gctggtggac 780

```
accaaacagc tcatcaaggc gctgcaggcg ctgaacccca cggtggcggt gctggtactg    840
ggcagccgcg gcgggcccat gggcgcggtg gcggcgctgc aggcgggcgc ggcggactac    900
atggtgaagc cgctggatct ggatgaggtg gttgcccgcg tggagcgaca cgtgcagcga    960
cagcactgca tcaagttgga aatggaaaag gcgctggagc acgccaagga gatgatgcag   1020
cagctcatgc cggcatcact actcggggac gtgatgttgc ggaaagacgg cagcgccgcg   1080
ggcggcgcgc cggcgggcgg caaggcgagt ctcaacagcg tggcggagac cgactttgag   1140
gagcagatga gcgagctgag cgaggagaac caccgcttgg gccagaaggt gcaggagatg   1200
gagcgcaagc ttgagctcaa ggaccaggag aaccgcgacc tggaagccaa actcaacgcc   1260
atcgaccgca aagtcagcgc gctggccgcc agccgcgaga tgggcggcgg caacggcggc   1320
ggcaacggcg gcggcggggg gtcgggctgc acggccgtgg ggcctgagca gcgtgccgcg   1380
gcgcagcagg cggcgcaggc ggcccaggcc tcgttgcagg ggcagctgaa cagcgtggca   1440
caggccaacg aggacctccg acataaagtg gacgagctgg agcggctgat gcagtcgcac   1500
acaggcgtca ccagcgccag caaccaaaac ctgcgcctga gcgtcaacgg tgggcagcag   1560
cagggctagc tgcagcccgc gggcctgtcg cacagcggca gcggtgctgt cgagcagcat   1620
tagcagcggc gctggcggcc gcattagcat tagcattagc agcaggagca gcagcggaac   1680
gctgcaggcg gcaggcaggc tttgcaatgg gcaaaagggc tcctgctgcg tgtggccacg   1740
ggcaggagct ctagaactgc actgagtcgt agaggcactg ccgcccctgc tctcggagca   1800
gcaccgggat ggccgggcac gctgtggccg gactggtgac aggtggcgca gcggaccgct   1860
gctcttgtac ccaagtgctg ccgccggcga tgcatcaggc gctggcgagc gtcagttaca   1920
tcatcggaat tgaacggagc gctgcagtct cggcgaggag taaagcagca cgacaaggac   1980
tgcggcagaa gtcacgctgg gcagtgcagc gcaacggcat tgcatgagcg gtggtggctg   2040
gcgcgcggct gcagctggcc gcccggactg tcgagcttct ggtgggctta catggcctgg   2100
cccagcaacc aggagcgtgt gcatggcgtc acagctgccg ttctggggct gcatgcacgt   2160
gctaggtgca ccgggcgctc gggcagtagc gcgctgcctg gagatgcgtg tggtcgggtg   2220
gcatcacgcg cagacagctg ttcgtacttg cgacccactt acagggcatc aacaagtctt   2280
ctttacgtgc tccaacttgc tgcagaactg ggagttgagg atggggattt aagcataagc   2340
accgtgtggg gtgcaaggca aaaagtgtcg tactgtactt ctgaccccgt agcagcagac   2400
ccgggccccg cataggcctc tgccaggtct gaagctggcc aggtggagga actcaactgc   2460
ttgcttccag ttgcagcccg gcgcaatgtg ggcaggagag cgagaggctt tcggcaccgc   2520
tggaggtgtc acagaacatg ttcggtgatt atcggcgtac gagaaggggg gcgctgtaaa   2580
cggggcgcga gttagagtca gagtccccat gcaactcgga gtcaaataca tgaggtataa   2640
aatggttgtt gtgtgggcaa cagaccggga tgtgcgtcgt cagaaatggc actcgctcca   2700
tggcgaaatt tggtctcaac ccggagtctt tcctaacaca ggtccactgc attggtattt   2760
gcgtatgtgt gcgtgcgtgc gcgtgcctgt gttgcgcata ttcgcggtga aggggtgtgg   2820
gcggtagcgg ctcacaatgg gagtgatggg gcggcggacg gtagacctcg cgccgtcaca   2880
aatgctctaa ttaggggacc tcctggcgct aatggcttgt gcgcgcccct tccccggaag   2940
ctcactgcaa cagacaatgt gcgttggcac ggtgaactgc attacttggc tagggaggct   3000
gtgccttctc gagtacgatg gcaaaagctg cctggagcgt gctcagagag gaagtgtgag   3060
tgtgatggac caggcgaagt gggaggtatg aacattcgtc agcaagcatc atcatcgtgc   3120
ggctggtacg cgtgcttcca tttgaaatgc tgcaatgtat cacaacacag ttggcctcgt   3180
```

-continued cacaagaatg tatgacgtgg gcgaccctct gcacgtgatt ttcagtggca tgagcgggtc 3240
gtgtgcaatg aagcatacag tgacaggcaa ctcttgaaga tgacgcagcg cttggctgac 3300
aggcgctgaa aggatgcggg tagacaatga gctggggcac agctactggt gttacgatga 3360
taccgatacg ggagcagcac gtaggtcgcg tgttctcgtg gtctgtgtgc tgggccatca 3420
atgatatgcg cagcctgaca ggttgcaggg gtcgtgcagg aatgagcagc 3470

<210> SEQ ID NO 76
<211> LENGTH: 1311
<212> TYPE: DNA
<213> ORGANISM: Chlamydomonas reinhardtii

<400> SEQUENCE: 76
atggactcgg agcagcagcc ggccagcccg agggctgcgc ctggtgcaag cggaggccga 60
cgcttgcctg gtcggacacc ttctggtcta ttgggacagg cagcgcaggg gccgcagcaa 120
cctcagcccc aacttggcaa gggagcactt cagctcaatc agtccagcag cgcagcgaca 180
accgcgttgc cggtgaaacg tcgggggagt ttccagcagt tgaagaaaat aggtgccgcc 240
ggggggcgag atggcagctc ttcgcacctg gactcggact cggcaccatc aattttcgcc 300
attgtgaaaa agtccacaca ctgggaaaag tatggcacgg tgctcgtgct gctcgttgcc 360
gacgagctca gcagtgacaa ggaggcggtg gtgcagatgc tgagcgcaga gggatacgat 420
gaccagacgt cggacagcat cgaggaggcg gtgaagttgt tttcggaaag ggaggtgtac 480
ccggacattg ttattgttga ttcagacaat gagctggtgg acaccaaaca gctcatcaag 540
gcgctgcagg cgctgaaccc cacggtggcg gtgctggtac tgggcagccg cggcgggccc 600
atgggcgcgg tggcggcgct gcaggcgggc gcggcggact acatggtgaa gccgctggat 660
ctggatgagg tggttgcccg cgtggagcga cacgtgcagc gacagcactg catcaagttg 720
gaaatggaaa aggcgctgga gcacgccaag gagatgatgc agcagctcat gccggcatca 780
ctactcgggg acgtgatgtt gcggaaagac ggcagcgccg cgggcggcgc gccggcgggc 840
ggcaaggcga gtctcaacag cgtggcggag accgactttg aggagcagat gagcgagctg 900
agcgaggaga accaccgctt gggccagaag gtgcaggaga tggagcgcaa gcttgagctc 960
aaggaccagg agaaccgcga cctggaagcc aaactcaacg ccatcgaccg caaagtcagc 1020
gcgctggccg ccagccgcga gatgggcggc ggcaacggcg gcggcaacgg cggcggcggg 1080
gggtcgggct gcacggccgt ggggcctgag cagcgtgccg cggcgcagca ggcggcgcag 1140
gcggcccagg cctcgttgca ggggcagctg aacagcgtgg cacaggccaa cgaggacctc 1200
cgacataaag tggacgagct ggagcggctg atgcagtcgc acacaggcgt caccagcgcc 1260
agcaaccaaa acctgcgcct gagcgtcaac ggtgggcagc agcagggcta g 1311

<210> SEQ ID NO 77
<211> LENGTH: 436
<212> TYPE: PRT
<213> ORGANISM: Chlamydomonas reinhardtii

<400> SEQUENCE: 77

Met Asp Ser Glu Gln Gln Pro Ala Ser Pro Arg Ala Ala Pro Gly Ala
1 5 10 15

Ser Gly Gly Arg Arg Leu Pro Gly Arg Thr Pro Ser Gly Leu Leu Gly
20 25 30

Gln Ala Ala Gln Gly Pro Gln Gln Pro Gln Pro Gln Leu Gly Lys Gly
35 40 45

```
Ala Leu Gln Leu Asn Gln Ser Ser Ser Ala Ala Thr Thr Ala Leu Pro
    50                  55                  60

Val Lys Arg Arg Gly Ser Phe Gln Gln Leu Lys Lys Ile Gly Ala Ala
65                  70                  75                  80

Gly Gly Arg Asp Gly Ser Ser Ser His Leu Asp Ser Asp Ser Ala Pro
                85                  90                  95

Ser Ile Phe Ala Ile Val Lys Lys Ser Thr His Trp Glu Lys Tyr Gly
            100                 105                 110

Thr Val Leu Val Leu Leu Val Ala Asp Glu Leu Ser Ser Asp Lys Glu
        115                 120                 125

Ala Val Val Gln Met Leu Ser Ala Glu Gly Tyr Asp Asp Gln Thr Ser
    130                 135                 140

Asp Ser Ile Glu Glu Ala Val Lys Leu Phe Ser Glu Arg Glu Val Tyr
145                 150                 155                 160

Pro Asp Ile Val Ile Val Asp Ser Asp Asn Glu Leu Val Asp Thr Lys
                165                 170                 175

Gln Leu Ile Lys Ala Leu Gln Ala Leu Asn Pro Thr Val Ala Val Leu
            180                 185                 190

Val Leu Gly Ser Arg Gly Gly Pro Met Gly Ala Val Ala Ala Leu Gln
        195                 200                 205

Ala Gly Ala Ala Asp Tyr Met Val Lys Pro Leu Asp Leu Asp Glu Val
    210                 215                 220

Val Ala Arg Val Glu Arg His Val Gln Arg Gln His Cys Ile Lys Leu
225                 230                 235                 240

Glu Met Glu Lys Ala Leu Glu His Ala Lys Glu Met Met Gln Gln Leu
                245                 250                 255

Met Pro Ala Ser Leu Leu Gly Asp Val Met Leu Arg Lys Asp Gly Ser
            260                 265                 270

Ala Ala Gly Gly Ala Pro Ala Gly Gly Lys Ala Ser Leu Asn Ser Val
        275                 280                 285

Ala Glu Thr Asp Phe Glu Glu Gln Met Ser Glu Leu Ser Glu Glu Asn
    290                 295                 300

His Arg Leu Gly Gln Lys Val Gln Glu Met Glu Arg Lys Leu Glu Leu
305                 310                 315                 320

Lys Asp Gln Glu Asn Arg Asp Leu Glu Ala Lys Leu Asn Ala Ile Asp
                325                 330                 335

Arg Lys Val Ser Ala Leu Ala Ala Ser Arg Glu Met Gly Gly Gly Asn
            340                 345                 350

Gly Gly Gly Asn Gly Gly Gly Gly Gly Ser Gly Cys Thr Ala Val Gly
        355                 360                 365

Pro Glu Gln Arg Ala Ala Ala Gln Gln Ala Ala Gln Ala Ala Gln Ala
    370                 375                 380

Ser Leu Gln Gly Gln Leu Asn Ser Val Ala Gln Ala Asn Glu Asp Leu
385                 390                 395                 400

Arg His Lys Val Asp Glu Leu Glu Arg Leu Met Gln Ser His Thr Gly
                405                 410                 415

Val Thr Ser Ala Ser Asn Gln Asn Leu Arg Leu Ser Val Asn Gly Gly
            420                 425                 430

Gln Gln Gln Gly
        435
```

<210> SEQ ID NO 78
<211> LENGTH: 3846

<212> TYPE: DNA
<213> ORGANISM: Chlamydomonas reinhardtii

<400> SEQUENCE: 78
gcgacgcacg gctgggccaa attcgccaac ggcaggagac caaatcgatc gaggcgatct 60
tgcgaagttc tcggacaaat cgatcgcacc catagtgatt taagcattac atttgcccaa 120
ggcgtgagaa gtgcgaggcc cgaacggcta tgacgccaat gcgcagctta cgacatttaa 180
agcaaattat tcatacatca tacagcacgc ttatgtgaag aaagccagga ttttaggctc 240
tcgccccgat caagacgatc tccccattgc gaagttctcg gtttctttcc ggttcgcctg 300
ctccgtatga tttacctttg cgctacaaca gcgacttaaa cgacctacgt cgccttactg 360
tgtgcgcgta cgtgtttgta gctgtgagat agttttgtcc gcagcgtacc cgcaaataga 420
atgctcgcga gcacttacac gccctgtggc gttcgccagg tggcaggccg cacggttgca 480
gtgcccagca gcttggtcgc gccagtggca gtcgctcggt cgctggggtt ggcgccctac 540
gtccctgtat gtgagccttc tgcggcgctt ccggcctgcc agcagcctag cgggcgtcgt 600
catgttcaga ctgctgccac tctccgtgcc gacaacccca gctcggtcgc gcagctggtg 660
catcagaatg gaaaggggat gaaggttatt atcgccggcg cgggcatcgg cggcctggtg 720
ctagccgttg cacttctgaa gcagggcttc caggttcagg tctttgagcg cgacctgacg 780
gccatccgcg gcgagggcaa gtaccgtgga cccatccagg ttcaaagcaa tgcgctcgct 840
gcgctggagg ctatcgatcc cgaggtggcc gcggaggtgc tgcgcgaggg ctgcatcact 900
ggcgaccgta tcaacgggct ctgcgacggc ctgactggcg agtggtacgt caagttcgac 960
acgttccacc cggcggtcag caagggcctg ccggtgaccc gcgtcatcag ccgcctcacg 1020
ctgcagcaga tcctggccaa agccgtggag cgctacggcg gccccggcac catccagaac 1080
ggctgcaacg tgaccgagtt cacggagcgc cgcaacgaca ccaccggcaa caacgaggtg 1140
actgtgcagc tggaggacgg gcgcacgttt gcggccgacg tgctggtggg cgccgacggc 1200
atctggtcca agatccgtaa gcagctcatt ggcgagacca aggccaacta cagcgggtac 1260
acctgctaca ccggcatctc ggactttacg ccggcggaca ttgacattgt gggctaccgc 1320
gtgttcctgg gcaacggcca gtactttgtc agcagcgacg tgggcaacgg caagatgcag 1380
tggtacggct tccacaagga gccgtctggc ggcaccgacc ccgagggcag ccgcaaggcg 1440
cgcctgctgc agatctttgg ccactggaac gacaacgtgg tggacctgat caaggccacg 1500
cccgaggagg acgtgctgcg ccgcgacatc tttgacaggc cgcccatctt cacctggagc 1560
aagggccgcg tggccctgct gggcgacagc gcgcacgcca tgcagcccaa cctgggccag 1620
ggcggctgca tggccattga ggacgcctac gagctggcca tcgacctcag ccgcgccgtg 1680
tccgacaagg ccggaaacgc ggcggcggtg gacgtggagg gcgtgctgcg cagctaccag 1740
gacagccgca ttttgcgcgt cagcgccatt cacggcatgg cgggcatggc tgccttcatg 1800
gccagcacct acaagtgcta cctgggcgag ggctggagca agtgggttga ggggctgcgc 1860
atcccgcacc ccggccgcgt ggtggggcgg ctggtgatgc tgctcaccat gcccagcgtg 1920
ctggagtggg tgctgggcgg caacaccgac cacgtggcgc cgcaccgcac cagctactgc 1980
tcgctgggcg acaagcccaa ggctttcccc gagagccgct tccccgagtt catgaacaac 2040
gacgcctcca tcatccgctc ctcccacgcc gactggctgc tggtggcgga gcgcgacgcc 2100
gccacggccg ccgccgccaa cgtgaacgcc gccaccggca gcagcgccgc cgcggccgcc 2160
gccgccgacg tgaacagcag ctgccagtgc aagggcatct acatggcgga ctcggcggcc 2220
ctggtgggcc gctgcggcgc cacctcgcgc cccgcgctgg ccgtggacga cgtgcacgtc 2280
gccgagagtc acgcgcaggt ctggcgcggc ctcgccggcc tccccccctc ctcgtcgtcc 2340
gcctccaccg ccgccgcctc tgcgtccgcc gcctcctctg ccgccagcgg caccgccagc 2400
accctgggca gctcggaggg ctactggctc cgcgacctgg gcagcggccg cggcacctgg 2460
gtcaacggca agcgcctgcc cgacggcgcc acggtgcagc tgtggcccgg cgacgcggtg 2520
gagttcggcc ggcaccccag ccacgaggtg ttcaaggtga agatgcagca cgtgacgctg 2580
cgcagcgacg agctcagcgg ccaggcctac accacgctca tggtgggcaa gatccggaac 2640
aacgactacg tcatgcccga gtcgcggccg gacggcggca gccagcagcc gggccgcctg 2700
gtgacggctt aagcggcgcc gtgcgtaagg gccggcttac gggggcggca gtgtcgctgt 2760
ggagggatgg tctggggtgg gaggaatggg aggagagcgg cgggagcccg aggagcggag 2820
cgctggaggc ttgcggagcg gcagcttggg aagagctgcg gagagaggaa ggagcgcagg 2880
gcgcttggag cacgcgccag attacgatca cggcagcgcg aggcgcgcgt ctgacttcga 2940
agtggtaagg aagatttcat gtatgattgc gtcgagggac accgcaagtt ttacgcgcgg 3000
cggagggagc cttggggcat acaacagtac gagcgggcgt tggtgagaag gtggtcactc 3060
cgtatgagaa gatggttact ccgtaccttc gtgagaagct gctgcgcaca agttacgaac 3120
ctatctgtgt ggagagcccg gtagtatatc aggggcgagg gtcatgaacg cgagtggcga 3180
gtctgtgagc gccaatttgt tatgcggcat aatttcgcat cggggtatta cgtctacaaa 3240
atgttgagct ggcttagcgc aggaggcaac acctcaggca gaatgtacga atgtgtgcag 3300
aagggcagag tcaaggcaga ggcggagaag ttgtcagggc tgtgtgtggt ttggtcaggg 3360
cgtggctaga tggatatgag acccgccgcc gtctccagat tgtggcggag gtggaactct 3420
cggcccccgc gccagtcccc gcggccagcg catcccgcca tgcgggttgt tggctggtgc 3480
atcgcgcggg gtgtgctatg agtgtggaaa cactatgtcg cgtgtcgtgc tgaggtctgt 3540
tgagaggttt cgtcgtttgt gcatgtcctg tcccggttgg agtttgagcg aggtggttca 3600
aagtttttgg atcgcgtggg agagactgaa acggtttggt gagaatggtt gagacagagg 3660
ttgggcttgg aaactggagg agaggagcag cgtaactcga ggacgatgca gtagatgcac 3720
cacaacagtt gtggtgggcg cctggagtaa cacgcgtgcc accaacacgc aattacagag 3780
atccgtcata caggagggat catatgcgat ttaattttgg ttttgcattt gtaagacgtt 3840
ttcaca 3846

<210> SEQ ID NO 79
<211> LENGTH: 2292
<212> TYPE: DNA
<213> ORGANISM: Chlamydomonas reinhardtii

<400> SEQUENCE: 79
atgctcgcga gcacttacac gccctgtggc gttcgccagg tggcaggccg cacggttgca 60
gtgcccagca gcttggtcgc gccagtggca gtcgctcggt cgctggggtt ggcgccctac 120
gtccctgtat gtgagccttc tgcggcgctt ccggcctgcc agcagcctag cgggcgtcgt 180
catgttcaga ctgctgccac tctccgtgcc gacaacccca gctcggtcgc gcagctggtg 240
catcagaatg gaaaggggat gaaggttatt atcgccggcg cgggcatcgg cggcctggtg 300
ctagccgttg cacttctgaa gcagggcttc caggttcagg tctttgagcg cgacctgacg 360
gccatccgcg gcgagggcaa gtaccgtgga cccatccagg ttcaaagcaa tgcgctcgct 420
gcgctggagg ctatcgatcc cgaggtggcc gcggaggtgc tgcgcgaggg ctgcatcact 480

```
ggcgaccgta tcaacgggct ctgcgacggc ctgactggcg agtggtacgt caagttcgac    540

acgttccacc cggcggtcag caagggcctg ccggtgaccc gcgtcatcag ccgcctcacg    600

ctgcagcaga tcctggccaa agccgtggag cgctacggcg gccccggcac catccagaac    660

ggctgcaacg tgaccgagtt cacggagcgc cgcaacgaca ccaccggcaa caacgaggtg    720

actgtgcagc tggaggacgg gcgcacgttt gcggccgacg tgctggtggg cgccgacggc    780

atctggtcca agatccgtaa gcagctcatt ggcgagacca aggccaacta cagcgggtac    840

acctgctaca ccggcatctc ggactttacg ccggcggaca ttgacattgt gggctaccgc    900

gtgttcctgg gcaacggcca gtactttgtc agcagcgacg tgggcaacgg caagatgcag    960

tggtacggct tccacaagga gccgtctggc ggcaccgacc ccgagggcag ccgcaaggcg   1020

cgcctgctgc agatctttgg ccactggaac gacaacgtgg tggacctgat caaggccacg   1080

cccgaggagg acgtgctgcg ccgcgacatc tttgacaggc cgcccatctt cacctggagc   1140

aagggccgcg tggccctgct gggcgacagc gcgcacgcca tgcagcccaa cctgggccag   1200

ggcggctgca tggccattga ggacgcctac gagctggcca tcgacctcag ccgcgccgtg   1260

tccgacaagg ccggaaacgc ggcggcggtg gacgtggagg gcgtgctgcg cagctaccag   1320

gacagccgca ttttgcgcgt cagcgccatt cacggcatgg cgggcatggc tgccttcatg   1380

gccagcacct acaagtgcta cctgggcgag ggctggagca agtgggttga ggggctgcgc   1440

atcccgcacc ccggccgcgt ggtggggcgg ctggtgatgc tgctcaccat gcccagcgtg   1500

ctggagtggg tgctgggcgg caacaccgac cacgtggcgc cgcaccgcac cagctactgc   1560

tcgctgggcg acaagcccaa ggctttcccc gagagccgct tccccgagtt catgaacaac   1620

gacgcctcca tcatccgctc ctcccacgcc gactggctgc tggtggcgga gcgcgacgcc   1680

gccacggccg ccgccgccaa cgtgaacgcc gccaccggca gcagcgccgc cgcggccgcc   1740

gccgccgacg tgaacagcag ctgccagtgc aagggcatct acatggcgga ctcggcggcc   1800

ctggtgggcc gctgcggcgc cacctcgcgc cccgcgctgg ccgtggacga cgtgcacgtc   1860

gccgagagtc acgcgcaggt ctggcgcggc ctcgccggcc tccccccctc ctcgtcgtcc   1920

gcctccaccg ccgccgcctc tgcgtccgcc gcctcctctg ccgccagcgg caccgccagc   1980

accctgggca gctcggaggg ctactggctc cgcgacctgg gcagcggccg cggcacctgg   2040

gtcaacggca agcgcctgcc cgacggcgcc acggtgcagc tgtggcccgg cgacgcggtg   2100

gagttcggcc ggcaccccag ccacgaggtg ttcaaggtga agatgcagca cgtgacgctg   2160

cgcagcgacg agctcagcgg ccaggcctac accacgctca tggtgggcaa gatccggaac   2220

aacgactacg tcatgcccga gtcgcggccg gacggcggca gccagcagcc gggccgcctg   2280

gtgacggctt aa                                                       2292
```

<210> SEQ ID NO 80
<211> LENGTH: 763
<212> TYPE: PRT
<213> ORGANISM: Chlamydomonas reinhardtii

<400> SEQUENCE: 80

```
Met Leu Ala Ser Thr Tyr Thr Pro Cys Gly Val Arg Gln Val Ala Gly
1               5                   10                  15

Arg Thr Val Ala Val Pro Ser Ser Leu Val Ala Pro Val Ala Val Ala
            20                  25                  30

Arg Ser Leu Gly Leu Ala Pro Tyr Val Pro Val Cys Glu Pro Ser Ala
        35                  40                  45
```

-continued

```
Ala Leu Pro Ala Cys Gln Gln Pro Ser Gly Arg Arg His Val Gln Thr
    50                  55                  60

Ala Ala Thr Leu Arg Ala Asp Asn Pro Ser Ser Val Ala Gln Leu Val
65                  70                  75                  80

His Gln Asn Gly Lys Gly Met Lys Val Ile Ile Ala Gly Ala Gly Ile
                85                  90                  95

Gly Gly Leu Val Leu Ala Val Ala Leu Leu Lys Gln Gly Phe Gln Val
            100                 105                 110

Gln Val Phe Glu Arg Asp Leu Thr Ala Ile Arg Gly Glu Gly Lys Tyr
        115                 120                 125

Arg Gly Pro Ile Gln Val Gln Ser Asn Ala Leu Ala Ala Leu Glu Ala
    130                 135                 140

Ile Asp Pro Glu Val Ala Ala Glu Val Leu Arg Glu Gly Cys Ile Thr
145                 150                 155                 160

Gly Asp Arg Ile Asn Gly Leu Cys Asp Gly Leu Thr Gly Glu Trp Tyr
                165                 170                 175

Val Lys Phe Asp Thr Phe His Pro Ala Val Ser Lys Gly Leu Pro Val
            180                 185                 190

Thr Arg Val Ile Ser Arg Leu Thr Leu Gln Gln Ile Leu Ala Lys Ala
        195                 200                 205

Val Glu Arg Tyr Gly Gly Pro Gly Thr Ile Gln Asn Gly Cys Asn Val
    210                 215                 220

Thr Glu Phe Thr Glu Arg Arg Asn Asp Thr Thr Gly Asn Asn Glu Val
225                 230                 235                 240

Thr Val Gln Leu Glu Asp Gly Arg Thr Phe Ala Ala Asp Val Leu Val
                245                 250                 255

Gly Ala Asp Gly Ile Trp Ser Lys Ile Arg Lys Gln Leu Ile Gly Glu
            260                 265                 270

Thr Lys Ala Asn Tyr Ser Gly Tyr Thr Cys Tyr Thr Gly Ile Ser Asp
        275                 280                 285

Phe Thr Pro Ala Asp Ile Asp Ile Val Gly Tyr Arg Val Phe Leu Gly
    290                 295                 300

Asn Gly Gln Tyr Phe Val Ser Ser Asp Val Gly Asn Gly Lys Met Gln
305                 310                 315                 320

Trp Tyr Gly Phe His Lys Glu Pro Ser Gly Gly Thr Asp Pro Glu Gly
                325                 330                 335

Ser Arg Lys Ala Arg Leu Leu Gln Ile Phe Gly His Trp Asn Asp Asn
            340                 345                 350

Val Val Asp Leu Ile Lys Ala Thr Pro Glu Glu Asp Val Leu Arg Arg
        355                 360                 365

Asp Ile Phe Asp Arg Pro Pro Ile Phe Thr Trp Ser Lys Gly Arg Val
    370                 375                 380

Ala Leu Leu Gly Asp Ser Ala His Ala Met Gln Pro Asn Leu Gly Gln
385                 390                 395                 400

Gly Gly Cys Met Ala Ile Glu Asp Ala Tyr Glu Leu Ala Ile Asp Leu
                405                 410                 415

Ser Arg Ala Val Ser Asp Lys Ala Gly Asn Ala Ala Ala Val Asp Val
            420                 425                 430

Glu Gly Val Leu Arg Ser Tyr Gln Asp Ser Arg Ile Leu Arg Val Ser
        435                 440                 445

Ala Ile His Gly Met Ala Gly Met Ala Ala Phe Met Ala Ser Thr Tyr
    450                 455                 460
```

-continued

```
Lys Cys Tyr Leu Gly Glu Gly Trp Ser Lys Trp Val Glu Gly Leu Arg
465                 470                 475                 480

Ile Pro His Pro Gly Arg Val Val Gly Arg Leu Val Met Leu Leu Thr
                485                 490                 495

Met Pro Ser Val Leu Glu Trp Val Leu Gly Gly Asn Thr Asp His Val
            500                 505                 510

Ala Pro His Arg Thr Ser Tyr Cys Ser Leu Gly Asp Lys Pro Lys Ala
        515                 520                 525

Phe Pro Glu Ser Arg Phe Pro Glu Phe Met Asn Asn Asp Ala Ser Ile
    530                 535                 540

Ile Arg Ser Ser His Ala Asp Trp Leu Leu Val Ala Glu Arg Asp Ala
545                 550                 555                 560

Ala Thr Ala Ala Ala Ala Asn Val Asn Ala Ala Thr Gly Ser Ser Ala
                565                 570                 575

Ala Ala Ala Ala Ala Ala Asp Val Asn Ser Ser Cys Gln Cys Lys Gly
            580                 585                 590

Ile Tyr Met Ala Asp Ser Ala Ala Leu Val Gly Arg Cys Gly Ala Thr
        595                 600                 605

Ser Arg Pro Ala Leu Ala Val Asp Asp Val His Val Ala Glu Ser His
    610                 615                 620

Ala Gln Val Trp Arg Gly Leu Ala Gly Leu Pro Pro Ser Ser Ser Ser
625                 630                 635                 640

Ala Ser Thr Ala Ala Ala Ser Ala Ser Ala Ala Ser Ser Ala Ala Ser
                645                 650                 655

Gly Thr Ala Ser Thr Leu Gly Ser Ser Glu Gly Tyr Trp Leu Arg Asp
            660                 665                 670

Leu Gly Ser Gly Arg Gly Thr Trp Val Asn Gly Lys Arg Leu Pro Asp
        675                 680                 685

Gly Ala Thr Val Gln Leu Trp Pro Gly Asp Ala Val Glu Phe Gly Arg
    690                 695                 700

His Pro Ser His Glu Val Phe Lys Val Lys Met Gln His Val Thr Leu
705                 710                 715                 720

Arg Ser Asp Glu Leu Ser Gly Gln Ala Tyr Thr Thr Leu Met Val Gly
                725                 730                 735

Lys Ile Arg Asn Asn Asp Tyr Val Met Pro Glu Ser Arg Pro Asp Gly
            740                 745                 750

Gly Ser Gln Gln Pro Gly Arg Leu Val Thr Ala
        755                 760
```

<210> SEQ ID NO 81
<211> LENGTH: 16122
<212> TYPE: DNA
<213> ORGANISM: Chlamydomonas reinhardtii

<400> SEQUENCE: 81

```
cacattcaac actgccacga tgaagcaaac tgaacgggtt atgcaggagt cgcttgaagg      60

ggaagtacac ggccccactt caggctctta agcctcaggg gttcgtgtag gcgttgtatt     120

atcatgagtg ctagatataa gacggtatta tgtgtaaact gggagggagg gagctgcaag     180

tatggagacg cttgccagtt tgcgcacgga gcgcacgagc tacgatctcg gggcgaacag     240

gttgcgactg gcttggtggt cgcgccagta aggaccacac caaagcttgc aggtcaacct     300

gctcagtcgc tgcagaaaag gcagctctgc aaatggcacc aagtgggcgc ctgcagcttt     360

ggcgcccgct gcaagttcgc gcacagcgag catgagctgt gcgccccagg cggagcctac     420
```

-continued

```
ggtggcagca acagtcatgg gtcggcagtc tcccagaacg gcggtggagc ctttccgaca    480
tcaccgcagc ccgaggccgc gtcttctccc acgtcccaga ccccgcctcc cccgcctcct    540
ccgcttcccc tgccgcgcct gagccccgtg gaagttcata agatttacaa ggaggcactg    600
gtggcggcgc ggtcgggtga tgcggtcaag gtggggagca aggctggcga gctgctagcc    660
cgcgggccgg cgccgcacta cggcctgtcg cgcaaccagg tggccgacct gatcgccgcc    720
gccaccgccg agtaccccag cctgccctgc ctgaaggccc tgctgccgct ggcccagccc    780
ttcggcgact ggaccctcct gcaccggcag taccccacgg cctcccacca acaggccacc    840
ggccaggccg tgtactgcgg gctactgcac caggccgctc tgatgctgct ggagtggcac    900
aaggcgggcc tcgcgcaggc agccaccacc gggctggagg tgctgcgagc catctgtgcc    960
gcgcggcccg ccgccgtcgt ggacatgaag gcgccgggca tcctgtccac gccgctggag   1020
acggtgctgc tagccggcca ggagccgcgc ggcttcgtgg ctcggctgct gcgcgaggtg   1080
tcacccatca cctggctgca cacggcgccg gggcacgcgg cgcacctgcg cgcggtggag   1140
gtgtgcgagg cgctggcgga cgacgagggc tgcctggtgg cgcgcaacct gggcttcagc   1200
caggcctact tcctcacctg cgcctcggtg ctgcagggca tctatgaccg caagcggccc   1260
gcgtccgcct cctacgaggc ggtgccggag ccggtgccgc cgccggcgtc cggctacatc   1320
cagctgccgg ccctggagat ccccggcatc tcgcggacct tcaccggcgt acggacaggg   1380
gcgccgccgc cgccaccacc accgcatgca gcagcaagca gcgcttccgg gcatgtcaag   1440
gtgcacagcc agccggccac ggcgccggcg gctggcagca ctgcctccag cagctcagtg   1500
gcaaagcagc cacacacgca gcagctccag ttgccgtcgg gcgcacgcag cggcgccgcc   1560
tcctccgctt cctcggtgca gaagggccct gtggcagccg cggtcaagac gacagtcgcc   1620
agcgccgctg tggccgcggc tatcggtggc gctgttgccg ccgggcagcg cggcgcgcgc   1680
cagcggcagc agccgcagca agacgacgac gatgatgaag aggggccgcc cgcgctgctg   1740
gatgacaact cctcggatgg cgacggcgac agctcgggct ccgaagactt gctggggctg   1800
ctgctgcagc aaaagcagcc acccaactcc aaggctgctt tgaaacagca aacggcaggc   1860
aagcagagca acggcgcagc ggcggccagc agcggcttcg cgcgcggctt ccttggcggg   1920
ggcggagcca gcacgggcgc tgcagcgggc gcgggggggca aggccgctgg gcctgctccc   1980
caacccgcag ccgcaagcaa gccccaaggc cagcagcaga atgcgatgca gcaacagggg   2040
cagcaggcac gacaatcgca gcagcagcag cagcagcagc agcagcagca gcagcagcag   2100
gcacaggcca agccagccag cggcggcctt gcacgcggct tcctggctgg cggcgcaaca   2160
gggtcttccg gcacagctca ggccgctgcc agtgcggcag gcaaagcacc cgcagccagc   2220
gctacaggtg caagtgctgg tgcgcaggcg ctcgccgcca agagagcggc gggctccgcc   2280
ggcgcggctg ccgccaaaac ggtagtagcg gcccccgcgg cggcaacgac cccggccaaa   2340
ccggccaccg cgcagcccgc caaagcagtt gcagcagcag cggcagcagc cgccgccaag   2400
ccgttagcgc cgccgccgca gccggccggc gcgcaagtgc tgagggcact gctggcggag   2460
ctgacggcgg cggtggacgc gaacgccgcg ggcaaggtgg cagacgtcgt gaagcggctc   2520
aacaaggaga ccgcggcgtg cacgcctccg ctacctgtgg aaaaagcaat ccaggctcca   2580
tgctttgcgg ccacccatag cgcgaagcag aaggtcggag acctgacgcc gctgacgatc   2640
aaggatgacc cgctttgggc tgcggagaac gcggcgcggg ccgcggcgga gtctgccccg   2700
caggcggggc tgctggcgga actgcttgcc gcgctgcgca agtgcacctg gagggcggtg   2760
ctgggccaca tgtcgctctc catgctgcag gagctacgca taataaacat cccctgcggc   2820
```

-continued

```
attccatggt ggccggagat cctgcgtgac gcctctgtgc cggccgacca gccgtcaccc   2880
agcctgtttg agatgctgct ggagaagggc ggcgccgtcg ccagcgactt ggcggcgggc   2940
ctggtggaga agcacagcta cgtgctgctg tacgccaaca agagcccggt gtgcctggcc   3000
ctgacccgca agctgccgct gaacgacacc gactacatct tccgcatgag cctcgcctac   3060
cgctccaagg agaagggcgg cgccgccagg gagaccctca cggcggagct gcagctgccc   3120
gatccggccg cgccgcaggg ctggcgccgc cgccaagtga gcgccaccgc cttcggctgg   3180
tgggcgctgc tgccgcactg cagcaatgac gcccgggtgc tgtcgacgct gcgggccaag   3240
gtggacccca aggtggagct gcccgccttc gagggcctgc cgccgctgca cgtgctggtg   3300
cagtacgggc ggcggccgtg ggatggggtg gcaacggtgg ccacggaccg gcggctcagc   3360
gcgctgctgt tcacggatga gggcgtgtta atctcccggc tgctggagca agtggcgggc   3420
ggcatcacac cgctgtacag ggcggtgcgc gtgggcgaca tcccggcagt gacgtggctg   3480
cggcagcggg gcgcgagccc gctggtcagc tgcacggagg agggcgcggg cggatacagc   3540
gatacgccgc tacacctggc ggtgacgcgc aagagcgccg aggccgtgga ggcaatcatt   3600
aagcactccg cgcccgacat cctcaagaag ctggacacca catacgacag cgacggcgcc   3660
acacccctca tgctcgcggc ggagctgggc tacacccgca tcgtggacct gctgctggcg   3720
gcaggtgccg acccctccct gctgcacgac ctgccaaaca agggcgcgag caagtcaaag   3780
aaaggcggcg cggccggctc tacggacgcg ccgcggggca cacaccagtc ggtcctgtca   3840
cggacgctgc agctgcagga ggcggaggag gagcggcgga agaagcaggg cagcaacggt   3900
caggcgcagg gcgacgccaa gaagcccaac ccgcatgacg ctgtgctgga ggcgatcatc   3960
agcagttgga agcccctgtg gagtggtgcg gcgctgcagc gcgagctagg gccggacggg   4020
tgcgcacgtg tgcgggcctg gctgctgcag cacgcggaca cgacgctgtg gccagtgatc   4080
aaggagatgg gtgcgggcgg cgtgtcgcca ggcgtgctga cagccagcct cgtggcgctg   4140
ctgctggagg tgtgccgcac ggcaggtggc gccgactggc gcgtgccagg caccaccgac   4200
cccttcaagc ccgcgggcga aggcggcagc ggcagcagca cgtggacggg gccgaagggc   4260
acacacccgc ctcggtcgca gctgtcggtg tggtcactgg ttccggagtc agccgctgcc   4320
caggatcacg ccaaggccat agccgcaaag gagggcagcg gcagtttggc gccggcgtgg   4380
ctgacgctgc ccctgctgcg cgagatgctg cagcgcgggc tggcttcgcc gcatgagcgc   4440
ctgccgtcgt acggcatcat gtctgagctc tccaagggca gcaccctgct ccacaaggcc   4500
tgtttcatcg gcgacttgga catggcgctt ctgcttctgg aggcgggggc ggactggagc   4560
aggaaggacg acaacggcaa cacggtgctg cactacgtcg ccatgggcag cgccggttac   4620
ggcgagagcc gcgtgctggc gctgtggcgc ctcttcatgt ggggccgtgc ggaggggatt   4680
gcggcgggcg gcggcaaggg ctcggcagct gcggcgtcgg cgctgccgcc gctgctgatt   4740
gatccggagc gcctggcgct ggcgaccgca accaacacca agaagcgcat gccagaagac   4800
ctggcagccg ccaagatcaa gccggcgttg aagacagaga tacaggccct caagcagcgc   4860
gtgaacgcca agctgaagaa ccaggaggcc gcagccaagg ccggcggaaa ggccacaggc   4920
aactccagcg gcaaagcaga cagcaaggcg ggcgccgccg tggctgagca gccggccgct   4980
gacgcgggca cggccgccgc ggctgctgcc ccggaggccc cgggtgcggc tgcggccccg   5040
gctgtggccg tgctgagccc ggcggagcag ctgaaggcgc tgctggcgga cgacgaggcc   5100
ctggcctccg ctccgctggc gcaactggtg ggcgtgccgg aggagtcggc gctgcagcta   5160
```

-continued

```
gccacgcggc tggccaaggc cctgcccggt acgctgcttc gcggcaagcg ggcagcaggg   5220
gctcaaggag ccggcggcgg cgaggatggt ggcggcggcg acggcggcga tgacggcctg   5280
tcgcggctcc gggcggtggt ggaggagctg cgggaggagg acgacgaaca ggagaacggg   5340
gacgacggcg ccgagtacag cgaggacgac gcgccgccgc ccggtgagga gctgttggag   5400
gacgaggatg ccaacgcggc cgccatgcgg ggagtggccg gtgacgccgc ggctgcctca   5460
gcggccgccg cctccgccag cagcagcggc agcgcggccg cgaacggcgg cgcggcccag   5520
gcggtggcgg ctgcgaccga cttcgacaac cacccgctgc gcaacctggc ctggccgctg   5580
ctcatcacca aggaggccat cgcgggctgg ggcacgctga acgaccagtg gaggaagctg   5640
gtgatggccc ggctgcgcgt catcgggcag gggctgtggc cgcgctgccg cggcgccaag   5700
cgcatcacca gcgacgaccc actgctcatg ccgcaggagc tgtggcggct caagctcaca   5760
aagggcggcc gcatcctgtt cgaggtggcg gtggacgacc acgacagcaa gggcaccttc   5820
tgcgagatta tcagagtctg gtgcatcacg ctgaaccaca aggagtacga ggtgatgatt   5880
cagcgcgtgc agcgctcctt caccaactca ctgcgcatgc ggctgcgcaa gaagctgcag   5940
ccgctggagc aggaggggcc ggcagcggcc gcgaccgcgg ccggcacaaa gaaggcggcc   6000
ggcgccaagg cggcggcagc cggcgtcgtg gctgcgggcg gcgaccgcac ccggactcgc   6060
ctgccgcggt tttacaagga ggcggggctg gtggacggca gcggcgctgg ggatgcgggc   6120
ggcagcaagg ggcaggagca gggccaggtg atggtgctgc gggagcacta cccgcccgca   6180
agctgggccg acgacacgta caccacgctc aagttctaca cggtggacgg gctgctggtg   6240
aaggcggtca tgtcggggct ggcggaggcg caggtggact tcatgttcaa gctgagcccg   6300
caggagcgcg acctcatcac catggtgccc agcccgccct cctccatcat cctgctgggc   6360
cgcagcggca ccggcaagac cacatgcgcc gtgttccgcc tgtggaccgc ctggctggcg   6420
ccctacctca gccgcgcgca cgagacgccg cacaccgtgt tcgtcaccgc gtcggccacg   6480
ctgcgggagc aggtggcccg cgccttccgc aagctgcagc gcgccgcact gcgcgaccac   6540
gagtgggagc gcgcctccgc ggccttcaac accacctatc acaccttcaa ggacgtgccg   6600
cccgaggcct tcccgctctt cctgtccagc cgcacctacc tgcgcatgct ggacggcacc   6660
accgagcgcc ccttcttccc gcgcgccgcc aacggctcca tcattcaggt ggcgggcgac   6720
ggcgaggaag cggaccccga cggcgcggcg ctggtggtgg ccctgaacga ggacctgagt   6780
gacgaggagg acgaggagga cggcgccgcc gcggaccagg agcggcagcg cggcgggccg   6840
gacgaggatg gcggcggcca ggagggcggc gcggcgctgt ttgaggagga ggtggcggcg   6900
gcggacgcgg cgcggcggga ggaggcggcg cgcgcgcggc tgctgatgga catggaggga   6960
gcggaggcgg gcggcgcggc ggacggctac gggctgggcg tggcgggtcg cgcgcggctg   7020
aaccgcgagg tgacgtacca gcacttcgtc agtgccatgt ggcccaagat cacaaccccc   7080
gagcagcgca accaggtggc gcccgggcgc gtgtaccagg agattgtgag ctacatcaag   7140
ggcagcgcag aagccatctc cagtcccgac ggccacctca gccgcgagca gtacatggcg   7200
ctgggccgca agcgcgccgc caacttcagc gccgacatgc gcggcgacgt ggtgtggccc   7260
atcttcgaga agtacgagcg gctgaagcga caggagtggc gctacgacat gttggacctg   7320
gtgggccaca tctaccgcga gatgaccacc acgcccgggg gctacgccgg cacgcccgtg   7380
cacgcgctgt atcgtgacga ggtccaggac ttcacccagg gcgagctgct gctggacatg   7440
gtggtggccg ccgaccccaa cagcctcttc tactgcggcg acacggcgca gaccattgcg   7500
cgaggcatcg ggttccgctt tgctgacacg cgcacgctgt tccacgagga gaacacgcgg   7560
```

cgccaggagg cggcggcgcg gcggctggcg gcggaggcgg cggacgagga gtcggtgggc 7620
aaggcgctgg cgcggcgcgg ccacggaatg accatcgcca cgcctcccgt cctccagctg 7680
accatgaact accggacgca ccagggcgtg ctggacgtgg cggcggtggt ggtggaggcg 7740
ctgaggcgct acttcccact gcagattgac aagctggagc gcgagagcgc gcagttcccg 7800
ggccctcacc cgctgctgct cggcagcatc tccgccgacg acctcaccta cctgctcagt 7860
ggctccgaca agaagacgtc gcaggtggag ttcggcgcgc accaggtgat cctggtccgc 7920
agcatggcgg cggtggacca gctgccggag gagatccggg acagcaacgc catcatcatg 7980
accgtgccgc aggccaaggg gctggagttc gacgatgtgt tcctggtgga cttctttgcg 8040
gacagccagg ccaccgccga gtggcgcgtg ctgtgctcct acctggccga gctgcaggag 8100
cggggcggca aggggctgga cggcttccag tacggcctgc agcaggtcgc cccgacggac 8160
ccgggcgcgg tgcggcctct ggagttgaac gagggcacgc acgtggtgct ggccgaggag 8220
ctcaagcacc tgtacaccgc catcacgcgc gccaagaaca acgtggtcat cttcgaccgc 8280
aacgccgcca agcgcgcgcc cttctaccac ctgctgcaga gcctgggcat ggcgcgcacc 8340
gtgcacaagt cgctgctgga ggacggcgcg gacgccgcca agttcgggct gacgcagaag 8400
gccaccagca gccggcacga gtgggccaag cgcgcgcgca acctcatggg caaccgcaac 8460
tacgccatgg cgcgcaaggc cttcctgcag gcggaggacc aggtgcgcgc cgaggtggcg 8520
gacgcactgc tcaagcgcca gcgcgccggc caggagtcca tgccggacgt cgacaagcgg 8580
cggctgctgg cggcggcggc gctgcagctg ctggcggcca ccgcccgctg cggcgagtcg 8640
ccggaccctg tggagccgga ggagctgcgg cgctgggtgc gcgaggccag caagttcctg 8700
gagggttgcg gcaagagcat tgaggctgcg cagctcaagt tcaagctggg cacgcagcgc 8760
gccgtggcag cggcgctgcg cctgctggtg gacgccaagg agtacgccgc cgctgccgag 8820
tgctgcgtgc acatggcggc ggccgagctg gcggcggcgc gcgcccgcgc cgcggaggag 8880
gacgcggcgg cggcgggcag catgcagcgg ctgctgatga cggaggcgga gctggcggcg 8940
cagcgggagg cgcaggcgca ccaggcggcg gtgccgtggc tggccaaagc agtggagcag 9000
ttccagttcg cgggcaacag cacggccgtg ctggcgctgc tcgcgccgcc tggcttcggc 9060
ggcagcaagg gtagcgccac aggcgcgcat gctccgcttg cagcagcagc cggcattgac 9120
tcggaggacg atgatgatgc ggcggaggat gcggcggagg atgcggcgga ggacgtggag 9180
gaggatgagc agcagcagcg cgagctagag gcgcaggagc ggacggggcc gctggcactg 9240
tttgcgccgc tggcgccgcg gctgcacgcc atgctggcga ggcgctggca gggctacggc 9300
caggcgctga gggcggccgc catcgcgctg cactcgcgcg gctcgctgcg gcgggcgggc 9360
gccgtggcgc ggctggtgcc catgccgcag gagcgggaca cattgctgga gacgctcggc 9420
tactggcggg cgcgggcgcg ggcccgcagc gcggtggacc cgctgggcgc ggcgcaggtg 9480
ctgctggagc acggcgacac gcggcgggcg gtgcgcctgg tgctgcgctg cctggagccg 9540
ctgcccgcct cctcgggggg catggaggcg gccgaggccg gggcgcgggg cggcggcggc 9600
gaccggctga cccgggcggc gcggcagcag cagctgtatg agctgcagct gcggcaggag 9660
catgagcggc gtcagaagca ggtgctggag gccaacgcgc tggctgtgct gcaccggctc 9720
gtcgcggcgc agaccaaggc agcggaggcg acgcagctgc ggcgagcgct ggaggcttgg 9780
atggcgcggc aggcgaagtc ggaggagggc ggcaaggaag gtgaggaggg cgccggtctc 9840
accaagcgca tgctgcccat ccgcggccac gtgctgctgc tggaggcgcg cttgctgctg 9900

-continued

```
gagccatggg ccgcagccgc tgccgggggc gccaaaggcg ctgcaggtga cagcaaggag   9960
cagcaggcgg cggcagcggc ggtggccacc aacgcggcat tgcgcgatgc cgcatggctt  10020
gaggcccggc cgctgctctt gacggcggtt gagtgcttcc tgcgctgtga ccagtggccg  10080
ggcttcatgg aggcggctga gctgctgctg cgggccgccc ccgacgcggc agtcgcaagc  10140
cacacggccg cagggcagct ggcagacttc gagcaggcgc tgctgcaggc tatgcagcga  10200
ggcgcagagc gcgccggtga cagcgccaca gtggcggccg cggcttcgtc tcgcacggcc  10260
gcagccaagc aggccctggc ccggagcctc gtggtgccgg aggcggcgct caagctgatg  10320
cggaccacgc agaccgcgtg tgatgcgctc agcgtggggc taggcagcag tgcgggtagc  10380
aacgtctctc tccgcccagg cggtggactg gtgggccgcg ccggtggcgg cggcgaaagg  10440
tcgcgcgccg gcgccgcctc ttcattgagc aagccgcagc aggaggcgct gtcggcgctg  10500
gaggggctgc tgctgctgcc gggcctgtcg cggccgactg aggcgaagct gtcggcgcgc  10560
aacgccagcc acagctggtg ggcggcgctg gggcagcaga acacggatgc ggtgcggcgc  10620
gcggctgggc ccaaggcagc agccggctcc ggacaggatg gcaaggagaa ggaaaagacg  10680
tctgggcagt cgagctgggc ggcggtggct gccaagggcg cggccgcaac ggcgatggtg  10740
tgggatccgg aggtgcccgc gctcgcaccc acctcgcacc tgctgctgcg ttgccaccag  10800
accgccatgg ccctgggcga aggtggagcc atggcggcag ccgtggaggc ggcgggtgct  10860
ggtgccagtc agatgccgct gccgcgtgcc gccgtcgcgg cggtcgcggc tcggagcctg  10920
actatccggg ctgcctgcct ggcacacctg gcggcacgcg gcgccctggc tgcctacttg  10980
caccctgcgc cgccgcctca gcccgccctg cccgcgggcg ccggcggcaa ggctgcggag  11040
gagggcacgg agggtgatgc cggcaagcag gagcagccgg cggaggccgc ggcgccgctc  11100
agctgtgagg tggtcctgga ccggctgcgg ccgctggtgt gcgctgcccg ggcggtgcac  11160
ctggccaaga tgatggtcgg cagcgttggg caggccttct caatggccgc ggcggcgagc  11220
ctccgcaagt gcctagatgc gcagctgcgc tacttggcgg ctgctctggt cgcggcctcg  11280
ctgccgcctg cggctgcgcc cgagctgctc gcagagctgc tgcagccgcg gccgcagccg  11340
cagcgcaggc ctggcggcgg cggcgggccg cctcggcggg tcatgggcga tctgctagag  11400
ttgctggcgc gtgacggctt cccgcaccgc gagctggcgg actgggcgga gcacctgctg  11460
gtcaggtgca tgccgctgga actgcgcatg ccgctggcgc ctgccgtgtc gtacctggcg  11520
tgccgcacga tgatgctggt ggcacccgac agcgaggacc gcgcctccaa gctgtggttg  11580
atcaaggaca gcagtgcgaa ggcgaccgga gacgtgcccc cggagcggct ggtgcatgac  11640
gacaagaaga cggggccggc ggaggcgctg ctggtgtccg ccttccgcgc catggacagc  11700
tccccgctcc gcgccgtggg ggacctgctc tactacctgg cgtggtgcgc ccggagagac  11760
gggctggcgg cggtgacgcc cactgacgct gcggcggaag gcgcgcaggc gccggctggt  11820
gcagctgccg gcggcagcaa gcccggaagc ggtgcagcgg cagcagccgg gcccgtgggc  11880
ctgtcgctgc cgcttgaggc ctacgccgag ctggtggagg tgacggtggg gcagctgctg  11940
ctggcggcct gcgacaacgc gctgctgccc ggcaacgtgg cgggcaccct ctcggggctg  12000
ccgcgcgtca gtgaccctca ggcgggcctg aacggcgtgg cggacacctg ggcgcgagag  12060
ctgggcttcc ggggcccggc cgtgggcgaa ggagcaggcg gcggcggtgg cagcggctgg  12120
ggctggggcc gaggccgtgg cccgtcgccc aaggaggtgg cagaggctaa ggcgcgggcg  12180
gtgacggcgc gcaaggaggt ggcgggtcag ctgcgtctgg ccgcgcggat gacgttgttg  12240
ctggcgtccc acattgacca gcgcctgcag gacacggctg cgcccgctgc gggcggcgca  12300
```

```
ggcggcgact cggctgcgtc ccctccggag ctggagttgt tgcagcaaga ggtgctgccg  12360
ctgctggacg ccccggggcg gcgcgaggcg cacgagctgc tgaggcagcc cggcggccca  12420
ggggcgcagc ctcgccgggc gcagggcaag agtcgcggcg gtggagcgga ggccggcgtg  12480
ggctcgggtg cgtccgttgc accgccgtcc gcaggagcca gcgggctgcg cttgcgggcg  12540
attgcgcagc gcgtcctgct ggcggcaggc gcagcctacg tctcgctgga gctgcaagag  12600
agtgtggtga agccgcagcg gcagcagcag aaggcggcgg cggagcggca gcagaagctg  12660
gcgggcggcg gccctgtgcc ggagccgccg ccgctgcgcg ggggctggcc ggccgaggcc  12720
tccgcgggct ttcgggacgc atgcacgctg ctgcaggcgc gtgtggcgcc ggcctgcttc  12780
cagccggcca ccggcgcgac cgacctggcc tcggtggcgc aggctgcgga cgcgctggca  12840
cggctgtcgc agcgggtgtg ctaccccagc tcgcgcctga gcacgggcat gcggctggtg  12900
ggcccggacg ccaaccgcga gtacgagggc ctcagcggcg cgcggccgcc caagggcccc  12960
ctggcgctgc tgttccaggc ggcgcaggcc aagatgcagc tgcccaaggc ggcggcggac  13020
gcggggatag gaggccgcgt caaggccgcc agcgacgcgg tggcgcgtgt ggccgcccgc  13080
gacttccagg ccacggagga cgagcgcgtg cggcagcgcc acgcggcggc ggtgatccaa  13140
aagcggtggc gcgcctggag gcagcggcgc atcgaggcgg cggaggcaat gcggcggcgc  13200
cagctgcagg ccaacgcgct ggagaccctg cgccgctcca tacgcttccg ggtctgggtg  13260
cgtgcgcgcc ttgcaaacgc gcgcaaggcc ctggacgcgc ggcacttcgg ggagcgcttc  13320
accgcggggt gcgccgccgc ggtccagttc ggcgagcagg cgctgcacat ggcggacatc  13380
gaggcggtgc tgaaggcgcg gtttgtccag ttggaccggt gcccggtgtg ctctggcgag  13440
acgctgcgca aacagacgga ggagctgaag cagcagatgg cgcagcgggc tgcgggcaag  13500
ctcaagggcg cagcagcgga gttccgaccg cacaagaaca cggttgatca cctggaggcc  13560
gccaactcct tcacaacctt ccgggacgtc tacaacggcg acctgccgac gcggctgggc  13620
ggcagcgccg cgcacatgga ccagctgcgt gccagcctag accgcttgga gcagctcggc  13680
gtcagcgacg cttcgctgat caagggccga ctcgtggcgg aggcggacct ggctctgcgc  13740
ggcgtggagc aggcccgtgc tgcgctggag gccagtctgc ggcagctggt ggaggagcgc  13800
gtctgggacg tgggtgtcct cgcatcgagg atgtttccgc agtacacctc gcttgacgcg  13860
gccgtgcagc gggttgacat gatgcgggtc cacgtggagg gactggccgc agctgcgcgc  13920
cgcacggcgc tgctgccccc tgacgagcag ctggcagcca ttcagcccaa gcagcagccc  13980
cagccccagc tgcagcagcc acaggagcag gaccagcacc aggagcagga gcaggagcag  14040
gcgctgcggt tgccaagcgg tgaagtccca gagcaggagc aggcgcagga gcaggtgcag  14100
gcgcaggagc agcagcctgt gggagtcttt gcggctggcc ttgatgtcag acctgctgac  14160
ggcatggcag cgcatgcagc cgccgccgcc gcctctccgg ccaagcaggc cgtgcccgcg  14220
ttagaggggc cgccggggac tcggcctggc ctgcagcagc ccttcagctc accgacacac  14280
cagcagcagg ggtccgcatg ggcggcgcag aagcctgtta ttcaattcac accgccgccg  14340
atgccgccaa tgccttcggc gctgctgcag cagctgtcac aggggcaagg gcagagctac  14400
gctgttgccg cccaggcggg cgccggcggc caggcagtta gtccctacag caaccagtcg  14460
cacgcgcagg ccgctcacac gatggggtac aatcaagtct atggcggtct gggtggcata  14520
ggcgcagacc tgcctccggg cctgtcgcaa acacctggtt acggcgcggc tgcagctggc  14580
tcaacggccg ggtatgctgc gtccgggttc gcgccgccca actttacggc gcaggctgga  14640
```

-continued

```
ttcccgttcc aacagcagca gcagttccag caacagcagc agcagcagca acagtatcaa  14700
tacttgccgc acatgcagca acagcagcag caacagcagc agcaacagta tcagccgtac  14760
ttgcagcagc agtaccagcc gccgtcgcct ggcatgaacg cttccatggt gtctccaggc  14820
ggcatgcctg gcttcatgcc gcagcagtac ggcatcggct acttcccaag cggagctgca  14880
ggtggaggag cggcggcagg gatgcaagga gtggctgcag ctgcagccat gggcgcggcg  14940
gcgcagttcg gtgctatggg cggcgcaggg ggctttccgg caggggagcc gggcacggac  15000
gccatcctgc aaggcgcact gatggaggac gatgacgagg acgacgacga gtggcagcag  15060
agccggcggc atggccgata tgacggcggg ggccggggcg ggggccgggg cgggcggggc  15120
cggggtcaca gcgcagggcc gcatgggagt ccctacgggc cgccaggccg tggacctgga  15180
ggcggtggag gccgcggtgg ccgcggcgcc ggtggatatg gcggtggcta tggcggtggg  15240
cgcggcagca acgtgtatga ggcgctgcgg ggtgccaatg ccacaccttc cagggccgcg  15300
cagcggatgg gcttgagcta atgttatttg agccaagccc gcatgactcc atgagcccat  15360
atgtgacgtg agcagatggc ggcagcaggt ggctatacgt tttagacaca tgcagtttgc  15420
tttcggagtg cggcgtgatg cgcagccggg aaaggagggt ggcggaagga ggaccgtgtc  15480
gctcattgct cttacagaca agaagcccct ggtgctggcc gacatgcctc atgtatgtga  15540
gcactgacac gtggtaggta gtgacagtgc gggatagggt gcgatgggac aggataaggg  15600
gcaggctggg gtagcaccgt tgtgtgcagc gtgttcccag accccgacat tcaattcaag  15660
ttgctgtacc gtattgagac atcgctgact ggctggcagg ctgggagtgt gctgatgcgc  15720
aatcctcacg atccgggcgc ccggcgaggc gaggcgatag caccacacac acacacacac  15780
acacacacac acacacacac acacacacac acacacacac acacacaaac atgcacacac  15840
agtggaggct ggcatggtgg tcgcaactgg cacggtctgt agcagctgcc gagtcatagg  15900
gcaggcgcac ggcgtctggg ctcacgaaga gttgaggcca gaccccggcc gggggcagaa  15960
ggcatgcgag tcgttagagc gaggcgagac agcctggcac acaaccacgg acagacaatg  16020
cccagacagc ctggcacaca gccacggaca gacaatgccc actccagggg ctggggtttc  16080
tgacggcggc acgtgtggca cgcaatgtaa aataccaggc ga                    16122
```

<210> SEQ ID NO 82
<211> LENGTH: 15198
<212> TYPE: DNA
<213> ORGANISM: Chlamydomonas reinhardtii

<400> SEQUENCE: 82

```
atgagtgcta gatataagac ggtattatgt gtaaactggg agggagggag ctgcaagtat     60
ggagacgctt gccagtttgc gcacggagcg cacgagctac gatctcgggg cgaacaggtt    120
gcgactggct tggtggtcgc gccagtaagg accacaccaa agcttgcagg tcaacctgct    180
cagtcgctgc agaaaaggca gctctgcaaa tggcaccaag tgggcgcctg cagctttggc    240
gcccgctgca agttcgcgca cagcgagcat gagctgtgcg ccccaggcgg agcctacggt    300
ggcagcaaca gtcatgggtc ggcagtctcc cagaacggcg gtggagcctt tccgacatca    360
ccgcagcccg aggccgcgtc ttctcccacg tcccagaccc cgcctccccc gcctcctccg    420
cttcccctgc cgcgcctgag ccccgtggaa gttcataaga tttacaagga ggcactggtg    480
gcggcgcggt cgggtgatgc ggtcaaggtg gggagcaagg ctggcgagct gctagcccgc    540
gggccggcgc cgcactacgg cctgtcgcgc aaccaggtgg ccgacctgat cgccgccgcc    600
accgccgagt accccagcct gccctgcctg aaggccctgc tgccgctggc ccagcccttc    660
```

```
ggcgactgga ccctcctgca ccggcagtac cccacggcct cccaccaaca ggccaccggc    720
caggccgtgt actgcgggct actgcaccag gccgctctga tgctgctgga gtggcacaag    780
gcgggcctcg cgcaggcagc caccaccggg ctggaggtgc tgcgagccat ctgtgccgcg    840
cggcccgccg ccgtcgtgga catgaaggcg ccgggcatcc tgtccacgcc gctggagacg    900
gtgctgctag ccggccagga gccgcgcggc ttcgtggctc ggctgctgcg cgaggtgtca    960
cccatcacct ggctgcacac ggcgccgggg cacgcggcgc acctgcgcgc ggtggaggtg   1020
tgcgaggcgc tggcggacga cgagggctgc ctggtggcgc gcaacctggg cttcagccag   1080
gcctacttcc tcacctgcgc ctcggtgctg cagggcatct atgaccgcaa gcggcccgcg   1140
tccgcctcct acgaggcggt gccggagccg gtgccgccgc cggcgtccgg ctacatccag   1200
ctgccggccc tggagatccc cggcatctcg cggaccttca ccggcgtacg gacaggggcg   1260
ccgccgccgc caccaccacc gcatgcagca gcaagcagcg cttccgggca tgtcaaggtg   1320
cacagccagc cggccacggc gccggcggct ggcagcactg cctccagcag ctcagtggca   1380
aagcagccac acacgcagca gctccagttg ccgtcgggcg cacgcagcgg cgccgcctcc   1440
tccgcttcct cggtgcagaa gggccctgtg gcagccgcgg tcaagacgac agtcgccagc   1500
gccgctgtgg ccgcggctat cggtggcgct gttgccgccg ggcagcgcgg cgcgcgccag   1560
cggcagcagc cgcagcaaga cgacgacgat gatgaagagg ggccgcccgc gctgctggat   1620
gacaactcct cggatggcga cggcgacagc tcgggctccg aagacttgct ggggctgctg   1680
ctgcagcaaa agcagccacc caactccaag gctgctttga aacagcaaac ggcaggcaag   1740
cagagcaacg gcgcagcggc ggccagcagc ggcttcgcgc gcggcttcct tggcgggggc   1800
ggagccagca cgggcgctgc agcgggcgcg gggggcaagg ccgctgggcc tgctccccaa   1860
cccgcagccg caagcaagcc ccaaggccag cagcagaatg cgatgcagca acaggggcag   1920
caggcacgac aatcgcagca gcagcagcag cagcagcagc agcagcagca gcagcaggca   1980
caggccaagc cagccagcgg cggccttgca cgcggcttcc tggctggcgg cgcaacaggg   2040
tcttccggca cagctcaggc cgctgccagt gcggcaggca aagcacccgc agccagcgct   2100
acaggtgcaa gtgctggtgc gcaggcgctc gccgccaaga gagcggcggg ctccgccggc   2160
gcggctgccg ccaaaacggt agtagcggcc cccgcggcgg caacgacccc ggccaaaccg   2220
gccaccgcgc agcccgccaa agcagttgca gcagcagcgg cagcagccgc cgccaagccg   2280
ttagcgccgc cgccgcagcc ggccggcgcg caagtgctga gggcactgct ggcggagctg   2340
acggcggcgg tggacgcgaa cgccgcgggc aaggtggcag acgtcgtgaa gcggctcaac   2400
aaggagaccg cggcgtgcac gcctccgcta cctgtggaaa aagcaatcca ggctccatgc   2460
tttgcggcca cccatagcgc gaagcagaag gtcggagacc tgacgccgct gacgatcaag   2520
gatgacccgc tttgggctgc ggagaacgcg gcgcgggccg cggcggagtc tgccccgcag   2580
gcggggctgc tggcggaact gcttgccgcg ctgcgcaagt gcacctggag ggcggtgctg   2640
ggccacatgt cgctctccat gctgcaggag ctacgcataa taaacatccc ctgcggcatt   2700
ccatggtggc cggagatcct gcgtgacgcc tctgtgccgg ccgaccagcc gtcacccagc   2760
ctgtttgaga tgctgctgga gaagggcggc gccgtcgcca gcgacttggc ggcgggcctg   2820
gtggagaagc acagctacgt gctgctgtac gccaacaaga gcccggtgtg cctggccctg   2880
acccgcaagc tgccgctgaa cgacaccgac tacatcttcc gcatgagcct cgcctaccgc   2940
tccaaggaga agggcggcgc cgccagggag accctcacgg cggagctgca gctgcccgat   3000
```

-continued

```
ccggccgcgc cgcagggctg gcgccgccgc caagtgagcg ccaccgcctt cggctggtgg   3060
gcgctgctgc cgcactgcag caatgacgcc cgggtgctgt cgacgctgcg ggccaaggtg   3120
gaccccaagg tggagctgcc cgccttcgag ggcctgccgc cgctgcacgt gctggtgcag   3180
tacgggcggc ggccgtggga tggggtggca acggtggcca cggaccggcg gctcagcgcg   3240
ctgctgttca cggatgaggg cgtgttaatc tcccggctgc tggagcaagt ggcgggcggc   3300
atcacaccgc tgtacagggc ggtgcgcgtg ggcgacatcc cggcagtgac gtggctgcgg   3360
cagcggggcg cgagcccgct ggtcagctgc acggaggagg gcgcgggcgg atacagcgat   3420
acgccgctac acctggcggt gacgcgcaag agcgccgagg ccgtggaggc aatcattaag   3480
cactccgcgc ccgacatcct caagaagctg gacaccacat acgacagcga cggcgccaca   3540
cccctcatgc tcgcggcgga gctgggctac acccgcatcg tggacctgct gctggcggca   3600
ggtgccgacc cctccctgct gcacgacctg ccaaacaagg gcgcgagcaa gtcaaagaaa   3660
ggcggcgcgg ccggctctac ggacgcgccg cggggcacac accagtcggt cctgtcacgg   3720
acgctgcagc tgcaggaggc ggaggaggag cggcggaaga agcagggcag caacggtcag   3780
gcgcagggcg acgccaagaa gcccaacccg catgacgctg tgctggaggc gatcatcagc   3840
agttggaagc ccctgtggag tggtgcggcg ctgcagcgcg agctagggcc ggacgggtgc   3900
gcacgtgtgc gggcctggct gctgcagcac gcggacacga cgctgtggcc agtgatcaag   3960
gagatgggtg cgggcggcgt gtcgccaggc gtgctgacag ccagcctcgt ggcgctgctg   4020
ctggaggtgt gccgcacggc aggtggcgcc gactggcgcg tgccaggcac caccgacccc   4080
ttcaagcccg cgggcgaagg cggcagcggc agcagcacgt ggacggggcc gaagggcaca   4140
cacccgcctc ggtcgcagct gtcggtgtgg tcactggttc cggagtcagc cgctgcccag   4200
gatcacgcca aggccatagc cgcaaaggag ggcagcggca gtttggcgcc ggcgtggctg   4260
acgctgcccc tgctgcgcga gatgctgcag cgcgggctgg cttcgccgca tgagcgcctg   4320
ccgtcgtacg gcatcatgtc tgagctctcc aagggcagca ccctgctcca caaggcctgt   4380
ttcatcggcg acttggacat ggcgcttctg cttctggagg cgggggcgga ctggagcagg   4440
aaggacgaca acggcaacac ggtgctgcac tacgtcgcca tgggcagcgc cggttacggc   4500
gagagccgcg tgctggcgct gtggcgcctc ttcatgtggg gccgtgcgga ggggattgcg   4560
gcgggcggcg gcaagggctc ggcagctgcg gcgtcggcgc tgccgccgct gctgattgat   4620
ccggagcgcc tggcgctggc gaccgcaacc aacaccaaga agcgcatgcc agaagacctg   4680
gcagccgcca agatcaagcc ggcgttgaag acagagatac aggccctcaa gcagcgcgtg   4740
aacgccaagc tgaagaacca ggaggccgca gccaaggccg gcggaaaggc cacaggcaac   4800
tccagcggca aagcagacag caaggcgggc gccgccgtgg ctgagcagcc ggccgctgac   4860
gcgggcacgg ccgccgcggc tgctgccccg gaggccccgg gtgcggctgc ggccccggct   4920
gtggccgtgc tgagcccggc ggagcagctg aaggcgctgc tggcggacga cgaggccctg   4980
gcctccgctc cgctggcgca actggtgggc gtgccggagg agtcggcgct gcagctagcc   5040
acgcggctgg ccaaggccct gcccggtacg ctgcttcgcg gcaagcgggc agcaggggct   5100
caaggagccg gcggcggcga ggatggtggc ggcggcgacg gcggcgatga cggcctgtcg   5160
cggctccggg cggtggtgga ggagctgcgg gaggaggacg acgaacagga gaacggggac   5220
gacggcgccg agtacagcga ggacgacgcg ccgccgcccg gtgaggagct gttggaggac   5280
gaggatgcca acgcggccgc catgcgggga gtggccggtg acgccgcggc tgcctcagcg   5340
gccgccgcct ccgccagcag cagcggcagc gcggccgcga acggcggcgc ggcccaggcg   5400
```

-continued

```
gtggcggctg cgaccgactt cgacaaccac ccgctgcgca acctggcctg gccgctgctc   5460
atcaccaagg aggccatcgc gggctggggc acgctgaacg accagtggag gaagctggtg   5520
atggcccggc tgcgcgtcat cgggcagggg ctgtggccgc gctgccgcgg cgccaagcgc   5580
atcaccagcg acgacccact gctcatgccg caggagctgt ggcggctcaa gctcacaaag   5640
ggcggccgca tcctgttcga ggtggcggtg gacgaccacg acagcaaggg caccttctgc   5700
gagattatca gagtctggtg catcacgctg aaccacaagg agtacgaggt gatgattcag   5760
cgcgtgcagc gctccttcac caactcactg cgcatgcggc tgcgcaagaa gctgcagccg   5820
ctggagcagg aggggccggc agcggccgcg accgcggccg gcacaaagaa ggcggccggc   5880
gccaaggcgg cggcagccgg cgtcgtggct gcgggcggcg accgcacccg gactcgcctg   5940
ccgcggtttt acaaggaggc ggggctggtg gacggcagcg gcgctgggga tgcgggcggc   6000
agcaaggggc aggagcaggg ccaggtgatg gtgctgcggg agcactaccc gcccgcaagc   6060
tgggccgacg acacgtacac cacgctcaag ttctacacgg tggacgggct gctggtgaag   6120
gcggtcatgt cggggctggc ggaggcgcag gtggacttca tgttcaagct gagcccgcag   6180
gagcgcgacc tcatcaccat ggtgcccagc ccgccctcct ccatcatcct gctgggccgc   6240
agcggcaccg gcaagaccac atgcgccgtg ttccgcctgt ggaccgcctg gctggcgccc   6300
tacctcagcc gcgcgcacga gacgccgcac accgtgttcg tcaccgcgtc ggccacgctg   6360
cgggagcagg tggcccgcgc cttccgcaag ctgcagcgcg ccgcactgcg cgaccacgag   6420
tgggagcgcg cctccgcggc cttcaacacc acctatcaca ccttcaagga cgtgccgccc   6480
gaggccttcc cgctcttcct gtccagccgc acctacctgc gcatgctgga cggcaccacc   6540
gagcgcccct tcttcccgcg cgccgccaac ggctccatca ttcaggtggc gggcgacggc   6600
gaggaagcgg accccgacgg cgcggcgctg gtggtggccc tgaacgagga cctgagtgac   6660
gaggaggacg aggaggacgg cgccgccgcg gaccaggagc ggcagcgcgg cgggccggac   6720
gaggatggcg gcggccagga gggcggcgcg gcgctgtttg aggaggaggt ggcggcggcg   6780
gacgcggcgc ggcgggagga ggcggcgcgc gcgcggctgc tgatggacat ggagggagcg   6840
gaggcgggcg gcgcggcgga cggctacggg ctgggcgtgg cgggtcgcgc gcggctgaac   6900
cgcgaggtga cgtaccagca cttcgtcagt gccatgtggc ccaagatcac aacccccgag   6960
cagcgcaacc aggtggcgcc cgggcgcgtg taccaggaga ttgtgagcta catcaagggc   7020
agcgcagaag ccatctccag tcccgacggc cacctcagcc gcgagcagta catggcgctg   7080
ggccgcaagc gcgccgccaa cttcagcgcc gacatgcgcg gcgacgtggt gtggcccatc   7140
ttcgagaagt acgagcggct gaagcgacag gagtggcgct acgacatgtt ggacctggtg   7200
ggccacatct accgcgagat gaccaccacg cccgggggct acgccggcac gcccgtgcac   7260
gcgctgtatc gtgacgaggt ccaggacttc acccagggcg agctgctgct ggacatggtg   7320
gtggccgccg accccaacag cctcttctac tgcggcgaca cggcgcagac cattgcgcga   7380
ggcatcgggt tccgctttgc tgacacgcgc acgctgttcc acgaggagaa cacgcggcgc   7440
caggaggcgg cggcgcggcg gctggcggcg gaggcggcgg acgaggagtc ggtgggcaag   7500
gcgctggcgc ggcgcggcca cggaatgacc atcgccacgc ctcccgtcct ccagctgacc   7560
atgaactacc ggacgcacca gggcgtgctg gacgtggcgg cggtggtggt ggaggcgctg   7620
aggcgctact tcccactgca gattgacaag ctggagcgcg agagcgcgca gttcccgggc   7680
cctcacccgc tgctgctcgg cagcatctcc gccgacgacc tcacctacct gctcagtggc   7740
```

-continued tccgacaaga agacgtcgca ggtggagttc ggcgcgcacc aggtgatcct ggtccgcagc 7800
atggcggcgg tggaccagct gccggaggag atccgggaca gcaacgccat catcatgacc 7860
gtgccgcagg ccaaggggct ggagttcgac gatgtgttcc tggtggactt ctttgcggac 7920
agccaggcca ccgccgagtg gcgcgtgctg tgctcctacc tggccgagct gcaggagcgg 7980
ggcggcaagg ggctggacgg cttccagtac ggcctgcagc aggtcgcccc gacggacccg 8040
ggcgcggtgc ggcctctgga gttgaacgag ggcacgcacg tggtgctggc cgaggagctc 8100
aagcacctgt acaccgccat cacgcgcgcc aagaacaacg tggtcatctt cgaccgcaac 8160
gccgccaagc gcgcgccctt ctaccacctg ctgcagagcc tgggcatggc gcgcaccgtg 8220
cacaagtcgc tgctggagga cggcgcggac gccgccaagt tcgggctgac gcagaaggcc 8280
accagcagcc ggcacgagtg ggccaagcgc gcgcgcaacc tcatgggcaa ccgcaactac 8340
gccatggcgc gcaaggcctt cctgcaggcg gaggaccagg tgcgcgccga ggtggcggac 8400
gcactgctca agcgccagcg cgccggccag gagtccatgc cggacgtcga caagcggcgg 8460
ctgctggcgg cggcggcgct gcagctgctg gcggccaccg cccgctgcgg cgagtcgccg 8520
gaccctgtgg agccggagga gctgcggcgc tgggtgcgcg aggccagcaa gttcctggag 8580
ggttgcggca agagcattga ggctgcgcag ctcaagttca agctgggcac gcagcgcgcc 8640
gtggcagcgg cgctgcgcct gctggtggac gccaaggagt acgccgccgc tgccgagtgc 8700
tgcgtgcaca tggcggcggc cgagctggcg gcggcgcgcg cccgcgccgc ggaggaggac 8760
gcggcggcgg cgggcagcat gcagcggctg ctgatgacgg aggcggagct ggcggcgcag 8820
cgggaggcgc aggcgcacca ggcggcggtg ccgtggctgg ccaaagcagt ggagcagttc 8880
cagttcgcgg gcaacagcac ggccgtgctg gcgctgctcg cgccgcctgg cttcggcggc 8940
agcaagggta gcgccacagg cgcgcatgct ccgcttgcag cagcagccgg cattgactcg 9000
gaggacgatg atgatgcggc ggaggatgcg gcggaggatg cggcggagga cgtggaggag 9060
gatgagcagc agcagcgcga gctagaggcg caggagcgga cggggccgct ggcactgttt 9120
gcgccgctgg cgccgcggct gcacgccatg ctggcgaggc gctggcaggg ctacggccag 9180
gcgctgaggg cggccgccat cgcgctgcac tcgcgcggct cgctgcggcg ggcgggcgcc 9240
gtggcgcggc tggtgcccat gccgcaggag cgggacacat tgctggagac gctcggctac 9300
tggcgggcgc gggcgcgggc ccgcagcgcg gtggacccgc tgggcgcggc gcaggtgctg 9360
ctggagcacg gcgacacgcg gcgggcggtg cgcctggtgc tgcgctgcct ggagccgctg 9420
cccgcctcct cggggggcat ggaggcggcc gaggccgggg gcgcgggcgg cggcggcgac 9480
cggctgaccc gggcggcgcg gcagcagcag ctgtatgagc tgcagctgcg gcaggagcat 9540
gagcggcgtc agaagcaggt gctggaggcc aacgcgctgg ctgtgctgca ccggctcgtc 9600
gcggcgcaga ccaaggcagc ggaggcgacg cagctgcggc gagcgctgga ggcttggatg 9660
gcgcggcagg cgaagtcgga ggagggcggc aaggaaggtg aggagggcgc cggtctcacc 9720
aagcgcatgc tgcccatccg cggccacgtg ctgctgctgg aggcgcgctt gctgctggag 9780
ccatgggccg cagccgctgc cgggggcgcc aaaggcgctg caggtgacag caaggagcag 9840
caggcggcgg cagcggcggt ggccaccaac gcggcattgc gcgatgccgc atggcttgag 9900
gcccggccgc tgctcttgac ggcggttgag tgcttcctgc gctgtgacca gtggccgggc 9960
ttcatggagg cggctgagct gctgctgcgg gccgcccccg acgcggcagt cgcaagccac 10020
acggccgcag ggcagctggc agacttcgag caggcgctgc tgcaggctat gcagcgaggc 10080
gcagagcgcg ccggtgacag cgccacagtg gcggccgcgg cttcgtctcg cacggccgca 10140
gccaagcagg ccctggcccg gagcctcgtg gtgccggagg cggcgctcaa gctgatgcgg 10200
accacgcaga ccgcgtgtga tgcgctcagc gtggggctag gcagcagtgc gggtagcaac 10260
gtctctctcc gcccaggcgg tggactggtg ggccgcgccg gtggcggcgg cgaaaggtcg 10320
cgcgccggcg ccgcctcttc attgagcaag ccgcagcagg aggcgctgtc ggcgctggag 10380
gggctgctgc tgctgccggg cctgtcgcgg ccgactgagg cgaagctgtc ggcgcgcaac 10440
gccagccaca gctggtgggc ggcgctgggg cagcagaaca cggatgcggt gcggcgcgcg 10500
gctgggccca aggcagcagc cggctccgga caggatggca aggagaagga aaagacgtct 10560
gggcagtcga gctgggcggc ggtggctgcc aagggcgcgg ccgcaacggc gatggtgtgg 10620
gatccggagg tgcccgcgct cgcacccacc tcgcacctgc tgctgcgttg ccaccagacc 10680
gccatggccc tgggcgaagg tggagccatg gcggcagccg tggaggcggc gggtgctggt 10740
gccagtcaga tgccgctgcc gcgtgccgcc gtcgcggcgg tcgcggctcg gagcctgact 10800
atccgggctg cctgcctggc acacctggcg gcacgcggcg ccctggctgc ctacttgcac 10860
cctgcgccgc cgcctcagcc cgccctgccc gcgggcgccg gcggcaaggc tgcggaggag 10920
ggcacggagg gtgatgccgg caagcaggag cagccggcgg aggccgcggc gccgctcagc 10980
tgtgaggtgg tcctggaccg gctgcggccg ctggtgtgcg ctgcccgggc ggtgcacctg 11040
gccaagatga tggtcggcag cgttgggcag gccttctcaa tggccgcggc ggcgagcctc 11100
cgcaagtgcc tagatgcgca gctgcgctac ttggcggctg ctctggtcgc ggcctcgctg 11160
ccgcctgcgg ctgcgcccga gctgctcgca gagctgctgc agccgcggcc gcagccgcag 11220
cgcaggcctg gcggcggcgg cgggccgcct cggcgggtca tgggcgatct gctagagttg 11280
ctggcgcgtg acggcttccc gcaccgcgag ctggcggact gggcggagca cctgctggtc 11340
aggtgcatgc cgctggaact gcgcatgccg ctggcgcctg ccgtgtcgta cctggcgtgc 11400
cgcacgatga tgctggtggc acccgacagc gaggaccgcg cctccaagct gtggttgatc 11460
aaggacagca gtgcgaaggc gaccggagac gtgcccccgg agcggctggt gcatgacgac 11520
aagaagacgg ggccggcgga ggcgctgctg gtgtccgcct tccgcgccat ggacagctcc 11580
ccgctccgcg ccgtggggga cctgctctac tacctggcgt ggtgcgcccg gagagacggg 11640
ctggcggcgg tgacgcccac tgacgctgcg gcggaaggcg cgcaggcgcc ggctggtgca 11700
gctgccggcg gcagcaagcc cggaagcggt gcagcggcag cagccgggcc cgtgggcctg 11760
tcgctgccgc ttgaggccta cgccgagctg gtggaggtga cggtggggca gctgctgctg 11820
gcggcctgcg acaacgcgct gctgcccggc aacgtggcgg gcaccctctc ggggctgccg 11880
cgcgtcagtg accctcaggc gggcctgaac ggcgtggcgg acacctgggc gcgagagctg 11940
ggcttccggg gcccggccgt gggcgaagga gcaggcggcg gcggtggcag cggctggggc 12000
tggggccgag gccgtggccc gtcgcccaag gaggtggcag aggctaaggc gcgggcggtg 12060
acggcgcgca aggaggtggc gggtcagctg cgtctggccg cgcggatgac gttgttgctg 12120
gcgtcccaca ttgaccagcg cctgcaggac acggctgcgc ccgctgcggg cggcgcaggc 12180
ggcgactcgg ctgcgtcccc tccggagctg gagttgttgc agcaagaggt gctgccgctg 12240
ctggacgccc cggggcggcg cgaggcgcac gagctgctga ggcagcccgg cggcccaggg 12300
gcgcagcctc gccgggcgca gggcaagagt cgcggcggtg gagcggaggc cggcgtgggc 12360
tcgggtgcgt ccgttgcacc gccgtccgca ggagccagcg ggctgcgctt gcgggcgatt 12420
gcgcagcgcg tcctgctggc ggcaggcgca gcctacgtct cgctggagct gcaagagagt 12480

-continued

```
gtggtgaagc cgcagcggca gcagcagaag gcggcggcgg agcggcagca gaagctggcg  12540
ggcggcggcc ctgtgccgga gccgccgccg ctgcgcgggg gctggccggc cgaggcctcc  12600
gcgggctttc gggacgcatg cacgctgctg caggcgcgtg tggcgccggc ctgcttccag  12660
ccggccaccg gcgcgaccga cctggcctcg gtggcgcagg ctgcggacgc gctggcacgg  12720
ctgtcgcagc gggtgtgcta ccccagctcg cgcctgagca cgggcatgcg gctggtgggc  12780
ccggacgcca accgcgagta cgagggcctc agcggcgcgc ggccgcccaa gggcccccctg  12840
gcgctgctgt tccaggcggc gcaggccaag atgcagctgc ccaaggcggc ggcggacgcg  12900
gggataggag gccgcgtcaa ggccgccagc gacgcggtgg cgcgtgtggc cgcccgcgac  12960
ttccaggcca cggaggacga gcgcgtgcgg cagcgccacg cggcggcggt gatccaaaag  13020
cggtggcgcg cctggaggca gcggcgcatc gaggcggcgg aggcaatgcg gcggcgccag  13080
ctgcaggcca acgcgctgga gaccctgcgc cgctccatac gcttccgggt ctgggtgcgt  13140
gcgcgccttg caaacgcgcg caaggccctg gacgcgcggc acttcgggga gcgcttcacc  13200
gcggggtgcg ccgccgcggt ccagttcggc gagcaggcgc tgcacatggc ggacatcgag  13260
gcggtgctga aggcgcggtt tgtccagttg gaccggtgcc cggtgtgctc tggcgagacg  13320
ctgcgcaaac agacggagga gctgaagcag cagatggcgc agcgggctgc gggcaagctc  13380
aagggcgcag cagcggagtt ccgaccgcac aagaacacgg ttgatcacct ggaggccgcc  13440
aactccttca caaccttccg ggacgtctac aacggcgacc tgccgacgcg gctgggcggc  13500
agcgccgcgc acatggacca gctgcgtgcc agcctagacc gcttggagca gctcggcgtc  13560
agcgacgctt cgctgatcaa gggccgactc gtggcggagg cggacctggc tctgcgcggc  13620
gtggagcagg cccgtgctgc gctggaggcc agtctgcggc agctggtgga ggagcgcgtc  13680
tgggacgtgg gtgtcctcgc atcgaggatg tttccgcagt acacctcgct tgacgcggcc  13740
gtgcagcggg ttgacatgat gcgggtccac gtggagggac tggccgcagc tgcgcgccgc  13800
acggcgctgc tgccccctga cgagcagctg gcagccattc agcccaagca gcagccccag  13860
ccccagctgc agcagccaca ggagcaggac cagcaccagg agcaggagca ggagcaggcg  13920
ctgcggttgc caagcggtga agtcccagag caggagcagg cgcaggagca ggtgcaggcg  13980
caggagcagc agcctgtggg agtctttgcg gctggccttg atgtcagacc tgctgacggc  14040
atggcagcgc atgcagccgc cgccgccgcc tctccggcca agcaggccgt gcccgcgtta  14100
gaggggccgc cggggactcg gcctggcctg cagcagccct tcagctcacc gacacaccag  14160
cagcaggggt ccgcatgggc ggcgcagaag cctgttattc aattcacacc gccgccgatg  14220
ccgccaatgc cttcggcgct gctgcagcag ctgtcacagg ggcaagggca gagctacgct  14280
gttgccgccc aggcgggcgc cggcggccag gcagttagtc cctacagcaa ccagtcgcac  14340
gcgcaggccg ctcacacgat ggggtacaat caagtctatg gcggtctggg tggcataggc  14400
gcagacctgc ctccgggcct gtcgcaaaca cctggttacg gcgcggctgc agctggctca  14460
acggccgggt atgctgcgtc cgggttcgcg ccgcccaact ttacggcgca ggctggattc  14520
ccgttccaac agcagcagca gttccagcaa cagcagcagc agcagcaaca gtatcaatac  14580
ttgccgcaca tgcagcaaca gcagcagcaa cagcagcagc aacagtatca gccgtacttg  14640
cagcagcagt accagccgcc gtcgcctggc atgaacgctt ccatggtgtc tccaggcggc  14700
atgcctggct tcatgccgca gcagtacggc atcggctact tcccaagcgg agctgcaggt  14760
ggaggagcgg cggcagggat gcaaggagtg gctgcagctg cagccatggg cgcggcggcg  14820
cagttcggtg ctatgggcgg cgcagggggc tttccggcag gggagccggg cacggacgcc  14880
```

atcctgcaag gcgcactgat ggaggacgat gacgaggacg acgacgagtg gcagcagagc 14940
cggcggcatg gccgatatga cggcgggggc cggggcgggg gccggggcgg gcggggccgg 15000
ggtcacagcg cagggccgca tgggagtccc tacgggccgc caggccgtgg acctggaggc 15060
ggtggaggcc gcggtggccg cggcgccggt ggatatggcg gtggctatgg cggtgggcgc 15120
ggcagcaacg tgtatgaggc gctgcggggt gccaatgcca caccttccag ggccgcgcag 15180
cggatgggct tgagctaa 15198

<210> SEQ ID NO 83
<211> LENGTH: 5065
<212> TYPE: PRT
<213> ORGANISM: Chlamydomonas reinhardtii

<400> SEQUENCE: 83

Met Ser Ala Arg Tyr Lys Thr Val Leu Cys Val Asn Trp Glu Gly Gly
1 5 10 15

Ser Cys Lys Tyr Gly Asp Ala Cys Gln Phe Ala His Gly Ala His Glu
20 25 30

Leu Arg Ser Arg Gly Glu Gln Val Ala Thr Gly Leu Val Val Ala Pro
35 40 45

Val Arg Thr Thr Pro Lys Leu Ala Gly Gln Pro Ala Gln Ser Leu Gln
50 55 60

Lys Arg Gln Leu Cys Lys Trp His Gln Val Gly Ala Cys Ser Phe Gly
65 70 75 80

Ala Arg Cys Lys Phe Ala His Ser Glu His Glu Leu Cys Ala Pro Gly
85 90 95

Gly Ala Tyr Gly Gly Ser Asn Ser His Gly Ser Ala Val Ser Gln Asn
100 105 110

Gly Gly Gly Ala Phe Pro Thr Ser Pro Gln Pro Glu Ala Ala Ser Ser
115 120 125

Pro Thr Ser Gln Thr Pro Pro Pro Pro Pro Pro Pro Leu Pro Leu Pro
130 135 140

Arg Leu Ser Pro Val Glu Val His Lys Ile Tyr Lys Glu Ala Leu Val
145 150 155 160

Ala Ala Arg Ser Gly Asp Ala Val Lys Val Gly Ser Lys Ala Gly Glu
165 170 175

Leu Leu Ala Arg Gly Pro Ala Pro His Tyr Gly Leu Ser Arg Asn Gln
180 185 190

Val Ala Asp Leu Ile Ala Ala Ala Thr Ala Glu Tyr Pro Ser Leu Pro
195 200 205

Cys Leu Lys Ala Leu Leu Pro Leu Ala Gln Pro Phe Gly Asp Trp Thr
210 215 220

Leu Leu His Arg Gln Tyr Pro Thr Ala Ser His Gln Gln Ala Thr Gly
225 230 235 240

Gln Ala Val Tyr Cys Gly Leu Leu His Gln Ala Ala Leu Met Leu Leu
245 250 255

Glu Trp His Lys Ala Gly Leu Ala Gln Ala Ala Thr Thr Gly Leu Glu
260 265 270

Val Leu Arg Ala Ile Cys Ala Ala Arg Pro Ala Ala Val Val Asp Met
275 280 285

Lys Ala Pro Gly Ile Leu Ser Thr Pro Leu Glu Thr Val Leu Leu Ala
290 295 300

Gly Gln Glu Pro Arg Gly Phe Val Ala Arg Leu Leu Arg Glu Val Ser

-continued

```
305                 310                 315                 320

Pro Ile Thr Trp Leu His Thr Ala Pro Gly His Ala Ala His Leu Arg
                325                 330                 335

Ala Val Glu Val Cys Glu Ala Leu Ala Asp Asp Glu Gly Cys Leu Val
            340                 345                 350

Ala Arg Asn Leu Gly Phe Ser Gln Ala Tyr Phe Leu Thr Cys Ala Ser
        355                 360                 365

Val Leu Gln Gly Ile Tyr Asp Arg Lys Arg Pro Ala Ser Ala Ser Tyr
    370                 375                 380

Glu Ala Val Pro Glu Pro Val Pro Pro Pro Ala Ser Gly Tyr Ile Gln
385                 390                 395                 400

Leu Pro Ala Leu Glu Ile Pro Gly Ile Ser Arg Thr Phe Thr Gly Val
                405                 410                 415

Arg Thr Gly Ala Pro Pro Pro Pro Pro Pro Pro His Ala Ala Ala Ser
            420                 425                 430

Ser Ala Ser Gly His Val Lys Val His Ser Gln Pro Ala Thr Ala Pro
        435                 440                 445

Ala Ala Gly Ser Thr Ala Ser Ser Ser Ser Val Ala Lys Gln Pro His
    450                 455                 460

Thr Gln Gln Leu Gln Leu Pro Ser Gly Ala Arg Ser Gly Ala Ala Ser
465                 470                 475                 480

Ser Ala Ser Ser Val Gln Lys Gly Pro Val Ala Ala Ala Val Lys Thr
                485                 490                 495

Thr Val Ala Ser Ala Ala Val Ala Ala Ala Ile Gly Gly Ala Val Ala
            500                 505                 510

Ala Gly Gln Arg Gly Ala Arg Gln Arg Gln Gln Pro Gln Gln Asp Asp
        515                 520                 525

Asp Asp Asp Glu Glu Gly Pro Pro Ala Leu Leu Asp Asp Asn Ser Ser
    530                 535                 540

Asp Gly Asp Gly Asp Ser Ser Gly Ser Glu Asp Leu Leu Gly Leu Leu
545                 550                 555                 560

Leu Gln Gln Lys Gln Pro Pro Asn Ser Lys Ala Ala Leu Lys Gln Gln
                565                 570                 575

Thr Ala Gly Lys Gln Ser Asn Gly Ala Ala Ala Ala Ser Ser Gly Phe
            580                 585                 590

Ala Arg Gly Phe Leu Gly Gly Gly Gly Ala Ser Thr Gly Ala Ala Ala
        595                 600                 605

Gly Ala Gly Gly Lys Ala Ala Gly Pro Ala Pro Gln Pro Ala Ala Ala
    610                 615                 620

Ser Lys Pro Gln Gly Gln Gln Gln Asn Ala Met Gln Gln Gln Gly Gln
625                 630                 635                 640

Gln Ala Arg Gln Ser Gln Gln Gln Gln Gln Gln Gln Gln Gln Gln Gln
                645                 650                 655

Gln Gln Gln Ala Gln Ala Lys Pro Ala Ser Gly Gly Leu Ala Arg Gly
            660                 665                 670

Phe Leu Ala Gly Gly Ala Thr Gly Ser Ser Gly Thr Ala Gln Ala Ala
        675                 680                 685

Ala Ser Ala Ala Gly Lys Ala Pro Ala Ala Ser Ala Thr Gly Ala Ser
    690                 695                 700

Ala Gly Ala Gln Ala Leu Ala Ala Lys Arg Ala Ala Gly Ser Ala Gly
705                 710                 715                 720

Ala Ala Ala Ala Lys Thr Val Val Ala Ala Pro Ala Ala Ala Thr Thr
                725                 730                 735
```

Pro Ala Lys Pro Ala Thr Ala Gln Pro Ala Lys Ala Val Ala Ala Ala
740 745 750

Ala Ala Ala Ala Ala Ala Lys Pro Leu Ala Pro Pro Pro Gln Pro Ala
755 760 765

Gly Ala Gln Val Leu Arg Ala Leu Leu Ala Glu Leu Thr Ala Ala Val
770 775 780

Asp Ala Asn Ala Ala Gly Lys Val Ala Asp Val Val Lys Arg Leu Asn
785 790 795 800

Lys Glu Thr Ala Ala Cys Thr Pro Pro Leu Pro Val Glu Lys Ala Ile
805 810 815

Gln Ala Pro Cys Phe Ala Ala Thr His Ser Ala Lys Gln Lys Val Gly
820 825 830

Asp Leu Thr Pro Leu Thr Ile Lys Asp Asp Pro Leu Trp Ala Ala Glu
835 840 845

Asn Ala Ala Arg Ala Ala Ala Glu Ser Ala Pro Gln Ala Gly Leu Leu
850 855 860

Ala Glu Leu Leu Ala Ala Leu Arg Lys Cys Thr Trp Arg Ala Val Leu
865 870 875 880

Gly His Met Ser Leu Ser Met Leu Gln Glu Leu Arg Ile Ile Asn Ile
885 890 895

Pro Cys Gly Ile Pro Trp Trp Pro Glu Ile Leu Arg Asp Ala Ser Val
900 905 910

Pro Ala Asp Gln Pro Ser Pro Ser Leu Phe Glu Met Leu Leu Glu Lys
915 920 925

Gly Gly Ala Val Ala Ser Asp Leu Ala Ala Gly Leu Val Glu Lys His
930 935 940

Ser Tyr Val Leu Leu Tyr Ala Asn Lys Ser Pro Val Cys Leu Ala Leu
945 950 955 960

Thr Arg Lys Leu Pro Leu Asn Asp Thr Asp Tyr Ile Phe Arg Met Ser
965 970 975

Leu Ala Tyr Arg Ser Lys Glu Lys Gly Gly Ala Ala Arg Glu Thr Leu
980 985 990

Thr Ala Glu Leu Gln Leu Pro Asp Pro Ala Ala Pro Gln Gly Trp Arg
995 1000 1005

Arg Arg Gln Val Ser Ala Thr Ala Phe Gly Trp Trp Ala Leu Leu
1010 1015 1020

Pro His Cys Ser Asn Asp Ala Arg Val Leu Ser Thr Leu Arg Ala
1025 1030 1035

Lys Val Asp Pro Lys Val Glu Leu Pro Ala Phe Glu Gly Leu Pro
1040 1045 1050

Pro Leu His Val Leu Val Gln Tyr Gly Arg Arg Pro Trp Asp Gly
1055 1060 1065

Val Ala Thr Val Ala Thr Asp Arg Arg Leu Ser Ala Leu Leu Phe
1070 1075 1080

Thr Asp Glu Gly Val Leu Ile Ser Arg Leu Leu Glu Gln Val Ala
1085 1090 1095

Gly Gly Ile Thr Pro Leu Tyr Arg Ala Val Arg Val Gly Asp Ile
1100 1105 1110

Pro Ala Val Thr Trp Leu Arg Gln Arg Gly Ala Ser Pro Leu Val
1115 1120 1125

Ser Cys Thr Glu Glu Gly Ala Gly Gly Tyr Ser Asp Thr Pro Leu
1130 1135 1140

```
His Leu  Ala Val Thr Arg Lys  Ser Ala Glu Ala Val  Glu Ala Ile
    1145                 1150                 1155

Ile Lys  His Ser Ala Pro Asp  Ile Leu Lys Lys Leu  Asp Thr Thr
    1160                 1165                 1170

Tyr Asp  Ser Asp Gly Ala Thr  Pro Leu Met Leu Ala  Ala Glu Leu
    1175                 1180                 1185

Gly Tyr  Thr Arg Ile Val Asp  Leu Leu Leu Ala Ala  Gly Ala Asp
    1190                 1195                 1200

Pro Ser  Leu Leu His Asp Leu  Pro Asn Lys Gly Ala  Ser Lys Ser
    1205                 1210                 1215

Lys Lys  Gly Gly Ala Ala Gly  Ser Thr Asp Ala Pro  Arg Gly Thr
    1220                 1225                 1230

His Gln  Ser Val Leu Ser Arg  Thr Leu Gln Leu Gln  Glu Ala Glu
    1235                 1240                 1245

Glu Glu  Arg Arg Lys Lys Gln  Gly Ser Asn Gly Gln  Ala Gln Gly
    1250                 1255                 1260

Asp Ala  Lys Lys Pro Asn Pro  His Asp Ala Val Leu  Glu Ala Ile
    1265                 1270                 1275

Ile Ser  Ser Trp Lys Pro Leu  Trp Ser Gly Ala Ala  Leu Gln Arg
    1280                 1285                 1290

Glu Leu  Gly Pro Asp Gly Cys  Ala Arg Val Arg Ala  Trp Leu Leu
    1295                 1300                 1305

Gln His  Ala Asp Thr Thr Leu  Trp Pro Val Ile Lys  Glu Met Gly
    1310                 1315                 1320

Ala Gly  Gly Val Ser Pro Gly  Val Leu Thr Ala Ser  Leu Val Ala
    1325                 1330                 1335

Leu Leu  Leu Glu Val Cys Arg  Thr Ala Gly Gly Ala  Asp Trp Arg
    1340                 1345                 1350

Val Pro  Gly Thr Thr Asp Pro  Phe Lys Pro Ala Gly  Glu Gly Gly
    1355                 1360                 1365

Ser Gly  Ser Ser Thr Trp Thr  Gly Pro Lys Gly Thr  His Pro Pro
    1370                 1375                 1380

Arg Ser  Gln Leu Ser Val Trp  Ser Leu Val Pro Glu  Ser Ala Ala
    1385                 1390                 1395

Ala Gln  Asp His Ala Lys Ala  Ile Ala Ala Lys Glu  Gly Ser Gly
    1400                 1405                 1410

Ser Leu  Ala Pro Ala Trp Leu  Thr Leu Pro Leu Leu  Arg Glu Met
    1415                 1420                 1425

Leu Gln  Arg Gly Leu Ala Ser  Pro His Glu Arg Leu  Pro Ser Tyr
    1430                 1435                 1440

Gly Ile  Met Ser Glu Leu Ser  Lys Gly Ser Thr Leu  Leu His Lys
    1445                 1450                 1455

Ala Cys  Phe Ile Gly Asp Leu  Asp Met Ala Leu Leu  Leu Leu Glu
    1460                 1465                 1470

Ala Gly  Ala Asp Trp Ser Arg  Lys Asp Asp Asn Gly  Asn Thr Val
    1475                 1480                 1485

Leu His  Tyr Val Ala Met Gly  Ser Ala Gly Tyr Gly  Glu Ser Arg
    1490                 1495                 1500

Val Leu  Ala Leu Trp Arg Leu  Phe Met Trp Gly Arg  Ala Glu Gly
    1505                 1510                 1515

Ile Ala  Ala Gly Gly Gly Lys  Gly Ser Ala Ala Ala  Ala Ser Ala
    1520                 1525                 1530

Leu Pro  Pro Leu Leu Ile Asp  Pro Glu Arg Leu Ala  Leu Ala Thr
```

```
    1535                1540                1545

Ala Thr  Asn Thr Lys Lys Arg  Met Pro Glu Asp Leu  Ala Ala Ala
    1550                1555                1560

Lys Ile  Lys Pro Ala Leu Lys  Thr Glu Ile Gln Ala  Leu Lys Gln
    1565                1570                1575

Arg Val  Asn Ala Lys Leu Lys  Asn Gln Glu Ala Ala  Ala Lys Ala
    1580                1585                1590

Gly Gly  Lys Ala Thr Gly Asn  Ser Ser Gly Lys Ala  Asp Ser Lys
    1595                1600                1605

Ala Gly  Ala Ala Val Ala Glu  Gln Pro Ala Ala Asp  Ala Gly Thr
    1610                1615                1620

Ala Ala  Ala Ala Ala Ala Pro  Glu Ala Pro Gly Ala  Ala Ala Ala
    1625                1630                1635

Pro Ala  Val Ala Val Leu Ser  Pro Ala Glu Gln Leu  Lys Ala Leu
    1640                1645                1650

Leu Ala  Asp Asp Glu Ala Leu  Ala Ser Ala Pro Leu  Ala Gln Leu
    1655                1660                1665

Val Gly  Val Pro Glu Glu Ser  Ala Leu Gln Leu Ala  Thr Arg Leu
    1670                1675                1680

Ala Lys  Ala Leu Pro Gly Thr  Leu Leu Arg Gly Lys  Arg Ala Ala
    1685                1690                1695

Gly Ala  Gln Gly Ala Gly Gly  Gly Glu Asp Gly Gly  Gly Gly Asp
    1700                1705                1710

Gly Gly  Asp Asp Gly Leu Ser  Arg Leu Arg Ala Val  Val Glu Glu
    1715                1720                1725

Leu Arg  Glu Glu Asp Asp Glu  Gln Glu Asn Gly Asp  Asp Gly Ala
    1730                1735                1740

Glu Tyr  Ser Glu Asp Asp Ala  Pro Pro Pro Gly Glu  Glu Leu Leu
    1745                1750                1755

Glu Asp  Glu Asp Ala Asn Ala  Ala Ala Met Arg Gly  Val Ala Gly
    1760                1765                1770

Asp Ala  Ala Ala Ala Ser Ala  Ala Ala Ala Ser Ala  Ser Ser Ser
    1775                1780                1785

Gly Ser  Ala Ala Ala Asn Gly  Gly Ala Ala Gln Ala  Val Ala Ala
    1790                1795                1800

Ala Thr  Asp Phe Asp Asn His  Pro Leu Arg Asn Leu  Ala Trp Pro
    1805                1810                1815

Leu Leu  Ile Thr Lys Glu Ala  Ile Ala Gly Trp Gly  Thr Leu Asn
    1820                1825                1830

Asp Gln  Trp Arg Lys Leu Val  Met Ala Arg Leu Arg  Val Ile Gly
    1835                1840                1845

Gln Gly  Leu Trp Pro Arg Cys  Arg Gly Ala Lys Arg  Ile Thr Ser
    1850                1855                1860

Asp Asp  Pro Leu Leu Met Pro  Gln Glu Leu Trp Arg  Leu Lys Leu
    1865                1870                1875

Thr Lys  Gly Gly Arg Ile Leu  Phe Glu Val Ala Val  Asp Asp His
    1880                1885                1890

Asp Ser  Lys Gly Thr Phe Cys  Glu Ile Ile Arg Val  Trp Cys Ile
    1895                1900                1905

Thr Leu  Asn His Lys Glu Tyr  Glu Val Met Ile Gln  Arg Val Gln
    1910                1915                1920

Arg Ser  Phe Thr Asn Ser Leu  Arg Met Arg Leu Arg  Lys Lys Leu
    1925                1930                1935
```

Gln Pro Leu Glu Gln Glu Gly Pro Ala Ala Ala Ala Thr Ala Ala
1940 1945 1950

Gly Thr Lys Lys Ala Ala Gly Ala Lys Ala Ala Ala Ala Gly Val
1955 1960 1965

Val Ala Ala Gly Gly Asp Arg Thr Arg Thr Arg Leu Pro Arg Phe
1970 1975 1980

Tyr Lys Glu Ala Gly Leu Val Asp Gly Ser Gly Ala Gly Asp Ala
1985 1990 1995

Gly Gly Ser Lys Gly Gln Glu Gln Gly Gln Val Met Val Leu Arg
2000 2005 2010

Glu His Tyr Pro Pro Ala Ser Trp Ala Asp Asp Thr Tyr Thr Thr
2015 2020 2025

Leu Lys Phe Tyr Thr Val Asp Gly Leu Leu Val Lys Ala Val Met
2030 2035 2040

Ser Gly Leu Ala Glu Ala Gln Val Asp Phe Met Phe Lys Leu Ser
2045 2050 2055

Pro Gln Glu Arg Asp Leu Ile Thr Met Val Pro Ser Pro Pro Ser
2060 2065 2070

Ser Ile Ile Leu Leu Gly Arg Ser Gly Thr Gly Lys Thr Thr Cys
2075 2080 2085

Ala Val Phe Arg Leu Trp Thr Ala Trp Leu Ala Pro Tyr Leu Ser
2090 2095 2100

Arg Ala His Glu Thr Pro His Thr Val Phe Val Thr Ala Ser Ala
2105 2110 2115

Thr Leu Arg Glu Gln Val Ala Arg Ala Phe Arg Lys Leu Gln Arg
2120 2125 2130

Ala Ala Leu Arg Asp His Glu Trp Glu Arg Ala Ser Ala Ala Phe
2135 2140 2145

Asn Thr Thr Tyr His Thr Phe Lys Asp Val Pro Pro Glu Ala Phe
2150 2155 2160

Pro Leu Phe Leu Ser Ser Arg Thr Tyr Leu Arg Met Leu Asp Gly
2165 2170 2175

Thr Thr Glu Arg Pro Phe Phe Pro Arg Ala Ala Asn Gly Ser Ile
2180 2185 2190

Ile Gln Val Ala Gly Asp Gly Glu Glu Ala Asp Pro Asp Gly Ala
2195 2200 2205

Ala Leu Val Val Ala Leu Asn Glu Asp Leu Ser Asp Glu Glu Asp
2210 2215 2220

Glu Glu Asp Gly Ala Ala Ala Asp Gln Glu Arg Gln Arg Gly Gly
2225 2230 2235

Pro Asp Glu Asp Gly Gly Gly Gln Glu Gly Gly Ala Ala Leu Phe
2240 2245 2250

Glu Glu Glu Val Ala Ala Ala Asp Ala Ala Arg Arg Glu Glu Ala
2255 2260 2265

Ala Arg Ala Arg Leu Leu Met Asp Met Glu Gly Ala Glu Ala Gly
2270 2275 2280

Gly Ala Ala Asp Gly Tyr Gly Leu Gly Val Ala Gly Arg Ala Arg
2285 2290 2295

Leu Asn Arg Glu Val Thr Tyr Gln His Phe Val Ser Ala Met Trp
2300 2305 2310

Pro Lys Ile Thr Thr Pro Glu Gln Arg Asn Gln Val Ala Pro Gly
2315 2320 2325

-continued

```
Arg Val  Tyr Gln Glu Ile Val  Ser Tyr Ile Lys Gly  Ser Ala Glu
    2330                 2335                 2340

Ala Ile  Ser Ser Pro Asp Gly  His Leu Ser Arg Glu  Gln Tyr Met
    2345                 2350                 2355

Ala Leu  Gly Arg Lys Arg Ala  Ala Asn Phe Ser Ala  Asp Met Arg
    2360                 2365                 2370

Gly Asp  Val Val Trp Pro Ile  Phe Glu Lys Tyr Glu  Arg Leu Lys
    2375                 2380                 2385

Arg Gln  Glu Trp Arg Tyr Asp  Met Leu Asp Leu Val  Gly His Ile
    2390                 2395                 2400

Tyr Arg  Glu Met Thr Thr Thr  Pro Gly Gly Tyr Ala  Gly Thr Pro
    2405                 2410                 2415

Val His  Ala Leu Tyr Arg Asp  Glu Val Gln Asp Phe  Thr Gln Gly
    2420                 2425                 2430

Glu Leu  Leu Leu Asp Met Val  Val Ala Ala Asp Pro  Asn Ser Leu
    2435                 2440                 2445

Phe Tyr  Cys Gly Asp Thr Ala  Gln Thr Ile Ala Arg  Gly Ile Gly
    2450                 2455                 2460

Phe Arg  Phe Ala Asp Thr Arg  Thr Leu Phe His Glu  Glu Asn Thr
    2465                 2470                 2475

Arg Arg  Gln Glu Ala Ala Ala  Arg Arg Leu Ala Ala  Glu Ala Ala
    2480                 2485                 2490

Asp Glu  Glu Ser Val Gly Lys  Ala Leu Ala Arg Arg  Gly His Gly
    2495                 2500                 2505

Met Thr  Ile Ala Thr Pro Pro  Val Leu Gln Leu Thr  Met Asn Tyr
    2510                 2515                 2520

Arg Thr  His Gln Gly Val Leu  Asp Val Ala Ala Val  Val Val Glu
    2525                 2530                 2535

Ala Leu  Arg Arg Tyr Phe Pro  Leu Gln Ile Asp Lys  Leu Glu Arg
    2540                 2545                 2550

Glu Ser  Ala Gln Phe Pro Gly  Pro His Pro Leu Leu  Leu Gly Ser
    2555                 2560                 2565

Ile Ser  Ala Asp Asp Leu Thr  Tyr Leu Leu Ser Gly  Ser Asp Lys
    2570                 2575                 2580

Lys Thr  Ser Gln Val Glu Phe  Gly Ala His Gln Val  Ile Leu Val
    2585                 2590                 2595

Arg Ser  Met Ala Ala Val Asp  Gln Leu Pro Glu Glu  Ile Arg Asp
    2600                 2605                 2610

Ser Asn  Ala Ile Ile Met Thr  Val Pro Gln Ala Lys  Gly Leu Glu
    2615                 2620                 2625

Phe Asp  Asp Val Phe Leu Val  Asp Phe Phe Ala Asp  Ser Gln Ala
    2630                 2635                 2640

Thr Ala  Glu Trp Arg Val Leu  Cys Ser Tyr Leu Ala  Glu Leu Gln
    2645                 2650                 2655

Glu Arg  Gly Gly Lys Gly Leu  Asp Gly Phe Gln Tyr  Gly Leu Gln
    2660                 2665                 2670

Gln Val  Ala Pro Thr Asp Pro  Gly Ala Val Arg Pro  Leu Glu Leu
    2675                 2680                 2685

Asn Glu  Gly Thr His Val Val  Leu Ala Glu Glu Leu  Lys His Leu
    2690                 2695                 2700

Tyr Thr  Ala Ile Thr Arg Ala  Lys Asn Asn Val Val  Ile Phe Asp
    2705                 2710                 2715

Arg Asn  Ala Ala Lys Arg Ala  Pro Phe Tyr His Leu  Leu Gln Ser
```

2720 2725 2730

Leu Gly Met Ala Arg Thr Val His Lys Ser Leu Leu Glu Asp Gly
2735 2740 2745

Ala Asp Ala Ala Lys Phe Gly Leu Thr Gln Lys Ala Thr Ser Ser
2750 2755 2760

Arg His Glu Trp Ala Lys Arg Ala Arg Asn Leu Met Gly Asn Arg
2765 2770 2775

Asn Tyr Ala Met Ala Arg Lys Ala Phe Leu Gln Ala Glu Asp Gln
2780 2785 2790

Val Arg Ala Glu Val Ala Asp Ala Leu Leu Lys Arg Gln Arg Ala
2795 2800 2805

Gly Gln Glu Ser Met Pro Asp Val Asp Lys Arg Arg Leu Leu Ala
2810 2815 2820

Ala Ala Ala Leu Gln Leu Leu Ala Ala Thr Ala Arg Cys Gly Glu
2825 2830 2835

Ser Pro Asp Pro Val Glu Pro Glu Glu Leu Arg Arg Trp Val Arg
2840 2845 2850

Glu Ala Ser Lys Phe Leu Glu Gly Cys Gly Lys Ser Ile Glu Ala
2855 2860 2865

Ala Gln Leu Lys Phe Lys Leu Gly Thr Gln Arg Ala Val Ala Ala
2870 2875 2880

Ala Leu Arg Leu Leu Val Asp Ala Lys Glu Tyr Ala Ala Ala Ala
2885 2890 2895

Glu Cys Cys Val His Met Ala Ala Ala Glu Leu Ala Ala Ala Arg
2900 2905 2910

Ala Arg Ala Ala Glu Glu Asp Ala Ala Ala Ala Gly Ser Met Gln
2915 2920 2925

Arg Leu Leu Met Thr Glu Ala Glu Leu Ala Ala Gln Arg Glu Ala
2930 2935 2940

Gln Ala His Gln Ala Ala Val Pro Trp Leu Ala Lys Ala Val Glu
2945 2950 2955

Gln Phe Gln Phe Ala Gly Asn Ser Thr Ala Val Leu Ala Leu Leu
2960 2965 2970

Ala Pro Pro Gly Phe Gly Gly Ser Lys Gly Ser Ala Thr Gly Ala
2975 2980 2985

His Ala Pro Leu Ala Ala Ala Ala Gly Ile Asp Ser Glu Asp Asp
2990 2995 3000

Asp Asp Ala Ala Glu Asp Ala Ala Glu Asp Ala Ala Glu Asp Val
3005 3010 3015

Glu Glu Asp Glu Gln Gln Gln Arg Glu Leu Glu Ala Gln Glu Arg
3020 3025 3030

Thr Gly Pro Leu Ala Leu Phe Ala Pro Leu Ala Pro Arg Leu His
3035 3040 3045

Ala Met Leu Ala Arg Arg Trp Gln Gly Tyr Gly Gln Ala Leu Arg
3050 3055 3060

Ala Ala Ala Ile Ala Leu His Ser Arg Gly Ser Leu Arg Arg Ala
3065 3070 3075

Gly Ala Val Ala Arg Leu Val Pro Met Pro Gln Glu Arg Asp Thr
3080 3085 3090

Leu Leu Glu Thr Leu Gly Tyr Trp Arg Ala Arg Ala Arg Ala Arg
3095 3100 3105

Ser Ala Val Asp Pro Leu Gly Ala Ala Gln Val Leu Leu Glu His
3110 3115 3120

```
Gly Asp  Thr Arg Arg Ala Val  Arg Leu Val Leu Arg  Cys Leu Glu
    3125                 3130                 3135

Pro Leu  Pro Ala Ser Ser Gly  Gly Met Glu Ala Ala  Glu Ala Gly
    3140                 3145                 3150

Gly Ala  Gly Gly Gly Gly Asp  Arg Leu Thr Arg Ala  Ala Arg Gln
    3155                 3160                 3165

Gln Gln  Leu Tyr Glu Leu Gln  Leu Arg Gln Glu His  Glu Arg Arg
    3170                 3175                 3180

Gln Lys  Gln Val Leu Glu Ala  Asn Ala Leu Ala Val  Leu His Arg
    3185                 3190                 3195

Leu Val  Ala Ala Gln Thr Lys  Ala Ala Glu Ala Thr  Gln Leu Arg
    3200                 3205                 3210

Arg Ala  Leu Glu Ala Trp Met  Ala Arg Gln Ala Lys  Ser Glu Glu
    3215                 3220                 3225

Gly Gly  Lys Glu Gly Glu Glu  Gly Ala Gly Leu Thr  Lys Arg Met
    3230                 3235                 3240

Leu Pro  Ile Arg Gly His Val  Leu Leu Leu Glu Ala  Arg Leu Leu
    3245                 3250                 3255

Leu Glu  Pro Trp Ala Ala Ala  Ala Ala Gly Gly Ala  Lys Gly Ala
    3260                 3265                 3270

Ala Gly  Asp Ser Lys Glu Gln  Gln Ala Ala Ala Ala  Ala Val Ala
    3275                 3280                 3285

Thr Asn  Ala Ala Leu Arg Asp  Ala Ala Trp Leu Glu  Ala Arg Pro
    3290                 3295                 3300

Leu Leu  Leu Thr Ala Val Glu  Cys Phe Leu Arg Cys  Asp Gln Trp
    3305                 3310                 3315

Pro Gly  Phe Met Glu Ala Ala  Glu Leu Leu Leu Arg  Ala Ala Pro
    3320                 3325                 3330

Asp Ala  Ala Val Ala Ser His  Thr Ala Ala Gly Gln  Leu Ala Asp
    3335                 3340                 3345

Phe Glu  Gln Ala Leu Leu Gln  Ala Met Gln Arg Gly  Ala Glu Arg
    3350                 3355                 3360

Ala Gly  Asp Ser Ala Thr Val  Ala Ala Ala Ala Ser  Ser Arg Thr
    3365                 3370                 3375

Ala Ala  Ala Lys Gln Ala Leu  Ala Arg Ser Leu Val  Val Pro Glu
    3380                 3385                 3390

Ala Ala  Leu Lys Leu Met Arg  Thr Thr Gln Thr Ala  Cys Asp Ala
    3395                 3400                 3405

Leu Ser  Val Gly Leu Gly Ser  Ser Ala Gly Ser Asn  Val Ser Leu
    3410                 3415                 3420

Arg Pro  Gly Gly Gly Leu Val  Gly Arg Ala Gly Gly  Gly Gly Glu
    3425                 3430                 3435

Arg Ser  Arg Ala Gly Ala Ala  Ser Ser Leu Ser Lys  Pro Gln Gln
    3440                 3445                 3450

Glu Ala  Leu Ser Ala Leu Glu  Gly Leu Leu Leu Leu  Pro Gly Leu
    3455                 3460                 3465

Ser Arg  Pro Thr Glu Ala Lys  Leu Ser Ala Arg Asn  Ala Ser His
    3470                 3475                 3480

Ser Trp  Trp Ala Ala Leu Gly  Gln Gln Asn Thr Asp  Ala Val Arg
    3485                 3490                 3495

Arg Ala  Ala Gly Pro Lys Ala  Ala Ala Gly Ser Gly  Gln Asp Gly
    3500                 3505                 3510
```

Lys Glu Lys Glu Lys Thr Ser Gly Gln Ser Ser Trp Ala Ala Val
3515 3520 3525

Ala Ala Lys Gly Ala Ala Ala Thr Ala Met Val Trp Asp Pro Glu
3530 3535 3540

Val Pro Ala Leu Ala Pro Thr Ser His Leu Leu Leu Arg Cys His
3545 3550 3555

Gln Thr Ala Met Ala Leu Gly Glu Gly Gly Ala Met Ala Ala Ala
3560 3565 3570

Val Glu Ala Ala Gly Ala Gly Ala Ser Gln Met Pro Leu Pro Arg
3575 3580 3585

Ala Ala Val Ala Ala Val Ala Ala Arg Ser Leu Thr Ile Arg Ala
3590 3595 3600

Ala Cys Leu Ala His Leu Ala Ala Arg Gly Ala Leu Ala Ala Tyr
3605 3610 3615

Leu His Pro Ala Pro Pro Pro Gln Pro Ala Leu Pro Ala Gly Ala
3620 3625 3630

Gly Gly Lys Ala Ala Glu Glu Gly Thr Glu Gly Asp Ala Gly Lys
3635 3640 3645

Gln Glu Gln Pro Ala Glu Ala Ala Ala Pro Leu Ser Cys Glu Val
3650 3655 3660

Val Leu Asp Arg Leu Arg Pro Leu Val Cys Ala Ala Arg Ala Val
3665 3670 3675

His Leu Ala Lys Met Met Val Gly Ser Val Gly Gln Ala Phe Ser
3680 3685 3690

Met Ala Ala Ala Ala Ser Leu Arg Lys Cys Leu Asp Ala Gln Leu
3695 3700 3705

Arg Tyr Leu Ala Ala Ala Leu Val Ala Ala Ser Leu Pro Pro Ala
3710 3715 3720

Ala Ala Pro Glu Leu Leu Ala Glu Leu Leu Gln Pro Arg Pro Gln
3725 3730 3735

Pro Gln Arg Arg Pro Gly Gly Gly Gly Gly Pro Pro Arg Arg Val
3740 3745 3750

Met Gly Asp Leu Leu Glu Leu Leu Ala Arg Asp Gly Phe Pro His
3755 3760 3765

Arg Glu Leu Ala Asp Trp Ala Glu His Leu Leu Val Arg Cys Met
3770 3775 3780

Pro Leu Glu Leu Arg Met Pro Leu Ala Pro Ala Val Ser Tyr Leu
3785 3790 3795

Ala Cys Arg Thr Met Met Leu Val Ala Pro Asp Ser Glu Asp Arg
3800 3805 3810

Ala Ser Lys Leu Trp Leu Ile Lys Asp Ser Ser Ala Lys Ala Thr
3815 3820 3825

Gly Asp Val Pro Pro Glu Arg Leu Val His Asp Asp Lys Lys Thr
3830 3835 3840

Gly Pro Ala Glu Ala Leu Leu Val Ser Ala Phe Arg Ala Met Asp
3845 3850 3855

Ser Ser Pro Leu Arg Ala Val Gly Asp Leu Leu Tyr Tyr Leu Ala
3860 3865 3870

Trp Cys Ala Arg Arg Asp Gly Leu Ala Ala Val Thr Pro Thr Asp
3875 3880 3885

Ala Ala Ala Glu Gly Ala Gln Ala Pro Ala Gly Ala Ala Ala Gly
3890 3895 3900

Gly Ser Lys Pro Gly Ser Gly Ala Ala Ala Ala Ala Gly Pro Val

```
    3905                3910                3915

Gly Leu  Ser Leu Pro Leu Glu  Ala Tyr Ala Glu Leu  Val Glu Val
    3920                3925                3930

Thr Val  Gly Gln Leu Leu Leu  Ala Ala Cys Asp Asn  Ala Leu Leu
    3935                3940                3945

Pro Gly  Asn Val Ala Gly Thr  Leu Ser Gly Leu Pro  Arg Val Ser
    3950                3955                3960

Asp Pro  Gln Ala Gly Leu Asn  Gly Val Ala Asp Thr  Trp Ala Arg
    3965                3970                3975

Glu Leu  Gly Phe Arg Gly Pro  Ala Val Gly Glu Gly  Ala Gly Gly
    3980                3985                3990

Gly Gly  Gly Ser Gly Trp Gly  Trp Gly Arg Gly Arg  Gly Pro Ser
    3995                4000                4005

Pro Lys  Glu Val Ala Glu Ala  Lys Ala Arg Ala Val  Thr Ala Arg
    4010                4015                4020

Lys Glu  Val Ala Gly Gln Leu  Arg Leu Ala Ala Arg  Met Thr Leu
    4025                4030                4035

Leu Leu  Ala Ser His Ile Asp  Gln Arg Leu Gln Asp  Thr Ala Ala
    4040                4045                4050

Pro Ala  Ala Gly Gly Ala Gly  Gly Asp Ser Ala Ala  Ser Pro Pro
    4055                4060                4065

Glu Leu  Glu Leu Leu Gln Gln  Glu Val Leu Pro Leu  Leu Asp Ala
    4070                4075                4080

Pro Gly  Arg Arg Glu Ala His  Glu Leu Leu Arg Gln  Pro Gly Gly
    4085                4090                4095

Pro Gly  Ala Gln Pro Arg Arg  Ala Gln Gly Lys Ser  Arg Gly Gly
    4100                4105                4110

Gly Ala  Glu Ala Gly Val Gly  Ser Gly Ala Ser Val  Ala Pro Pro
    4115                4120                4125

Ser Ala  Gly Ala Ser Gly Leu  Arg Leu Arg Ala Ile  Ala Gln Arg
    4130                4135                4140

Val Leu  Leu Ala Ala Gly Ala  Ala Tyr Val Ser Leu  Glu Leu Gln
    4145                4150                4155

Glu Ser  Val Val Lys Pro Gln  Arg Gln Gln Gln Lys  Ala Ala Ala
    4160                4165                4170

Glu Arg  Gln Gln Lys Leu Ala  Gly Gly Gly Pro Val  Pro Glu Pro
    4175                4180                4185

Pro Pro  Leu Arg Gly Gly Trp  Pro Ala Glu Ala Ser  Ala Gly Phe
    4190                4195                4200

Arg Asp  Ala Cys Thr Leu Leu  Gln Ala Arg Val Ala  Pro Ala Cys
    4205                4210                4215

Phe Gln  Pro Ala Thr Gly Ala  Thr Asp Leu Ala Ser  Val Ala Gln
    4220                4225                4230

Ala Ala  Asp Ala Leu Ala Arg  Leu Ser Gln Arg Val  Cys Tyr Pro
    4235                4240                4245

Ser Ser  Arg Leu Ser Thr Gly  Met Arg Leu Val Gly  Pro Asp Ala
    4250                4255                4260

Asn Arg  Glu Tyr Glu Gly Leu  Ser Gly Ala Arg Pro  Pro Lys Gly
    4265                4270                4275

Pro Leu  Ala Leu Leu Phe Gln  Ala Ala Gln Ala Lys  Met Gln Leu
    4280                4285                4290

Pro Lys  Ala Ala Ala Asp Ala  Gly Ile Gly Gly Arg  Val Lys Ala
    4295                4300                4305
```

-continued

```
Ala Ser Asp Ala Val Ala Arg Val Ala Ala Arg Asp Phe Gln Ala
    4310                4315                4320

Thr Glu Asp Glu Arg Val Arg Gln Arg His Ala Ala Ala Val Ile
    4325                4330                4335

Gln Lys Arg Trp Arg Ala Trp Arg Gln Arg Arg Ile Glu Ala Ala
    4340                4345                4350

Glu Ala Met Arg Arg Arg Gln Leu Gln Ala Asn Ala Leu Glu Thr
    4355                4360                4365

Leu Arg Arg Ser Ile Arg Phe Arg Val Trp Val Arg Ala Arg Leu
    4370                4375                4380

Ala Asn Ala Arg Lys Ala Leu Asp Ala Arg His Phe Gly Glu Arg
    4385                4390                4395

Phe Thr Ala Gly Cys Ala Ala Ala Val Gln Phe Gly Glu Gln Ala
    4400                4405                4410

Leu His Met Ala Asp Ile Glu Ala Val Leu Lys Ala Arg Phe Val
    4415                4420                4425

Gln Leu Asp Arg Cys Pro Val Cys Ser Gly Glu Thr Leu Arg Lys
    4430                4435                4440

Gln Thr Glu Glu Leu Lys Gln Gln Met Ala Gln Arg Ala Ala Gly
    4445                4450                4455

Lys Leu Lys Gly Ala Ala Ala Glu Phe Arg Pro His Lys Asn Thr
    4460                4465                4470

Val Asp His Leu Glu Ala Ala Asn Ser Phe Thr Thr Phe Arg Asp
    4475                4480                4485

Val Tyr Asn Gly Asp Leu Pro Thr Arg Leu Gly Gly Ser Ala Ala
    4490                4495                4500

His Met Asp Gln Leu Arg Ala Ser Leu Asp Arg Leu Glu Gln Leu
    4505                4510                4515

Gly Val Ser Asp Ala Ser Leu Ile Lys Gly Arg Leu Val Ala Glu
    4520                4525                4530

Ala Asp Leu Ala Leu Arg Gly Val Glu Gln Ala Arg Ala Ala Leu
    4535                4540                4545

Glu Ala Ser Leu Arg Gln Leu Val Glu Glu Arg Val Trp Asp Val
    4550                4555                4560

Gly Val Leu Ala Ser Arg Met Phe Pro Gln Tyr Thr Ser Leu Asp
    4565                4570                4575

Ala Ala Val Gln Arg Val Asp Met Met Arg Val His Val Glu Gly
    4580                4585                4590

Leu Ala Ala Ala Ala Arg Arg Thr Ala Leu Leu Pro Pro Asp Glu
    4595                4600                4605

Gln Leu Ala Ala Ile Gln Pro Lys Gln Gln Pro Gln Pro Gln Leu
    4610                4615                4620

Gln Gln Pro Gln Glu Gln Asp Gln His Gln Glu Gln Glu Gln Glu
    4625                4630                4635

Gln Ala Leu Arg Leu Pro Ser Gly Glu Val Pro Glu Gln Glu Gln
    4640                4645                4650

Ala Gln Glu Gln Val Gln Ala Gln Glu Gln Gln Pro Val Gly Val
    4655                4660                4665

Phe Ala Ala Gly Leu Asp Val Arg Pro Ala Asp Gly Met Ala Ala
    4670                4675                4680

His Ala Ala Ala Ala Ala Ala Ser Pro Ala Lys Gln Ala Val Pro
    4685                4690                4695
```

Ala Leu Glu Gly Pro Pro Gly Thr Arg Pro Gly Leu Gln Gln Pro
4700 4705 4710

Phe Ser Ser Pro Thr His Gln Gln Gln Gly Ser Ala Trp Ala Ala
4715 4720 4725

Gln Lys Pro Val Ile Gln Phe Thr Pro Pro Pro Met Pro Pro Met
4730 4735 4740

Pro Ser Ala Leu Leu Gln Gln Leu Ser Gln Gly Gln Gly Gln Ser
4745 4750 4755

Tyr Ala Val Ala Ala Gln Ala Gly Ala Gly Gly Gln Ala Val Ser
4760 4765 4770

Pro Tyr Ser Asn Gln Ser His Ala Gln Ala Ala His Thr Met Gly
4775 4780 4785

Tyr Asn Gln Val Tyr Gly Gly Leu Gly Gly Ile Gly Ala Asp Leu
4790 4795 4800

Pro Pro Gly Leu Ser Gln Thr Pro Gly Tyr Gly Ala Ala Ala Ala
4805 4810 4815

Gly Ser Thr Ala Gly Tyr Ala Ala Ser Gly Phe Ala Pro Pro Asn
4820 4825 4830

Phe Thr Ala Gln Ala Gly Phe Pro Phe Gln Gln Gln Gln Gln Phe
4835 4840 4845

Gln Gln Gln Gln Gln Gln Gln Gln Gln Tyr Gln Tyr Leu Pro His
4850 4855 4860

Met Gln Gln Gln Gln Gln Gln Gln Gln Gln Gln Gln Tyr Gln Pro
4865 4870 4875

Tyr Leu Gln Gln Gln Tyr Gln Pro Pro Ser Pro Gly Met Asn Ala
4880 4885 4890

Ser Met Val Ser Pro Gly Gly Met Pro Gly Phe Met Pro Gln Gln
4895 4900 4905

Tyr Gly Ile Gly Tyr Phe Pro Ser Gly Ala Ala Gly Gly Gly Ala
4910 4915 4920

Ala Ala Gly Met Gln Gly Val Ala Ala Ala Ala Ala Met Gly Ala
4925 4930 4935

Ala Ala Gln Phe Gly Ala Met Gly Gly Ala Gly Gly Phe Pro Ala
4940 4945 4950

Gly Glu Pro Gly Thr Asp Ala Ile Leu Gln Gly Ala Leu Met Glu
4955 4960 4965

Asp Asp Asp Glu Asp Asp Asp Glu Trp Gln Gln Ser Arg Arg His
4970 4975 4980

Gly Arg Tyr Asp Gly Gly Gly Arg Gly Gly Gly Arg Gly Gly Arg
4985 4990 4995

Gly Arg Gly His Ser Ala Gly Pro His Gly Ser Pro Tyr Gly Pro
5000 5005 5010

Pro Gly Arg Gly Pro Gly Gly Gly Gly Gly Arg Gly Gly Arg Gly
5015 5020 5025

Ala Gly Gly Tyr Gly Gly Gly Tyr Gly Gly Gly Arg Gly Ser Asn
5030 5035 5040

Val Tyr Glu Ala Leu Arg Gly Ala Asn Ala Thr Pro Ser Arg Ala
5045 5050 5055

Ala Gln Arg Met Gly Leu Ser
5060 5065

<210> SEQ ID NO 84
<211> LENGTH: 2827
<212> TYPE: DNA

<213> ORGANISM: Chlamydomonas reinhardtii

<400> SEQUENCE: 84
ttatatggcc ctatagtttg caccttgaaa gagcccggaa caacataact tcgcccgggc 60
cattgctccg ctcgcgaacg accacgcttg gagcgagctg ctgccgacga ggacaggcgc 120
gctgaacacg agccttgtgt acacgtcccg tgctcccggc ttggggcttg gcggcggcgc 180
caaggggcga caccgggctc cggtcacgca cgcgacccgg tgggacacag cacggcacgg 240
ccaccccgtg cgccgtcggg ggcgggccgg acatcgccgt ggtcgccaaa catgtctgaa 300
aggtcccagg tcctgtgcaa gtaccacatc tccggtgcct gccggttcgg ctcggactgc 360
gccttctcgc acaacctgtc cgacctgccc agccaggtct gcaagttcta cctagccggg 420
aactgcgcct acggcgaccg ctgccgctac gaccaccgcc ggccggactg gtccaaagcc 480
gggcagctac ggcagcagca gcagcagcac gtacagcccg cacagccgca cgctagctcc 540
gcgggggctg ccgggcccag ctcccgagct ctgcgcgggg acccatatgt ggcggtgtgg 600
gatgcgcggg agcccaccga cccttcgcgc ctccccccag cccttgcggc agcggcagcg 660
gcagcctccc cctcggggcc agccccctca gggcctggcg ccgcgccttc agcgactgcg 720
agcaggggcc cggcctgggg cttagccgcc ggcgccaagg cgcccgtcgc aacaggagcg 780
gcagcaggcc gtgcagcggg tggtggcggc ggcgctgagc cggcggacga gtgggagcac 840
gtcgccgagg ccgttgcggc ggcggaggcg gcggaagcgg cagctgcggc tgggcggcgc 900
ggactggtgc tgattgatga cgatgtgggt ctggagcagg aggcgcggcg gctggagcag 960
gagcgagggc agcgggcagc ggagggggca ggcgcgaggc cgtcagtggt gtcaggagcc 1020
gcagcggcgg cggcgggggc ggcgggcgcc gccggctcac ttccctggtc cccggacttg 1080
gatccctggg accagcgggg cggggcgggt ggggaacgcg aggcaggcgg ggaggaaggg 1140
tactacgacc cgtactacga cgagtatggg gagtacggcg aaggcgagga ggggcatgag 1200
ggggaggagc aggcgggcta tgaggccggc ggcgaggagg ggcaggaggg cccggcgggt 1260
caaggcgcgg gctggtggag tggcgccggt gctggtgctg gtgcaggggg tgaagcggtg 1320
gaccccgcgg acctggagct gtgtccggcg tttgcgctgc acggccggtg tgcggagggc 1380
gaggactgcc ccctcataca cggcctggag tgcgagacgt gccacaagtg gcggatacac 1440
ccctacaacg aggcggcggc ggcggagcac gcggcggagt gccggctgcg gcatgcgcgg 1500
ctggaggcgc ggctgcgcag tgcagacgtg gagtgcggca tctgcctgga gcacgtgatg 1560
cacaagccca gtgtgtcgga ccggcgcttc ggactgatgg actgcgacca cgccttctgc 1620
ctggcctgca tccgctcctg gcgagagcgc aacacagacg ccagcctggc cacggacacg 1680
gctgtgcgca cctgccccat ttgccgcacg tgcacgcact tcgtgacgcc ctccctggtg 1740
tggccggcca cggccgagga gaaggaggcc atcgtgggcg cctacaaggc caaactgggc 1800
accatcgact gccggcactt cgcatttggc gacggcacat gccccttctc cacctcctgc 1860
ttctaccgcc atgcctaccg cgatggccga ctagaggtgc cggtactgcg gcgcgccggc 1920
aacgcggacg gcgaggtgcg ggtggtggcg ccgctgcggc tgtccgcctt cctggacaca 1980
ccgcaggcgc agcggctgct gggcggccgc aggcggtgaa caggggtgca gcgggcggca 2040
gggtaagggg caggtgacga ggggtgaaca gggcggcagg cgggtaaggg atgctggatg 2100
gcagggtggc agagtggcag agatttacag gtattgtcag gcaggcagtt tgtgagtgta 2160
ggcgactaag caactaggca gcactaggca tagacgtgta ggaatgcatg ggtgttcccc 2220
gaggaccggg ccacgcccac agccacgccc acagccacta gagccgtgga ggagggccgt 2280

```
gcccgcgcac tcccgctggc aagctggtgg gccgtagcag atactaccaa ggtgttttga   2340

tggctaacgt tcattgagag atgtagcagg cgggtttggc gggaacatgg atccggccaa   2400

ccgcttaaaa ttgtgcactt gtgcaccagg gaattgtggc ccagggacgt atctattcaa   2460

tacttacgag ccgtgacact ccaaacttca caaaatgtcg ggcattgaca agtgtcttgg   2520

cccgggacgg ggaatcggca aaggcggcaa gcggcaccgc aaggttctgc gcgaaagcat   2580

caacacagct ctgacgcaag gctccattcg ccgcctggct cgccgtggcg gcgtgaagcg   2640

gctcagtggg cttgtctaca acgagattcg ctcggtcctc cgaggattcc tggaggcctt   2700

ggtcagggac acgatcacgt acacggagca cgcgcgtcgc caacatgtca agttaatgga   2760

tgtcatgtac gctcttaagc gtcaaggccg gactttgtat gggttcggcg tcttttaatt   2820

gcgccaa                                                             2827
```

<210> SEQ ID NO 85
<211> LENGTH: 1728
<212> TYPE: DNA
<213> ORGANISM: Chlamydomonas reinhardtii

<400> SEQUENCE: 85

```
atgtctgaaa ggtcccaggt cctgtgcaag taccacatct ccggtgcctg ccggttcggc     60

tcggactgcg ccttctcgca caacctgtcc gacctgccca gccaggtctg caagttctac    120

ctagccggga actgcgccta cggcgaccgc tgccgctacg accaccgccg gccggactgg    180

tccaaagccg ggcagctacg gcagcagcag cagcagcacg tacagcccgc acagccgcac    240

gctagctccg cgggggctgc cgggcccagc tcccgagctc tgcgcgggga cccatatgtg    300

gcggtgtggg atgcgcggga gcccaccgac ccttcgcgcc tccccccagc ccttgcggca    360

gcggcagcgg cagcctcccc ctcggggcca gcccccctcag ggcctggcgc cgcgccttca   420

gcgactgcga gcaggggccc ggcctggggc ttagccgccg gcgccaaggc gcccgtcgca    480

acaggagcgg cagcaggccg tgcagcgggt ggtggcggcg gcgctgagcc ggcggacgag    540

tgggagcacg tcgccgaggc cgttgcggcg gcggaggcgg cggaagcggc agctgcggct    600

gggcggcgcg gactggtgct gattgatgac gatgtgggtc tggagcagga ggcgcggcgg    660

ctggagcagg agcgagggca gcgggcagcg gagggggcag gcgcgaggcc gtcagtggtg    720

tcaggagccg cagcggcggc ggcgggggcg gcgggcgccg ccggctcact tccctggtcc    780

ccggacttgg atccctggga ccagcggggc ggggcgggtg gggaacgcga ggcaggcggg    840

gaggaagggt actacgaccc gtactacgac gagtatgggg agtacggcga aggcgaggag    900

gggcatgagg gggaggagca ggcgggctat gaggccggcg gcgaggaggg gcaggagggc    960

ccggcgggtc aaggcgcggg ctggtggagt ggcgccggtg ctggtgctgg tgcagggggt   1020

gaagcggtgg accccgcgga cctggagctg tgtccggcgt ttgcgctgca cggccggtgt   1080

gcggagggcg aggactgccc cctcatacac ggcctggagt gcgagacgtg ccacaagtgg   1140

cggatacacc cctacaacga ggcggcggcg gcggagcacg cggcggagtg ccggctgcgg   1200

catgcgcggc tggaggcgcg gctgcgcagt gcagacgtgg agtgcggcat ctgcctggag   1260

cacgtgatgc acaagcccag tgtgtcggac cggcgcttcg gactgatgga ctgcgaccac   1320

gccttctgcc tggcctgcat ccgctcctgg cgagagcgca acacagacgc cagcctggcc   1380

acggacacgg ctgtgcgcac ctgccccatt tgccgcacgt gcacgcactt cgtgacgccc   1440

tccctggtgt ggccggccac ggccgaggag aaggaggcca tcgtgggcgc ctacaaggcc   1500
```

```
aaactgggca ccatcgactg ccggcacttc gcatttggcg acggcacatg ccccttctcc   1560

acctcctgct tctaccgcca tgcctaccgc gatggccgac tagaggtgcc ggtactgcgg   1620

cgcgccggca acgcggacgg cgaggtgcgg gtggtggcgc cgctgcggct gtccgccttc   1680

ctggacacac cgcaggcgca gcggctgctg ggcggccgca ggcggtga                1728


<210> SEQ ID NO 86
<211> LENGTH: 575
<212> TYPE: PRT
<213> ORGANISM: Chlamydomonas reinhardtii

<400> SEQUENCE: 86

Met Ser Glu Arg Ser Gln Val Leu Cys Lys Tyr His Ile Ser Gly Ala
1               5                   10                  15

Cys Arg Phe Gly Ser Asp Cys Ala Phe Ser His Asn Leu Ser Asp Leu
            20                  25                  30

Pro Ser Gln Val Cys Lys Phe Tyr Leu Ala Gly Asn Cys Ala Tyr Gly
        35                  40                  45

Asp Arg Cys Arg Tyr Asp His Arg Arg Pro Asp Trp Ser Lys Ala Gly
    50                  55                  60

Gln Leu Arg Gln Gln Gln Gln Gln His Val Gln Pro Ala Gln Pro His
65                  70                  75                  80

Ala Ser Ser Ala Gly Ala Ala Gly Pro Ser Ser Arg Ala Leu Arg Gly
                85                  90                  95

Asp Pro Tyr Val Ala Val Trp Asp Ala Arg Glu Pro Thr Asp Pro Ser
            100                 105                 110

Arg Leu Pro Pro Ala Leu Ala Ala Ala Ala Ala Ala Ala Ser Pro Ser
        115                 120                 125

Gly Pro Ala Pro Ser Gly Pro Gly Ala Ala Pro Ser Ala Thr Ala Ser
    130                 135                 140

Arg Gly Pro Ala Trp Gly Leu Ala Ala Gly Ala Lys Ala Pro Val Ala
145                 150                 155                 160

Thr Gly Ala Ala Ala Gly Arg Ala Ala Gly Gly Gly Gly Gly Ala Glu
                165                 170                 175

Pro Ala Asp Glu Trp Glu His Val Ala Glu Ala Val Ala Ala Ala Glu
            180                 185                 190

Ala Ala Glu Ala Ala Ala Ala Ala Gly Arg Arg Gly Leu Val Leu Ile
        195                 200                 205

Asp Asp Asp Val Gly Leu Glu Gln Glu Ala Arg Arg Leu Glu Gln Glu
    210                 215                 220

Arg Gly Gln Arg Ala Ala Glu Gly Ala Gly Ala Arg Pro Ser Val Val
225                 230                 235                 240

Ser Gly Ala Ala Ala Ala Ala Ala Gly Ala Ala Gly Ala Ala Gly Ser
                245                 250                 255

Leu Pro Trp Ser Pro Asp Leu Asp Pro Trp Asp Gln Arg Gly Gly Ala
            260                 265                 270

Gly Gly Glu Arg Glu Ala Gly Gly Glu Glu Gly Tyr Tyr Asp Pro Tyr
        275                 280                 285

Tyr Asp Glu Tyr Gly Glu Tyr Gly Glu Gly Glu Glu Gly His Glu Gly
    290                 295                 300

Glu Glu Gln Ala Gly Tyr Glu Ala Gly Gly Glu Glu Gly Gln Glu Gly
305                 310                 315                 320

Pro Ala Gly Gln Gly Ala Gly Trp Trp Ser Gly Ala Gly Ala Gly Ala
                325                 330                 335
```

-continued

```
Gly Ala Gly Gly Glu Ala Val Asp Pro Ala Asp Leu Glu Leu Cys Pro
            340                 345                 350

Ala Phe Ala Leu His Gly Arg Cys Ala Glu Gly Glu Asp Cys Pro Leu
        355                 360                 365

Ile His Gly Leu Glu Cys Glu Thr Cys His Lys Trp Arg Ile His Pro
    370                 375                 380

Tyr Asn Glu Ala Ala Ala Ala Glu His Ala Ala Glu Cys Arg Leu Arg
385                 390                 395                 400

His Ala Arg Leu Glu Ala Arg Leu Arg Ser Ala Asp Val Glu Cys Gly
                405                 410                 415

Ile Cys Leu Glu His Val Met His Lys Pro Ser Val Ser Asp Arg Arg
            420                 425                 430

Phe Gly Leu Met Asp Cys Asp His Ala Phe Cys Leu Ala Cys Ile Arg
        435                 440                 445

Ser Trp Arg Glu Arg Asn Thr Asp Ala Ser Leu Ala Thr Asp Thr Ala
    450                 455                 460

Val Arg Thr Cys Pro Ile Cys Arg Thr Cys Thr His Phe Val Thr Pro
465                 470                 475                 480

Ser Leu Val Trp Pro Ala Thr Ala Glu Glu Lys Glu Ala Ile Val Gly
                485                 490                 495

Ala Tyr Lys Ala Lys Leu Gly Thr Ile Asp Cys Arg His Phe Ala Phe
            500                 505                 510

Gly Asp Gly Thr Cys Pro Phe Ser Thr Ser Cys Phe Tyr Arg His Ala
        515                 520                 525

Tyr Arg Asp Gly Arg Leu Glu Val Pro Val Leu Arg Arg Ala Gly Asn
    530                 535                 540

Ala Asp Gly Glu Val Arg Val Val Ala Pro Leu Arg Leu Ser Ala Phe
545                 550                 555                 560

Leu Asp Thr Pro Gln Ala Gln Arg Leu Leu Gly Gly Arg Arg Arg
                565                 570                 575
```

<210> SEQ ID NO 87
<211> LENGTH: 16
<212> TYPE: PRT
<213> ORGANISM: Artificial Sequence
<220> FEATURE:
<223> OTHER INFORMATION: antibody

<400> SEQUENCE: 87

```
Gln Gln Gln Gly Leu Ala Leu Gly Gly Tyr Gly Leu Thr Gln Gln Pro
1               5                   10                  15
```

<210> SEQ ID NO 88
<211> LENGTH: 16
<212> TYPE: PRT
<213> ORGANISM: Artificial Sequence
<220> FEATURE:
<223> OTHER INFORMATION: Antibody

<400> SEQUENCE: 88

```
Leu Gln His Gln Pro Gln Leu Leu Gln Pro Gln Gly Ser Leu Pro Ala
1               5                   10                  15
```

<210> SEQ ID NO 89
<211> LENGTH: 31
<212> TYPE: DNA
<213> ORGANISM: Artificial Sequence
<220> FEATURE:
<223> OTHER INFORMATION: Primer

<400> SEQUENCE: 89
ggaattccat atgctgtcgc agcatcaaga c 31

<210> SEQ ID NO 90
<211> LENGTH: 30
<212> TYPE: DNA
<213> ORGANISM: Artificial Sequence
<220> FEATURE:
<223> OTHER INFORMATION: Primer

<400> SEQUENCE: 90
acaggatcct caatgggctt cagaggaacc 30

<210> SEQ ID NO 91
<211> LENGTH: 60
<212> TYPE: DNA
<213> ORGANISM: Artificial Sequence
<220> FEATURE:
<223> OTHER INFORMATION: Primer

<400> SEQUENCE: 91
tggagagcaa cccgggcccc ctcgaggaca aagctgaacg cgctgctggt ggccctaacg 60

<210> SEQ ID NO 92
<211> LENGTH: 59
<212> TYPE: DNA
<213> ORGANISM: Artificial Sequence
<220> FEATURE:
<223> OTHER INFORMATION: Primer

<400> SEQUENCE: 92
gagtgggtcg acgtcggaga ggtaccctat ggctccactc gctgccgctt tgcgcgatc 59

<210> SEQ ID NO 93
<211> LENGTH: 24
<212> TYPE: DNA
<213> ORGANISM: Artificial Sequence
<220> FEATURE:
<223> OTHER INFORMATION: Primer

<400> SEQUENCE: 93
gacaaagctg aacgcgctgc tggt 24

<210> SEQ ID NO 94
<211> LENGTH: 25
<212> TYPE: DNA
<213> ORGANISM: Artificial Sequence
<220> FEATURE:
<223> OTHER INFORMATION: Primer

<400> SEQUENCE: 94
ctatggctcc actcgctgcc gcttt 25

<210> SEQ ID NO 95
<211> LENGTH: 18
<212> TYPE: DNA
<213> ORGANISM: Artificial Sequence
<220> FEATURE:
<223> OTHER INFORMATION: Primer

<400> SEQUENCE: 95
atgggcagta cttcatgc 18

<210> SEQ ID NO 96
<211> LENGTH: 16

<212> TYPE: DNA
<213> ORGANISM: Artificial Sequence
<220> FEATURE:
<223> OTHER INFORMATION: Primer

<400> SEQUENCE: 96
tgacgaagcg gttgtg 16

<210> SEQ ID NO 97
<211> LENGTH: 24
<212> TYPE: DNA
<213> ORGANISM: Artificial Sequence
<220> FEATURE:
<223> OTHER INFORMATION: Primer

<400> SEQUENCE: 97
gccacaccga gtgggtgtcg tgcg 24

<210> SEQ ID NO 98
<211> LENGTH: 24
<212> TYPE: DNA
<213> ORGANISM: Artificial Sequence
<220> FEATURE:
<223> OTHER INFORMATION: Primer

<400> SEQUENCE: 98
ccttgccgcc cgaggcgcac agcg 24

<210> SEQ ID NO 99
<211> LENGTH: 752
<212> TYPE: PRT
<213> ORGANISM: Chlamydomonas reinhardtii

<400> SEQUENCE: 99

Met Asp Lys Ala Glu Arg Ala Ala Gly Gly Pro Asn Ala Ala Ser Glu
1 5 10 15

Asp Asp Trp Leu Leu Glu Phe Trp Pro Glu Pro Ala Ala Asp Phe Pro
20 25 30

Ala Pro Val Ala Pro Met Leu Ser Gln His Gln Asp Ala Ala Gln Leu
35 40 45

Pro Glu Ala Met Pro Gln Gln Gln Gly Leu Ala Leu Gly Gly Tyr Gly
50 55 60

Leu Thr Gln Gln Pro Ser Asp Phe Met Gln Thr Gly Met Pro Gly Phe
65 70 75 80

Asp Ala Phe Ser Ser Gly Lys Ala Ala Thr Leu Gly Leu Pro Leu Leu
85 90 95

Ala Asp Pro Gln Arg Ala Ser Thr Asp Gly Ala Ser Ala Leu Met Asn
100 105 110

Ala Ala Gln Gln Ser Ser Glu Tyr Met Leu Ala Pro Gly Met Gly Gly
115 120 125

Met Pro His Leu Leu Ala Pro Ser Val Gly Thr Ala Leu Pro Gly Thr
130 135 140

Gly His Thr Gly Phe Ala Asp Leu Ser Met Gly Gly Met Ala Gly Gly
145 150 155 160

Ile Pro Gly Leu Gly Gly Pro Gly Ile Met His Gly Gln Tyr Phe Met
165 170 175

Gln Pro Gln Arg Ala Ala Thr Gly Pro Ala Lys Ser Arg Leu Arg Trp
180 185 190

Thr Pro Glu Leu His Asn Arg Phe Val Asn Ala Val Asn Ser Leu Gly
195 200 205

-continued

```
Gly Pro Asp Lys Ala Thr Pro Lys Gly Ile Leu Lys Leu Met Gly Val
    210                 215                 220

Asp Gly Leu Thr Ile Tyr His Ile Lys Ser His Leu Gln Lys Tyr Arg
225                 230                 235                 240

Leu Asn Ile Arg Leu Pro Gly Glu Ser Gly Leu Ala Gly Asp Ser Ala
                245                 250                 255

Asp Gly Ser Asp Gly Glu Arg Ser Asp Gly Glu Gly Gly Val Arg Arg
            260                 265                 270

Ala Thr Ser Leu Glu Arg Ala Asp Thr Met Ser Gly Met Ala Gly Gly
        275                 280                 285

Ala Ala Ala Ala Leu Gly Arg Ala Gly Gly Thr Pro Gly Gly Ala Leu
    290                 295                 300

Ile Ser Pro Gly Leu Ala Gly Gly Thr Ser Ser Thr Gly Gly Met Ala
305                 310                 315                 320

Ala Gly Gly Gly Gly Gly Gly Gly Leu Val Thr Glu Pro Ser Ile Ser
                325                 330                 335

Arg Gly Thr Val Leu Asn Ala Ala Gly Ala Val Ala Thr Ala Ala Pro
            340                 345                 350

Ala Ala Ala Ala Pro Ala Gly Gly Ser Ala Ala Val Lys Arg Pro Ala
        355                 360                 365

Gly Thr Ser Leu Ser Ser Gly Ser Thr Ala Ser Ala Thr Arg Arg Asn
    370                 375                 380

Leu Glu Glu Ala Leu Leu Phe Gln Met Glu Leu Gln Lys Lys Leu His
385                 390                 395                 400

Glu Gln Leu Glu Thr Gln Arg Gln Leu Gln Leu Ser Leu Glu Ala His
                405                 410                 415

Gly Arg Tyr Ile Ala Ser Leu Met Glu Gln Glu Gly Leu Thr Ser Arg
            420                 425                 430

Leu Pro Glu Leu Ser Gly Gly Ala Pro Ala Ala Ala Pro Val Ala Ala
        435                 440                 445

Gly Gly Ala Ala Gly Gly Met Ile Ala Pro Pro Pro Pro Gln Gln Gln
    450                 455                 460

Leu Gln His Gln Pro Gln Leu Leu Gln Pro Gln Gly Ser Leu Pro Ala
465                 470                 475                 480

Gly Gly Ser Ser Glu Ala His Ala Ala Ala Gly Ala Gly Thr Met Val
                485                 490                 495

Val His Gln Gln Gln Gln Gln His Val His His His His Gln Gln Gln
            500                 505                 510

Gln Val Gln Met Gln Gln His Ala Arg His Cys Asp Thr Cys Gly Ala
        515                 520                 525

Gly Gly Ala Gly Gly Ala Pro Ser Gly Gly Ser Ser Met Gln Gln Leu
    530                 535                 540

Gln Ala Ala Glu Gln Gln Arg Thr Glu Leu Val Val Ala Gly Arg Leu
545                 550                 555                 560

Gly Ser Met Pro Ala Pro Ala Ser Ser Ser Pro Leu Ala Gly Gln Ala
                565                 570                 575

His Gln Gln Gln Pro Leu Ala Gly Gly Ala Ala His Leu Val His Val
            580                 585                 590

His Ser His Thr Pro Gly Gly Gln Pro His Val Gln His Gln Asp Ala
        595                 600                 605

Phe Ala Gly Ala Ala Thr Ala Ala Ala His Ala Ser Pro Gly Leu Pro
    610                 615                 620
```

```
Gln Ser His Ser His Leu Leu Pro Ala Asp Leu Ser Ser Asn Ala Gly
625                 630                 635                 640

Pro Asp Thr Ser Ala Gly Gln Ile Lys Pro Glu Pro Asp Met Ser Gln
                645                 650                 655

Gln Gln Gln Gln Gln Glu Gln Gln Glu Ala Glu Gln Leu Ala Gln Gly
            660                 665                 670

Leu Leu Asn Asp Ser Ser Ala Gly Ala Gly Ala Val Ser Gly Ser Asp
        675                 680                 685

Gly Gly Gly Leu Gly Asp Phe Asp Phe Gly Asp Phe Gly Asp Leu Asp
    690                 695                 700

Gly Gly Ala Gln Gly Gly Leu Leu Gly Pro Gly Asp Leu Ile Gly Ile
705                 710                 715                 720

Ala Glu Leu Glu Ala Ala Ala Ala His Glu Gln Gln Gln Glu Gln Glu
                725                 730                 735

His Asp Pro Leu Asp Ala Asp Arg Ala Lys Arg Gln Arg Val Glu Pro
            740                 745                 750


<210> SEQ ID NO 100
<211> LENGTH: 6
<212> TYPE: DNA
<213> ORGANISM: Chlamydomonas reinhardtii

<400> SEQUENCE: 100

ccctaa                                                                 6


<210> SEQ ID NO 101
<211> LENGTH: 8
<212> TYPE: DNA
<213> ORGANISM: Chlamydomonas reinhardtii

<400> SEQUENCE: 101

rtaccgta                                                               8


<210> SEQ ID NO 102
<211> LENGTH: 8
<212> TYPE: DNA
<213> ORGANISM: Chlamydomonas reinhardtii

<400> SEQUENCE: 102

rtacvgta                                                               8


<210> SEQ ID NO 103
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (9)..(9)
<223> OTHER INFORMATION: ACETYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
```

```
<222> LOCATION: (10)..(10)
<223> OTHER INFORMATION: PHOSPHORYLATION
<220> FEATURE:
<221> NAME/KEY: MOD_RES
<222> LOCATION: (14)..(14)
<223> OTHER INFORMATION: ACETYLATION
<220> FEATURE:
<221> NAME/KEY: MOD_RES
<222> LOCATION: (17)..(17)
<223> OTHER INFORMATION: METHYLATION
<220> FEATURE:
<221> NAME/KEY: MOD_RES
<222> LOCATION: (18)..(18)
<223> OTHER INFORMATION: ACETYLATION
<220> FEATURE:
<221> NAME/KEY: MOD_RES
<222> LOCATION: (23)..(23)
<223> OTHER INFORMATION: ACETYLATION
<220> FEATURE:
<221> NAME/KEY: MOD_RES
<222> LOCATION: (26)..(27)
<223> OTHER INFORMATION: METHYLATION
<220> FEATURE:
<221> NAME/KEY: MOD_RES
<222> LOCATION: (28)..(28)
<223> OTHER INFORMATION: PHOSPHORYLATION
<220> FEATURE:
<221> NAME/KEY: MOD_RES
<222> LOCATION: (36)..(36)
<223> OTHER INFORMATION: METHYLATION

<400> SEQUENCE: 103

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His
        35

<210> SEQ ID NO 104
<211> LENGTH: 18
<212> TYPE: DNA
<213> ORGANISM: Artificial Sequence
<220> FEATURE:
<223> OTHER INFORMATION: Synthetic construct

<400> SEQUENCE: 104

gtacggtagg catacaat                                               18
```